US012767647B2

(12) United States Patent
Beckwith et al.

(10) Patent No.: US 12,767,647 B2
(45) Date of Patent: Oct. 20, 2026

(54) GLUE DEGRADERS AND METHODS OF USE THEREOF

(71) Applicant: NOVARTIS AG, Basel (CH)

(72) Inventors: Rohan Eric John Beckwith, San Diego, CA (US); Simone Bonazzi, Cambridge, MA (US); Nicole Buschmann, Basel (CH); Artiom Cernijenko, Cambridge, MA (US); Aleem Fazal, Wilmington, MA (US); Matthew James Hesse, Oakland, CA (US); Julie Lachal, Bartenheim (FR); Hasnain Ahmed Malik, Boston, MA (US); James R. Manning, Emeryville, CA (US); Pierre Nimsgern, Saint Louis (FR); Gary O'Brien, Maynard, MA (US); Anna Vulpetti, Basel (CH); Junping Zhao, Arlington, MA (US)

(73) Assignee: NOVARTIS AG, Basel (CH)

( * ) Notice: Subject to any disclaimer, the term of this patent is extended or adjusted under 35 U.S.C. 154(b) by 994 days.

(21) Appl. No.: 17/642,292

(22) PCT Filed: Sep. 16, 2020

(86) PCT No.: PCT/IB2020/058641

§ 371 (c)(1),
(2) Date: Mar. 11, 2022

(87) PCT Pub. No.: WO2021/053555

PCT Pub. Date: Mar. 25, 2021

(65) Prior Publication Data

US 2022/0363671 A1 Nov. 17, 2022

Related U.S. Application Data

(60) Provisional application No. 62/901,229, filed on Sep. 16, 2019.

(51) Int. Cl.

| | |
|---|---|
| ***C07D 405/04*** | (2006.01) |
| ***A61K 31/513*** | (2006.01) |
| ***A61P 11/00*** | (2006.01) |
| ***A61P 25/00*** | (2006.01) |
| ***A61P 29/00*** | (2006.01) |
| ***A61P 31/00*** | (2006.01) |
| ***A61P 35/00*** | (2006.01) |
| ***A61P 37/02*** | (2006.01) |
| ***C07D 401/04*** | (2006.01) |
| ***C07D 401/14*** | (2006.01) |
| ***C07D 403/04*** | (2006.01) |
| ***C07D 403/14*** | (2006.01) |
| ***C07D 413/04*** | (2006.01) |
| ***C07D 413/12*** | (2006.01) |
| ***C07D 471/04*** | (2006.01) |

(52) U.S. Cl.
CPC .......... *C07D 405/04* (2013.01); *A61K 31/513* (2013.01); *C07D 401/14* (2013.01); *C07D 413/04* (2013.01); *C07D 471/04* (2013.01)

(58) Field of Classification Search
CPC .. C07D 405/04; C07D 401/14; C07D 413/04; C07D 471/04; A61K 31/513
See application file for complete search history.

(56) References Cited

U.S. PATENT DOCUMENTS

| | | | |
|---|---|---|---|
| 8,796,254 B2 | 8/2014 | Payan et al. | |
| 9,511,058 B2 | 12/2016 | Payan et al. | |
| 9,694,084 B2 | 7/2017 | Bradner et al. | |
| 9,750,816 B2 | 9/2017 | Bradner et al. | |
| 9,770,512 B2 | 9/2017 | Bradner et al. | |
| 9,796,698 B2 | 10/2017 | Muller et al. | |
| 9,821,068 B2 | 11/2017 | Bradner et al. | |
| 9,968,596 B2 | 5/2018 | Cathers et al. | |
| 10,660,968 B2 | 5/2020 | Phillips et al. | |
| 10,849,980 B2 | 12/2020 | Bradner et al. | |
| 11,185,592 B2 | 11/2021 | Phillips et al. | |
| 11,285,218 B2 | 3/2022 | Buckley et al. | |
| 11,292,792 B2 | 4/2022 | Ji et al. | |
| 11,293,023 B2 | 4/2022 | Buckley et al. | |
| 2009/0118276 A1 | 5/2009 | Gopalsamy et al. | |
| 2016/0176916 A1 | 6/2016 | Bradner et al. | |
| 2018/0099940 A1 | 4/2018 | Crew et al. | |
| 2018/0155322 A1 | 6/2018 | Crew et al. | |
| 2018/0215731 A1 * | 8/2018 | Crew | A61K 47/55 |

(Continued)

FOREIGN PATENT DOCUMENTS

| | | |
|---|---|---|
| CN | 106932576 A | 7/2017 |
| EP | 2177615 A1 | 4/2010 |
| EP | 2682750 A1 | 1/2014 |

(Continued)

OTHER PUBLICATIONS

Norris, S. et. al. J. Med. Chem. 2023, 66, 16388-16409. (Year: 2023).*

(Continued)

*Primary Examiner* — Clinton A Brooks
*Assistant Examiner* — Kendall Nicole Heitmeier
(74) *Attorney, Agent, or Firm* — Emily T. Wu

(57) ABSTRACT

Described herein are glue degrader compounds comprising pyrimidine-2,4-dione and dihydropyrimidine-2,4-dione, their various targets, their preparation, pharmaceutical compositions comprising them, and their use in the treatment or prevention of conditions, diseases, and disorders mediated by various target proteins.

9 Claims, No Drawings

(56) References Cited

U.S. PATENT DOCUMENTS

| | | | |
|---|---|---|---|
| 2021/0002285 | A1 | 1/2021 | Arista et al. |

FOREIGN PATENT DOCUMENTS

| | | | | |
|---|---|---|---|---|
| EP | 3050570 | A1 | 8/2016 | |
| EP | 3061758 | A1 | 8/2016 | |
| EP | 3202461 | A1 | 8/2017 | |
| EP | 3061758 | B1 | 1/2018 | |
| EP | 3272739 | A1 | 1/2018 | |
| JP | 2009092508 | A | 4/2009 | |
| KR | 20070120709 | A | 12/2007 | |
| KR | 20090071808 | A | 7/2009 | |
| WO | 9116315 | A1 | 10/1991 | |
| WO | 9854170 | A1 | 12/1998 | |
| WO | 0244372 | A2 | 6/2002 | |
| WO | 03014315 | A2 | 2/2003 | |
| WO | 2004029041 | A1 | 4/2004 | |
| WO | 2004078163 | A2 | 9/2004 | |
| WO | 2005044178 | A2 | 5/2005 | |
| WO | 2006028964 | A1 | 3/2006 | |
| WO | 2006060507 | A2 | 6/2006 | |
| WO | 2006060507 | A3 | 6/2006 | |
| WO | 2006061216 | A2 | 6/2006 | |
| WO | 2007079182 | A2 | 7/2007 | |
| WO | 2008115516 | A2 | 9/2008 | |
| WO | 2008145562 | A1 | 12/2008 | |
| WO | 2009039127 | A1 | 3/2009 | |
| WO | 2009039135 | A1 | 3/2009 | |
| WO | 2009094592 | A2 | 7/2009 | |
| WO | 2009137095 | A2 | 11/2009 | |
| WO | 2010053732 | A1 | 5/2010 | |
| WO | 2010142656 | A1 | 12/2010 | |
| WO | 2011015037 | A1 | 2/2011 | |
| WO | 2011056505 | A1 | 5/2011 | |
| WO | 2011100380 | A1 | 8/2011 | |
| WO | 2012054509 | A2 | 4/2012 | |
| WO | 2012175613 | A1 | 12/2012 | |
| WO | 2013006474 | A2 | 1/2013 | |
| WO | 2013008095 | A1 | 1/2013 | |
| WO | 2013037118 | A1 | 3/2013 | |
| WO | 2013157021 | A1 | 10/2013 | |
| WO | 2014039960 | A1 | 3/2014 | |
| WO | 2014200952 | A2 | 12/2014 | |
| WO | 2015050875 | A1 | 4/2015 | |
| WO | 2015107196 | A1 | 7/2015 | |
| WO | 2015109212 | A1 | 7/2015 | |
| WO | 2015160845 | A2 | 10/2015 | |
| WO | 2015160845 | A3 | 10/2015 | |
| WO | 2015197028 | A1 | 12/2015 | |
| WO | 2016105518 | A1 | 6/2016 | |
| WO | 2016118666 | A1 | 7/2016 | |
| WO | 2016139361 | A1 | 9/2016 | |
| WO | 2016140974 | A1 | 9/2016 | |
| WO | 2016169989 | A1 | 10/2016 | |
| WO | 2016196580 | A1 | 12/2016 | |
| WO | 2016196912 | A1 | 12/2016 | |
| WO | 2016197032 | A1 | 12/2016 | |
| WO | 2016209806 | A1 | 12/2016 | |
| WO | 2017042337 | A1 | 3/2017 | |
| WO | 2017044979 | A2 | 3/2017 | |
| WO | 2017058881 | A1 | 4/2017 | |
| WO | 2017100726 | A1 | 6/2017 | |
| WO | 2017161001 | A1 | 9/2017 | |
| WO | WO-2017161119 | A1 * | 9/2017 | ................ A61P 3/10 |
| WO | 2017176958 | A1 | 10/2017 | |
| WO | 2017184746 | A1 | 10/2017 | |
| WO | 2017185023 | A1 | 10/2017 | |
| WO | 2017185031 | A1 | 10/2017 | |
| WO | 2017185034 | A1 | 10/2017 | |
| WO | 2017223452 | A1 | 12/2017 | |
| WO | 2018033556 | A1 | 2/2018 | |
| WO | 2018064589 | A1 | 4/2018 | |
| WO | 2018071606 | A1 | 4/2018 | |
| WO | 2018098288 | A1 | 5/2018 | |
| WO | 2018102725 | A1 | 6/2018 | |
| WO | 2018119448 | A1 | 6/2018 | |
| WO | 2018140809 | A1 | 8/2018 | |
| WO | 2018144649 | A1 | 8/2018 | |
| WO | 2018148440 | A1 | 8/2018 | |
| WO | 2018148443 | A1 | 8/2018 | |
| WO | 2018187506 | A1 | 10/2018 | |
| WO | 2019014429 | A1 | 1/2019 | |
| WO | 2019023553 | A1 | 1/2019 | |
| WO | 2019025467 | A1 | 2/2019 | |
| WO | 2019034690 | A1 | 2/2019 | |
| WO | 2019034693 | A1 | 2/2019 | |
| WO | 2019038717 | A1 | 2/2019 | |
| WO | 2019060693 | A1 | 3/2019 | |
| WO | 2019079569 | A1 | 4/2019 | |
| WO | 2019092170 | A1 | 5/2019 | |
| WO | 2019099868 | A2 | 5/2019 | |
| WO | 2019099926 | A1 | 5/2019 | |
| WO | 2019121562 | A1 | 6/2019 | |
| WO | 2019140387 | A1 | 7/2019 | |
| WO | 2019165229 | A1 | 8/2019 | |
| WO | 2019186343 | A1 | 10/2019 | |
| WO | 2019186358 | A1 | 10/2019 | |
| WO | 2019191112 | A1 | 10/2019 | |
| WO | 2019242625 | A1 | 12/2019 | |
| WO | 2020041308 | A1 | 2/2020 | |
| WO | 2020051235 | A1 | 3/2020 | |
| WO | 2020051564 | A1 | 3/2020 | |
| WO | 2020081556 | A2 | 4/2020 | |
| WO | 2020132561 | A1 | 6/2020 | |
| WO | 2020160192 | A1 | 8/2020 | |
| WO | 2020160196 | A1 | 8/2020 | |
| WO | 2020160198 | A1 | 8/2020 | |
| WO | 2020181232 | A1 | 9/2020 | |
| WO | 2021011913 | A1 | 1/2021 | |
| WO | 2021018018 | A1 | 2/2021 | |
| WO | 2021022163 | A2 | 2/2021 | |
| WO | 2021053495 | A1 | 3/2021 | |
| WO | 2021055295 | A1 | 3/2021 | |
| WO | 2021087093 | A1 | 5/2021 | |
| WO | 2021101919 | A1 | 5/2021 | |
| WO | 2021155100 | A1 | 8/2021 | |
| WO | 2021155225 | A1 | 8/2021 | |
| WO | 2021168197 | A1 | 8/2021 | |
| WO | 2021178920 | A1 | 9/2021 | |
| WO | 2021194914 | A1 | 9/2021 | |
| WO | 2021219070 | A1 | 11/2021 | |
| WO | 2022025880 | A1 | 2/2022 | |
| WO | 2022065962 | A1 | 3/2022 | |
| WO | 2022069520 | A1 | 4/2022 | |

OTHER PUBLICATIONS

Zoppi, V. et. al. J. Med. Chem. 2019, 62, 699-726 (Year: 2019).*

Najjar, A. & Karaman, R. Expert Opinion on Drug Discovery, 2018, 14(3), 199-220 (Year: 2018).*

Sasso, J. M. et. al. Biochemistry, 2023, 62, 601-623 (Year: 2023).*

Burris, et al., Phase II Study of Capecitabine in Combination With Thalidomide in Patients With Metastatic Breast Cancer, Cancer Investigation, 28(4), 408-412, Apr. 22, 2010.

Dyson, et al., Chemistry of Synthetic Drugs, 12-19, 1964.

Mashkovsky, Medicaments, vol. 1, p. 8, 1998.

Pokrovsky, Antitumor Agents, Small Medical Encyclopedia, 5, 90-96, 1996.

Pokrovsky, Popular Medical Encyclopedia, Popular Medical Encyclopedia, 4th edition, p. 317, 1997.

Bahl, et al., Scaffold-hopping with zwitterionic CCR3 antagonists: Identification and optimisation of a series with good potency and pharmacokinetics leading to the discovery of AZ12436092, Bioorganic & Medicinal Chemistry Letters, Sep. 11, 2012, 6694-6699, 22.

Bian, et al., Discovery of NAD(P)H: quinone oxidoreductase 1 (NQ01) inhibitors woth novel chemical scaffolds by shape-based virtual screning combined with cascade docking, RSC Advances, 2015, 49471-49479, 5.

Cheung, et al., Discovery of Small Molecule Splicing Modulators of Survival Motor Neuron-2 (SMN2) for the Treatment of Spinal Muscular Atrophy (SMA), J Med. Chem., Nov. 8, 2018, 11021-11036, 61.

(56) References Cited

OTHER PUBLICATIONS

Coll, et al., A small-molecule inhibitor of the NLRP3 inflammasome for the treatment of inflammatory diseases, Nature Medicine, Mar. 2015, 248-255, 21(3).
Doig, et al., Rational design of inhibitors of the bacterical cell wall synthetic enzyme GlmU using virtual screening and lead-hopping, Bioorganic & Medicinal Chemisty Letters, Sep. 16, 2014, 6256-6269, 22.
Donner, et al., High potency improvements to weak aryl uracil HCV polymerase inhibitor leads, Bioorganic & Medicinal Chemisty Letters, Jun. 4, 2013, 4367-4369, 23.
Gupta, et al., Discovery of dual binding site acetylcholinesterase inhibitiors identified byb pharmacophore modelling and sequential virtual screening techniques, Bioorganic & medicinal chemistry letters, Jan. 1, 2011, 1105-1112, 21.
Hansen, et al., Protein Degradation via CRL4CRBN Ubiquitin Ligase: Discovery and Structure-Activity Relationships of Novel Glutarimide Analogs That Promote Degradation of Aiolos and/or GSPT1, Journal of Medicinal Chemistry, 2018, 492-503, 61.
Harada, et al., Expansion of Th1-like Vγ9Vδ2T cells by new-generation IMiDs, lenalidomide and pomalidomide, in combination with zoledronic acid, Leukemia, 2017, 234-265, 31.
Huang, et al., A Chemoproteomic Approach to Query the Degradable Kinome Using a Multi-kinase Degrader, Cell Chemical Biology, Jan. 18, 2018, 1-12, e1-e6, 25.
Ilyin, et al., Synthesis of Heterocyclic Compounds Possessing the 4H-Thieno[3,2-b]Pyrrole Moiety, Journal of Combinatorial Chemistry, 2007, 96-106, 9(1).
Jones, et al., Lenalidomide, Thalidomide, and Pomalidomide Reactivate the Epstein-Barr Virus Lytic Cycle Through Phosphoinositide 3-kinase Signaling and Ikaros Expression, Clin Cancer Res, Oct. 1, 2016, 4901-4912, 22(19).
Kim, et al., Discovery of thienopyrrolotriazine derivatives to protect mitochondrial function against Abeta-induced neurotoxicity, European Journal of Medicinal Chemistry, Sep. 21, 2017, 240-256, 141.
Kronke, et al., IKZF1 expression is a prognostic marker in newly diagnosed standard-risk multiple myeloma treated with lenalidomide and intensive chemotherapy: a study of the German Myeloma Study Group (DSMM), Leukemia, 2017, 1363-1367, 31.
Kronke, et al., Lenalidomide Causes Selective Degradation of IKZF1 and IKZF3 in Multiple Myeloma Cells, Science, Jan. 17, 2014, 301-305, 343.
Lu, et al., Hijacking the E3 Ubiquitin Ligase Cereblon to Efficiently Target BRD4, Chemistry & Biology, Jun. 18, 2015, 755-763, 22.
Matyskiela, et al., A Cereblon Modulator (CC-220) with Improved Degradation of Ikaros and Aiolos, Journal of Medicinal Chemistry, 2018, 535-542, 61.
Nakayama, et al., Aiolos Overexpression in Systemic Lupus Erythematosus B Cell Subtypes and BAFF-Induced Memory B Cell Differentiation Are Reduced by CC-220 Modulation of Cereblon Activity, The Journal of Immunology, 2007, 2388-2407, 199.
Randolph, et al., Synthesis and Biological Characterization of Aryl Uracil Inhibitors of Hepatitis C Virus NS5B Polymerase: Discovery od ABT-072, a trans-Stilbene Analog with Good Oral Bioavailability, Journal of Medicinal Chemistry, Jan. 17, 2018, 1153-1163, 61.
Registry No. 1448326-82-6, entered Aug. 14, 2013—Registry No. 959150-73-3, entered Dec. 21, 2007.
Registry No. 1500994-95-5, entered Dec. 22, 2013.
Registry No. 1711790-34-9, entered May 25, 2015.
Registry No. 2154353-25-8, entered Dec. 8, 2017—Registry No. 959150-73-3, entered Dec. 21, 2007.
Registry No. 2222115-39-9.
Registry No. 2241326-47-4.
Remillard, et al., Degradation of the BAF Complex Factor BRD9 by Heterobifunctional Ligands, Angew. Chem. Int. Ed., 2017, 5738-5743, 56.
Schafer, et al., Cereblon modulator iberdomide induces degradation of the transcription factors Ikaros and Aiolos: Immunomodulation in healthy volunteers and relevance to systemic lupus erythematosus, Ann Rheum Dis., Jun. 26, 2018, 1516-1523, 77.
Stewart, et al., New thalidomide analogues derived through Sonogashira or Suzuki reactions and their TNF expression inhibition profiles, Bioorganic & Medicinal Chemistry, 2010, 650-662, 18.
Stewart, et al., Synthesis and TNF expression inhibitory properties of new thalidomide analogues derived via Heck cross coupling, Bioorganic & Medicinal Chemistry Letters, 2007, 5819-5824, 17.
Talamas, et al., Discovery of N-[4-[6-tert-Butyl-5-methoxy-8-(6-methoxy-2-oxo-1H-pyridin-3-yl)-3-quinolyl]phenyl] methanesulfonamide (RG7109), A Potent Inhibitor of the Hepatitis C Virus NS5B Polymerase, Journal of Medicinal Chemistry, Nov. 6, 2013, 1914-1931, 57.
Voskiene, et al., Synthesis, chemical properties, and antimicrobial activity of 2- and 2,3-substituted [(tetrahydro-2,4-dioxopyrimidin-1(2H)-yl)-phenoxy]naphthalene-1,4-diones, Monatsh Chem, Mar. 18, 2011, 529-537, 142.
Woo, et al., Identification of a thalidomide derivative that selectively targets tumorigenic liver progenitor cells and comparing its effects with lenalidomide and sorafenib, European Journal of Medicinal Chemistry, Mar. 9, 2016, 275-283, 120.
Yeung, et al., Novel thalidomide analogues with potent NFκB and TNF expression inhibition, Med. Chem. Commun., 2011, 1073-1078, 2.
Zoppi, et al., Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7, J Med Chem, 2019, 699-726, 62.
Boichenko, et al., Chemical Ligand Space of Cereblon, ACS Omega, 3, 11163-11171, Sep. 14, 2018.
Belikov, Relationship between the chemical structure, properties of compounds and their action on the body, Pharmaceutical Chemistry, 2007, 27-29, chapter 2.6.
Chhabra, et al., A review of drug isomerism and its significance, International Journal of Applied Basic Medical Research, 3(1), 16-18, 2013.
Clinical Trial NCT02452268, Dec. 17, 2017, available on a href= "https://www.clinicaltrials.gov/ct2/show/NCT02452268" target="_blank"https://www.clinicaltrials.gov/ct2/show/NCT02452268/a.
STN Online Search, CAS reg. No. 2305255-85-8, 1557538-44-9, 1554775-93-7, 1521243-81-1, 1512199-69-7, 1566374-86-4, 1541832-69-2, 1700060-22-5, etc. entered on Apr. 24, 2019, pp. 36.

* cited by examiner

GLUE DEGRADERS AND METHODS OF USE THEREOF

RELATED APPLICATIONS

This application is a U.S. National Phase filing of International Application Serial No. PCT/IB2020/058641, filed 16 Sep. 2020, which claims priority to U.S. Provisional application No. 62/901,229, filed 16 Sep. 2019, respectively, each of which are incorporated herein by reference in their entireties.

FIELD OF THE DISCLOSURE

Described herein are glue degrader compounds, their various targets, their preparation, pharmaceutical compositions comprising them, and their use in the treatment of conditions, diseases, and disorders mediated by various target proteins.

BACKGROUND OF THE DISCLOSURE

The Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity.

Cereblon (CRBN) interacts with damaged DNA binding protein 1 and forms an E3 ubiquitin ligase complex with Cullin 4 where it functions as a substrate receptor in which the proteins recognized by CRBN might be ubiquitinated and degraded by proteasomes.

Proteasome-mediated degradation of unneeded or damaged proteins plays a very important role in maintaining regular function of a cell, such as cell survival, proliferation and growth. A new role for CRBN has been identified; i.e., the binding of immunomodulatory drugs (IMiDs), e.g., thalidomide, to CRBN has now been associated with teratogenicity and also the cytotoxicity of IMiDs, including lenalidomide, which are widely used to treat multiple myeloma patients. CRBN is likely a key player in the binding, ubiquitination, and degradation of factors involved in maintaining function of myeloma cells.

Glue degrader compounds that bind to and alter the specificity of a cereblon complex have been shown to induce proteasome-mediated degradation of selected proteins. These molecules can been used to modulate protein expression and may be useful as biochemicals or therapeutics for the treatment of diseases or disorders. There is a need for glue degrader compounds for targeting proteins for degradation. The present application addresses the need for glue degrader molecules that are directed to a variety of protein targets.

SUMMARY OF THE DISCLOSURE

A first aspect of the present disclosure relates to compounds or a pharmaceutically acceptable salts, hydrates, solvates, prodrugs, stereoisomers, or tautomers thereof that bind to and alter the specificity of a cereblon complex to induce ubiquitination and degradation of a complex-associated protein.

In another aspect, the disclosure relates to compounds that comprises, (i) a tris-tryptophan Pocket Binder moiety that binds to the tris-tryptophan pocket of Cereblon E3 ligase; and (ii) a target affinity moiety attached covalently to the tris-tryptophan Pocket Binder moiety that interacts with the surface of the Cereblon E3 ligase altering its surface and causing the ligase to have affinity for a Target Protein.

Another aspect of the present disclosure relates to compounds of Formula (I)

(I)

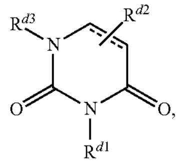

or a pharmaceutically acceptable salt, hydrate, solvate, prodrug, stereoisomer, or tautomer thereof, wherein:

⎓ is a single bond or a double bond;

$R^{d1}$ is H, $—CH_2OC(O)R^{15}$, $—CH_2OP(O)OHOR^{15}$, or $—CH_2OP(O)(R^{15})_2$;

$R^{d2}$ is H, $C_{1-6}$ alkyl, halogen, $C_{1-6}$ haloalkyl, or $C_{1-6}$ heteroalkyl;

$R^{d3}$ is

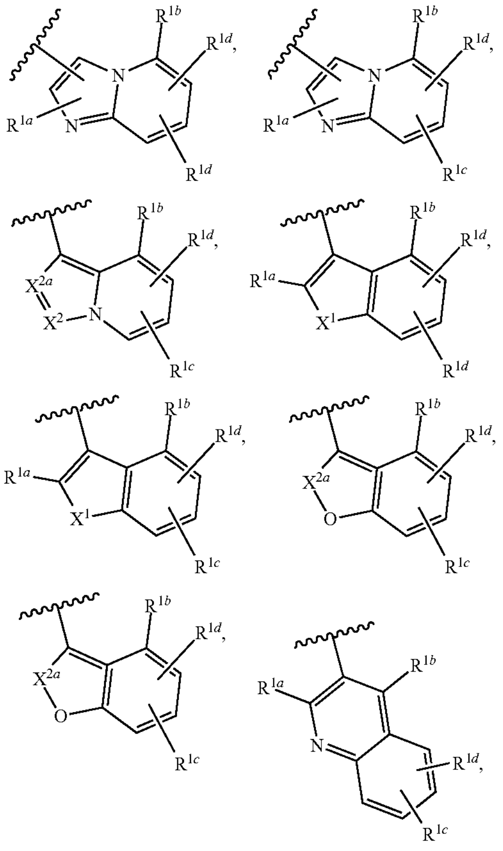

-continued
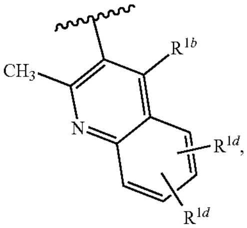
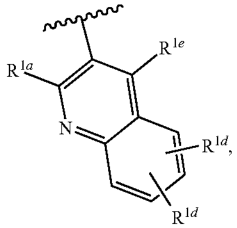
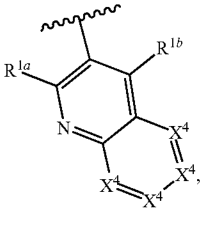
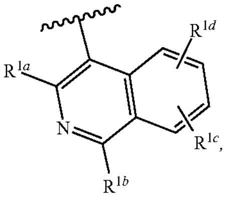
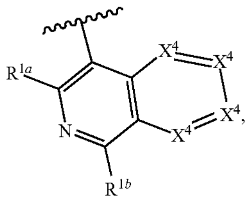
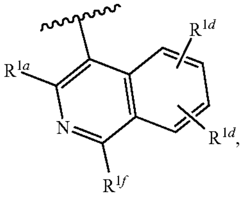
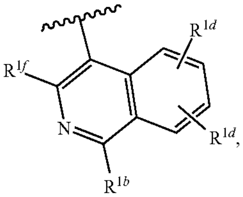
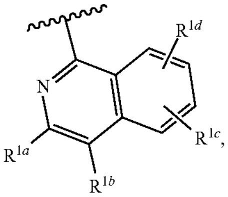
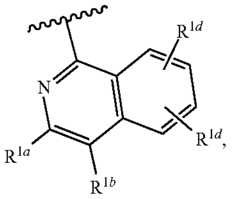
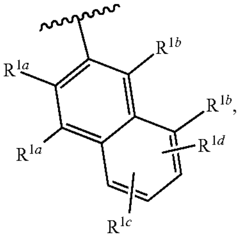
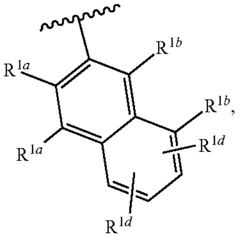
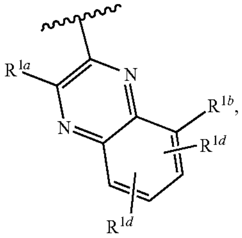
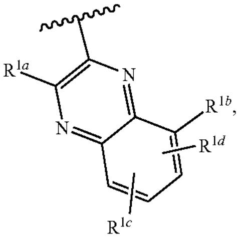
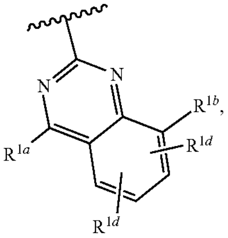
-continued
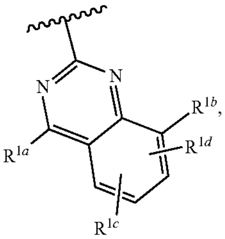
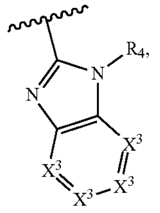
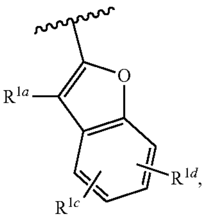
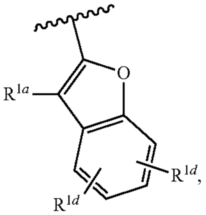
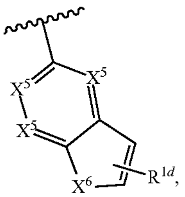
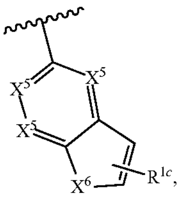
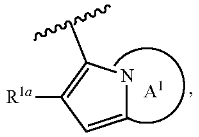
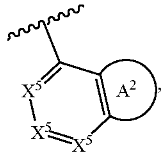
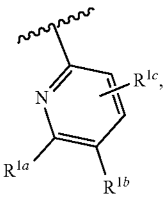
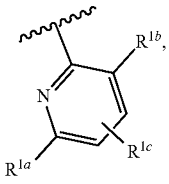
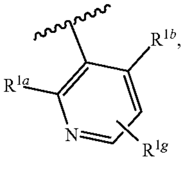
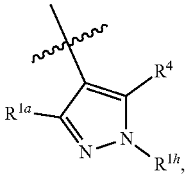
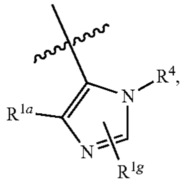
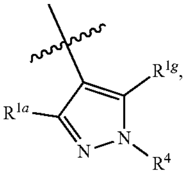
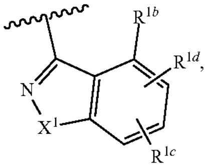
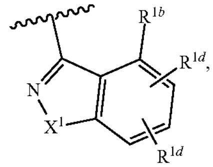

-continued

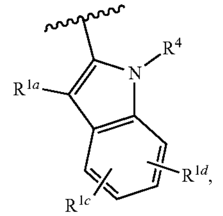

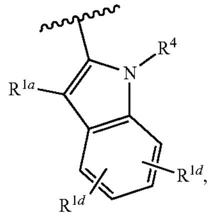

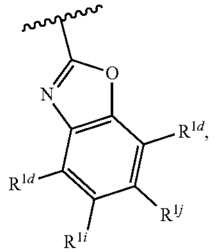

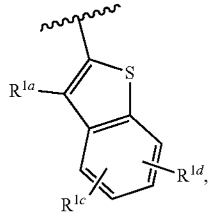

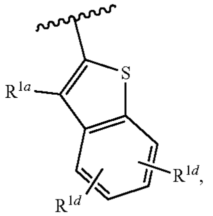

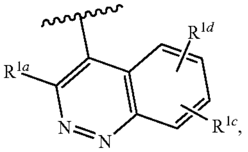

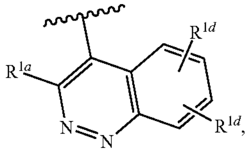

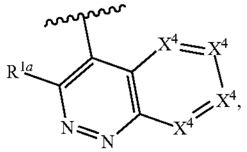

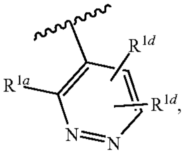

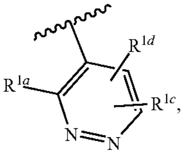

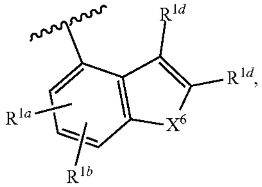

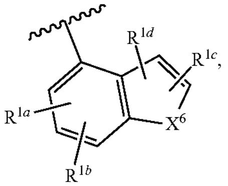

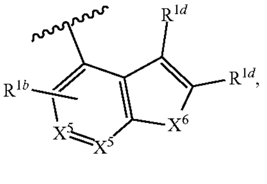

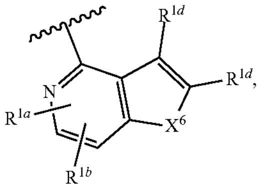

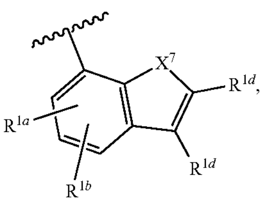

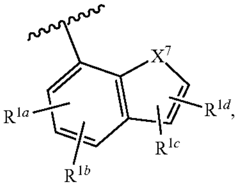

-continued

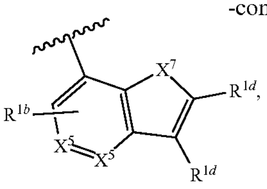

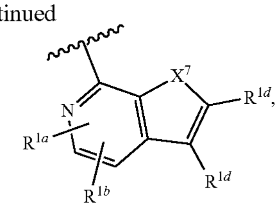

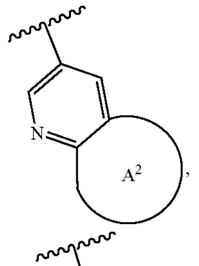

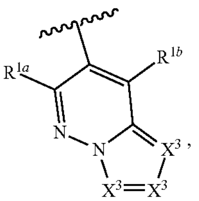

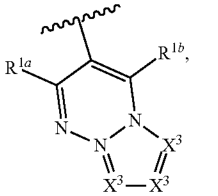

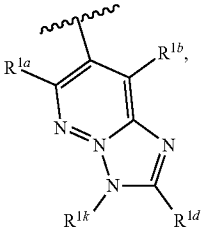

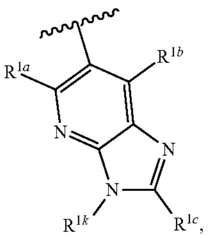

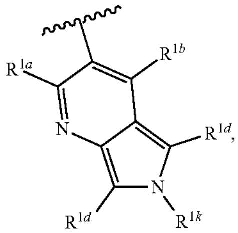

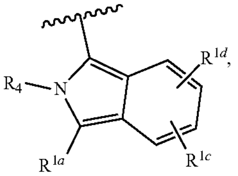

or

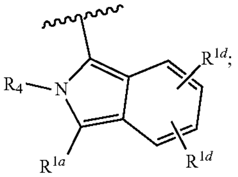

$A^1$ is a 5- or 6-membered heterocyclyl optionally comprising 1-3 additional heteroatoms selected from O, N, and S, or 5-membered heteroaryl optionally comprising 1-3 additional heteroatoms selected from N, $NR^{1k}$, O, and S and substituted with one to three $R^{1d}$;

$A^2$ is a $C_{5-7}$ carbocyclyl or 5- to 7-membered heterocyclyl comprising 1-3 heteroatoms selected from N, $NR^{1k}$, O, and S, wherein the carbocyclyl and heterocyclyl are substituted with one to three $R^{1d}$;

$X^1$ is $NR^4$ or S;

$X^2$ and $X^{2a}$ are each independently $CR^{1a}$ or N;

each $X^3$ is independently $CR^{1d}$ or N, wherein no more than two $X^3$ are N;

each $X^4$ is independently $CR^{1d}$ or N, wherein at least one $X^4$ is N and wherein no more than two $X^4$ are N;

each $X^5$ is independently $CR^{1a}$ or N, wherein no more than two $X^5$ are N;

$X^6$ is $NR^{1k}$, O, or S;

$X^7$ is $NR^4$, O, or S;

$R^{1a}$ and $R^{1b}$ are each independently H, $C_{1-3}$ alkyl, $C_{1-3}$ haloalkyl, $C_{1-3}$ alkoxy, $C_{1-3}$ haloalkoxy, —$NH_2$, —NH($C_{1-3}$ alkyl), —N($C_{1-3}$ alkyl)$_2$, —CN, F, or Cl;

$R^{1c}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR_3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR_3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

each $R^{1d}$ is independently is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR^3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1e}$ is $C_{2-3}$ alkyl, $C_{1-3}$ haloalkyl, $C_{1-3}$ alkoxy, $C_{1-3}$ haloalkoxy, —CN, F, or Cl;

$R^{1f}$ is $C_{1-3}$ alkyl, $C_{1-3}$ haloalkyl, $C_{1-3}$ alkoxy, $C_{1-3}$ haloalkoxy, —CN, F, or Cl;

$R^{1g}$ is $C_{2-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR_3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1h}$ is $C_{4-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$C_{6-10}$ aryl, —$(CH_2)_{2-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR^3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1i}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR_3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR_3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$;

$R^{1j}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}$ $C_{6-10}$ aryl, $-(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR_3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$;

wherein $R^{1d}$, $R^{1i}$, and $R^{1j}$ on the benzoxazole ring are not all simultaneously H;

each $R^{1k}$ is independently is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}$ $C_{6-10}$ aryl, $-(CH_2)_{0-6}$-5- or 6-membered heteroaryl comprising 1-3 heteroatoms selected from O, N, and S, $-C(O)O(CH_2)_{0-4}-C_{3-7}$ carbocyclyl, $-C(O)O(CH_2)_{0-4}$-5- to 7-membered heterocyclyl comprising 1-3 heteroatoms selected from O, N, and S, $-C(O)O(CH_2)_{0-4}-C_{6-10}$ aryl, or $-C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

each $R^2$ is independently $NH_2$, $-NH(C_{1-6}$ alkyl), $-N(C_{1-6}$ alkyl$)_2$, $-C(O)NH_2$, $-C(O)NH(C_{1-6}$ alkyl), $-C(O)N(C_{1-6}$ alkyl$)_2$, $-NHC(O)R^9$, $-N(R^9)C(O)(R^9)$, $-NHS(O)_2R^9$, or $-NR^9S(O)_2R^9$;

$R^3$ is H or $C_{1-6}$ alkyl;

$R^4$ is H or $C_{1-6}$ alkyl;

each $R^5$ is independently $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, $-OH$, $-C(O)H$, $-C(O)(C_{1-6}$ alkyl), $-C(O)(C_{6-10}$ aryl), $-C(O)$(5- or 6-membered heteroaryl), $-C(O)(C_{3-7}$ carbocyclyl), $-C(O)$(5- to 7-membered heterocyclyl), $-(CH_2)_{0-3}C(O)OC_{1-6}$ alkyl, $-C(O)NH_2$, $-C(O)NH(C_{1-6}$ alkyl), $-C(O)N(C_{1-6}$ alkyl$)_2$, $-NHC(O)R^9$, $-N(R^9)C(O)(R^9)$, $-NH_2$, $-NH(C_{1-6}$ alkyl), $-N(C_{1-6}$ alkyl$)_2$, $-NHC(O)O(R^9)$, $-N(R^9)C(O)O(R^9)$, $-NHS(O)_2R^9$, $NR^9S(O)_2R^9$, $-S(O)_qNHR^9$, $-S(O)_qN(R^9)_2$, $-S(O)^qR^9$, $C_{1-6}$ hydroxyalkyl, $-O(CH_2)_{1-3}CN$, CN, $-O(CH_2)_{0-6}-C_{3-7}$ carbocyclyl, $-O(CH_2)_{0-6}$-5- to 7-membered heterocyclyl comprising 1-3 heteroatoms selected from O, N, and S, $-O(CH_2)_{0-3}(C_6$-$C_{10})$aryl, adamantyl, $-O(CH_2)_{0-3}$-5- or 6-membered heteroaryl comprising 1-3 heteroatoms selected from O, N, and S, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}-C_{6-10}$ aryl, and $-(CH_2)_{0-6}$-5- or 6-membered heteroaryl comprising 1-3 heteroatoms selected from O, N, and S, wherein the alkyl is optionally substituted with one to three $R^6$, and the carbocyclyl, heterocyclyl, aryl, and heteroaryl are optionally substituted with one to four $R^8$; or two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$; or two $R^5$ when on adjacent atoms, together with the atoms to which they are attached form a $C_{6-10}$ aryl or a 5- or 6-membered heteroaryl comprising 1-3 heteroatoms selected from O, N, and S; or two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$; or two $R^5$ when on the same carbon atom form $=(O)$;

$R^6$ is $-NH_2$, $-NH(C_{1-6}$ alkyl), $-N(C_{1-6}$ alkyl$)_2$, $C_{6-10}$ aryl, or a 5- or 6-membered heteroaryl comprising 1-3 heteroatoms selected from O, N, and S, wherein the aryl and heteroaryl are optionally substituted with one to three $R^7$;

each $R^7$ is independently $C_{1-6}$ alkyl, $C_{1-6}$ haloalkyl, $C_{1-6}$ alkoxy, $C_{1-3}$ haloalkoxy, halogen, or $C_{6-10}$ aryl;

each $R^8$ is independently $C_{1-6}$ alkyl, $C_{1-6}$ haloalkyl, $C_{1-6}$ alkoxy, $C_{1-6}$ haloalkoxy, halogen, or $-OH$;

$R^9$ is $C_{1-6}$ alkyl, $C_{1-6}$ haloalkyl, 5- to 7-membered heterocyclyl comprising 1-3 heteroatoms selected from O, N, and S, $C_{6-10}$ aryl, or a 5- or 6-membered heteroaryl comprising 1-3 heteroatoms selected from O, N, and S, wherein the aryl and heteroaryl are optionally substituted with one to three $R^{11}$;

each $R^{10}$ is $C_{1-6}$ alkyl, $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S;

each $R^{11}$ is independently $C_{1-6}$ alkyl, $C_{1-6}$ haloalkyl, $C_{1-6}$ alkoxy, $C_{1-6}$ haloalkoxy, —NHC(O)($C_{1-6}$ alkyl), —N($C_{1-6}$ alkyl)C(O)($C_{1-6}$alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$;

each $R^{12}$ is independently $C_{1-6}$ alkyl, $C_{1-6}$ haloalkyl, $C_{1-6}$ alkoxy, or $C_{1-3}$ haloalkoxy;

$R^{13}$ is independently at each occurrence $C_{1-6}$ alkyl, $C_{1-6}$ haloalkyl, $C_{6-10}$ aryl, or a 5- or 6-membered heteroaryl comprising 1-3 heteroatoms selected from O, N, and S, wherein the alkyl is optionally substituted with one to two $C_{1-6}$ alkoxy and the aryl and heteroaryl are optionally substituted with one to three $R^{14}$;

each $R^{14}$ is independently $C_{1-6}$ alkyl, $C_{1-6}$ haloalkyl, $C_{1-6}$ alkoxy, $C_{1-3}$ haloalkoxy, halogen, $C_{6-10}$ aryl, or a 5- or 6-membered heteroaryl comprising 1-3 heteroatoms selected from O, N, and S;

$R^{15}$ is H or $C_{1-6}$ alkyl; and q is 0, 1, or 2.

In another aspect, the present disclosure relates to compounds of Formula (I)

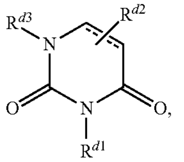

(I)

or a pharmaceutically acceptable salt, hydrate, solvate, prodrug, stereoisomer, or tautomer thereof, wherein:

⎓ is a single bond or a double bond;

$R^{d1}$ is H, —$CH_2OC(O)R^{15}$, —$CH_2OP(O)OHOR^{15}$, or —$CH_2OP(O)(R^{15})_2$;

$R^{d2}$ is H, $C_{1-6}$ alkyl, halogen, $C_{1-6}$ haloalkyl, or $C_{1-6}$ heteroalkyl;

$R^{d3}$ is

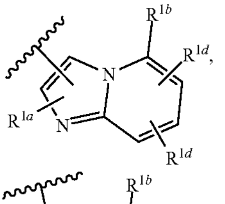
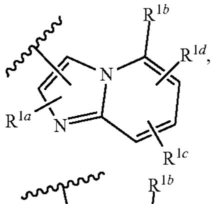
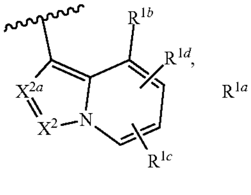
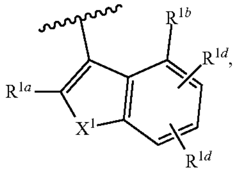

-continued

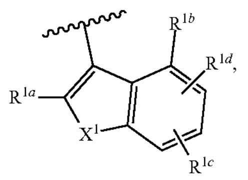
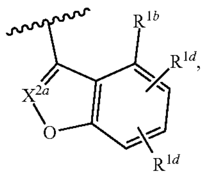
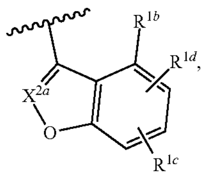
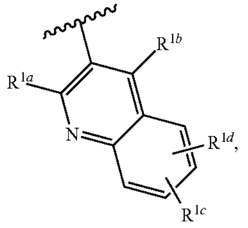
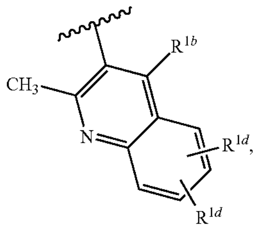
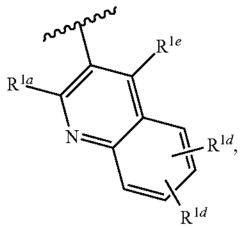
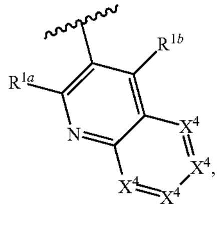
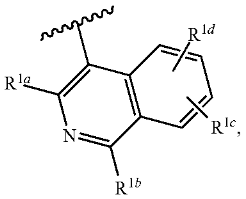
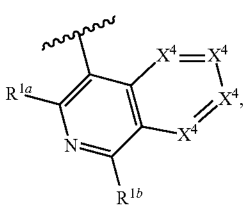
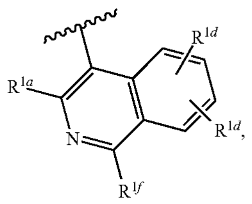
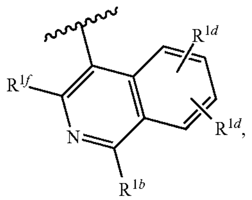
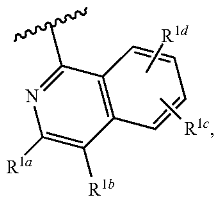
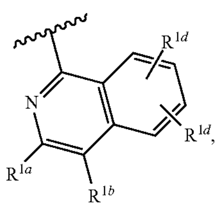
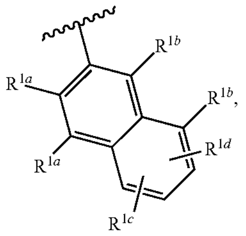

-continued
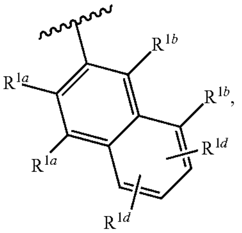
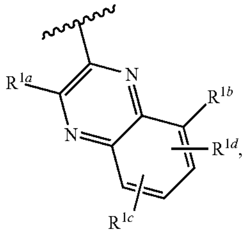
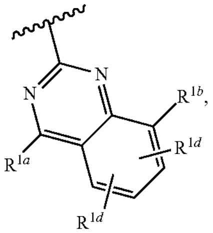
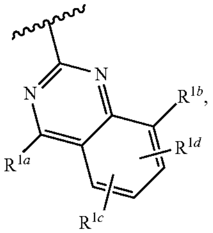
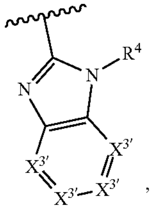
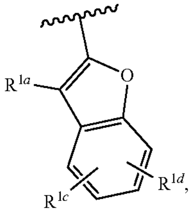
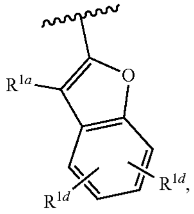
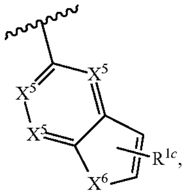
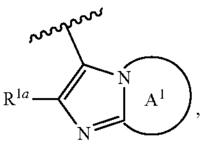
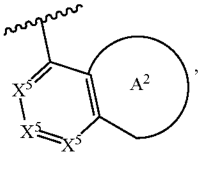
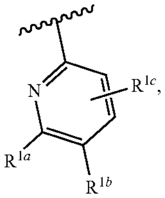
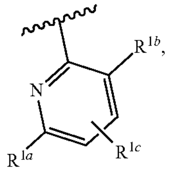
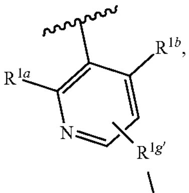
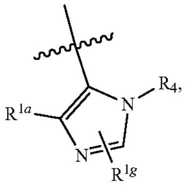
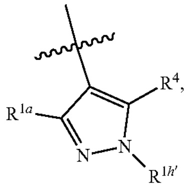
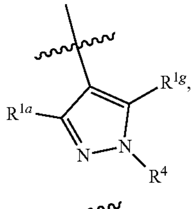
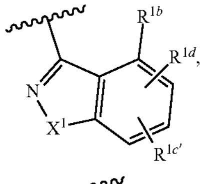
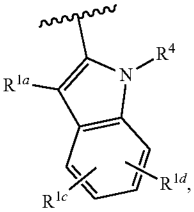
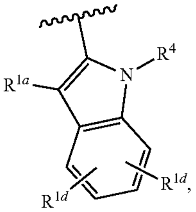
-continued
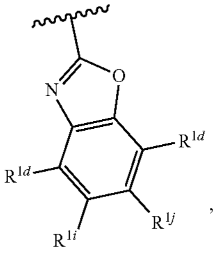
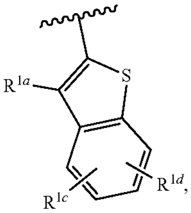
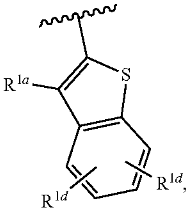
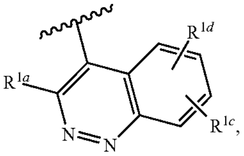
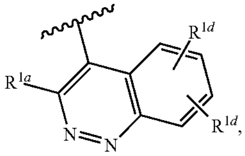
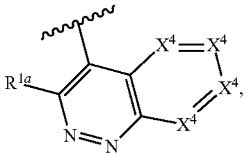
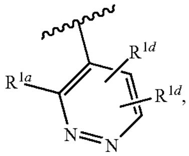
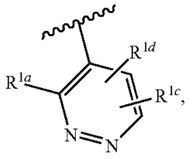
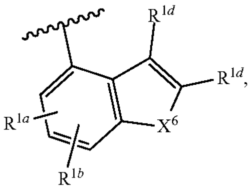
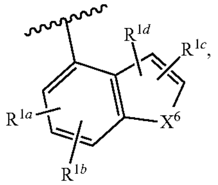
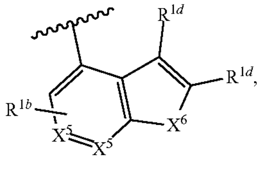
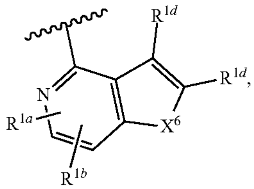
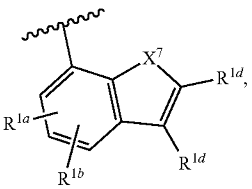
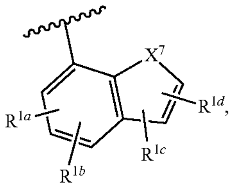
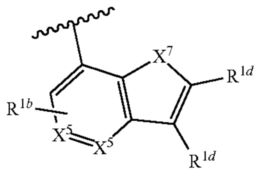

-continued

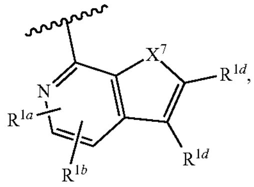

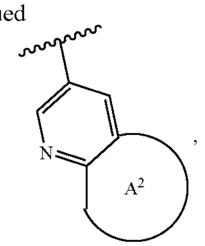

,

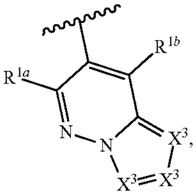

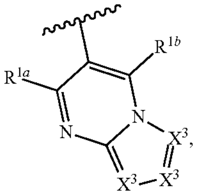

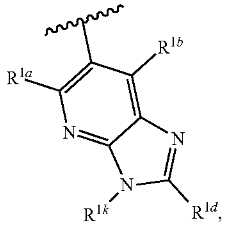

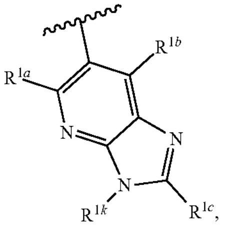

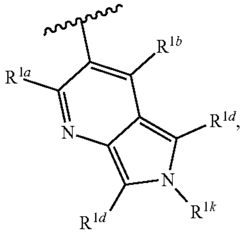

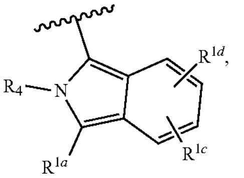

or

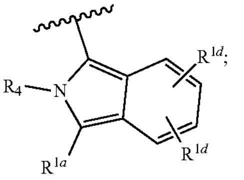

$A^1$ is a 5- or 6-membered heterocyclyl optionally comprising 1-3 additional heteroatoms selected from O, N, and S, or 5-membered heteroaryl optionally comprising 1-3 additional heteroatoms selected from N, $NR^{1k}$, O, and S and substituted with one to three $R^{1d}$;

$A^2$ is a $C_{5-7}$ carbocyclyl or 5- to 7-membered heterocyclyl comprising 1-3 heteroatoms selected from N, $NR^{1k}$ O, and S, wherein the carbocyclyl and heterocyclyl are substituted with one to three $R^{1d}$;

$X^1$ is $NR^4$ or S;

$X^2$ and $X^{2a}$ are each independently $CR^{1a}$ or N;

each $X^3$ is independently $CR^{1d}$ or N, wherein no more than two $X^3$ are N;

each $X^{3'}$ is independently $CR^{1d}$, $CR^{1c}$ or N, wherein no more than two $X^3$ are N and wherein at least one $X^{3'}$ is $CR^{1c}$;

each $X^4$ is independently $CR^{1d}$ or N, wherein at least one $X^4$ is N and wherein no more than two $X^4$ are N;

each $X^5$ is independently $CR^{1a}$ or N, wherein no more than two $X^5$ are N;

$X^6$ is $NR^{1k}$, O, or S;

$X^7$ is $NR^4$, O, or S;

$R^{1a}$ and $R^{1c}$ are each independently H, $C_{1-3}$ alkyl, $C_{1-3}$ haloalkyl, $C_{1-3}$ alkoxy, $C_{1-3}$ haloalkoxy, —$NH_2$, —NH($C_{1-3}$ alkyl), —N($C_{1-3}$ alkyl)$_2$, —CN, F, or Cl;

$R^{1c}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$$NR^3$$(CH_2)_{0-4}$—$C_{3-7}$ carbocyclyl, —$(CH_2)_{0-4}$$NR^3$$(CH_2)_{0-4}$-5- to 7-membered heterocyclyl comprising 1-3 heteroatoms selected from O, N, and S, —$(CH_2)_{0-4}$$NR^3$$(CH_2)_{0-4}$—$C_{6-10}$ aryl, —$(CH_2)_{0-4}$$NR^3$$(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR^3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1c}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, F, Cl, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$$NR^3$$(CH_2)_{0-4}$—$C_{3-7}$ carbocyclyl, —$(CH_2)_{0-4}$$NR^3$$(CH_2)_{0-4}$-5- to 7-membered heterocyclyl comprising 1-3 heteroatoms selected from O, N, and S, —$(CH_2)_{0-4}$$NR^3$$(CH_2)_{0-4}$—$C_{6-10}$ aryl, —$(CH_2)_{0-4}$$NR^3$$(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR^3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

each $R^{1d}$ is independently is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1e}$ is $C_{2-3}$ alkyl, $C_{1-3}$ haloalkyl, $C_{1-3}$ alkoxy, $C_{1-3}$ haloalkoxy, —CN, F, or Cl;

$R^{1f}$ is $C_{1-3}$ alkyl, $C_{1-3}$ haloalkyl, $C_{1-3}$ alkoxy, $C_{1-3}$ haloalkoxy, —CN, F, or Cl;

$R^{1g}$ is $C_{2-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1g'}$ is $C_{2-6}$ alkyl, $C_{2-6}$ alkenyl, $C_{2-6}$ alkynyl, $C_{2-6}$ haloalkyl, $C_{2-6}$ alkoxy, $C_{1-3}$ haloalkoxy, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$, the heterocyclyl is substituted with one to five $R^5$ and the carbocyclyl, aryl, and heteroaryl are optionally substituted with one to five $R^5$;

$R^{1h}$ is $C_{4-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$C_{6-10}$ aryl, —$(CH_2)_{2-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1h'}$ is $C_{4-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$C_{6-10}$ aryl, —$(CH_2)_{2-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, $—(CH_2)_{0-4}—NR^3C(O)—C_{3-7}$ carbocyclyl, $—(CH_2)_{0-4}—NR^3C(O)$-5- to 7-membered heterocyclyl comprising 1-3 heteroatoms selected from O, N, and S, $—(CH_2)_{0-4}—NR^3C(O)—C_{6-10}$ aryl, $—(CH_2)_{0-4}—NR^3C(O)$-5- or 6-membered heteroaryl comprising 1-3 heteroatoms selected from O, N, and S, $—NR^3C(O)O(CH_2)_{0-4}—C_{3-7}$ carbocyclyl, $—NR^3C(O)O(CH_2)_{0-4}$-5- to 7-membered heterocyclyl comprising 1-3 heteroatoms selected from O, N, and S, $—NR^3C(O)O(CH_2)_{0-4}—C_{6-10}$ aryl, or $—NR^3C(O)O(CH_2)_{0-4}$-5- or 6-membered heteroaryl comprising 1-3 heteroatoms selected from O, N, and S, wherein the alkynyl is optionally substituted with one to three $R^2$, the heterocyclyl is substituted with one to five $R^5$, and the carbocyclyl, aryl, and heteroaryl are optionally substituted with one to five $R^5$;

$R^{1i}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, CN, —C(O)OH, $—C(O)OC_{1-6}$ alkyl, $—(CH_2)_{0-4}—C(O)NH_2$, $—(CH_2)_{0-4}—C(O)NH(R^{13})$, $—(CH_2)_{0-4}—C(O)N(R^{13})_2$, $—(CH_2)_{0-6}—C_{3-7}$ carbocyclyl, $—(CH_2)_{0-6}$-5- to 7-membered heterocyclyl comprising 1-3 heteroatoms selected from O, N, and S, $—(CH_2)_{0-6}$ $C_{6-10}$ aryl, $—(CH_2)_{0-6}$-5- or 6-membered heteroaryl comprising 1-3 heteroatoms selected from O, N, and S, $—(CH_2)_{0-4}NR^3(CH_2)_{0-4}—C_{3-7}$ carbocyclyl, $—(CH_2)_{0-4}NR^3(CH_2)_{0-4}$-5- to 7-membered heterocyclyl comprising 1-3 heteroatoms selected from O, N, and S, $—(CH_2)_{0-4}NR^3(CH_2)_{0-4}—C_{6-10}$ aryl, $—(CH_2)_{0-4}NR^3(CH_2)_{0-4}$-5- or 6-membered heteroaryl comprising 1-3 heteroatoms selected from O, N, and S, $—(CH_2)_{0-4}—NR^3C(O)—C_{3-7}$ carbocyclyl, $—(CH_2)_{0-4}—NR^3C(O)$-5- to 7-membered heterocyclyl comprising 1-3 heteroatoms selected from O, N, and S, $—(CH_2)_{0-4}—NR^3C(O)—C_{6-10}$ aryl, $—(CH_2)_{0-4}—NR^3C(O)$-5- or 6-membered heteroaryl comprising 1-3 heteroatoms selected from O, N, and S, $—NR^3C(O)O(CH_2)_{0-4}—C_{3-7}$ carbocyclyl, $—NR^3C(O)O(CH_2)_{0-4}$-5- to 7-membered heterocyclyl comprising 1-3 heteroatoms selected from O, N, and S, $—NR^3C(O)O(CH_2)_{0-4}—C_{6-10}$ aryl, or $—NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$;

$R^{1j}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, $—C(O)OC_{1-6}$ alkyl, $—(CH_2)_{0-4}—C(O)NH_2$, $—(CH_2)_{0-4}—C(O)NH(R^{13})$, $—(CH_2)_{0-4}—C(O)N(R^{13})_2$, $—(CH_2)_{0-6}—C_{3-7}$ carbocyclyl, $—(CH_2)_{0-6}$-5- to 7-membered heterocyclyl comprising 1-3 heteroatoms selected from O, N, and S, $—(CH_2)_{0-6}$ $C_{6-10}$ aryl, $—(CH_2)_{0-6}$-5- or 6-membered heteroaryl comprising 1-3 heteroatoms selected from O, N, and S, $—(CH_2)_{0-4}NR^3(CH_2)_{0-4}—C_{3-7}$ carbocyclyl, $—(CH_2)_{0-4}NR^3(CH_2)_{0-4}$-5- to 7-membered heterocyclyl comprising 1-3 heteroatoms selected from O, N, and S, $—(CH_2)_{0-4}NR^3(CH_2)_{0-4}—C_{6-10}$ aryl, $—(CH_2)_{0-4}NR^3(CH_2)_{0-4}$-5- or 6-membered heteroaryl comprising 1-3 heteroatoms selected from O, N, and S, $—(CH_2)_{0-4}—NR^3C(O)—C_{3-7}$ carbocyclyl, $—(CH_2)_{0-4}—NR^3C(O)$-5- to 7-membered heterocyclyl comprising 1-3 heteroatoms selected from O, N, and S, $—(CH_2)_{0-4}—NR^3C(O)—C_{6-10}$ aryl, $—(CH_2)_{0-4}—NR^3C(O)$-5- or 6-membered heteroaryl comprising 1-3 heteroatoms selected from O, N, and S, $—NR^3C(O)O(CH_2)_{0-4}—C_{3-7}$ carbocyclyl, $—NR^3C(O)O(CH_2)_{0-4}$-5- to 7-membered heterocyclyl comprising 1-3 heteroatoms selected from O, N, and S, $—NR^3C(O)O(CH_2)_{0-4}—C_{6-10}$ aryl, or $—NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$;

wherein $R^{1d}$, $R^{1i}$, and $R^{1j}$ on the benzoxazole ring are not all simultaneously H;

each $R^{1k}$ is independently is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, $—C(O)OC_{1-6}$ alkyl, $—(CH_2)_{0-4}—C(O)NH_2$, $—(CH_2)_{0-4}—C(O)NH(R^{13})$, $—(CH_2)_{0-4}—C(O)N(R^{13})_2$, $—(CH_2)_{0-6}—C_{3-7}$ carbocyclyl, $—(CH_2)_{0-6}$-5- to 7-membered heterocyclyl comprising 1-3 heteroatoms selected from O, N, and S, $—(CH_2)_{0-6}$ $C_{6-10}$ aryl, $—(CH_2)_{0-6}$-5- or 6-membered heteroaryl comprising 1-3 heteroatoms selected from O, N, and S, $—C(O)O(CH_2)_{0-4}—C_{3-7}$ carbocyclyl, $—C(O)O(CH_2)_{0-4}$-5- to 7-membered heterocyclyl comprising 1-3 heteroatoms selected from O, N, and S, $—C(O)O(CH_2)_{0-4}—C_{6-10}$ aryl, or $—C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

each $R^2$ is independently $NH_2$, $—NH(C_{1-6}$ alkyl), $—N(C_{1-6}$ alkyl$)_2$, $—C(O)NH_2$, $—C(O)NH(C_{1-6}$ alkyl), $—C(O)N(C_{1-6}$ alkyl$)_2$, $—NHC(O)R^9$, $—N(R^9)C(O)(R^9)$, $—NHS(O)_2R^9$, or $—NR^9S(O)_2R^9$;

$R^3$ is H or $C_{1-6}$ alkyl;

$R^4$ is H or $C_{1-6}$ alkyl;

each $R^5$ is independently $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, —OH, —C(O)H, $—C(O)(C_{1-6}$ alkyl), $—C(O)(C_{6-10}$ aryl), —C(O)(5- or 6-membered heteroaryl), $—C(O)(C_{3-7}$ carbocyclyl), —C(O)(5- to 7-membered heterocyclyl), $—(CH_2)_{0-3}C(O)OC_{1-6}$ alkyl, $—C(O)NH_2$, $—C(O)NH(C_{1-6}$ alkyl), $—C(O)N(C_{1-6}$ alkyl$)_2$, $—NHC(O)R^9$, $—N(R^9)C(O)(R^9)$, $—NH_2$, $—NH(C_{1-6}$ alkyl), $—N(C_{1-6}$ alkyl$)_2$, $—NHC(O)O(R^9)$, $—N(R^9)C(O)O(R^9)$, $—NHS(O)_2R^9$, $—NR^9S(O)_2R^9$, $—S(O)_qNHR^9$, $—S(O)_qN(R^9)_2$, $—S(O)_qR^9$, $C_{1-6}$ hydroxyalkyl, $—O(CH_2)_{1-3}CN$, CN, $—O(CH_2)_{0-6}—C_{3-7}$ carbocyclyl, $—O(CH_2)_{0-6}$-5- to 7-membered heterocyclyl comprising 1-3 heteroatoms selected from O, N, and S, $—O(CH_2)_{0-3}(C_6-C_{10})$aryl, adamantyl, $—O(CH_2)_{0-3}$-5- or 6-membered heteroaryl comprising 1-3 heteroatoms selected from O, N, and S, $—(CH_2)_{0-6}—C_{3-7}$ carbocyclyl, $—(CH_2)_{0-6}$-5- to 7-membered heterocyclyl comprising 1-3 heteroatoms selected from O, N, and S, $—(CH_2)_{0-6}—C_{6-10}$ aryl, and $—(CH_2)_{0-6}$-5- or 6-membered heteroaryl comprising 1-3 heteroatoms selected from O, N, and S, wherein the alkyl is optionally substituted with one to three $R^6$, and the carbocyclyl, heterocyclyl, aryl, and heteroaryl are optionally substituted with one to four $R^8$; or two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$; or two $R^5$ when on adjacent atoms, together with the atoms to which they are attached form a $C_{6-10}$ aryl or a 5- or 6-membered heteroaryl comprising 1-3 heteroatoms selected from O, N, and S; or two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$; or two $R^5$ when on the same carbon atom form =(O);

$R^6$ is —$NH_2$, —NH($C_{1-6}$ alkyl), —N($C_{1-6}$ alkyl)$_2$, $C_{6-10}$ aryl, or a 5- or 6-membered heteroaryl comprising 1-3 heteroatoms selected from O, N, and S, wherein the aryl and heteroaryl are optionally substituted with one to three $R^7$;

each $R^7$ is independently $C_{1-6}$ alkyl, $C_{1-6}$ haloalkyl, $C_{1-6}$ alkoxy, $C_{1-3}$ haloalkoxy, halogen, or $C_{6-10}$ aryl;

each $R^8$ is independently $C_{1-6}$ alkyl, $C_{1-6}$ haloalkyl, $C_{1-6}$ alkoxy, $C_{1-6}$ haloalkoxy, halogen, or —OH;

$R^9$ is $C_{1-6}$ alkyl, $C_{1-6}$ haloalkyl, 5- to 7-membered heterocyclyl comprising 1-3 heteroatoms selected from O, N, and S, $C_{6-10}$ aryl, or a 5- or 6-membered heteroaryl comprising 1-3 heteroatoms selected from O, N, and S, wherein the aryl and heteroaryl are optionally substituted with one to three $R^{11}$;

each $R^{10}$ is $C_{1-6}$ alkyl, $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S;

each $R^{11}$ is independently $C_{1-6}$ alkyl, $C_{1-6}$ haloalkyl, $C_{1-6}$ alkoxy, $C_{1-6}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$;

each $R^{12}$ is independently $C_{1-6}$ alkyl, $C_{1-6}$ haloalkyl, $C_{1-6}$ alkoxy, or $C_{1-3}$ haloalkoxy;

$R^{13}$ is independently at each occurrence $C_{1-6}$ alkyl, $C_{1-6}$ haloalkyl, $C_{6-10}$ aryl, or a 5- or 6-membered heteroaryl comprising 1-3 heteroatoms selected from O, N, and S, wherein the alkyl is optionally substituted with one to two $C_{1-6}$ alkoxy and the aryl and heteroaryl are optionally substituted with one to three $R^{14}$;

each $R^{14}$ is independently $C_{1-6}$ alkyl, $C_{1-6}$ haloalkyl, $C_{1-6}$ alkoxy, $C_{1-3}$ haloalkoxy, halogen, $C_{6-10}$ aryl, or a 5- or 6-membered heteroaryl comprising 1-3 heteroatoms selected from O, N, and S;

$R^{15}$ is H or $C_{1-6}$ alkyl; and q is 0, 1, or 2.

In one aspect of the disclosure, the hydrogens in the compound of Formula (I) are present in their normal isotopic abundances. In a preferred aspect of the disclosure, the hydrogens are isotopically enriched in deuterium (D), and in a particularly preferred aspect of the invention the hydrogen at position $R_x$ is enriched in D, as discussed in more detail concerning isotopes and isotopic enrichment below.

Another aspect of the present disclosure relates to a pharmaceutical composition comprising a therapeutically effective amount of a compound of Formula (I), or a pharmaceutically acceptable salt, hydrate, solvate, prodrug, stereoisomer, or tautomer thereof, and a pharmaceutically acceptable carrier or excipient. The pharmaceutical composition is useful in the treatment or prevention of a cereblon-mediated disorder, disease, or condition. The pharmaceutical composition may further comprise at least one additional pharmaceutical agent.

In another aspect, the disclosure relates to a method of modulating cereblon in a biological sample comprising contacting the sample with a compound of Formula (I), or a pharmaceutically acceptable salt, hydrate, solvate, prodrug, stereoisomer, or tautomer thereof Another aspect of the present disclosure relates to a method of inhibiting cereblon in a biological sample comprising contacting the sample with a compound of Formula (I), or a pharmaceutically acceptable salt, hydrate, solvate, prodrug, stereoisomer, or tautomer thereof.

In another aspect, the disclosure relates to a method of modulating a target protein in a biological sample comprising contacting the sample with a compound of Formula (I), or a pharmaceutically acceptable salt, hydrate, solvate, prodrug, stereoisomer, or tautomer thereof.

Another aspect of the present disclosure relates to a method of inhibiting target protein in a biological sample comprising contacting the sample with a compound of Formula (I), or a pharmaceutically acceptable salt, hydrate, solvate, prodrug, stereoisomer, or tautomer thereof.

Another aspect of the present disclosure relates to a method of binding to and altering the specificity of a cereblon complex to induce the ubiquitination and degradation of a complex-associated protein selected from the group listed in TABLE 1 in a biological sample, comprising contacting the sample with a compound of Formula (I), or a pharmaceutically acceptable salt, hydrate, solvate, prodrug, stereoisomer, or tautomer thereof.

In another aspect, the disclosure relates to a method of treating or preventing a cereblon-mediated disorder, disease, or condition in a subject comprising administering to the subject a compound of Formula (I), or a pharmaceutically acceptable salt, hydrate, solvate, prodrug, stereoisomer, or tautomer thereof.

Another aspect of the present disclosure relates to a method of treating or preventing a respiratory disorder, a proliferative disorder, an autoimmune disorder, an autoinflammatory disorder, an inflammatory disorder, a neurological disorder, and an infectious disease or disorder in a subject in need thereof, the method comprising administering to the subject a therapeutically effective amount of a compound of Formula (I), or a pharmaceutically acceptable salt, hydrate, solvate, prodrug, stereoisomer, or tautomer thereof.

In another aspect, the disclosure relates to the use of a compound of Formula (I), or a pharmaceutically acceptable salt, hydrate, solvate, prodrug, stereoisomer, or tautomer thereof in the preparation of a medicament for treating or preventing a respiratory disorder, a proliferative disorder, an autoimmune disorder, an autoinflammatory disorder, an inflammatory disorder, a neurological disorder, and an infectious disease or disorder in a subject in need thereof.

Another aspect of the present disclosure relates to the use of a compound of Formula (I), or a pharmaceutically acceptable salt, hydrate, solvate, prodrug, stereoisomer, or tautomer thereof for treating or preventing cancer.

In another aspect, the disclosure relates to a method of degrading a target protein in a biological sample comprising contacting a compound of Formula (I), or a pharmaceutically acceptable salt, hydrate, solvate, prodrug, stereoisomer, or tautomer thereof, wherein the target protein is selected from the group listed in TABLE 1.

Another aspect of the present disclosure relates to a method of treating or preventing a target protein-mediated disorder, disease, or condition in a subject comprising administering to the subject a compound of Formula (I), or a pharmaceutically acceptable salt, hydrate, solvate, prodrug, stereoisomer, or tautomer thereof.

In another aspect, the disclosure relates to a method of treating or preventing a cancer in a subject comprising administering to the subject a compound of Formula (I), or a pharmaceutically acceptable salt, hydrate, solvate, prodrug, stereoisomer, or tautomer thereof.

Another aspect of the present disclosure relates to the use of a compound of Formula (I), or a pharmaceutically acceptable salt, hydrate, solvate, prodrug, stereoisomer, or tautomer thereof in the preparation of a medicament for treating or preventing a cereblon-mediated disorder, disease, or condition in a subject in need thereof.

In another aspect, the disclosure relates to a compound of Formula (I), or a pharmaceutically acceptable salt, hydrate, solvate, prodrug, stereoisomer, or tautomer thereof for use in the treatment or prevention of a cereblon-mediated disorder, disease, or condition in a subject in need thereof.

Another aspect of the present disclosure relates to a compound of Formula (I), or a pharmaceutically acceptable salt, hydrate, solvate, prodrug, stereoisomer, or tautomer thereof for use in the treatment or prevention of cancer.

In another aspect, the disclosure relates to the use of a compound of Formula (I), or a pharmaceutically acceptable salt, hydrate, solvate, prodrug, stereoisomer, or tautomer thereof in the preparation of a medicament for treating or preventing a target protein-mediated disorder, disease, or condition in a subject.

Another aspect of the present disclosure relates to a compound of Formula (I), or a pharmaceutically acceptable salt, hydrate, solvate, prodrug, stereoisomer, or tautomer thereof for use in the treatment or prevention of a target protein-mediated disorder, disease, or condition in a subject.

DETAILED DESCRIPTION OF THE DISCLOSURE

The present disclosure relates to compounds and compositions that are capable of modulating or inhibiting a Target Protein by binding to and altering the specificity of a cereblon complex to induce ubiquitination and degradation of a complex-associated protein. The disclosure features methods of treating, preventing, or ameliorating a cereblon-mediated disorder, disease, or condition by administering to a subject in need thereof a therapeutically effective amount of a compound of Formula (I), or a pharmaceutically acceptable salt, hydrate, solvate, prodrug, stereoisomer, or tautomer thereof. The methods of the present disclosure can be used in the treatment of a variety of a cereblon-mediated disorder, disease, or condition diseases and disorders by modulating the Target Protein levels. Modulation of protein levels through degradation provides a novel approach to the treatment, prevention, or amelioration of diseases including, but not limited to, respiratory disorders, proliferative disorders, autoimmune disorders, autoinflammatory disorders, inflammatory disorders, neurological disorders, infectious diseases or disorders, and other cereblon-mediated disorders, diseases, or conditions.

In a first aspect of the disclosure, the compounds of Formula (I) are described:

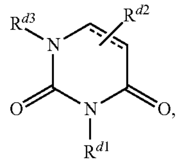

(I)

or pharmaceutically acceptable salts, hydrates, solvates, prodrugs, stereoisomers, and tautomers thereof, wherein $R^{d1}$, $R^{d2}$, and $R^{d3}$ are as described herein above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $(C_{1-10})$alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-. Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "optionally substituted" means that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon).

Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups.

Suitable substituents used in the optional substitution of the described groups include, without limitation, halogen, oxo, —OH, —CN, —COOH, —$CH_2$CN, —O—$C_{1-6}$ alkyl, $C_{1-6}$ alkyl, $C_{1-6}$ alkoxy, $C_{1-6}$ haloalkyl, $C_{1-6}$ haloalkoxy, —O—$C_{2-6}$ alkenyl, —O—$C_{2-6}$ alkynyl, $C_{2-6}$ alkenyl, $C_{2-6}$ alkynyl, —OH, —OP(O)$(OH)_2$, —OC(O)$C_{1-6}$ alkyl, —C(O)$C_{1-6}$ alkyl, —OC(O)O$C_{1-6}$ alkyl, —$NH_2$, —NH($C_{1-6}$ alkyl), —N($C_{1-6}$ alkyl$)_2$, —NHC(O)$C_{1-6}$ alkyl, —C(O)NH ($C_{1-6}$ alkyl), —S$(O)_2C_{1-6}$ alkyl, —S(O)NH($C_{1-6}$ alkyl), and S(O)N($C_{1-6}$ alkyl$)_2$. The substituents can themselves be optionally substituted. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

Unless otherwise specifically defined, "aryl" means a cyclic, aromatic hydrocarbon group having 1 to 3 aromatic rings, including monocyclic or bicyclic groups such as phenyl, biphenyl, or naphthyl. When containing two aromatic rings (bicyclic, etc.), the aromatic rings of the aryl group are optionally joined at a single point (e.g., biphenyl), or fused (e.g., naphthyl). The aryl group is optionally substituted by one or more substituents, e.g., 1 to 5 substituents, at any point of attachment. Exemplary substituents include, but are not limited to, —H, -halogen, —CN, —O—$C_{1-6}$ alkyl, $C_{1-6}$ alkyl, —O—$C_2$-$C_6$ alkenyl, —O—$C_{2-6}$ alkynyl, $C_{2-6}$ alkenyl, $C_{2-6}$ alkynyl, —OH, —OP (O)$(OH)_2$, —OC(O)$C_{1-6}$ alkyl, —C(O)$C_{1-6}$ alkyl, —OC(O) O($C_{1-6}$ alkyl), $NH_2$, NH($C_{1-6}$ alkyl), N($C_{1-6}$ alkyl$)_2$, —S$(O)_2$—$C_{1-6}$ alkyl, —S(O)NH($C_{1-6}$alkyl), and S(O)N ($C_{1-6}$ alkyl$)_2$. The substituents are themselves optionally substituted. Furthermore, when containing two fused rings, the aryl groups optionally have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b] pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo [de]isoquinolinyl, pyrido[4,3-b][1,6]naphthyridinyl, thieno [2,3-b]pyrazinyl, quinazolinyl, tetrazolo[1,5-a]pyridinyl, [1,2,4]triazolo[4,3-a]pyridinyl, isoindolyl, pyrrolo[2,3-b] pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\Delta^2$-pyrrolo [2,1-b]pyrimidine, dibenzo[b,d]thiophene, pyridin-2-one, furo[3,2-c]pyridinyl, furo[2,3-c]pyridinyl, 1H-pyrido[3,4-b] [1,4]thiazinyl, benzooxazolyl, benzoisoxazolyl, furo[2,3-b] pyridinyl, benzothiophenyl, 1,5-naphthyridinyl, furo[3,2-b] pyridine, [1,2,4]triazolo[1,5-a]pyridinyl, benzo[1,2,3] triazolyl, imidazo[1,2-a]pyrimidinyl, [1,2,4]triazolo[4,3-b] pyridazinyl, benzo[c][1,2,5]thiadiazolyl, benzo[c][1,2,5] oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4 d]thiazolyl, imidazo[2,1-b][1,3,4]thiadiazolyl, thieno[2,3-b]pyrrolyl, 3H-indolyl, and derivatives thereof. Furthermore, when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" mean fluorine, chlorine, bromine, or iodine.

"Alkyl" means a straight or branched chain saturated hydrocarbon containing 1-12 carbon atoms. Examples of a $C_{1-6}$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" means a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

"Alkenyl" means a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted and may be straight or branched.

"Alkynyl" means a straight or branched chain unsaturated hydrocarbon containing 2-12 carbon atoms. The "alkynyl" group contains at least one triple bond in the chain. Examples of alkenyl groups include ethynyl, propargyl, n-butynyl, isobutynyl, pentynyl, or hexynyl. An alkynyl group can be unsubstituted or substituted.

"Alkylene" or "alkylenyl" means a divalent alkyl radical. Any of the above mentioned monovalent alkyl groups may be an alkylene by abstraction of a second hydrogen atom from the alkyl. As herein defined, alkylene may also be a $C_{1-6}$ alkylene. An alkylene may further be a $C_{1-4}$ alkylene. Typical alkylene groups include, but are not limited to, —$CH_2$—, —CH($CH_3$)—, —C$(CH_3)_2$—, —$CH_2CH_2$—, $—CH_2CH(CH_3)—$, $—CH_2C(CH_3)_2—$, $—CH_2CH_2CH_2—$, $—CH_2CH_2CH_2CH—$, and the like.

"Cycloalkyl" or "carbocyclyl" means a monocyclic or polycyclic saturated or partially unsaturated carbon ring containing 3-18 carbon atoms wherein there is not delocalized n electrons (aromaticity) shared among the ring carbon. Examples of cycloalkyl groups include, without limitations, cyclopropenyl, cyclopropyl cyclobutyl, cyclobutenyl, cyclopentyl, cyclohexyl, cycloheptanyl, cyclooctanyl, norboranyl, norborenyl, bicyclo[2.2.2]octanyl, or bicyclo[2.2.2] octenyl and derivatives thereof. A $C_{3-8}$ cycloalkyl is a cycloalkyl group containing between 3 and 8 carbon atoms. A cycloalkyl group can be fused (e.g., decalin) or bridged (e.g., norbomane).

"Heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

"Heterocyclyl" means a saturated or partially saturated monocyclic or polycyclic ring containing carbon and at least one heteroatom selected from oxygen, nitrogen, or sulfur (O, N, or S) and wherein there is not delocalized n electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, imidazolinyl, dithiolanyl, and homotropanyl.

"Hydroxyalkyl" means an alkyl group substituted with one or more —OH groups. Examples of hydroxyalkyl groups include $HO—CH_2—$, $HO—CH_2CH_2—$, and $CH_2—CH(OH)—$.

"Haloalkyl" means an alkyl group substituted with one or more halogens. Examples of haloalkyl groups include, but are not limited to, trifluoromethyl, difluoromethyl, pentafluoroethyl, trichloromethyl, etc.

"Haloalkoxy" means an alkoxy group substituted with one or more halogens. Examples of haloalkyl groups include, but are not limited to, trifluoromethoxy, difluoromethoxy, pentafluoroethoxy, trichloromethoxy, etc.

"Cyano" means a substituent having a carbon atom joined to a nitrogen atom by a triple bond, e.g., C≡N.

"Amino" means a substituent containing at least one nitrogen atom (e.g., $NH_2$).

"Alkylamino" means an amino or $NH_2$ group where one of the hydrogens is replaced with an alkyl group, e.g., —NH(alkyl). Examples of alkylamino groups include, but are not limited to, methylamino (e.g., $—NH(CH_3)$), ethylamino, propylamino, iso-propylamino, n-butylamino, sec-butylamino, tert-butylamino, etc.

"Dialkylamino" means an amino or $NH_2$ group where both of the hydrogens are replaced with alkyl groups, e.g., $—N(alkyl)_2$. The alkyl groups on the amino group are the same or different alkyl groups. Examples of dialkylamino groups include, but are not limited to, dimethylamino (e.g., $—N(CH_3)_2$), diethylamino, dipropylamino, diiso-propylamino, di-n-butylamino, di-sec-butylamino, di-tert-butylamino, methyl(ethyl)amino, methyl(butylamino), etc.

"Spirocarbocyclyl" means a carbocyclyl bicyclic ring system with both rings connected through a single atom. The rings can be different in size and nature, or identical in size and nature. Examples include spiropentane, spirohexane, spiroheptane, spirooctane, spirononane, or spirodecane. One or both of the rings in a spirocycle can be fused to another ring carbocyclic, heterocyclic, aromatic, or heteroaromatic ring. A $C_{3-12}$ spirocycloalkyl is a spirocycle containing between 3 and 12 carbon atoms.

"Spiroheterocycloalkyl" or "spiroheterocyclyl" means a spirocarbocyclyl wherein at least one of the rings is a heterocycle one or more of the carbon atoms can be substituted with a heteroatom (e.g., one or more of the carbon atoms can be substituted with a heteroatom in at least one of the rings). One or both of the rings in a spiroheterocycle can be fused to another ring carbocyclic, heterocyclic, aromatic, or heteroaromatic ring.

B. Salt, Prodrug, Derivative, and Solvate Terms and Conventions

"Prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

"Pharmaceutically acceptable prodrug" as used herein means a prodrug of a compound of the disclosure which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

"Salt" means an ionic form of the parent compound or the product of the reaction between the parent compound with a suitable acid or base to make the acid salt or base salt of the parent compound. Salts of the compounds of the present disclosure can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

"Pharmaceutically acceptable salt" means a salt of a compound of the disclosure which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present disclosure are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

"Pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

"Pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

"Solvate" means a complex of variable stoichiometry formed by a solute, for example, a compound of Formula (I)) and solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, such solvents selected for the purpose of the disclosure do not interfere with the biological activity of the solute. Solvates encompasses both solution-phase and isolatable solvates. Representative solvates include hydrates, ethanolates, methanolates, and the like.

"Hydrate" means a solvate wherein the solvent molecule (s) is/are water.

The compounds of the present disclosure as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

"Isomers" means compounds having the same number and kind of atoms, and hence the same molecular weight, but differing with respect to the arrangement or configuration of the atoms in space. The term includes stereoisomers and geometric isomers.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

"Enantiomers" means a pair of stereoisomers that are non-superimposable mirror images of each other.

"Diastereoisomers" or "diastereomers" mean optical isomers which are not mirror images of each other.

"Racemic mixture" or "racemate" mean a mixture containing equal parts of individual enantiomers.

"Non-racemic mixture" means a mixture containing unequal parts of individual enantiomers.

"Geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C═N double bonds, cyclic structures, and the like may be present in the compounds of the disclosure, the disclosure contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, Advanced Organic Chemistry: Reactions, Mechanisms, and Structure, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^{1}H$ NMR, and $^{13}C$ NMR.

Some of the compounds of the disclosure can exist in more than one tautomeric form. As mentioned above, the compounds of the disclosure include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the disclosure from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

D. Pharmaceutical Administration and Treatment Terms and Conventions

A "patient" or "subject" is a mammal, e.g., a human, mouse, rat, guinea pig, dog, cat, horse, cow, pig, or nonhuman primate, such as a monkey, chimpanzee, baboon or, rhesus. In certain embodiments, the subject is a primate. In yet other embodiments, the subject is a human.

An "effective amount" or "therapeutically effective amount" when used in connection with a compound means an amount of a compound of the present disclosure that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "pharmaceutically effective amount" or "therapeutically effective amount" means an amount of a compound according to the disclosure which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the disclosure which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the disclosure, and the age, body weight, general health, sex, and diet of the patient. Such a therapeutically effective amount can be determined routinely by one of ordinary skill in the art having regard to their own knowledge, the prior art, and this disclosure.

As used herein, the term "pharmaceutical composition" refers to a compound of the disclosure, or a pharmaceutically acceptable salt, hydrate, solvate, prodrug, stereoisomer, or tautomer thereof, together with at least one pharmaceutically acceptable carrier, in a form suitable for oral or parenteral administration.

"Carrier" encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

A subject is "in need of" a treatment if such subject would benefit biologically, medically, or in quality of life from such treatment (preferably, a human).

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

"Pharmaceutically acceptable" means that the substance or composition must be compatible chemically and/or toxicologically, with the other ingredients comprising a formulation, and/or the mammal being treated therewith.

"Disorder" means, and is used interchangeably with, the terms disease, condition, or illness, unless otherwise indicated.

"Administer", "administering", or "administration" means to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

"Prodrug" means a compound which is convertible in vivo by metabolic means (e.g., by hydrolysis) to a disclosed compound.

"Compounds of the present disclosure", "Compounds of Formula (I)", "compounds of the disclosure", and equivalent expressions (unless specifically identified otherwise) refer to compounds of Formulae (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), and (Iam) as herein described including the tautomers, the prodrugs, salts particularly the pharmaceutically acceptable salts, and the solvates and hydrates thereof, where the context so permits thereof, as well as all stereoisomers (including diastereoisomers and enantiomers), rotamers, tautomers, and isotopically labelled compounds (including deuterium substitutions), as well as inherently formed moieties (e.g., polymorphs, solvates and/or hydrates). For purposes of this disclosure, solvates and hydrates are generally considered compositions. In general and preferably, the compounds of the disclosure and the formulas designating the compounds of the disclosure are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

"Stable compound" or "stable structure" means a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the disclosure.

Provided compounds are binders of CRBN and are therefore useful for treating one or more disorders associated with activity of CRBN or mutants thereof. Thus, in certain embodiments, the present disclosure provides a method for treating a CRBN-mediated disorder comprising the step of administering to a patient in need thereof a compound of the disclosure, or pharmaceutically acceptable composition thereof.

As used herein, the term "CRBN-mediated" disorders, diseases, and/or conditions means any disease, condition, or disorder in which CRBN or a mutant thereof is known to play a role. Accordingly, another embodiment relates to treating tor preventing one or more diseases in which CRBN, or a mutant thereof, is known to play a role. Such CRBN-mediated disorders include but are not limited respiratory disorders, proliferative disorders, autoimmune disorders, autoinflammatory disorders, inflammatory disorders, neurological disorders, or infectious diseases or disorders.

In a specific embodiment, the term "about" or "approximately" means within 20%, preferably within 10%, and more preferably within 5% of a given value or range.

The yield of each of the reactions described herein is expressed as a percentage of the theoretical yield.

D. Specific Embodiments and Methods for Testing Compounds of Formula (I)

The present disclosure relates compounds or pharmaceutically acceptable salts, hydrates, solvates, prodrugs, stereoisomers, or tautomers thereof, which are useful for the treatment or prevention of diseases and disorders associated with modulation of protein levels through the binding to and altering of the specificity of a cereblon complex to induce proteasome-mediated degradation of the selected proteins. The disclosure further relates to compounds, or pharmaceutically acceptable salts, hydrates, solvates, prodrugs, stereoisomers, or tautomers thereof, which are useful for the treatment or prevention of diseases and disorders associated with reducing or decreasing protein levels through the binding to and altering of the specificity of a cereblon complex to induce proteasome-mediated degradation of the selected proteins.

In one embodiment, the compounds of Formula (I) have a formula selected from:

(Ia)

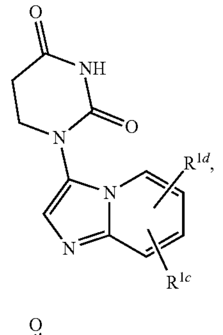

(Ib)

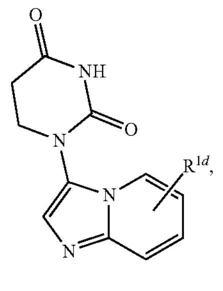

-continued (Ic)

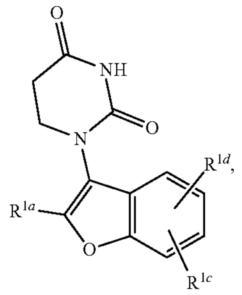

(Id)

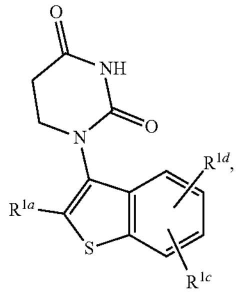

(Ie)

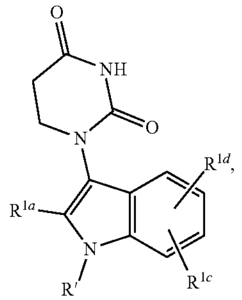

(If)

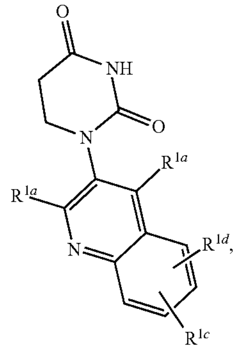

(Ig)

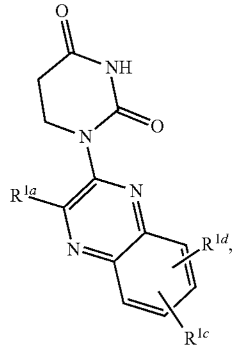

-continued
(Ih)
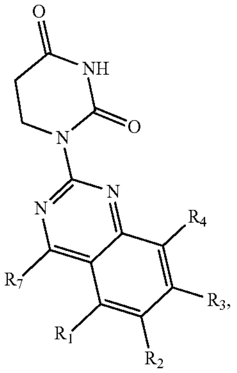
(Ii)
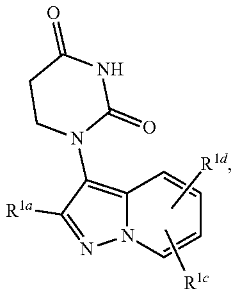
(Ij)
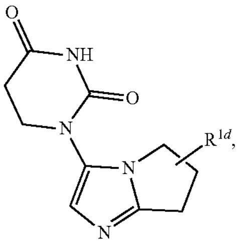
(Ik)
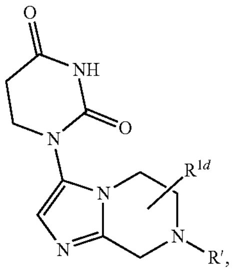
(Il)
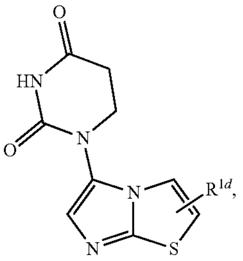
-continued
(Im)
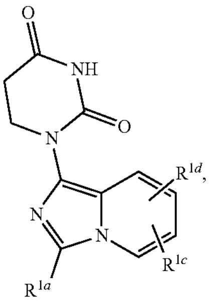
(In)
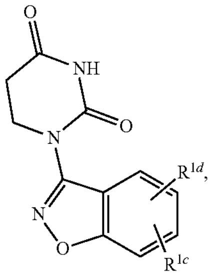
(Io)
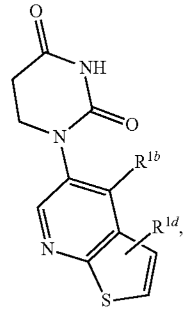
(Ip)
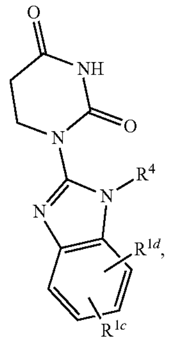
(Ia)
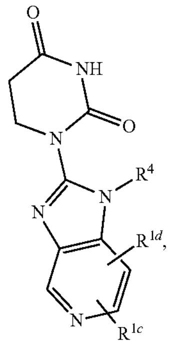

-continued
(Ir)
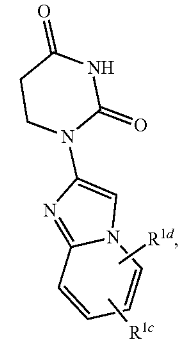
(Is)
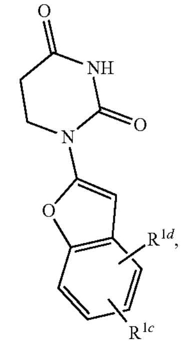
(It)
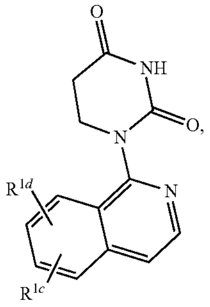
(Iu)
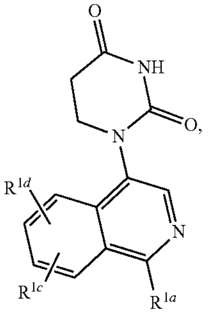
(Iv)
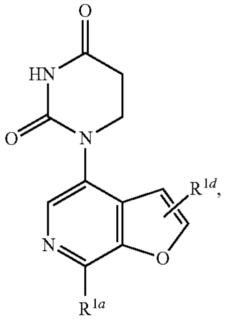
-continued
(Iw)
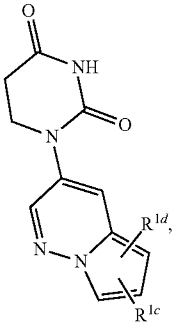
(Ix)
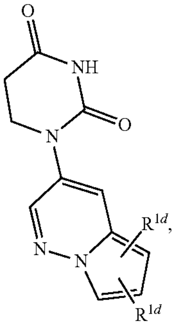
(Iy)
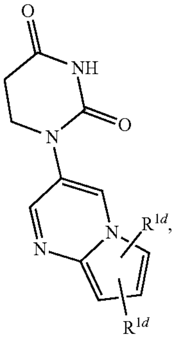
(Iz)
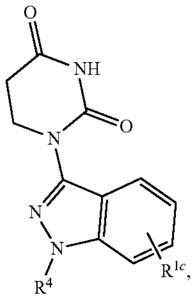
(Iaa)
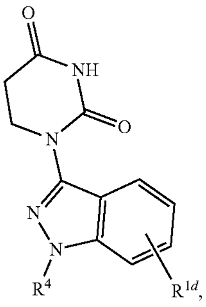

-continued
(Iab)
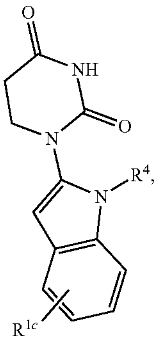
(Iac)
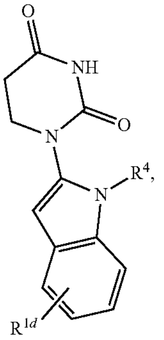
(Iad)
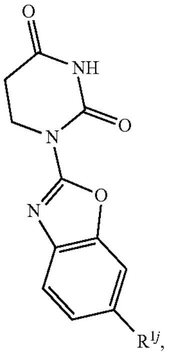
(Iae)
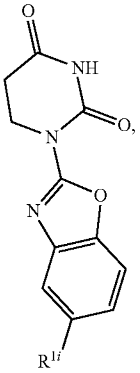
-continued
(Iaf)
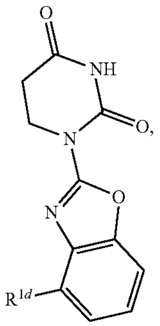
(Iag)
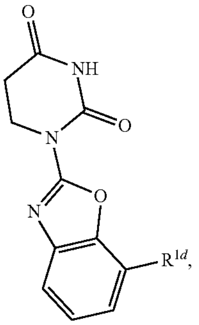
(Iah)
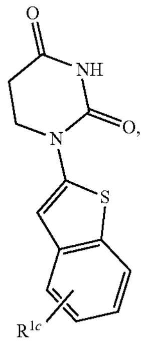
(Iai)
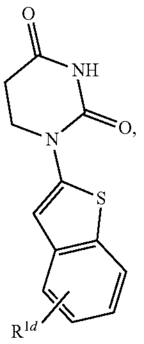

-continued (Iaj)

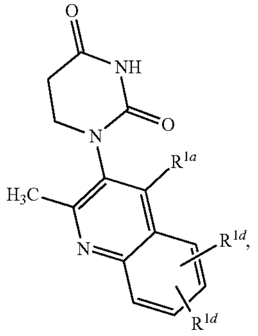

(Iak)

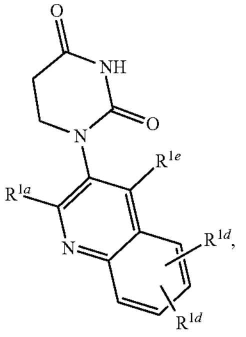

(Ial)

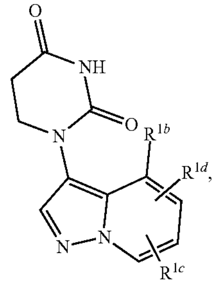

and (Iam)

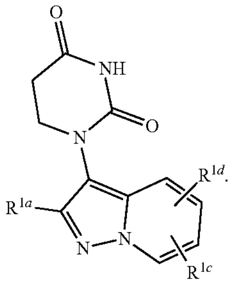

or pharmaceutically acceptable salts, hydrates, solvates, prodrugs, stereoisomers, and tautomers thereof.

In some embodiments of the formulae above (i.e., Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (TI), Formula (Im), Formula (In), Formula (Io), Formula (Ip), Formula (Iq), Formula (Ir), Formula (Is), Formula (It), Formula (Iu), Formula (Iv), Formula (Iw), Formula (Ix), Formula (Iy), Formula (Iz), Formula (Iaa), Formula (Iab), Formula (Iac), Formula (Iad), Formula (Iae), Formula (Iaf), Formula (Iag), Formula (Iah), Formula (Iai), Formula (Iaj), Formula (Iak), Formula (Ial), and/or Formula (Iam)), $=\!=$ is a double bond. In another embodiment, $=\!=$ is a single bond In some embodiments of the formulae above, $R^{d1}$ is —$CH_2OC(O)R^{15}$, —$CH_2OP(O)OHOR^{15}$, or $CH_2OP(O)(R^{15})_2$. In another embodiment, $R^{d1}$ is H, —$CH_2OC(O)R^{15}$, or —$CH_2OP(O)OHOR^{15}$. In yet another embodiment, $R^{d1}$ is H, —$CH_2OC(O)R^{15}$, or —$CH_2OP(O)(R^{15})_2$. In another embodiment, $R^{d1}$ is H, —$CH_2OP(O)OHOR^{15}$, or —$CH_2OP(O)(R^{15})_2$. In yet another embodiment, $R^{d1}$ is H or —$CH_2OC(O)R^{15}$. In another embodiment, $R^{d1}$ is H or —$CH_2OP(O)OHOR^{15}$. In yet another embodiment, $R^{d1}$ is H or —$CH_2OP(O)(R^{15})_2$. In another embodiment, $R^{d1}$ is H.

In some embodiments of the formulae above, $R^{d2}$ is H, $C_{1-3}$ alkyl, halogen, $C_{1-3}$ haloalkyl, or $C_{1-3}$ heteroalkyl. In another embodiment, $R^{d2}$ is H, $C_{1-3}$ alkyl, halogen, or $C_{1-3}$ haloalkyl. In yet another embodiment, $R^{d2}$ is H, $C_{1-6}$ alkyl, halogen, or $C_{1-6}$ heteroalkyl. In another embodiment, $R^{d2}$ is H, $C_{1-6}$ alkyl, $C_{1-6}$ haloalkyl, or $C_{1-6}$ heteroalkyl. In yet another embodiment, $R^{d2}$ is H, halogen, $C_{1-6}$ haloalkyl, or $C_{1-6}$ heteroalkyl. In another embodiment, $R^{d2}$ is H, $C_{1-6}$ alkyl, or halogen. In yet another embodiment, $R^{d2}$ is H, $C_{1-6}$ alkyl, or $C_{1-6}$ haloalkyl. In another embodiment, $R^{d2}$ is H, $C_{1-6}$ alkyl, or $C_{1-6}$ heteroalkyl. In yet another embodiment, $R^{d2}$ is H or halogen. In yet another embodiment, $R^{d2}$ is H or $C_{1-6}$ haloalkyl. In another embodiment, $R^{d2}$ is H or $C_{1-6}$ heteroalkyl. In yet another embodiment, $R^{d2}$ is H or $C_{1-6}$ alkyl. In another embodiment, $R^{d2}$ is H or $C_{1-3}$ alkyl. In yet another embodiment, $R^{d2}$ is H, methyl, ethyl, n-propyl, or i-propyl. In another embodiment, $R^{d2}$ is H, methyl or ethyl. In yet another embodiment, $R^{d2}$ is H or methyl. In another embodiment, $R^{d2}$ is H, methyl, or F. In yet another embodiment, $R^{d2}$ is H.

In some embodiments of the formulae above, $R^{d3}$ is

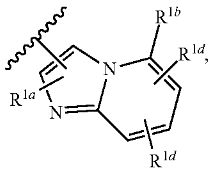

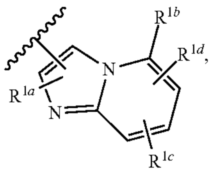

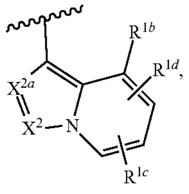

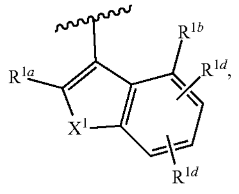

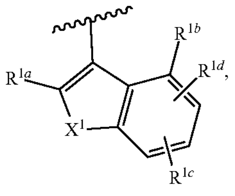

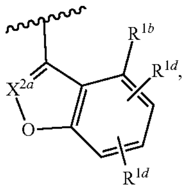

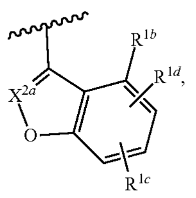

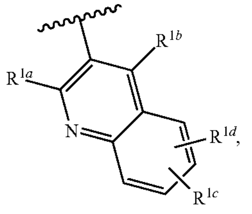

-continued
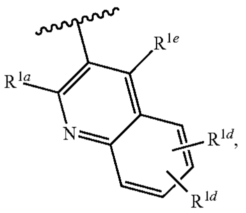
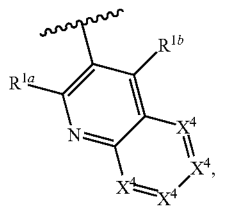
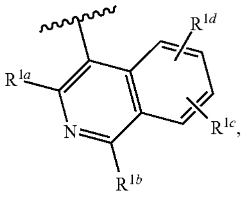
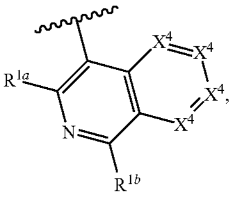
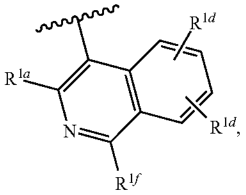
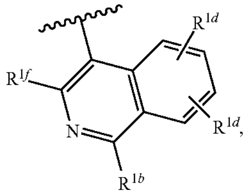
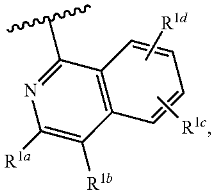
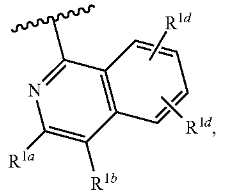
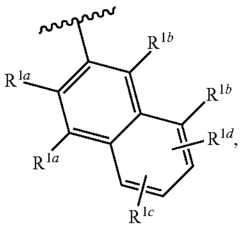
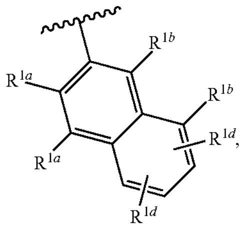
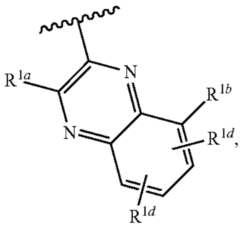
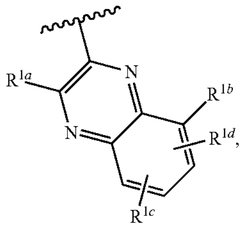
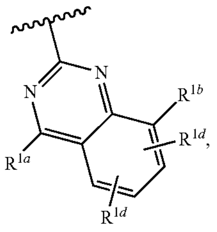
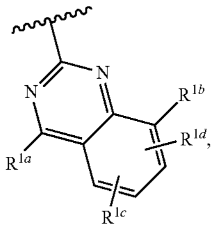
-continued
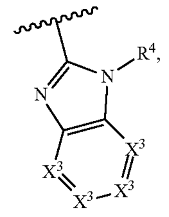
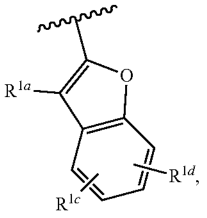
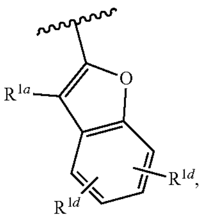
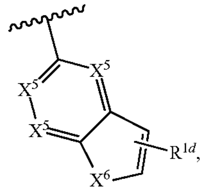
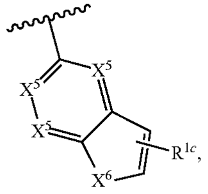
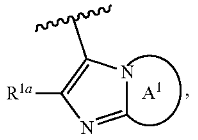
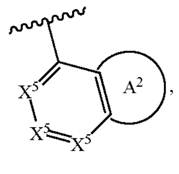
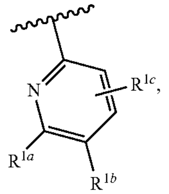
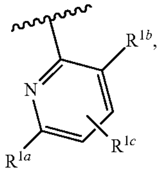
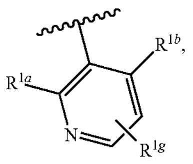
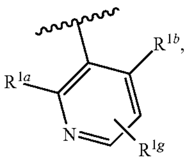
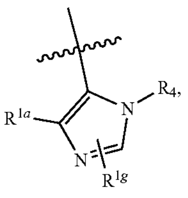
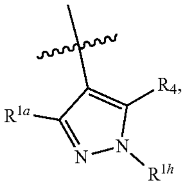
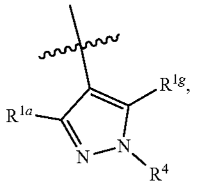
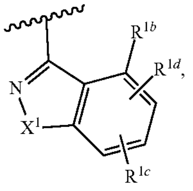
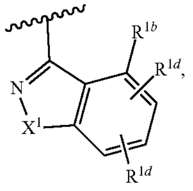

-continued
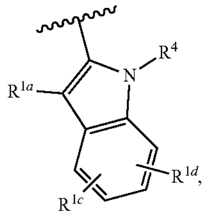
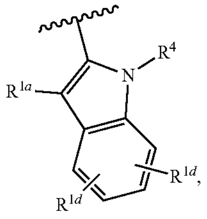
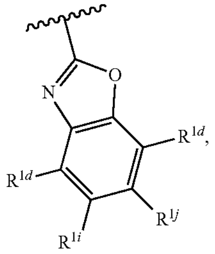
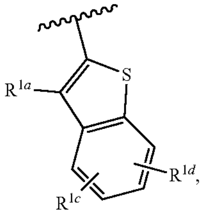
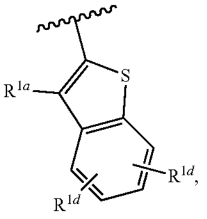
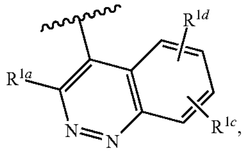
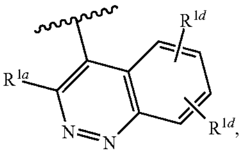
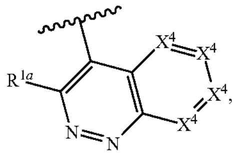
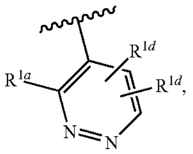
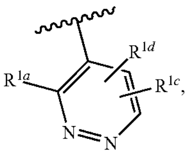
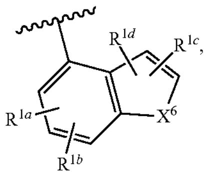
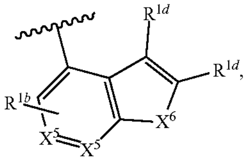
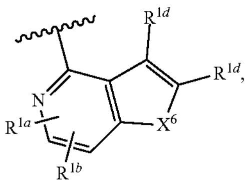
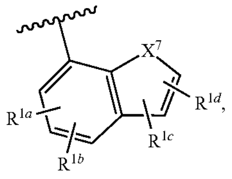
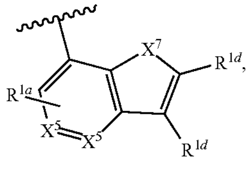
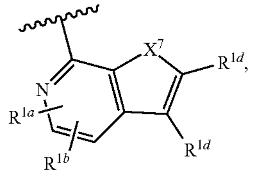
-continued
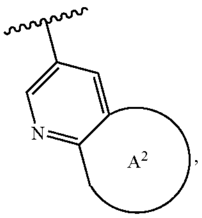
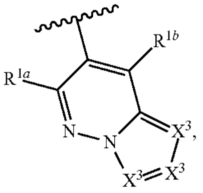
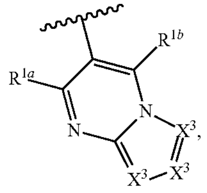
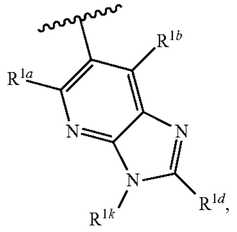
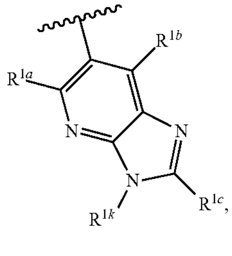
or
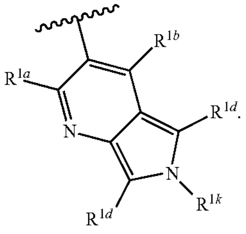
In another embodiment, $R^{d3}$ is
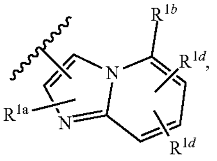
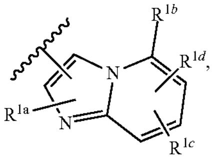
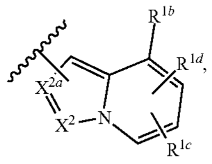
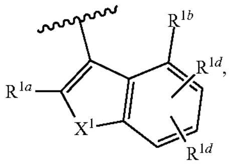
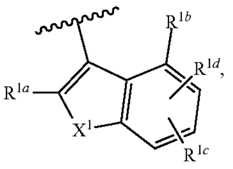
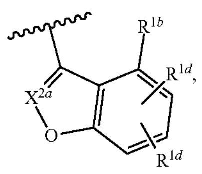
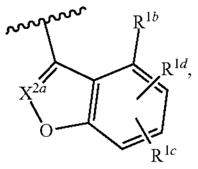
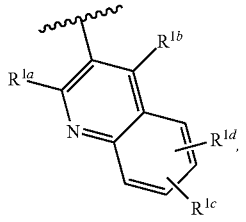

-continued
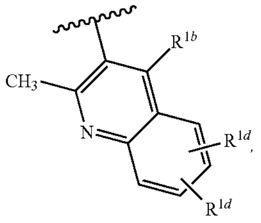
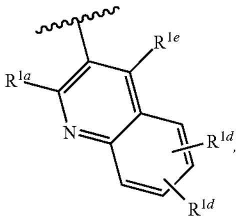
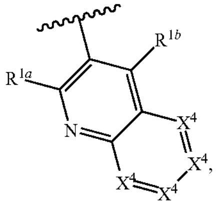
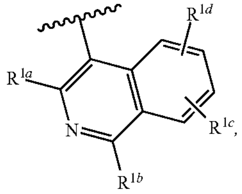
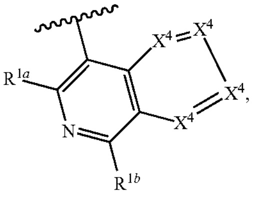
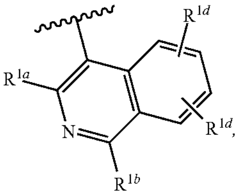
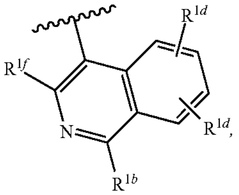
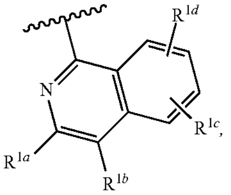
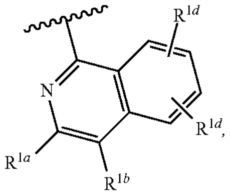
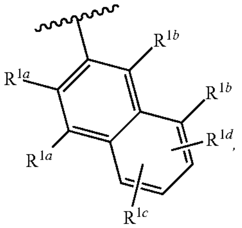
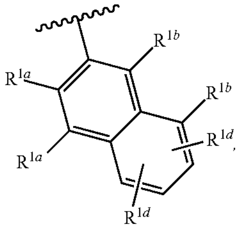
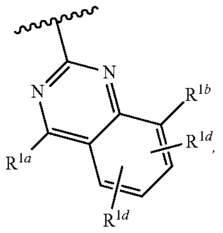
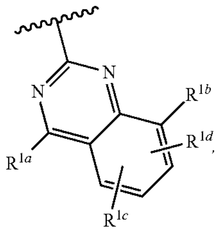
-continued
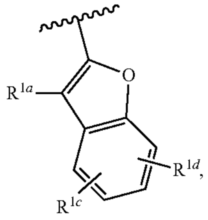
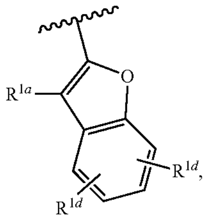
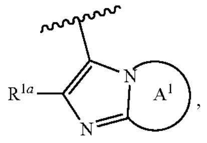
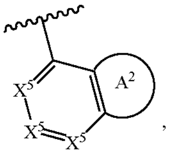
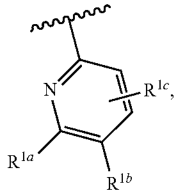
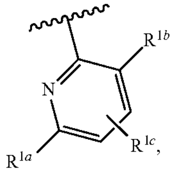
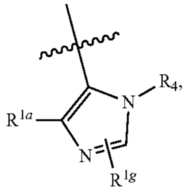
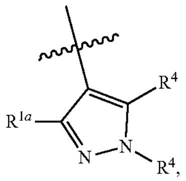
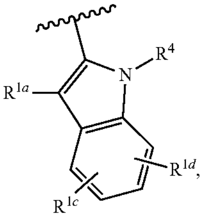
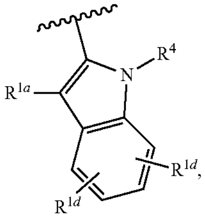
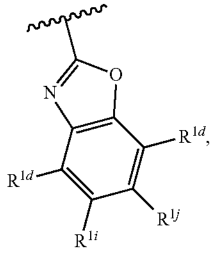
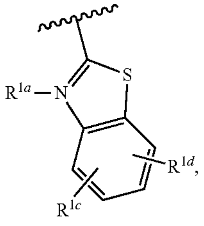
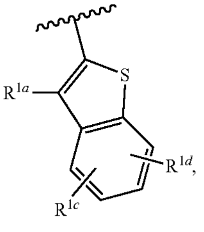
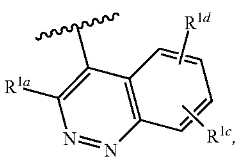

-continued
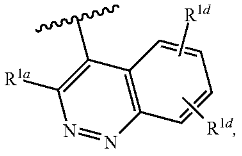
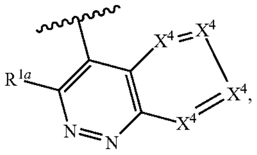
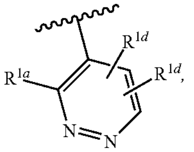
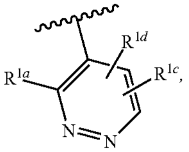
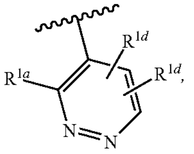
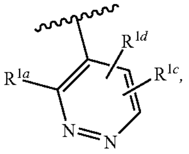
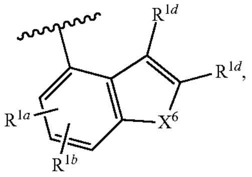
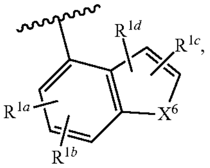
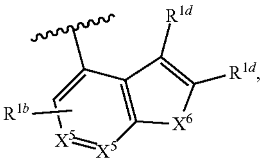
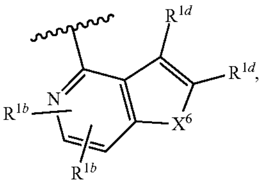
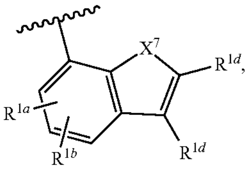
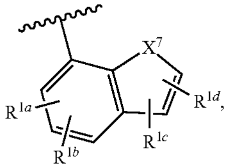
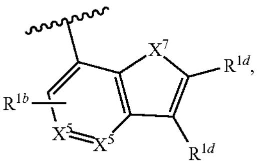
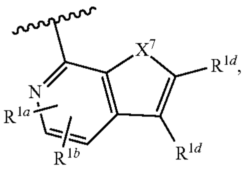
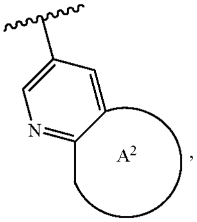
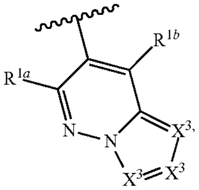
-continued
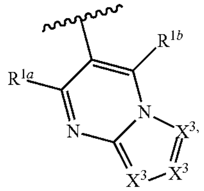
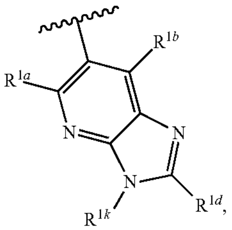
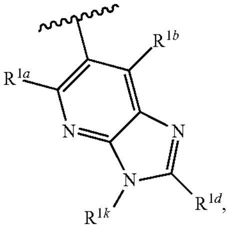
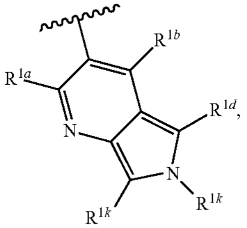
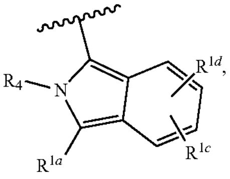
or
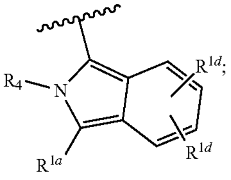
In another embodiment, $R^{d3}$ is
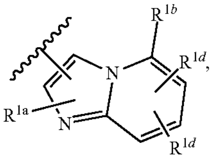
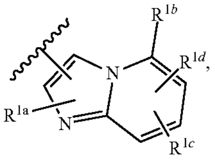
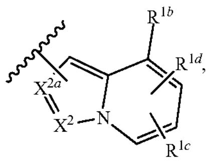
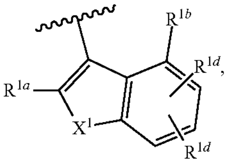
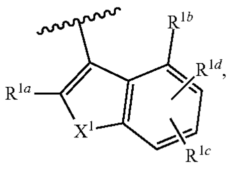
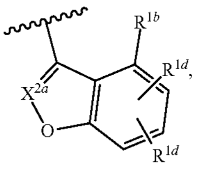
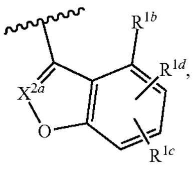
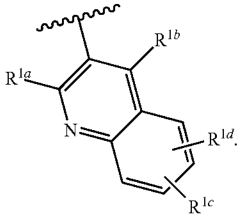

-continued
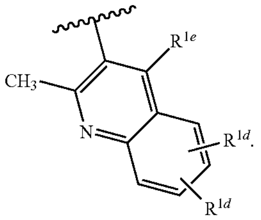
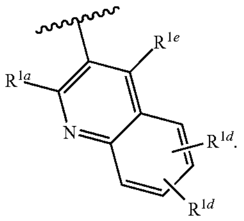
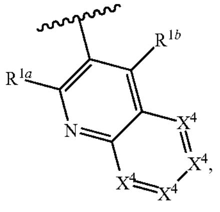
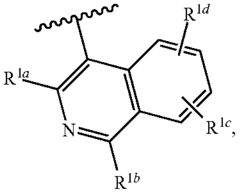
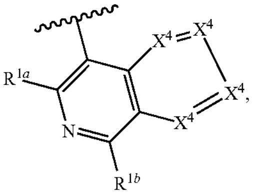
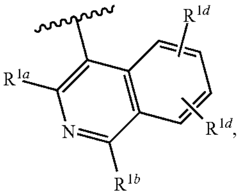
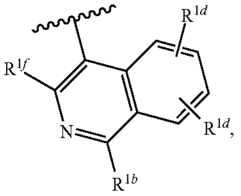
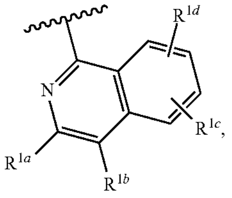
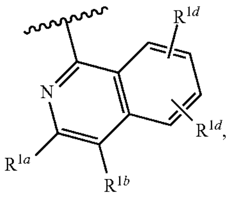
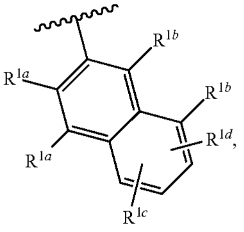
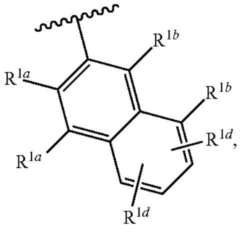
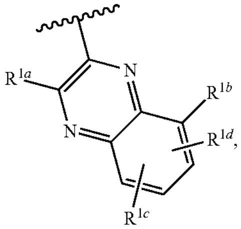
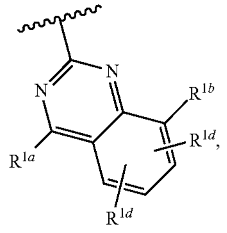
-continued
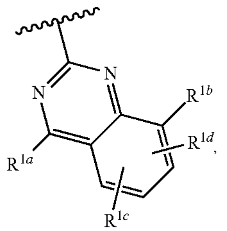
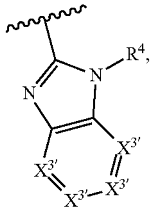
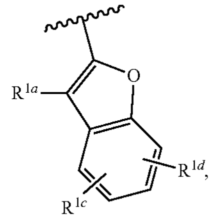
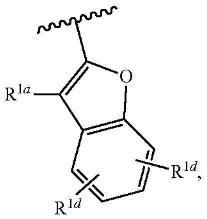
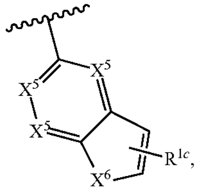
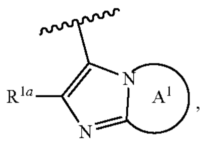
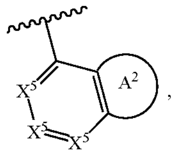
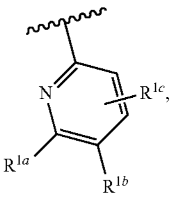
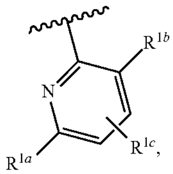
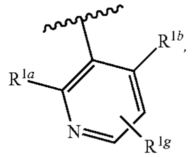
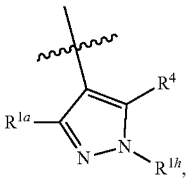
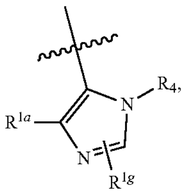
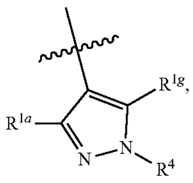
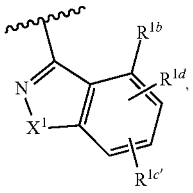

-continued
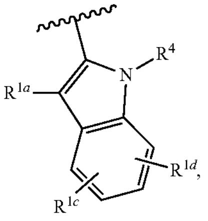
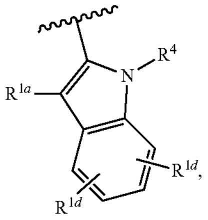
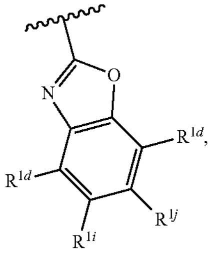
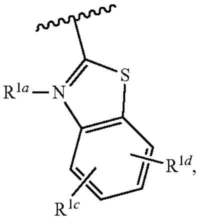
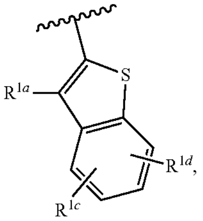
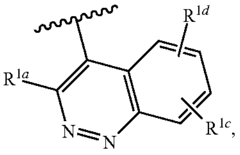
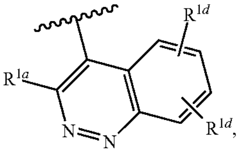
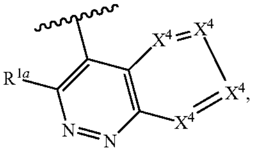
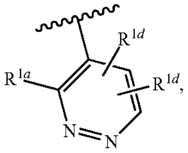
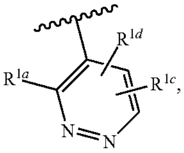
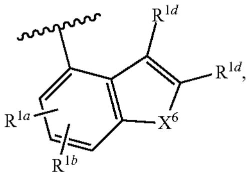
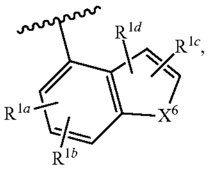
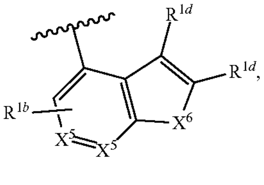
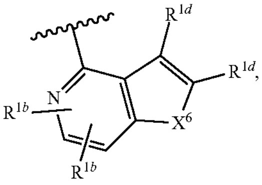
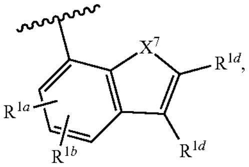
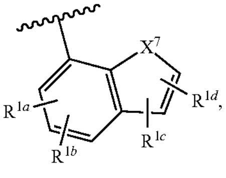
-continued
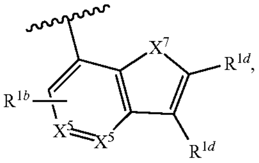
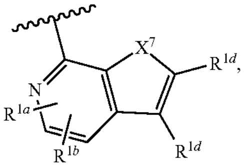
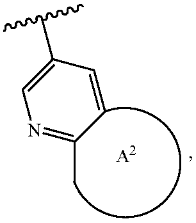
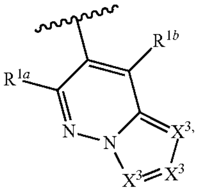
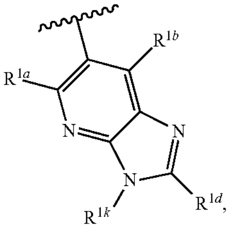
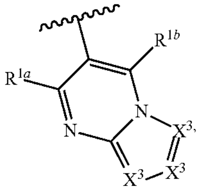
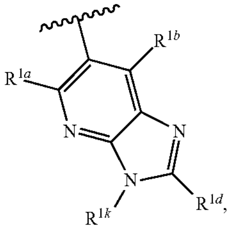
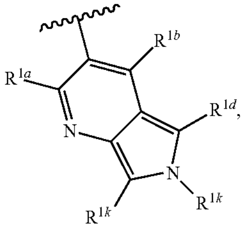
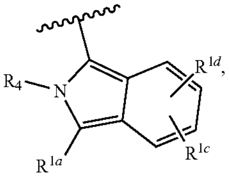
or
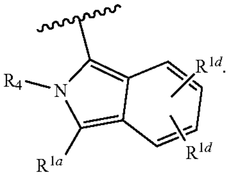
In another embodiment, $R^{d3}$ is
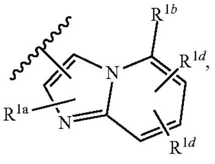
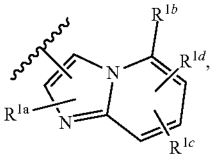
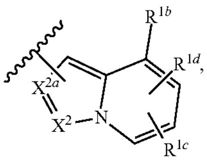
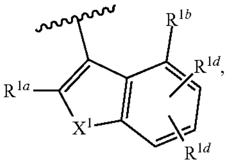

-continued
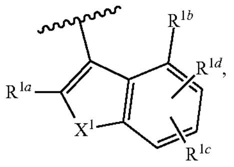
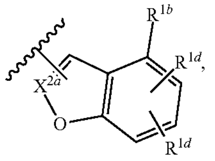
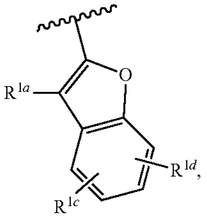
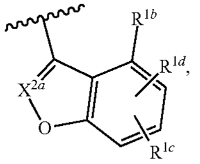
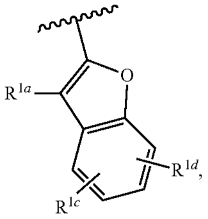
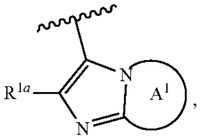
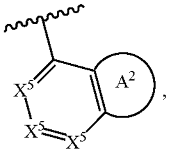
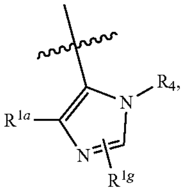
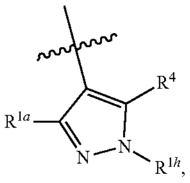
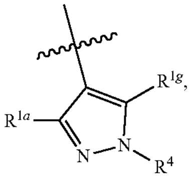
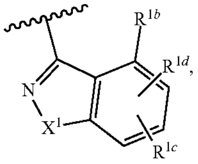
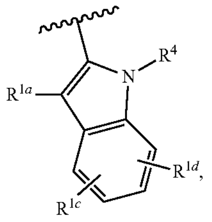
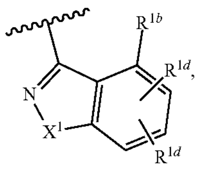
-continued
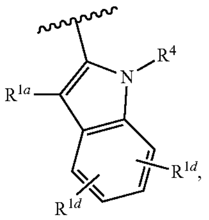
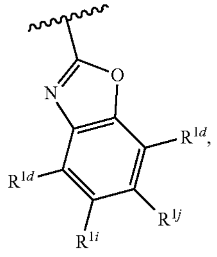
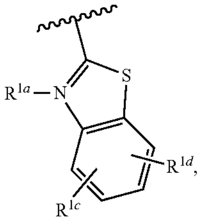
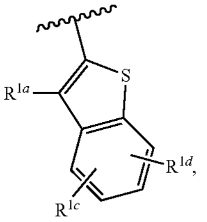
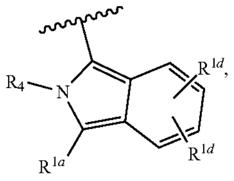
or
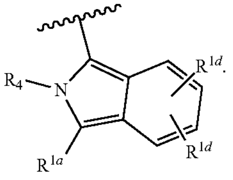
In another embodiment, $R^{d3}$ is
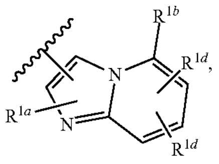
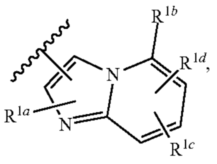
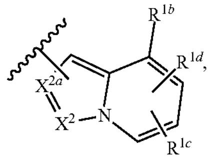
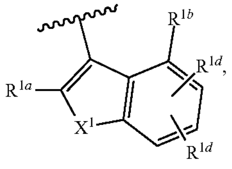
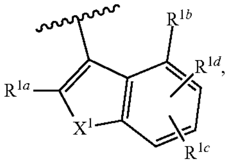
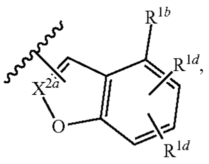
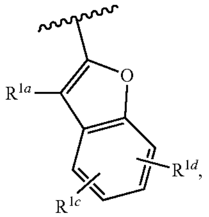
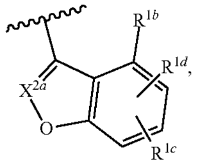

-continued
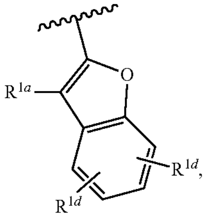
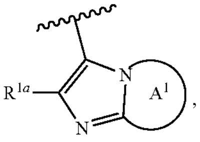
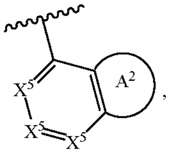
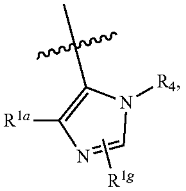
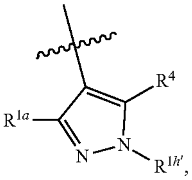
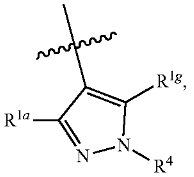
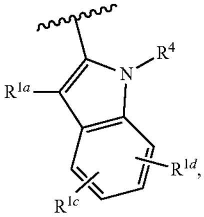
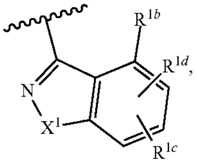
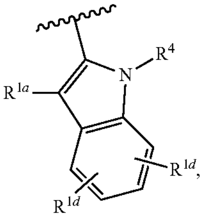
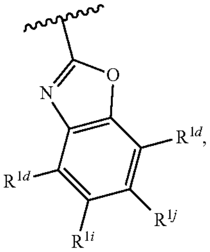
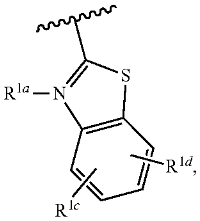
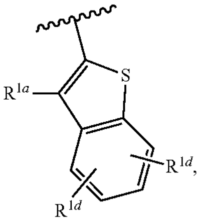
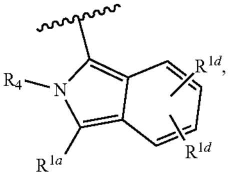
or
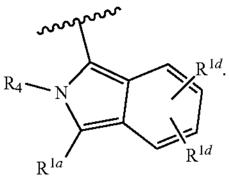
In another embodiment, $R^{d3}$ is
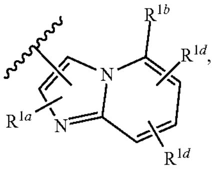
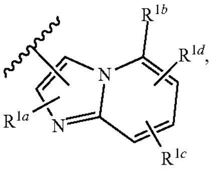
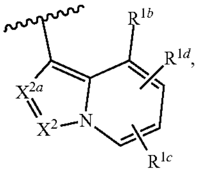
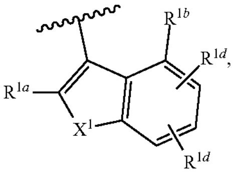
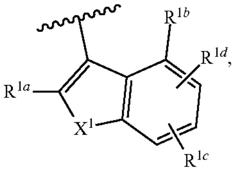
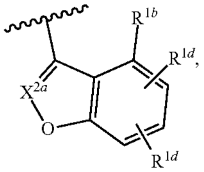
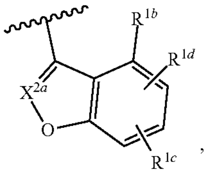
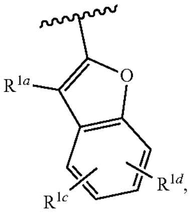
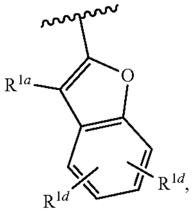
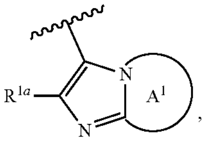
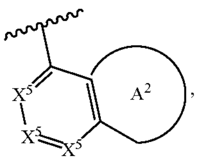
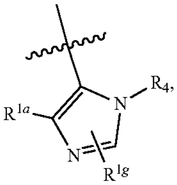
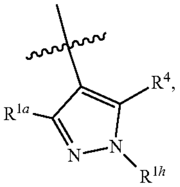
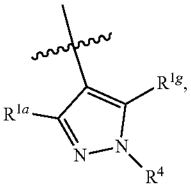
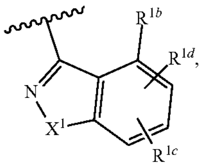
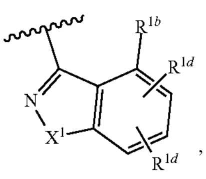
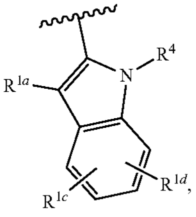

-continued
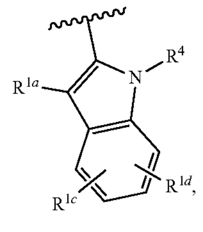
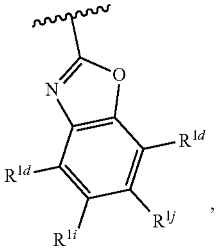
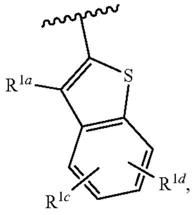
or
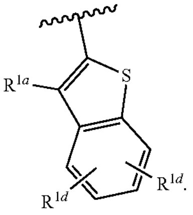
In another embodiment, $R^{d3}$ is
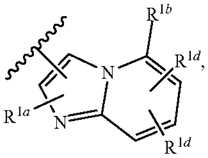
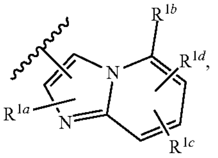
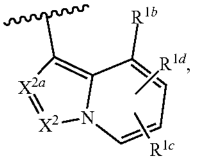
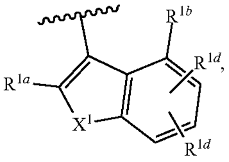
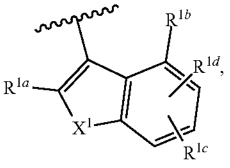
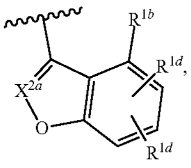
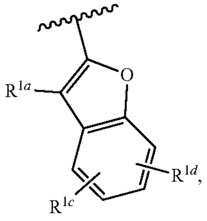
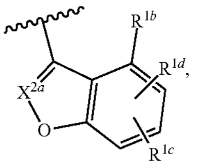
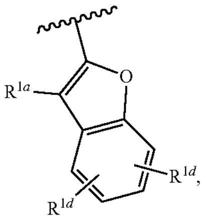
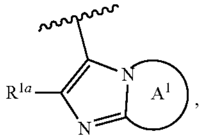
-continued
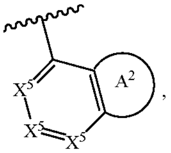
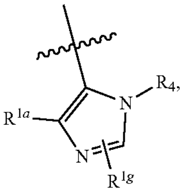
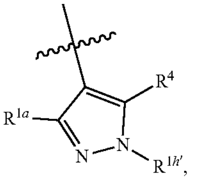
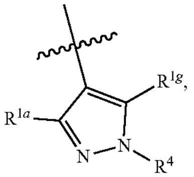
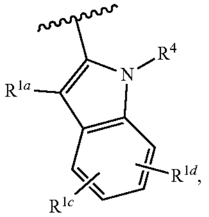
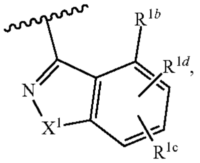
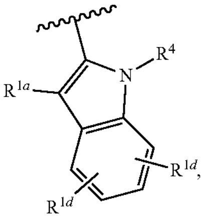
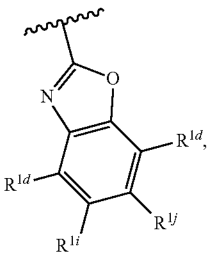
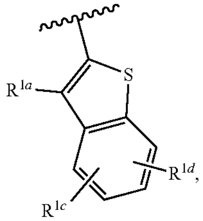
or
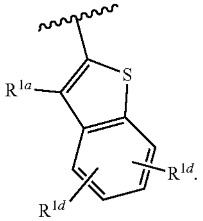
In another embodiment, $R^{d3}$ is
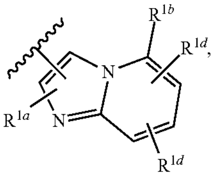
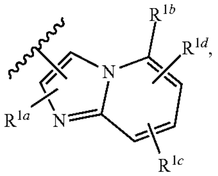
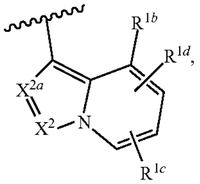
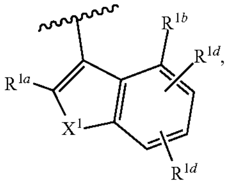

-continued
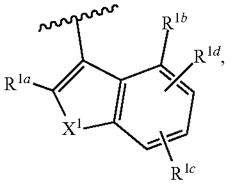
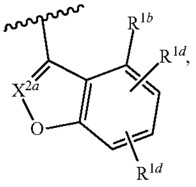
or
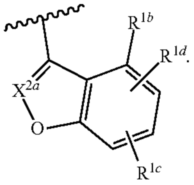
In another embodiment, $R^{d3}$ is
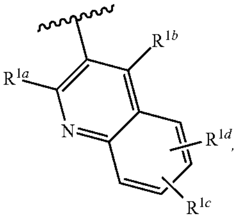
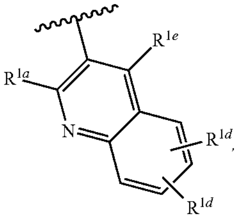
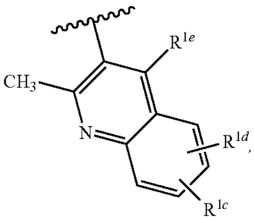
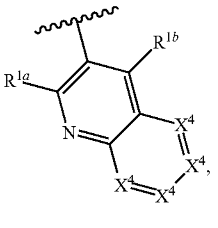
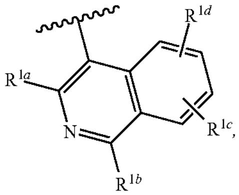
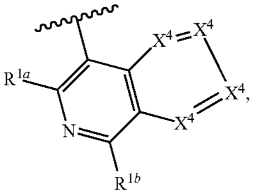
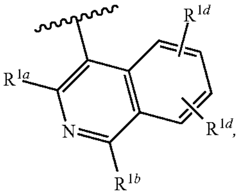
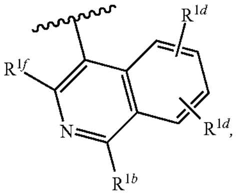
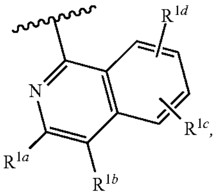
or
-continued
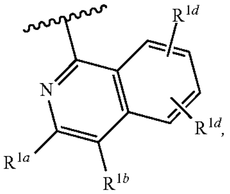
In another embodiment, $R^{d3}$ is
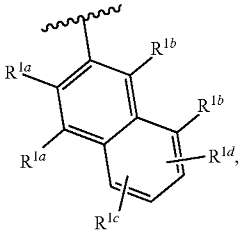
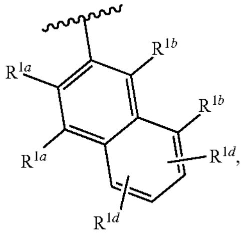
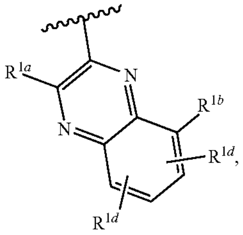
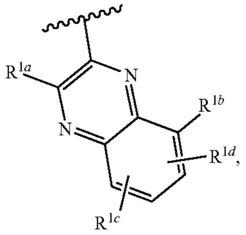
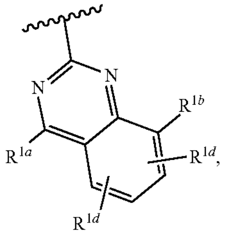
or
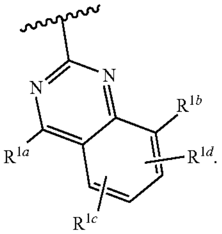
In another embodiment, $R^{d3}$ is
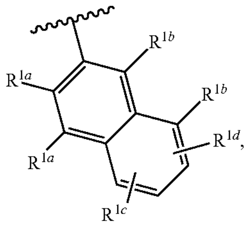
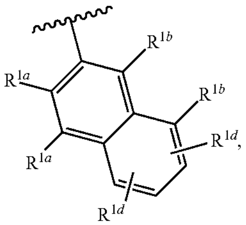
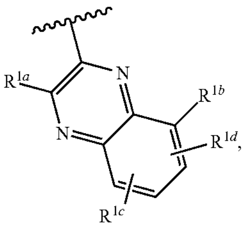
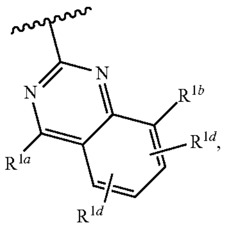
or -continued
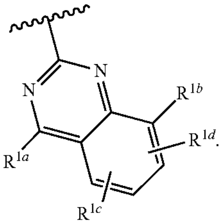
In another embodiment, $R^{d3}$ is
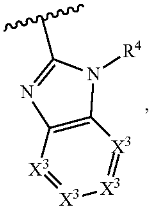,
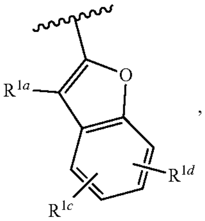,
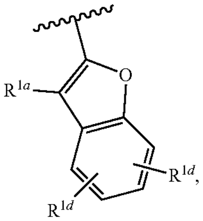
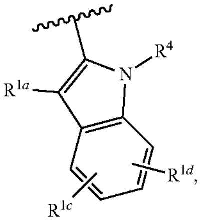
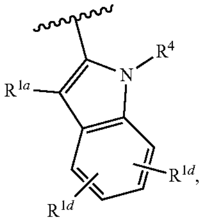
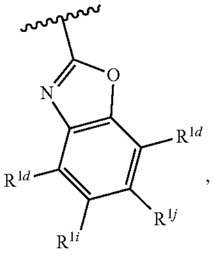,
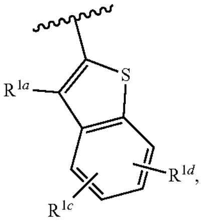 or 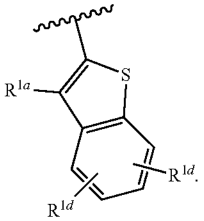
In another embodiment, $R^{d3}$ is
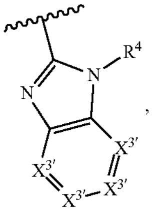,
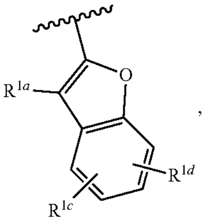,
-continued
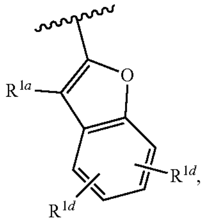
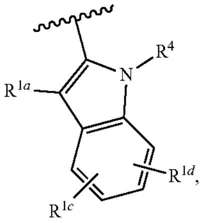
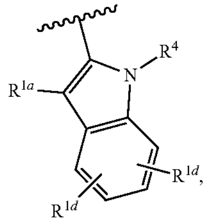
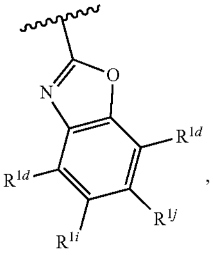,
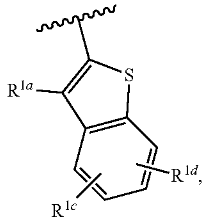 or 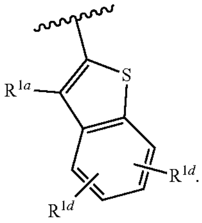
In another embodiment, $R^{d3}$ is
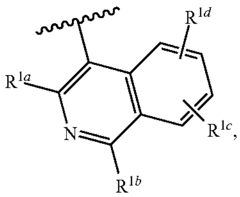
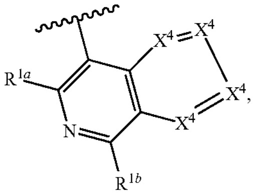
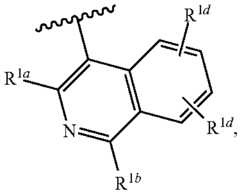
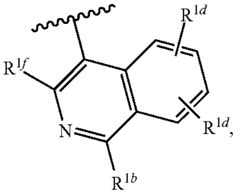
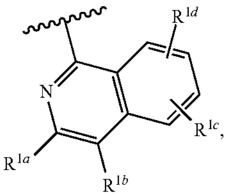
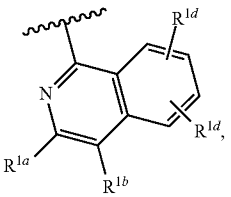
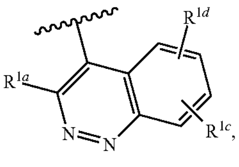
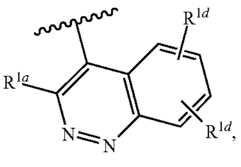 or -continued
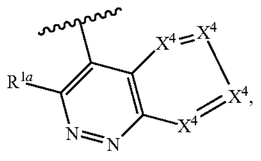
In another embodiment, $R^{d3}$ is
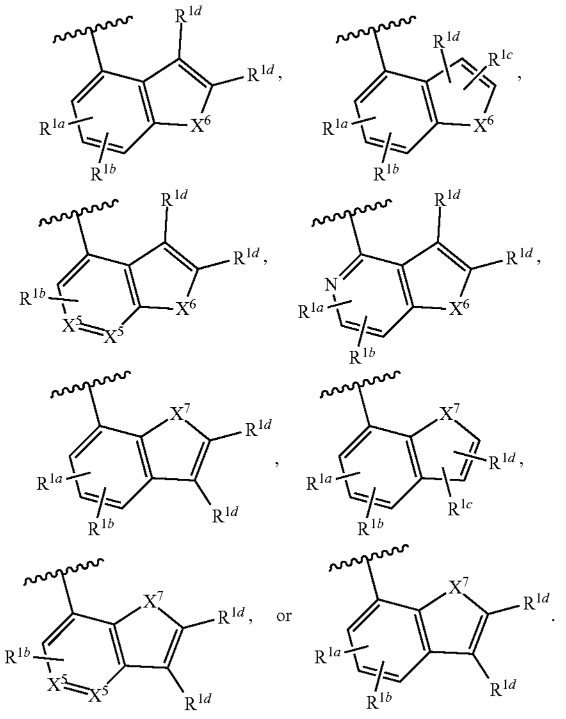
or
In another embodiment, $R^{d3}$ is
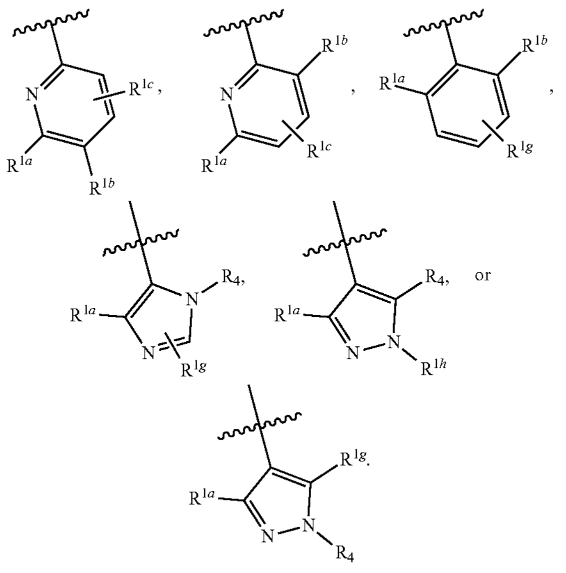
or
In another embodiment, $R^{d3}$ is
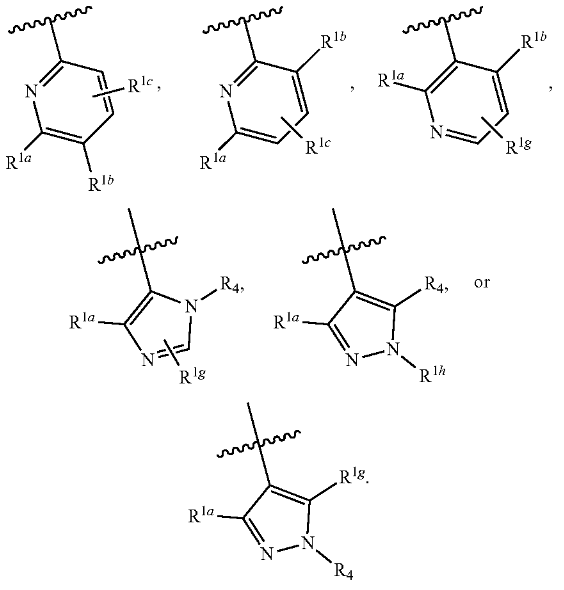
or
In another embodiment, $R^{d3}$ is
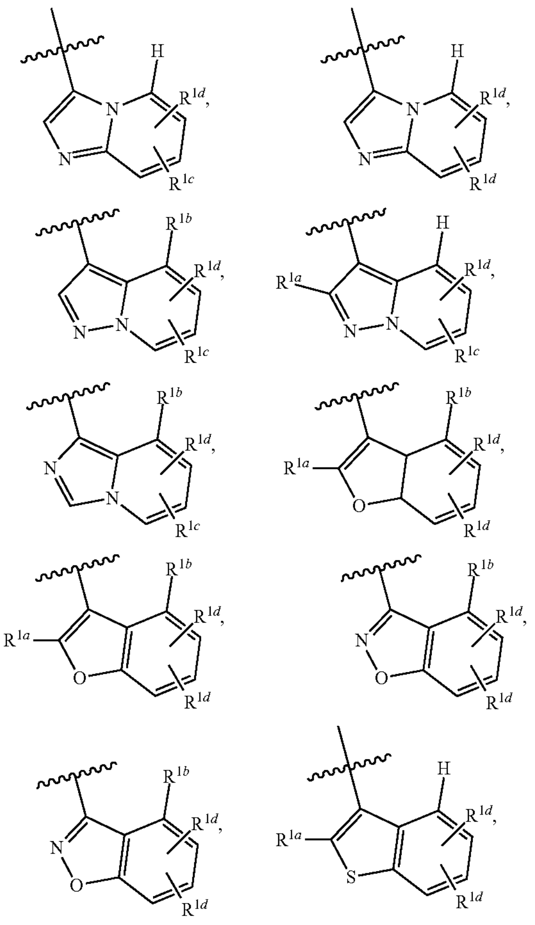

-continued
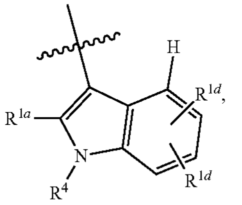
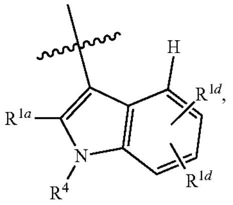
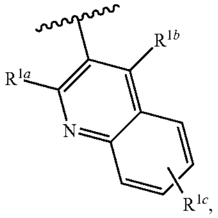
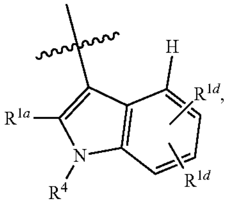
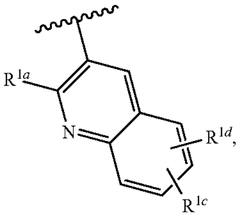
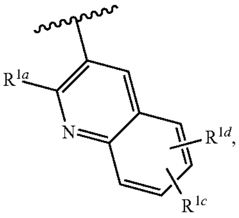
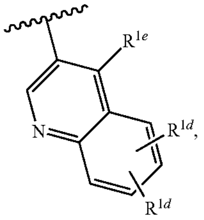
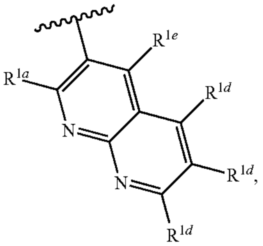
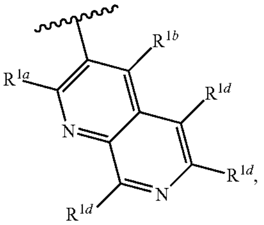
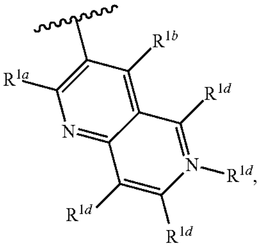
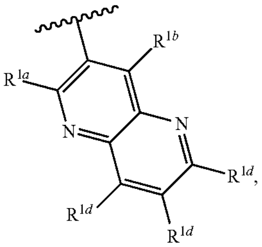
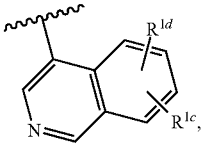
-continued
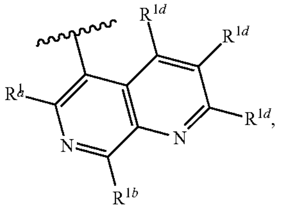
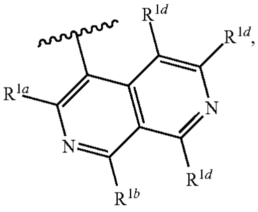
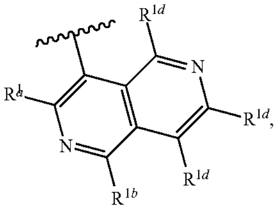
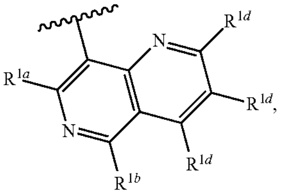
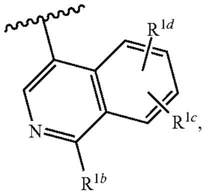
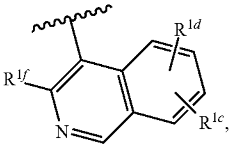
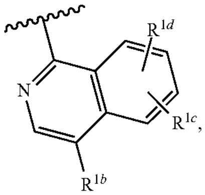
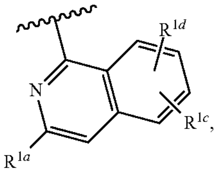
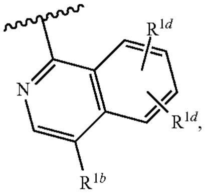
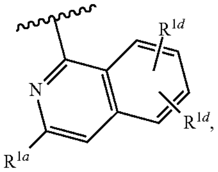
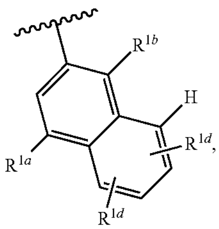
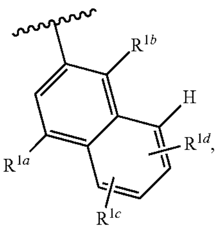
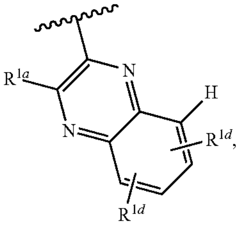
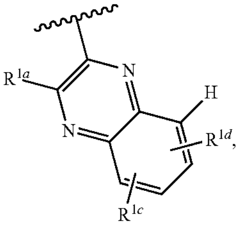

-continued
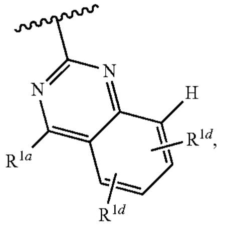
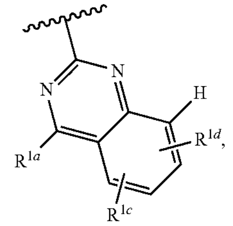
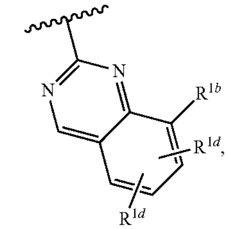
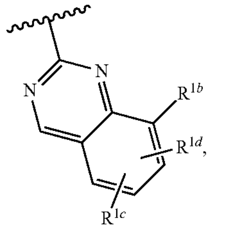
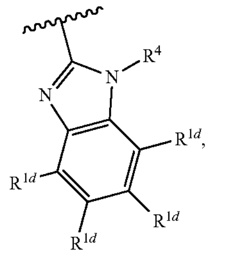
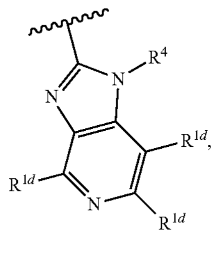
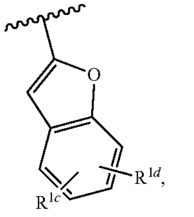
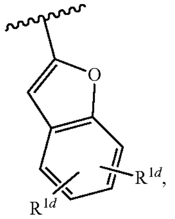
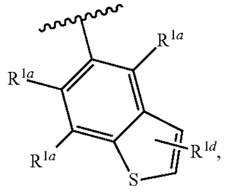
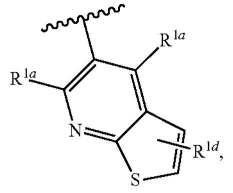
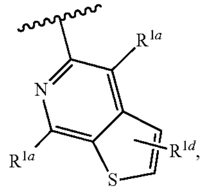
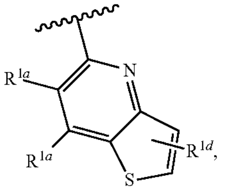
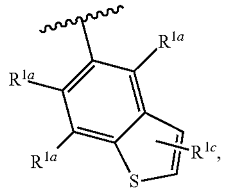
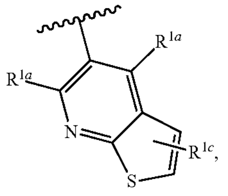
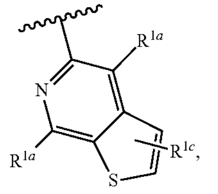
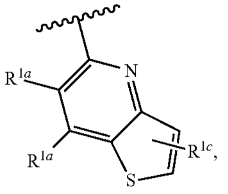
-continued
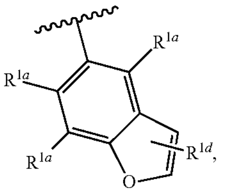
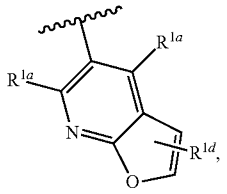
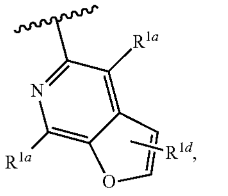
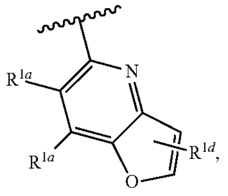
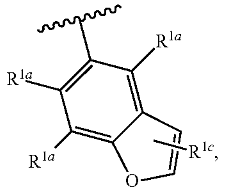
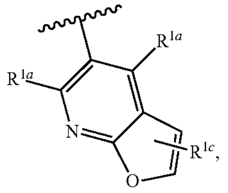
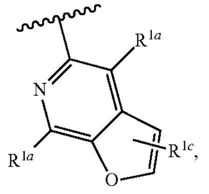
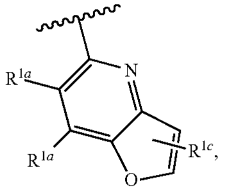
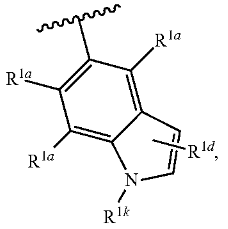
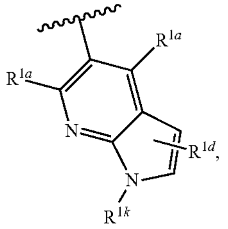
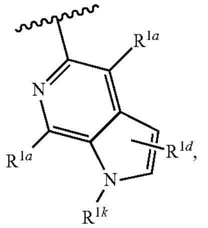
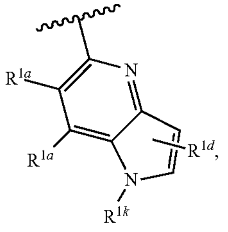
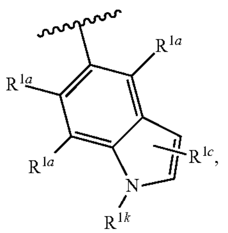
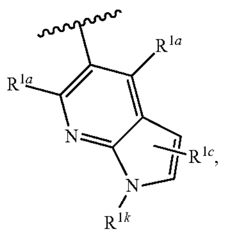
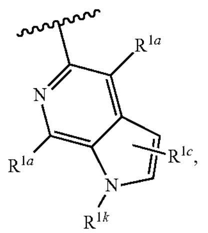
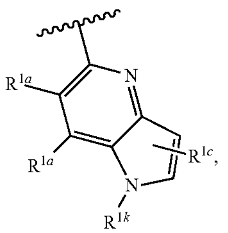

-continued
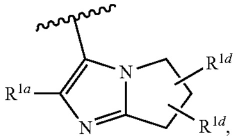
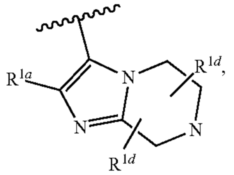
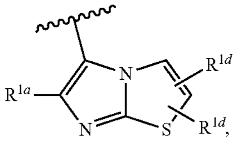
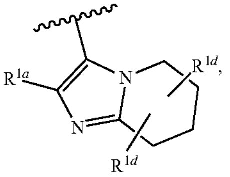
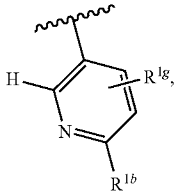
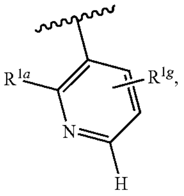
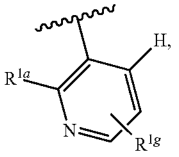
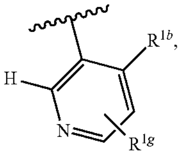
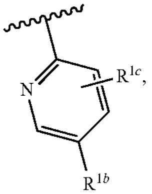
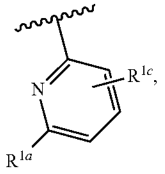
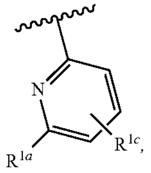
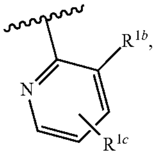
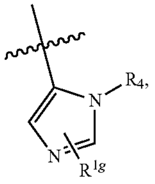
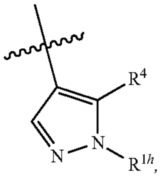
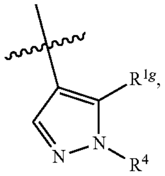
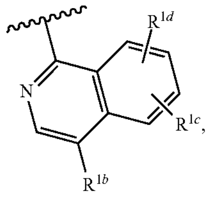
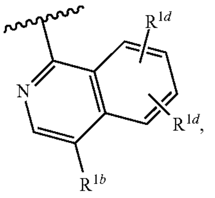
-continued
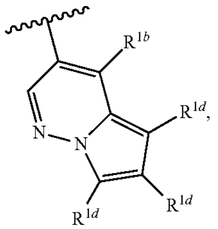
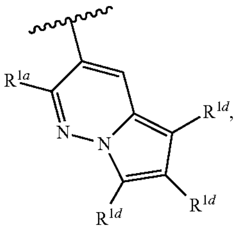
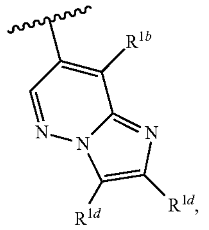
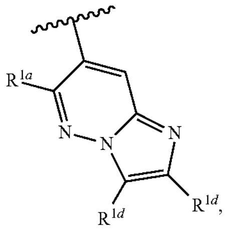
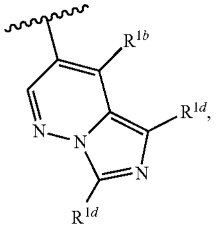
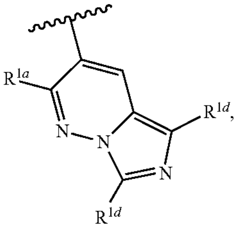
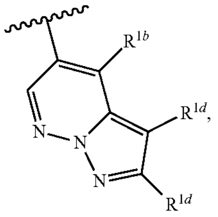
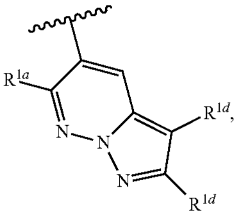
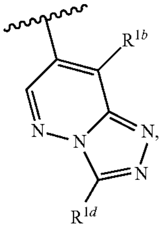
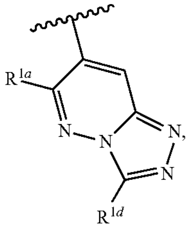
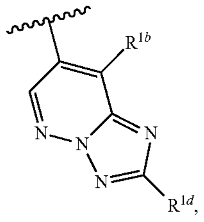
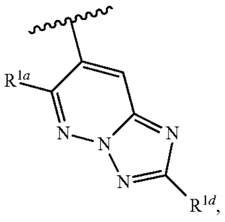
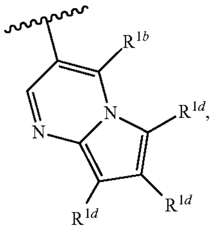
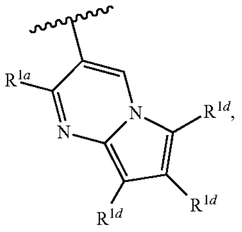

-continued
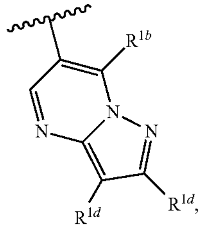
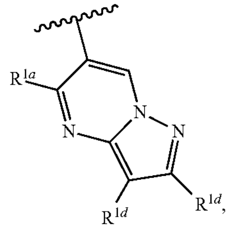
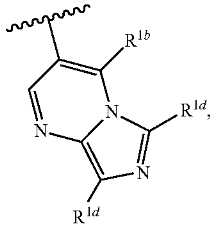
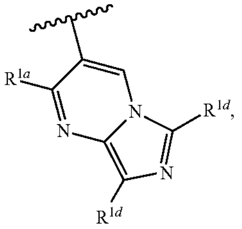
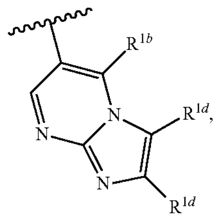
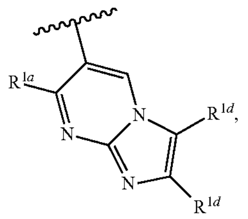
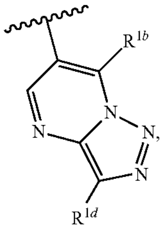
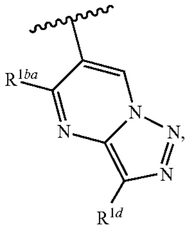
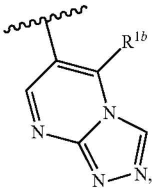
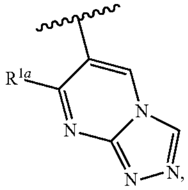
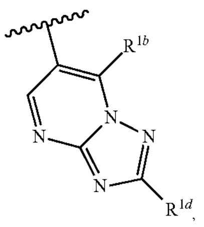
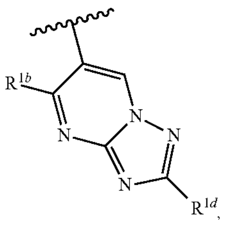
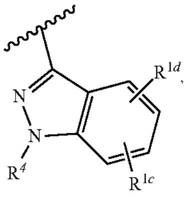
-continued
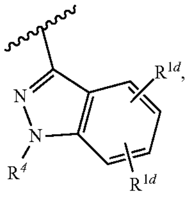
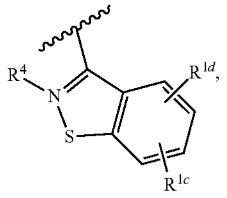
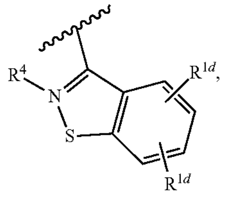
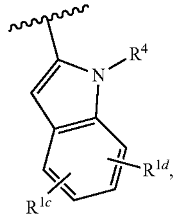
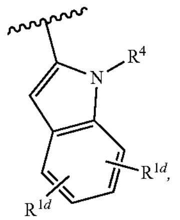
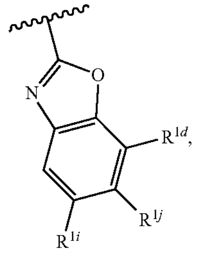
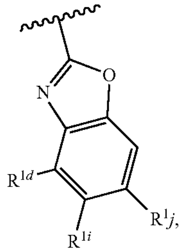
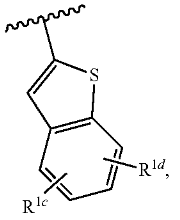
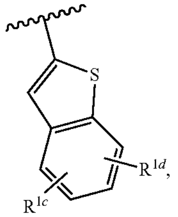
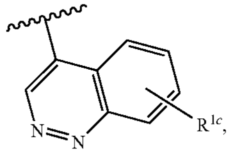
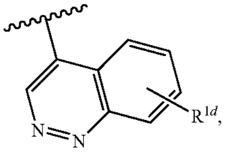
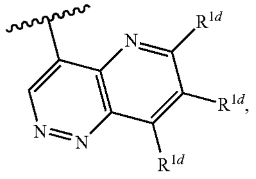
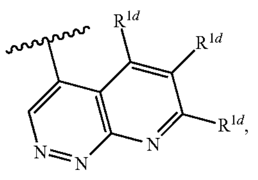

-continued
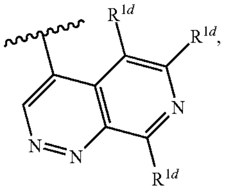
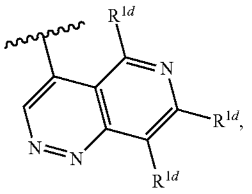
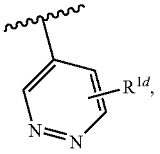
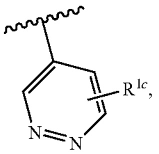
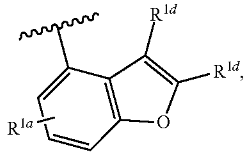
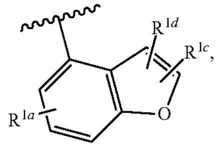
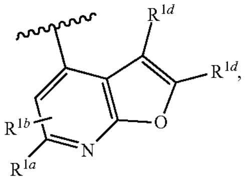
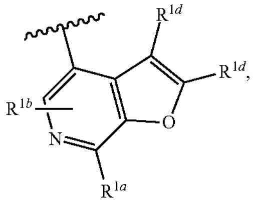
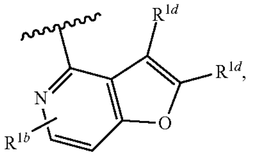
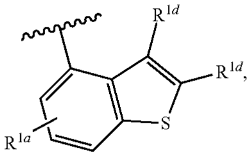
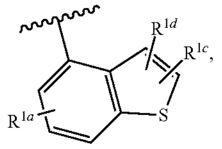
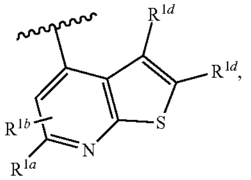
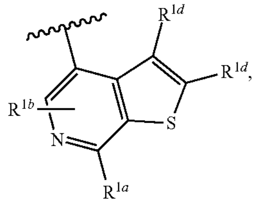
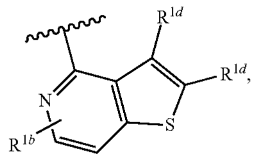
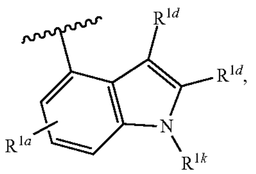
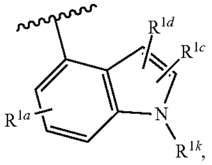
-continued
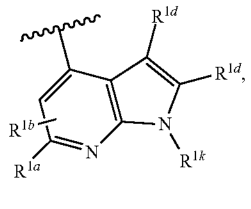
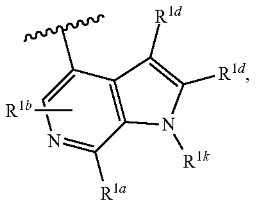
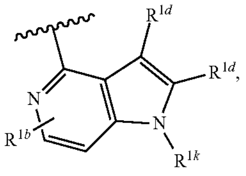
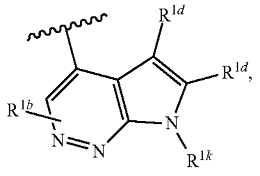
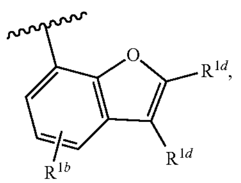
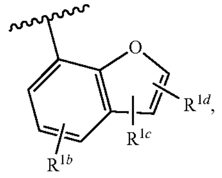
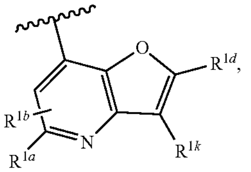
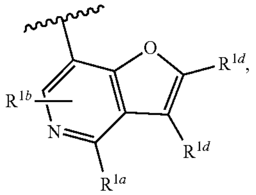
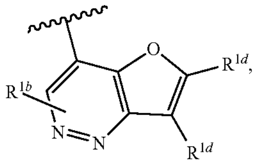
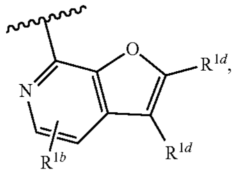
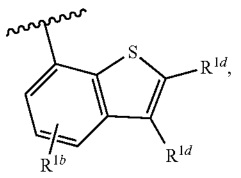
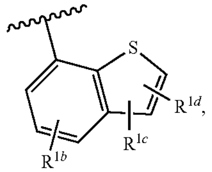
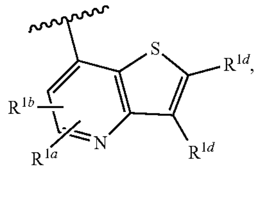
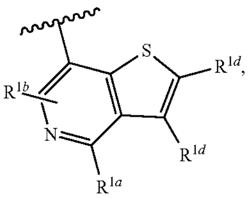
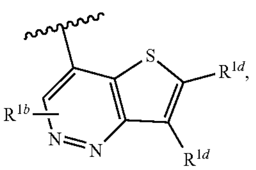
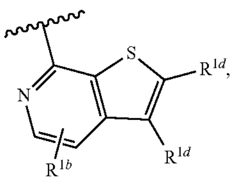

-continued
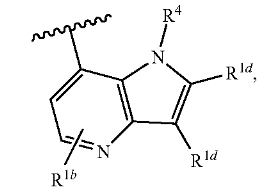
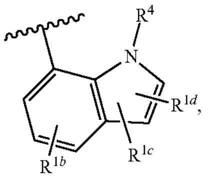
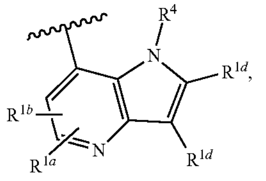
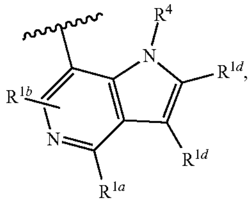
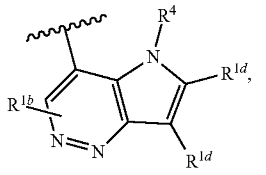
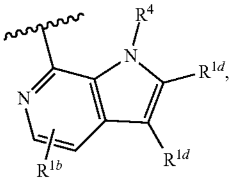
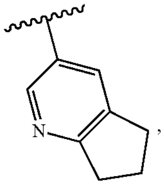
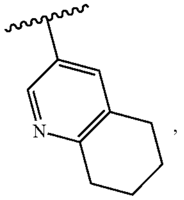
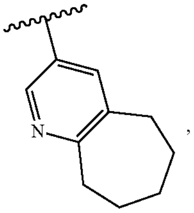
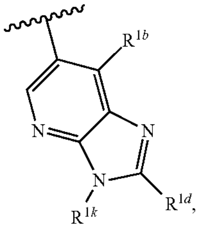
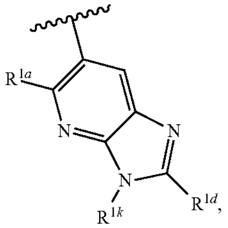
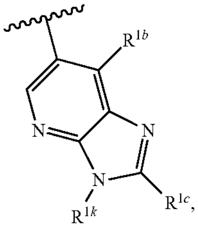
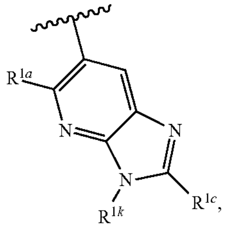
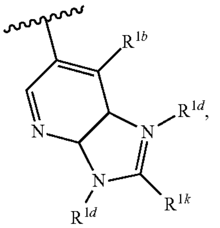
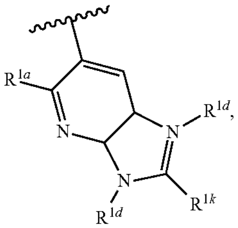
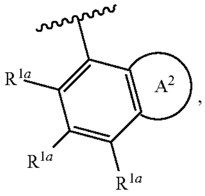
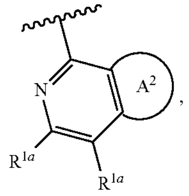
-continued
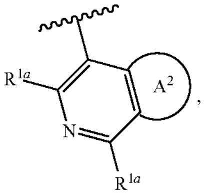
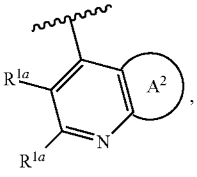
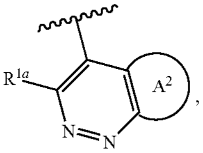
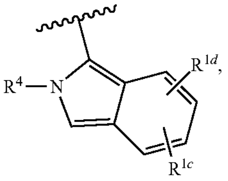
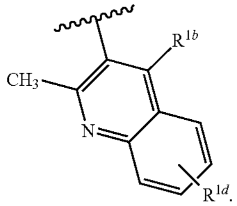
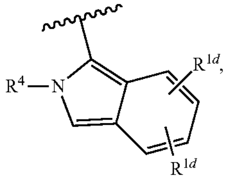
or
In another embodiment, $R^{d3}$ is
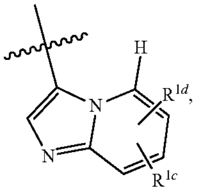
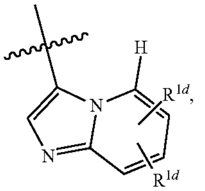
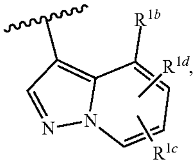
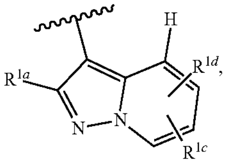
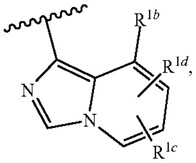
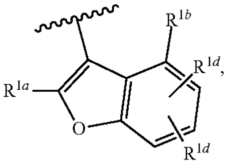
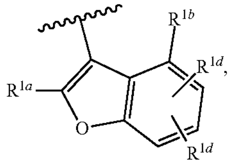
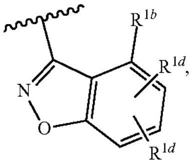
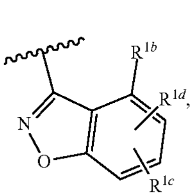
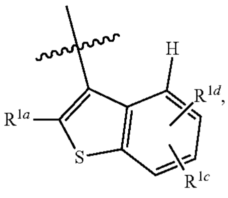

-continued
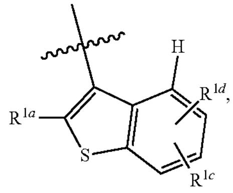
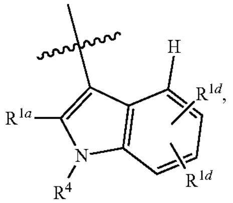
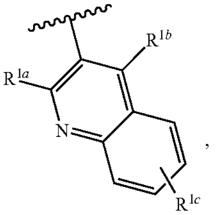
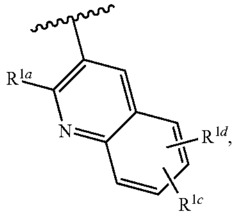
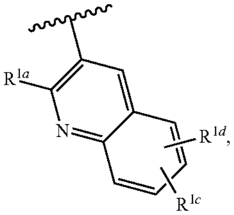
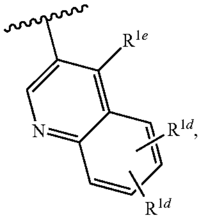
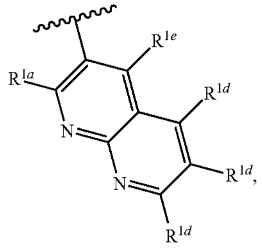
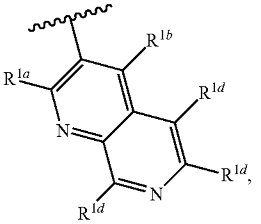
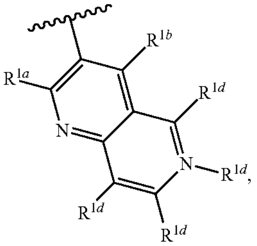
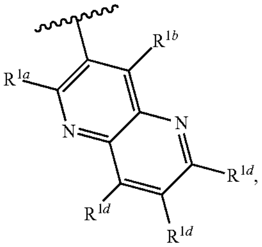
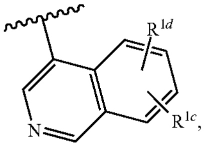
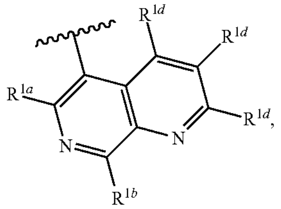
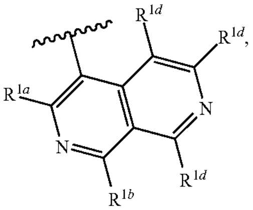
-continued
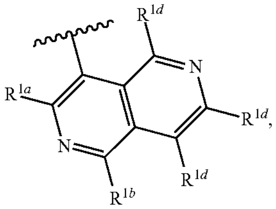
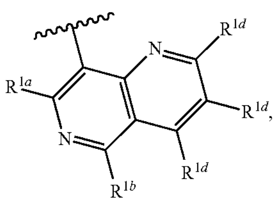
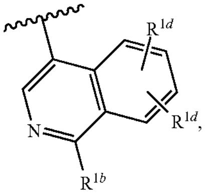
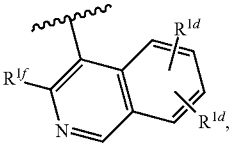
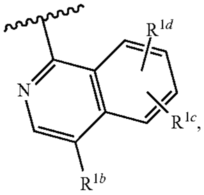
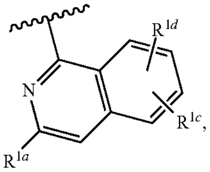
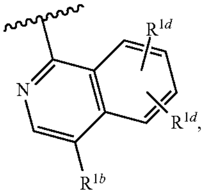
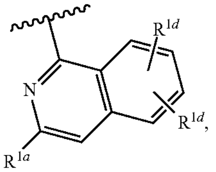
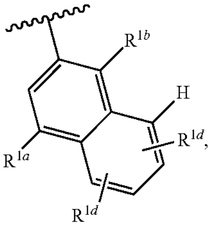
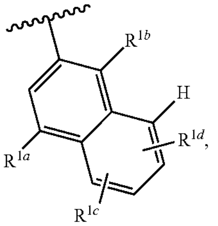
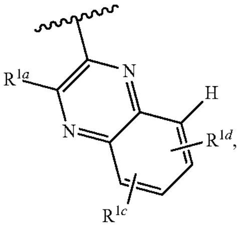
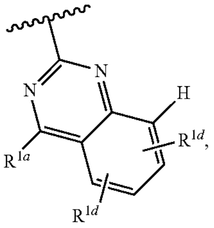
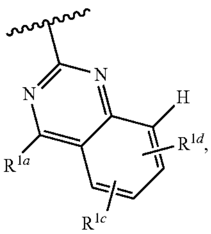
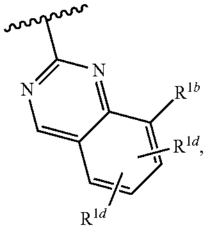
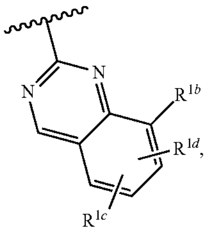
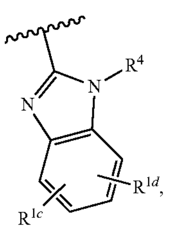

-continued
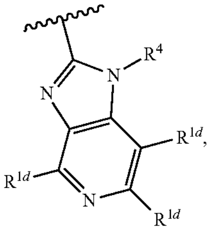
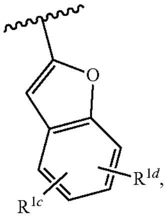
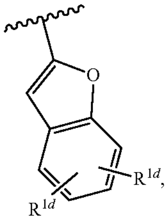
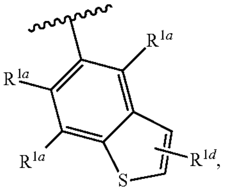
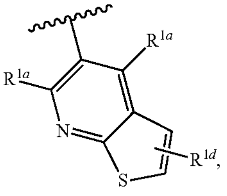
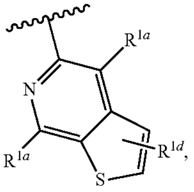
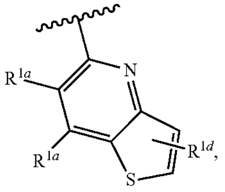
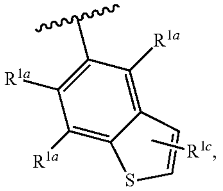
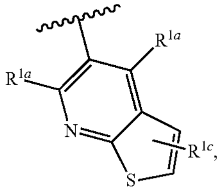
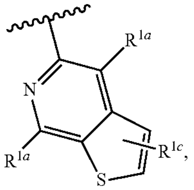
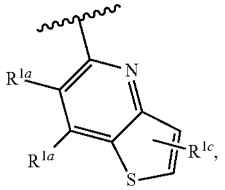
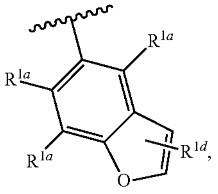
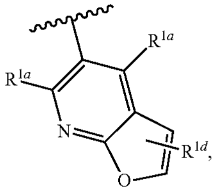
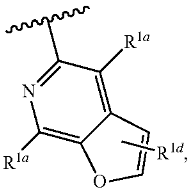
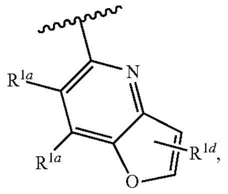
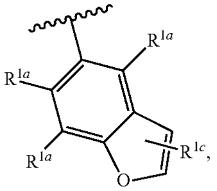
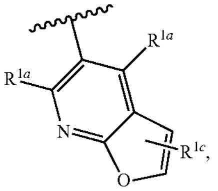
-continued
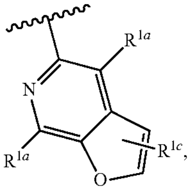
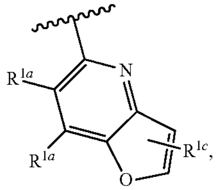
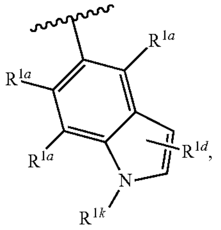
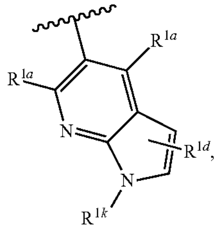
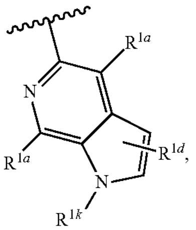
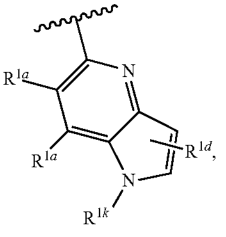
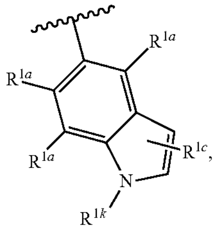
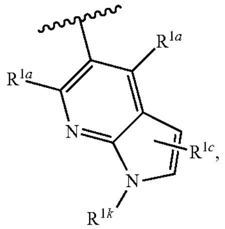
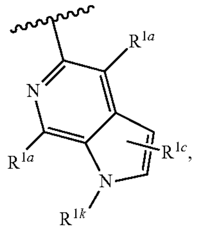
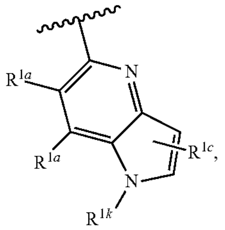
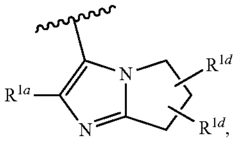
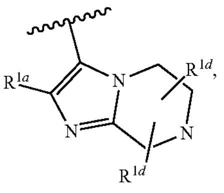
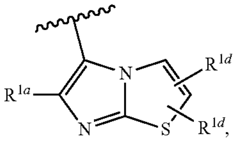
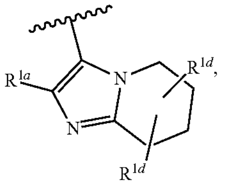

-continued
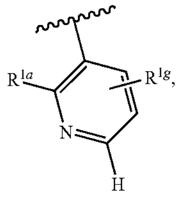
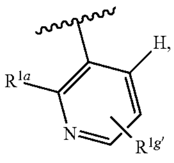
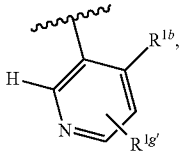
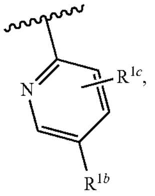
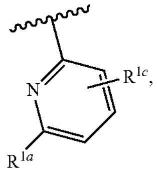
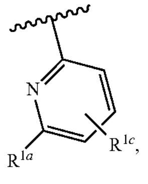
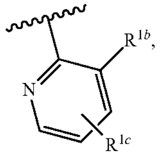
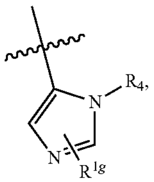
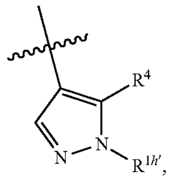
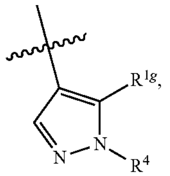
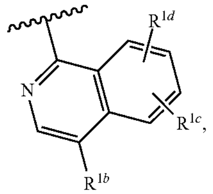
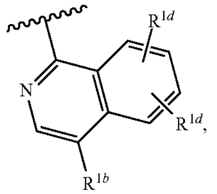
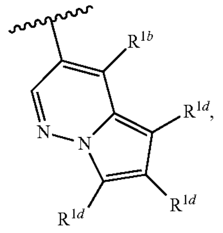
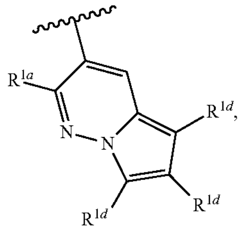
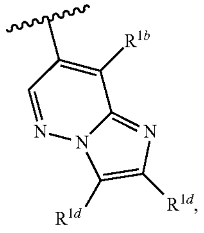
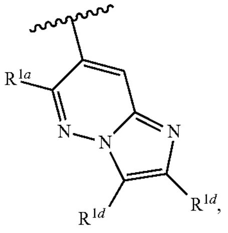
-continued
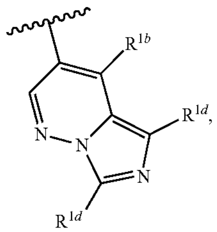
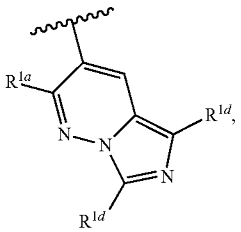
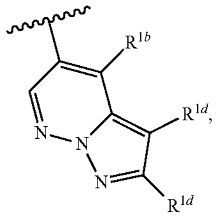
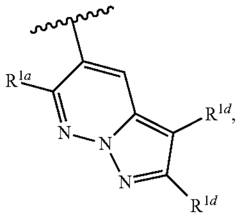
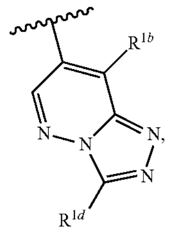
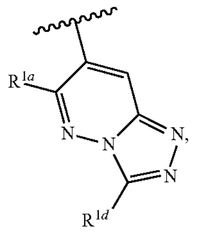
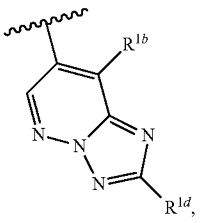
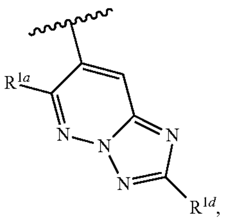
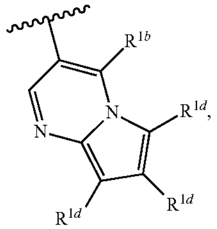
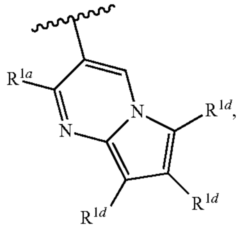
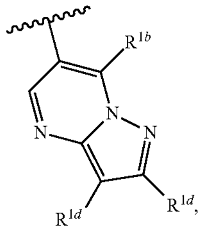
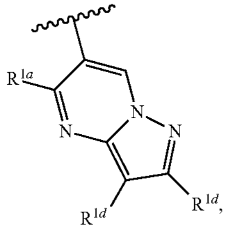
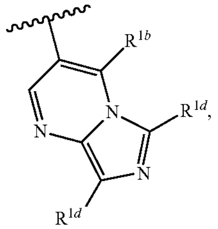
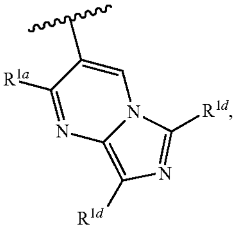

-continued
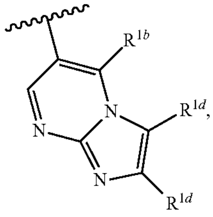
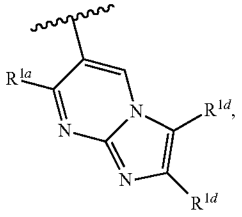
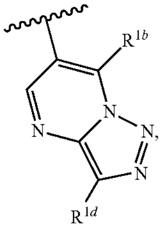
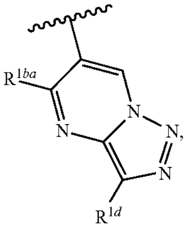
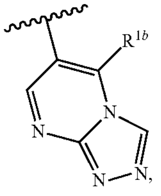
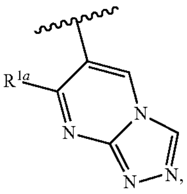
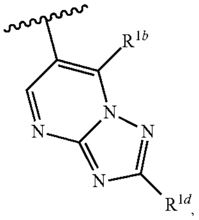
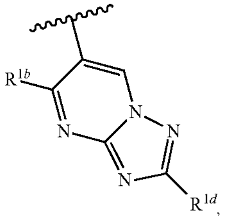
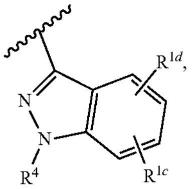
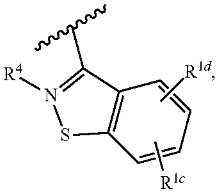
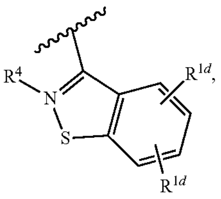
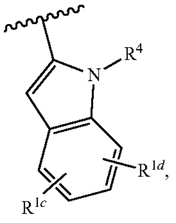
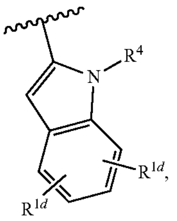
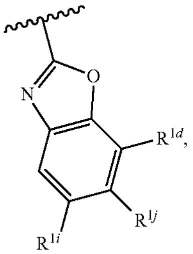
-continued
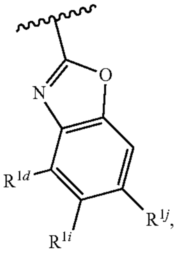
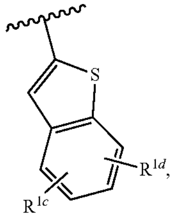
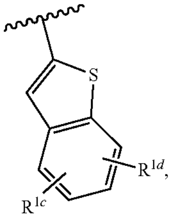
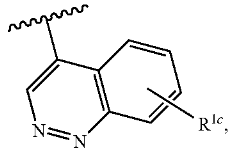
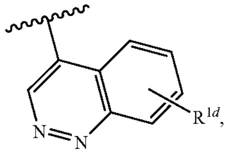
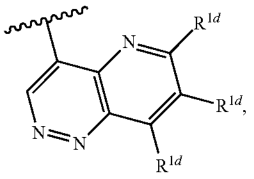
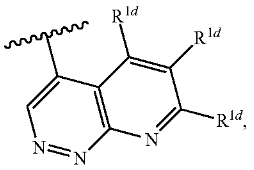
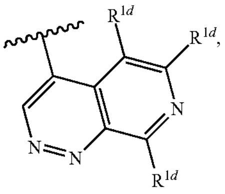
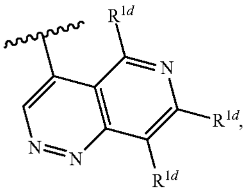
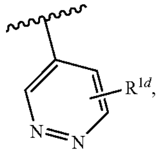
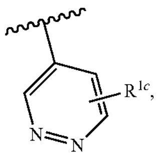
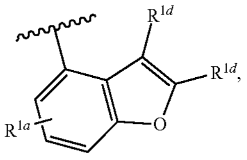
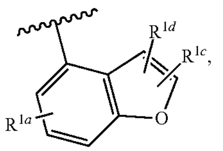
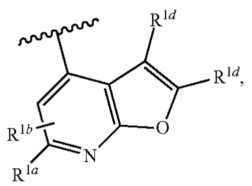
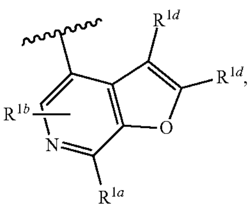
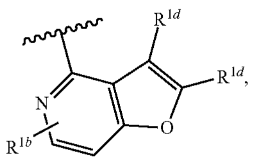
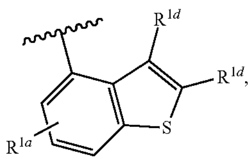

-continued
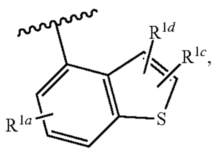
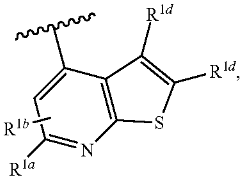
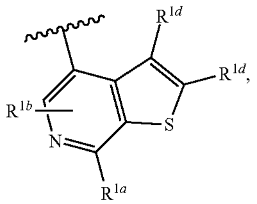
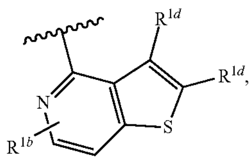
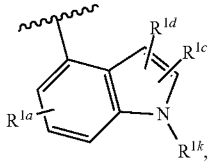
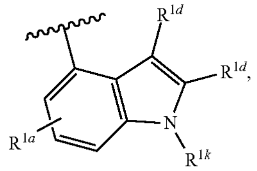
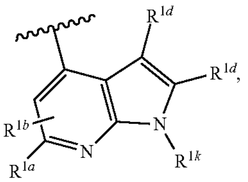
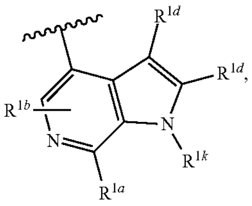
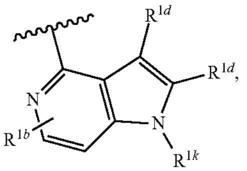
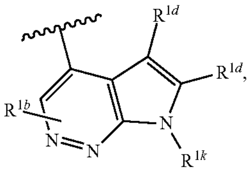
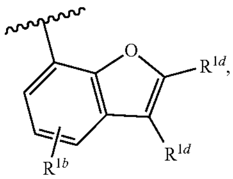
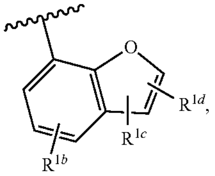
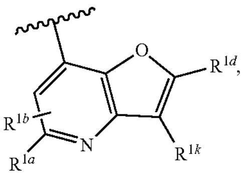
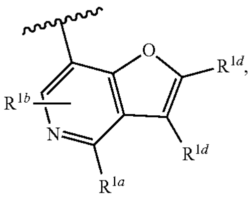
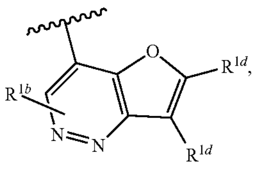
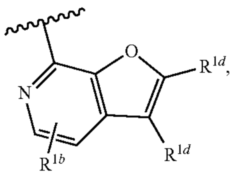
-continued
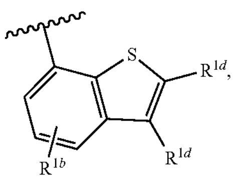
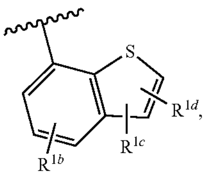
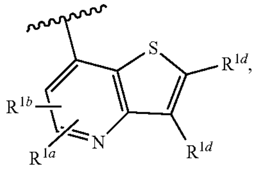
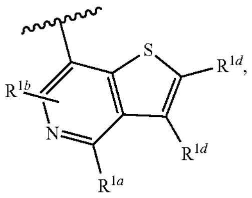
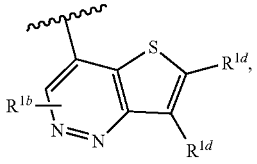
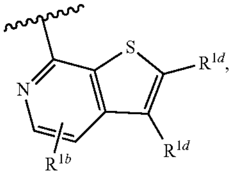
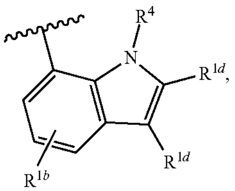
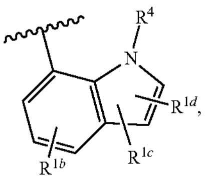
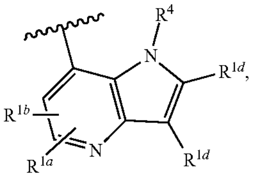
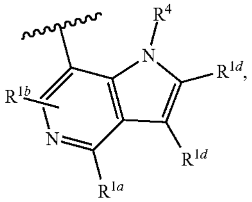
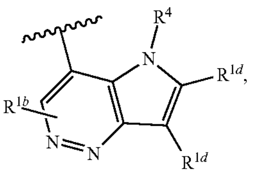
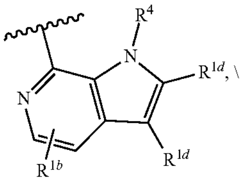
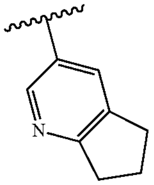
,
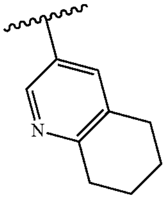
,
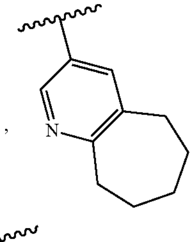
,
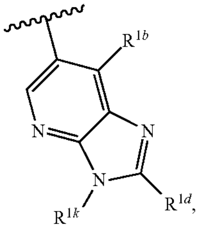
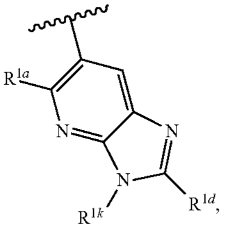

-continued
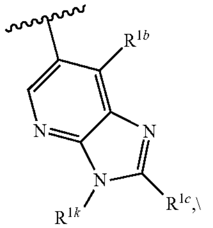
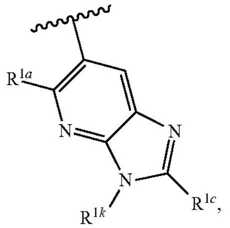
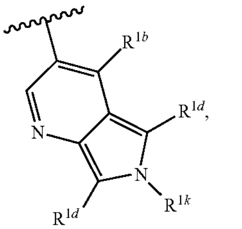
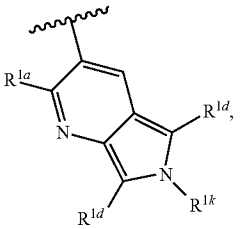
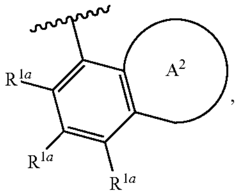
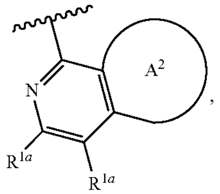
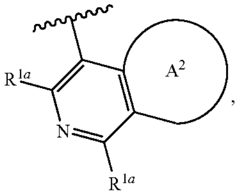
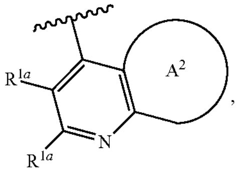
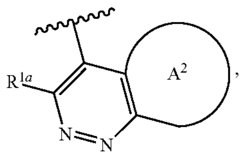
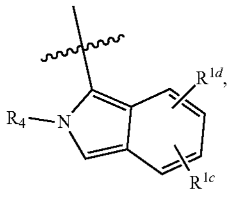
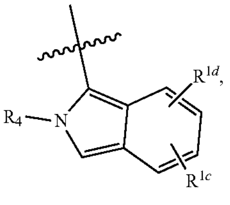
or
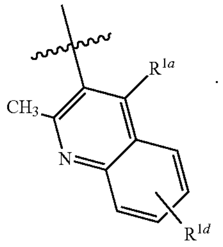
In another embodiment, $R^{d3}$ is
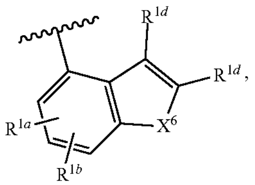
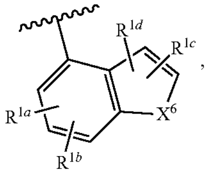
-continued
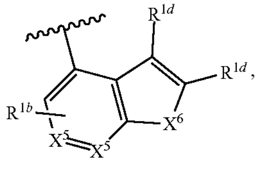
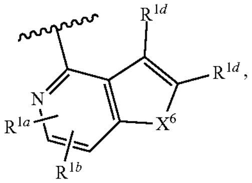
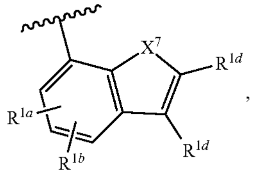
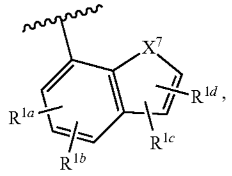
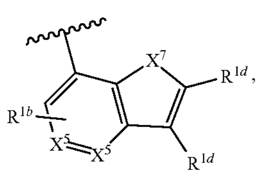
or
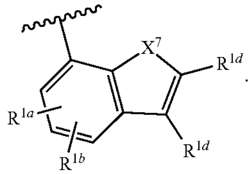
In another embodiment, $R^{d3}$ is
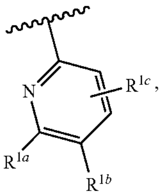
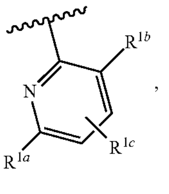
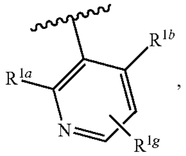
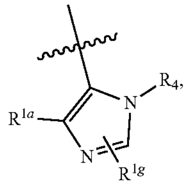
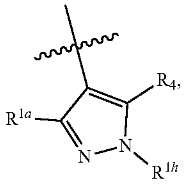
or
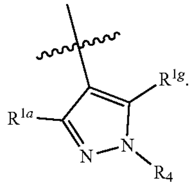
In another embodiment, $R^{d3}$ is
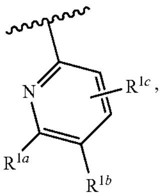
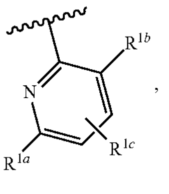
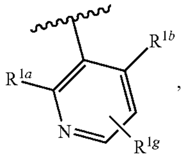
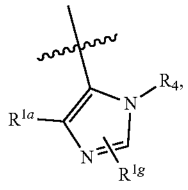
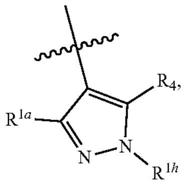
or -continued
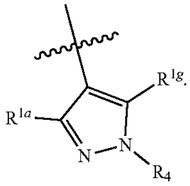
In another embodiment, $R^{d3}$ is
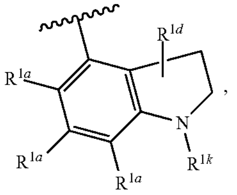
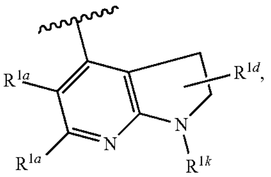
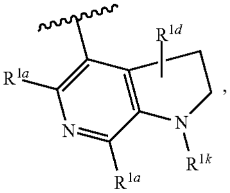
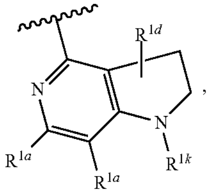
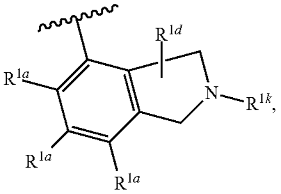
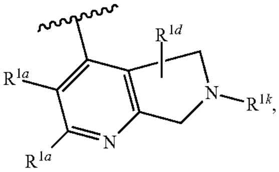
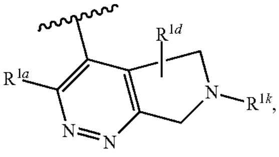
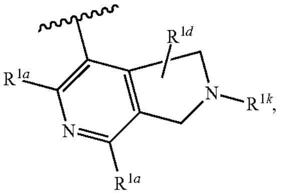
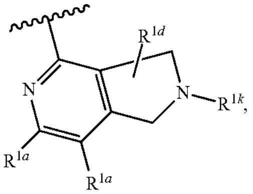
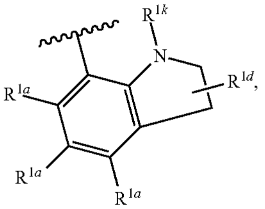
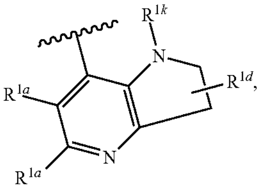
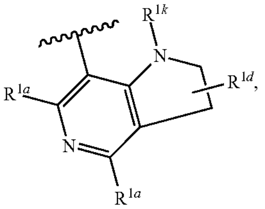
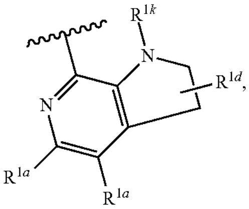
-continued
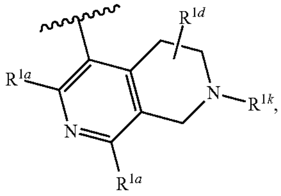
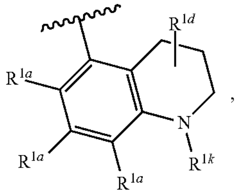
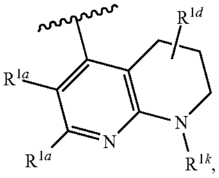
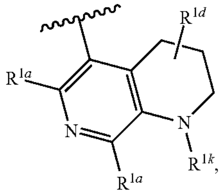
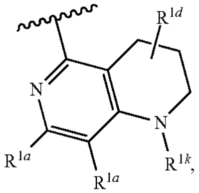
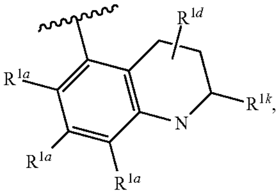
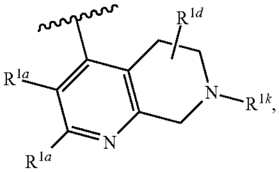
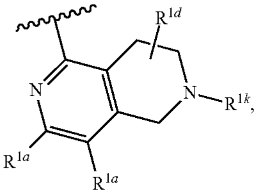
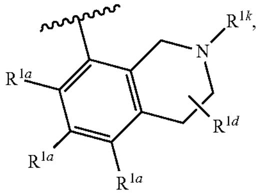
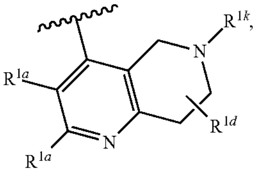
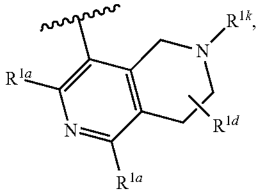
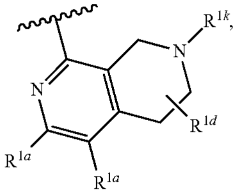
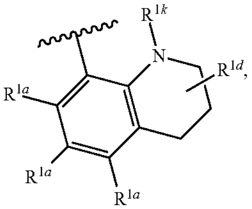
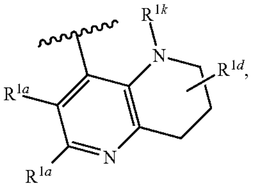
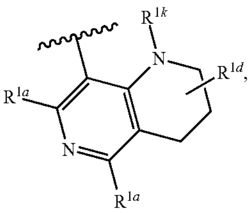
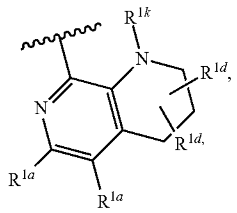

-continued
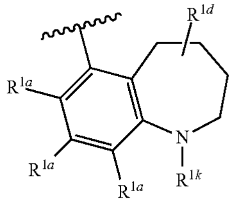 ,
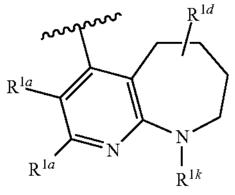 ,
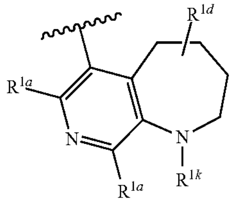 ,
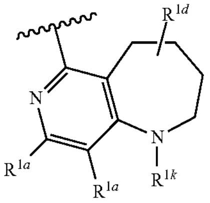 ,
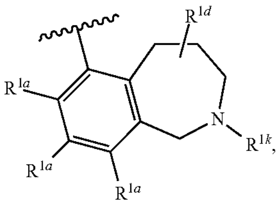
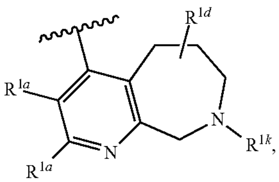
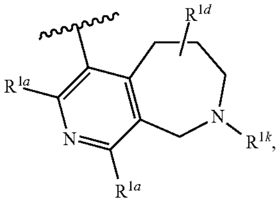
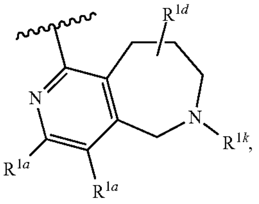
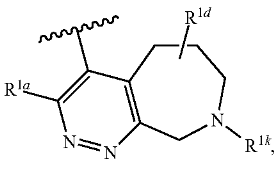
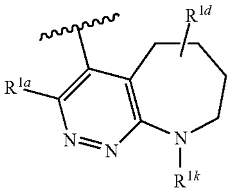 ,
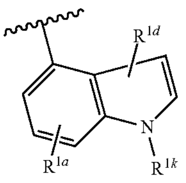 ,
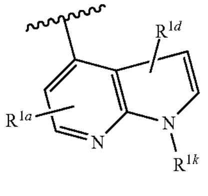 ,
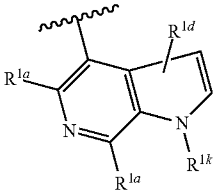 ,
-continued
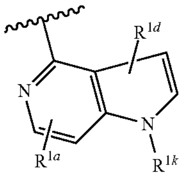 ,
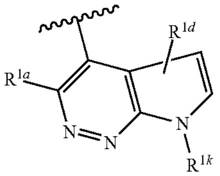 ,
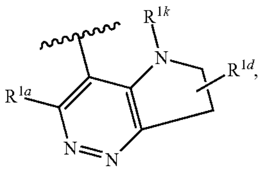
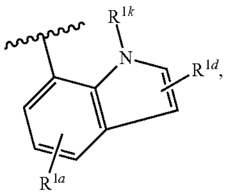
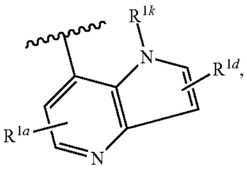
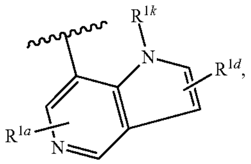
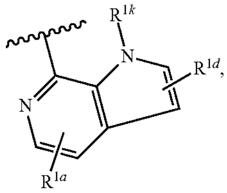
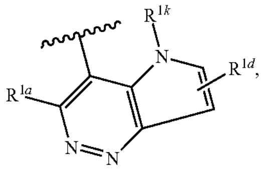
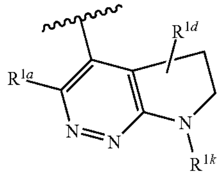 ,
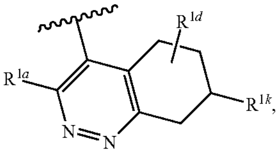
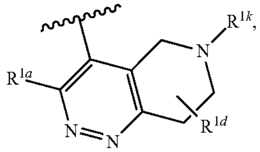
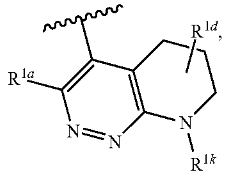
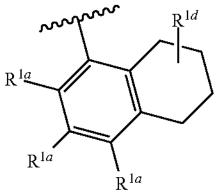 ,
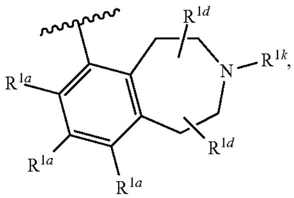
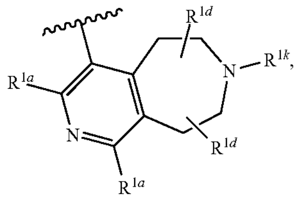

-continued
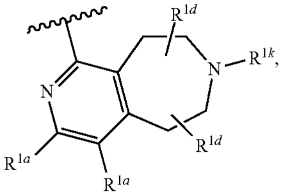
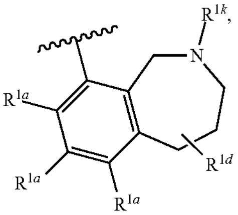
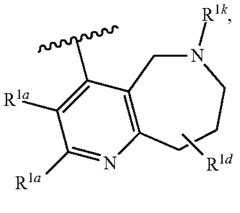
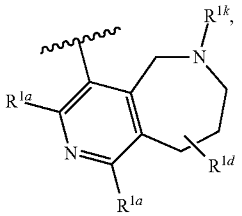
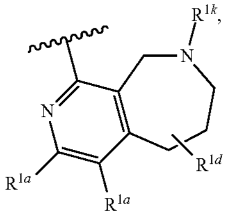
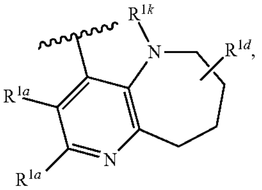
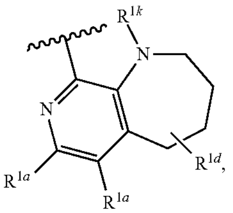
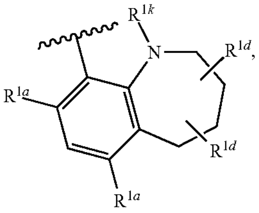
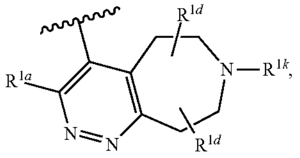
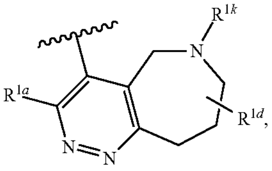
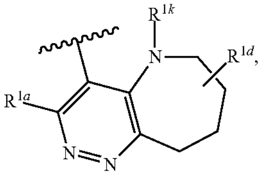
or
-continued
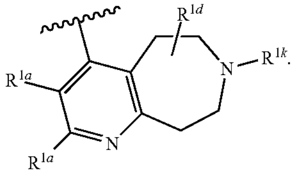
In another embodiment, $R^{d3}$ is
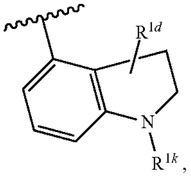
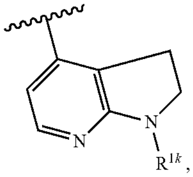
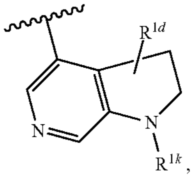
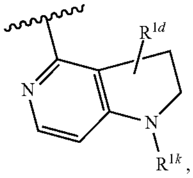
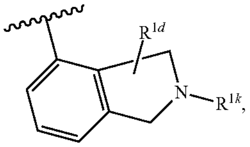
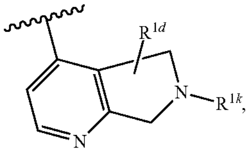
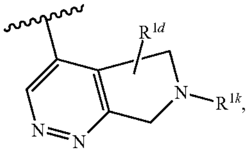
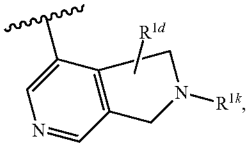
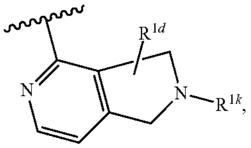
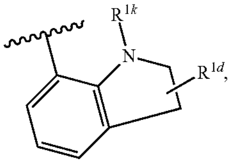
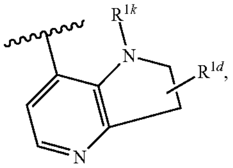
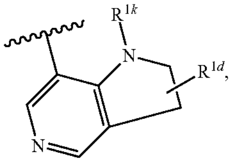
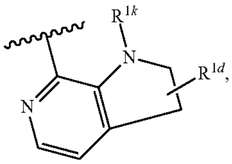
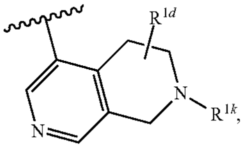
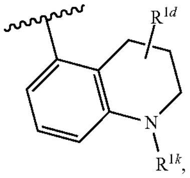
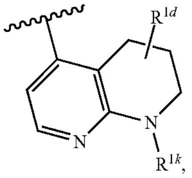

-continued
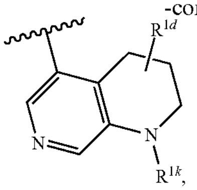
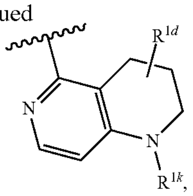
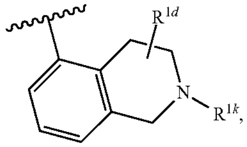
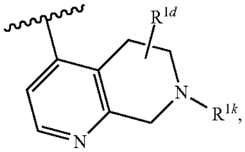
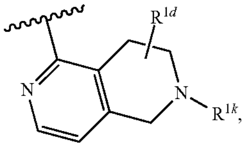
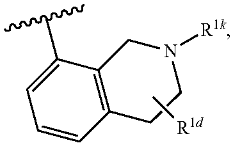
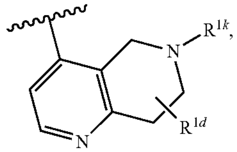
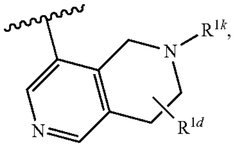
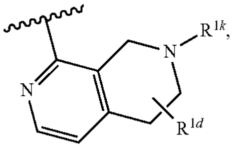
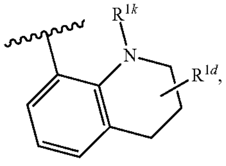
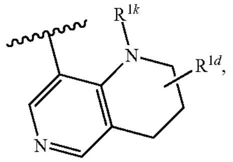
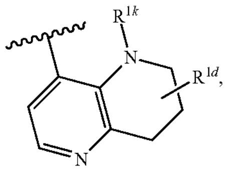
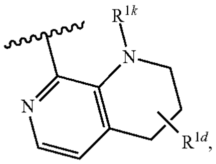
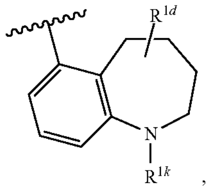
,
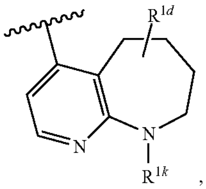
,
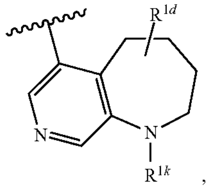
,
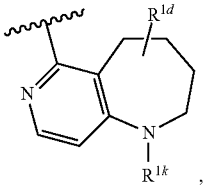
,
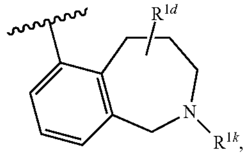
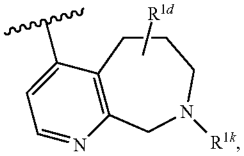
-continued
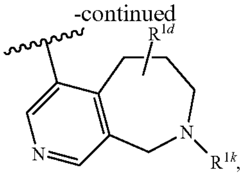
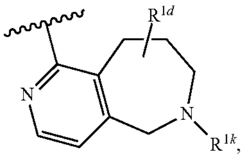
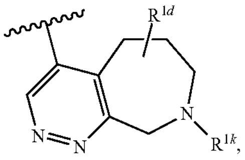
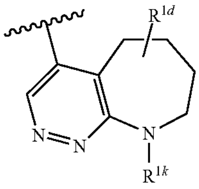
,
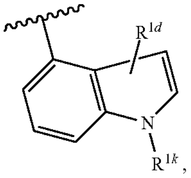
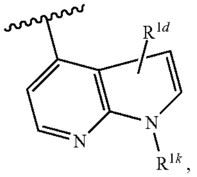
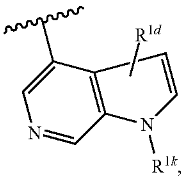
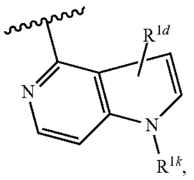
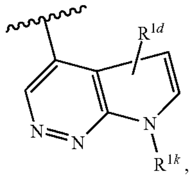
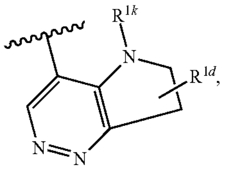
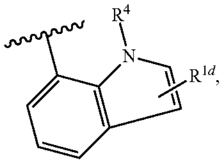
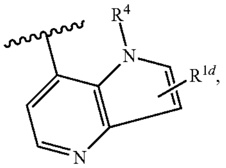
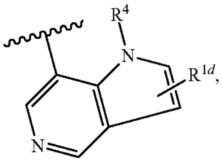
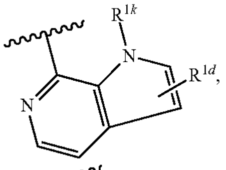
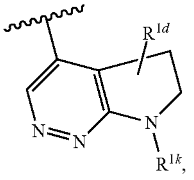
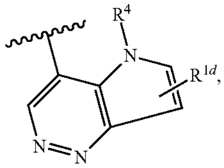

-continued
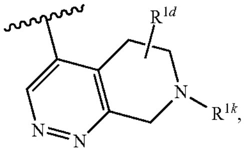
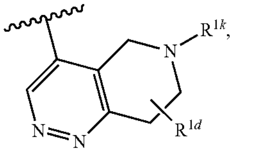
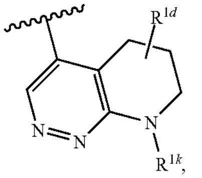
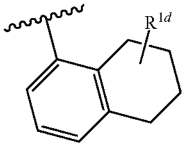
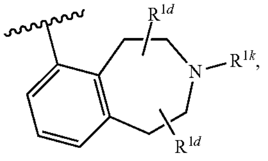
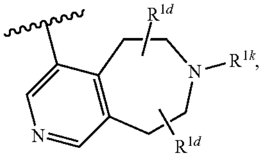
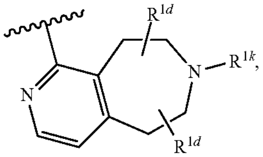
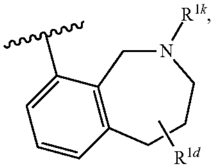
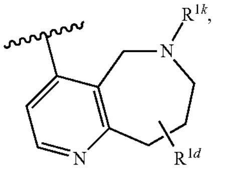
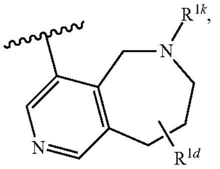
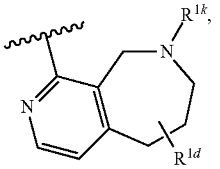
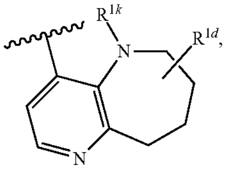
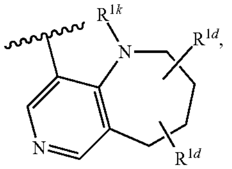
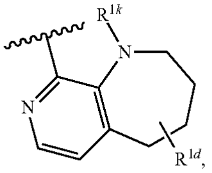
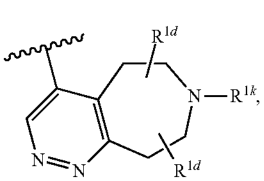
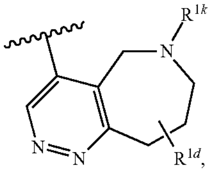
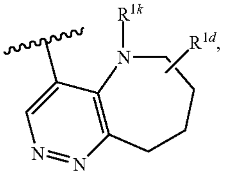
or
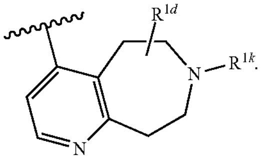
In another embodiment, $R^{d3}$ is
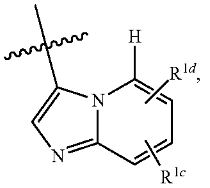
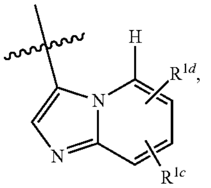
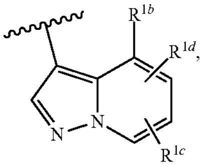
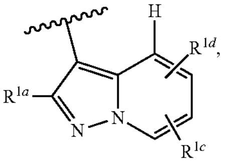
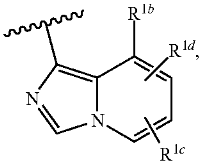
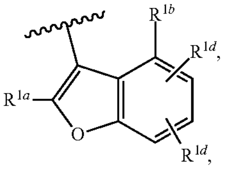
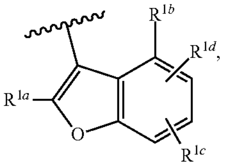
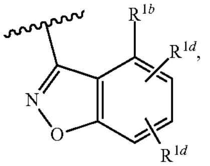
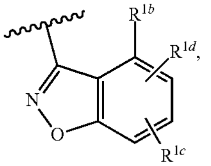
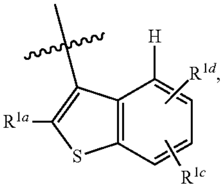
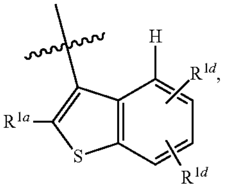
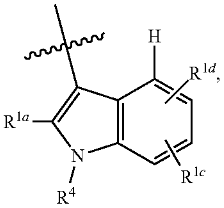
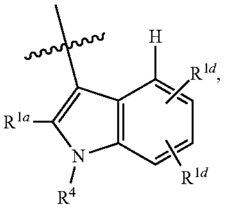
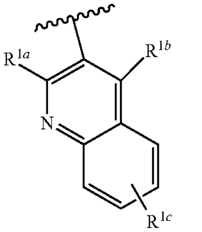
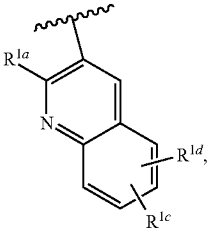
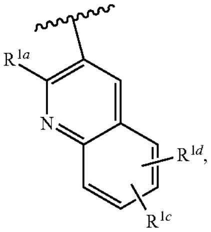
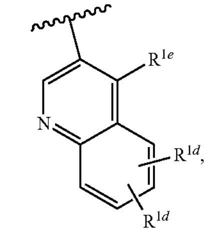

-continued
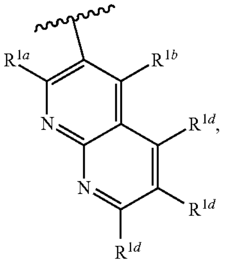
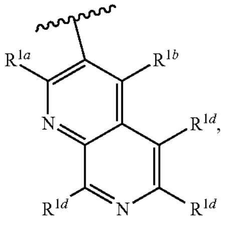
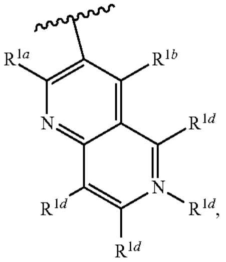
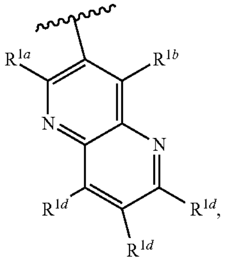
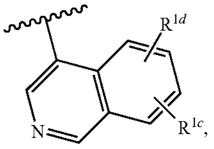
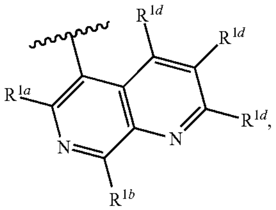
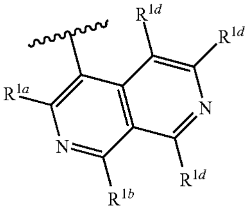
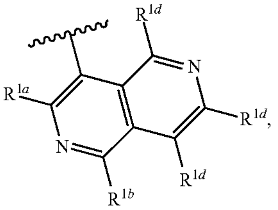
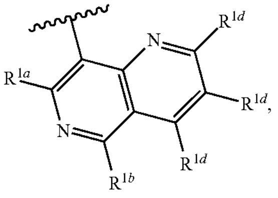
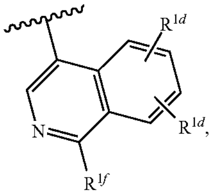
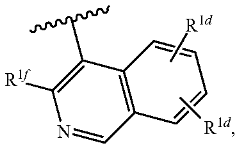
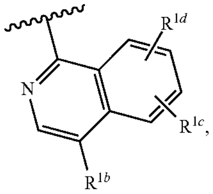
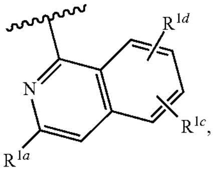
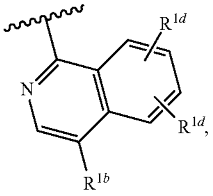
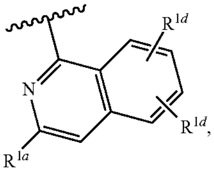
-continued
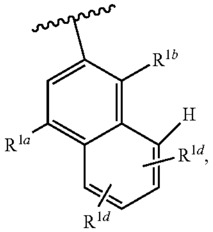
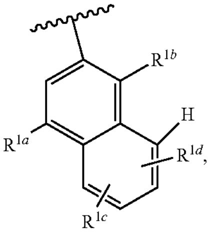
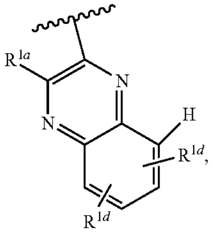
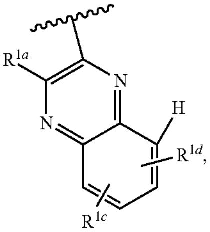
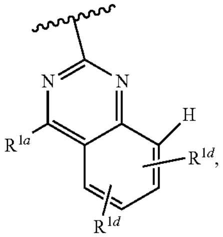
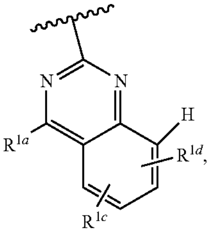
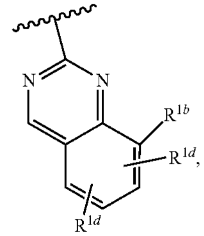
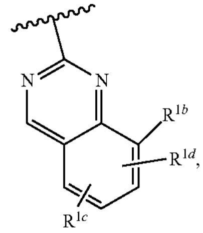
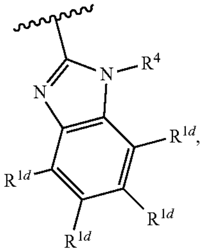
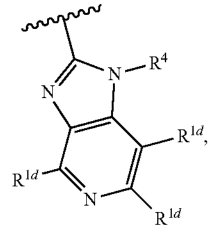
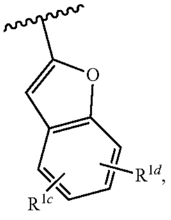
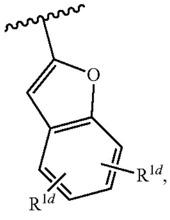
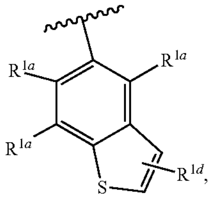
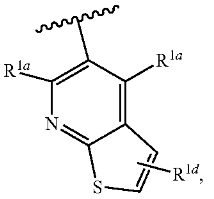

-continued
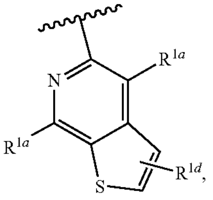
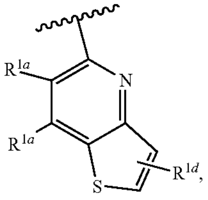
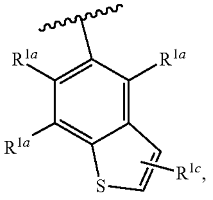
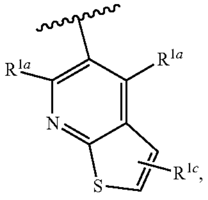
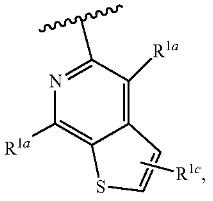
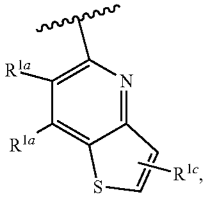
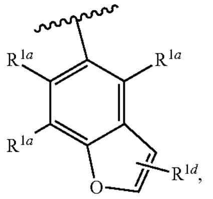
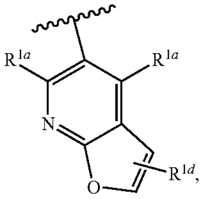
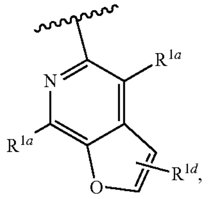
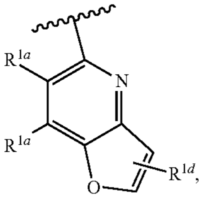
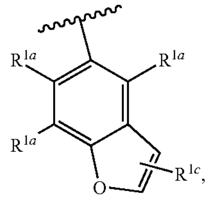
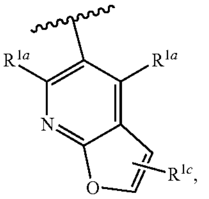
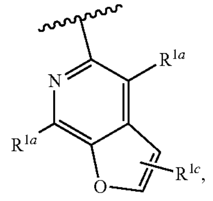
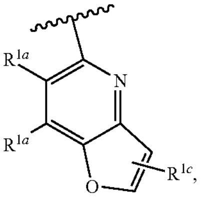
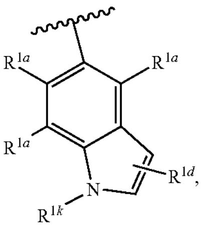
-continued
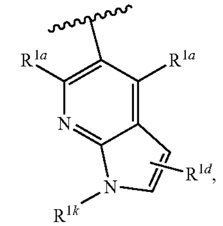
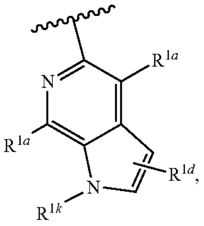
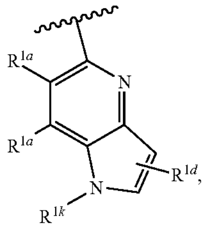
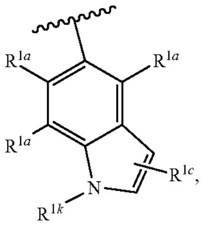
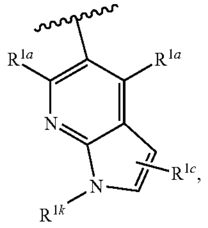
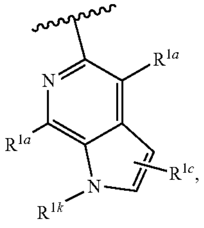
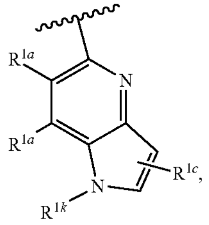
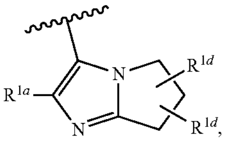
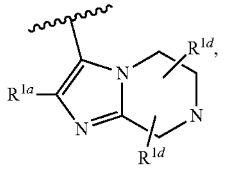
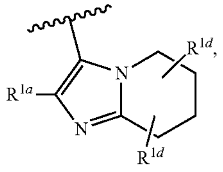
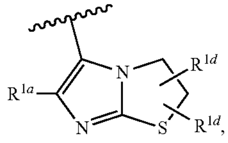
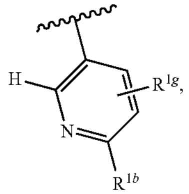
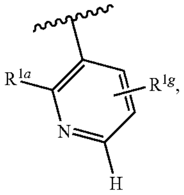
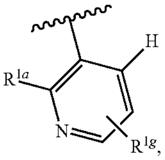
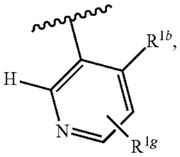

-continued
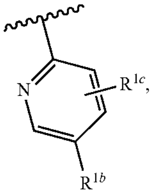
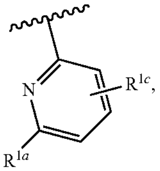
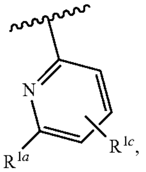
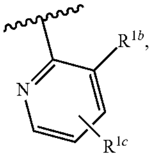
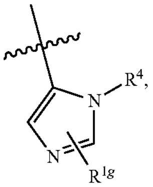
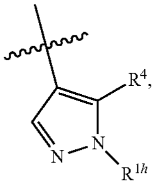
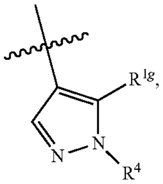
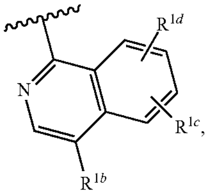
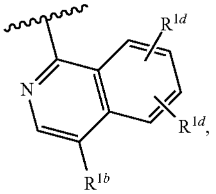
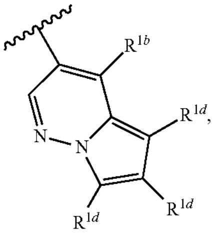
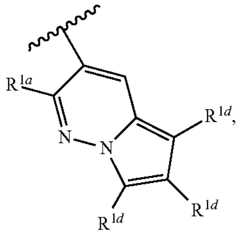
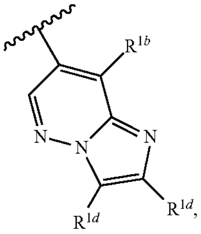
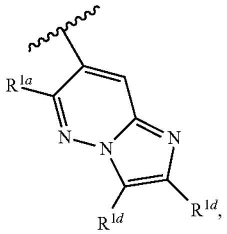
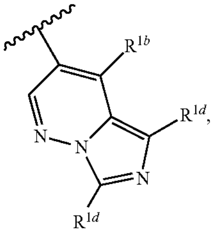
-continued
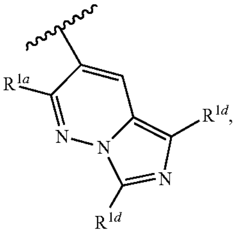
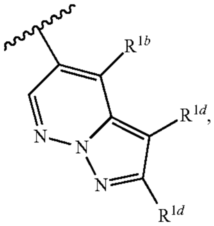
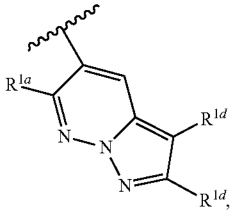
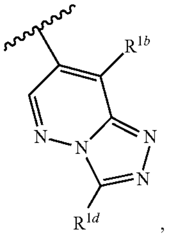
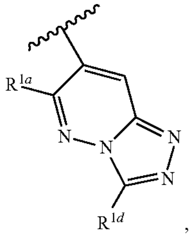
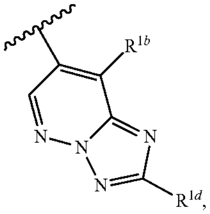
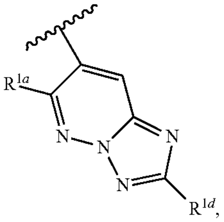
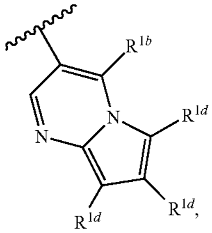
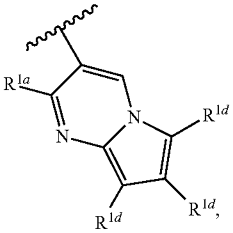
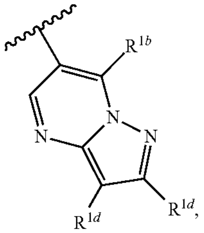
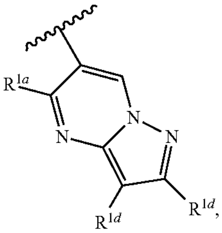
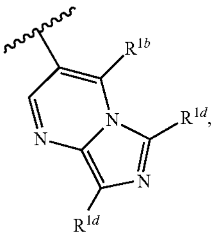

-continued
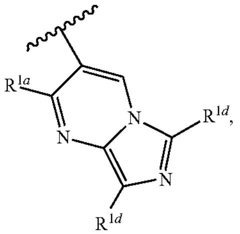
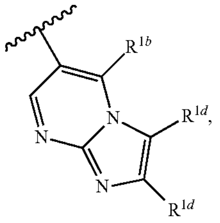
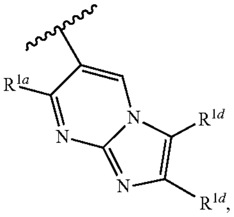
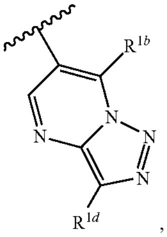
,
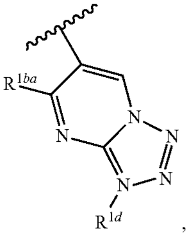
,
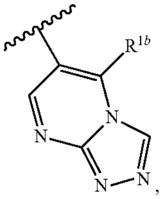
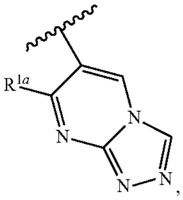
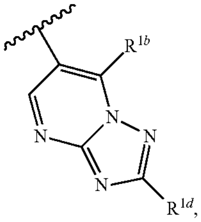
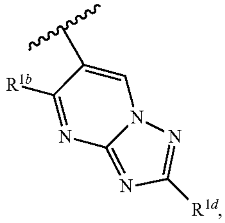
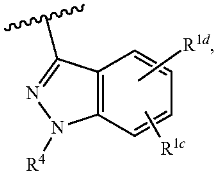
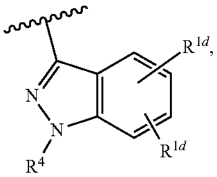
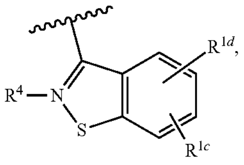
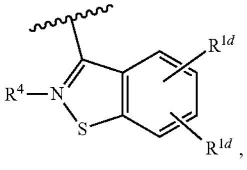
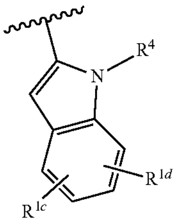
,
-continued
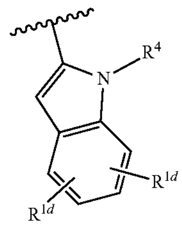
,
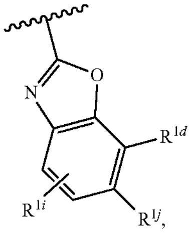
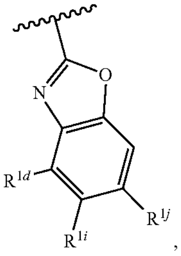
,
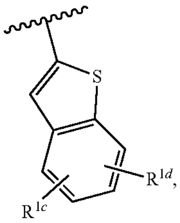
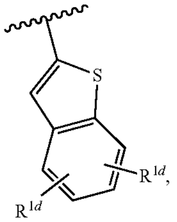
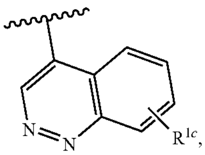
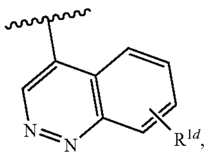
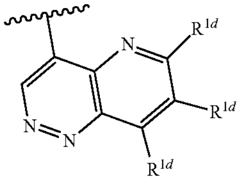
,
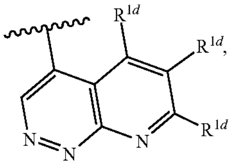
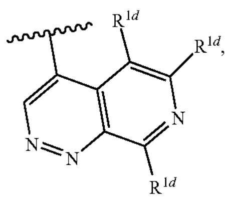
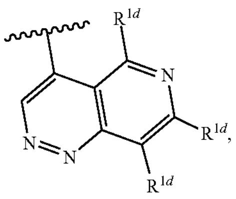
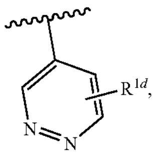
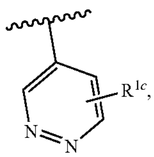
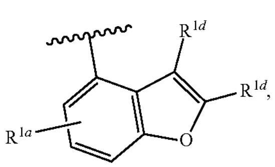
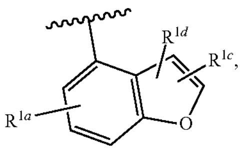
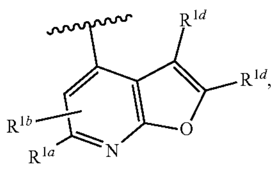

-continued
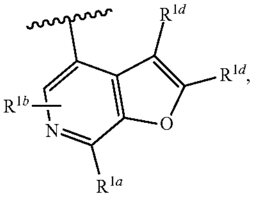
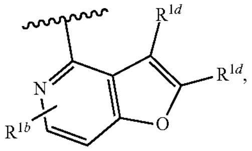
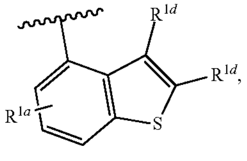
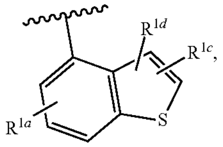
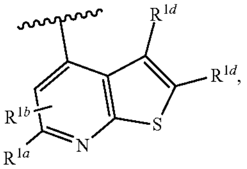
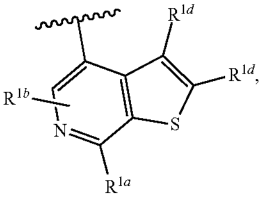
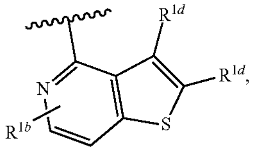
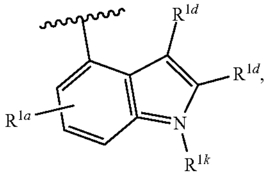
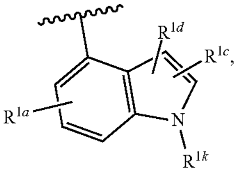
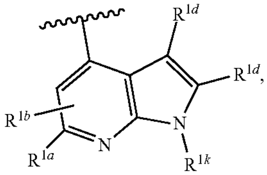
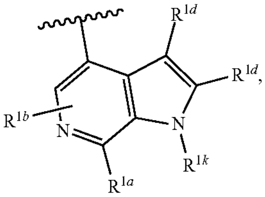
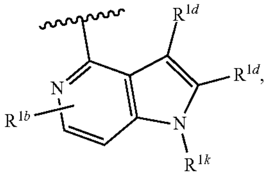
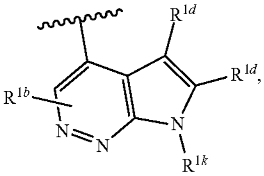
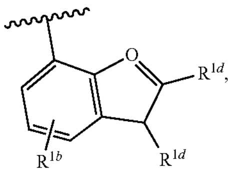
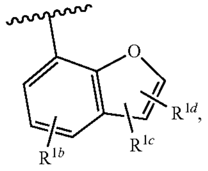
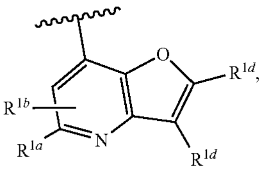
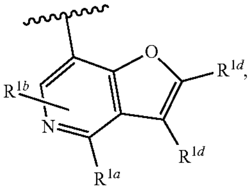
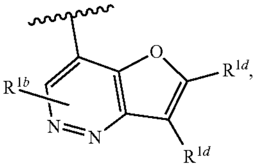
-continued
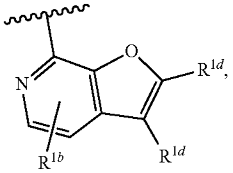
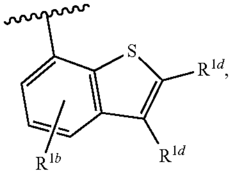
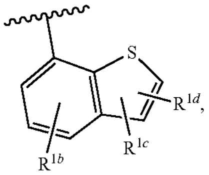
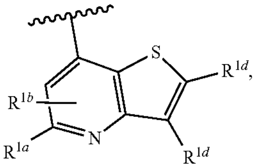
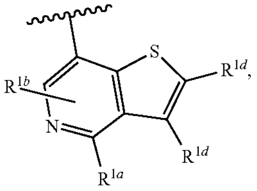
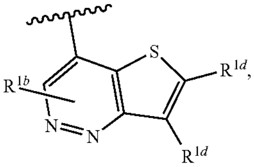
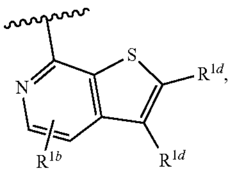
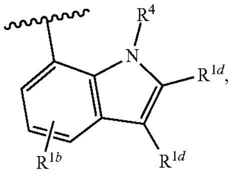
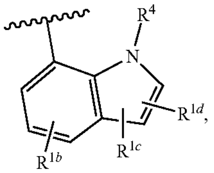
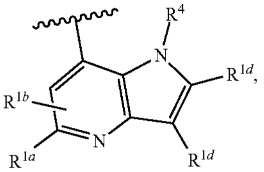
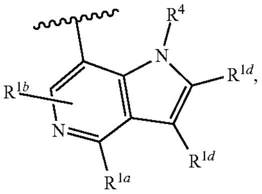
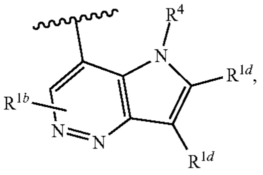
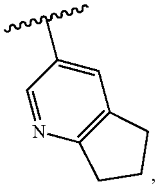
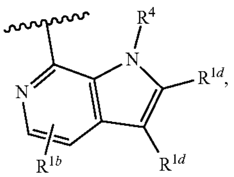
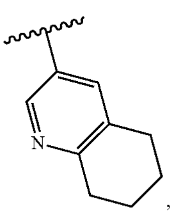
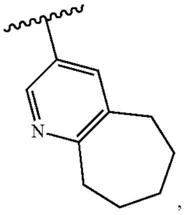

-continued
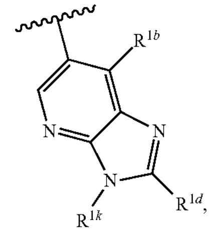
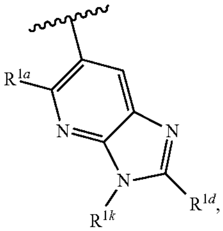
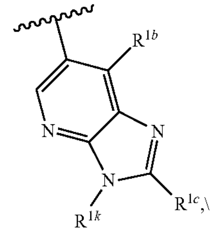
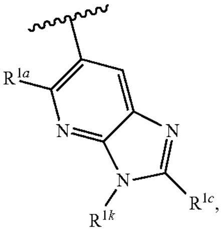
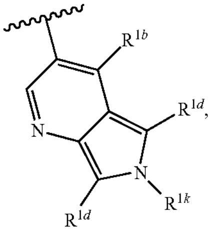
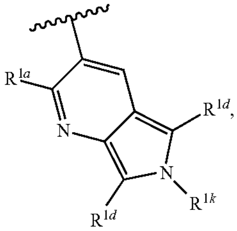
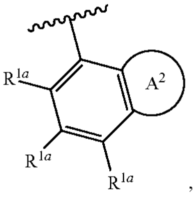
,
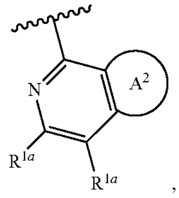
,
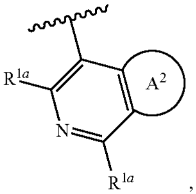
,
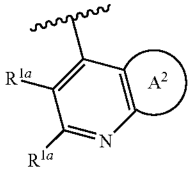
,
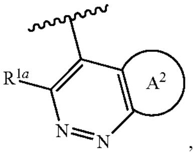
, or
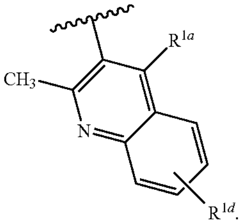
In another embodiment, $R^{d3}$ is
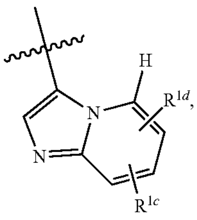
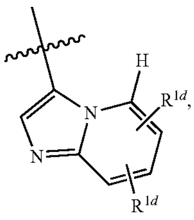
-continued
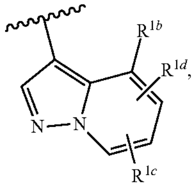
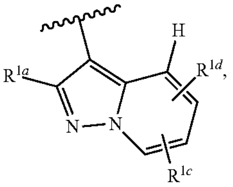
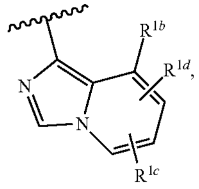
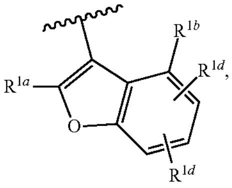
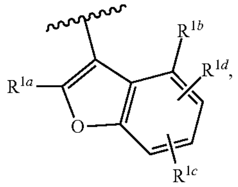
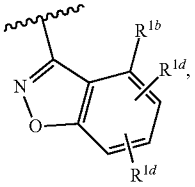
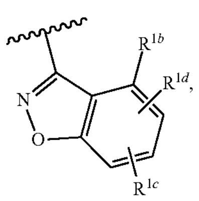
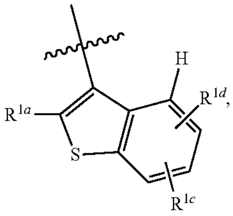
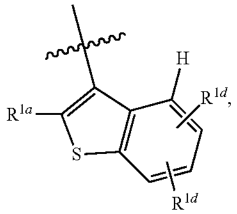
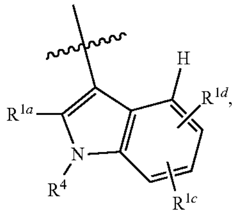
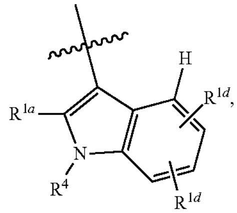
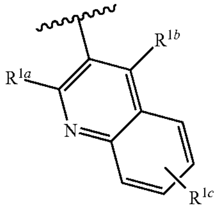
,
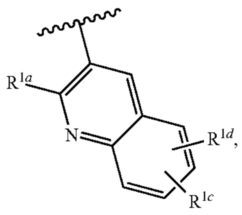
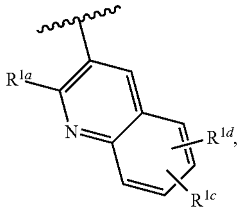
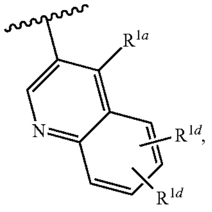
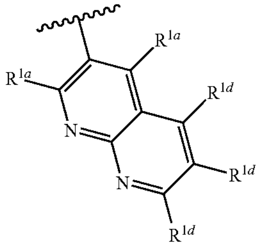
, -continued
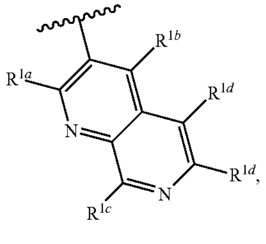
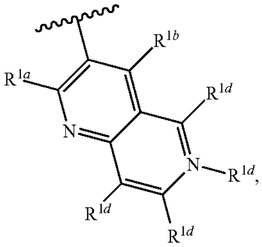
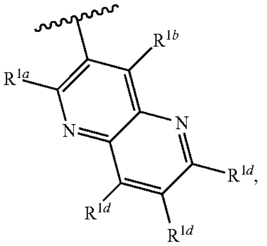
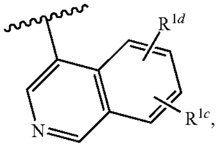
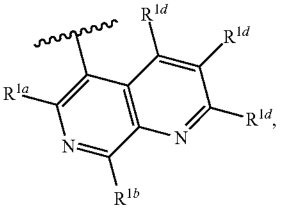
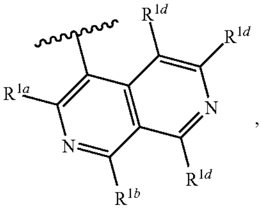
,
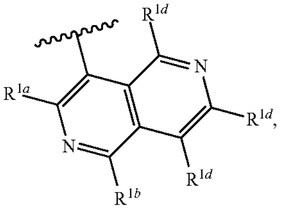
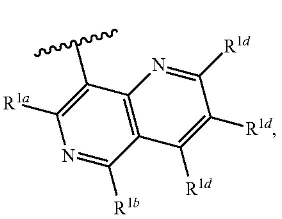
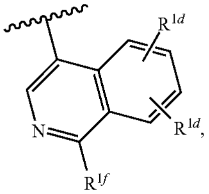
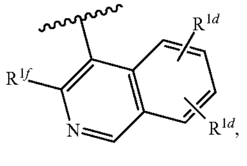
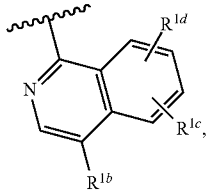
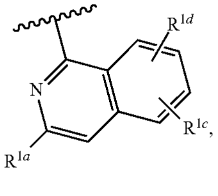
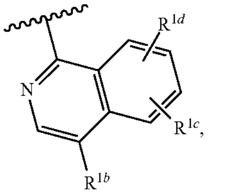
-continued
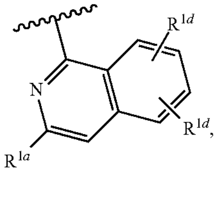
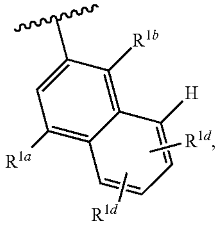
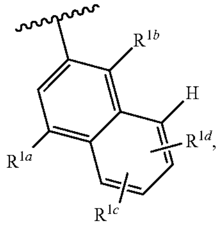
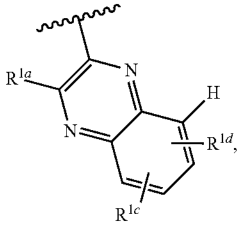
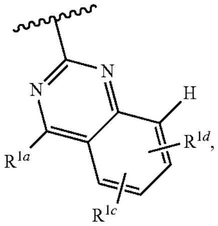
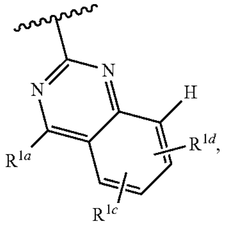
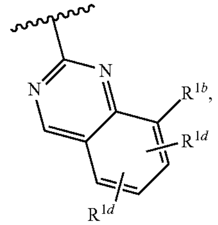
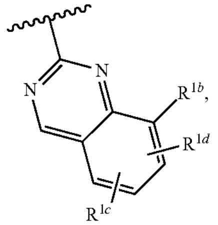
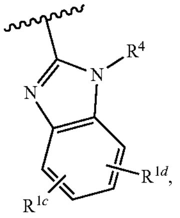
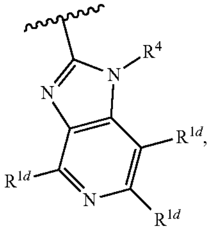
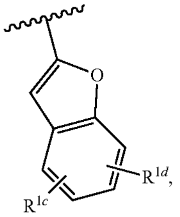
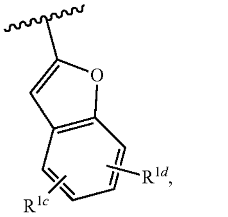
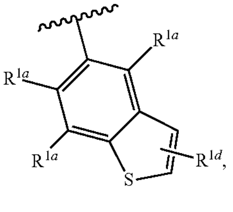
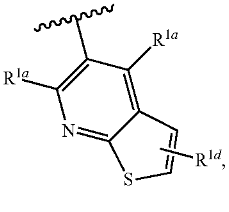

-continued
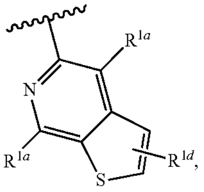
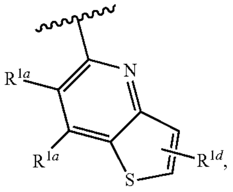
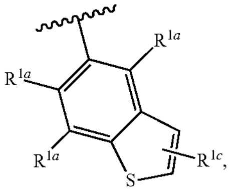
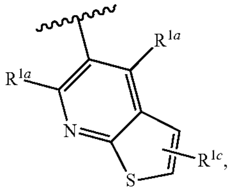
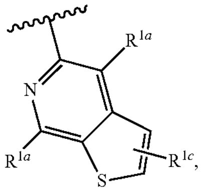
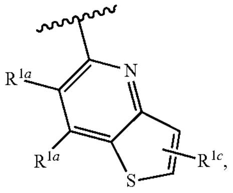
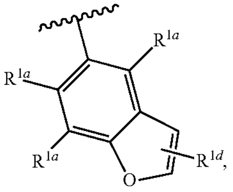
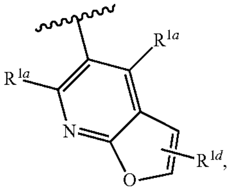
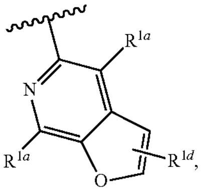
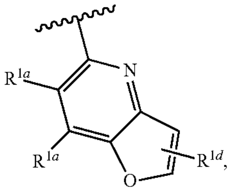
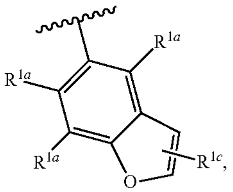
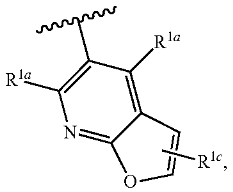
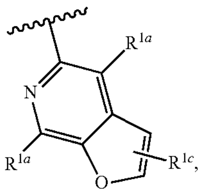
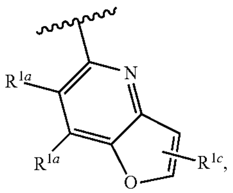
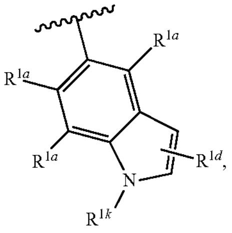
-continued
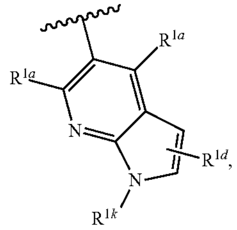
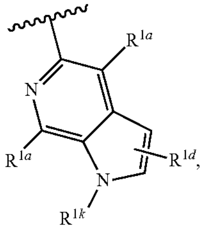
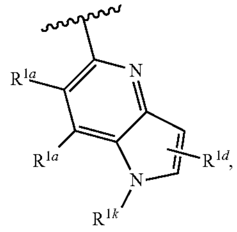
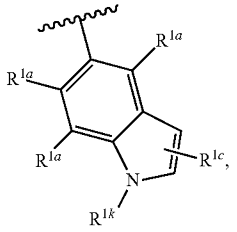
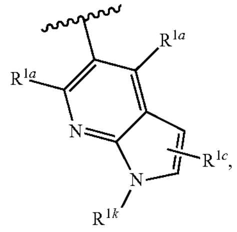
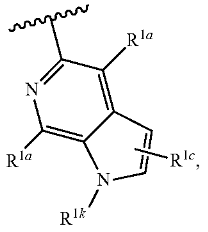
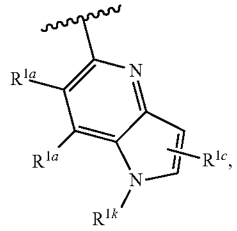
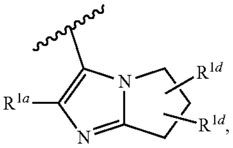
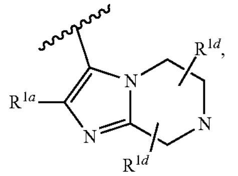
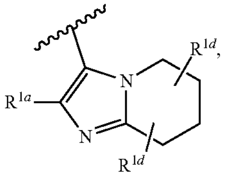
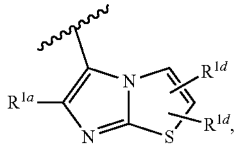
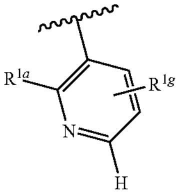
,
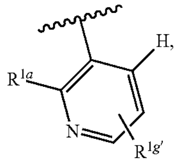
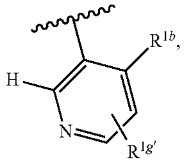
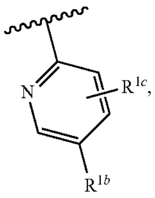
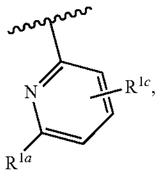
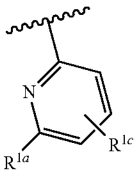
, -continued
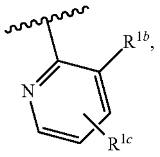
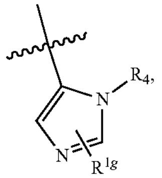
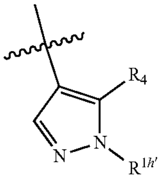
,
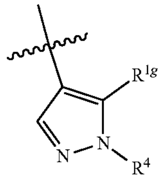
,
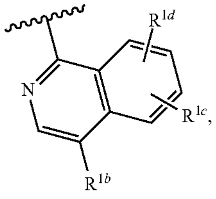
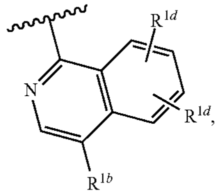
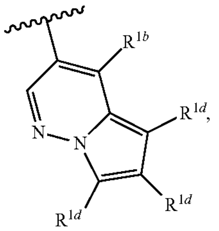
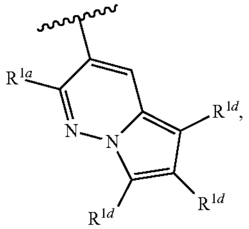
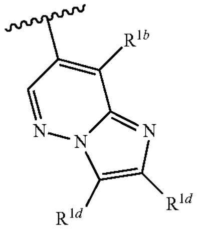
,
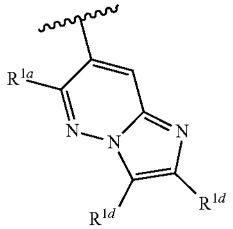
,
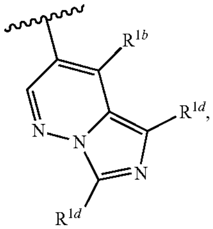
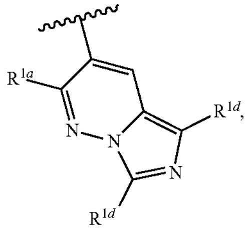
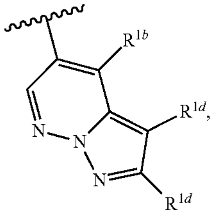
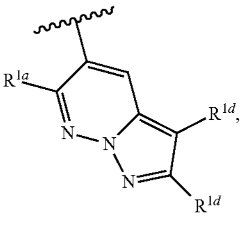
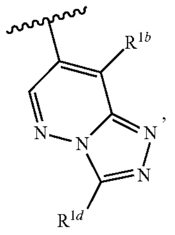
-continued
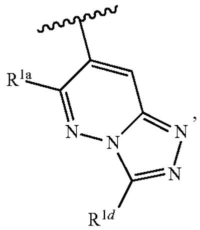
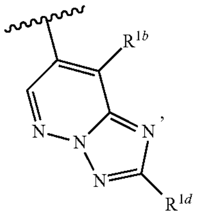
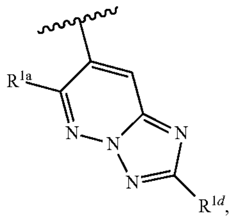
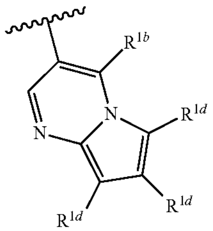
,
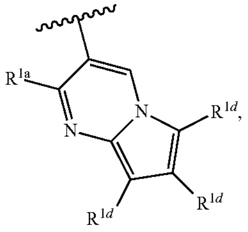
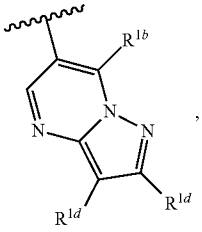
,
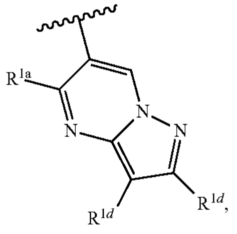
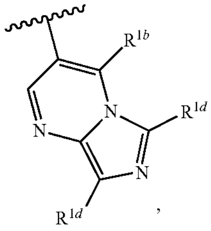
,
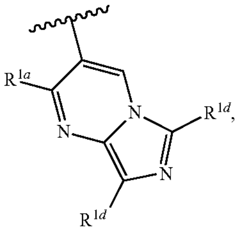
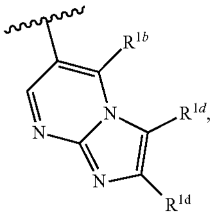
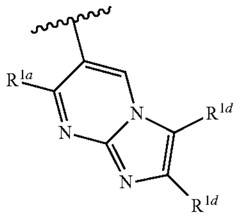
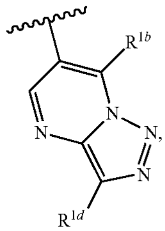
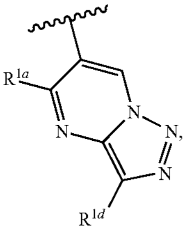

-continued
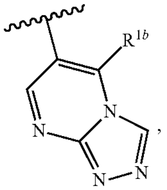
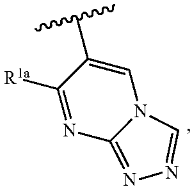
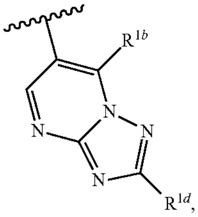
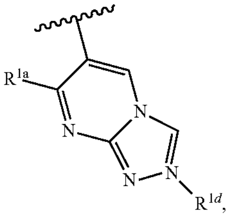
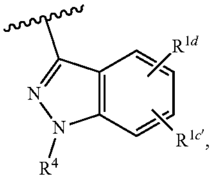
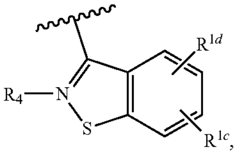
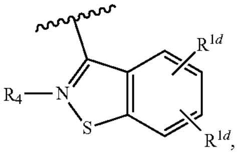
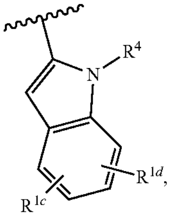
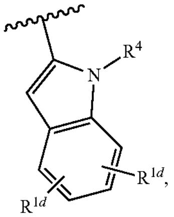
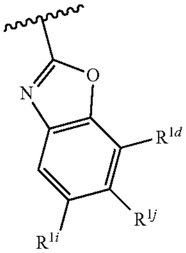
,
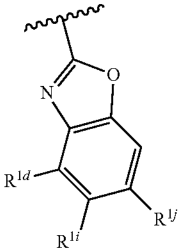
,
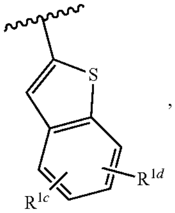
,
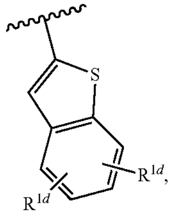
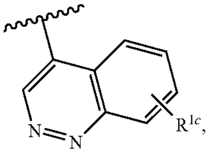
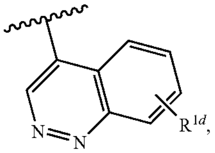
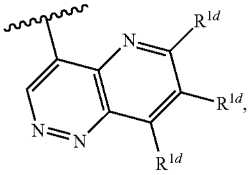
-continued
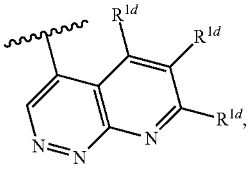
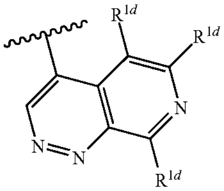
,
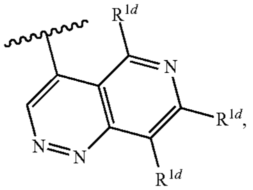
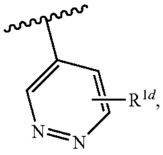
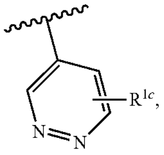
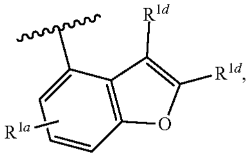
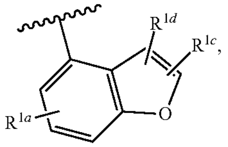
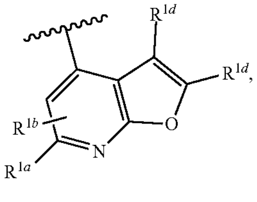
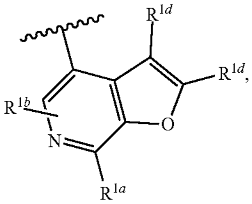
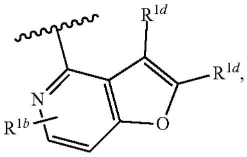
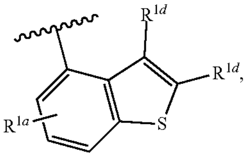
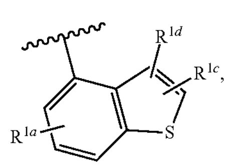
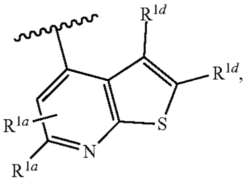
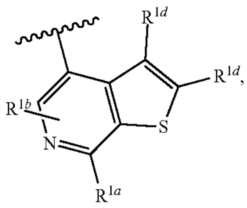
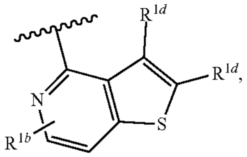
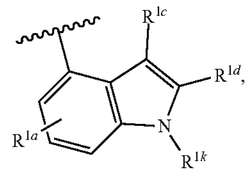
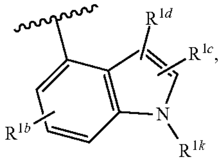

-continued
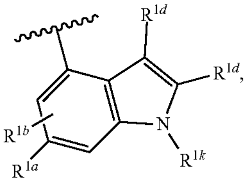
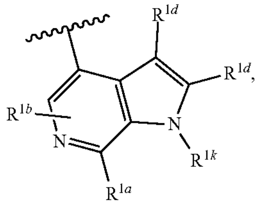
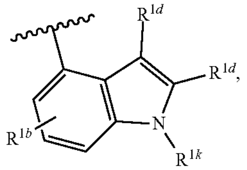
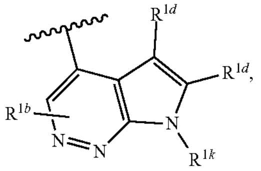
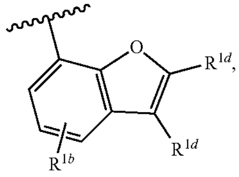
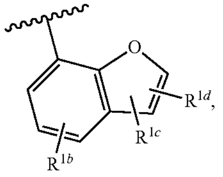
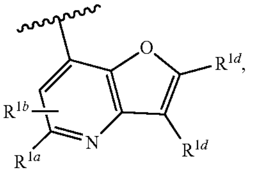
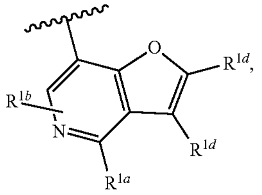
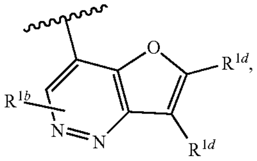
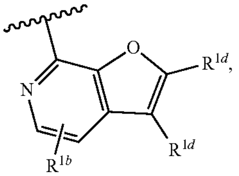
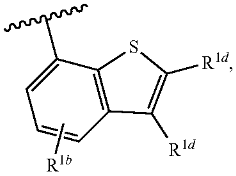
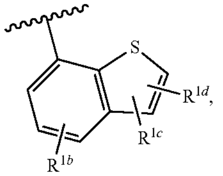
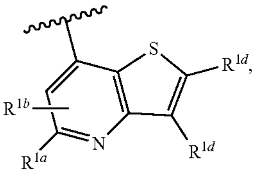
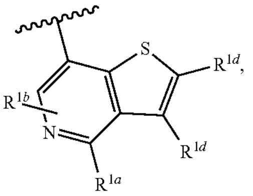
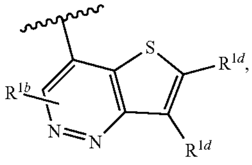
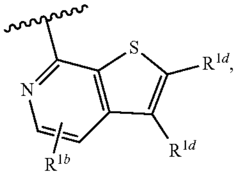
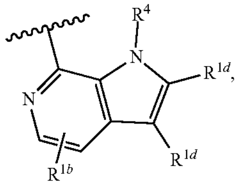
-continued
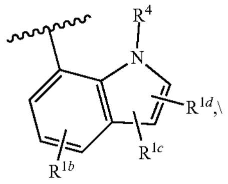
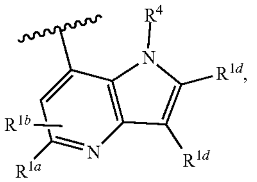
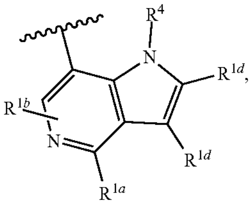
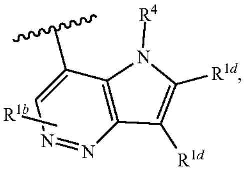
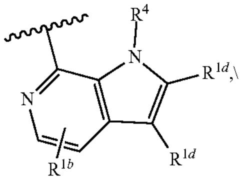
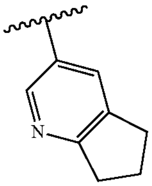
,
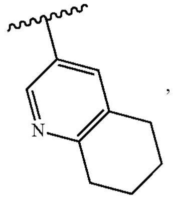
,
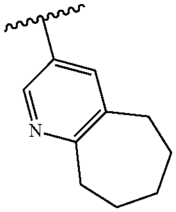
,
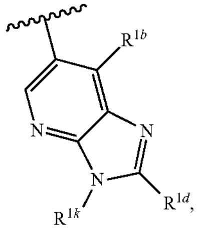
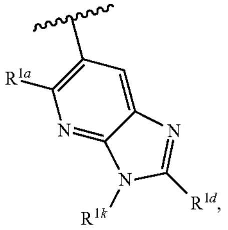
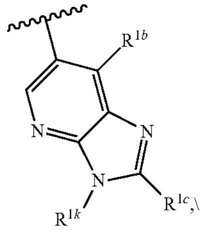
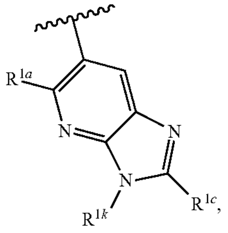
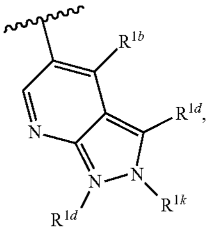
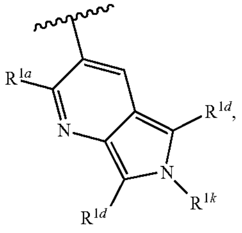
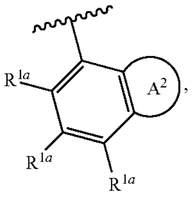
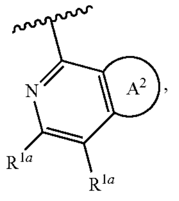

-continued
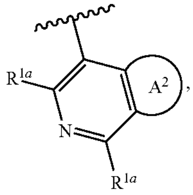
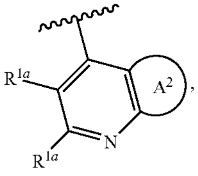
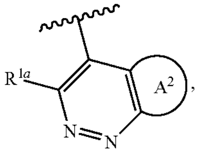
or
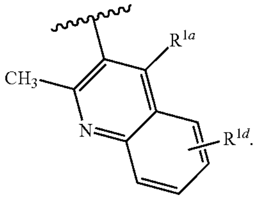
In another embodiment, $R^{d3}$ is
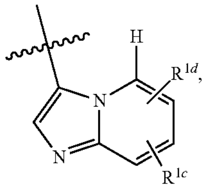
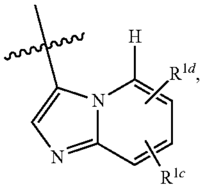
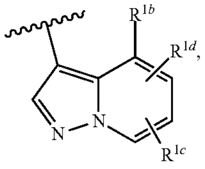
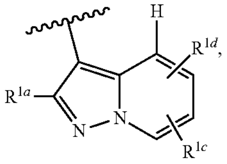
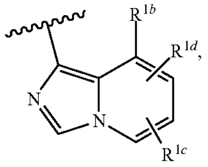
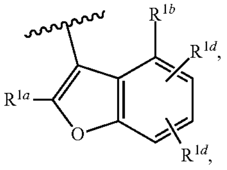
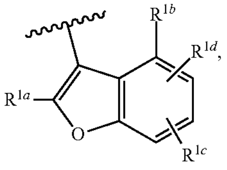
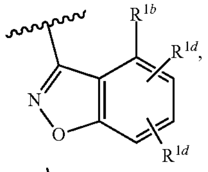
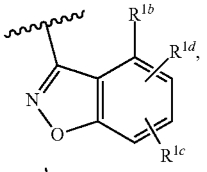
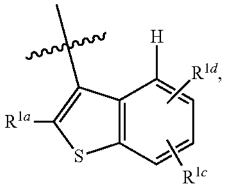
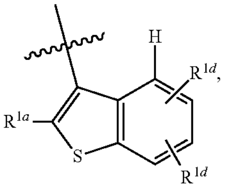
-continued
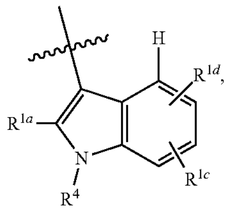
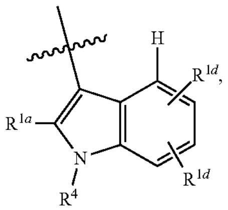
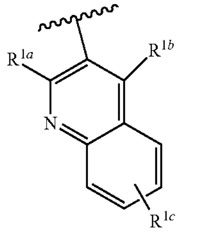
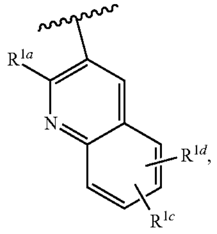
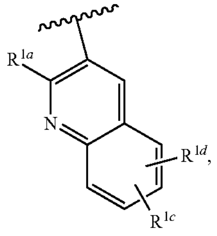
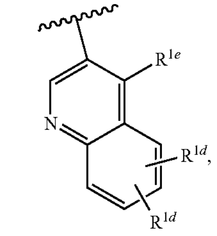
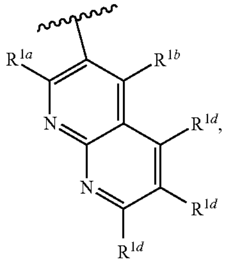
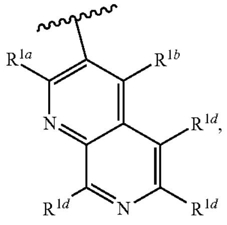
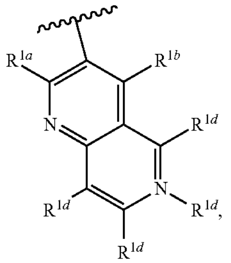
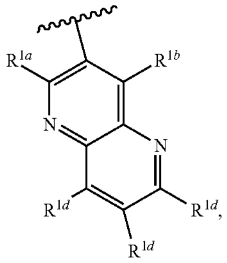
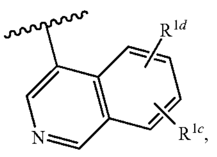
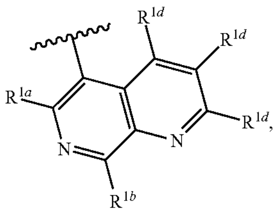
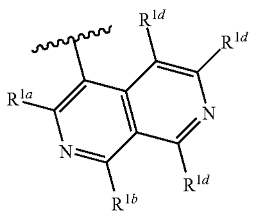
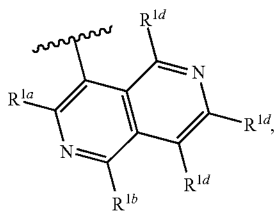

-continued
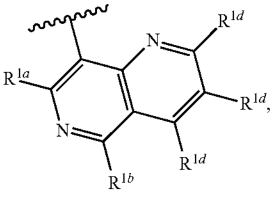
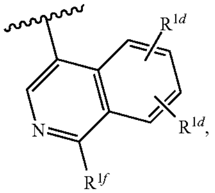
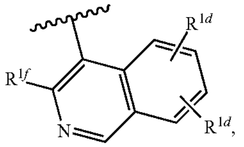
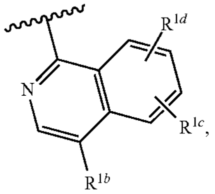
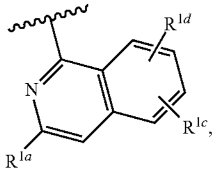
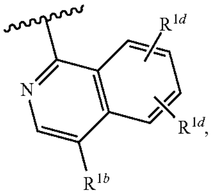
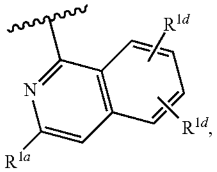
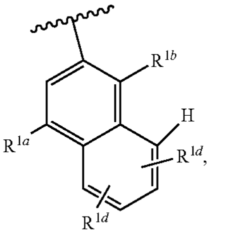
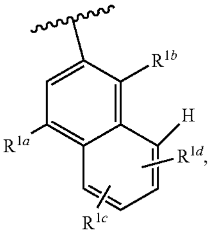
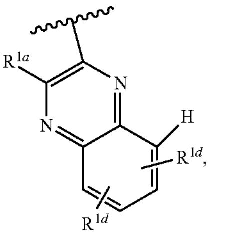
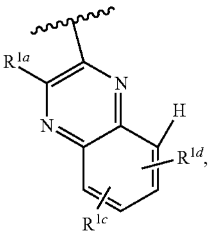
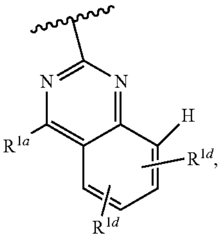
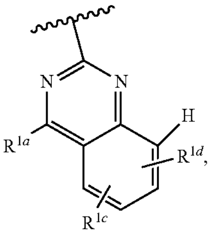
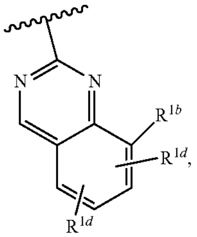
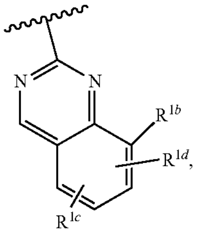
-continued
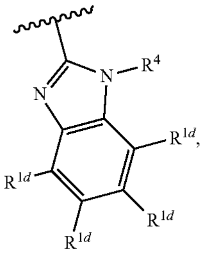
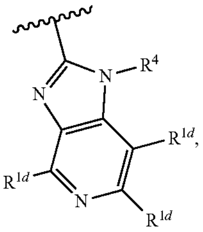
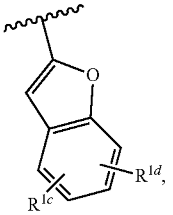
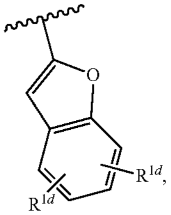
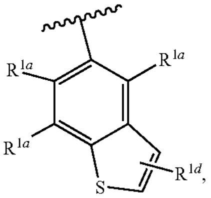
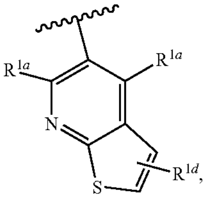
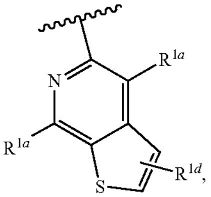
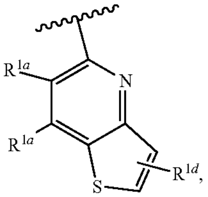
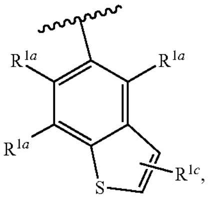
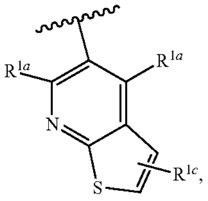
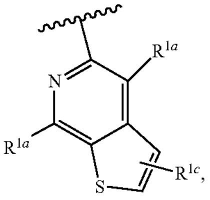
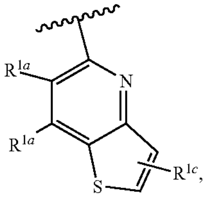
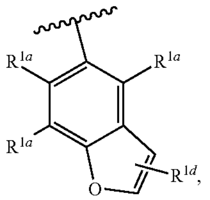
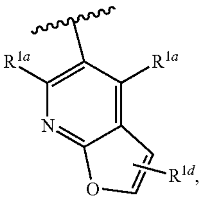
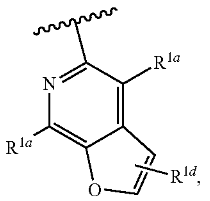
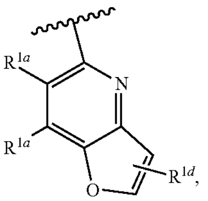

-continued
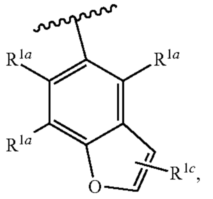
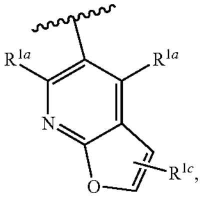
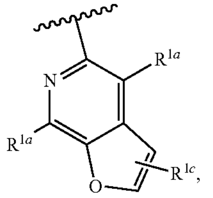
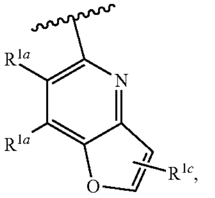
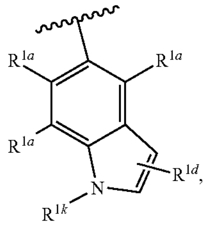
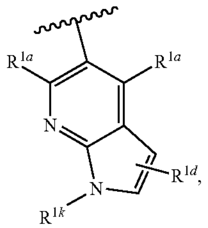
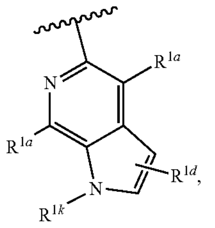
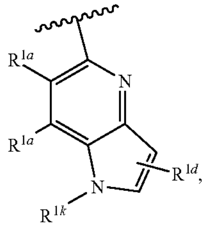
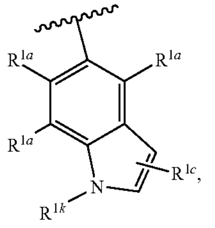
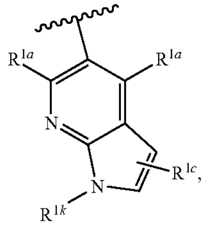
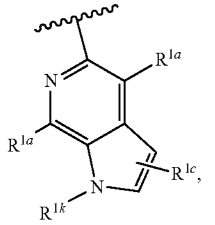
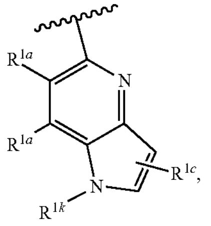
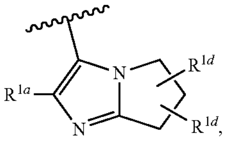
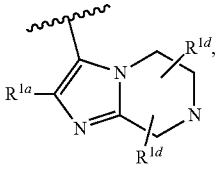
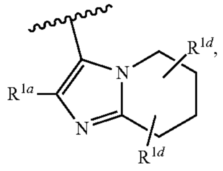
-continued
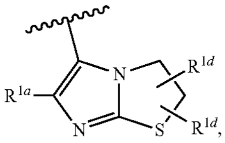
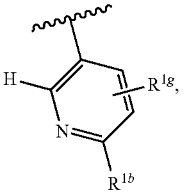
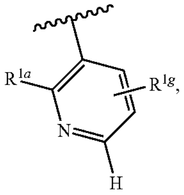
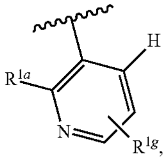
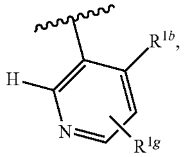
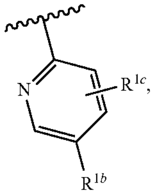
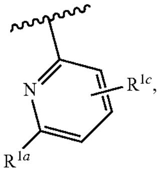
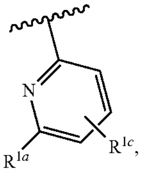
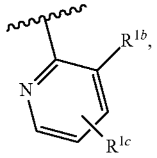
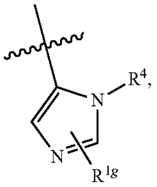
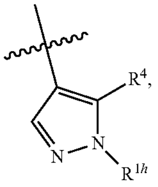
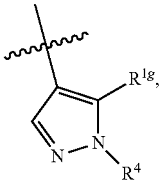
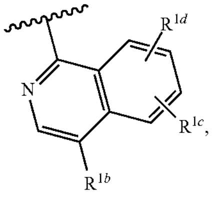
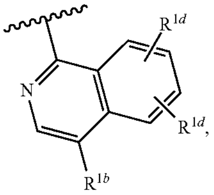
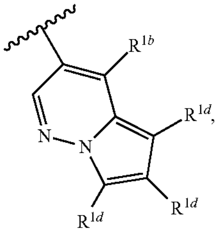

-continued
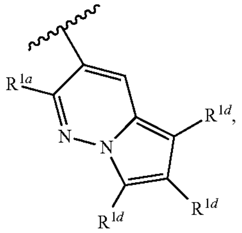
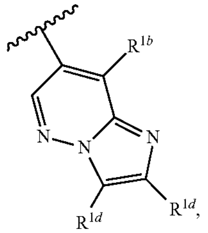
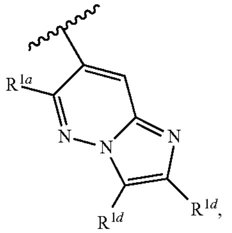
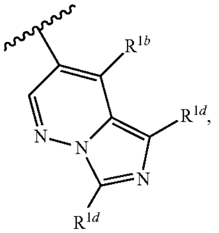
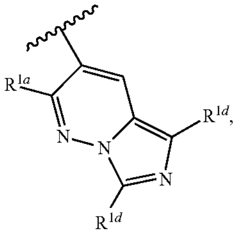
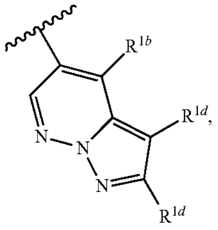
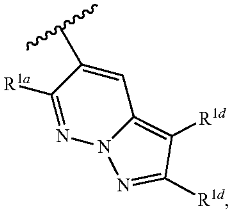
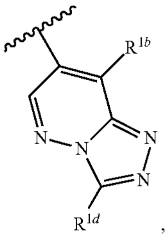
,
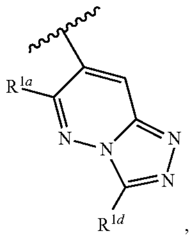
,
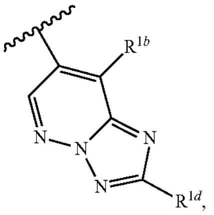
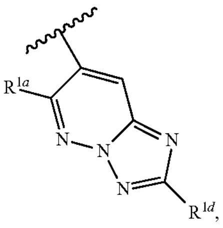
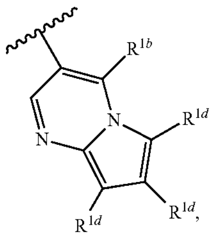
-continued
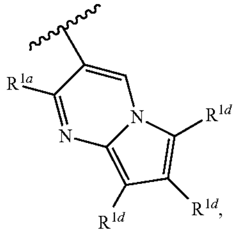
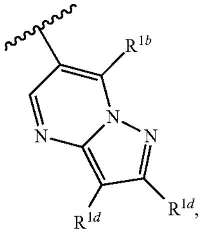
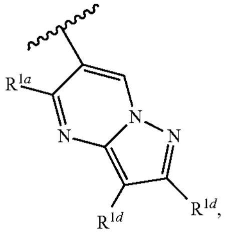
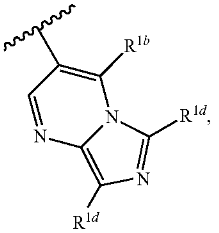
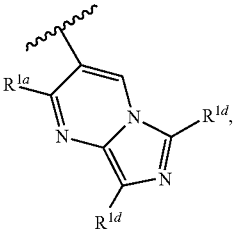
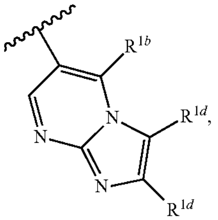
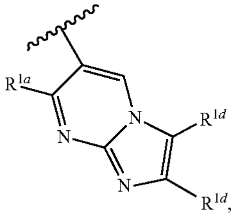
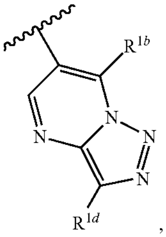
,
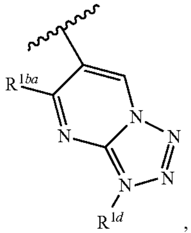
,
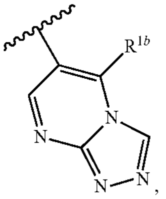
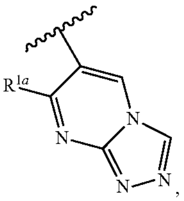
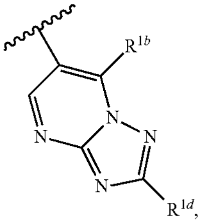

-continued
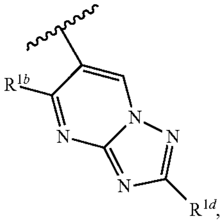
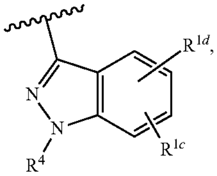
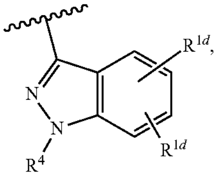
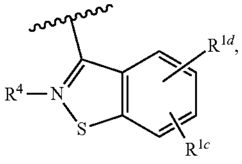
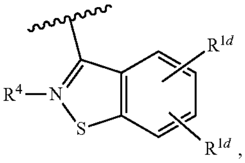
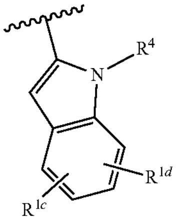
,
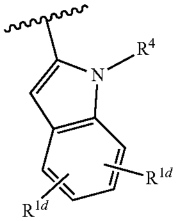
,
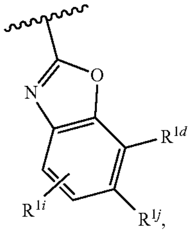
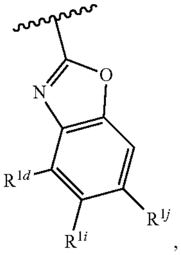
,
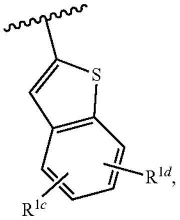
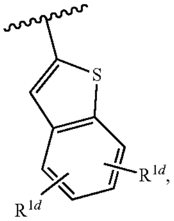
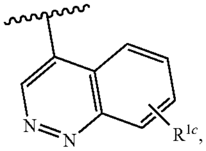
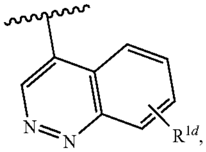
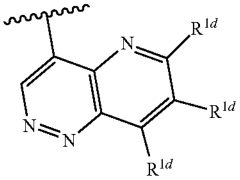
,
-continued
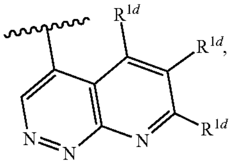
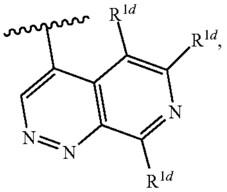
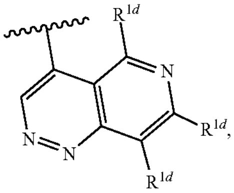
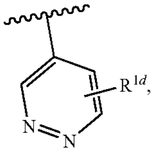
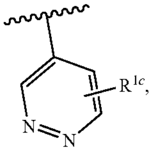
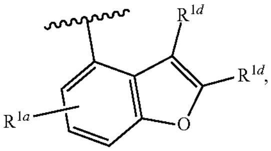
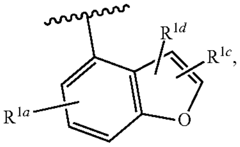
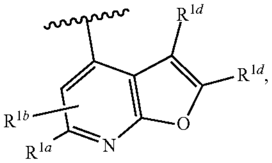
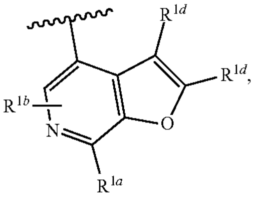
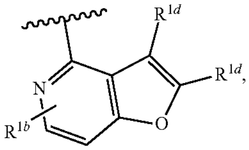
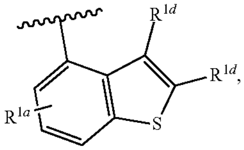
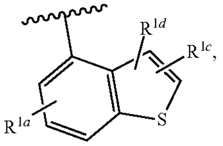
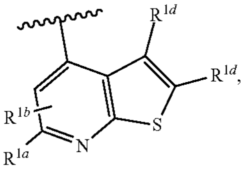
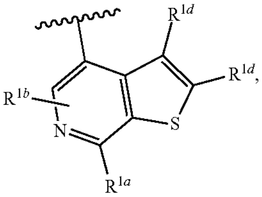
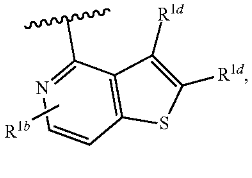
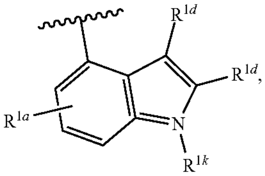
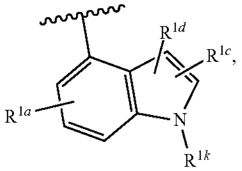
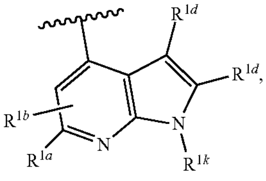

-continued
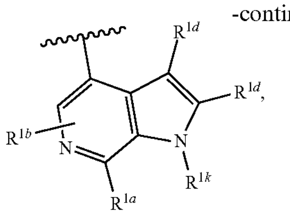
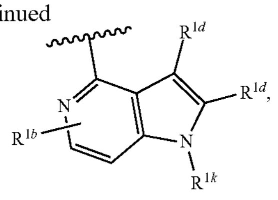
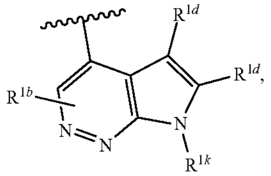
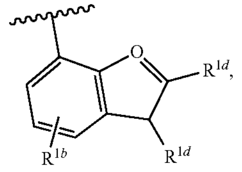
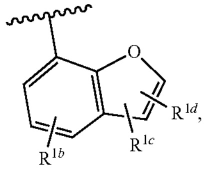
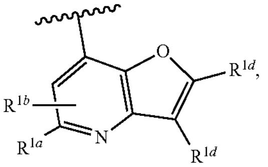
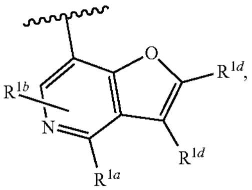
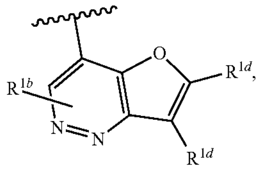
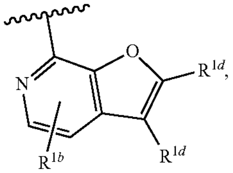
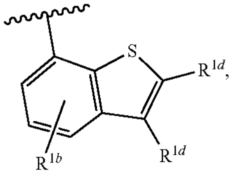
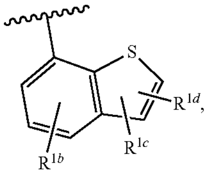
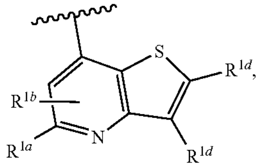
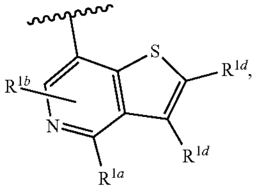
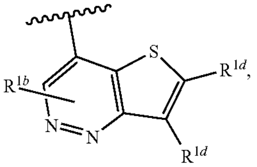
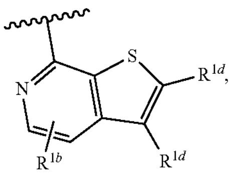
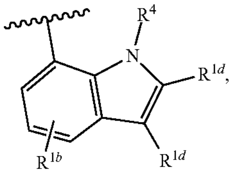
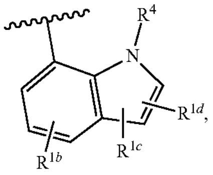
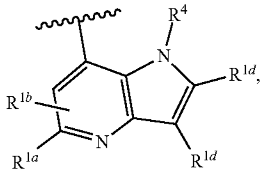
-continued
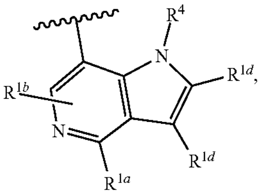
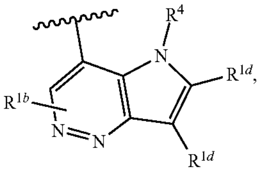
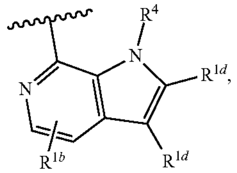
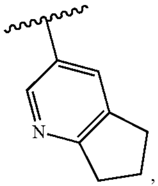
,
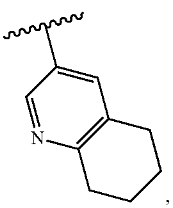
,
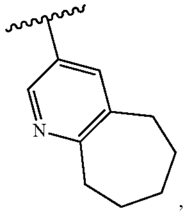
,
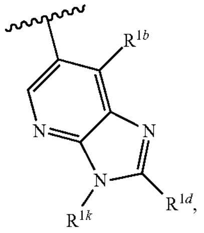
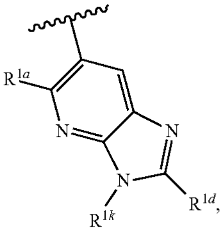
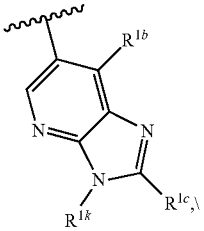
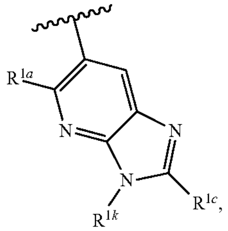
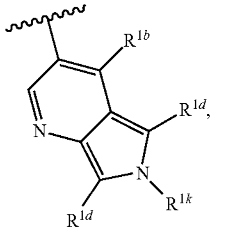
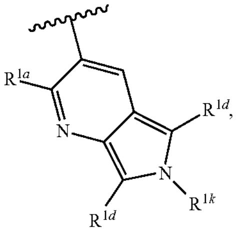
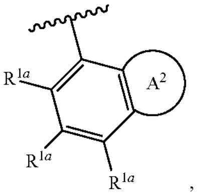
,
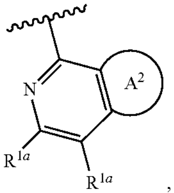
, -continued
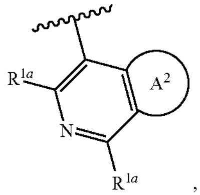
,
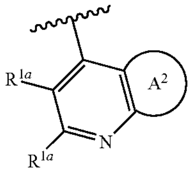
,
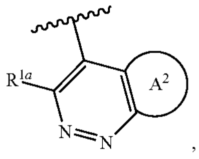
, or
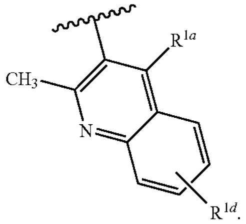
In another embodiment, $R^{d3}$ is
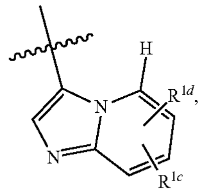
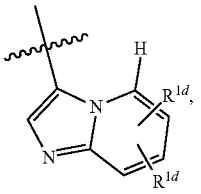
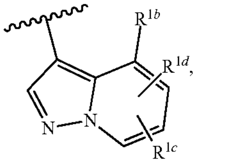
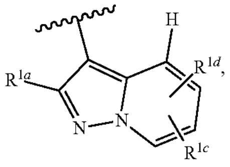
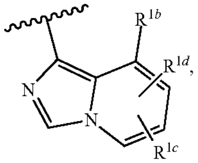
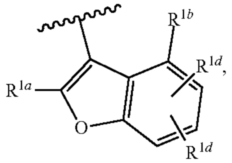
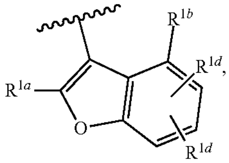
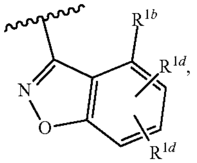
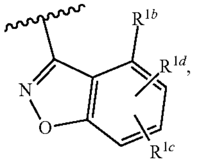
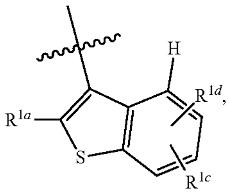
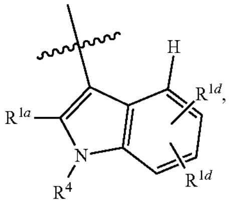
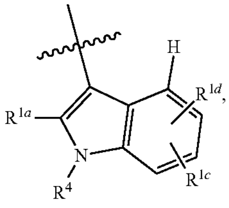
-continued
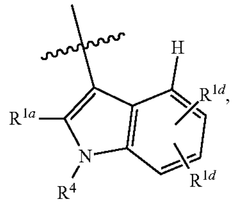
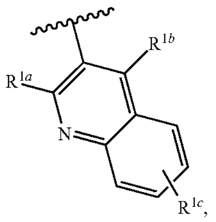
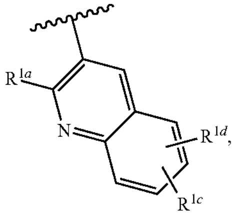
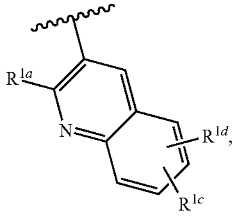
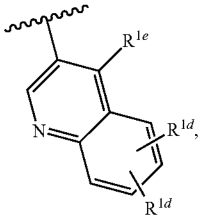
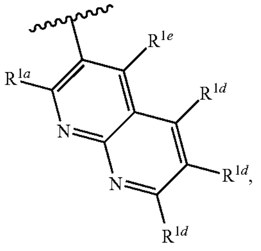
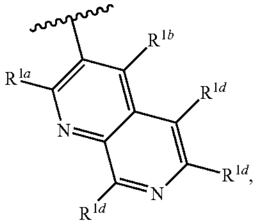
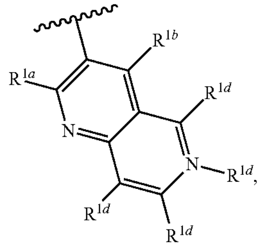
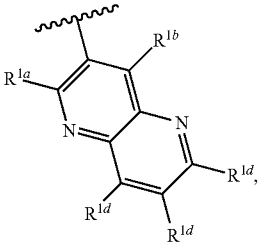
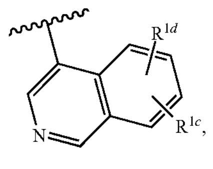
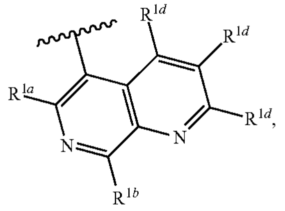
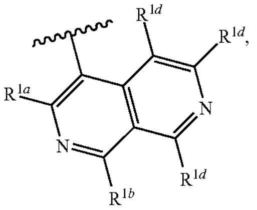

-continued
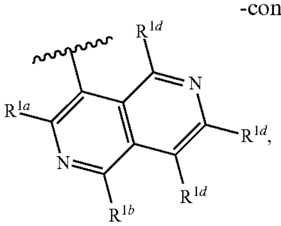
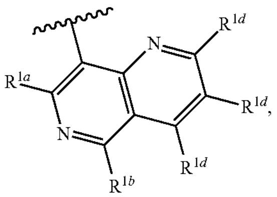
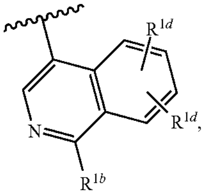
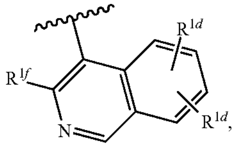
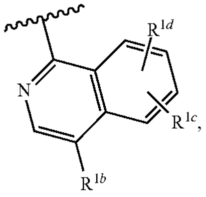
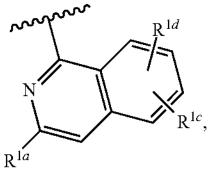
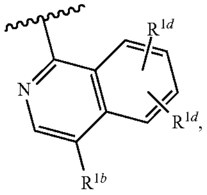
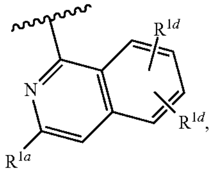
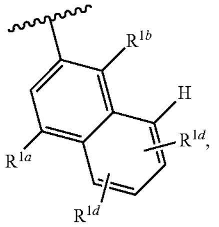
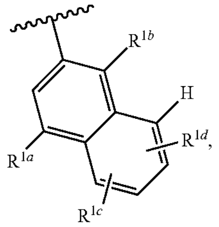
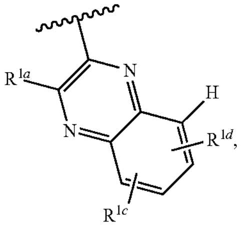
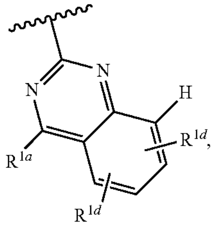
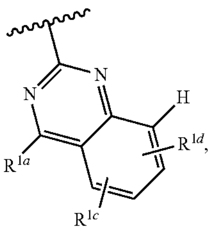
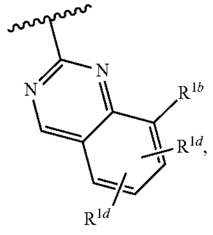
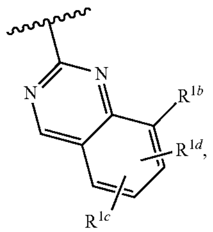
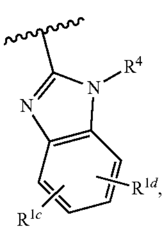
-continued
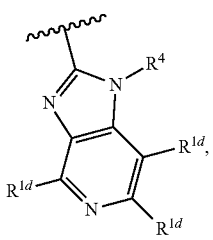
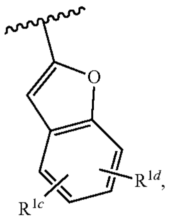
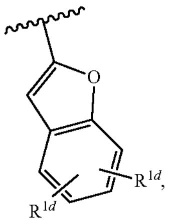
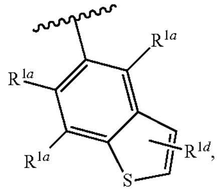
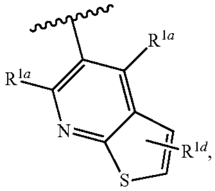
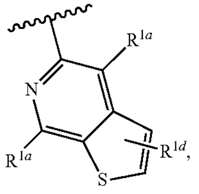
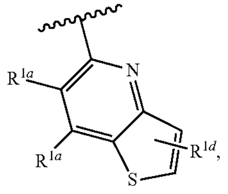
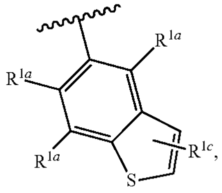
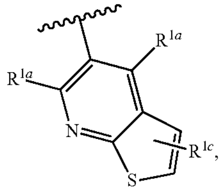
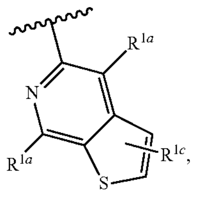
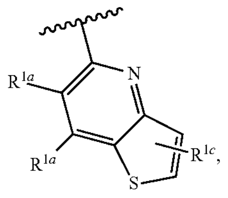
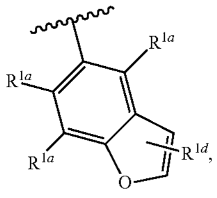
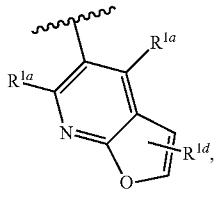
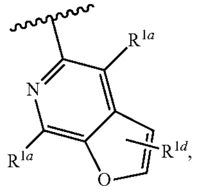
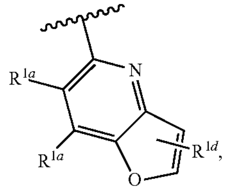
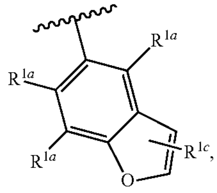
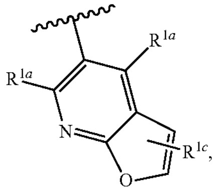

-continued
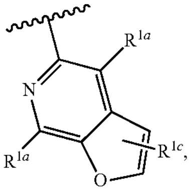
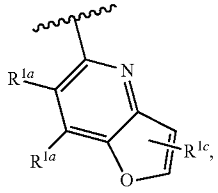
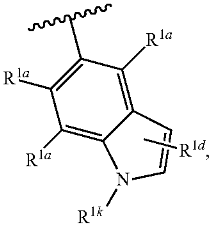
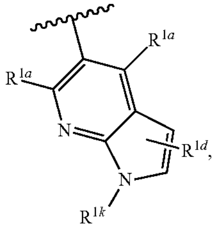
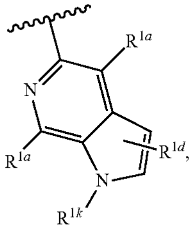
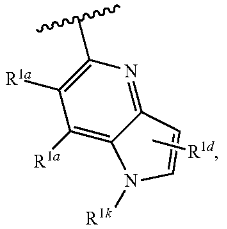
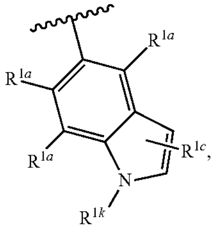
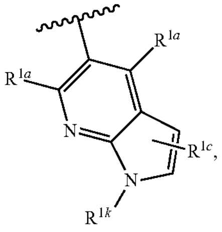
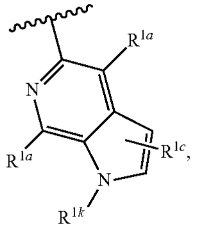
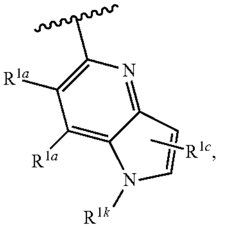
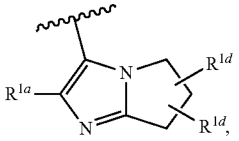
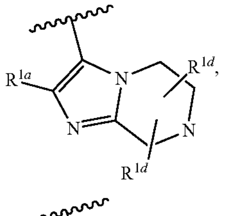
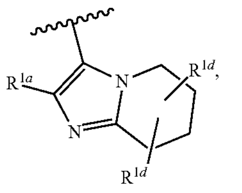
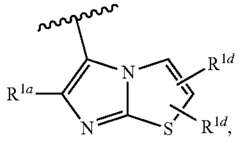
-continued
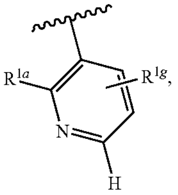
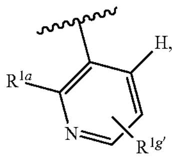
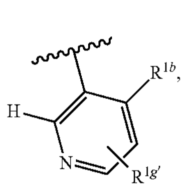
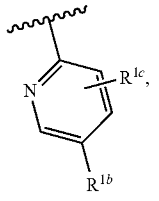
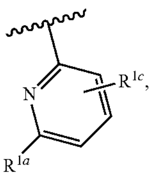
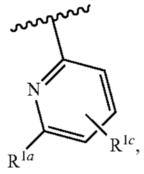
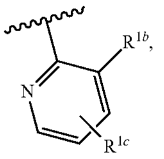
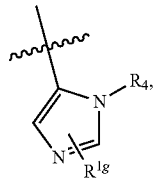
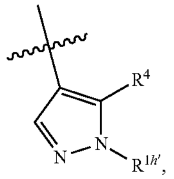
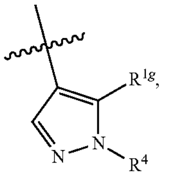
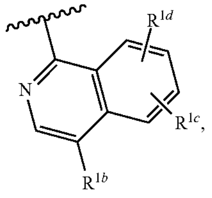
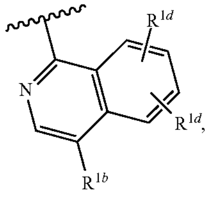
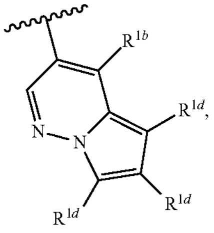
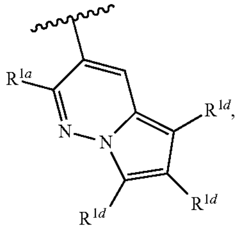
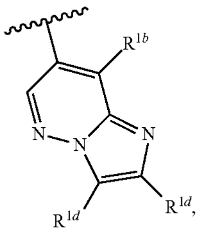
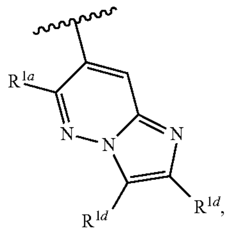

-continued
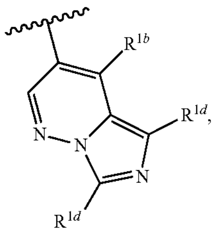
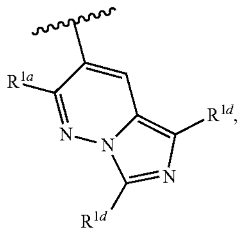
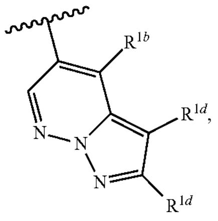
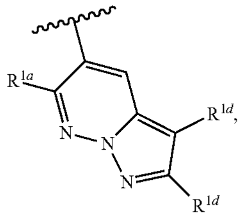
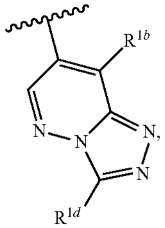
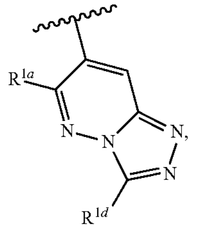
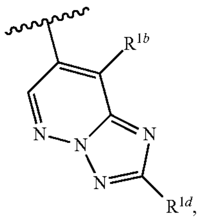
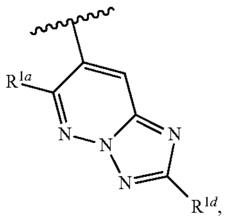
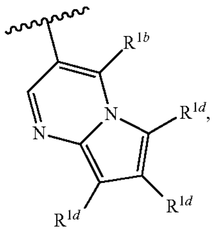
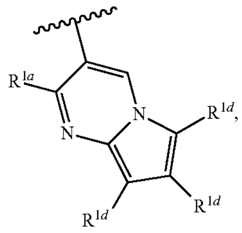
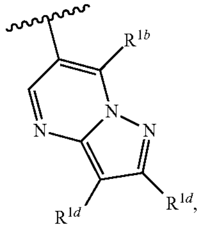
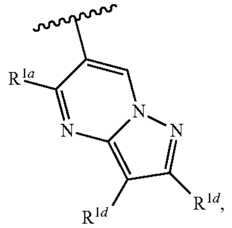
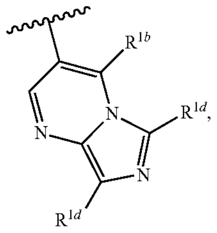
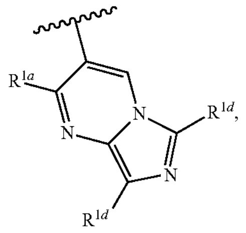
-continued
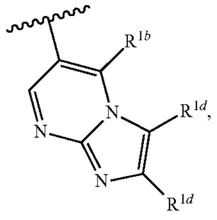
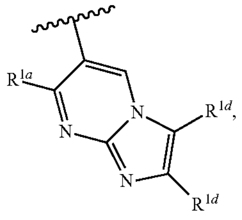
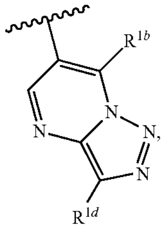
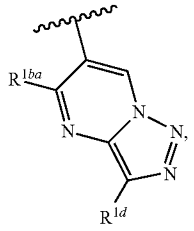
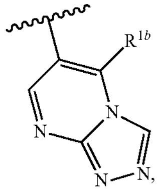
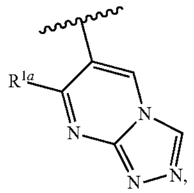
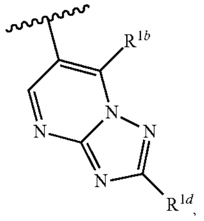
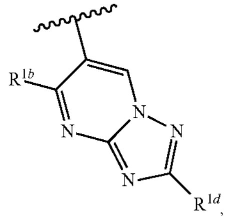
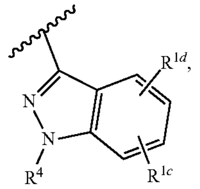
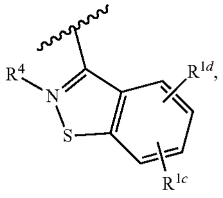
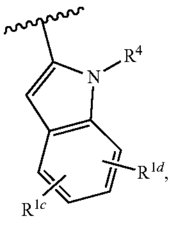
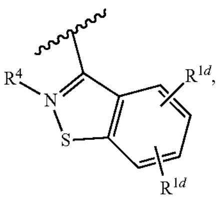
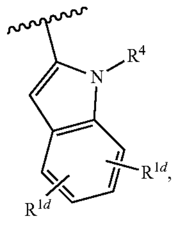
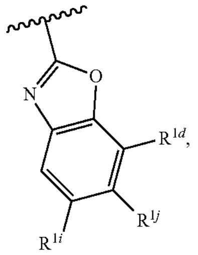

-continued
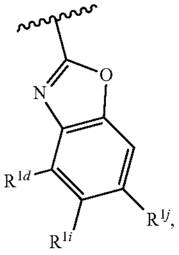
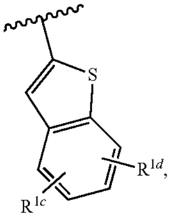
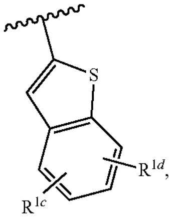
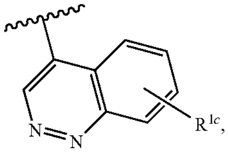
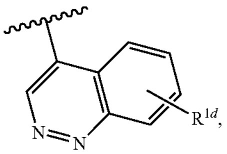
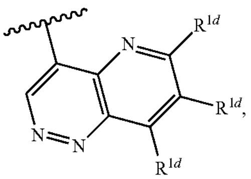
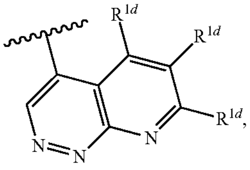
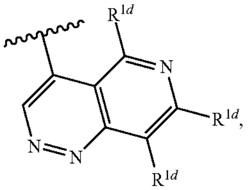
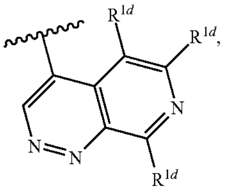
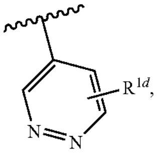
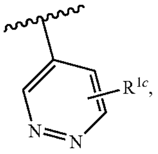
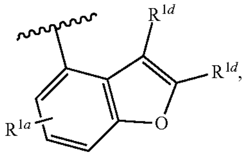
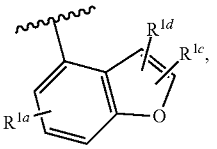
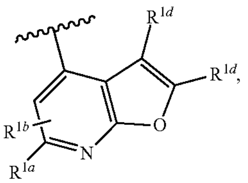
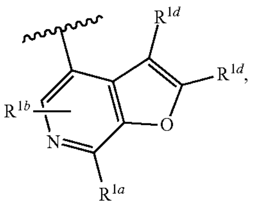
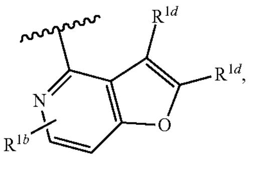
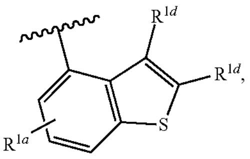
-continued
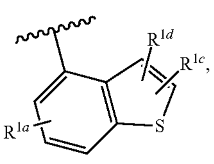
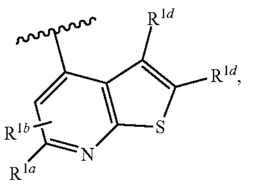
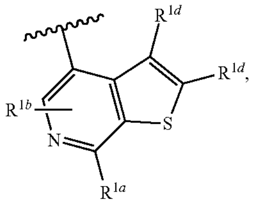
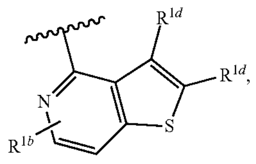
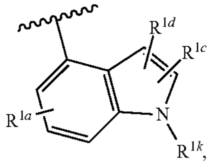
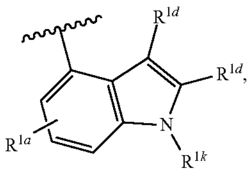
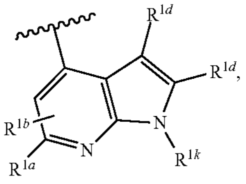
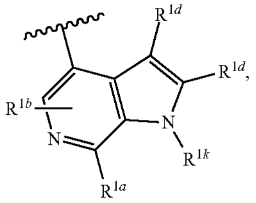
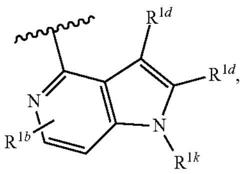
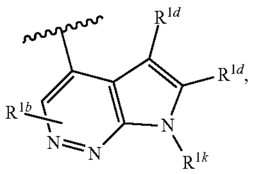
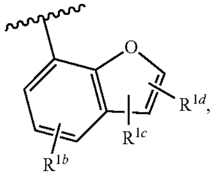
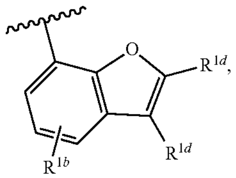
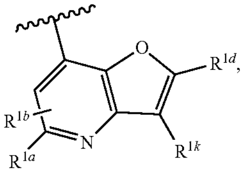
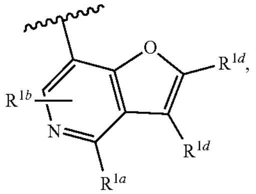
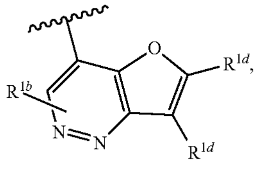
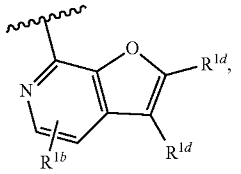

-continued
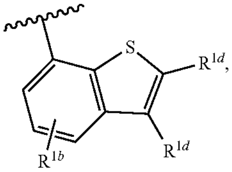
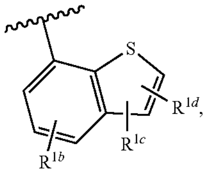
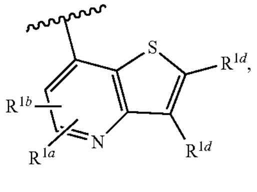
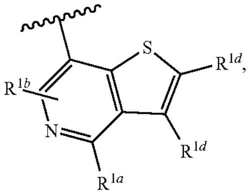
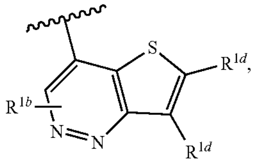
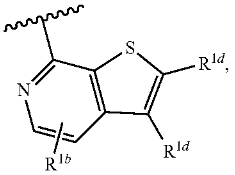
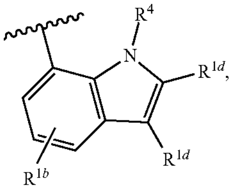
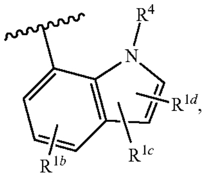
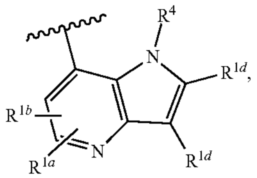
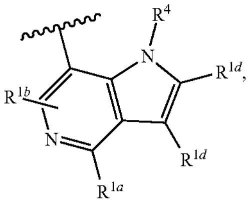
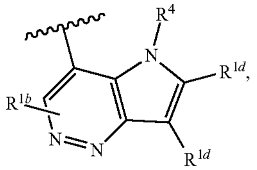
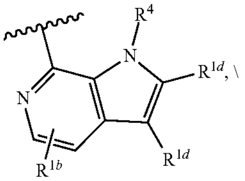
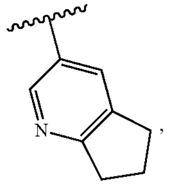
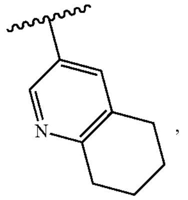
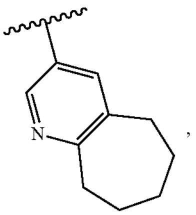
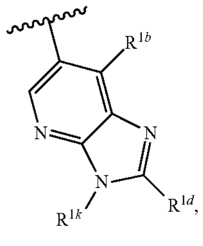
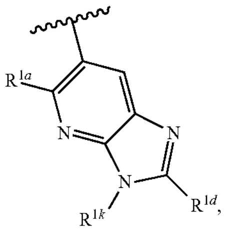
-continued
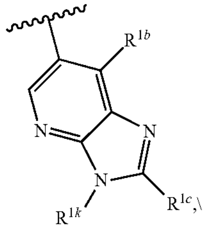
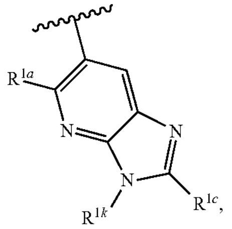
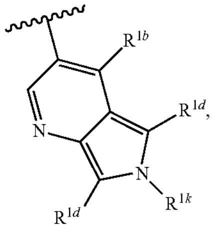
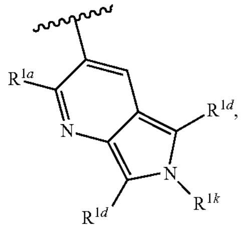
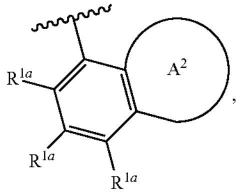
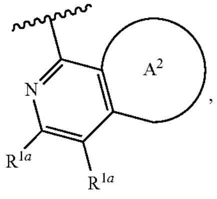
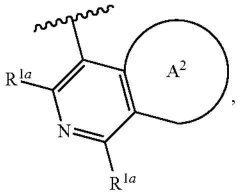
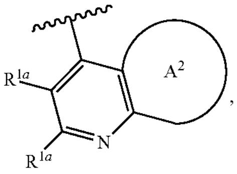
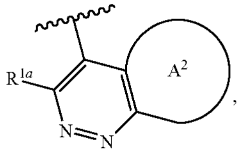
or
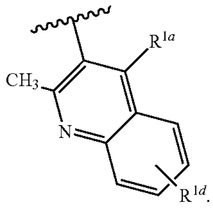
In another embodiment, $R^{d3}$ is
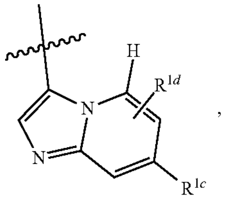
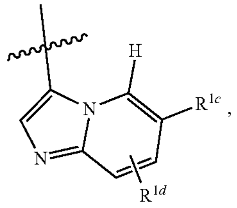
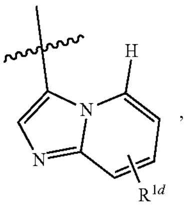
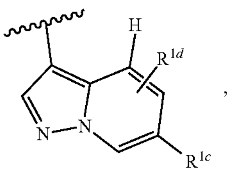

-continued
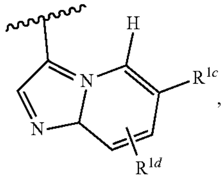,
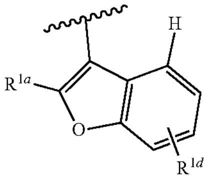,
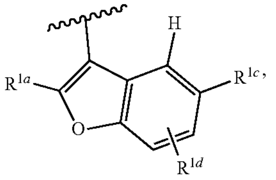
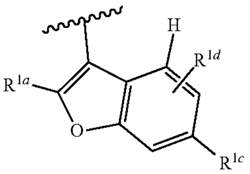,
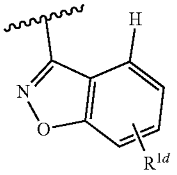,
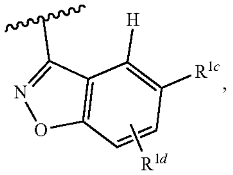
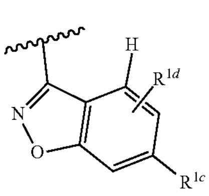,
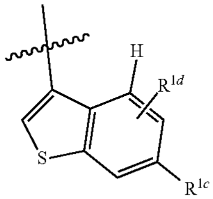,
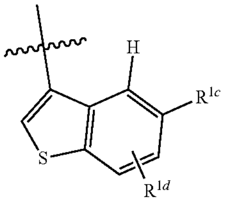,
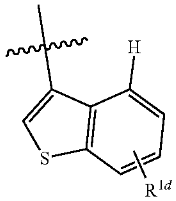,
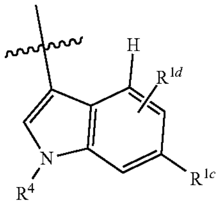
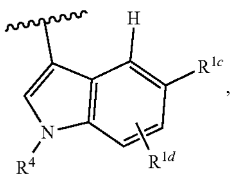,
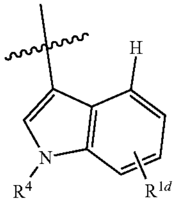,
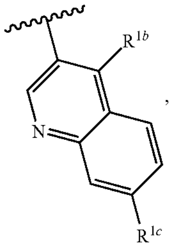,
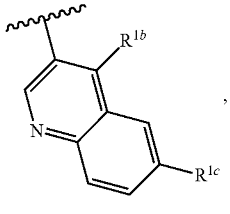,
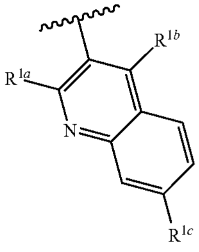,
-continued
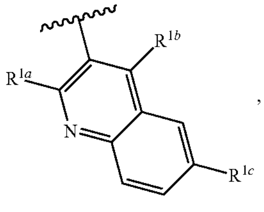,
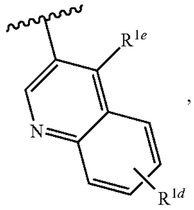,
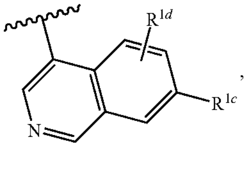
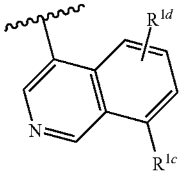
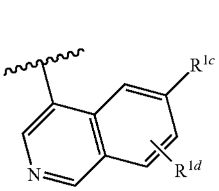,
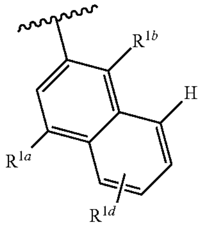
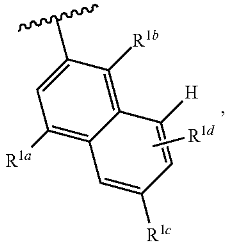
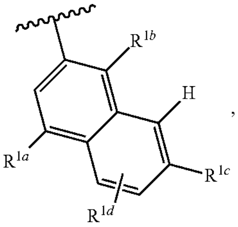,
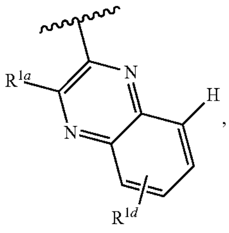
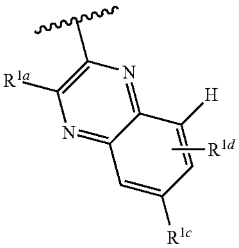
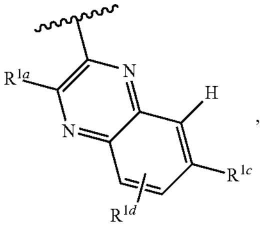,
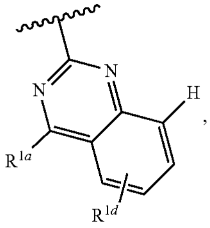
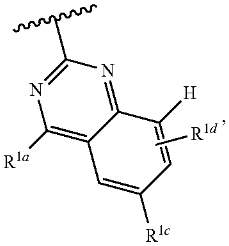
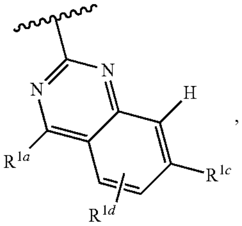, -continued
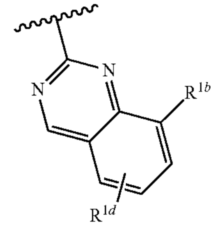,
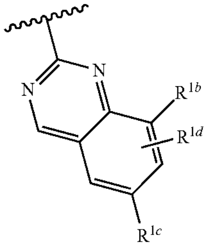,
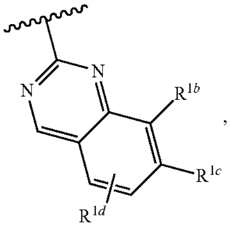,
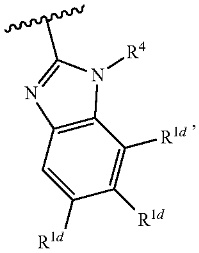,
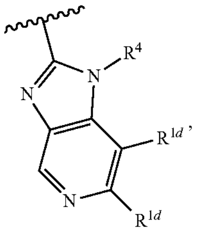,
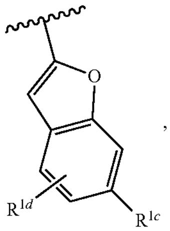,
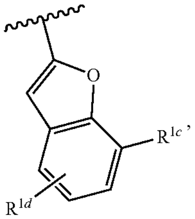,
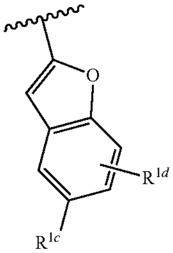,
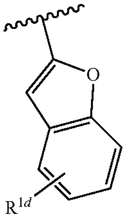,
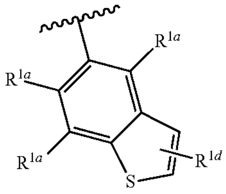,
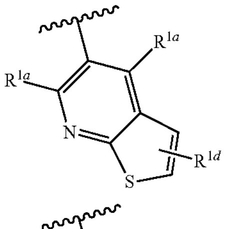,
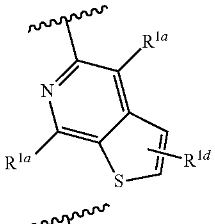,
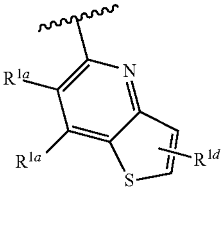,
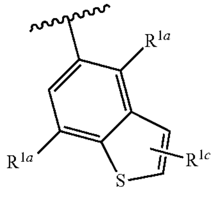,
-continued
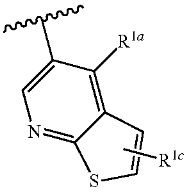,
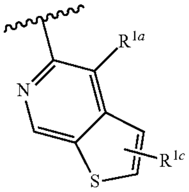,
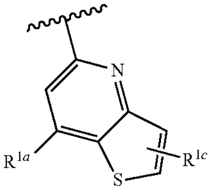,
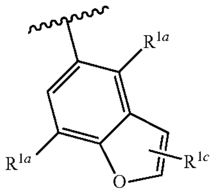,
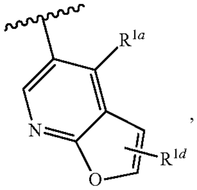,
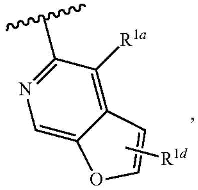,
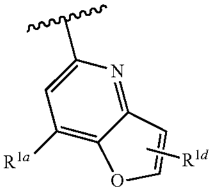,
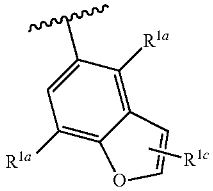,
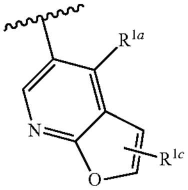,
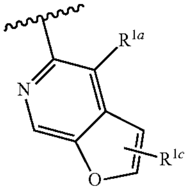,
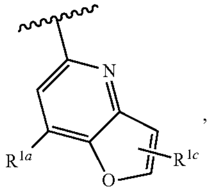,
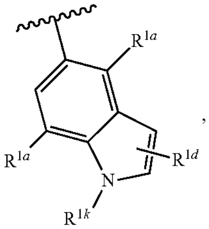,
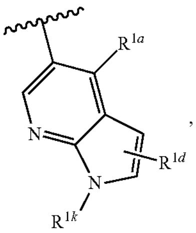,
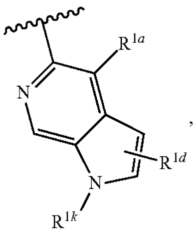,
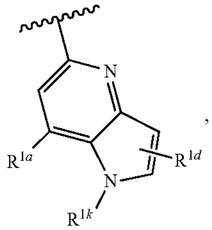,
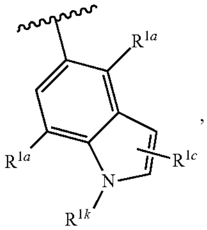, -continued
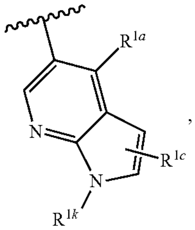, 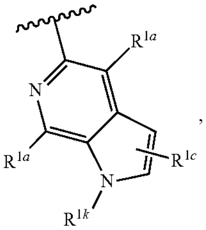,
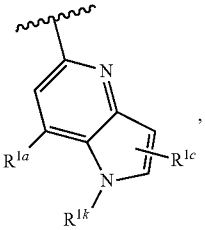, 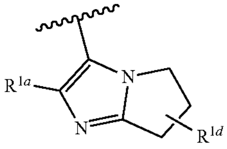,
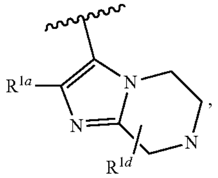, 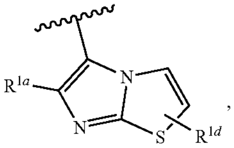,
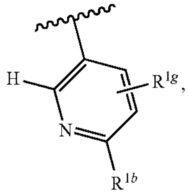 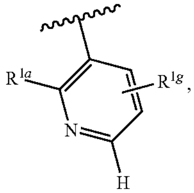
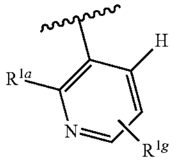, 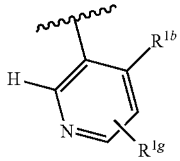,
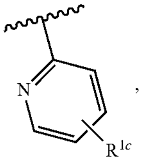, 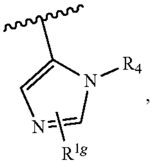, 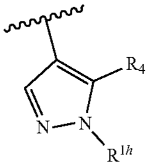,
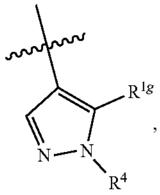, 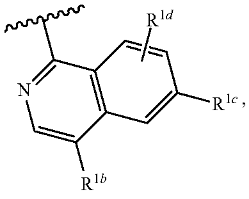
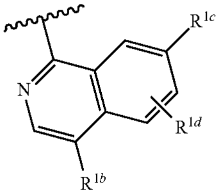, 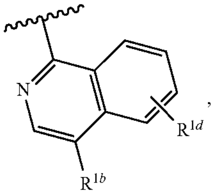,
-continued
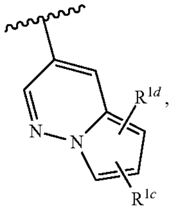 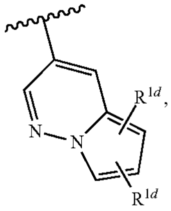 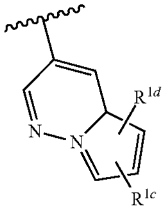
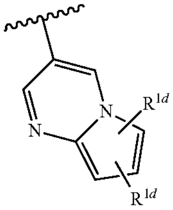 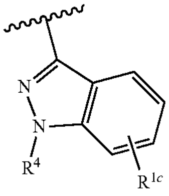,
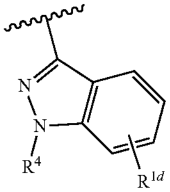, 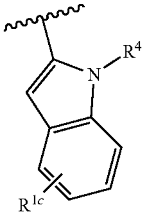,
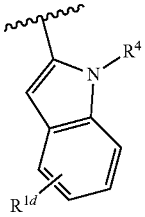, 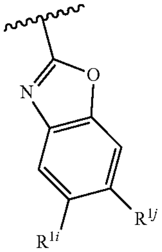,
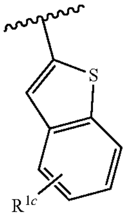, or 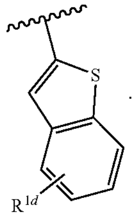.
In another embodiment, $R^{d3}$ is
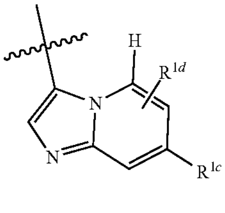, 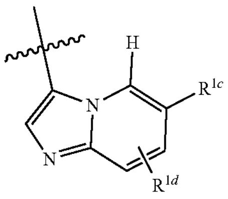,
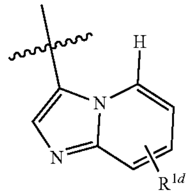, 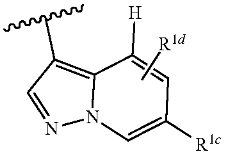, -continued
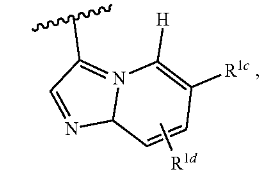,
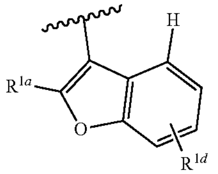,
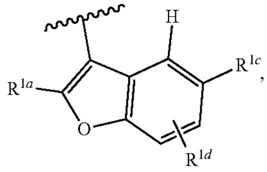,
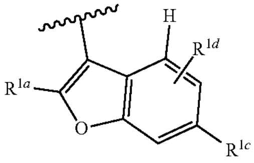,
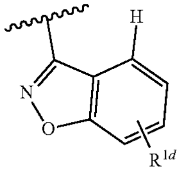,
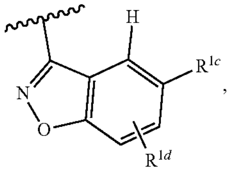,
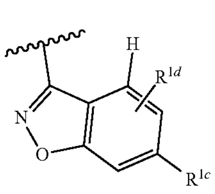,
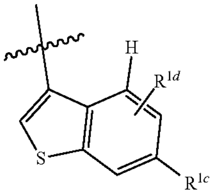,
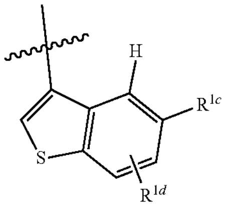,
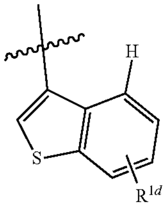,
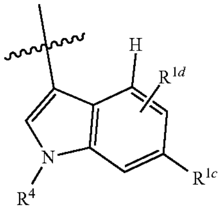,
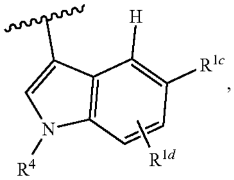,
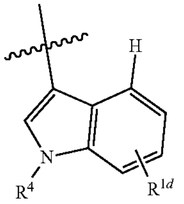,
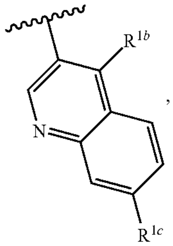,
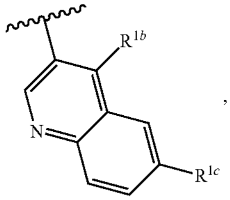,
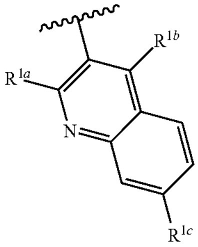,
-continued
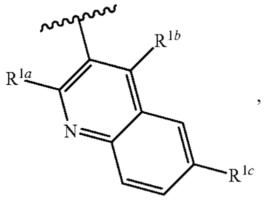,
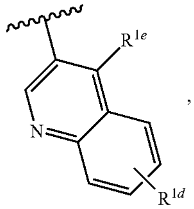,
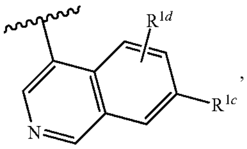,
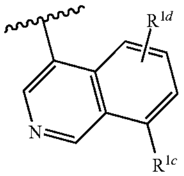,
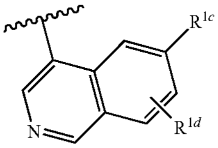,
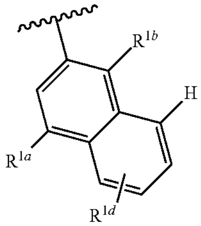,
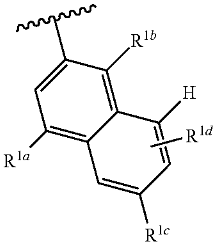,
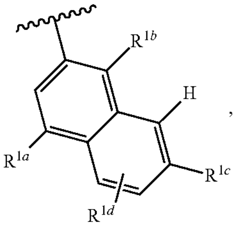,
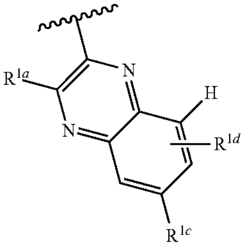,
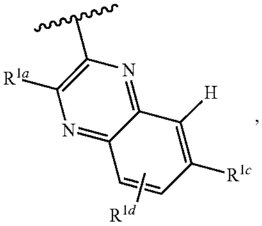,
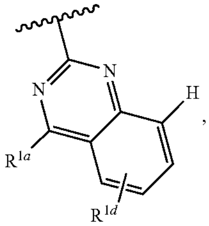,
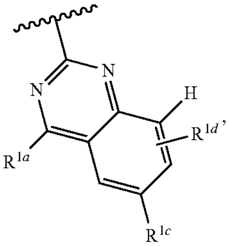,
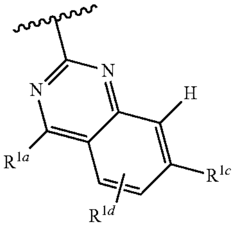,
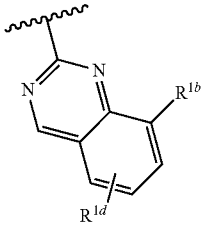, -continued
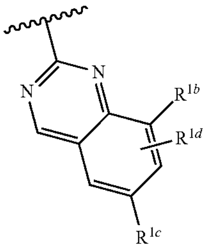,
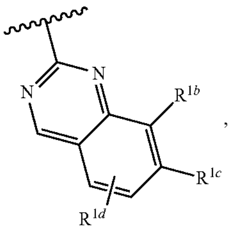,
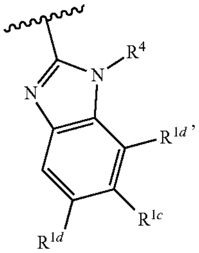,
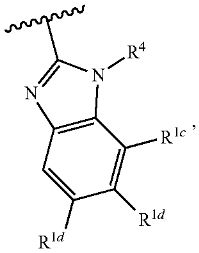,
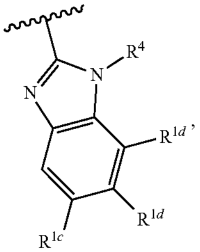,
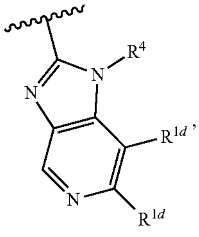,
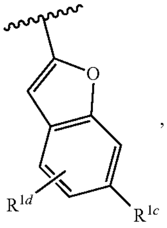,
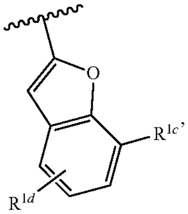,
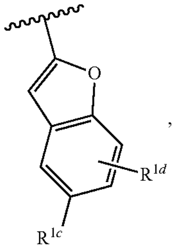,
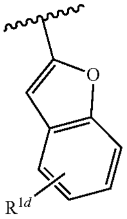,
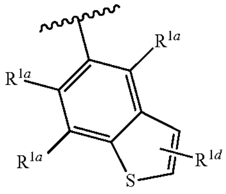,
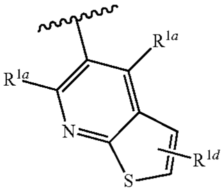,
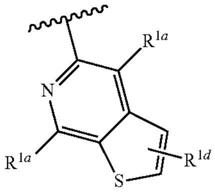,
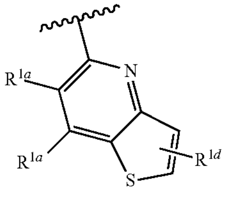,
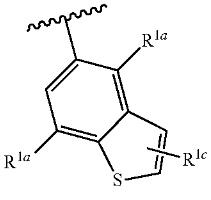,
-continued
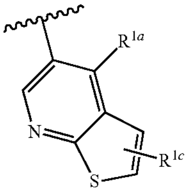,
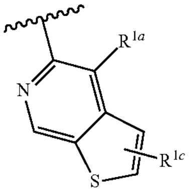,
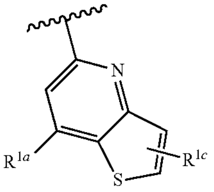,
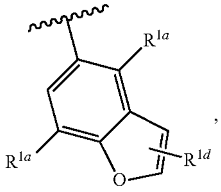,
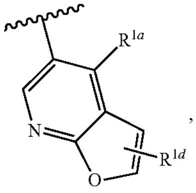,
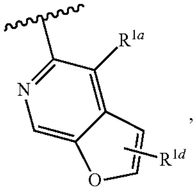,
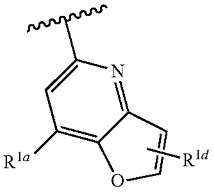,
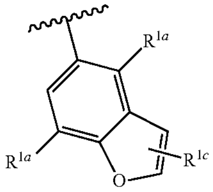,
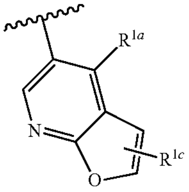,
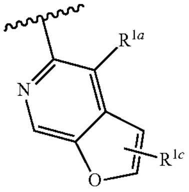,
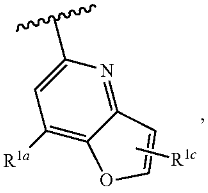,
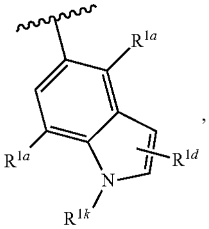,
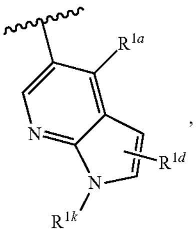,
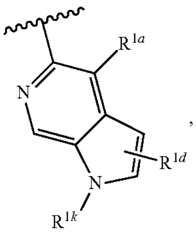,
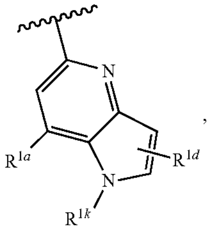,
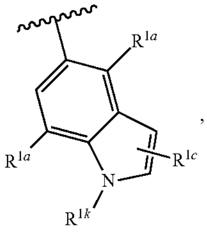, -continued
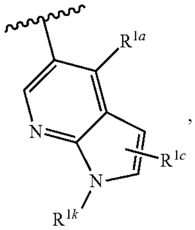,
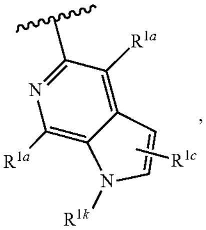,
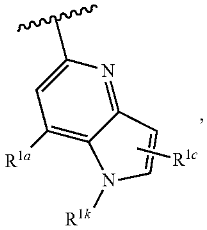,
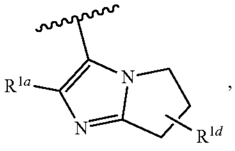,
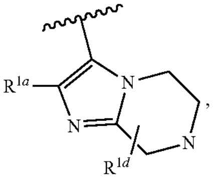,
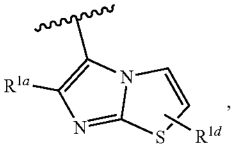,
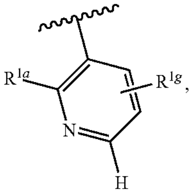
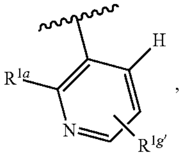,
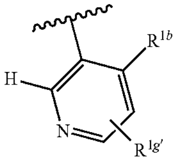,
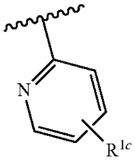,
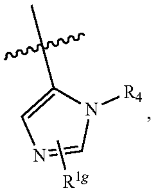
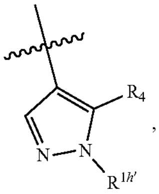,
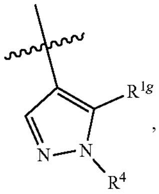,
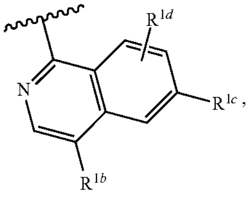
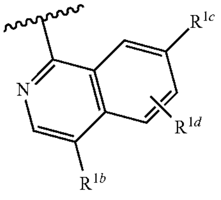,
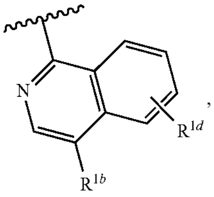
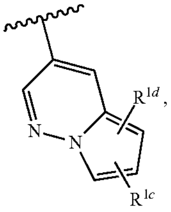
-continued
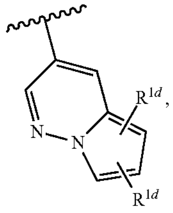
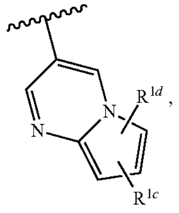
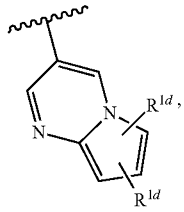
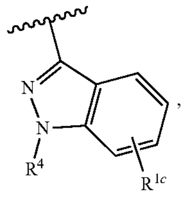,
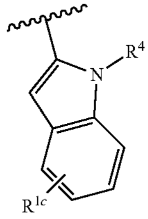,
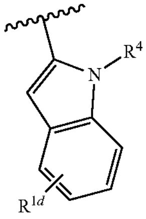,
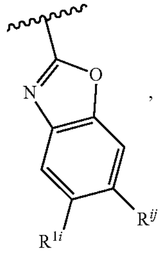,
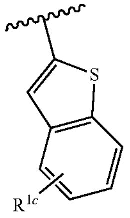, or
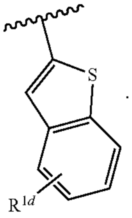.
In another embodiment, $R^{d3}$ is
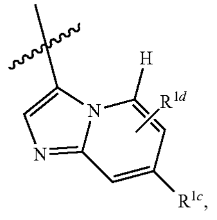
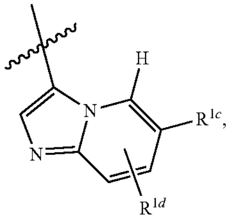
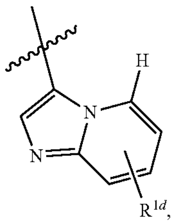
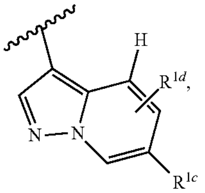
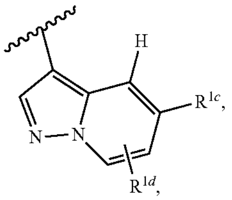
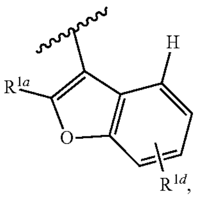

-continued

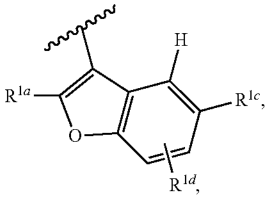

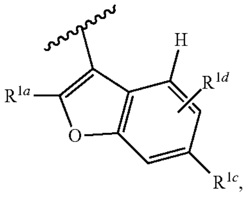

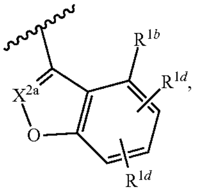

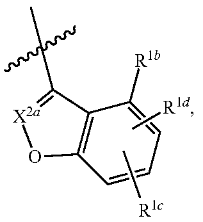

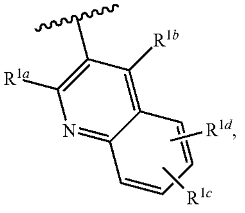

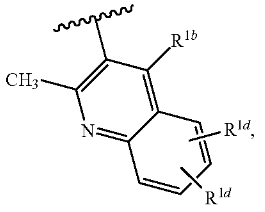

or

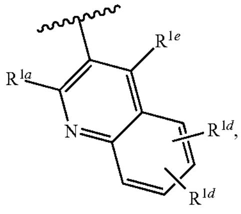

In another embodiment, $R^{d3}$ is

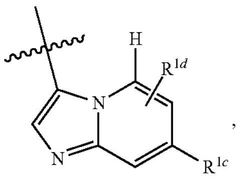

,

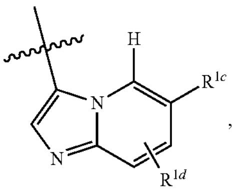

,

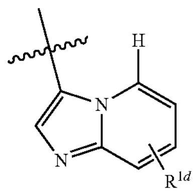

,

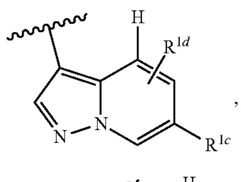

,

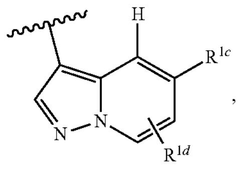

,

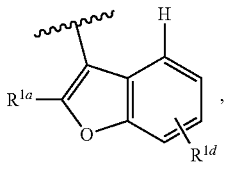

,

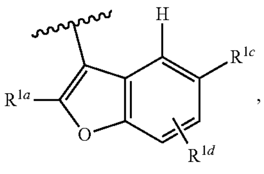

,

-continued

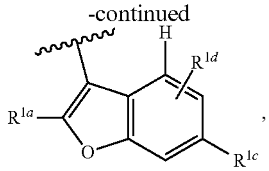

,

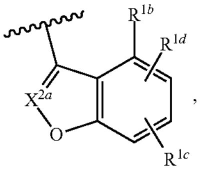

, or

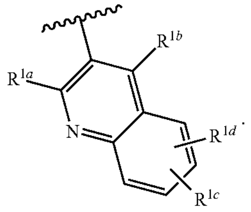

In another embodiment, $R^{d3}$ is

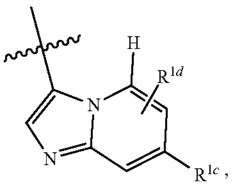

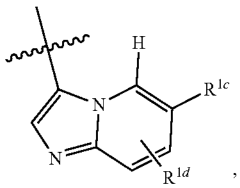

,

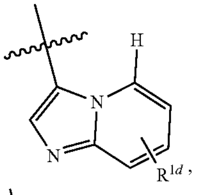

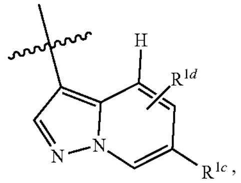

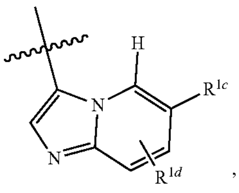

,

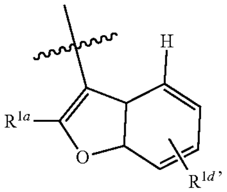

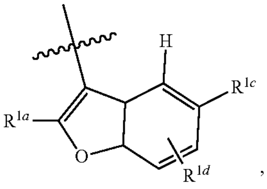

, or

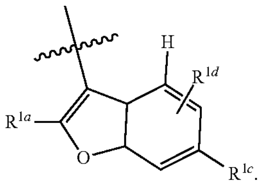

In some embodiments of the formulae above, $A^1$ is a 5- or 6-membered heterocyclyl optionally comprising 1-3 additional heteroatoms selected from O, N, and S or 5-membered heteroaryl optionally comprising 1-3 additional heteroatoms selected from N, $NR^{1k}$, O, and S and substituted with one to two $R^{1d}$. In another embodiment, $A^1$ is a 5- or 6-membered heterocyclyl optionally comprising 1-3 additional heteroatoms selected from O, N, and S or 5-membered heteroaryl optionally comprising 1-3 additional heteroatoms selected from N, $NR^{1k}$, O, and S. In yet another embodiment, $A^1$ is a 5-membered heterocyclyl optionally comprising 1-3 additional heteroatoms selected from O, N, and S or 5-membered heteroaryl optionally comprising 1-3 additional heteroatoms selected from N, $NR^{1k}$, O, and S and substituted with one to three $R^{1d}$. In another embodiment, $A^1$ is a 5-membered heterocyclyl optionally comprising 1-3 additional heteroatoms selected from O, N, and S or 5-membered heteroaryl optionally comprising 1-3 additional heteroatoms selected from N, $NR^{1k}$, O, and S. In yet another embodiment, $A^1$ is a 6-membered heterocyclyl optionally comprising 1-3 additional heteroatoms selected from O, N, and S or 5-membered heteroaryl optionally comprising 1-3 additional heteroatoms selected from N, $NR^{1k}$, O, and S and substituted with one to three $R^{1d}$. In another embodiment, $A^1$ is a 6-membered heterocyclyl optionally comprising 1-3 additional heteroatoms selected from O, N, and S or 5-membered heteroaryl optionally comprising 1-3 additional heteroatoms selected from N, $NR^{1k}$, O, and S.

In another embodiment, $A^1$ is a 5- or 6-membered heterocyclyl optionally comprising 1-3 additional heteroatoms selected from N, $NR^{1k}$, O, and S and substituted with one to two $R^{1d}$. In another embodiment, $A^1$ is a 5- or 6-membered heterocyclyl optionally comprising 1-3 additional heteroatoms selected from N, $NR^{1k}$, O, and S. In yet another embodiment, $A^1$ is a 5-membered heterocyclyl optionally comprising 1-3 additional heteroatoms selected from N, $NR^{1k}$, O, and S and substituted with one to three $R^{1d}$. In another embodiment, $A^1$ is a 5-membered heterocyclyl optionally comprising 1-3 additional heteroatoms selected from N, $NR^{1k}$, O, and S. In yet another embodiment, $A^1$ is a 6-membered heterocyclyl optionally comprising 1-3 additional heteroatoms selected from N, $NR^{1k}$, O, and S and substituted with one to three $R^{1d}$. In another embodiment, $A^1$ is a 6-membered heterocyclyl optionally comprising 1-3 additional heteroatoms selected from N, $NR^{1k}$, O, and S.

In another embodiment, $A^1$ is a 5-membered heteroaryl optionally comprising 1-3 additional heteroatoms selected from N, $NR^{1k}$, O, and S and substituted with one to three $R^{1d}$. In another embodiment, $A^1$ is a 5-membered heteroaryl optionally comprising 1-3 additional heteroatoms selected from N, $NR^{1k}$, O, and S.

In some embodiments of the formulae above, $A^2$ is a $C_{5-7}$ carbocyclyl or 5- to 7-membered heterocyclyl comprising 1-3 heteroatoms selected from N, $NR^{1k}$, O, and S, wherein the carbocyclyl and heterocyclyl are substituted with one to three $R^{1d}$.

In some embodiments of the formulae above, $X^1$ is $NR^4$. In another embodiment, $X^1$ is S.

In some embodiments of the formulae above, $X^2$ is $CR^{1a}$ or N. In another embodiment, $X^2$ is $CR^{1a}$.

In yet another embodiment, $X^2$ is N.

In some embodiments of the formulae above, $X^{2a}$ is $CR^{1a}$ or N. In another embodiment, $X^{2a}$ is $CR^{1a}$. In yet another embodiment, $X^{2a}$ is N.

In some embodiments of the formulae above, $X^2$ is $CR^{1a}$ or N and $X^{2a}$ is $CR^{1a}$. In another embodiment, $X^2$ is $CR^{1a}$ or N and $X^{2a}$ is N. In yet another embodiment, $X^{2a}$ is $CR^{1a}$ or N and $X^2$ is $CR^{1a}$. In another embodiment, $X^{2a}$ is $CR^{1a}$ or N and $X^2$ is N. In yet another embodiment, $X^{2a}$ is $CR^{1a}$ and $X^2$ is N. In another embodiment, $X^{2a}$ is N and $X^2$ is N. In yet another embodiment, $X^{2a}$ is $CR^{1a}$ and $X^2$ is N.

In some embodiments of the formulae above, each $X^3$ is independently $CR^{1d}$ or N; wherein no more than two $X^3$ are N.

In some embodiments of the formulae above, each $X^{3'}$ is independently $CR^{1d}$, $CR^{1c}$ or N, wherein no more than two $X^3$ are N and wherein at least one $X^{3'}$ is $CR^{1c}$. In another embodiment, each $X^{3'}$ is independently $CR^{1d}$ or $CR^{1c}$, wherein at least one $X^{3'}$ is $CR^{1c}$. In another embodiment, each $X^{3'}$ is independently $CR^{1c}$ or N, wherein no more than two $X^3$ are N.

In some embodiments of the formulae above, each $X^4$ is independently $CR^{1d}$ or N, wherein at least one $X^4$ is N and wherein no more than two $X^4$ are N.

In some embodiments of the formulae above, each $X^5$ is independently $CR^{1a}$ or N; wherein no more than two $X^5$ are N.

In some embodiments of the formulae above, $X^6$ is $NR^{1k}$ or O. In another embodiment, $X^6$ is $NR^{1k}$ or S. In yet another embodiment, $X^6$ is O or S. In another embodiment, $X^6$ is $NR^{1k}$. In yet another embodiment, $X^6$ is O. In another embodiment, $X^6$ is S.

In some embodiments of the formulae above, $X^7$ is $NR^4$ or O. In another embodiment, $X^7$ is N $NR^4$ or S. In yet another embodiment, $X^7$ is O or S. In another embodiment, $X^7$ is $NR^4$. In yet another embodiment, $X^7$ is O. In another embodiment, $X^7$ is S.

In some embodiments of the formulae above, $R^{1a}$ is $C_{1-3}$ alkyl, $C_{1-3}$ haloalkyl, $C_{1-3}$ alkoxy, $C_{1-3}$ haloalkoxy, —$NH_2$, —$NH(C_{1-3}$ alkyl), —$N(C_{1-3}$ alkyl$)_2$, —CN, F, or Cl. In another embodiment, $R^{1a}$ is H, $C_{2-4}$ alkyl, $C_{1-3}$ haloalkyl, $C_{1-3}$ alkoxy, $C_{1-3}$ haloalkoxy, —$NH_2$, —$NH(C_{1-3}$ alkyl), —$N(C_{1-3}$ alkyl$)_2$, —CN, F, or Cl. In yet another embodiment, $R^{1a}$ is H, $C_{1-3}$ alkyl, $C_{1-3}$ haloalkyl, $C_{1-3}$ alkoxy, or $C_{1-3}$ haloalkoxy. In another embodiment, $R^{1a}$ is $C_{1-3}$ alkyl, $C_{1-3}$ haloalkyl, $C_{1-3}$ alkoxy, or $C_{1-3}$ haloalkoxy. In yet another embodiment, $R^{1a}$ is —$NH_2$, —$NH(C_{1-3}$ alkyl), —$N(C_{1-3}$ alkyl$)_2$, —CN, F, or Cl. In another embodiment, $R^{1a}$ is H, $C_{1-3}$ alkyl, $C_{1-3}$ haloalkyl, $C_{1-3}$ alkoxy, $C_{1-3}$ haloalkoxy, —CN, F, or Cl. In yet another embodiment, $R^{1a}$ is $C_{1-3}$ alkyl, $C_{1-3}$ haloalkyl, $C_{1-3}$ alkoxy, $C_{1-3}$ haloalkoxy, —CN, F, or Cl. In another embodiment, $R^{1a}$ is H, $C_{1-3}$ alkyl, $C_{1-3}$ haloalkyl, $C_{1-3}$ alkoxy, $C_{1-3}$ haloalkoxy, F, or Cl. In yet another embodiment, Ria is $C_{1-3}$ alkyl, $C_{1-3}$ haloalkyl, $C_{1-3}$ alkoxy, $C_{1-3}$ haloalkoxy, F, or Cl. In another embodiment, $R^{1a}$ is H, $C_{1-3}$ alkyl, $C_{1-3}$ haloalkyl, —$NH_2$, —$NH(C_{1-3}$ alkyl), —$N(C_{1-3}$ alkyl$)_2$, —CN, F, or Cl. In yet another embodiment, $R^{1a}$ is $C_{1-3}$ alkyl, $C_{1-3}$ haloalkyl, —$NH_2$, —NH ($C_{1-3}$ alkyl), —$N(C_{1-3}$ alkyl$)_2$, —CN, F, or Cl. In another embodiment, $R^{1a}$ is H, $C_{1-3}$ alkyl, $C_{1-3}$ haloalkyl, $C_{1-3}$ alkoxy, $C_{1-3}$ haloalkoxy, —$NH_2$, —$NH(C_{1-3}$ alkyl), —$N(C_{1-3}$ alkyl$)_2$, or —CN. In yet another embodiment, $R^{1a}$ is $C_{1-3}$ alkyl, $C_{1-3}$ haloalkyl, $C_{1-3}$ alkoxy, $C_{1-3}$ haloalkoxy, —$NH_2$, —$NH(C_{1-3}$ alkyl), —$N(C_{1-3}$ alkyl$)_2$, or —CN. In another embodiment, $R^{1a}$ is H, $C_{1-3}$ alkyl, $C_{1-3}$ haloalkyl, $C_{1-3}$ alkoxy, $C_{1-3}$ haloalkoxy, or F. In yet another embodiment, $R^{1a}$ is $C_{1-3}$ alkyl, $C_{1-3}$ haloalkyl, $C_{1-3}$ alkoxy, $C_{1-3}$ haloalkoxy, or F. In another embodiment, $R^{1a}$ is H, $C_{1-3}$ alkyl, $C_{1-3}$ haloalkyl, or F. In yet another embodiment, $R^{1a}$ is $C_{1-3}$ alkyl, $C_{1-3}$ haloalkyl, or F.

In some embodiments of the formulae above, $R^{1b}$ is $C_{1-3}$ alkyl, $C_{1-3}$ haloalkyl, $C_{1-3}$ alkoxy, $C_{1-3}$ haloalkoxy, —$NH_2$, —$NH(C_{1-3}$ alkyl), —$N(C_{1-3}$ alkyl$)_2$, —CN, F, or Cl. In another embodiment, $R^{1b}$ is H, $C_{2-4}$ alkyl, $C_{1-3}$ haloalkyl, $C_{1-3}$ alkoxy, $C_{1-3}$ haloalkoxy, —$NH_2$, —$NH(C_{1-3}$ alkyl), —$N(C_{1-3}$ alkyl$)_2$, —CN, F, or Cl. In yet another embodiment, $R^{1b}$ is H, $C_{1-3}$ alkyl, $C_{1-3}$ haloalkyl, $C_{1-3}$ alkoxy, or $C_{1-3}$ haloalkoxy. In another embodiment, $R^{1b}$ is $C_{1-3}$ alkyl, $C_{1-3}$ haloalkyl, $C_{1-3}$ alkoxy, or $C_{1-3}$ haloalkoxy. In yet another embodiment, $R^{1b}$ is —$NH_2$, —$NH(C_{1-3}$ alkyl), —$N(C_{1-3}$ alkyl$)_2$, —CN, F, or Cl. In another embodiment, $R^{1b}$ is H, $C_{1-3}$ alkyl, $C_{1-3}$ haloalkyl, $C_{1-3}$ alkoxy, $C_{1-3}$ haloalkoxy, —CN, F, or Cl. In yet another embodiment, $R^{1b}$ is $C_{1-3}$ alkyl, $C_{1-3}$ haloalkyl, $C_{1-3}$ alkoxy, $C_{1-3}$ haloalkoxy, —CN, F, or Cl. In another embodiment, $R^{1b}$ is H, $C_{1-3}$ alkyl, $C_{1-3}$ haloalkyl, $C_{1-3}$ alkoxy, $C_{1-3}$ haloalkoxy, F, or Cl. In yet another embodiment, $R^{1b}$ is $C_{1-3}$ alkyl, $C_{1-3}$ haloalkyl, $C_{1-3}$ alkoxy, $C_{1-3}$ haloalkoxy, F, or Cl. In another embodiment, $R^{1b}$ is H, $C_{1-3}$ alkyl, $C_{1-3}$ haloalkyl, —$NH_2$, —NH($C_{1-3}$ alkyl), —N($C_{1-3}$ alkyl)$_2$, —CN, F, or Cl. In yet another embodiment, $R^{1b}$ is $C_{1-3}$ alkyl, $C_{1-3}$ haloalkyl, —$NH_2$, —NH ($C_{1-3}$ alkyl), —N($C_{1-3}$ alkyl)$_2$, —CN, F, or Cl. In another embodiment, $R^{1b}$ is H, $C_{1-3}$ alkyl, $C_{1-3}$ haloalkyl, $C_{1-3}$ alkoxy, $C_{1-3}$ haloalkoxy, —$NH_2$, —NH($C_{1-3}$ alkyl), —N($C_{1-3}$ alkyl)$_2$, or —CN. In yet another embodiment, $R^{1b}$ is $C_{1-3}$ alkyl, $C_{1-3}$ haloalkyl, $C_{1-3}$ alkoxy, $C_{1-3}$ haloalkoxy, —$NH_2$, —NH($C_{1-3}$ alkyl), —N($C_{1-3}$ alkyl)$_2$, or —CN. In another embodiment, $R^{1b}$ is H, $C_{1-3}$ alkyl, $C_{1-3}$ haloalkyl, $C_{1-3}$ alkoxy, $C_{1-3}$ haloalkoxy, or F. In yet another embodiment, $R^{1b}$ is $C_{1-3}$ alkyl, $C_{1-3}$ haloalkyl, $C_{1-3}$ alkoxy, $C_{1-3}$ haloalkoxy, or F. In another embodiment, $R^{1b}$ is H, $C_{1-3}$ alkyl, $C_{1-3}$ haloalkyl, or F. In yet another embodiment, $R^{1b}$ is $C_{1-3}$ alkyl, $C_{1-3}$ haloalkyl, or F.

In some embodiments of the formulae above, $R^{1c}$ is $C_{1-6}$ alkyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)O$C_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$N$R^3$$(CH_2)_{0-4}$—$C_{3-7}$ carbocyclyl, —$(CH_2)_{0-4}$N$R^3$$(CH_2)_{0-4}$-5- to 7-membered heterocyclyl comprising 1-3 heteroatoms selected from O, N, and S, —$(CH_2)_{0-4}$N$R^3$$(CH_2)_{0-4}$—$C_{6-10}$ aryl, —$(CH_2)_{0-4}$N$R^3$$(CH_2)_{0-4}$-5- or 6-membered heteroaryl comprising 1-3 heteroatoms selected from O, N, and S, —$(CH_2)_{0-4}$—N$R^3$C(O)—$C_{3-7}$ carbocyclyl, —$(CH_2)_{0-4}$—N$R^3$C(O)-5- to 7-membered heterocyclyl comprising 1-3 heteroatoms selected from O, N, and S, —$(CH_2)_{0-4}$—N$R^3$C(O)—$C_{6-10}$ aryl, —$(CH_2)_{0-4}$—N$R^3$C(O)-5- or 6-membered heteroaryl comprising 1-3 heteroatoms selected from O, N, and S, —N$R^3$C(O)O$(CH_2)_{0-4}$—$C_{3-7}$ carbocyclyl, —N$R^3$C(O)O$(CH_2)_{0-4}$-5- to 7-membered heterocyclyl comprising 1-3 heteroatoms selected from O, N, and S, —N$R^3$C(O)O$(CH_2)_{0-4}$—$C_{6-10}$ aryl, or —N$R^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$. In another embodiment, $R^{1c}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)O$C_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, wherein the alkynyl is optionally substituted with one to three $R^2$.

In another embodiment, $R^{1c}$ is, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$N$R^3$$(CH_2)_{0-4}$—$C_{3-7}$ carbocyclyl, —$(CH_2)_{0-4}$N$R^3$$(CH_2)_{0-4}$-5- to 7-membered heterocyclyl comprising 1-3 heteroatoms selected from O, N, and S, —$(CH_2)_{0-4}$N$R^3$$(CH_2)_{0-4}$—$C_{6-10}$ aryl, —$(CH_2)_{0-4}$N$R^3$$(CH_2)_{0-4}$-5- or 6-membered heteroaryl comprising 1-3 heteroatoms selected from O, N, and S, —$(CH_2)_{0-4}$—N$R^3$C(O)—$C_{3-7}$ carbocyclyl, —$(CH_2)_{0-4}$—N$R^3$C(O)-5- to 7-membered heterocyclyl comprising 1-3 heteroatoms selected from O, N, and S, —$(CH_2)_{0-4}$—N$R^3$C(O)—$C_{6-10}$ aryl, —$(CH_2)_{0-4}$—N$R^3$C(O)-5- or 6-membered heteroaryl comprising 1-3 heteroatoms selected from O, N, and S, —N$R^3$C(O)O$(CH_2)_{0-4}$—$C_{3-7}$ carbocyclyl, —N$R^3$C(O)O$(CH_2)_{0-4}$-5- to 7-membered heterocyclyl comprising 1-3 heteroatoms selected from O, N, and S, —N$R^3$C(O)O$(CH_2)_{0-4}$—$C_{6-10}$ aryl, or —N$R^3$C(O)O$(CH_2)_{0-4}$-5- or 6-membered heteroaryl comprising 1-3 heteroatoms selected from O, N, and S, wherein the carbocyclyl, heterocyclyl, aryl, and heteroaryl are optionally substituted with one to five $R^5$.

In another embodiment, $R^{1c}$ is $C_{1-6}$ alkyl, $C_{2-6}$ alkynyl, $C_{1-6}$ haloalkyl, halogen, CN, —C(O)OH, —C(O)O$C_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$N$R^3$$(CH_2)_{0-4}$—$C_{3-7}$ carbocyclyl, —$(CH_2)_{0-4}$N$R^3$$(CH_2)_{0-4}$-5- to 7-membered heterocyclyl comprising 1-3 heteroatoms selected from O, N, and S, —$(CH_2)_{0-4}$N$R^3$$(CH_2)_{0-4}$—$C_{6-10}$ aryl, —$(CH_2)_{0-4}$N$R^3$$(CH_2)_{0-4}$-5- or 6-membered heteroaryl comprising 1-3 heteroatoms selected from O, N, and S, —$(CH_2)_{0-4}$—N$R^3$C(O)—$C_{3-7}$ carbocyclyl, —$(CH_2)_{0-4}$—N$R^3$C(O)-5- to 7-membered heterocyclyl comprising 1-3 heteroatoms selected from O, N, and S, —$(CH_2)_{0-4}$—N$R^3$C(O)—$C_{6-10}$ aryl, —$(CH_2)_{0-4}$—N$R^3$C(O)-5- or 6-membered heteroaryl comprising 1-3 heteroatoms selected from O, N, and S, —N$R^3$C(O)O$(CH_2)_{0-4}$—$C_{3-7}$ carbocyclyl, —N$R^3$C(O)O$(CH_2)_{0-4}$-5- to 7-membered heterocyclyl comprising 1-3 heteroatoms selected from O, N, and S, —N$R^3$C(O)O$(CH_2)_{0-4}$—$C_{6-10}$ aryl, or —N$R^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$.

In some embodiments of the formulae above, $R^{1c'}$ is $C_{1-6}$ alkyl, $C_{2-6}$ alkynyl, $C_{1-6}$ haloalkyl, $C_{1-6}$ alkoxy, $C_{1-3}$ haloalkoxy, F, Cl, CN, —C(O)OH, —C(O)O$C_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$N$R^3$$(CH_2)_{0-4}$—$C_{3-7}$ carbocyclyl, —$(CH_2)_{0-4}$N$R^3$$(CH_2)_{0-4}$-5- to 7-membered heterocyclyl comprising 1-3 heteroatoms selected from O, N, and S, —$(CH_2)_{0-4}$N$R^3$$(CH_2)_{0-4}$—$C_{6-10}$ aryl, —$(CH_2)_{0-4}$N$R^3$$(CH_2)_{0-4}$-5- or 6-membered heteroaryl comprising 1-3 heteroatoms selected from O, N, and S, —$(CH_2)_{0-4}$—N$R^3$C(O)—$C_{3-7}$ carbocyclyl, —$(CH_2)_{0-4}$—N$R^3$C(O)-5- to 7-membered heterocyclyl comprising 1-3 heteroatoms selected from O, N, and S, —$(CH_2)_{0-4}$—N$R^3$C(O)—$C_{6-10}$ aryl, —$(CH_2)_{0-4}$—N$R^3$C(O)-5- or 6-membered heteroaryl comprising 1-3 heteroatoms selected from O, N, and S, —N$R^3$C(O)O$(CH_2)_{0-4}$—$C_{3-7}$ carbocyclyl, —N$R^3$C(O)O$(CH_2)_{0-4}$-5- to 7-membered heterocyclyl comprising 1-3 heteroatoms selected from O, N, and S, —N$R^3$C(O)O$(CH_2)_{0-4}$—$C_{6-10}$ aryl, or —N$R^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$. In another embodiment, $R^{1c'}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, F, Cl, CN, —C(O)OH, —C(O)O$C_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, wherein the alkynyl is optionally substituted with one to three $R^2$.

In another embodiment, $R^{1c'}$ is, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the carbocyclyl, heterocyclyl, aryl, and heteroaryl are optionally substituted with one to five $R^5$.

In another embodiment, $R^{1c'}$ is $C_{1-6}$ alkyl, $C_{2-6}$ alkynyl, $C_{1-6}$ haloalkyl, F, Cl, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$.

In some embodiments of the formulae above, $R^{1d}$ is H, $C_{1-6}$ alkyl, $C_{2-6}$ alkynyl, $C_{1-6}$ haloalkyl, $C_{1-6}$ alkoxy, $C_{1-3}$ haloalkoxy, halogen, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$. In another embodiment, $R^{1d}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, wherein the alkynyl is optionally substituted with one to three $R^2$.

In another embodiment, $R^{1d}$ is, H, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the carbocyclyl, heterocyclyl, aryl, and heteroaryl are optionally substituted with one to five $R^5$.

In another embodiment, $R^{1d}$ is H, $C_{1-6}$ alkyl, $C_{2-6}$ alkynyl, $C_{1-6}$ haloalkyl, halogen, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$ In some embodiments of the formulae above, $R^{1e}$ is $C_{2-3}$ alkyl, $C_{1-3}$ haloalkyl, $C_{1-3}$ alkoxy, $C_{1-3}$ haloalkoxy, —CN, or F. In another embodiment, $R^{1e}$ is $C_{2-3}$ alkyl, $C_{1-3}$ haloalkyl, $C_{1-3}$ alkoxy, $C_{1-3}$ haloalkoxy, —CN, or Cl. In yet another embodiment, $R^{1e}$ is $C_{2-3}$ alkyl, $C_{1-3}$ haloalkyl, $C_{1-3}$ alkoxy, $C_{1-3}$ haloalkoxy, F, or Cl. In another embodiment, $R^{1e}$ is $C_{2-3}$ alkyl, $C_{1-3}$ haloalkyl, $C_{1-3}$ alkoxy, —CN, F, or Cl. In yet another embodiment, $R^{1e}$ is $C_{2-3}$ alkyl, $C_{1-3}$ haloalkyl, $C_{1-3}$ haloalkoxy, —CN, F, or Cl. In another embodiment, $R^{1e}$ is $C_{2-3}$ alkyl, $C_{1-3}$ alkoxy, $C_{1-3}$ haloalkoxy, —CN, F, or Cl. In yet another embodiment, $R^{1e}$ is $C_{1-3}$ haloalkyl, $C_{1-3}$ alkoxy, $C_{1-3}$ haloalkoxy, —CN, F, or Cl. In another embodiment, $R^{1e}$ is $C_{2-3}$ alkyl, $C_{1-3}$ haloalkyl, $C_{1-3}$ alkoxy, $C_{1-3}$ haloalkoxy, or —CN. In yet another embodiment, $R^{1e}$ is $C_{2-3}$ alkyl, $C_{1-3}$ haloalkyl, —CN, F, or Cl. In another embodiment, $R^{1e}$ is $C_{1-3}$ alkoxy, $C_{1-3}$ haloalkoxy, —CN, F, or Cl. In yet another embodiment, $R^{1e}$ is $C_{2-3}$ alkyl, $C_{1-3}$ haloalkyl, F, or Cl.

In some embodiments of the formulae above, $R^{1f}$ is $C_{1-3}$ alkyl, $C_{1-3}$ haloalkyl, $C_{1-3}$ alkoxy, $C_{1-3}$ haloalkoxy, —CN, or F. In another embodiment, $R^{1f}$ is $C_{1-3}$ alkyl, $C_{1-3}$ haloalkyl, $C_{1-3}$ alkoxy, $C_{1-3}$ haloalkoxy, —CN, or Cl. In yet another embodiment, $R^{1f}$ is $C_{1-3}$ alkyl, $C_{1-3}$ haloalkyl, $C_{1-3}$ alkoxy, $C_{1-3}$ haloalkoxy, F, or Cl. In another embodiment, $R^{1f}$ is $C_{1-3}$ alkyl, $C_{1-3}$ haloalkyl, $C_{1-3}$ alkoxy, —CN, F, or Cl. In yet another embodiment, $R^{f}$ is $C_{1-3}$ alkyl, $C_{1-3}$ haloalkyl, $C_{1-3}$ haloalkoxy, —CN, F, or Cl. In another embodiment, $R^{f}$ is $C_{1-3}$ alkyl, $C_{1-3}$ alkoxy, $C_{1-3}$ haloalkoxy, —CN, F, or Cl. In yet another embodiment, $R^{f}$ is $C_{1-3}$ haloalkyl, $C_{1-3}$ alkoxy, $C_{1-3}$ haloalkoxy, —CN, F, or Cl. In another embodiment, $R^{f}$ is $C_{1-3}$ alkyl, $C_{1-3}$ haloalkyl, $C_{1-3}$ alkoxy, $C_{1-3}$ haloalkoxy, or —CN. In yet another embodiment, $R^{1f}$ is $C_{1-3}$ alkyl, $C_{1-3}$ haloalkyl, —CN, F, or Cl. In another embodiment, $R^{1f}$ is $C_{1-3}$ alkoxy, $C_{1-3}$ haloalkoxy, —CN, F, or Cl. In yet another embodiment, $R^{1f}$ is $C_{1-3}$ alkyl, $C_{1-3}$ haloalkyl, F, or Cl.

In some embodiments of the formulae above, $R^9$ is $C_{2-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, wherein the alkynyl is optionally substituted with one to three $R^2$.

In another embodiment, $R^9$ is —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$NR$^3$$(CH_2)_{0-4}$—$C_{3-7}$ carbocyclyl, —$(CH_2)_{0-4}$NR$^3$$(CH_2)_{0-4}$-5- to 7-membered heterocyclyl comprising 1-3 heteroatoms selected from O, N, and S, —$(CH_2)_{0-4}$NR$^3$$(CH_2)_{0-4}$—$C_{6-10}$ aryl, —$(CH_2)_{0-4}$NR$^3$$(CH_2)_{0-4}$-5- or 6-membered heteroaryl comprising 1-3 heteroatoms selected from O, N, and S, —$(CH_2)_{0-4}$—NR$^3$C(O)—$C_{3-7}$ carbocyclyl, —$(CH_2)_{0-4}$—NR$^3$C(O)-5- to 7-membered heterocyclyl comprising 1-3 heteroatoms selected from O, N, and S, —$(CH_2)_{0-4}$—NR$^3$C(O)—$C_{6-10}$ aryl, —$(CH_2)_{0-4}$—NR$^3$C(O)-5- or 6-membered heteroaryl comprising 1-3 heteroatoms selected from O, N, and S, —NR$^3$C(O)O$(CH_2)_{0-4}$—$C_{3-7}$ carbocyclyl, —NR$^3$C(O)O$(CH_2)_{0-4}$-5- to 7-membered heterocyclyl comprising 1-3 heteroatoms selected from O, N, and S, —NR$^3$C(O)O$(CH_2)_{0-4}$—$C_{6-10}$ aryl, or —NR$^3$C(O)O$(CH_2)_{0-4}$-5- or 6-membered heteroaryl comprising 1-3 heteroatoms selected from O, N, and S, wherein the carbocyclyl, heterocyclyl, aryl, and heteroaryl are optionally substituted with one to five $R^5$.

In another embodiment, $R^9$ is $C_{3-6}$ alkyl, $C_{2-6}$ alkenyl, $C_{2-6}$ alkynyl, $C_{2-6}$ haloalkyl, $C_{1-6}$ alkoxy, $C_1$. 3 haloalkoxy, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$NR$^3$$(CH_2)_{0-4}$—$C_{3-7}$ carbocyclyl, —$(CH_2)_{0-4}$NR$^3$$(CH_2)_{0-4}$-5- to 7-membered heterocyclyl comprising 1-3 heteroatoms selected from O, N, and S, —$(CH_2)_{0-4}$NR$^3$$(CH_2)_{0-4}$—$C_{6-10}$ aryl, —$(CH_2)_{0-4}$NR$^3$$(CH_2)_{0-4}$-5- or 6-membered heteroaryl comprising 1-3 heteroatoms selected from O, N, and S, —$(CH_2)_{0-4}$—NR$^3$C(O)—$C_{3-7}$ carbocyclyl, —$(CH_2)_{0-4}$—NR$^3$C(O)-5- to 7-membered heterocyclyl comprising 1-3 heteroatoms selected from O, N, and S, —$(CH_2)_{0-4}$—NR$^3$C(O)—$C_{6-10}$ aryl, —$(CH_2)_{0-4}$—NR$^3$C(O)-5- or 6-membered heteroaryl comprising 1-3 heteroatoms selected from O, N, and S, —NR$^3$C(O)O$(CH_2)_{0-4}$—$C_{3-7}$ carbocyclyl, —NR$^3$C(O)O$(CH_2)_{0-4}$-5- to 7-membered heterocyclyl comprising 1-3 heteroatoms selected from O, N, and S, —NR$^3$C(O)O$(CH_2)_{0-4}$—$C_{6-10}$ aryl, or —NR$^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$.

In another embodiment, $R^{1g}$ is $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$NR$^3$$(CH_2)_{0-4}$—$C_{3-7}$ carbocyclyl, —$(CH_2)_{0-4}$NR$^3$$(CH_2)_{0-4}$-5- to 7-membered heterocyclyl comprising 1-3 heteroatoms selected from O, N, and S, —$(CH_2)_{0-4}$NR$^3$$(CH_2)_{0-4}$—$C_{6-10}$ aryl, —$(CH_2)_{0-4}$NR$^3$$(CH_2)_{0-4}$-5- or 6-membered heteroaryl comprising 1-3 heteroatoms selected from O, N, and S, —$(CH_2)_{0-4}$—NR$^3$C(O)—$C_{3-7}$ carbocyclyl, —$(CH_2)_{0-4}$—NR$^3$C(O)-5- to 7-membered heterocyclyl comprising 1-3 heteroatoms selected from O, N, and S, —$(CH_2)_{0-4}$—NR$^3$C(O)—$C_{6-10}$ aryl, —$(CH_2)_{0-4}$—NR$^3$C(O)-5- or 6-membered heteroaryl comprising 1-3 heteroatoms selected from O, N, and S, —NR$^3$C(O)O$(CH_2)_{0-4}$—$C_{3-7}$ carbocyclyl, —NR$^3$C(O)O$(CH_2)_{0-4}$-5- to 7-membered heterocyclyl comprising 1-3 heteroatoms selected from O, N, and S, —NR$^3$C(O)O$(CH_2)_{0-4}$—$C_{6-10}$ aryl, or —NR$^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$.

In another embodiment, Rig is $C_{2-6}$ alkyl, $C_{2-6}$ alkynyl, $C_{2-6}$ haloalkyl, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}$NR$^3$$(CH_2)_{0-4}$—$C_{3-7}$ carbocyclyl, —$(CH_2)_{0-4}$NR$^3$$(CH_2)_{0-4}$-5- to 7-membered heterocyclyl comprising 1-3 heteroatoms selected from O, N, and S, —$(CH_2)_{0-4}$NR$^3$$(CH_2)_{0-4}$—$C_{6-10}$ aryl, —$(CH_2)_{0-4}$NR$^3$$(CH_2)_{0-4}$-5- or 6-membered heteroaryl comprising 1-3 heteroatoms selected from O, N, and S, —$(CH_2)_{0-4}$—NR$^3$C(O)—$C_{3-7}$ carbocyclyl, —$(CH_2)_{0-4}$—NR$^3$C(O)-5- to 7-membered heterocyclyl comprising 1-3 heteroatoms selected from O, N, and S, —$(CH_2)_{0-4}$—NR$^3$C (O)—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_6$. 10 aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$.

In some embodiments of the formulae above, $R^{1g'}$ is $C_{2-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —C(O)O$C_{1-6}$ alkyl, —$(CH_2)_{0-4}$—$C(O)NH_2$, —$(CH_2)_{0-4}$—$C(O)NH(R^{13})$, or —$(CH_2)_{0-4}$—$C(O)N(R^{13})_2$, wherein the alkynyl is optionally substituted with one to three $R^2$.

In another embodiment, $R^{1g'}$ is —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the heterocyclyl is substituted with one to five $R^5$ and the carbocyclyl, aryl, and heteroaryl are optionally substituted with one to five $R^5$.

In another embodiment, $R^{1g'}$ is $C_{3-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —C(O)O$C_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$, the heterocyclyl is substituted with one to five $R^5$, and the carbocyclyl, aryl, and heteroaryl are optionally substituted with one to five $R^5$.

In another embodiment, $R^{1g'}$ is $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —C(O)O$C_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$, the heterocyclyl is substituted with one to five $R^5$, and the carbocyclyl, aryl, and heteroaryl are optionally substituted with one to five $R^5$.

In another embodiment, $R^{1i'}$ is $C_{2-6}$ alkyl, $C_{2-6}$ alkynyl, $C_{2-6}$ haloalkyl, CN, —C(O)OH, —C(O)O$C_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$, the heterocyclyl is substituted with one to five $R^5$, and the carbocyclyl, aryl, and heteroaryl are optionally substituted with one to five $R^5$.

In some embodiments of the formulae above, $R^{1h}$ is $C_{4-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —C(O)O$C_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, wherein the alkynyl is optionally substituted with one to three $R^2$. In another embodiment, $R^{1h}$ is, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$C_{6-10}$ aryl, —$(CH_2)_{2-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the carbocyclyl, heterocyclyl, aryl, and heteroaryl are optionally substituted with one to five $R^5$.

In another embodiment, $R^{1h}$ is $C_{4-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$C_{6-10}$ aryl, —$(CH_2)_{2-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$.

In another embodiment, $R^{1h}$ is $C_{4-6}$ alkyl, $C_{2-6}$ alkenyl, $C_{2-6}$ alkynyl, $C_{2-6}$ haloalkyl, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$C_{6-10}$ aryl, —$(CH_2)_{2-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$.

In some embodiments of the formulae above, $R^{1h'}$ is $C_{4-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, or —$(CH_2)_{0-4}$—$C(O)N(R^{13})_2$, wherein the alkynyl is optionally substituted with one to three $R^2$.

In another embodiment, $R^{1h'}$ is, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$C_{6-10}$ aryl, —$(CH_2)_{2-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the heterocyclyl is substituted with one to five $R^5$, and the carbocyclyl, aryl, and heteroaryl are optionally substituted with one to five $R^5$.

In another embodiment, $R^{1h'}$ is $C_{4-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$C_{6-10}$ aryl, —$(CH_2)_{2-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$, the heterocyclyl is substituted with one to five $R^5$, and the carbocyclyl, aryl, and heteroaryl are optionally substituted with one to five $R^5$.

In another embodiment, $R^{1h'}$ is $C_{4-6}$ alkyl, $C_{2-6}$ alkenyl, $C_{2-6}$ alkynyl, $C_{2-6}$ haloalkyl, CN, —C(O)OH, —$C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-C_{6-10}$ aryl, $-(CH_2)_{2-6}$ $C_{6-10}$ aryl, $-(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR^3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$, the heterocyclyl is substituted with one to five $R^5$, and the carbocyclyl, aryl, and heteroaryl are optionally substituted with one to five $R^5$.

In some embodiments of the formulae above, $R^{1i}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, wherein the alkynyl is optionally substituted with one to three $R^2$. In another embodiment, $R^{1i}$ is $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}$ $C_{6-10}$ aryl, $-(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR^3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the carbocyclyl, heterocyclyl, aryl, and heteroaryl is optionally substituted with one to five $R^5$.

In another embodiment, $R^{1i}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}$ $C_{6-10}$ aryl, $-(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR^3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$.

In another embodiment, $R^{1i}$ is H, $C_{1-6}$ alkyl, $C_{2-6}$ alkenyl, $C_{2-6}$ alkynyl, $C_{1-6}$ haloalkyl, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}$ $C_{6-10}$ aryl, $-(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR^3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$.

In some embodiments of the formulae above, $R^{1j}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}$ $C_{6-10}$ aryl, $-(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR^3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$.

In another embodiment, $R^{1j}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)OC$_{1-6}$ alkyl, —$(CH_2)_{0-4}$—C(O)$NH_2$, —$(CH_2)_{0-4}$—C(O)NH($R^{13}$)—$(CH_2)_{0-4}$—C(O)N$(R^{13})_2$, wherein the alkynyl is optionally substituted with one to three $R^2$. In another embodiment, $R^J$ is —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}$ $NR^3(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR^3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the carbocyclyl, heterocyclyl, aryl, and heteroaryl is optionally substituted with one to five $R^5$.

In another embodiment, $R^J$ is H, $C_{1-6}$ alkyl, $C_{2-6}$ alkenyl, $C_{2-6}$ alkynyl, $C_{1-6}$ haloalkyl, halogen, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}$ $NR^3(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR^3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from 0, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$.

In some embodiments of the formulae above, $R^{1d}$, $R^{1i}$, and $R^{1j}$ on the benzoxazole ring are not all simultaneously H. In another embodiment, $R^{1d}$ and $R^{1h}$ are H and $R^{1i}$ is not H. In another embodiment, $R^{1i}$ and $R^{1j}$ are H and $R^{1d}$ is not H. In another embodiment, $R^{1d}$ and $R^{1i}$ are H and $R^{1i}$ is not H. In another embodiment, $R^{1d}$ is H and $R^{1i}$ and $R^{1j}$ are not H. In another embodiment, $R^{1i}$ is H and $R^{1d}$ and $R^{1j}$ are not H. In another embodiment, $R^{1j}$ is H and $R^{1d}$ and $R^{1i}$ are not H.

In some embodiments of the formulae above, each $R^{1k}$ is independently is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), wherein the alkynyl is optionally substituted with one to three $R^2$. In another embodiment, each $R^{1k}$ is independently is selected from H, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —C(O)O$(CH_2)_{0-4}$—$C_{3-7}$ carbocyclyl, —C(O)O$(CH_2)_{0-4}$-5- to 7-membered heterocyclyl comprising 1-3 heteroatoms selected from O, N, and S, —C(O)O$(CH_2)_{0-4}$—$C_{6-10}$ aryl, or —C(O)O$(CH_2)_{0-4}$-5- or 6-membered heteroaryl comprising 1-3 heteroatoms selected from O, N, and S, wherein the carbocyclyl, heterocyclyl, aryl, and heteroaryl are optionally substituted with one to five $R^5$.

In another embodiment, each $R^{1k}$ is independently is selected from $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)OC$_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, wherein the alkynyl is optionally substituted with one to three $R^2$. In yet another embodiment, each $R^{1k}$ is independently is selected from —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —C(O)O$(CH_2)_{0-4}$—$C_{3-7}$ carbocyclyl, —C(O)O$(CH_2)_{0-4}$-5- to 7-membered heterocyclyl comprising 1-3 heteroatoms selected from O, N, and S, —C(O)O$(CH_2)_{0-4}$—$C_{6-10}$ aryl, or —C(O)O$(CH_2)_{0-4}$-5- or 6-membered heteroaryl comprising 1-3 heteroatoms selected from O, N, and S, wherein the carbocyclyl, heterocyclyl, aryl, and heteroaryl are optionally substituted with one to five $R^5$ In some embodiments of the formulae above, each $R^2$ is independently $NH_2$, —NH($C_{1-4}$ alkyl), —N($C_1$. 4 alkyl)$_2$, —C(O)$NH_2$, —C(O)NH($C_{1-4}$ alkyl), —C(O)N($C_{1-4}$ alkyl)$_2$, —NHC(O)$R^9$, —N($R^9$)C(O)($R^9$), —NHS$(O)_2R^9$, or —$NR^9S(O)_2R^9$. In another embodiment, each $R^2$ is independently $NH_2$, —NH($C_{1-6}$ alkyl), —N($C_{1-6}$ alkyl)$_2$, —C(O)$NH_2$, —C(O)NH($C_{1-6}$ alkyl), —C(O)N($C_{1-6}$ alkyl)$_2$, —NHC(O)$R^9$, —N($R^9$)C(O)($R^9$), or —NHS$(O)_2R^9$. In yet another embodiment, each $R^2$ is independently $NH_2$, —NH($C_{1-6}$ alkyl), —N($C_{1-6}$ alkyl)$_2$, —C(O)$NH_2$, —C(O)NH($C_{1-6}$ alkyl), —C(O)N($C_{1-6}$ alkyl)$_2$, —NHC(O)$R^9$, —N($R^9$)C(O)($R^9$), or —$NR^9S(O)_2R^9$. In another embodiment, each $R^2$ is independently $NH_2$, —NH($C_{1-6}$ alkyl), —N($C_{1-6}$ alkyl)$_2$, —C(O)$NH_2$, —C(O)NH($C_{1-6}$ alkyl), —C(O)N($C_{1-6}$ alkyl)$_2$, —NHC(O)$R^9$, —NHS$(O)_2R^9$, or —$NR^9S(O)_2R^9$. In yet another embodiment, each $R^2$ is independently $NH_2$, —NH($C_{1-6}$ alkyl), —N($C_{1-6}$ alkyl)$_2$, —C(O)$NH_2$, —C(O)NH($C_{1-6}$ alkyl), —C(O)N($C_{1-6}$ alkyl)$_2$, —N($R^9$)C(O)($R^9$), —NHS$(O)_2R^9$, or —$NR^9S(O)_2R^9$. In another embodiment, each $R^2$ is independently $NH_2$, —NH($C_{1-6}$ alkyl), —N($C_{1-6}$ alkyl)$_2$, —C(O)$NH_2$, —C(O)NH($C_{1-6}$ alkyl), —NHC(O)$R^9$, —N($R^9$)C(O)($R^9$), —NHS$(O)_2R^9$, or —$NR^9S(O)_2R^9$. In another embodiment, each $R^2$ is independently $NH_2$, —NH($C_{1-6}$ alkyl), —N($C_{1-6}$alkyl)$_2$, —C(O)$NH_2$, —C(O)N($C_{1-6}$alkyl)$_2$, —NHC(O)$R^9$, —N($R^9$)C(O)($R^9$), —NHS$(O)_2R^9$, or —$NR^9S(O)_2R^9$.

In another embodiment, each $R^2$ is independently $NH_2$, —NH($C_{1-6}$ alkyl), —N($C_{1-6}$ alkyl)$_2$, —C(O)NH($C_{1-6}$ alkyl), —C(O)N($C_{1-6}$ alkyl)$_2$, —NHC(O)$R^9$, —N($R^9$)C(O)($R^9$), —NHS(O)$_2R^9$, or —N$R^9$S(O)$_2R^9$. In yet another embodiment, each $R^2$ is independently $NH_2$, —NH($C_{1-6}$ alkyl), —C(O)$NH_2$, —C(O)NH($C_{1-6}$ alkyl), —C(O)N($C_{1-6}$ alkyl)$_2$, —NHC(O)$R^9$, —N($R^9$)C(O)($R^9$), —NHS(O)$_2R^9$, or —N$R^9$S(O)$_2R^9$. In another embodiment, each $R^2$ is independently $NH_2$, —N($C_{1-6}$ alkyl)$_2$, —C(O)$NH_2$, —C(O)NH ($C_{1-6}$ alkyl), —C(O)N($C_{1-6}$ alkyl)$_2$, —NHC(O)$R^9$, —N($R^9$) C(O)($R^9$), —NHS(O)$_2R^9$, or —N$R^9$S(O)$_2R^9$. In yet another embodiment, each $R^2$ is independently —NH($C_{1-6}$ alkyl), —N($C_{1-6}$ alkyl)$_2$, —C(O)$NH_2$, —C(O)NH($C_{1-6}$ alkyl), —C(O)N($C_{1-6}$ alkyl)$_2$, —NHC(O)$R^9$, —N($R^9$)C(O)($R^9$), —NHS(O)$_2R^9$, or —N$R^9$S(O)$_2R^9$. In another embodiment, each $R^2$ is independently $NH_2$, —NH($C_{1-6}$ alkyl), —N($C_{1-6}$ alkyl)$_2$, —C(O)$NH_2$, —C(O)NH($C_{1-6}$ alkyl), —C(O)N($C_{1-6}$ alkyl)$_2$, —NHC(O)$R^9$, or —N($R^9$)C(O)($R^9$). In yet another embodiment, each $R^2$ is independently $NH_2$, —NH($C_{1-6}$alkyl), —N($C_{1-6}$ alkyl)$_2$, —C(O)$NH_2$, —C(O) NH($C_{1-6}$ alkyl), —C(O)N($C_{1-6}$ alkyl)$_2$, —NHS(O)$_2R^9$, or —N$R^9$S(O)$_2R^9$. In another embodiment, each $R^2$ is independently $NH_2$, —NH($C_{1-6}$ alkyl), —N($C_{1-6}$ alkyl)$_2$, —C(O) $NH_2$, —NHC(O)$R^9$, —N($R^9$)C(O)($R^9$), —NHS(O)$_2R^9$, or —N$R^9$S(O)$_2R^9$. In yet another embodiment, each $R^2$ is independently $NH_2$, —C(O)$NH_2$, —C(O)NH($C_{1-6}$ alkyl), —C(O)N($C_{1-6}$ alkyl)$_2$, —NHC(O)$R^9$, —N($R^9$)C(O)($R^9$), —NHS(O)$_2R^9$, or —N$R^9$S(O)$_2R^9$.

In some embodiments of the formulae above, $R^3$ is H or $C_{1-3}$ alkyl. In another embodiment, $R^3$ is $C_{1-6}$ alkyl. In yet another embodiment, $R^3$ is H or $C_{2-6}$ alkyl. In another embodiment, $R^3$ is H or $C_{3-6}$ alkyl. In yet another embodiment, $R^3$ is H, methyl, ethyl, n-propyl, or i-propyl. In another embodiment, $R^3$ is H, ethyl, n-propyl, or i-propyl. In yet another embodiment, $R^3$ is H, n-propyl, or i-propyl. In another embodiment, $R^3$ is H, methyl, or ethyl. In yet another embodiment, $R^3$ is H or methyl. In another embodiment, $R^3$ is H.

In some embodiments of the formulae above, $R^4$ is H or $C_{1-3}$ alkyl. In another embodiment, $R^4$ is $C_{1-6}$ alkyl. In yet another embodiment, $R^4$ is H or $C_{2-6}$ alkyl. In another embodiment, $R^4$ is H or $C_{3-6}$ alkyl.

In yet another embodiment, $R^4$ is H, methyl, ethyl, n-propyl, or i-propyl. In another embodiment, $R^4$ is H, ethyl, n-propyl, or i-propyl. In yet another embodiment, $R^4$ is H, n-propyl, or i-propyl. In another embodiment, $R^4$ is H, methyl, or ethyl. In yet another embodiment, $R^4$ is H or methyl. In another embodiment, $R^4$ is H.

In some embodiments of the formulae above, each $R^5$ is independently $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, —OH, —C(O)H, —C(O)($C_{1-6}$ alkyl), —C(O)($C_{6-10}$ aryl), —C(O) (5- or 6-membered heteroaryl), —C(O)($C_{3-7}$ carbocyclyl), —C(O)(5- to 7-membered heterocyclyl), —($CH_2$)$_{0-3}$C(O) O$C_{1-6}$ alkyl, —C(O)$NH_2$, —C(O)NH($C_{1-6}$ alkyl), —C(O)N ($C_{1-6}$ alkyl)$_2$, —NHC(O)$R^9$, —N($R^9$)C(O)($R^9$), —$NH_2$, —NH($C_{1-6}$ alkyl), —N($C_{1-6}$ alkyl)$_2$, —NHC(O)O($R^9$), —N($R^9$)C(O)O($R^9$), —NHS(O)$_2R^9$, —N$R^9$S(O)$_2R^9$, —S(O)$_q$NH$R^9$, —S(O)$_q$N($R^9$)$_2$, —S(O)$_qR^9$, $C_{1-6}$ hydroxyalkyl, —O($CH_2$)$_{1-3}$CN, —($CH_2$)$_{0-6}$—$C_{3-7}$ carbocyclyl, CN, —O($CH_2$)$_{0-3}$($C_6$-$C_{10}$)aryl, adamantyl, —O($CH_2$)$_{0-3}$-5- or 6-membered heteroaryl comprising 1-3 heteroatoms selected from O, N, and S, —($CH_2$)$_{0-6}$-5- to 7-membered heterocyclyl comprising 1-3 heteroatoms selected from O, N, and S, —($CH_2$)$_{0-6}$—$C_{6-10}$ aryl, and —($CH_2$)$_{0-6}$-5- or 6-membered heteroaryl comprising 1-3 heteroatoms selected from O, N, and S, wherein the alkyl is optionally substituted with one to three $R^6$, and the carbocyclyl, heterocyclyl, aryl, and heteroaryl are optionally substituted with one to four $R^8$; or two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$; or two $R^5$ when on adjacent atoms, together with the atoms to which they are attached form a $C_{6-10}$ aryl or a 5- or 6-membered heteroaryl comprising 1-3 heteroatoms selected from O, N, and S; or two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$; or two $R^5$ when on the same carbon atom form ═(O);

In another embodiment, each $R^5$ is independently $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, —OH, —C(O)H, —C(O)($C_{1-6}$ alkyl), —C(O)($C_{6-10}$ aryl), —C(O)(5- or 6-membered heteroaryl), —C(O)($C_{3-7}$ carbocyclyl), —C(O)(5- to 7-membered heterocyclyl)-($CH_2$)$_{0-3}$C(O)O$C_{1-6}$ alkyl, —C(O)$NH_2$, —C(O)NH($C_{1-6}$ alkyl), —C(O)N($C_{1-6}$ alkyl)$_2$, —NHC(O) $R^9$, —N($R^9$)C(O)($R^9$), —$NH_2$, —NH($C_{1-6}$ alkyl), —N($C_{1-6}$ alkyl)$_2$, —NHC(O)O($R^9$), —N($R^9$)C(O)O($R^9$), —NHS(O)$_2R^9$, —N$R^9$S(O)$_2R^9$, —S(O)$_q$NH$R^9$, —S(O)$_q$N ($R^9$)$_2$, —S(O)$_qR^9$, $C_{1-6}$ hydroxyalkyl, —O($CH_2$)$_{1-3}$CN, CN, —O($CH_2$)$_{0-6}$—$C_{3-7}$ carbocyclyl, —O($CH_2$)$_{0-6}$-5- to 7-membered heterocyclyl comprising 1-3 heteroatoms selected from O, N, and S, —O($CH_2$)$_{0-3}$($C_6$-$C_{10}$)aryl, adamantyl, —O($CH_2$)$_{0-3}$-5- or 6-membered heteroaryl comprising 1-3 heteroatoms selected from O, N, and S, —($CH_2$)$_{0-6}$—$C_{3-7}$ carbocyclyl, —($CH_2$)$_{0-6}$-5- to 7-membered heterocyclyl comprising 1-3 heteroatoms selected from O, N, and S, —($CH_2$)$_{0-6}$—$C_{6-10}$ aryl, and —($CH_2$)$_{0-6}$-5- or 6-membered heteroaryl comprising 1-3 heteroatoms selected from O, N, and S, wherein the alkyl is optionally substituted with one to three $R^6$, and the carbocyclyl, heterocyclyl, aryl, and heteroaryl are optionally substituted with one to four $R^8$; or two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$; or two $R^5$ when on adjacent atoms, together with the atoms to which they are attached form a $C_{6-10}$ aryl or a 5- or 6-membered heteroaryl comprising 1-3 heteroatoms selected from O, N, and S; or two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$; or two $R^5$ when on the same carbon atom form ═(O).

In another embodiment, each $R^5$ is independently $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, —OH, —C(O)H, —C(O)($C_{1-6}$ alkyl), —C(O)($C_{6-10}$ aryl), —C(O)(5- or 6-membered heteroaryl), —C(O)($C_{3-7}$ carbocyclyl), —C(O)(5- to 7-membered heterocyclyl)-($CH_2$)$_{0-3}$C(O)O$C_{1-6}$ alkyl, —C(O)$NH_2$, —C(O)NH($C_{1-6}$ alkyl), —C(O)N($C_{1-6}$ alkyl)$_2$, —NHC(O) $R^9$, —N($R^9$)C(O)($R^9$), —$NH_2$, —NH($C_{1-6}$ alkyl), —N($C_{1-6}$ alkyl)$_2$, —NHC(O)O($R^9$), —N($R^9$)C(O)O($R^9$), —NHS(O)$_2R^9$, —N$R^9$S(O)$_2R^9$, —S(O)$_q$NH$R^9$, —S(O)$_q$N ($R^9$)$_2$, —S(O)$_qR^9$, $C_{1-6}$ hydroxyalkyl, —O($CH_2$)$_{1-3}$CN, CN, —O($CH_2$)$_{0-6}$—$C_{3-7}$ carbocyclyl, —O($CH_2$)$_{0-6}$-5- to 7-membered heterocyclyl comprising 1-3 heteroatoms selected from O, N, and S, —$O(CH_2)_{0-3}(C_6-C_{10})$aryl, adamantyl, —$O(CH_2)_{0-3}$-5- or 6-membered heteroaryl comprising 1-3 heteroatoms selected from O, N, and S, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$—$C_{6-10}$ aryl, and —$(CH_2)_{0-6}$-5- or 6-membered heteroaryl comprising 1-3 heteroatoms selected from O, N, and S, wherein the alkyl is optionally substituted with one to three $R^6$, and the carbocyclyl, heterocyclyl, aryl, and heteroaryl are optionally substituted with one to four $R^8$.

In another embodiment, two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$; or two $R^5$ when on adjacent atoms, together with the atoms to which they are attached form a $C_{6-10}$ aryl or a 5- or 6-membered heteroaryl comprising 1-3 heteroatoms selected from O, N, and S; or two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$; or two $R^5$ when on the same carbon atom form ═(O).

In another embodiment, two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$. In yet another embodiment, two $R^5$ when on adjacent atoms, together with the atoms to which they are attached form a $C_{6-10}$ aryl or a 5- or 6-membered heteroaryl comprising 1-3 heteroatoms selected from O, N, and S. In another embodiment, two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$. In yet another embodiment, two $R^5$ when on the same carbon atom form ═(O).

In another embodiment, each $R^5$ is independently $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, —OH, —C(O)H, —$C(O)(C_{1-6}$ alkyl), —$C(O)(C_{6-10}$ aryl), —C(O)(5- or 6-membered heteroaryl), —$C(O)(C_{3-7}$ carbocyclyl), —C(O)(5- to 7-membered heterocyclyl)-$(CH_2)_{0-3}C(O)OC_{1-6}$ alkyl, —$C(O)NH_2$, —$C(O)NH(C_{1-6}$ alkyl), —$C(O)N(C_{1-6}$ alkyl$)_2$, —NHC(O)$R^9$, —$N(R^9)C(O)(R^9)$, —$NH_2$, —$NH(C_{1-6}$ alkyl), —$N(C_{1-6}$ alkyl$)_2$, —$NHC(O)O(R^9)$, —$N(R^9)C(O)O(R^9)$, —$NHS(O)_2R^9$, —$NR^9S(O)_2R^9$, —$S(O)_qNHR^9$, —$S(O)_qN(R^9)_2$, —$S(O)_qR^9$, $C_{1-6}$ hydroxyalkyl, —$O(CH_2)_{1-3}CN$, wherein the alkyl is optionally substituted with one to three $R^6$, and the carbocyclyl, heterocyclyl, aryl and heteroaryl ire optionally substituted with one to four $R^8$; or two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$; or two $R^5$ when on adjacent atoms, together with the atoms to which they are attached form a $C_{6-10}$ aryl or a 5- or 6-membered heteroaryl comprising 1-3 heteroatoms selected from O, N, and S; or two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$; or two $R^5$ when on the same carbon atom form ═(O).

In another embodiment, each $R^5$ is independently —$O(CH_2)_{0-6}$—$C_{3-7}$ carbocyclyl, —$O(CH_2)_{0-6}$-5- to 7-membered heterocyclyl comprising 1-3 heteroatoms selected from O, N, and S, —$O(CH_2)_{0-3}(C_6-C_{10})$aryl, adamantyl, —$O(CH_2)_{0-3}$-5- or 6-membered heteroaryl comprising 1-3 heteroatoms selected from O, N, and S, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$—$C_{6-10}$ aryl, and —$(CH_2)_{0-6}$-5- or 6-membered heteroaryl comprising 1-3 heteroatoms selected from O, N, and S, wherein the carbocyclyl, heterocyclyl, aryl, and heteroaryl are optionally substituted with one to four $R^8$; or two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$; or two $R^5$ when on adjacent atoms, together with the atoms to which they are attached form a $C_{6-10}$ aryl or a 5- or 6-membered heteroaryl comprising 1-3 heteroatoms selected from O, N, and S; or two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$; or two $R^5$ when on the same carbon atom form ═(O).

In some embodiments of the formulae above, $R^6$ is —$NH_2$, —$NH(C_{1-4}$ alkyl), —$N(C_{1-4}$ alkyl$)_2$, $C_{6-10}$ aryl, or a 5- or 6-membered heteroaryl comprising 1-3 heteroatoms selected from O, N, and S, wherein the aryl and heteroaryl are optionally substituted with one to three $R^7$. In another embodiment, $R^6$ is —$NH_2$, —$NH(C_{1-6}$ alkyl), or —$N(C_{1-6}$ alkyl$)_2$. In another embodiment, $R^6$ is $C_{6-10}$ aryl or a 5- or 6-membered heteroaryl comprising 1-3 heteroatoms selected from O, N, and S, wherein the aryl and heteroaryl are optionally substituted with one to three $R^7$. In yet another embodiment, $R^6$ is —$NH_2$, —$NH(C_{1-6}$ alkyl), —$N(C_{1-6}$ alkyl$)_2$phenyl, or a 5- or 6-membered heteroaryl comprising 1-3 heteroatoms selected from O, N, and S, wherein the aryl and heteroaryl are optionally substituted with one to three $R^7$. In another embodiment, $R^6$ is —$NH_2$, —$NH(C_{1-6}$ alkyl), —$N(C_{1-6}$ alkyl$)_2$, $C_{6-10}$ aryl, or a 5-membered heteroaryl comprising 1-3 heteroatoms selected from O, N, and S, wherein the aryl and heteroaryl are optionally substituted with one to three $R^7$.

In yet another embodiment, $R^6$ is —$NH_2$, —$NH(C_{1-6}$ alkyl), —$N(C_{1-6}$ alkyl$)_2$, $C_{6-10}$ aryl, or a 6-membered heteroaryl comprising 1-3 heteroatoms selected from O, N, and S, wherein the aryl and heteroaryl are optionally substituted with one to three $R^7$. In another embodiment, $R^6$ is —$NH_2$, —$NH(C_{1-6}$ alkyl), —$N(C_{1-6}$ alkyl$)_2$, phenyl, or a 5-membered heteroaryl comprising 1-3 heteroatoms selected from O, N, and S, wherein the phenyl and heteroaryl are optionally substituted with one to three $R^7$.

In another embodiment, $R^6$ is —$NH_2$, —$NH(C_{1-6}$ alkyl), —$N(C_{1-6}$ alkyl$)_2$, phenyl, or a 6-membered heteroaryl comprising 1-3 heteroatoms selected from O, N, and S, wherein the phenyl and heteroaryl are optionally substituted with one to three $R^7$. In yet another embodiment, $R^6$ is —$NH_2$, —$NH(C_{1-6}$ alkyl), —$N(C_{1-6}$ alkyl$)_2$, or $C_{6-10}$ aryl optionally substituted with one to three $R^7$. In another embodiment, $R^6$ is —$NH_2$, —$NH(C_{1-6}$ alkyl), —$N(C_{1-6}$ alkyl$)_2$, 5- or 6-membered heteroaryl comprising 1-3 heteroatoms selected from O, N, and S optionally substituted with one to three $R^7$. In another embodiment, $R^6$ is —$NH_2$, —$NH(C_{1-6}$ alkyl), —$N(C_{1-6}$ alkyl$)_2$, or phenyl optionally substituted with one to three $R^7$. In yet another embodiment, $R^6$ is —$NH_2$, —$NH(C_{1-6}$ alkyl), —$N(C_{1-6}$ alkyl$)_2$, 5-membered heteroaryl optionally substituted with one to three $R^7$. In another embodiment, $R^6$ is —$NH_2$, —$NH(C_{1-6}$ alkyl), —$N(C_{1-6}$ alkyl$)_2$, 6-membered heteroaryl optionally substituted with one to three $R^7$.

In some embodiments of the formulae above, each $R^7$ is independently $C_{1-4}$ alkyl, $C_{1-4}$ haloalkyl, $C_{1-4}$ alkoxy, $C_{1-4}$ haloalkoxy, halogen, or $C_{6-10}$ aryl. In another embodiment, each $R^7$ is independently $C_{1-6}$ alkyl, $C_{1-6}$ haloalkyl, $C_{1-6}$ alkoxy, $C_{1-3}$ haloalkoxy, halogen, or phenyl. In yet another embodiment, each $R^7$ is independently $C_{1-6}$ alkyl, $C_{1-6}$ haloalkyl, $C_{1-6}$ alkoxy, $C_{1-3}$ haloalkoxy, or halogen. In another embodiment, each $R^7$ is independently $C_{1-6}$ alkyl, $C_{1-6}$ haloalkyl, $C_{1-6}$ alkoxy, $C_{1-3}$ haloalkoxy, or $C_{6-10}$ aryl. In yet another embodiment, each $R^7$ is independently $C_{1-6}$ alkyl, $C_{1-6}$ haloalkyl, $C_{1-6}$ alkoxy, halogen, or $C_{6-10}$ aryl. In another embodiment, each $R^7$ is independently $C_{1-6}$ alkyl, $C_{1-6}$ haloalkyl, $C_{1-3}$ haloalkoxy, halogen, or $C_{6-10}$ aryl. In yet another embodiment, each $R^7$ is independently $C_{1-6}$ alkyl, $C_{1-6}$ alkoxy, $C_{1-3}$ haloalkoxy, halogen, or $C_{6-10}$ aryl. In another embodiment, each $R^7$ is independently $C_{1-6}$ haloalkyl, $C_{1-6}$ alkoxy, $C_{1-3}$ haloalkoxy, halogen, or $C_{6-10}$ aryl. In yet another embodiment, each $R^7$ is independently $C_{1-6}$ alkyl, $C_{1-6}$ haloalkyl, halogen, or $C_{6-10}$ aryl. In another embodiment, each $R^7$ is independently $C_{1-6}$ alkoxy, $C_{1-3}$ haloalkoxy, halogen, or $C_{6-10}$ aryl. In yet another embodiment, each $R^7$ is independently $C_{1-6}$ alkyl, $C_{1-6}$ alkoxy, halogen, or $C_{6-10}$ aryl. In another embodiment, each $R^7$ is independently $C_{1-6}$ alkyl, $C_{1-6}$ alkoxy, $C_{1-3}$ or $C_{6-10}$ aryl. In yet another embodiment, each $R^7$ is independently $C_{1-4}$ alkyl, $C_{1-4}$ haloalkyl, $C_{1-4}$ alkoxy, $C_{1-4}$ haloalkoxy, halogen, or phenyl.

In some embodiments of the formulae above, each $R^8$ is independently $C_{1-3}$ alkyl, $C_{1-3}$ haloalkyl, $C_{1-3}$ alkoxy, $C_{1-3}$ haloalkoxy, halogen, or —OH. In another embodiment, each $R^8$ is independently $C_{1-6}$ alkyl, $C_{1-6}$ haloalkyl, $C_{1-6}$ alkoxy, $C_{1-6}$ haloalkoxy, or halogen. In yet another embodiment, each $R^8$ is independently $C_{1-6}$ alkyl, $C_{1-6}$ haloalkyl, $C_{1-6}$ alkoxy, $C_{1-6}$ haloalkoxy, or —OH. In another embodiment, each $R^8$ is independently $C_{1-6}$ alkyl, $C_{1-6}$ haloalkyl, $C_{1-6}$ alkoxy, halogen, or —OH. In yet another embodiment, each $R^8$ is independently $C_{1-6}$ alkyl, $C_{1-6}$ haloalkyl, $C_{1-6}$ haloalkoxy, halogen, or —OH. In another embodiment, each $R^8$ is independently $C_{1-6}$ alkyl, $C_{1-6}$ alkoxy, $C_{1-6}$ haloalkoxy, halogen, or —OH. In yet another embodiment, each $R^8$ is independently $C_{1-6}$ haloalkyl, $C_{1-6}$ alkoxy, $C_{1-6}$ haloalkoxy, halogen, or —OH.

In another embodiment, each $R^8$ is independently $C_{1-6}$ alkyl, $C_{1-6}$ haloalkyl, halogen, or —OH. In yet another embodiment, each $R^8$ is independently $C_{1-6}$ alkoxy, $C_{1-6}$ haloalkoxy, halogen, or —OH. In another embodiment, each $R^8$ is independently $C_{1-6}$ alkyl, $C_{1-6}$ alkoxy, halogen, or —OH. In yet another embodiment, each $R^8$ is independently halogen, or —OH. In another embodiment, each $R^8$ is independently $C_{1-6}$ alkyl, $C_{1-6}$ haloalkyl, or halogen.

In some embodiments of the formulae above, $R^9$ is $C_{1-4}$ alkyl, $C_{1-4}$ haloalkyl, 5- to 7-membered heterocyclyl comprising 1-3 heteroatoms selected from O, N, and S, $C_{6-10}$ aryl, or a 5- or 6-membered heteroaryl comprising 1-3 heteroatoms selected from O, N, and S, wherein the aryl and heteroaryl are optionally substituted with one to three $R^{11}$. In another embodiment, $R^9$ is $C_{1-6}$ alkyl, $C_{1-6}$ haloalkyl, 5- to 7-membered heterocyclyl comprising 1-3 heteroatoms selected from O, N, and S, phenyl, or a 5- or 6-membered heteroaryl comprising 1-3 heteroatoms selected from O, N, and S, wherein the phenyl and heteroaryl are optionally substituted with one to three $R^{11}$. In another embodiment, $R^9$ is $C_{1-6}$ alkyl, or $C_{1-6}$ haloalkyl. In yet another embodiment, $R^9$ is 5- to 7-membered heterocyclyl comprising 1-3 heteroatoms selected from O, N, and S, $C_{6-10}$ aryl, or a 5- or 6-membered heteroaryl comprising 1-3 heteroatoms selected from O, N, and S, wherein the aryl and heteroaryl are optionally substituted with one to three $R^{11}$. In another embodiment, $R^9$ is $C_{1-6}$ alkyl, $C_{1-6}$ haloalkyl, $C_{6-10}$ aryl, or a 5- or 6-membered heteroaryl comprising 1-3 heteroatoms selected from O, N, and S, wherein the aryl and heteroaryl are optionally substituted with one to three $R^9$. In yet another embodiment, $R^9$ is $C_{1-6}$ alkyl, $C_{1-6}$ haloalkyl, 5- to 7-membered heterocyclyl comprising 1-3 heteroatoms selected from O, N, and S, or a 5- or 6-membered heteroaryl comprising 1-3 heteroatoms selected from O, N, and S, wherein the heteroaryl is optionally substituted with one to three $R^{11}$. In another embodiment, $R^9$ is $C_{1-6}$ alkyl, $C_{1-6}$ haloalkyl, 5- to 7-membered heterocyclyl comprising 1-3 heteroatoms selected from O, N, and S, or a 5- or 6-membered heteroaryl, wherein the heteroaryl is optionally substituted with one to three $R^{11}$.

In another embodiment, $R^9$ is $C_{1-6}$ alkyl, $C_{1-6}$ haloalkyl, 5- to 7-membered heterocyclyl comprising 1-3 heteroatoms selected from O, N, and S, phenyl, or a 5- or 6-membered heteroaryl comprising 1-3 heteroatoms selected from O, N, and S, wherein the phenyl and heteroaryl are optionally substituted with one to three $R^{11}$. In yet another embodiment, $R^9$ is $C_{1-6}$ alkyl, $C_{1-6}$ haloalkyl, 5- to 7-membered heterocyclyl comprising 1-3 heteroatoms selected from O, N, and S, phenyl, or a 6-membered heteroaryl comprising 1-3 heteroatoms selected from O, N, and S, wherein the aryl and heteroaryl are optionally substituted with one to three $R^{11}$. In another embodiment, $R^9$ is $C_{1-6}$ alkyl, $C_{1-6}$ haloalkyl, 5- to 7-membered heterocyclyl comprising 1-3 heteroatoms selected from O, N, and S, phenyl, or a 5-membered heteroaryl comprising 1-3 heteroatoms selected from O, N, and S, wherein the phenyl and heteroaryl are optionally substituted with one to three $R^{11}$. In yet another embodiment, $R^9$ is $C_{1-6}$ alkyl, $C_{1-6}$ haloalkyl, 5- or 6-membered heterocyclyl comprising 1-3 heteroatoms selected from O, N, and S, phenyl, or a 5- or 6-membered heteroaryl comprising 1-3 heteroatoms selected from O, N, and S, wherein the phenyl and heteroaryl are optionally substituted with one to three $R^{11}$. In another embodiment, $R^9$ is $C_{1-6}$ alkyl, $C_{1-6}$ haloalkyl, 6- or 7-membered heterocyclyl comprising 1-3 heteroatoms selected from O, N, and S, phenyl, or a 5- or 6-membered heteroaryl comprising 1-3 heteroatoms selected from O, N, and S, wherein the phenyl and heteroaryl are optionally substituted with one to three $R^{11}$. In yet another embodiment, $R^9$ is $C_{1-6}$ alkyl, $C_{1-6}$ haloalkyl, 5- to 7-membered heterocyclyl comprising 1-3 heteroatoms selected from O, N, and S, phenyl, or a 5- or 6-membered heteroaryl comprising 1-3 heteroatoms selected from O, N, and S, wherein the aryl and heteroaryl are optionally substituted with one to three $R^{11}$. In another embodiment, $R^9$ is $C_{1-6}$ alkyl, $C_{1-6}$ haloalkyl, or 5- to 7-membered heterocyclyl comprising 1-3 heteroatoms selected from O, N, and S. In yet another embodiment, $R^9$ is $C_{1-6}$ alkyl, $C_{1-6}$ haloalkyl, or phenyl optionally substituted with one to three $R^{11}$. In another embodiment, $R^9$ is $C_{1-6}$ alkyl, $C_{1-6}$ haloalkyl, or a 5- or 6-membered heteroaryl comprising 1-3 heteroatoms selected from O, N, and S, wherein the heteroaryl is optionally substituted with one to three $R^{11}$.

In some embodiments of the formulae above, each $R^1$ is $C_{1-6}$ alkyl, $C_{1-4}$ haloalkyl, $C_{1-4}$ alkoxy, $C_{1-4}$ haloalkoxy, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S. In another embodiment, each $R^{10}$ is $C_{1-6}$ alkyl, $C_{1-6}$ haloalkyl, $C_{1-6}$ alkoxy, $C_{1-3}$ haloalkoxy, or halogen. In yet another embodiment, each $R^{10}$ is $C_{1-6}$ alkyl, $C_{1-6}$ haloalkyl, $C_{1-6}$ alkoxy, or $C_{1-6}$ haloalkoxy; or two $R^{10}$, when on adjacent atoms, together with the atoms to which they are attached form a $C_{6-10}$ aryl or a 5- or 6-membered heteroaryl comprising 1-3 heteroatoms selected from O, N, and S. In another embodiment, each $R^{10}$ is $C_{1-6}$ alkyl, $C_{1-6}$ haloalkyl, $C_{1-6}$ haloalkoxy, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S. In yet another embodiment, each $R^{10}$ is $C_{1-6}$ alkyl, $C_{1-6}$ alkoxy, $C_{1-6}$ haloalkoxy, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S.

In another embodiment, each $R^{10}$ is $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S. In yet another embodiment, each $R^{10}$ is $C_{1-6}$ alkyl, $C_{1-6}$ haloalkyl, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S. In another embodiment, each $R^{10}$ is $C_{1-6}$ alkoxy, $C_{1-6}$ haloalkoxy, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S. In yet another embodiment, each $R^{10}$ is $C_{1-6}$ alkyl, $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a phenyl or a 5- or 6-membered heteroaryl comprising 1-3 heteroatoms selected from O, N, and S.

In another embodiment, each $R^{10}$ is $C_{1-6}$ alkyl, $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a $C_{6-10}$ aryl or a 5-membered heteroaryl comprising 1-3 heteroatoms selected from O, N, and S. In yet another embodiment, each $R^{10}$ is $C_{1-6}$ alkyl, $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a $C_{6-10}$ aryl or a 6-membered heteroaryl comprising 1-3 heteroatoms selected from O, N, and S. In another embodiment, each $R^{10}$ is $C_{1-6}$ alkyl, $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a phenyl or a 5-membered heteroaryl comprising 1-3 heteroatoms selected from O, N, and S. In another embodiment, each $R^{10}$ is $C_{1-6}$ alkyl, $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a phenyl or a 6-membered heteroaryl comprising 1-3 heteroatoms selected from O, N, and S. In yet another embodiment, two $R^{10}$, when on adjacent atoms, together with the atoms to which they are attached form a $C_{6-10}$ aryl or a 5- or 6-membered heteroaryl comprising 1-3 heteroatoms selected from O, N, and S. In another embodiment, two $R^{10}$, when on adjacent atoms, together with the atoms to which they are attached form a phenyl or a 5- or 6-membered heteroaryl comprising 1-3 heteroatoms selected from O, N, and S. In yet another embodiment, two $R^{10}$, when on adjacent atoms, together with the atoms to which they are attached form a $C_{6-10}$ aryl. In another embodiment, two $R^{10}$, when on adjacent atoms, together with the atoms to which they are attached form a 5- or 6-membered heteroaryl comprising 1-3 heteroatoms selected from O, N, and S.

In some embodiments of the formulae above, each $R^{11}$ is independently $C_{1-4}$ alkyl, $C_{1-4}$ haloalkyl, $C_{1-4}$ alkoxy, $C_{1-4}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$. In another embodiment, each $R^{11}$ is independently $C_{1-6}$ alkyl, $C_{1-6}$ haloalkyl, $C_{1-6}$ alkoxy, $C_{1-4}$ haloalkoxy, —NHC(O)($C_{1-6}$ alkyl), or —N($C_{1-6}$ alkyl)C(O)($C_{1-6}$ alkyl); or two $R^{11}$, when on adjacent atoms, together with the atoms to which they are attached form a $C_6$. 10 aryl or a 5- or 6-membered heteroaryl comprising 1-3 heteroatoms selected from O, N, and S, wherein the aryl and heteroaryl are optionally substituted with one to three $R^{12}$. In yet another embodiment, each $R^{11}$ is independently $C_{1-6}$ alkyl, $C_{1-6}$ haloalkyl, $C_{1-6}$ alkoxy, $C_{1-4}$ haloalkoxy, —NHC(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$. In another embodiment, each $R^{11}$ is independently $C_{1-6}$ alkyl, $C_{1-6}$ haloalkyl, $C_{1-6}$ alkoxy, $C_{1-4}$ haloalkoxy, —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$.

In another embodiment, each $R^{11}$ is independently $C_{1-6}$ alkyl, $C_{1-6}$ haloalkyl, $C_{1-6}$ alkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$. In yet another embodiment, each $R^{11}$ is independently $C_{1-6}$ alkyl, $C_{1-6}$ haloalkyl, $C_{1-4}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$. In another embodiment, each $R^{11}$ is independently $C_{1-6}$ alkyl, $C_{1-6}$ alkoxy, $C_{1-4}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$.

In another embodiment, each $R^{11}$ is independently $C_{1-6}$ haloalkyl, $C_{1-6}$ alkoxy, $C_{1-4}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$. In yet another embodiment, each $R^{11}$ is independently $C_{1-6}$ alkyl, $C_{1-6}$ haloalkyl, $C_{1-6}$ alkoxy, $C_{1-4}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$. In another embodiment, each $R^{11}$ is independently $C_{1-6}$ alkyl, $C_{1-6}$ haloalkyl, $C_{1-6}$ alkoxy, $C_{1-4}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$.

In another embodiment, each $R^{11}$ is independently $C_{1-6}$ alkyl, $C_{1-6}$ haloalkyl, $C_{1-6}$ alkoxy, $C_{1-4}$ haloalkoxy, —NHC(O)($C_{1-6}$ alkyl), —N($C_{1-6}$ alkyl)C(O)($C_{1-6}$ alkyl), or halogen. In yet another embodiment, each $R^{11}$ is independently $C_{1-6}$ alkyl, $C_{1-6}$ haloalkyl, $C_{1-6}$ alkoxy, $C_{1-4}$ haloalkoxy, or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$. In another embodiment, each $R^{11}$ is independently $C_{1-6}$ alkyl, $C_{1-6}$ haloalkyl, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$. In yet another embodiment, each $R^{11}$ is independently $C_{1-6}$ alkoxy, $C_{1-4}$ haloalkoxy, —NHC(O)($C_{1-6}$alkyl), —N($C_{1-6}$alkyl)C(O)($C_{1-6}$alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$.

In another embodiment, each $R^{11}$ is independently $C_{1-6}$ alkyl, $C_{1-6}$ haloalkyl, $C_{1-6}$ alkoxy, $C_{1-4}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a phenyl or a 5- or 6-membered heteroaryl comprising 1-3 heteroatoms selected from O, N, and S, wherein the phenyl and heteroaryl are optionally substituted with one to three $R^{12}$. In yet another embodiment, each $R^{11}$ is independently $C_{1-6}$ alkyl, $C_{1-6}$ haloalkyl, $C_{1-6}$ alkoxy, $C_{1-4}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a phenyl or a 5-membered heteroaryl comprising 1-3 heteroatoms selected from O, N, and S, wherein the phenyl and heteroaryl are optionally substituted with one to three $R^{12}$. In another embodiment, each $R^{11}$ is independently $C_{1-6}$ alkyl, $C_{1-6}$ haloalkyl, $C_{1-6}$ alkoxy, $C_{1-4}$ haloalkoxy, —NHC(O)($C_{1-6}$ alkyl), —N($C_{1-6}$ alkyl)C(O)($C_{1-6}$ alkyl), or halogen; or two $R^{11}$, when on adjacent atoms, together with the atoms to which they are attached form a phenyl or a 6-membered heteroaryl comprising 1-3 heteroatoms selected from O, N, and S, wherein the phenyl and heteroaryl are optionally substituted with one to three $R^{12}$. In yet another embodiment, two $R^{11}$, when on adjacent atoms, together with the atoms to which they are attached form a phenyl or a 5- or 6-membered heteroaryl comprising 1-3 heteroatoms selected from O, N, and S, wherein the phenyl and heteroaryl are optionally substituted with one to three $R^{12}$. In another embodiment, two $R^{11}$, when on adjacent atoms, together with the atoms to which they are attached form a phenyl optionally substituted with one to three $R^{12}$. In another embodiment, two $R^{11}$, when on adjacent atoms, together with the atoms to which they are attached form a 5- or 6-membered heteroaryl comprising 1-3 heteroatoms selected from O, N, and S and optionally substituted with one to three $R^{12}$.

In some embodiments of the formulae above, each $R^{12}$ is independently $C_{1-3}$ alkyl, $C_{1-3}$ haloalkyl, $C_{1-3}$ alkoxy, or $C_{1-3}$ haloalkoxy. In another embodiment, each $R^{12}$ is independently $C_{1-6}$ alkyl, $C_{1-6}$ haloalkyl, or $C_{1-6}$ alkoxy. In yet another embodiment, each $R^{12}$ is independently $C_{1-6}$ alkyl, $C_{1-6}$ haloalkyl, or $C_{1-3}$ haloalkoxy. In another embodiment, each $R^{12}$ is independently $C_{1-6}$ alkyl, $C_{1-6}$ alkoxy, or $C_{1-3}$ haloalkoxy.

In yet another embodiment, each $R^{12}$ is independently $C_{1-6}$ haloalkyl, $C_{1-6}$ alkoxy, or $C_{1-3}$ haloalkoxy. In another embodiment, each $R^{12}$ is independently $C_{1-6}$ alkyl or $C_{1-6}$ haloalkyl. In yet another embodiment, each $R^{12}$ is independently $C_{1-6}$ alkyl or $C_{1-6}$ alkoxy. In another embodiment, each $R^{12}$ is independently $C_{1-6}$ alkyl or $C_{1-3}$ haloalkoxy. In yet another embodiment, each $R^{12}$ is independently $C_{1-6}$ haloalkyl or $C_{1-6}$ alkoxy. In another embodiment, each $R^{12}$ is independently $C_{1-6}$ haloalkyl or $C_{1-3}$ haloalkoxy. In yet another embodiment, each $R^{12}$ is independently $C_{1-6}$ alkoxy, or $C_{1-3}$ haloalkoxy. In another embodiment, each $R^{12}$ is independently $C_{1-6}$ alkyl. In yet another embodiment, each $R^{12}$ is independently $C_{1-6}$ haloalkyl. In another embodiment, each $R^{12}$ is independently $C_{1-3}$ haloalkoxy. In yet another embodiment, each $R^{12}$ is independently $C_{1-6}$ alkoxy.

In some embodiments of the formulae above, $R^{13}$ is independently at each occurrence $C_{1-4}$ alkyl, $C_{1-4}$ haloalkyl, $C_{6-10}$ aryl, or a 5- or 6-membered heteroaryl comprising 1-3 heteroatoms selected from O, N, and S, wherein the alkyl is optionally substituted with one to two $C_{1-6}$ alkoxy and the aryl and heteroaryl are optionally substituted with one to three $R^{14}$. In another embodiment, $R^{13}$ is independently at each occurrence $C_{1-6}$ alkyl or $C_{1-6}$ haloalkyl, wherein the alkyl is optionally substituted with one to two $C_{1-6}$ alkoxy. In yet another embodiment, $R^{13}$ is independently at each occurrence $C_{6-10}$ aryl or a 5- or 6-membered heteroaryl comprising 1-3 heteroatoms selected from O, N, and S, wherein the aryl and heteroaryl are optionally substituted with one to three $R^{14}$. In another embodiment, $R^{13}$ is independently at each occurrence $C_{1-6}$ alkyl, $C_{1-6}$ haloalkyl, phenyl, or a 5- or 6-membered heteroaryl comprising 1-3 heteroatoms selected from O, N, and S, wherein the alkyl is optionally substituted with one to two $C_{1-6}$ alkoxy and the phenyl and heteroaryl are optionally substituted with one to three $R^{14}$. In yet another embodiment, $R^{13}$ is independently at each occurrence $C_{1-6}$ alkyl, $C_{6-10}$ aryl, or a 5- or 6-membered heteroaryl comprising 1-3 heteroatoms selected from O, N, and S, wherein the alkyl is optionally substituted with one to two $C_{1-6}$ alkoxy and the aryl and heteroaryl are optionally substituted with one to three $R^{14}$.

In another embodiment, $R^{13}$ is independently at each occurrence $C_{1-6}$ alkyl, $C_{1-6}$ haloalkyl, $C_{6-10}$ aryl, or a 5-membered heteroaryl comprising 1-3 heteroatoms selected from O, N, and S, wherein the alkyl is optionally substituted with one to two $C_{1-6}$ alkoxy and the aryl and heteroaryl are optionally substituted with one to three $R^{14}$. In yet another embodiment, $R^{13}$ is independently at each occurrence $C_{1-6}$ alkyl, $C_{1-6}$ haloalkyl, phenyl, or a 5-membered heteroaryl comprising 1-3 heteroatoms selected from O, N, and S, wherein the alkyl is optionally substituted with one to two $C_{1-6}$ alkoxy and the phenyl and heteroaryl are optionally substituted with one to three $R^{14}$. In another embodiment, $R^{13}$ is independently at each occurrence $C_{1-6}$ alkyl, $C_{1-6}$ haloalkyl, $C_{6-10}$ aryl, or a 6-membered heteroaryl comprising 1-3 heteroatoms selected from O, N, and S, wherein the alkyl is optionally substituted with one to two $C_{1-6}$ alkoxy and the aryl and heteroaryl are optionally substituted with one to three $R^{14}$. In yet another embodiment, $R^{13}$ is independently at each occurrence $C_{1-6}$ alkyl, $C_{1-6}$ haloalkyl, phenyl, or a 6-membered heteroaryl comprising 1-3 heteroatoms selected from O, N, and S, wherein the alkyl is optionally substituted with one to two $C_{1-6}$ alkoxy and the phenyl and heteroaryl are optionally substituted with one to three $R^{14}$.

In some embodiments of the formulae above, each $R^{14}$ is independently $C_{1-4}$ alkyl, $C_{1-4}$ haloalkyl, $C_{1-4}$ alkoxy, $C_{1-4}$ haloalkoxy, halogen, $C_{6-10}$ aryl, or a 5- or 6-membered heteroaryl comprising 1-3 heteroatoms selected from O, N, and S. In another embodiment, each $R^{14}$ is independently $C_{1-6}$ alkyl, $C_{1-6}$ haloalkyl, $C_{1-6}$ alkoxy, $C_{1-3}$ haloalkoxy, or halogen. In another embodiment, each $R^{14}$ is independently $C_6$. 10 aryl, or a 5- or 6-membered heteroaryl comprising 1-3 heteroatoms selected from O, N, and S. In another embodiment, each $R^{14}$ is independently $C_{1-6}$ alkyl, $C_{1-6}$ haloalkyl, $C_{1-6}$ alkoxy, $C_{1-3}$ haloalkoxy, halogen, phenyl, or a 5- or 6-membered heteroaryl comprising 1-3 heteroatoms selected from O, N, and S. In another embodiment, each $R^{14}$ is independently $C_{1-6}$ alkyl, $C_{1-6}$ haloalkyl, $C_{1-6}$ alkoxy, $C_{1-3}$ haloalkoxy, $C_{6-10}$ aryl, or a 5- or 6-membered heteroaryl comprising 1-3 heteroatoms selected from O, N, and S. In another embodiment, each $R^{14}$ is independently $C_{1-6}$ alkyl, $C_{1-6}$ haloalkyl, $C_{1-6}$ alkoxy, $C_{1-3}$ halogen, $C_{6-10}$ aryl, or a 5- or 6-membered heteroaryl comprising 1-3 heteroatoms selected from O, N, and S. In another embodiment, each $R^{14}$ is independently $C_{1-6}$ alkyl, $C_{1-6}$ haloalkyl, $C_{1-3}$ haloalkoxy, halogen, $C_{6-10}$ aryl, or a 5- or 6-membered heteroaryl comprising 1-3 heteroatoms selected from O, N, and S;

In another embodiment, each $R^{14}$ is independently $C_{1-6}$ alkyl, $C_{1-6}$ alkoxy, $C_{1-3}$ haloalkoxy, halogen, $C_{6-10}$ aryl, or a 5- or 6-membered heteroaryl comprising 1-3 heteroatoms selected from O, N, and S. In another embodiment, each $R^{14}$ is independently $C_{1-6}$ haloalkyl, $C_{1-6}$ alkoxy, $C_{1-3}$ haloalkoxy, halogen, $C_{6-10}$ aryl, or a 5- or 6-membered heteroaryl comprising 1-3 heteroatoms selected from O, N, and S. In another embodiment, each $R^{14}$ is independently $C_{1-6}$ alkyl, $C_{1-6}$ haloalkyl, halogen, $C_{6-10}$ aryl, or a 5- or 6-membered heteroaryl comprising 1-3 heteroatoms selected from O, N, and S. In another embodiment, each $R^{14}$ is independently $C_{1-6}$ alkoxy, $C_{1-3}$ haloalkoxy, halogen, $C_{6-10}$ aryl, or a 5- or 6-membered heteroaryl comprising 1-3 heteroatoms selected from O, N, and S. In another embodiment, each $R^{14}$ is independently $C_{1-6}$ alkyl, $C_{1-6}$ alkoxy, halogen, $C_{6-10}$ aryl, or a 5- or 6-membered heteroaryl comprising 1-3 heteroatoms selected from O, N, and S. In another embodiment, each $R^{14}$ is independently $C_{1-6}$ haloalkyl, $C_{1-3}$ haloalkoxy, halogen, $C_{6-10}$ aryl, or a 5- or 6-membered heteroaryl comprising 1-3 heteroatoms selected from O, N, and S. In another embodiment, each $R^{14}$ is independently $C_{1-6}$ alkyl, $C_{1-6}$ haloalkyl, $C_{1-6}$ alkoxy, $C_{1-3}$ haloalkoxy, halogen, phenyl, or a 6-membered heteroaryl comprising 1-3 heteroatoms selected from O, N, and S. In another embodiment, each $R^{14}$ is independently $C_{1-6}$ alkyl, $C_{1-6}$ haloalkyl, $C_{1-6}$ alkoxy, $C_{1-3}$ haloalkoxy, halogen, phenyl or a 6-membered heteroaryl comprising 1-3 heteroatoms selected from O, N, and S.

In some embodiments of the formulae above, $R^{15}$ is H or $C_{1-3}$ alkyl. In another embodiment, $R^{15}$ is $C_{1-6}$ alkyl. In yet another embodiment, $R^{11}$ is H or $C_{2-6}$ alkyl. In another embodiment, $R^{11}$ is H or $C_{3-6}$ alkyl. In yet another embodiment, $R^{15}$ is H, methyl, ethyl, n-propyl, or i-propyl. In another embodiment, $R^{15}$ is H, ethyl, n-propyl, or i-propyl. In yet another embodiment, $R^{15}$ is H, n-propyl, or i-propyl. In another embodiment, $R^{15}$ is H, methyl, or ethyl. In yet another embodiment, $R^{15}$ is H or methyl. In another embodiment, $R^{15}$ is H.

In some embodiments of the formulae above, q is 0 or 1. In another embodiment, q is 1 or 2. In another embodiment, q is 0 or 2. In another embodiment, q is 0. In another embodiment, q is 1. In another embodiment, q is 2.

In some embodiments of the formulae above, $R^{d1}$ is H.

In some embodiments of the formulae above, $R^{d1}$ is H and $R^{d2}$ is H.

In some embodiments of the formulae above, $R^{d1}$ is H and === is a double bond.

In some embodiments of the formulae above, $R^{d1}$ is H and === is a single bond.

In some embodiments of the formulae above, $R^{d2}$ is H and === is a double bond.

In some embodiments of the formulae above, $R^{d2}$ is H and === is a single bond.

In some embodiments of the formulae above, $R^{d1}$ is H, $R^{d2}$ is H, and === is a double bond.

In some embodiments of the formulae above, $R^{d1}$ is H, $R^{d2}$ is H, and === is a single bond.

In an embodiment, the compounds disclosed herein, e.g., a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, can be used as a Targeting Ligase Binder to prepare a bifunctional degrader. In an embodiment, the bifunctional degrader is a compound of Formula (A):

(A)

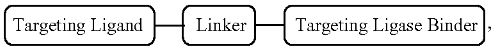

, wherein:

the Targeting Ligand is a group that is capable of binding to a Target Protein, e.g., a Target protein disclosed herein in Table 1;

the Linker is a absent or a group that covalently links the Targeting Ligand to the Targeting Ligase Binder; and the Targeting Ligase Binder is a group that is capable of binding to a ligase (e.g., Cereblon E3 Ubiquitin ligase), wherein the Targeting Ligase Binder is, a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof.

Examples of Linkers and Target Ligands and synthesis thereof is provided in related U.S. Provisional Application entitled "BIFUNCTIONAL DEGRADERS AND THEIR METHODS OF USE" filed on Sep. 16, 2019, and assigned U.S. Ser. No. 62/901,161 which is incorporated herein in its entirety.

Embodiment 1: A compound or a pharmaceutically acceptable salt, hydrate, solvate, prodrug, stereoisomer, or tautomer thereof, capable of binding to and altering the specificity of a cereblon complex to induce ubiquitination and degradation of a complex-associated protein.

Embodiment 2: The compound of Embodiment 1, wherein the compound comprises, (i) a tris-tryptophan Pocket Binder moiety that binds to the tris-tryptophan pocket of Cereblon E3 ligase; and (ii) a target affinity moiety attached covalently to the tris-tryptophan Pocket Binder moiety that interacts with the surface of the Cereblon E3 ligase altering its surface and causing the ligase to have affinity for a Target Protein.

Embodiment 3: The compound of Embodiment 1 or 2, wherein the compound has a Formula (I):

(I)

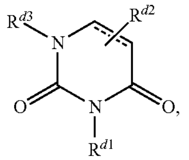

or a pharmaceutically acceptable salt, hydrate, solvate, prodrug, stereoisomer, or tautomer thereof, wherein:

⁼⁼⁼ is optionally a double bond;

$R^{d1}$ is H, $—CH_2OC(O)R^{15}$, $—CH_2OP(O)OHOR^{15}$, or $—CH_2OP(O)(R^{15})_2$;

$R^{d2}$ is H, $C_{1-6}$ alkyl, halogen $C_{1-6}$ haloalkyl, or $C_{1-6}$ heteroalkyl;

$R^{d3}$ is

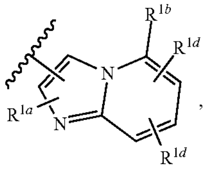,
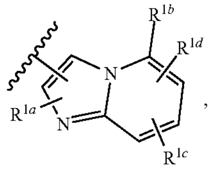,
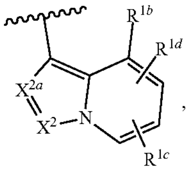,
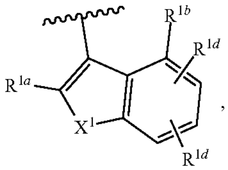,
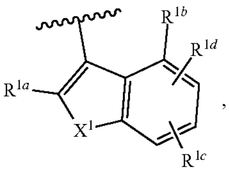,
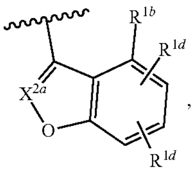, -continued

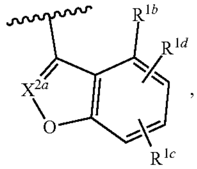,
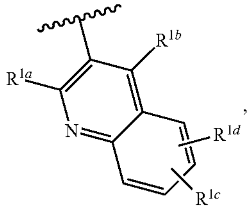,
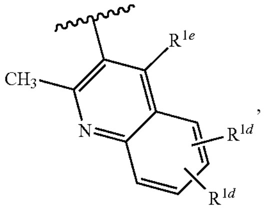,
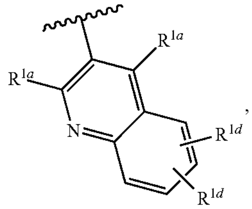,
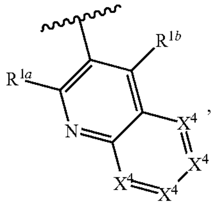,
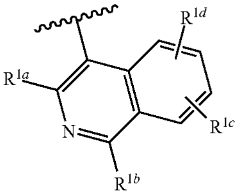,
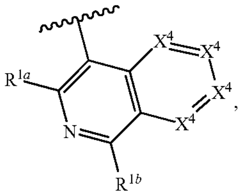,
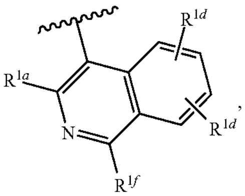,
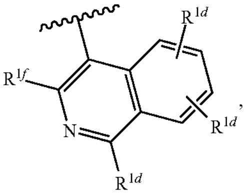,
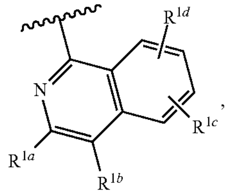,
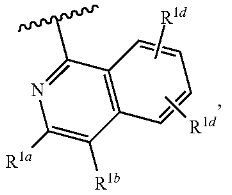,
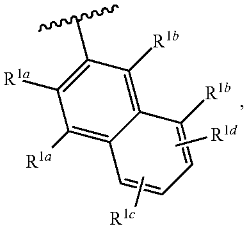,
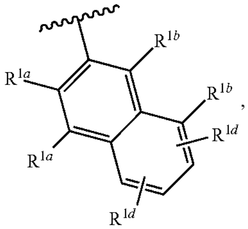,
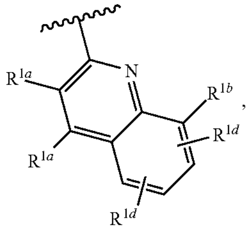,
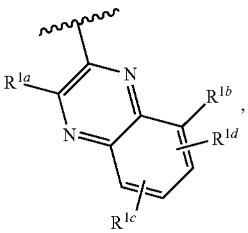,
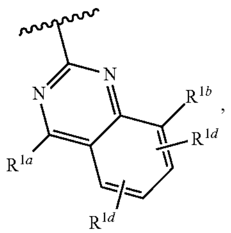, -continued
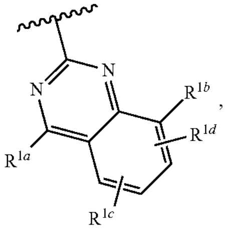,
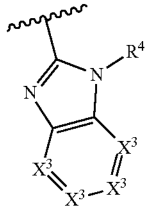,
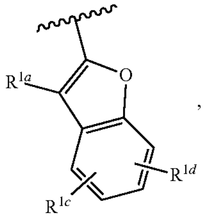,
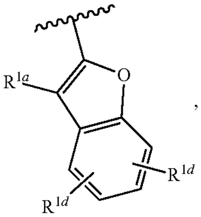,
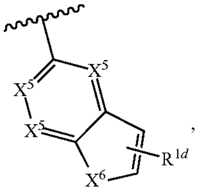,
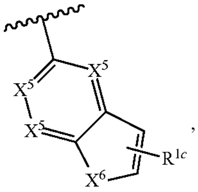,
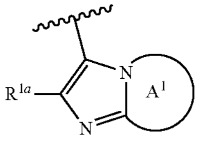,
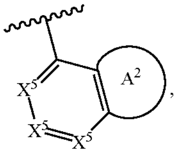,
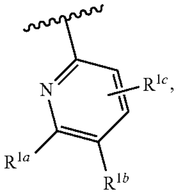,
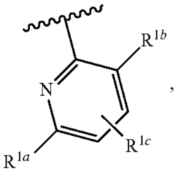,
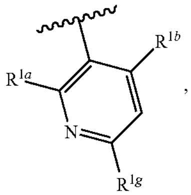,
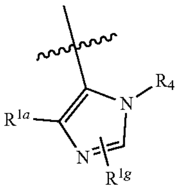,
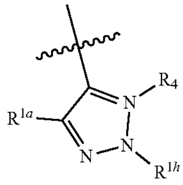,
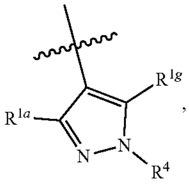,
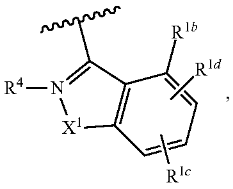,
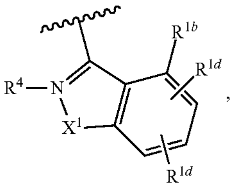,
-continued
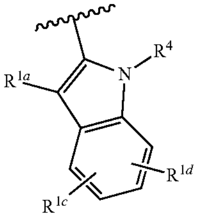,
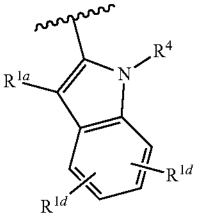,
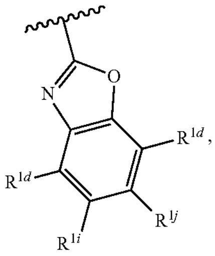,
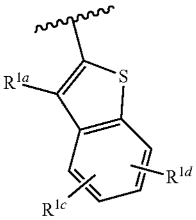,
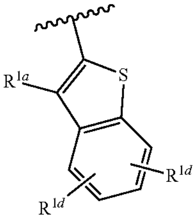,
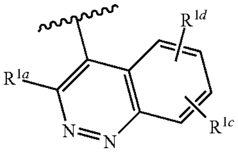,
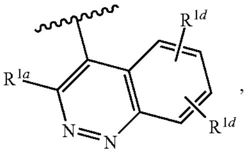,
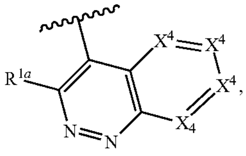,
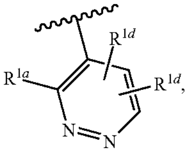,
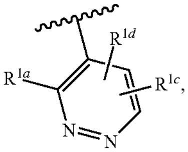,
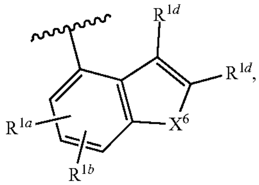,
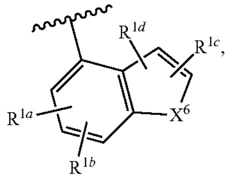,
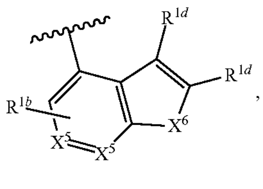,
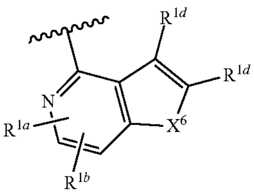,
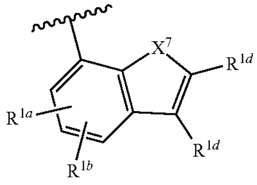,
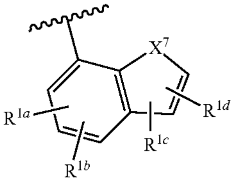, -continued

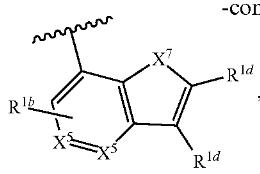
,
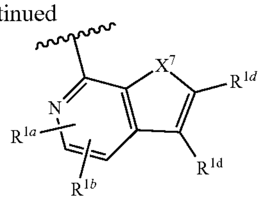
,
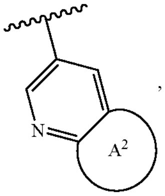
,
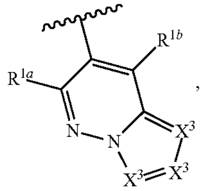
,
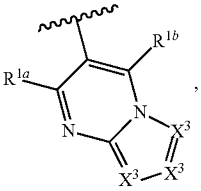
,
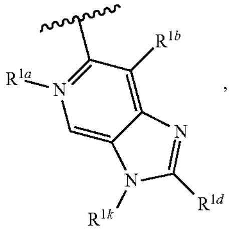
,
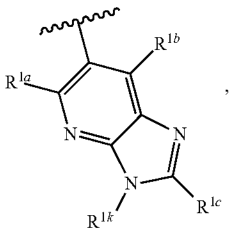
,
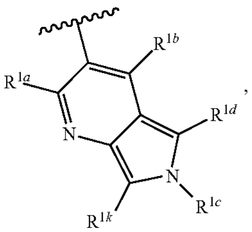
,
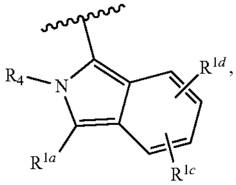
, or
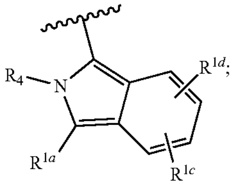
;

$A^1$ is a 5- or 6-membered heterocyclyl optionally comprising 1-3 additional heteroatoms selected from O, N, and S or 5-membered heteroaryl optionally comprising 1-3 additional heteroatoms selected from $NR^{1k}$, O, and S and substituted with one to three $R^{1d}$;

$A^2$ is a $C_{5-7}$carbocyclyl or 5- to 7-membered heterocyclyl comprising 1-3 heteroatoms selected from N, $NR^{1k}$, O, and S, wherein the carbocyclyl and heterocyclyl are substituted with one to three $R^{1d}$;

$X^1$ is $NR^4$ or S;

$X^2$ and $X^{2a}$ are each independently $CR^{1a}$ or N;

each $X^3$ is independently $CR^{1d}$ or N; wherein no more than two $X^3$ are N;

each $X^4$ is independently $CR^{1d}$ or N, wherein at least one $X^4$ is N and wherein no more than two $X^4$ are N;

each $X^5$ is independently $CR^{1a}$ or N; wherein no more than two $X^5$ are N;

$X^6$ is $NR^{1k}$, O, or S;

$X^7$ is $NR^4$, O, or S;

$R^{1a}$ and $R^{1c}$ are each independently H, $C_{1-3}$ alkyl, $C_{1-3}$ haloalkyl, $C_{1-3}$ alkoxy, $C_{1-3}$ haloalkoxy, —$NH_2$, —NH($C_{1-3}$ alkyl), —N($C_{1-3}$ alkyl)$_2$, —CN, F, or Cl;

$R^{1c}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)O$C_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR^3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

each $R^{1d}$ is independently is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)O$C_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR^3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1e}$ is $C_{2-3}$ alkyl, $C_{1-3}$ haloalkyl, $C_{1-3}$ alkoxy, $C_{1-3}$ haloalkoxy, —CN, F, or Cl;

$R^{1f}$ is $C_{1-3}$ alkyl, $C_{1-3}$ haloalkyl, $C_{1-3}$ alkoxy, $C_{1-3}$ haloalkoxy, —CN, F, or Cl;

$R^{1g}$ is $C_{2-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —C(O)O$C_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N($R^{13}$)$_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1h}$ is $C_{4-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$C_{6-10}$ aryl, —$(CH_2)_{2-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1i}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$;

$R^{1j}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$—$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR_3(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$;

wherein $R^{1d}$, $R^{1i}$, and $R^{1j}$ on the benzoxazole ring are not all simultaneously H;

each $R^{1k}$ is independently is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —$C(O)OC_{1-6}$ alkyl, —$(CH_2)_{0-4}$—$C(O)NH_2$, —$(CH_2)_{0-4}$—$C(O)NH(R^{13})$, —$(CH_2)_{0-4}$—$C(O)N(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$C(O)O(CH_2)_{0-4}$—$C_{3-7}$ carbocyclyl, —$C(O)O(CH_2)_{0-4}$-5- to 7-membered heterocyclyl comprising 1-3 heteroatoms selected from O, N, and S, —$C(O)O(CH_2)_{0-4}$—$C_{6-10}$ aryl, or —$C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

each $R^2$ is independently $NH_2$, —$NH(C_{1-6}$ alkyl), —$N(C_{1-6}$ alkyl$)_2$, —$C(O)NH_2$, —$C(O)NH(C_{1-6}$ alkyl), —C(O)N($C_{1-6}$ alkyl)$_2$, —NHC(O)$R^9$, —N($R^9$)C(O)($R^9$), —NHS(O)$_2R^9$, or —N$R^9$S(O)$_2R^9$;

$R^3$ is H or $C_{1-6}$ alkyl;

$R^4$ is H or $C_{1-6}$ alkyl;

each $R^5$ is independently $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, —OH, —C(O)H, —C(O)($C_{1-6}$ alkyl), —C(O)($C_{6-10}$ aryl), —C(O)(5- or 6-membered heteroaryl), —C(O)($C_{3-7}$ carbocyclyl), —C(O)(5- to 7-membered heterocyclyl)-(CH$_2$)$_{0-3}$C(O)O$C_{1-6}$ alkyl, —C(O)NH$_2$, —C(O)NH($C_{1-6}$ alkyl), —C(O)N($C_{1-6}$ alkyl)$_2$, —NHC(O)$R^9$, —N($R^9$)C(O)($R^9$), —NH$_2$, —NH($C_{1-6}$ alkyl), —N($C_{1-6}$ alkyl)$_2$, —NHC(O)O($R^9$), —N($R^9$)C(O)O($R^9$), —NHS(O)$_2R^9$, —N$R^9$S(O)$_2R^9$, —S(O)$_q$NH$R^9$, —S(O)$_q$N($R^9$)$_2$, —S(O)$_qR^9$, $C_{1-6}$ hydroxyalkyl, —O(CH$_2$)$_{1-3}$CN, CN, —O(CH$_2$)$_{0-6}$—$C_{3-7}$ carbocyclyl, —O(CH$_2$)$_{0-6}$-5- to 7-membered heterocyclyl comprising 1-3 heteroatoms selected from O, N, and S, —O(CH$_2$)$_{0-3}$($C_6$-$C_{10}$)aryl, adamantyl, —O(CH$_2$)$_{0-3}$-5- or 6-membered heteroaryl comprising 1-3 heteroatoms selected from O, N, and S, —(CH$_2$)$_{0-6}$—$C_{3-7}$ carbocyclyl, —(CH$_2$)$_{0-6}$-5- to 7-membered heterocyclyl comprising 1-3 heteroatoms selected from O, N, and S, —(CH$_2$)$_{0-6}$—$C_{6-10}$ aryl, and —(CH$_2$)$_{0-6}$-5- or 6-membered heteroaryl comprising 1-3 heteroatoms selected from O, N, and S, wherein the alkyl is optionally substituted with one to three $R^6$, and the carbocyclyl, heterocyclyl, aryl, and heteroaryl are optionally substituted with one to four $R^8$; or two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$; or two $R^5$ when on adjacent atoms, together with the atoms to which they are attached form a $C_{6-10}$ aryl or a 5- or 6-membered heteroaryl comprising 1-3 heteroatoms selected from O, N, and S; or two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$; or two $R^5$ when on the same carbon atom form ═(O);

$R^6$ is —NH$_2$, —NH($C_{1-6}$ alkyl), —N($C_{1-6}$ alkyl)$_2$, $C_{6-10}$ aryl, or a 5- or 6-membered heteroaryl comprising 1-3 heteroatoms selected from O, N, and S, wherein the aryl and heteroaryl are optionally substituted with one to three $R^7$;

each $R^7$ is independently $C_{1-6}$ alkyl, $C_{1-6}$ haloalkyl, $C_{1-6}$ alkoxy, $C_{1-3}$ haloalkoxy, halogen, or $C_{6-10}$ aryl;

each $R^8$ is independently $C_{1-6}$ alkyl, $C_{1-6}$ haloalkyl, $C_{1-6}$ alkoxy, $C_{1-6}$ haloalkoxy, halogen, or —OH;

$R^9$ is $C_{1-6}$ alkyl, $C_{1-6}$ haloalkyl, 5- to 7-membered heterocyclyl comprising 1-3 heteroatoms selected from O, N, and S, $C_{6-10}$ aryl, or a 5- or 6-membered heteroaryl comprising 1-3 heteroatoms selected from O, N, and S, wherein the aryl and heteroaryl are optionally substituted with one to three $R^{11}$;

each $R^{10}$ is $C_{1-6}$ alkyl, $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S;

each $R^{11}$ is independently $C_{1-6}$ alkyl, $C_{1-6}$ haloalkyl, $C_{1-6}$ alkoxy, $C_{1-6}$ haloalkoxy, —NHC(O)($C_{1-6}$ alkyl), —N($C_{1-6}$alkyl)C(O)($C_{1-6}$alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$;

each $R^{12}$ is independently $C_{1-6}$ alkyl, $C_{1-6}$ haloalkyl, $C_{1-6}$ alkoxy, or $C_{1-3}$ haloalkoxy;

$R^{13}$ is independently at each occurrence $C_{1-6}$ alkyl, $C_{1-6}$ haloalkyl, $C_{6-10}$ aryl, or a 5- or 6-membered heteroaryl comprising 1-3 heteroatoms selected from O, N, and S, wherein the alkyl is optionally substituted with one to two $C_{1-6}$ alkoxy and the aryl and heteroaryl are optionally substituted with one to three $R^{14}$;

each $R^{14}$ is independently $C_{1-6}$ alkyl, $C_{1-6}$ haloalkyl, $C_{1-6}$ alkoxy, $C_{1-3}$ haloalkoxy, halogen, $C_{6-10}$ aryl, or a 5- or 6-membered heteroaryl comprising 1-3 heteroatoms selected from O, N, and S;

$R^{15}$ is H or $C_{1-6}$ alkyl; and q is 0, 1, or 2.

Embodiment 4: The compound of Embodiment 3, wherein $R^{d1}$ is H.

Embodiment 5: The compound of Embodiment 3, wherein $R^{d1}$ is —CH$_2$OC(O)$R^5$, —CH$_2$OP(O)OHO$R^{15}$, or —CH$_2$OP(O)($R^{15}$)$_2$.

Embodiment 6: The compound of any one of Embodiments 1-5, wherein $R^{d2}$ is H.

Embodiment 7: The compound of any one of Embodiments 1-6, wherein $R^{d1}$ and $R^{d2}$ are each independently H.

Embodiment 8: The compound of any one of Embodiments 1-7, wherein $R^{1d}$ is H.

Embodiment 9: The compound of any one of Embodiments 1-8, wherein $R^{d3}$ is

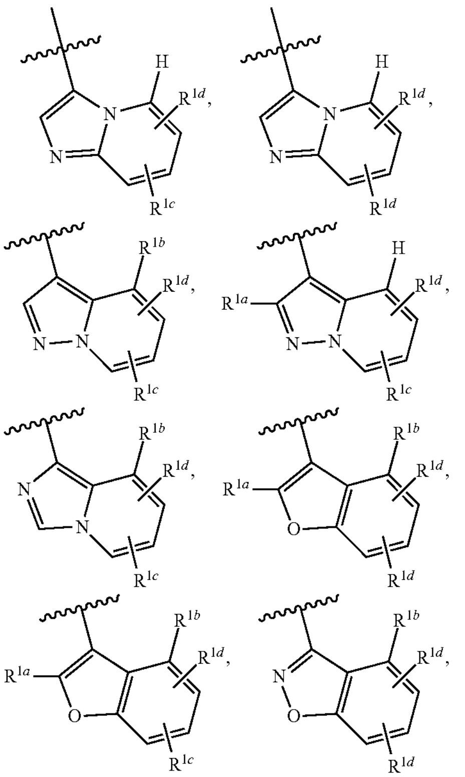

-continued
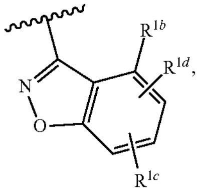
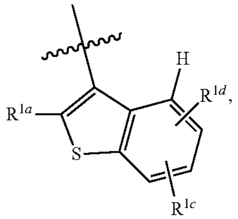
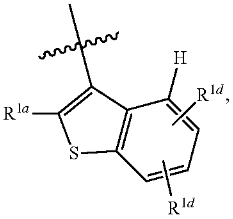
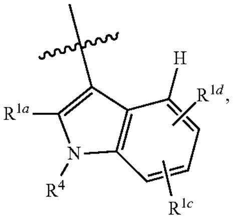
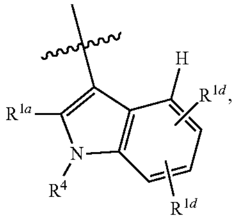
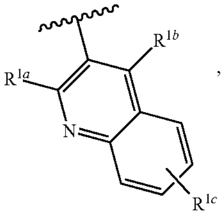
,
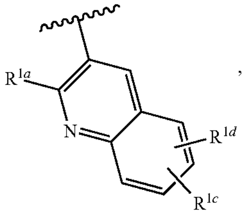
,
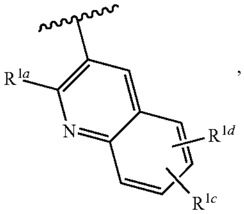
,
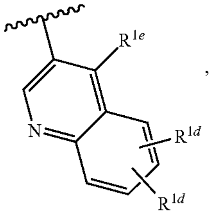
,
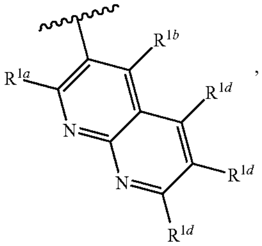
,
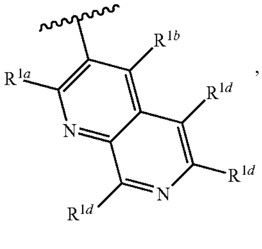
,
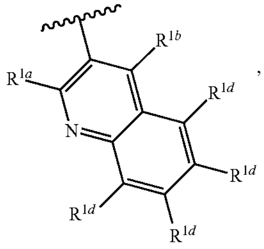
,
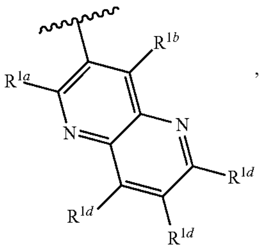
,
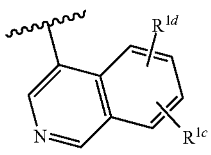
,
-continued
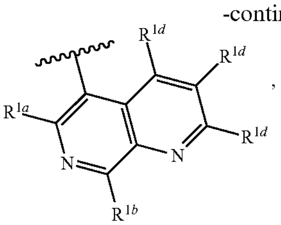
,
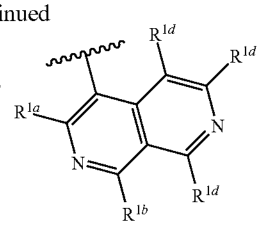
,
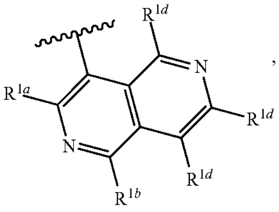
,
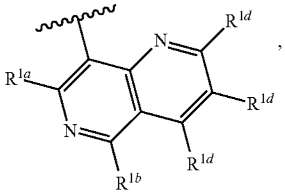
,
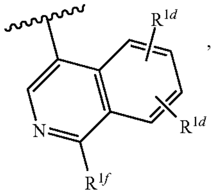
,
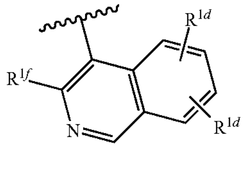
,
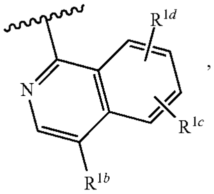
,
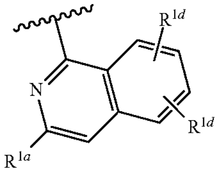
,
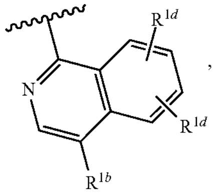
,
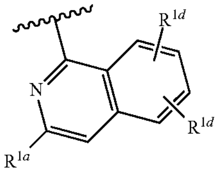
,
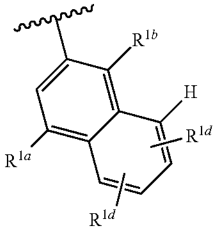
,
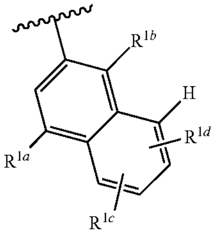
,
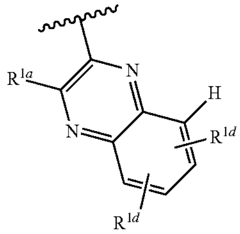
,
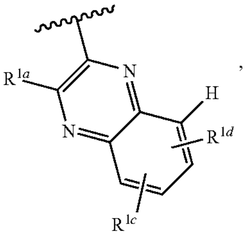
,
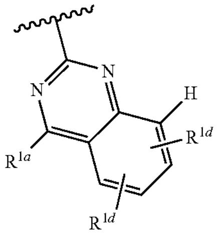
, -continued
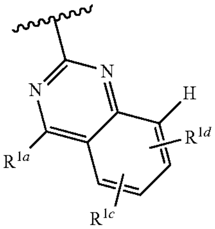
,
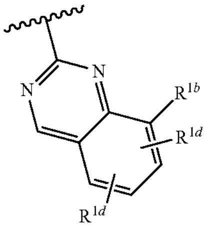
,
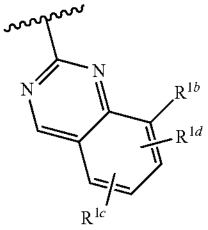
,
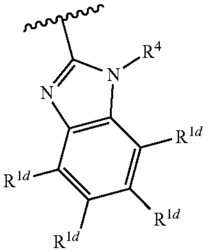
,
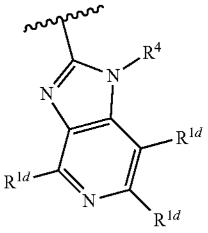
,
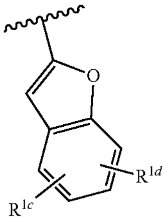
,
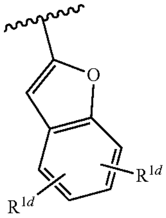
,
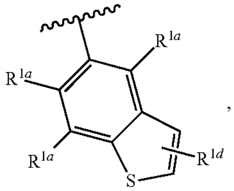
,
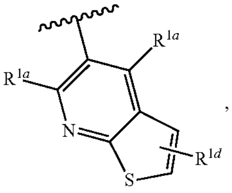
,
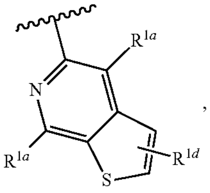
,
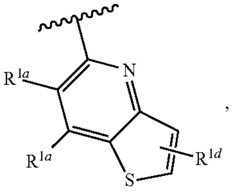
,
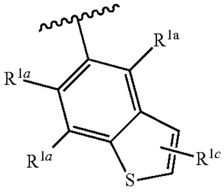
,
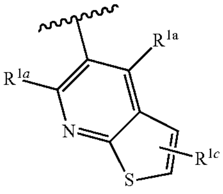
,
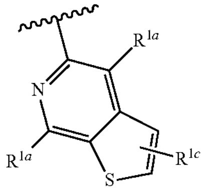
,
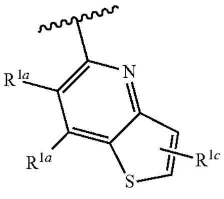
,
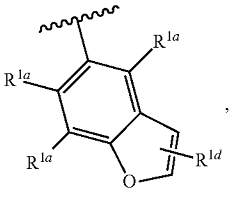
,
-continued
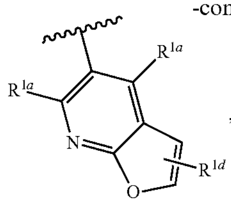
,
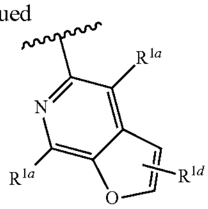
,
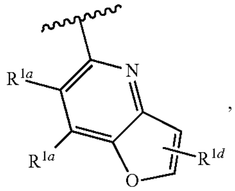
,
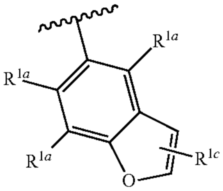
,
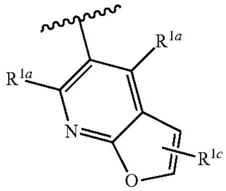
,
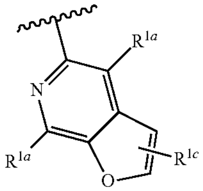
,
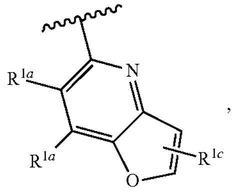
,
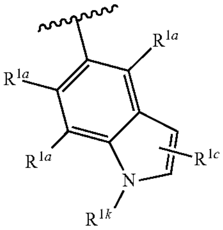
,
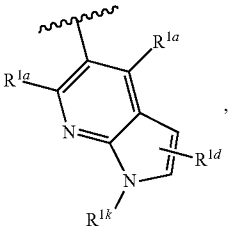
,
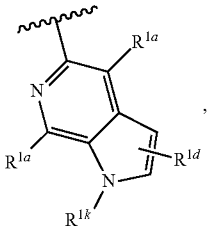
,
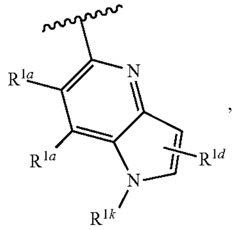
,
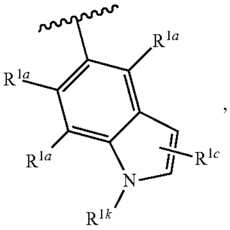
,
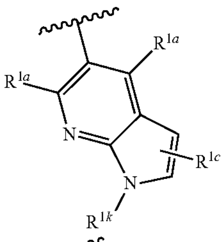
,
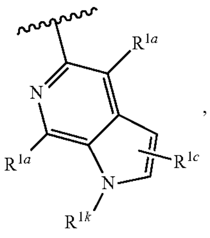
,
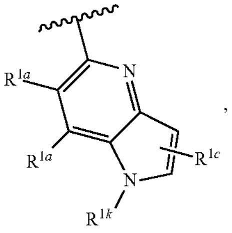
,
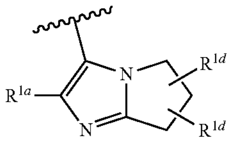
, -continued
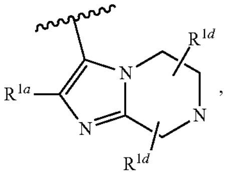 , 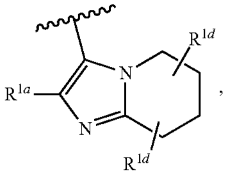 ,
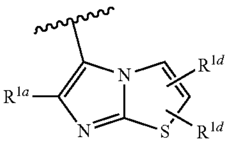 , 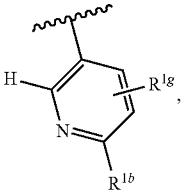 ,
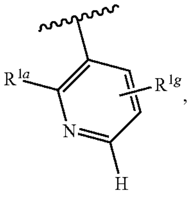 , 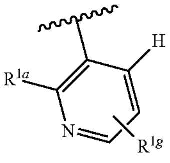 ,
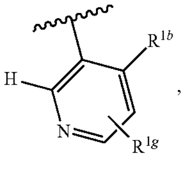 , 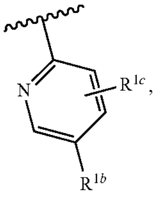 , 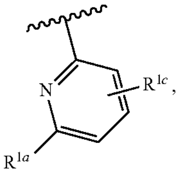 ,
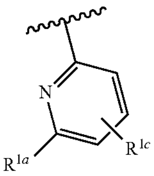 , 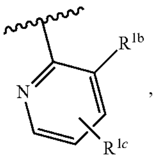 , 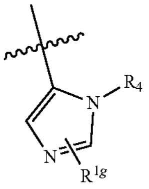
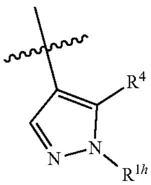 , 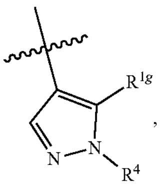 ,
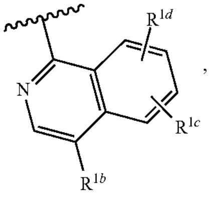 , 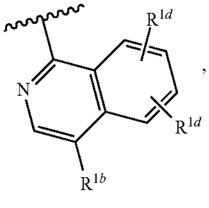 ,
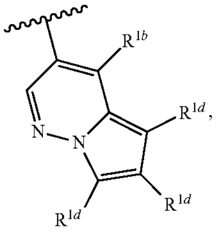 , 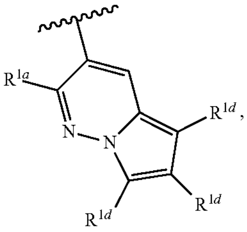 ,
-continued
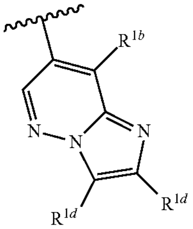 , 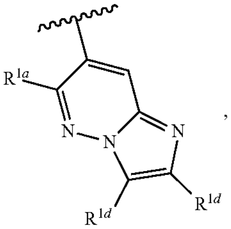 ,
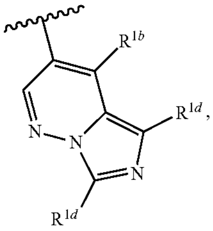 , 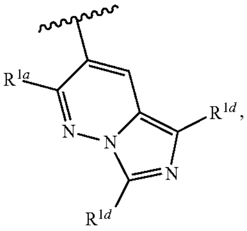 ,
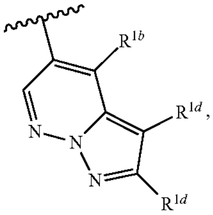 , 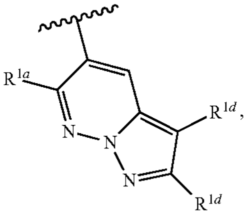 ,
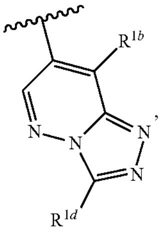 , 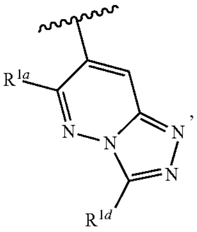 ,
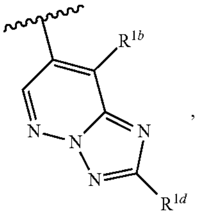 , 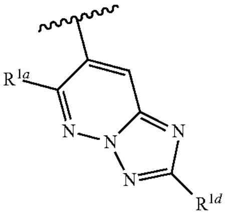 ,
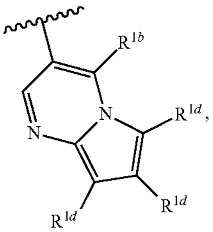 , 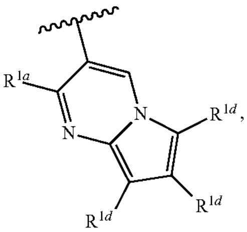 ,
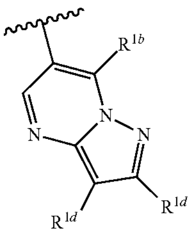 , 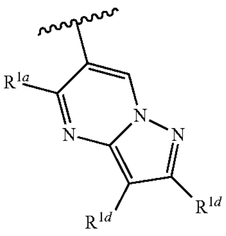 , -continued
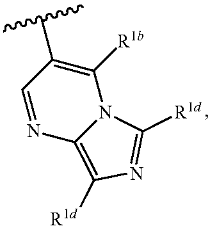
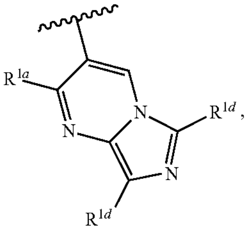
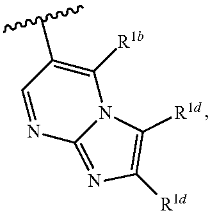
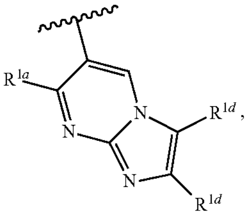
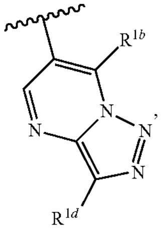
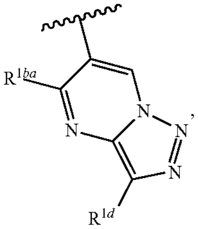
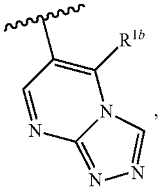
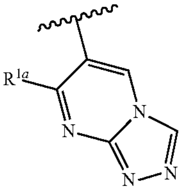
,
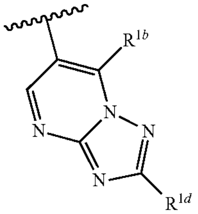
,
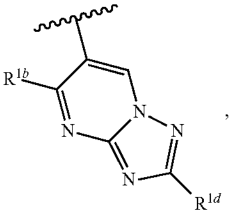
,
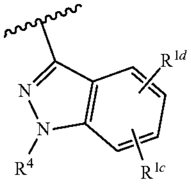
,
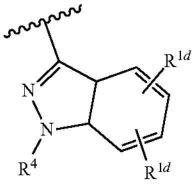
,
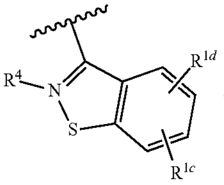
,
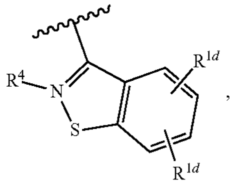
,
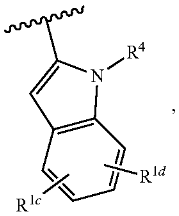
,
-continued
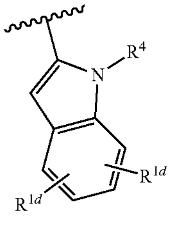
,
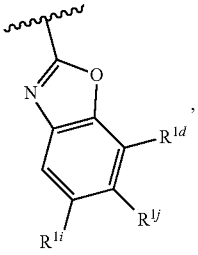
,
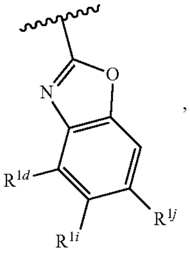
,
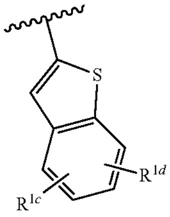
,
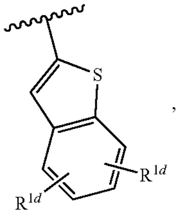
,
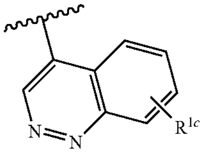
,
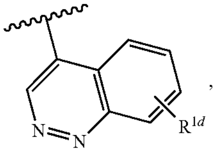
,
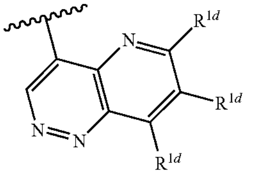
,
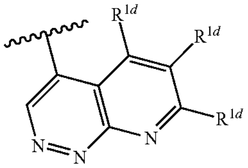
,
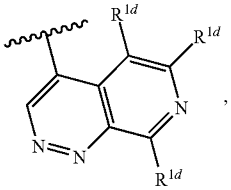
,
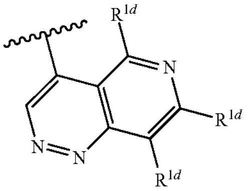
,
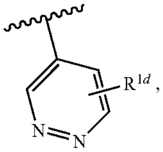
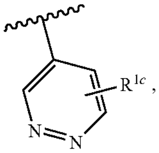
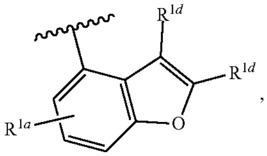
,
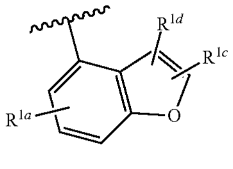
,
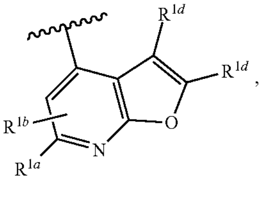

-continued
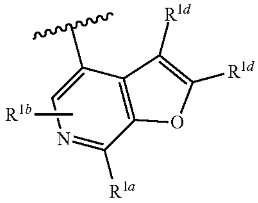,
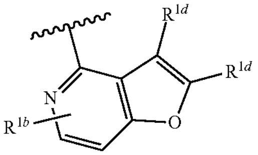,
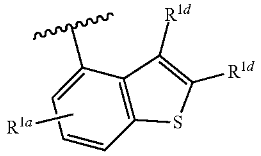,
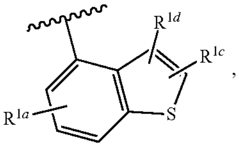,
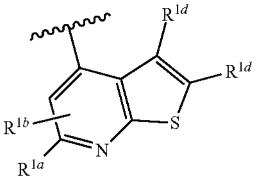,
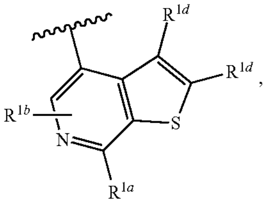,
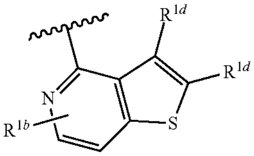,
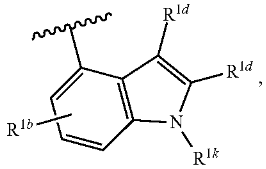,
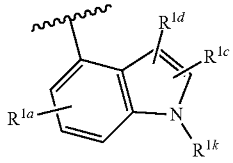,
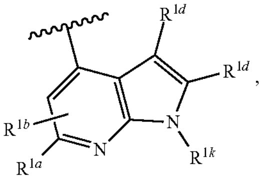,
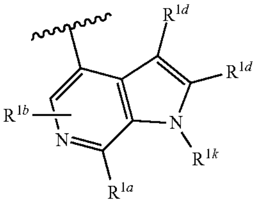,
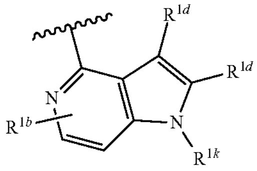,
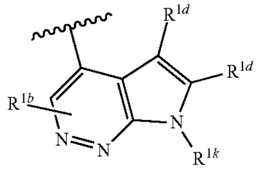,
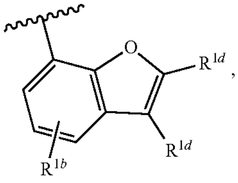,
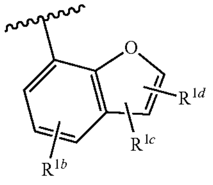,
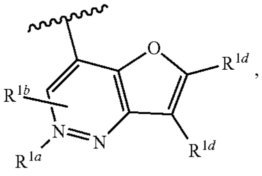,
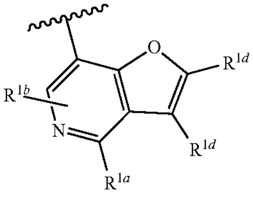,
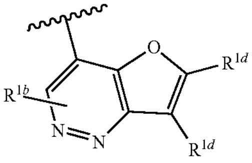,
-continued
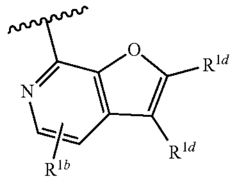,
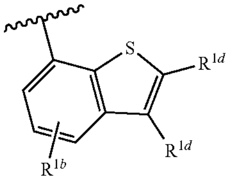,
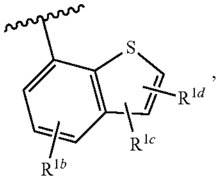,
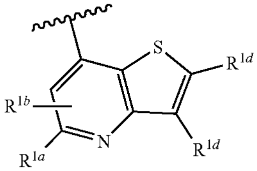,
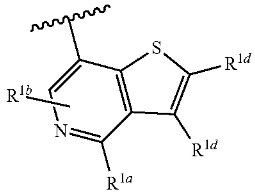,
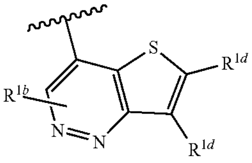,
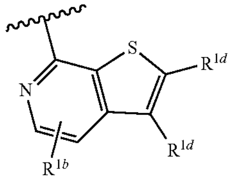,
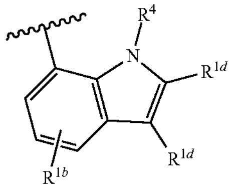,
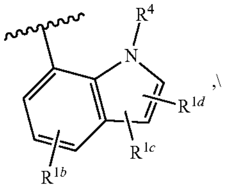,\
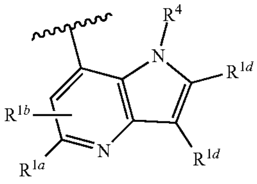,
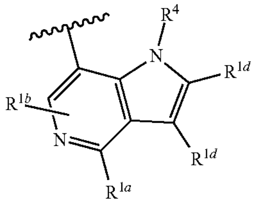,
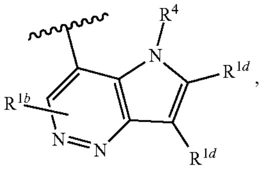,
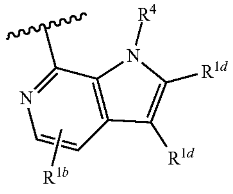,\
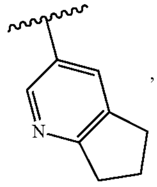,
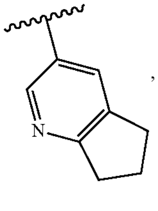,
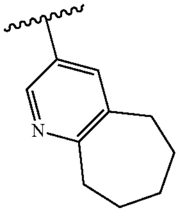, -continued
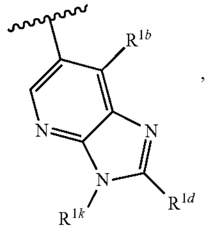, 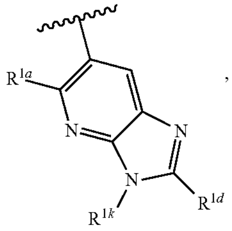,
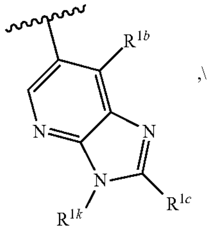, 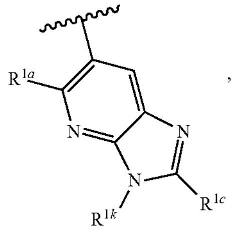,
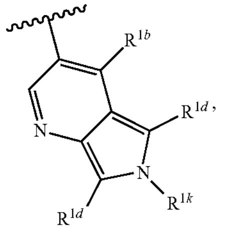 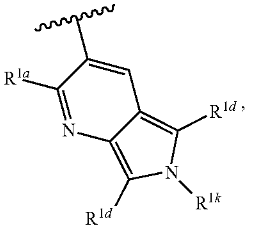
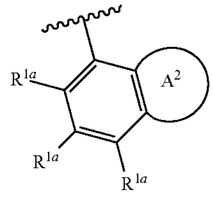, 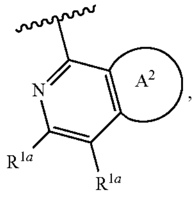,
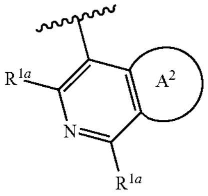, 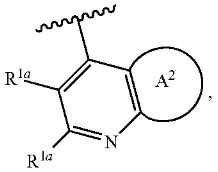,
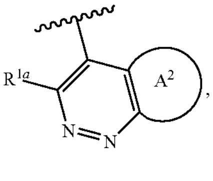, 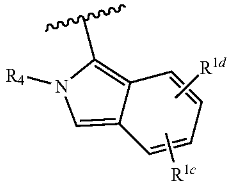,
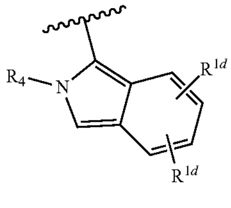, or 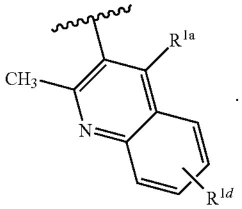.
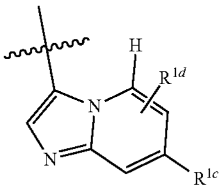, 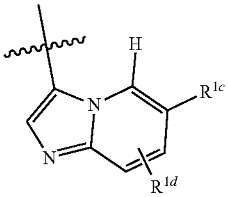,
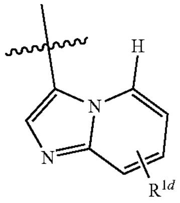, 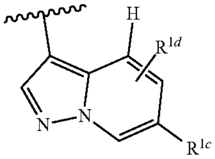,
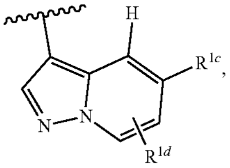 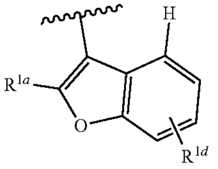,
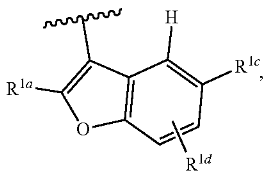 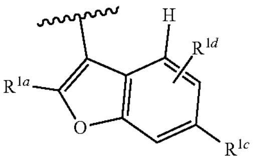,
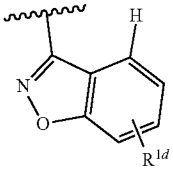, 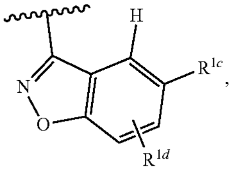
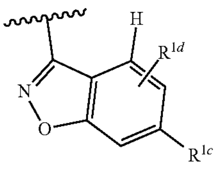, 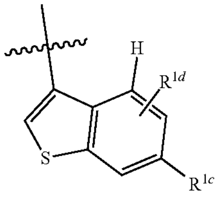,
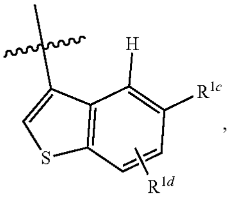, 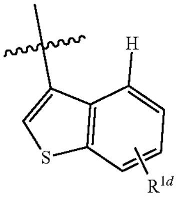,
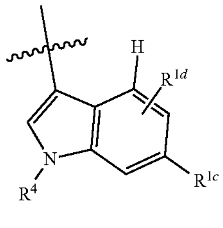 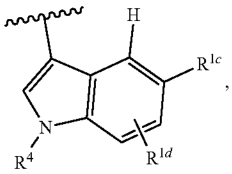,
Embodiment 10: The compound of any one of Embodiments 1-9, wherein $R^{d3}$ is -continued
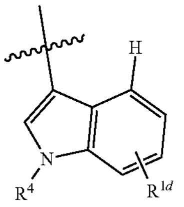,
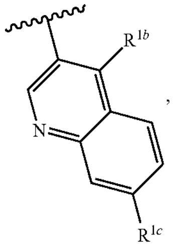,
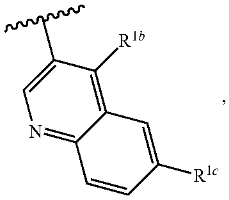,
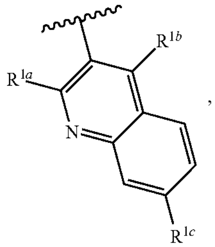,
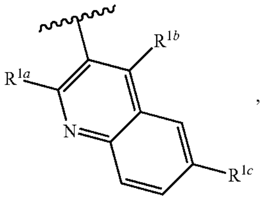,
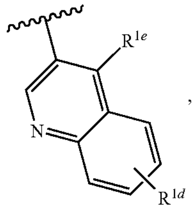,
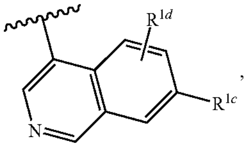,
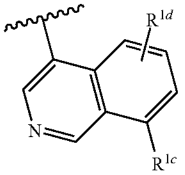,
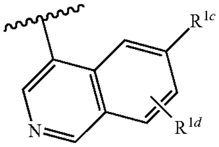,
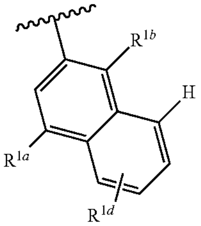,
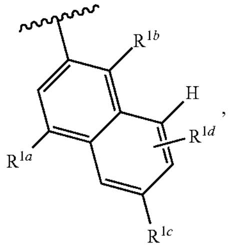,
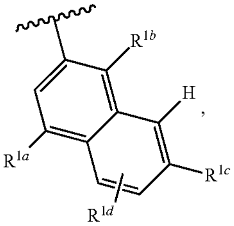,
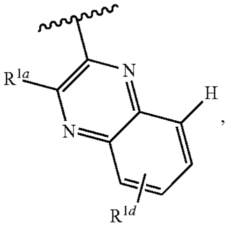,
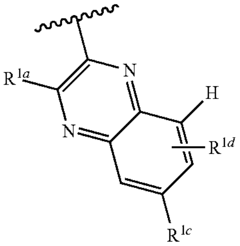,
-continued
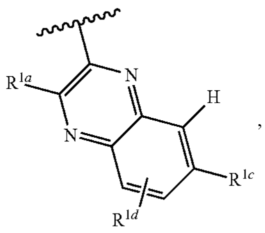,
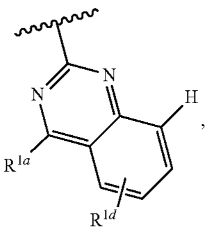,
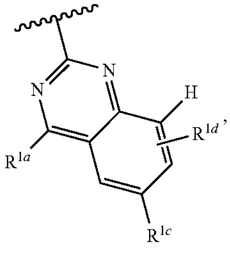,
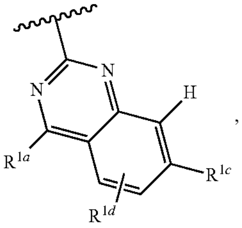,
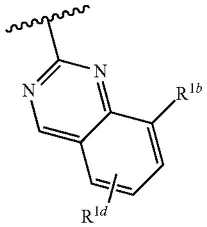,
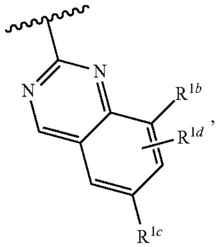,
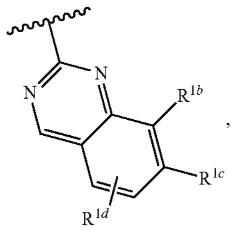,
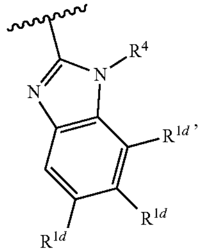,
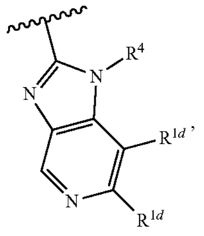,
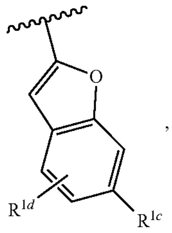,
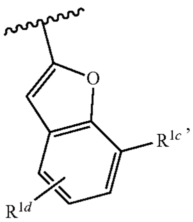,
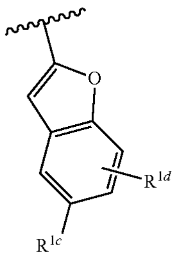,
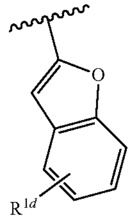,
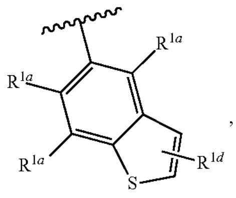, -continued
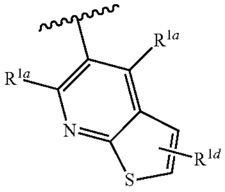,
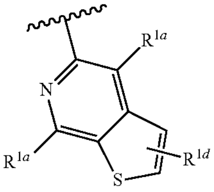,
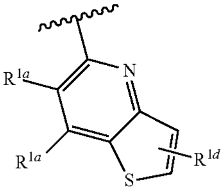,
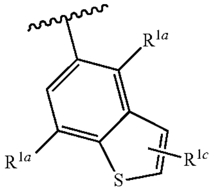,
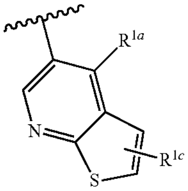,
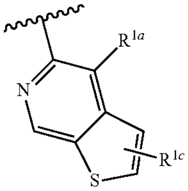,
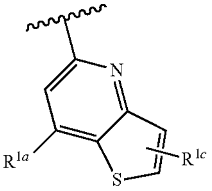,
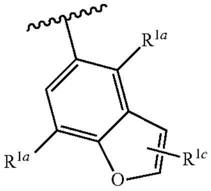,
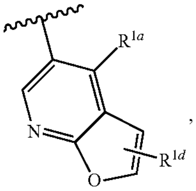,
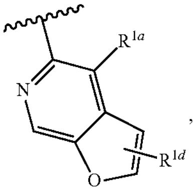,
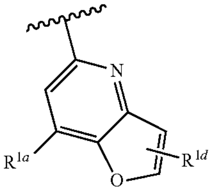,
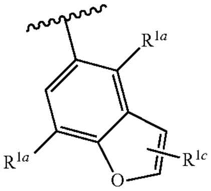,
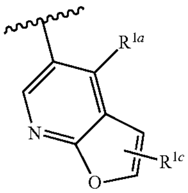,
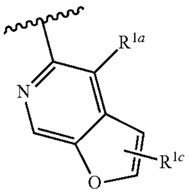,
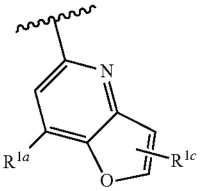,
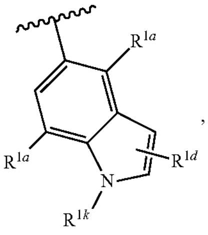,
-continued
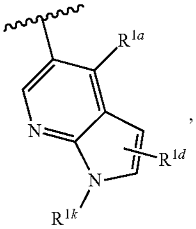,
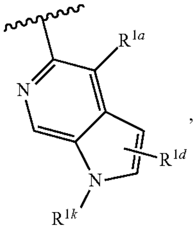,
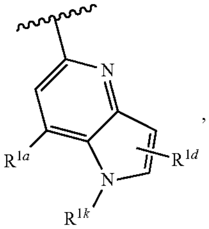,
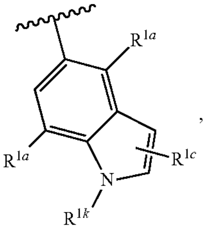,
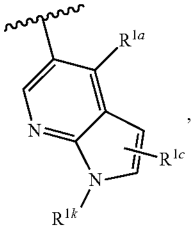,
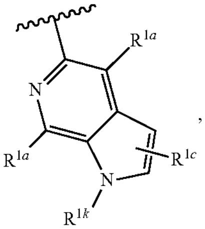,
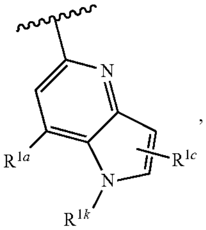,
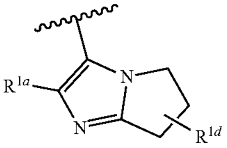,
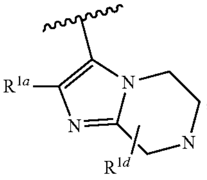,
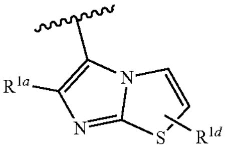,
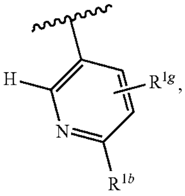,
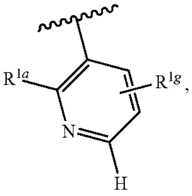,
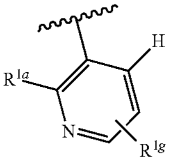,
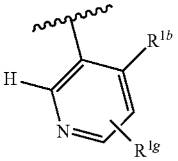,
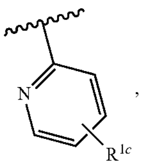,
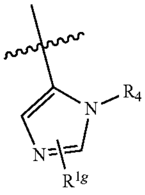,
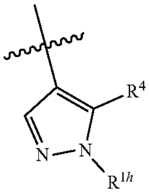, -continued
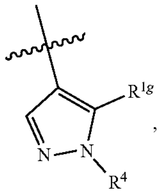,
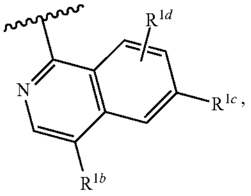,
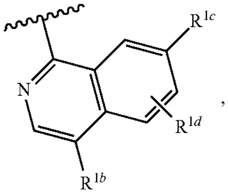,
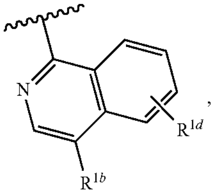,
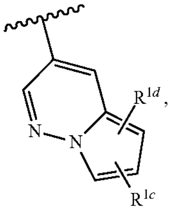,
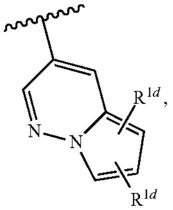,
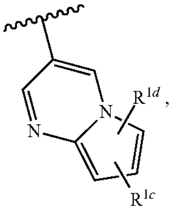,
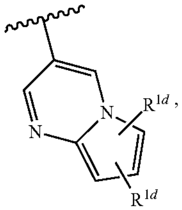,
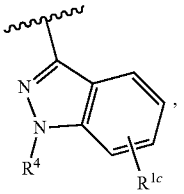,
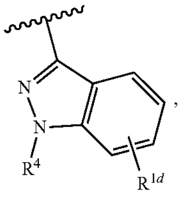,
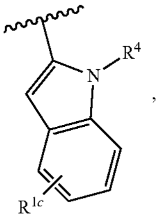,
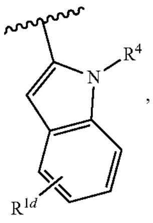,
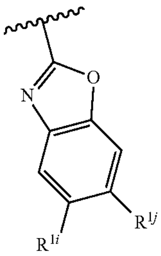,
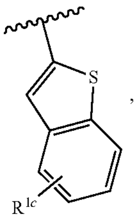,
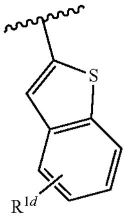, or
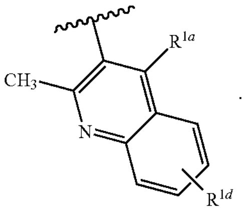.
Embodiment 11: The compound of any one of Embodiments 1-10, wherein the compound has a formula selected from:
(Ia)
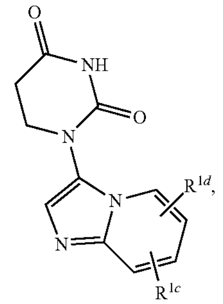
(Ib)
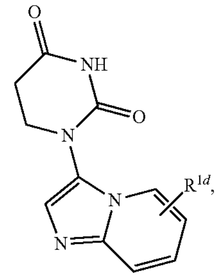
(Ic)
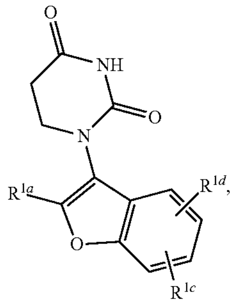
(Id)
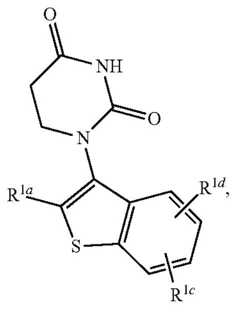
(Ie)
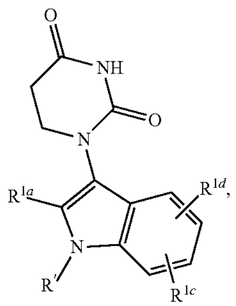

-continued
(If)
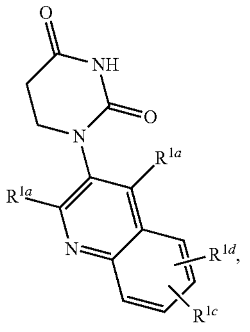
(Ig)
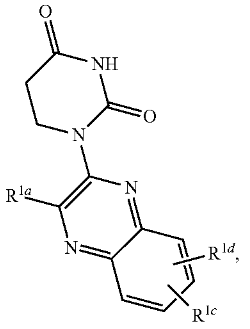
(Ih)
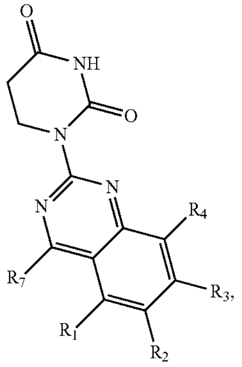
(Ii)
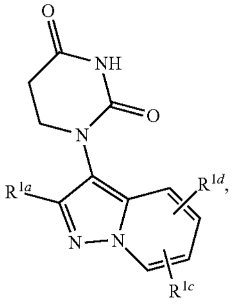
(Ij)
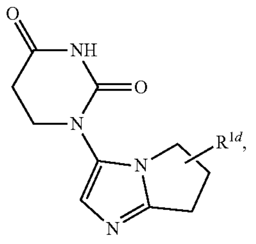
-continued
(Ik)
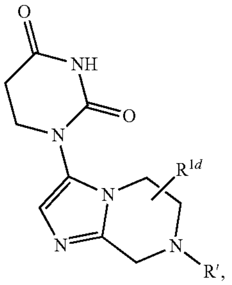
(Il)
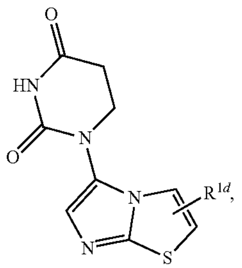
(Im)
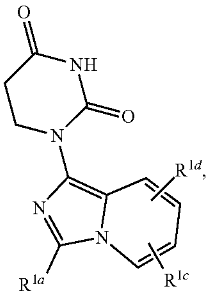
(In)
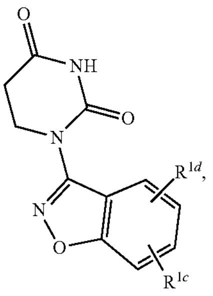
(Io)
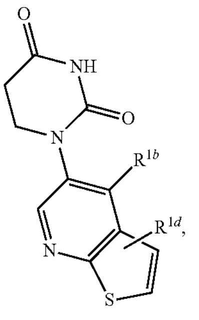

-continued
(Ip)
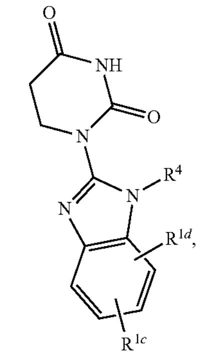
(Ia)
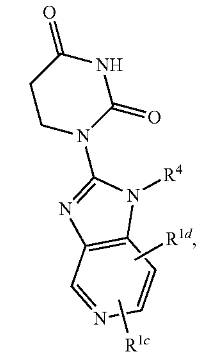
(Ir)
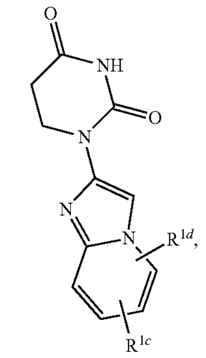
(Is)
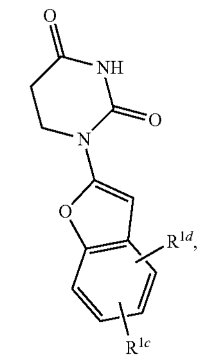
-continued
(It)
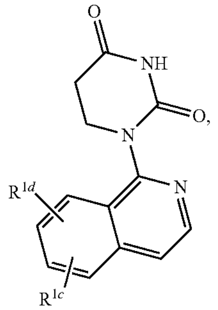
(Iu)
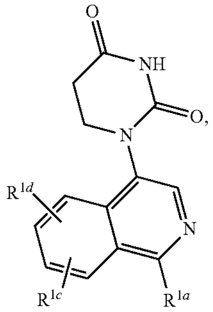
(Iv)
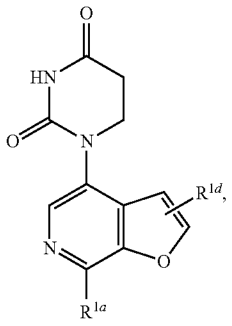
(Iw)
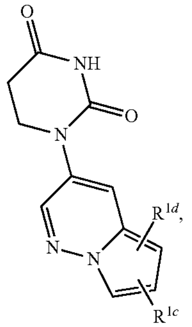
(Ix)
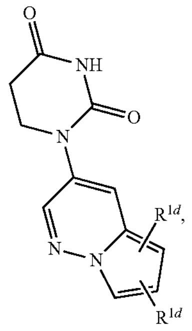

-continued
(Iy)
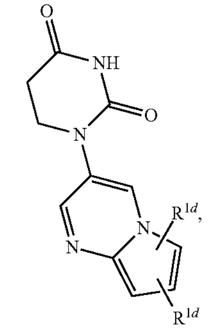
(Iz)
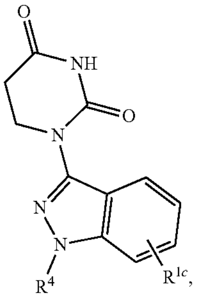
(Iaa)
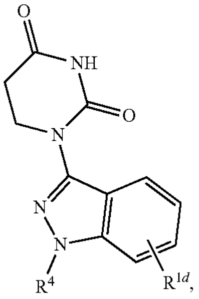
(Iab)
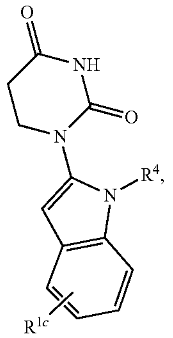
(Iac)
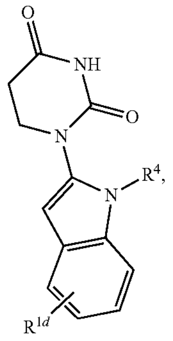
-continued
(Iad)
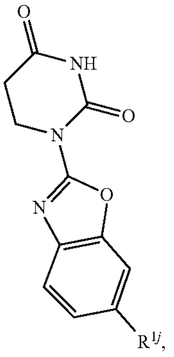
(Iae)
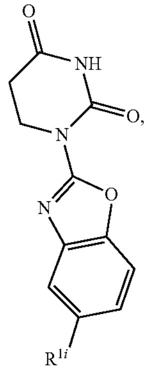
(Iaf)
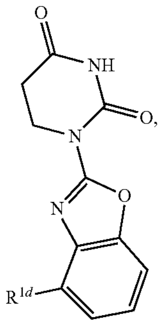
(Iag)
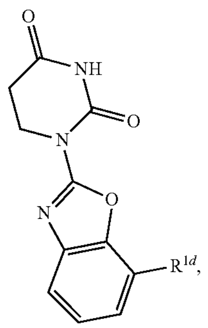

-continued (Iah)

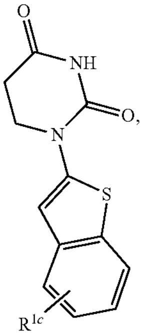

(Iai)

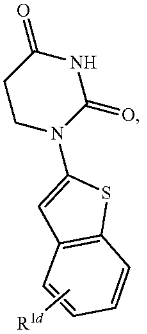

(Iaj)

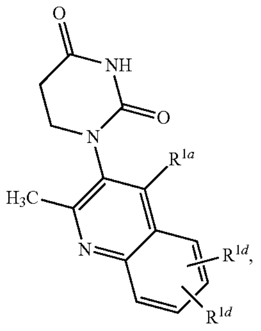

(Iak)

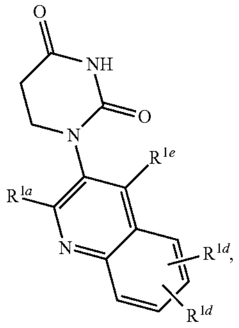

(Ial)

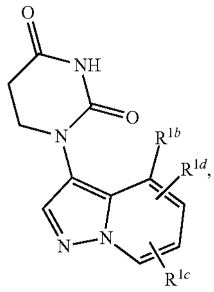

and

-continued (Iam)

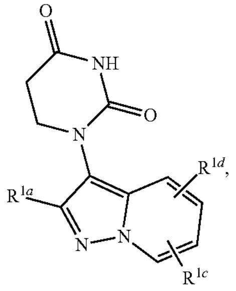

or a pharmaceutically acceptable salt, hydrate, solvate, prodrug, stereoisomer, or tautomer thereof.

Embodiment 12: The compound of any one of the Embodiments 1-11, wherein the compound is selected from:

1-(benzofuran-3-yl)dihydropyrimidine-2,4(1H,3H)-dione;

1-(6-ethynylbenzofuran-3-yl)dihydropyrimidine-2,4(1H, 3H)-dione;

1-(5-methylbenzofuran-3-yl)dihydropyrimidine-2,4(1H, 3H)-dione;

1-(5-iodobenzofuran-3-yl)dihydropyrimidine-2,4(1H,3H)-dione;

1-(6-iodobenzofuran-3-yl)dihydropyrimidine-2,4(1H,3H)-dione; phenyl (3-(2,4-dioxotetrahydropyrimidin-1(2H)-yl)benzofuran-5-yl)carbamate;

1-(6-chloropyrazolo[1,5-a]pyridin-3-yl)dihydropyrimidine-2,4(1H,3H)-dione;

1-(7-(1-benzyl-1,2,3,6-tetrahydropyridin-4-yl)imidazo[1,2-a]pyridin-3-yl)dihydropyrimidine-2,4(1H,3H)-dione;

1-(7-(1-(4-(tert-butyl)benzoyl)-1,2,3,6-tetrahydropyridin-4-yl)imidazo[1,2-a]pyridin-3-yl)dihydropyrimidine-2,4 (1H,3H)-dione; and 1-(6-(1-benzylpiperidin-4-yl)imidazo[1,2-a]pyridin-3-yl)dihydropyrimidine-2,4(1H,3H)-dione;

or a pharmaceutically acceptable salt, hydrate, solvate, prodrug, stereoisomer, or tautomer thereof.

Embodiment 13: A pharmaceutical composition comprising a compound of any one of Embodiments 1-12, or a pharmaceutically acceptable salt, hydrate, solvate, prodrug, stereoisomer, or tautomer thereof, and a pharmaceutically acceptable carrier or excipient.

Embodiment 14: The pharmaceutical composition of Embodiment 13 further comprising at least one additional pharmaceutical agent.

Embodiment 15: The pharmaceutical composition of Embodiment 13 or Embodiment 14 for use in the treatment or prevention of a cereblon-mediated disorder, disease, or condition.

Embodiment 16: The pharmaceutical composition of Embodiment 13 or Embodiment 14 for use in the treatment or prevention of a respiratory disorder, a proliferative disorder, an autoimmune disorder, an autoinflammatory disorder, an inflammatory disorder, a neurological disorder, and an infectious disease or disorder.

Embodiment 17: A method of modulating cereblon in a biological sample comprising contacting the sample with a compound of any one of Embodiments 1-12, or a pharmaceutically acceptable salt thereof.

Embodiment 18: A method of binding to and altering the specificity of a cereblon complex to induce the ubiquitination and degradation of a complex-associated protein selected from the group listed in TABLE 1 in a biological sample, comprising contacting the sample with a compound of any one of Embodiments 1-12, or a pharmaceutically acceptable salt, hydrate, solvate, prodrug, stereoisomer, or tautomer thereof.

Embodiment 19: A method of treating or preventing a cereblon-mediated disorder, disease, or condition in a subject comprising administering to the subject a compound of any one of Embodiments 1-12, or a pharmaceutically acceptable salt, hydrate, solvate, prodrug, stereoisomer, or tautomer thereof.

Embodiment 20: The method of Embodiment 19, wherein the disorder, disease, or condition is a respiratory disorder, a proliferative disorder, an autoimmune disorder, an autoinflammatory disorder, an inflammatory disorder, a neurological disorder, or an infectious disease or disorder.

Embodiment 21: The method of Embodiment 20, wherein the disorder, disease, or condition is a proliferative disorder.

Embodiment 22: The method of Embodiment 21, wherein the proliferative disorder is cancer.

Embodiment 23: The method of Embodiment 20, wherein the disorder, disease, or condition is a neurological disorder.

Embodiment 24: A method of treating or preventing a respiratory disorder, a proliferative disorder, an autoimmune disorder, an autoinflammatory disorder, an inflammatory disorder, a neurological disorder, or an infectious disease or disorder in a subject in need thereof, the method comprising administering to the subject a therapeutically effective amount of a compound of any one of Embodiments 1-12, or a pharmaceutically acceptable salt thereof.

Embodiment 25: The method of Embodiment 24, wherein the disorder or disease is a proliferative disorder.

Embodiment 26: The method of Embodiment 25, wherein the proliferative disorder is cancer.

Embodiment 27: The method of Embodiment 24, wherein the disorder or disease is a neurological disorder.

Embodiment 28: Use of a compound of any one of Embodiments 1-12, or a pharmaceutically acceptable salt, hydrate, solvate, prodrug, stereoisomer, or tautomer thereof in the preparation of a medicament for treating or preventing a respiratory disorder, a proliferative disorder, an autoimmune disorder, an autoinflammatory disorder, an inflammatory disorder, a neurological disorder, or an infectious disease or disorder in a subject in need thereof.

Embodiment 29: Use of a compound of Embodiments 1-12, or a pharmaceutically acceptable salt, hydrate, solvate, prodrug, stereoisomer, or tautomer thereof for treating or preventing cancer.

Embodiment 30: A method of degrading a target protein in a biological sample comprising contacting the compound of any one of Embodiments 1-12, or a pharmaceutically acceptable salt, hydrate, solvate, prodrug, stereoisomer, or tautomer thereof, wherein the target protein is selected from the group listed in TABLE 1.

Embodiment 31: A method of treating or preventing a target protein-mediated disorder, disease, or condition in a subject comprising administering to the subject the compound of any one of Embodiments 1-12, or a pharmaceutically acceptable salt, hydrate, solvate, prodrug, stereoisomer, or tautomer thereof.

Embodiment 32: The method of Embodiment 31, wherein the disorder, disease, or condition is a proliferative disorder.

Embodiment 33: The method of Embodiment 32, wherein the proliferative disorder is cancer.

Embodiment 34: The method of Embodiment 31, wherein the disorder, disease, or condition is a neurological disorder.

Embodiment 35: A compound selected from:

| Cmpd No. | Structure | Compound Name |
| --- | --- | --- |
| I-1 | 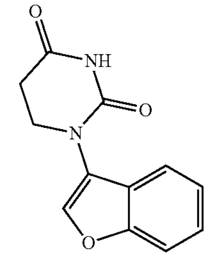 [SMILES: O=C1CCN(c2coc3ccccc23)C(=O)N1] | 1-(benzofuran-3-yl)dihydropyrimidine-2,4(1H,3H)-dione; |
| I-2 | 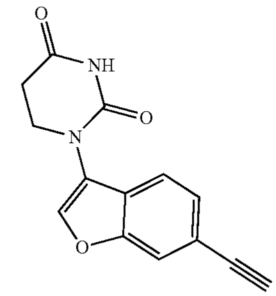 [SMILES: C#Cc1ccc2c(N3CCC(=O)NC3=O)coc2c1] | 1-(6-ethynylbenzofuran-3-yl)dihydropyrimidine-2,4(1H,3H)-dione; |

-continued
| Cmpd No. | Structure | Compound Name |
|---|---|---|
| I-3 | 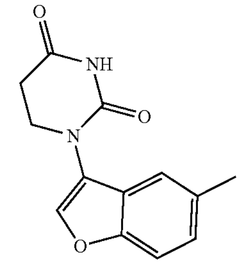 [SMILES: Cc1ccc2occ(N3CCC(=O)NC3=O)c2c1] | 1-(5-methylbenzofuran-3-yl)dihydropyrimidine-2,4(1H,3H)-dione; |
| I-4 | 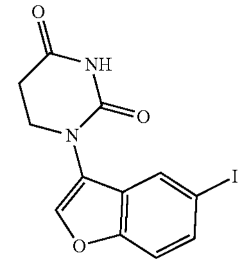 [SMILES: O=C1CCN(c2coc3ccc(I)cc23)C(=O)N1] | 1-(5-iodobenzofuran-3-yl)dihydropyrimidine-2,4(1H,3H)-dione; |
| I-5 | 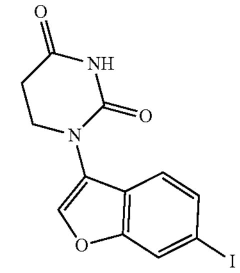 [SMILES: O=C1CCN(c2coc3cc(I)ccc23)C(=O)N1] | 1-(6-iodobenzofuran-3-yl)dihydropyrimidine-2,4(1H,3H)-dione: |
| I-6 | 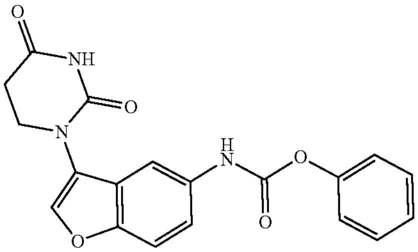 [SMILES: O=C1CCN(c2coc3ccc(NC(=O)Oc4ccccc4)cc23)C(=O)N1] | phenyl (3-(2,4-dioxotetrahydropyrimidin-1(2H)-yl)benzofuran-5-yl)carbamate; |
| I-7 | 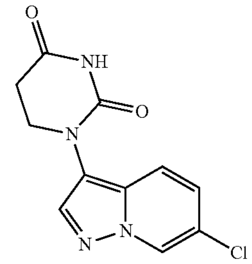 [SMILES: O=C1CCN(c2cnn3cc(Cl)ccc23)C(=O)N1] | 1-(6-chloropyrazolo[1,5-a]pyridin-3-yl)dihydropyrimidine-2,4(1H,3H)-dione |

-continued

| Cmpd No. | Structure | Compound Name |
|---|---|---|
| I-8 | 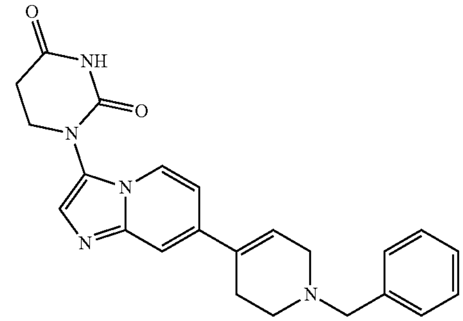 [SMILES: O=C1CCN(c2cnc3cc(C4=CCN(Cc5ccccc5)CC4)ccn23)C(=O)N1] | 1-(7-(1-benzyl-1,2,3,6-tetrahydropyridin-4-yl)imidazo[1,2-a]pyridin-3-yl)dihydropyrimidine-2,4(1H,3H)-dione; |
| I-9 | 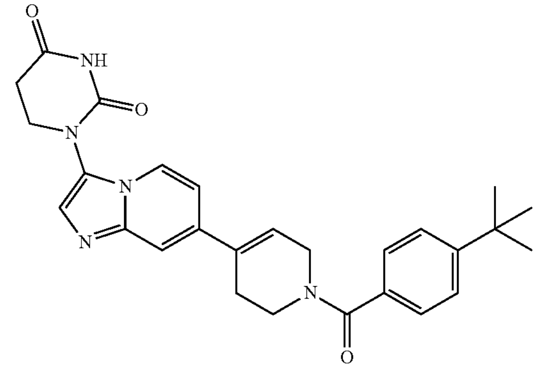 [SMILES: CC(C)(C)c1ccc(C(=O)N2CC=C(c3ccn4c(N5CCC(=O)NC5=O)cnc4c3)CC2)cc1] | 1-(7-(1-(4-(tert-butyl)benzoyl)-1,2,3,6-tetrahydropyridin-4-yl)imidazo[1,2-a]pyridin-3-yl)dihydropyrimidine-2,4(1H,3H)-dione; and |
| I-10 | 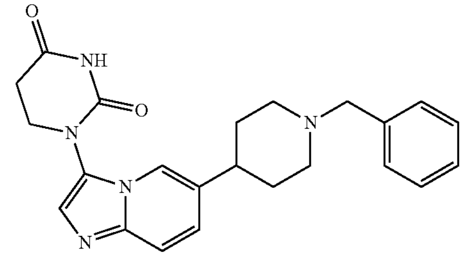 [SMILES: O=C1CCN(c2cnc3ccc(C4CCN(Cc5ccccc5)CC4)cn23)C(=O)N1] | 1-(6-(1-benzylpiperidin-4-yl)imidazo[1,2-a]pyridin-3-yl)dihydropyrimidine-2,4(1H,3H)-dione. |

Embodiment 35A: A compound selected from:

| Cmpd No. | Structure | Compound Name |
|---|---|---|
| I-1 | 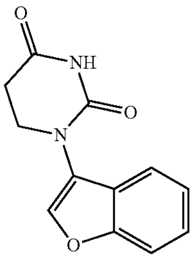 [SMILES: O=C1CCN(c2coc3ccccc23)C(=O)N1] | 1-(benzofuran-3-yl)dihydropyrimidine-2,4(1H,3H)-dione; |

-continued
| Cmpd No. | Structure | Compound Name |
| --- | --- | --- |
| I-2 | 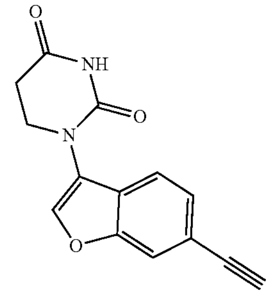 [SMILES: C#Cc1ccc2c(N3CCC(=O)NC3=O)coc2c1] | 1-(6-ethynylbenzofuran-3-yl)dihydropyrimidine-2,4(1H,3H)-dione; |
| I-3 | 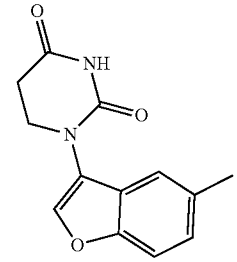 [SMILES: Cc1ccc2occ(N3CCC(=O)NC3=O)c2c1] | 1-(5-methylbenzofuran-3-yl)dihydropyrimidine-2,4(1H,3H)-dione; |
| I-4 | 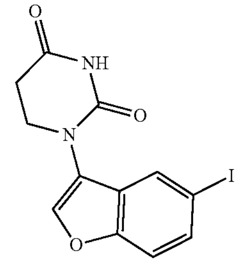 [SMILES: O=C1CCN(c2coc3ccc(I)cc23)C(=O)N1] | 1-(5-iodobenzofuran-3-yl)dihydropyrimidine-2,4(1H,3H)-dione; |
| I-5 | 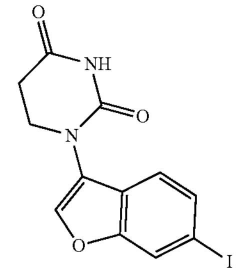 [SMILES: O=C1CCN(c2coc3cc(I)ccc23)C(=O)N1] | 1-(6-iodobenzofuran-3-yl)dihydropyrimidine-2,4(1H,3H)-dione; |
| I-6 | 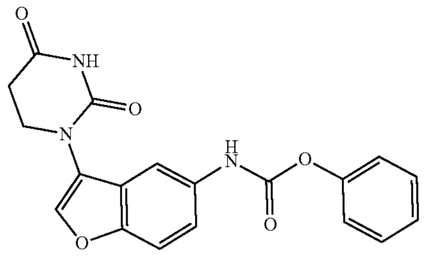 [SMILES: O=C1CCN(c2coc3ccc(NC(=O)Oc4ccccc4)cc23)C(=O)N1] | phenyl (3-(2,4-dioxotetrahydropyrimidin-1(2H)-yl)benzofuran-5-yl)carbamate; |

-continued

| Cmpd No. | Structure | Compound Name |
|---|---|---|
| I-7 | 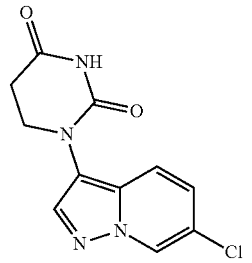 [SMILES: O=C1CCN(c2cnn3cc(Cl)ccc23)C(=O)N1] | 1-(6-chloropyrazolo[1,5-a]pyridin-3-yl)dihydropyrimidine-2,4(1H,3H)-dione |
| I-8 | 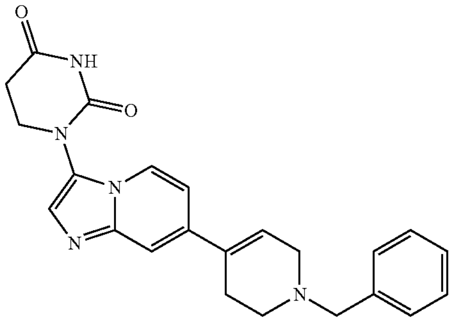 [SMILES: O=C1CCN(c2cnc3cc(C4=CCN(Cc5ccccc5)CC4)ccn23)C(=O)N1] | 1-(7-(1-benzyl-1,2,3,6-tetrahydropyridin-4-yl)imidazo[1,2-a]pyridin-3-yl)dihydropyrimidine-2,4(1H,3H)-dione; |
| I-9 | 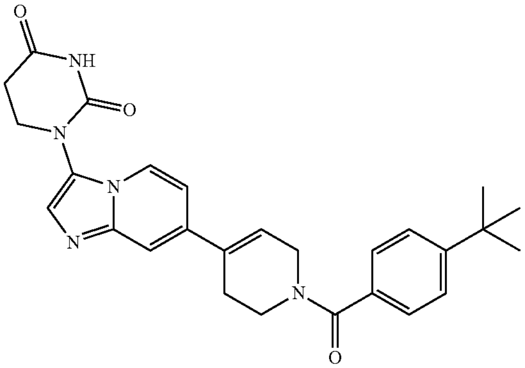 [SMILES: CC(C)(C)c1ccc(C(=O)N2CC=C(c3ccn4c(N5CCC(=O)NC5=O)cnc4c3)CC2)cc1] | 1-(7-(1-(4-(tert-butyl)benzoyl)-1,2,3,6-tetrahydropyridin-4-yl)imidazo[1,2-a]pyridin-3-yl)dihydropyrimidine-2,4(1H,3H)-dione; |
| I-10 | 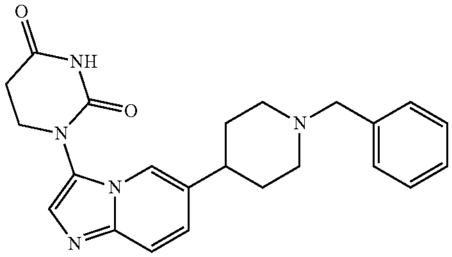 [SMILES: O=C1CCN(c2cnc3ccc(C4CCN(Cc5ccccc5)CC4)cn23)C(=O)N1] | 1-(6-(1-benzylpiperidin-4-yl)imidazo[1,2-a]pyridin-3-yl)dihydropyrimidine-2,4(1H,3H)-dione; |
| I-11 | 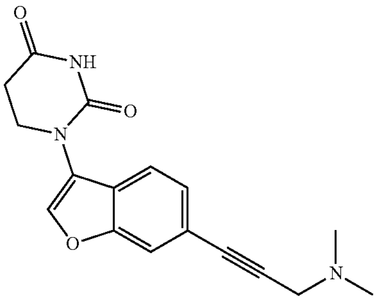 [SMILES: CN(C)CC#Cc1ccc2c(N3CCC(=O)NC3=O)coc2c1] | 1-(6-(3-(dimethylamino)prop-1-yn-1-yl)benzofuran-3-yl)dihydropyrimidine-2,4(1H,3H)-dione; |

-continued

| Cmpd No. | Structure | Compound Name |
|---|---|---|
| I-12 | 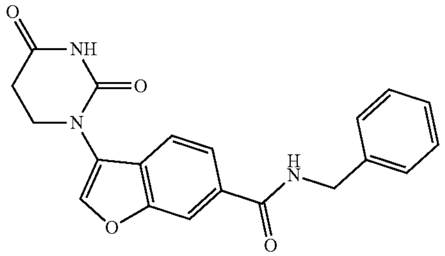 [SMILES: O=C1CCN(c2coc3cc(C(=O)NCc4ccccc4)ccc23)C(=O)N1] | N-benzyl-3-(2,4-dioxotetrahydropyrimidin-1(2H)-yl)benzofuran-6-carboxamide; |
| I-13 | 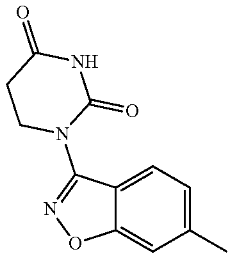 [SMILES: Cc1ccc2c(N3CCC(=O)NC3=O)noc2c1] | 1-(6-methylbenzo[d]isoxazol-3-yl)dihydropyrimidine-2,4(1H,3H)-dione; |
| I-14 | 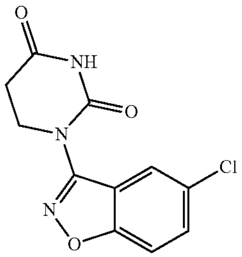 [SMILES: O=C1CCN(c2noc3ccc(Cl)cc23)C(=O)N1] | 1-(5-chlorobenzo[d]isoxazol-3-yl)dihydropyrimidine-2,4(1H,3H)-dione; |
| I-15 | 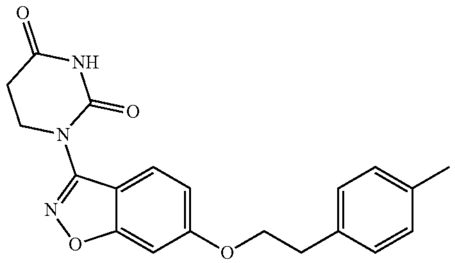 [SMILES: Cc1ccc(CCOc2ccc3c(N4CCC(=O)NC4=O)noc3c2)cc1] | 1-(6-(4-methylphenethoxy)benzo[d]isoxazol-3-yl)dihydropyrimidine-2,4(1H,3H)-dione; |
| I-16 | 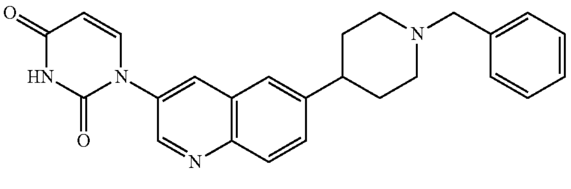 [SMILES: O=c1ccn(-c2cnc3ccc(C4CCN(Cc5ccccc5)CC4)cc3c2)c(=O)[nH]1] | 1-(6-(1-benzylpiperidin-4-yl)quinolin-3-yl)pyrimidine-2,4(1H,3H)-dione; |
| I-17 | 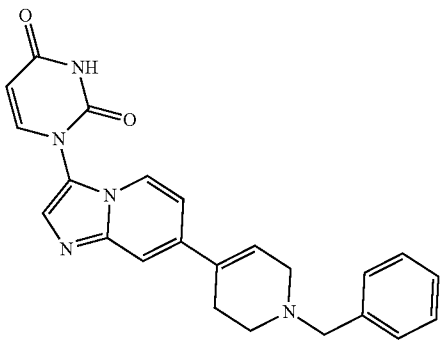 [SMILES: O=c1ccn(-c2cnc3cc(C4=CCN(Cc5ccccc5)CC4)ccn23)c(=O)[nH]1] | 1-(7-(1-benzyl-1,2,3,6-tetrahydropyridin-4-yl)imidazo[1,2-a]pyridin-3-yl)pyrimidine-2,4(1H,3H)-dione; and |

-continued

| Cmpd No. | Structure | Compound Name |
|---|---|---|
| I-18 | 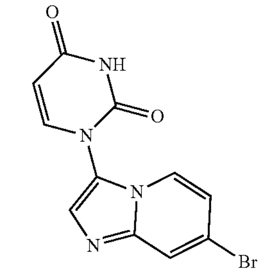 [SMILES: O=c1ccn(-c2cnc3cc(Br)ccn23)c(=O)[nH]1] | 1-(7-bromoimidazo[1,2-a]pyridin-3-yl)pyrimidine-2,4(1H,3H)-dione. |

or a pharmaceutically acceptable salt, hydrate, solvate, prodrug, stereoisomer, or tautomer thereof.

Embodiment 36: A pharmaceutical composition comprising a compound of Embodiment 35 or Embodiment 35A, or a pharmaceutically acceptable salt, hydrate, solvate, prodrug, stereoisomer, or tautomer thereof, and a pharmaceutically acceptable carrier or excipient.

Embodiment 37: The pharmaceutical composition of Embodiment 36 further comprising at least one additional pharmaceutical agent.

Embodiment 38: The pharmaceutical composition of Embodiment 36 or Embodiment 37 for use in the treatment or prevention of a cereblon-mediated disorder, disease, or condition.

Embodiment 39: The pharmaceutical composition of Embodiment 36 or Embodiment 37 for use in the treatment or prevention of a respiratory disorder, a proliferative disorder, an autoimmune disorder, an autoinflammatory disorder, an inflammatory disorder, a neurological disorder, or an infectious disease or disorder.

Embodiment 40: A method of inhibiting cereblon in a biological sample comprising contacting the sample with a compound of Embodiment 35 or Embodiment 35A, or a pharmaceutically acceptable salt thereof.

Embodiment 41: A method of binding to and altering the specificity of a cereblon complex to induce the ubiquitination and degradation of a complex-associated protein selected from the group listed in TABLE 1 in a biological sample, comprising contacting the sample with a compound of Embodiment 35 or Embodiment 35A, or a pharmaceutically acceptable salt, hydrate, solvate, prodrug, stereoisomer, or tautomer thereof.

Embodiment 42: A method of treating or preventing a cereblon-mediated disorder, disease, or condition in a subject comprising administering to the subject a compound of Embodiment 35 or Embodiment 35A, or a pharmaceutically acceptable salt, hydrate, solvate, prodrug, stereoisomer, or tautomer thereof.

Embodiment 43: The method of Embodiment 42, wherein the disorder, disease, or condition is a respiratory disorder, a proliferative disorder, an autoimmune disorder, an autoinflammatory disorder, an inflammatory disorder, a neurological disorder, or an infectious disease or disorder.

Embodiment 44: The method of Embodiment 43, wherein the disorder, disease, or condition is a proliferative disorder.

Embodiment 45: The method of Embodiment 44, wherein the proliferative disorder is cancer.

Embodiment 46: The method of Embodiment 43, wherein the disorder, disease, or condition is a neurological disorder.

Embodiment 47: A method of treating or preventing a respiratory disorder, a proliferative disorder, an autoimmune disorder, an autoinflammatory disorder, an inflammatory disorder, a neurological disorder, or an infectious disease or disorder in a subject in need thereof, the method comprising administering to the subject a therapeutically effective amount of a compound of Embodiment 35 or Embodiment 35A, or a pharmaceutically acceptable salt thereof.

Embodiment 48: The method of Embodiment 47, wherein the disorder or disease is a proliferative disorder.

Embodiment 49: The method of Embodiment 48, wherein the proliferative disorder is cancer.

Embodiment 50: The method of Embodiment 47, wherein the disorder or disease is a neurological disorder.

Embodiment 51: Use of a compound of Embodiment 35 or Embodiment 35A, or a pharmaceutically acceptable salt, hydrate, solvate, prodrug, stereoisomer, or tautomer thereof in the preparation of a medicament for treating or preventing a respiratory disorder, a proliferative disorder, an autoimmune disorder, an autoinflammatory disorder, an inflammatory disorder, a neurological disorder, or an infectious disease or disorder in a subject in need thereof.

Embodiment 52: Use of a compound of Embodiment 35 or Embodiment 35A, or a pharmaceutically acceptable salt, hydrate, solvate, prodrug, stereoisomer, or tautomer thereof for treating or preventing cancer.

Embodiment 53: A method of degrading a target protein in a biological sample comprising contacting a compound of Embodiment 35 or Embodiment 35A, or a pharmaceutically acceptable salt, hydrate, solvate, prodrug, stereoisomer, or tautomer thereof, wherein the target protein is selected from the group listed in TABLE 1.

Embodiment 54: A method of treating or preventing a target protein-mediated disorder, disease, or condition in a subject comprising administering to the subject a compound of Embodiment 35 or Embodiment 35A, or a pharmaceutically acceptable salt, hydrate, solvate, prodrug, stereoisomer, or tautomer thereof.

Embodiment 55: The method of Embodiment 54, wherein the disorder, disease, or condition is a proliferative disorder.

Embodiment 56: The method of Embodiment 55, wherein the proliferative disorder is cancer.

Embodiment 57: The method of Embodiment 54, wherein the disorder, disease, or condition is a neurological disorder.

Embodiment 58: A method of treating or preventing a cancer in a subject comprising administering to the subject a compound of Embodiment 35 or Embodiment 35A, or a pharmaceutically acceptable salt, hydrate, solvate, prodrug, stereoisomer, or tautomer thereof.

Embodiment 59: A compound of any one of Embodiments 1-12, or a pharmaceutically acceptable salt, hydrate, solvate, prodrug, stereoisomer, or tautomer thereof for use in the treatment or prevention of a respiratory disorder, a proliferative disorder, an autoimmune disorder, an autoinflammatory disorder, an inflammatory disorder, a neurological disorder, or an infectious disease or disorder in a subject in need thereof.

Embodiment 60: A compound of Embodiments 1-12, or a pharmaceutically acceptable salt, hydrate, solvate, prodrug, stereoisomer, or tautomer thereof for use in the treatment or prevention of cancer.

Embodiment 61: Use of a compound of Embodiments 1-12, or a pharmaceutically acceptable salt, hydrate, solvate, prodrug, stereoisomer, or tautomer thereof in the preparation of a medicament for treating or preventing a target protein-mediated disorder, disease, or condition in a subject.

Embodiment 62: A compound of Embodiments 1-12, or a pharmaceutically acceptable salt, hydrate, solvate, prodrug, stereoisomer, or tautomer thereof for use in the treatment or prevention of a target protein-mediated disorder, disease, or condition in a subject.

Embodiment 63: A compound of Embodiment 35 or Embodiment 35A, or a pharmaceutically acceptable salt, hydrate, solvate, prodrug, stereoisomer, or tautomer thereof for use in the treatment or prevention of a respiratory disorder, a proliferative disorder, an autoimmune disorder, an autoinflammatory disorder, an inflammatory disorder, a neurological disorder, and an infectious disease or disorder in a subject in need thereof.

Embodiment 64: A compound of Embodiment 35 or Embodiment 35A, or a pharmaceutically acceptable salt, hydrate, solvate, prodrug, stereoisomer, or tautomer thereof for use in the treatment or prevention of cancer.

Embodiment 65: Use of a compound of Embodiment 35 or Embodiment 35A, or a pharmaceutically acceptable salt, hydrate, solvate, prodrug, stereoisomer, or tautomer thereof in the preparation of a medicament for treating or preventing a target protein-mediated disorder, disease, or condition in a subject.

Embodiment 66: A compound of Embodiment 35 or Embodiment 35A, or a pharmaceutically acceptable salt, hydrate, solvate, prodrug, stereoisomer, or tautomer thereof for use in the treatment or prevention of a target protein-mediated disorder, disease, or condition in a subject.

Embodiment 67: A method of treating or preventing a cancer in a subject comprising administering to the subject a compound of any one of Embodiments 1-12, or a pharmaceutically acceptable salt, hydrate, solvate, prodrug, stereoisomer, or tautomer thereof.

Embodiment 68: A compound or a pharmaceutically acceptable salt, hydrate, solvate, prodrug, stereoisomer, or tautomer thereof, capable of binding to and altering the specificity of a cereblon complex to induce ubiquitination and degradation of a complex-associated protein.

Embodiment 69: The compound according to Embodiment 68, wherein the compound comprises, (i) a tris-tryptophan Pocket Binder moiety that binds to the tris-tryptophan pocket of Cereblon E3 ligase; and (ii) a target affinity moiety attached covalently to the tris-tryptophan Pocket Binder moiety that interacts with the surface of the Cereblon E3 ligase altering its surface and causing the ligase to have affinity for a Target Protein.

Embodiment 70: The compound according to Embodiment 68 or 69, wherein the compound has a Formula (I):

(I)

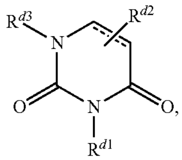

or a pharmaceutically acceptable salt, hydrate, solvate, prodrug, stereoisomer, or tautomer thereof, wherein:

⎓ is a single bond or a double bond;

$R^{d1}$ is H, $—CH_2OC(O)R^{15}$, $—CH_2OP(O)OHOR^{15}$, or $—CH_2OP(O)(R^{15})_2$;

$R^{12}$ is H, $C_{1-6}$ alkyl, halogen, $C_{1-6}$ haloalkyl, or $C_{1-6}$ heteroalkyl; $R^{d3}$ is

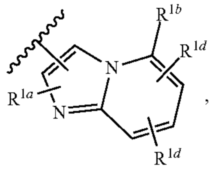,
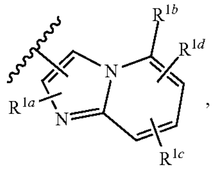,
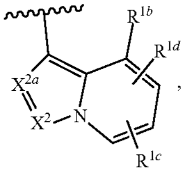,
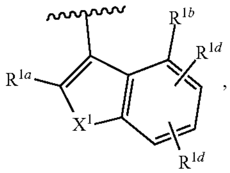,
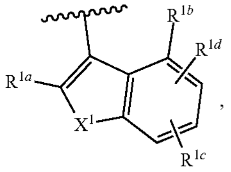,
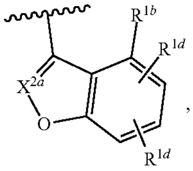,
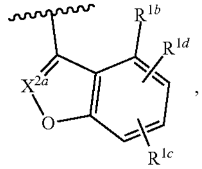,
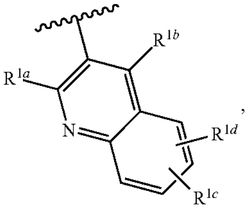,
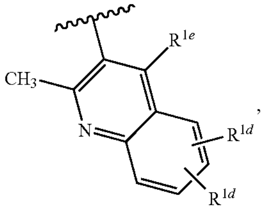,
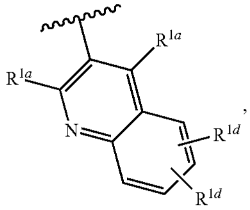,
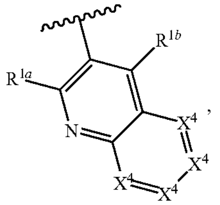,
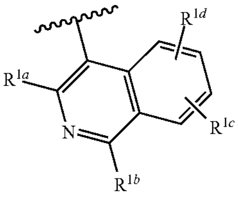, -continued
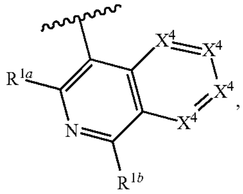,
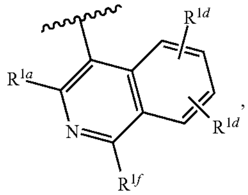,
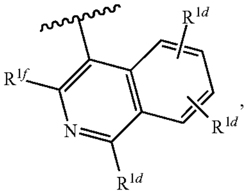,
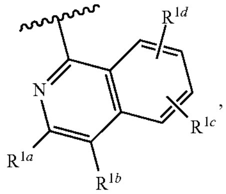,
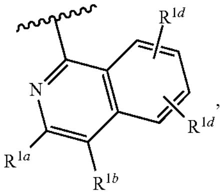,
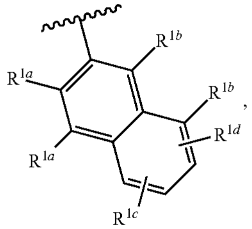,
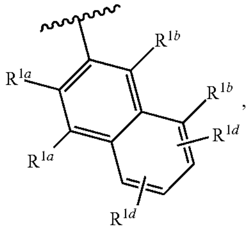,
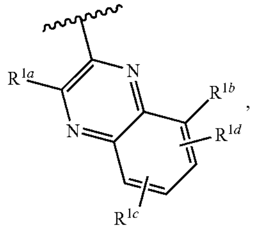,
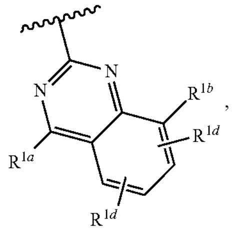,
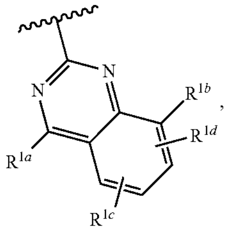,
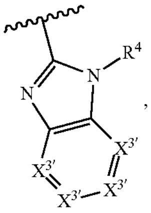,
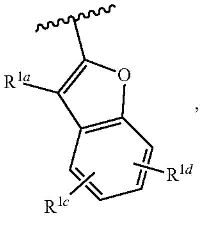,
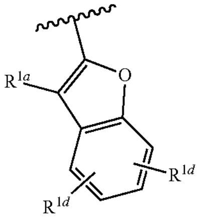,
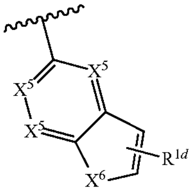,
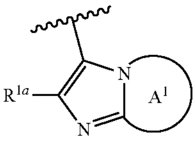,
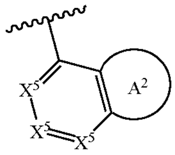,
-continued
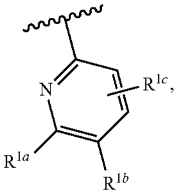,
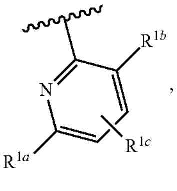,
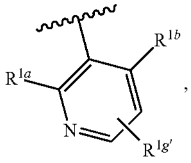,
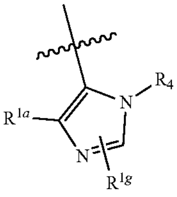,
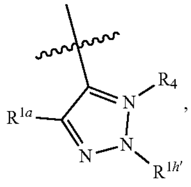,
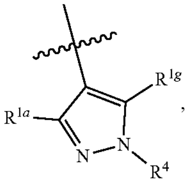,
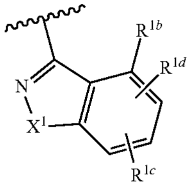,
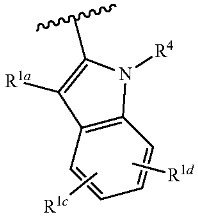,
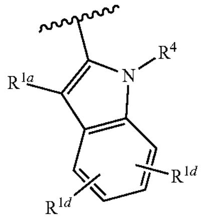,
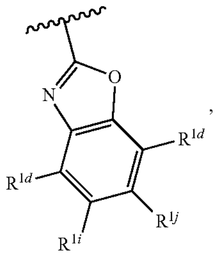,
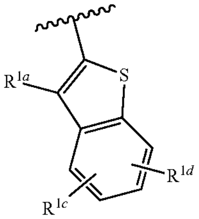,
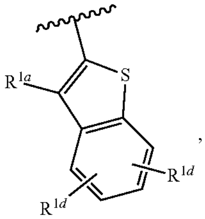,
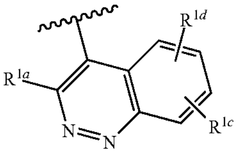,
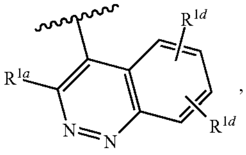,
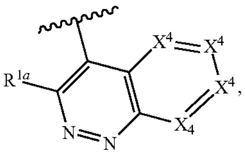,
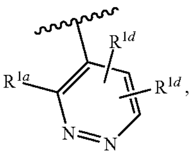, -continued

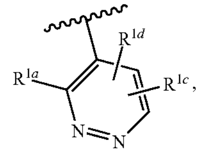

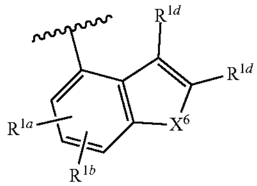
,

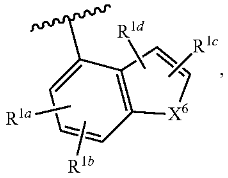
,

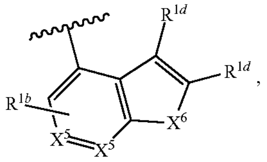

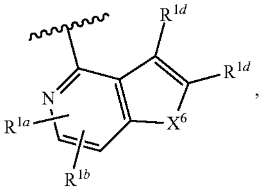
,

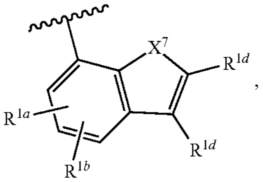
,

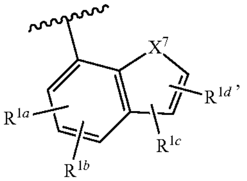

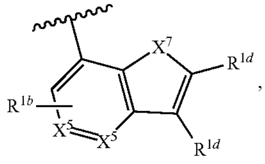
,

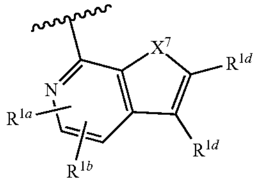

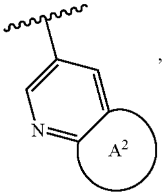
,

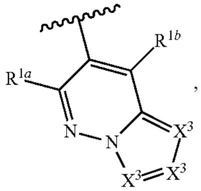
,

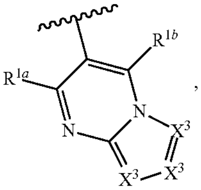
,

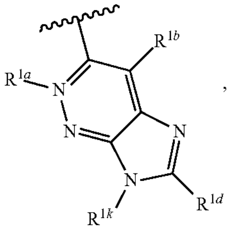
,

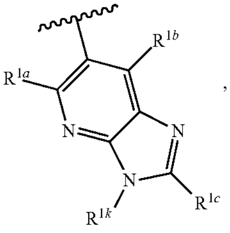
,

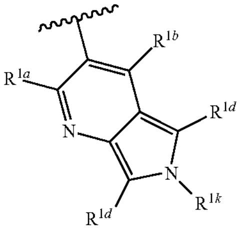
,

-continued

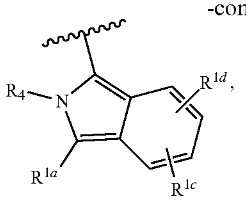
or

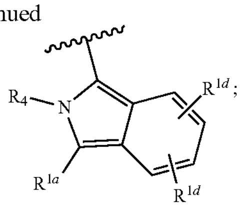
;

$A^1$ is a 5- or 6-member heterocyclyl optionally comprising 1-3 additional heteroatoms selected from O, N, and S or 5-membered heteroaryl optionally comprising 1-3 additional heteroatoms selected form $NR^{1k}$, O, and S and substituted with one to three $R^{1d}$.

$A^2$ is a $C_{5-7}$ carbocyclyl or 5- to 7-membered heterocyclyl comprising 1-3 heteroatoms selected from N, $NR^{1k}$, O, and S, wherein the carbocyclyl and heterocyclyl are substituted with one to three $R^{1d}$;

$X^1$ is $NR^4$ or S;

$X^2$ and $X^{2a}$ are each independently $CR^{1a}$ or N;

each $X^3$ is independently $CR^{1d}$ or N, wherein no more than two $X^3$ are N;

each $X^{3'}$ is independently $CR^{1d}$, $CR^{1c}$ or N, wherein no more than two $X^3$ are N and wherein at least one $X^{3'}$ is $CR^{1c}$;

each $X^4$ is independently $CR^{1d}$ or N, wherein at least one $X^4$ is N and wherein no more than two $X^4$ are N;

each $X^5$ is independently $CR^{1a}$ or N, wherein no more than two $X^5$ are N;

$X^6$ is $NR^{1k}$, O, or S;

$X^7$ is $NR^4$, O, or S;

$R^{1a}$ and $R^{1b}$ are each independently H, $C_{1-3}$ alkyl, $C_{1-3}$ haloalkyl, $C_{1-3}$ alkoxy, $C_{1-3}$ haloalkoxy, —$NH_2$, —NH($C_{1-3}$ alkyl), —N($C_{1-3}$ alkyl)$_2$, —CN, F, or Cl;

$R^{1c}$ is $C_{1-6}$ alkyl, $C_{2-6}$ alkenyl, $C_{2-6}$ alkynyl, $C_{1-6}$ haloalkyl, $C_{1-6}$ alkoxy, CI-3 haloalkoxy, halogen, CN, —C(O)OH, —C(O)O$C_{1-6}$ alkyl, —$(CH_2)_{0-4}$—C(O)$NH_2$, —$(CH_2)_{0-4}$—C(O)NH($R^{13}$), —$(CH_2)_{0-4}$—C(O)N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3(CH_2)_{0-4}$-5- to 7-membered heterocyclyl comprising 1-3 heteroatoms selected from O, N, and S, —$(CH_2)_{0-4}NR^3(CH_2)_{0-4}$—$C_{6-10}$ aryl, —$(CH_2)_{0-4}NR^3(CH_2)_{0-4}$-5- or 6-membered heteroaryl comprising 1-3 heteroatoms selected from O, N, and S, —$(CH_2)_{0-4}$—$NR^3$C(O)—$C_{3-7}$ carbocyclyl, —$(CH_2)_{0-4}$—$NR^3$C(O)-5- to 7-membered heterocyclyl comprising 1-3 heteroatoms selected from O, N, and S, —$(CH_2)_{0-4}$—$NR^3$C(O)—$C_{6-10}$ aryl, —$(CH_2)_{0-4}$—$NR^3$C(O)-5- or 6-membered heteroaryl comprising 1-3 heteroatoms selected from O, N, and S, —$NR^3$C(O)O$(CH_2)_{0-4}$—$C_{3-7}$ carbocyclyl, —$NR^3$C(O)O$(CH_2)_{0-4}$-5- to 7-membered heterocyclyl comprising 1-3 heteroatoms selected from O, N, and S, —$NR^3$C(O)O$(CH_2)_{0-4}$—$C_{6-10}$ aryl, or —$NR^3$C(O)O$(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1c'}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, F, Cl, CN, —C(O)OH, —C(O)O$C_{1-6}$ alkyl, —$(CH_2)_{0-4}$—C(O)$NH_2$, —(CH$_2$)$_{0-4}$—C(O)NH(R$^{13}$), —(CH$_2$)$_{0-4}$—C(O)N(R$^{13}$)$_2$, —(CH$_2$)$_{0-6}$—C$_{3-7}$ carbocyclyl, —(CH$_2$)$_{0-6}$-5- to 7-membered heterocyclyl comprising 1-3 heteroatoms selected from O, N, and S, —(CH$_2$)$_{0-6}$ C$_{6-10}$ aryl, —(CH$_2$)$_{0-6}$-5- or 6-membered heteroaryl comprising 1-3 heteroatoms selected from O, N, and S, —(CH$_2$)$_{0-4}$NR$^3$(CH$_2$)$_{0-4}$—C$_{3-7}$ carbocyclyl, —(CH$_2$)$_{0-4}$NR$^3$(CH$_2$)$_{0-4}$-5- to 7-membered heterocyclyl comprising 1-3 heteroatoms selected from O, N, and S, —(CH$_2$)$_{0-4}$NR$^3$(CH$_2$)$_{0-4}$—C$_{6-10}$ aryl, —(CH$_2$)$_{0-4}$NR$^3$(CH$_2$)$_{0-4}$-5- or 6-membered heteroaryl comprising 1-3 heteroatoms selected from O, N, and S, —(CH$_2$)$_{0-4}$—NR$^3$C(O)—C$_{3-7}$ carbocyclyl, —(CH$_2$)$_{0-4}$—NR$^3$C(O)-5- to 7-membered heterocyclyl comprising 1-3 heteroatoms selected from O, N, and S, —(CH$_2$)$_{0-4}$—NR$^3$C(O)—C$_{6-10}$ aryl, —(CH$_2$)$_{0-4}$—NR$^3$C(O)-5- or 6-membered heteroaryl comprising 1-3 heteroatoms selected from O, N, and S, —NR$^3$C(O)O(CH$_2$)$_{0-4}$—C$_{3-7}$ carbocyclyl, —NR$^3$C(O)O(CH$_2$)$_{0-4}$-5- to 7-membered heterocyclyl comprising 1-3 heteroatoms selected from O, N, and S, —NR$^3$C(O)O(CH$_2$)$_{0-4}$—C$_{6-10}$ aryl, or —NR$^3$C(O)O(CH$_2$)$_{0-4}$-5- or 6-membered heteroaryl comprising 1-3 heteroatoms selected from O, N, and S, wherein the alkynyl is optionally substituted with one to three R$^2$ and the carbocyclyl, heterocyclyl, aryl, and heteroaryl are optionally substituted with one to five R$^5$;

each R$^{1d}$ is independently is selected from H, C$_{1-6}$ alkyl, C$_{2-6}$ alkenyl, C$_{2-6}$ alkynyl, C$_{1-6}$ haloalkyl, C$_{1-6}$ alkoxy, C$_{1-3}$ haloalkoxy, halogen, CN, —C(O)OH, —C(O)OC$_{1-6}$ alkyl, —(CH$_2$)$_{0-4}$—C(O)NH$_2$, —(CH$_2$)$_{0-4}$—C(O)NH(R$^{13}$), —(CH$_2$)$_{0-4}$—C(O)N(R$^{13}$)$_2$, —(CH$_2$)$_{0-6}$—C$_{3-7}$ carbocyclyl, —(CH$_2$)$_{0-6}$-5- to 7-membered heterocyclyl comprising 1-3 heteroatoms selected from O, N, and S, —(CH$_2$)$_{0-6}$ C$_{6-10}$ aryl, —(CH$_2$)$_{0-6}$-5- or 6-membered heteroaryl comprising 1-3 heteroatoms selected from O, N, and S, —(CH$_2$)$_{0-4}$NR$^3$(CH$_2$)$_{0-4}$—C$_{3-7}$ carbocyclyl, —(CH$_2$)$_{0-4}$NR$^3$(CH$_2$)$_{0-4}$-5- to 7-membered heterocyclyl comprising 1-3 heteroatoms selected from O, N, and S, —(CH$_2$)$_{0-4}$NR$^3$(CH$_2$)$_{0-4}$—C$_{6-10}$ aryl, —(CH$_2$)$_{0-4}$NR$^3$(CH$_2$)$_{0-4}$-5- or 6-membered heteroaryl comprising 1-3 heteroatoms selected from O, N, and S, —(CH$_2$)$_{0-4}$—NR$^3$C(O)—C$_{3-7}$ carbocyclyl, —(CH$_2$)$_{0-4}$—NR$^3$C(O)-5- to 7-membered heterocyclyl comprising 1-3 heteroatoms selected from O, N, and S, —(CH$_2$)$_{0-4}$—NR$^3$C(O)—C$_{6-10}$ aryl, —(CH$_2$)$_{0-4}$—NR$^3$C(O)-5- or 6-membered heteroaryl comprising 1-3 heteroatoms selected from O, N, and S, —NR$^3$C(O)O(CH$_2$)$_{0-4}$—C$_{3-7}$ carbocyclyl, —NR$^3$C(O)O(CH$_2$)$_{0-4}$-5- to 7-membered heterocyclyl comprising 1-3 heteroatoms selected from O, N, and S, —NR$^3$C(O)O(CH$_2$)$_{0-4}$—C$_{6-10}$ aryl, or —NR$^3$C(O)O(CH$_2$)$_{0-4}$-5- or 6-membered heteroaryl comprising 1-3 heteroatoms selected from O, N, and S, wherein the alkynyl is optionally substituted with one to three R$^2$ and the carbocyclyl, heterocyclyl, aryl, and heteroaryl are optionally substituted with one to five R$^5$;

R$^{1e}$ is C$_{2-3}$ alkyl, C$_{1-3}$ haloalkyl, C$_{1-3}$ alkoxy, C$_{1-3}$ haloalkoxy, —CN, F, or Cl;

R$^{1f}$ is C$_{1-3}$ alkyl, C$_{1-3}$ haloalkyl, C$_{1-3}$ alkoxy, C$_{1-3}$ haloalkoxy, —CN, F, or Cl;

R$^{1g}$ is C$_{2-6}$ alkyl, C$_{2-6}$ alkenyl, C$_{2-6}$ alkynyl, C$_{2-6}$ haloalkyl, C$_{1-6}$ alkoxy, C$_{1-3}$ haloalkoxy, CN, —C(O)OH, —C(O)OC$_{1-6}$ alkyl, —(CH$_2$)$_{0-4}$—C(O)NH$_2$, —(CH$_2$)$_{0-4}$—C(O)NH(R$^{13}$), —(CH$_2$)$_{0-4}$—C(O)N(R$^{13}$)$_2$, —(CH$_2$)$_{0-6}$—C$_{3-7}$ carbocyclyl, —(CH$_2$)$_{0-6}$-5- to 7-membered heterocyclyl comprising 1-3 heteroatoms selected from O, N, and S, —(CH$_2$)$_{0-6}$ C$_{6-10}$ aryl, —(CH$_2$)$_{0-6}$-5- or 6-membered heteroaryl comprising 1-3 heteroatoms selected from O, N, and S, —(CH$_2$)$_{0-4}$NR$^3$(CH$_2$)$_{0-4}$—C$_{3-7}$ carbocyclyl, —(CH$_2$)$_{0-4}$NR$^3$(CH$_2$)$_{0-4}$-5- to 7-membered heterocyclyl comprising 1-3 heteroatoms selected from O, N, and S, —(CH$_2$)$_{0-4}$NR$^3$(CH$_2$)$_{0-4}$—C$_{6-10}$ aryl, —(CH$_2$)$_{0-4}$NR$^3$(CH$_2$)$_{0-4}$-5- or 6-membered heteroaryl comprising 1-3 heteroatoms selected from O, N, and S, —(CH$_2$)$_{0-4}$—NR$^3$C(O)—C$_{3-7}$ carbocyclyl, —(CH$_2$)$_{0-4}$—NR$^3$C(O)-5- to 7-membered heterocyclyl comprising 1-3 heteroatoms selected from O, N, and S, —(CH$_2$)$_{0-4}$—NR$^3$C(O)—C$_{6-10}$ aryl, —(CH$_2$)$_{0-4}$—NR$^3$C(O)-5- or 6-membered heteroaryl comprising 1-3 heteroatoms selected from O, N, and S, —NR$^3$C(O)O(CH$_2$)$_{0-4}$—C$_{3-7}$ carbocyclyl, —NR$^3$C(O)O(CH$_2$)$_{0-4}$-5- to 7-membered heterocyclyl comprising 1-3 heteroatoms selected from O, N, and S, —NR$^3$C(O)O(CH$_2$)$_{0-4}$—C$_{6-10}$ aryl, or —NR$^3$C(O)O(CH$_2$)$_{0-4}$-5- or 6-membered heteroaryl comprising 1-3 heteroatoms selected from O, N, and S, wherein the alkynyl is optionally substituted with one to three R$^2$ and the carbocyclyl, heterocyclyl, aryl, and heteroaryl are optionally substituted with one to five R$^5$;

R$^{1g'}$ is C$_{2-6}$ alkyl, C$_{2-6}$ alkenyl, C$_{2-6}$ alkynyl, C$_{2-6}$ haloalkyl, C$_{2-6}$ alkoxy, C$_{1-3}$ haloalkoxy, CN, —C(O)OH, —C(O)OC$_{1-6}$ alkyl, —(CH$_2$)$_{0-4}$—C(O)NH$_2$, —(CH$_2$)$_{0-4}$—C(O)NH(R$^{13}$), —(CH$_2$)$_{0-4}$—C(O)N(R$^{13}$)$_2$, —(CH$_2$)$_{0-6}$—C$_{3-7}$ carbocyclyl, —(CH$_2$)$_{0-6}$-5- to 7-membered heterocyclyl comprising 1-3 heteroatoms selected from O, N, and S, —(CH$_2$)$_{0-6}$ C$_{6-10}$ aryl, —(CH$_2$)$_{0-6}$-5- or 6-membered heteroaryl comprising 1-3 heteroatoms selected from O, N, and S, —(CH$_2$)$_{0-4}$NR$^3$(CH$_2$)$_{0-4}$—C$_{3-7}$ carbocyclyl, —(CH$_2$)$_{0-4}$NR$^3$(CH$_2$)$_{0-4}$-5- to 7-membered heterocyclyl comprising 1-3 heteroatoms selected from O, N, and S, —(CH$_2$)$_{0-4}$NR$^3$(CH$_2$)$_{0-4}$—C$_{6-10}$ aryl, —(CH$_2$)$_{0-4}$NR$^3$(CH$_2$)$_{0-4}$-5- or 6-membered heteroaryl comprising 1-3 heteroatoms selected from O, N, and S, —(CH$_2$)$_{0-4}$—NR$^3$C(O)—C$_{3-7}$ carbocyclyl, —(CH$_2$)$_{0-4}$—NR$^3$C(O)-5- to 7-membered heterocyclyl comprising 1-3 heteroatoms selected from O, N, and S, —(CH$_2$)$_{0-4}$—NR$^3$C(O)—C$_{6-10}$ aryl, —(CH$_2$)$_{0-4}$—NR$^3$C(O)-5- or 6-membered heteroaryl comprising 1-3 heteroatoms selected from O, N, and S, —NR$^3$C(O)O(CH$_2$)$_{0-4}$—C$_{3-7}$ carbocyclyl, —NR$^3$C(O)O(CH$_2$)$_{0-4}$-5- to 7-membered heterocyclyl comprising 1-3 heteroatoms selected from O, N, and S, —NR$^3$C(O)O(CH$_2$)$_{0-4}$—C$_{6-10}$ aryl, or —NR$^3$C(O)O(CH$_2$)$_{0-4}$-5- or 6-membered heteroaryl comprising 1-3 heteroatoms selected from O, N, and S, wherein the alkynyl is optionally substituted with one to three R$^2$, the heterocyclyl is substituted with one to five R$^5$ and the carbocyclyl, aryl, and heteroaryl are optionally substituted with one to five R$^5$;

R$^{1h}$ is C$_{4-6}$ alkyl, C$_{2-6}$ alkenyl, C$_{2-6}$ alkynyl, C$_{2-6}$ haloalkyl, C$_{1-6}$ alkoxy, C$_{1-3}$ haloalkoxy, CN, —C(O)OH, —C(O)OC$_{1-6}$ alkyl, —(CH$_2$)$_{0-4}$—C(O)NH$_2$, —(CH$_2$)$_{0-4}$—C(O)NH(R$^{13}$), —(CH$_2$)$_{0-4}$—C(O)N(R$^{13}$)$_2$, —(CH$_2$)$_{0-6}$—C$_{3-7}$ carbocyclyl, —(CH$_2$)$_{0-6}$-5- to 7-membered heterocyclyl comprising 1-3 heteroatoms selected from O, N, and S, —C$_{6-10}$ aryl, —(CH$_2$)$_{2-6}$ C$_{6-10}$ aryl, —(CH$_2$)$_{0-6}$-5- or 6-membered heteroaryl comprising 1-3 heteroatoms selected from O, N, and S, —(CH$_2$)$_{0-4}$NR$^3$(CH$_2$)$_{0-4}$—C$_{3-7}$ carbocyclyl, —(CH$_2$)$_{0-4}$NR$^3$(CH$_2$)$_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR^3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

$R^{1h'}$ is $C_{4-6}$ alkyl, $C_{2-6}$ alkenyl, $C_{2-6}$ alkynyl, $C_{2-6}$ haloalkyl, $C_{1-6}$ alkoxy, $C_{1-3}$ haloalkoxy, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-C_{6-10}$ aryl, $-(CH_2)_{2-6}$ $C_{6-10}$ aryl, $-(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR^3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$, the heterocyclyl is substituted with one to five $R^5$, and the carbocyclyl, aryl, and heteroaryl are optionally substituted with one to five $R^5$;

$R^{1i}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}$ $C_{6-10}$ aryl, $-(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR^3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$;

$R^{1j}$ is H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}$ $C_{6-10}$ aryl, $-(CH_2)_{0-6}$-5- or 6-membered heteroaryl comprising 1-3 heteroatoms selected from O, N, and S, $-(CH_2)_{0-4}NR^3(CH_2)_{0-4}-C_{3-7}$ carbocyclyl, $-(CH_2)_{0-4}NR^3(CH_2)_{0-4}$-5- to 7-membered heterocyclyl comprising 1-3 heteroatoms selected from O, N, and S, $-(CH_2)_{0-4}NR^3(CH_2)_{0-4}-C_{6-10}$ aryl, $-(CH_2)_{0-4}NR^3(CH_2)_{0-4}$-5- or 6-membered heteroaryl comprising 1-3 heteroatoms selected from O, N, and S, $-(CH_2)_{0-4}-NR^3C(O)-C_{3-7}$ carbocyclyl, $-(CH_2)_{0-4}-NR^3C(O)$-5- to 7-membered heterocyclyl comprising 1-3 heteroatoms selected from O, N, and S, $-(CH_2)_{0-4}-NR^3C(O)-C_{6-10}$ aryl, $-(CH_2)_{0-4}-NR^3C(O)$-5- or 6-membered heteroaryl comprising 1-3 heteroatoms selected from O, N, and S, $-NR^3C(O)O(CH_2)_{0-4}-C_{3-7}$ carbocyclyl, $-NR^3C(O)O(CH_2)_{0-4}$-5- to 7-membered heterocyclyl comprising 1-3 heteroatoms selected from O, N, and S, $-NR^3C(O)O(CH_2)_{0-4}-C_{6-10}$ aryl, or $-NR^3C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl is optionally substituted with one to five $R^5$;

wherein $R^{1d}$, $R^{1i}$, and $R^{1j}$ on the benzoxazole ring are not all simultaneously H;

each $R^{1k}$ is independently is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, $-C(O)OH$, $-C(O)OC_{1-6}$ alkyl, $-(CH_2)_{0-4}-C(O)NH_2$, $-(CH_2)_{0-4}-C(O)NH(R^{13})$, $-(CH_2)_{0-4}-C(O)N(R^{13})_2$, $-(CH_2)_{0-6}-C_{3-7}$ carbocyclyl, $-(CH_2)_{0-6}$-5- to 7-membered heterocyclyl comprising 1-3 heteroatoms selected from O, N, and S, $-(CH_2)_{0-6}$ $C_{6-10}$ aryl, $-(CH_2)_{0-6}$-5- or 6-membered heteroaryl comprising 1-3 heteroatoms selected from O, N, and S, $-C(O)O(CH_2)_{0-4}-C_{3-7}$ carbocyclyl, $-C(O)O(CH_2)_{0-4}$-5- to 7-membered heterocyclyl comprising 1-3 heteroatoms selected from O, N, and S, $-C(O)O(CH_2)_{0-4}-C_{6-10}$ aryl, or $-C(O)O(CH_2)_{0-4}$-5- or 6-membered heteroaryl comprising 1-3 heteroatoms selected from O, N, and S, wherein the alkynyl is optionally substituted with one to three $R^2$ and the carbocyclyl, heterocyclyl, aryl, and heteroaryl are optionally substituted with one to five $R^5$;

each $R^2$ is independently $NH_2$, $-NH(C_{1-6}$ alkyl), $-N(C_{1-6}$ alkyl$)_2$, $-C(O)NH_2$, $-C(O)NH(C_{1-6}$ alkyl), $-C(O)N(C_{1-6}$ alkyl$)_2$, $-NHC(O)R^9$, $-N(R^9)C(O)(R^9)$, $-NHS(O)_2R^9$, or $-NR^9S(O)_2R^9$;

$R^3$ is H or $C_{1-6}$ alkyl;

$R^4$ is H or $C_{1-6}$ alkyl;

each $R^5$ is independently $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, —OH, —C(O)H, —C(O)($C_{1-6}$ alkyl), —C(O)($C_{6-10}$ aryl), —C(O)(5- or 6-membered heteroaryl), —C(O)($C_{3-7}$ carbocyclyl), —C(O)(5- to 7-membered heterocyclyl), —$(CH_2)_{0-3}$C(O)O$C_{1-6}$ alkyl, —C(O)$NH_2$, —C(O)NH($C_{1-6}$ alkyl), —C(O)N($C_{1-6}$ alkyl)$_2$, —NHC(O)$R^9$, —N($R^9$)C(O)($R^9$), —$NH_2$, —NH($C_{1-6}$ alkyl), —N($C_{1-6}$ alkyl)$_2$, —NHC(O)O($R^9$), —N($R^9$)C(O)O($R^9$), —NHS(O)$_2R^9$, $NR^9S(O)_2R^9$, —S(O)$_q$NH$R^9$, —S(O)$_q$N($R^9$)$_2$, —S(O)$_q R^9$, $C_{1-6}$ hydroxyalkyl, —O$(CH_2)_{1-3}$CN, CN, —O$(CH_2)_{0-6}$—$C_{3-7}$ carbocyclyl, —O$(CH_2)_{0-6}$-5- to 7-membered heterocyclyl comprising 1-3 heteroatoms selected from O, N, and S, —O$(CH_2)_{0-3}$($C_6$-$C_{10}$)aryl, adamantyl, —O$(CH_2)_{0-3}$-5- or 6-membered heteroaryl comprising 1-3 heteroatoms selected from O, N, and S, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$—$C_{6-10}$ aryl, and —$(CH_2)_{0-6}$-5- or 6-membered heteroaryl comprising 1-3 heteroatoms selected from O, N, and S, wherein the alkyl is optionally substituted with one to three $R^6$, and the carbocyclyl, heterocyclyl, aryl, and heteroaryl are optionally substituted with one to four $R^8$; or two $R^5$ when on adjacent atoms, together with the atoms to which they are attached form a $C_{3-7}$ carbocyclyl or a 5- to 7-membered heterocyclyl comprising 1-3 heteroatoms selected from O, N, and S, wherein the carbocyclyl and heterocyclyl are optionally substituted with one to three $R^6$; or two $R^5$ when on adjacent atoms, together with the atoms to which they are attached form a $C_{6-10}$ aryl or a 5- or 6-membered heteroaryl comprising 1-3 heteroatoms selected from O, N, and S; or two $R^5$ when on the same atom, together with the atom to which they are attached form a $C_{3-7}$ spirocarbocyclyl or a 5- to 7-membered spiroheterocyclyl comprising 1-3 heteroatoms selected from O, N, and S, wherein the spirocarbocyclyl and spiroheterocyclyl are optionally substituted with one to four $R^{10}$; or two $R^5$ when on the same carbon atom form =(O);

$R^6$ is —$NH_2$, —NH($C_{1-6}$ alkyl), —N($C_{1-6}$ alkyl)$_2$, $C_{6-10}$ aryl, or a 5- or 6-membered heteroaryl comprising 1-3 heteroatoms selected from O, N, and S, wherein the aryl and heteroaryl are optionally substituted with one to three $R^7$;

each $R^7$ is independently $C_{1-6}$ alkyl, $C_{1-6}$ haloalkyl, $C_{1-6}$ alkoxy, $C_{1-3}$ haloalkoxy, halogen, or $C_{6-10}$ aryl;

each $R^8$ is independently $C_{1-6}$ alkyl, $C_{1-6}$ haloalkyl, $C_{1-6}$ alkoxy, $C_{1-6}$ haloalkoxy, halogen, or —OH;

$R^9$ is $C_{1-6}$ alkyl, $C_{1-6}$ haloalkyl, 5- to 7-membered heterocyclyl comprising 1-3 heteroatoms selected from O, N, and S, $C_{6-10}$ aryl, or a 5- or 6-membered heteroaryl comprising 1-3 heteroatoms selected from O, N, and S, wherein the aryl and heteroaryl are optionally substituted with one to three $R^{11}$;

each $R^{10}$ is $C_{1-6}$ alkyl, $C_{1-6}$ haloalkyl, $C_{1-6}$ alkoxy, $C_{1-6}$ haloalkoxy, or halogen; or two $R^{10}$, when on adjacent atoms, together with the atoms to which they are attached form a $C_{6-10}$ aryl or a 5- or 6-membered heteroaryl comprising 1-3 heteroatoms selected from O, N, and S; each $R^{11}$ is independently $C_{1-6}$ alkyl, $C_{1-6}$ haloalkyl, $C_{1-6}$ alkoxy, $C_{1-6}$ haloalkoxy, —NHC(O)($C_{1-6}$ alkyl), —N($C_{1-6}$ alkyl)C(O)($C_{1-6}$alkyl), or halogen; or two $R^{11}$, when on adjacent atoms, together with the atoms to which they are attached form a $C_{6-10}$ aryl or a 5- or 6-membered heteroaryl comprising 1-3 heteroatoms selected from O, N, and S, wherein the aryl and heteroaryl are optionally substituted with one to three $R^{12}$;

each $R^{12}$ is independently $C_{1-6}$ alkyl, $C_{1-6}$ haloalkyl, $C_{1-6}$ alkoxy, or $C_{1-3}$ haloalkoxy;

$R^{13}$ is independently at each occurrence $C_{1-6}$ alkyl, $C_{1-6}$ haloalkyl, $C_{6-10}$ aryl, or a 5- or 6-membered heteroaryl comprising 1-3 heteroatoms selected from O, N, and S, wherein the alkyl is optionally substituted with one to two $C_{1-6}$ alkoxy and the aryl and heteroaryl are optionally substituted with one to three $R^{14}$;

each $R^{14}$ is independently $C_{1-6}$ alkyl, $C_{1-6}$ haloalkyl, $C_{1-6}$ alkoxy, $C_{1-3}$ haloalkoxy, halogen, $C_{6-10}$ aryl, or a 5- or 6-membered heteroaryl comprising 1-3 heteroatoms selected from O, N, and S;

$R^{15}$ is H or $C_{1-6}$ alkyl; and q is 0, 1, or 2.

Embodiment 71: The compound according to Embodiment 70, wherein $R^{d1}$ is H.

Embodiment 72: The compound according to Embodiment 70, wherein $R^{d1}$ is —$CH_2$OC(O)$R^{15}$, —$CH_2$OP(O)OH$OR^{15}$, or —$CH_2$OP(O)($R^{15}$)$_2$.

Embodiment 73: The compound according to any one of Embodiments 70-72, wherein $R^{d2}$ is H.

Embodiment 74: The compound according to any one of Embodiments 70-73, wherein $R^{d1}$ and $R^{d2}$ are each independently H.

Embodiment 75: The compound according to any one of Embodiments 70-74, wherein $R^{1d}$ is H.

Embodiment 76: The compound according to any one of Embodiments 70-75, wherein $R^{d3}$ is

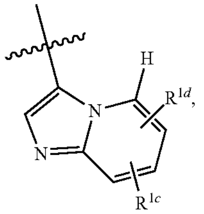
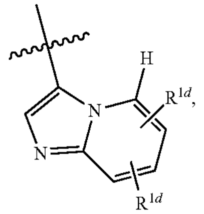
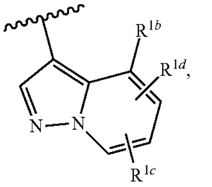
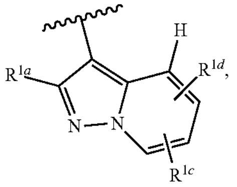
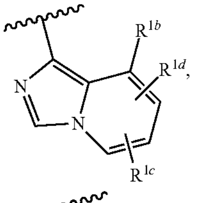
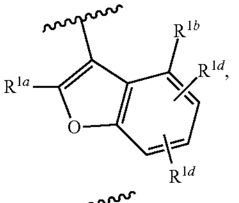
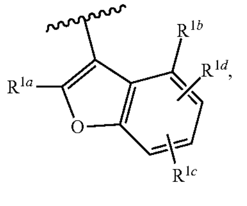
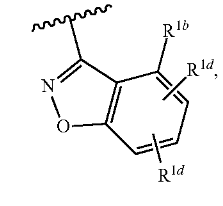

253
-continued
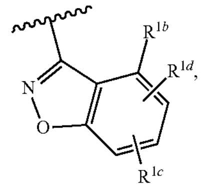
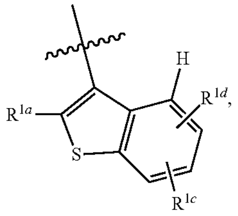
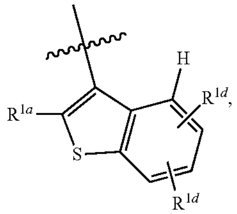
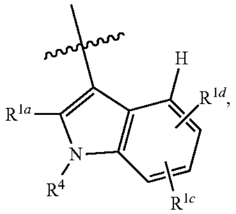
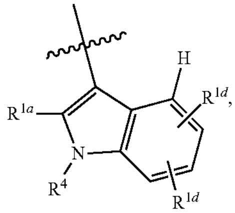
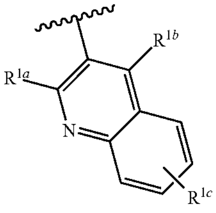
,
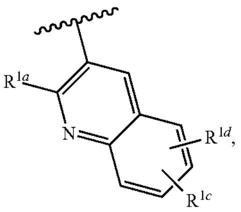
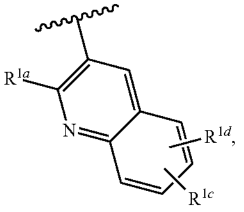
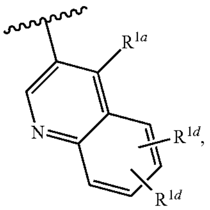
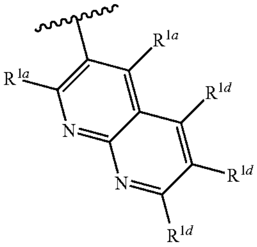
,
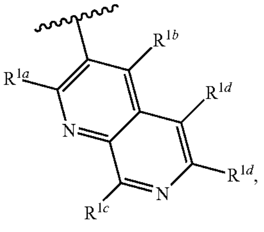
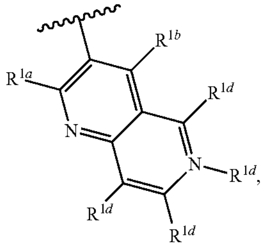
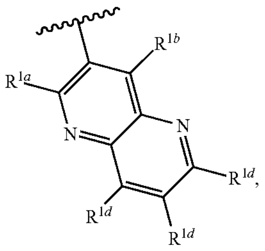
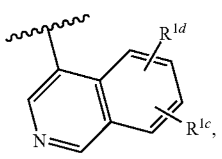
254
-continued
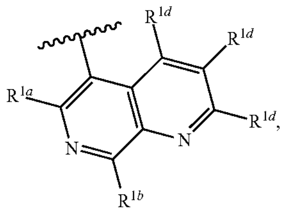
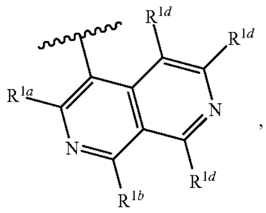
,
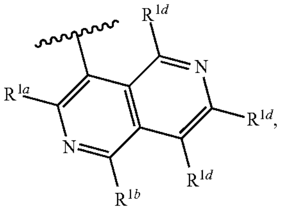
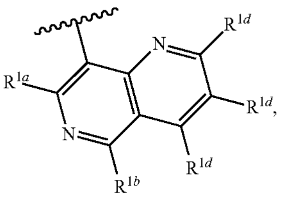
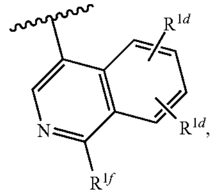
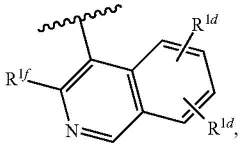
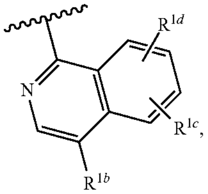
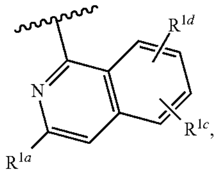
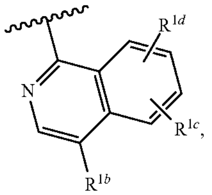
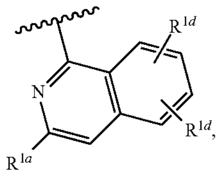
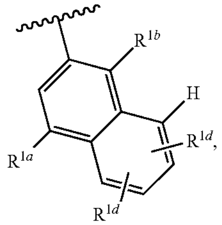
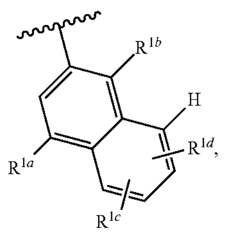
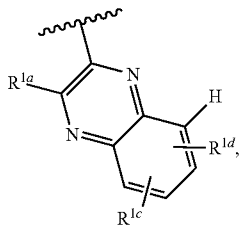
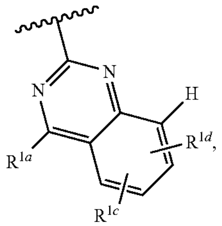
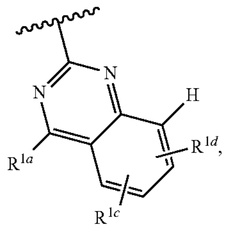

-continued
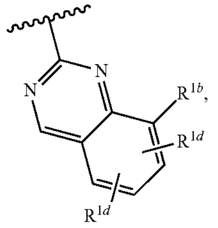
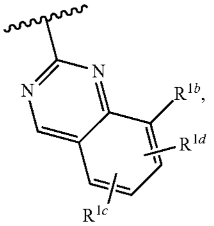
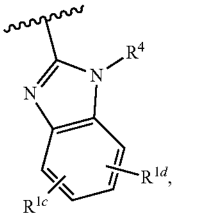
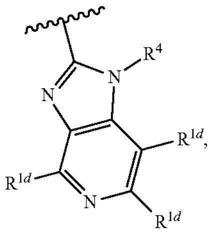
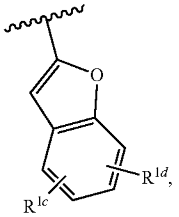
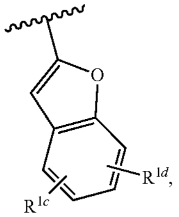
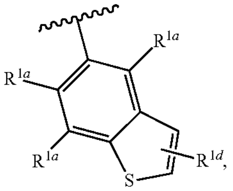
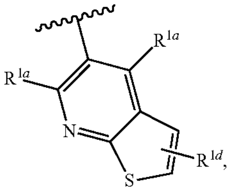
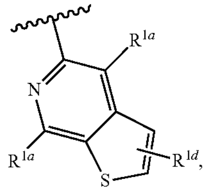
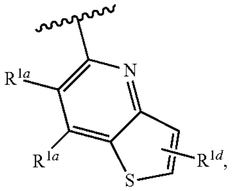
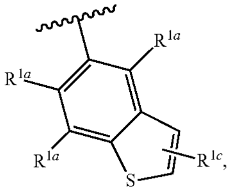
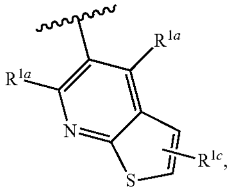
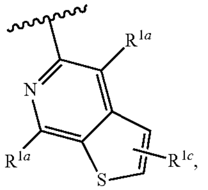
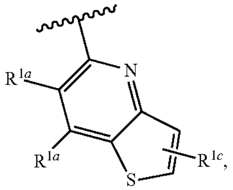
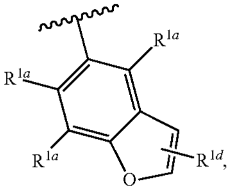
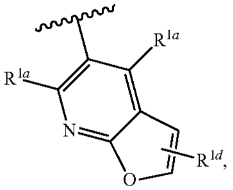
-continued
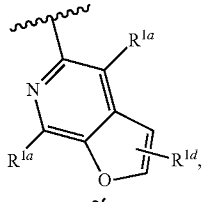
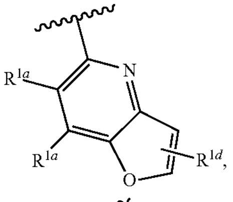
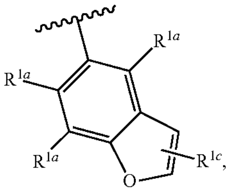
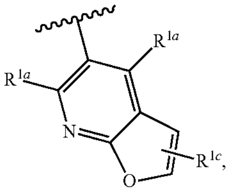
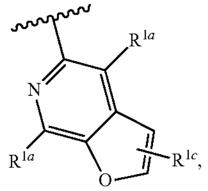
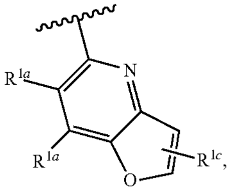
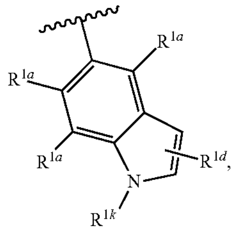
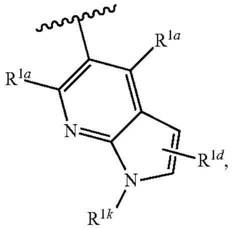
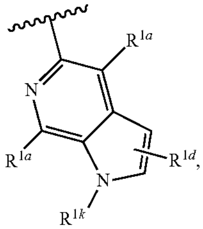
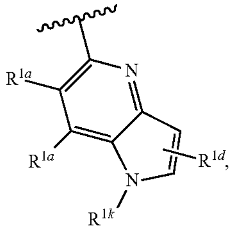
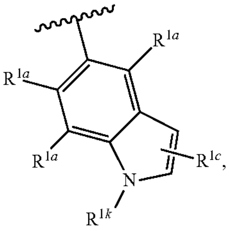
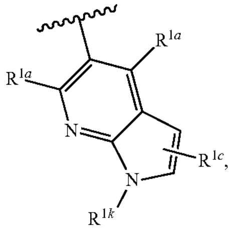
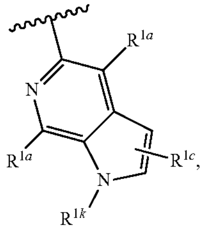
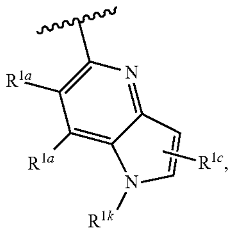
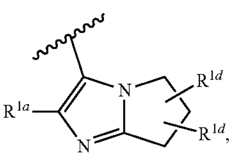

-continued
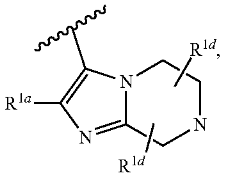
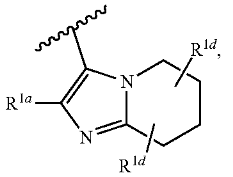
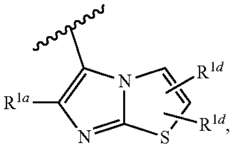
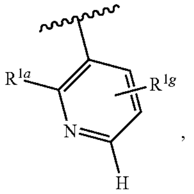
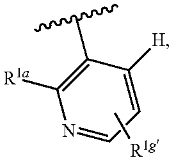
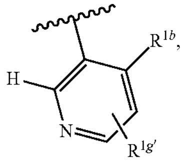
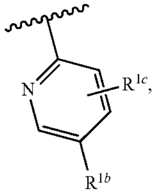
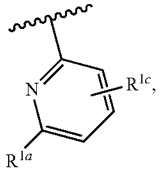
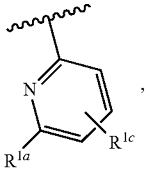
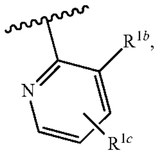
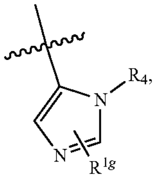
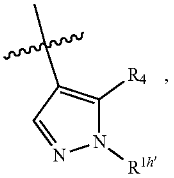
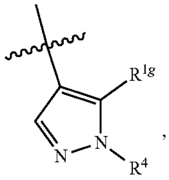
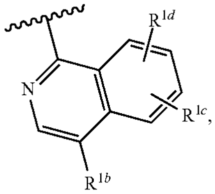
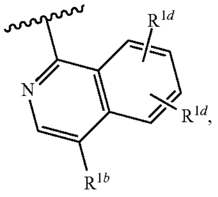
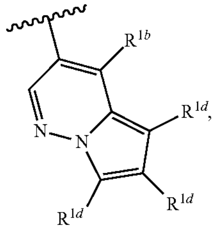
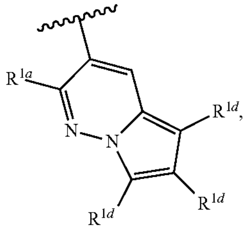
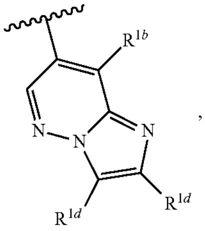
-continued
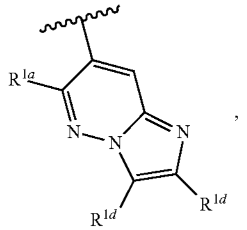
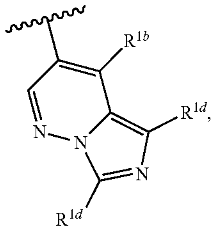
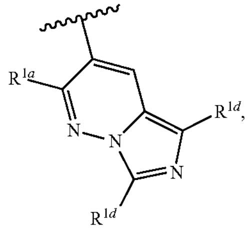
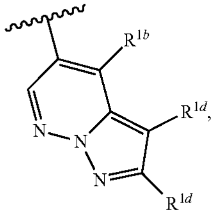
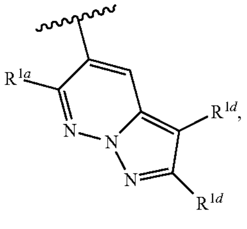
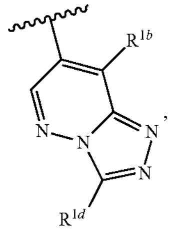
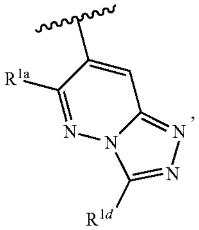
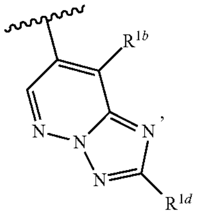
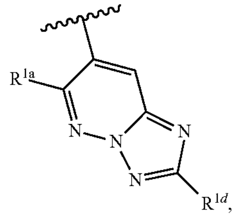
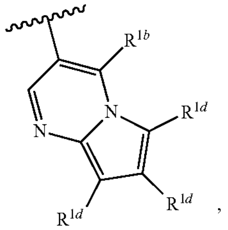
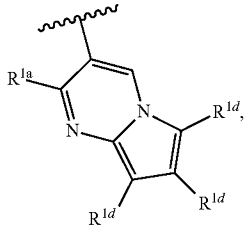
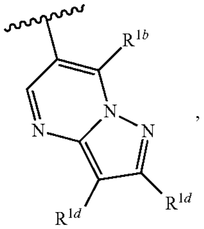
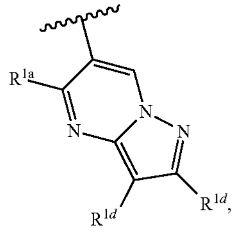
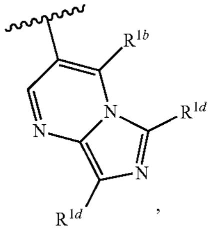

-continued
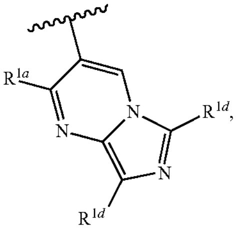
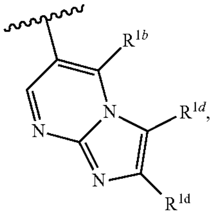
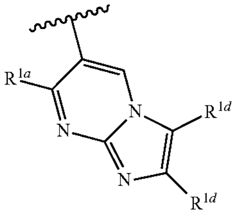
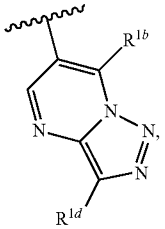
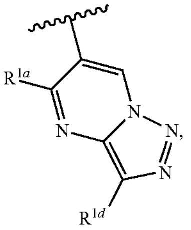
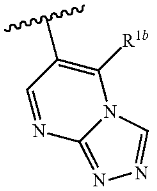
,
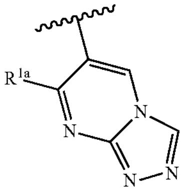
,
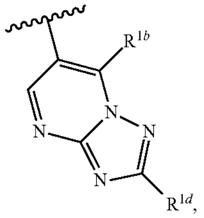
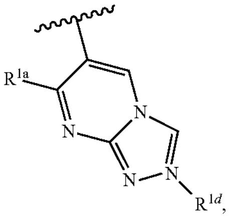
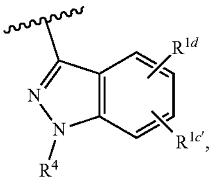
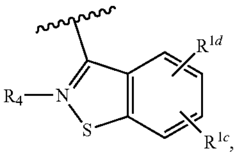
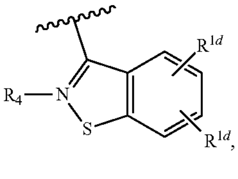
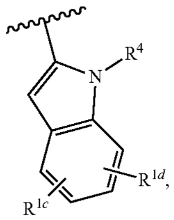
-continued
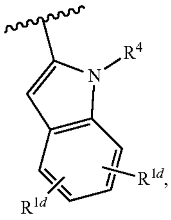
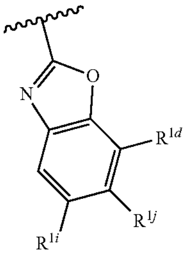
,
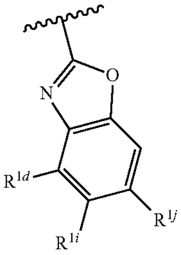
,
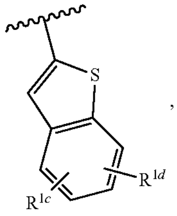
,
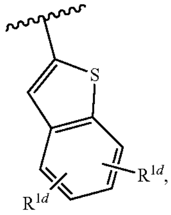
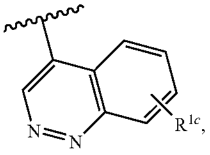
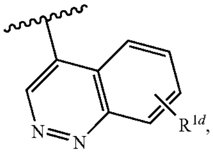
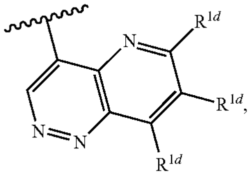
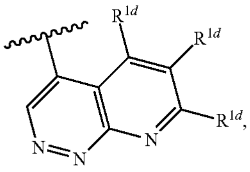
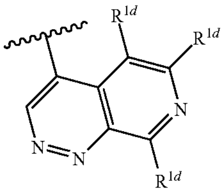
,
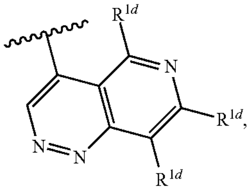
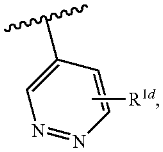
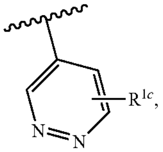
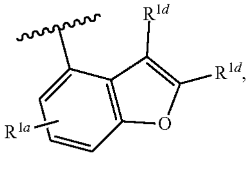
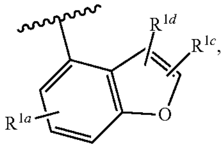

-continued
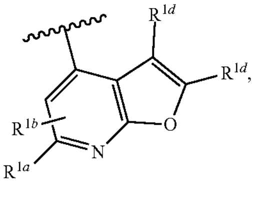
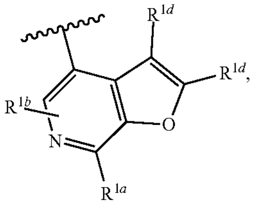
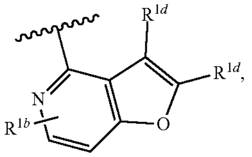
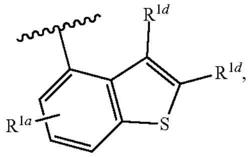
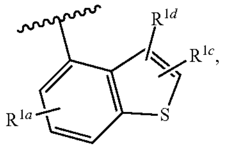
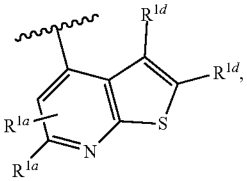
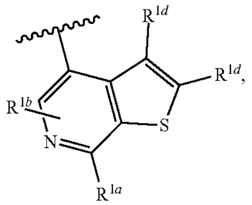
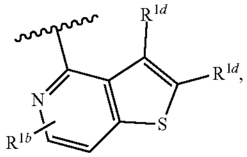
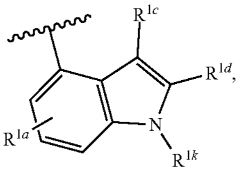
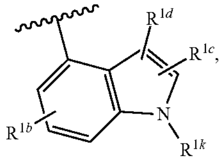
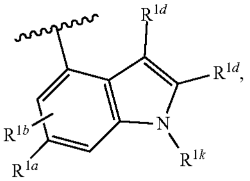
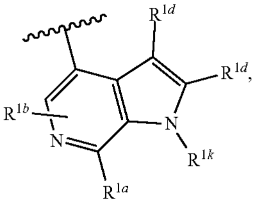
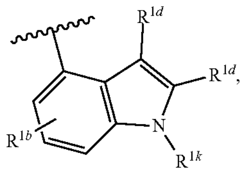
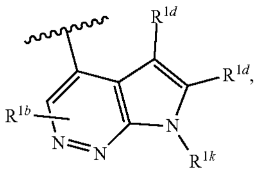
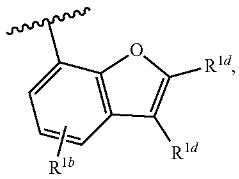
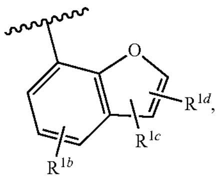
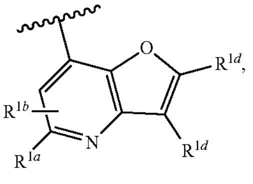
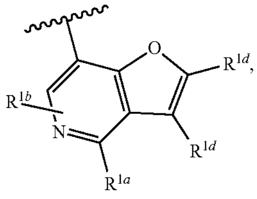
-continued
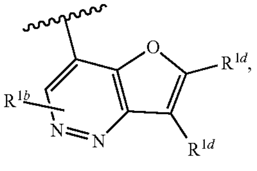
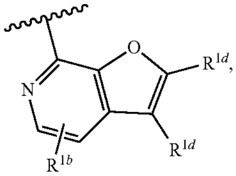
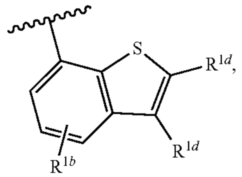
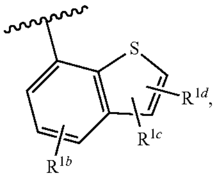
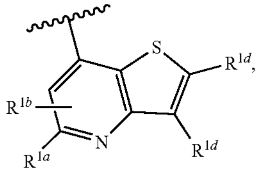
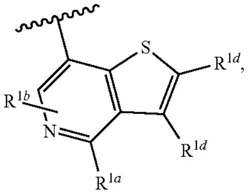
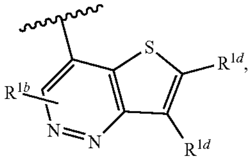
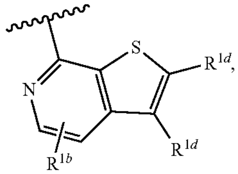
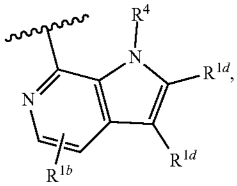
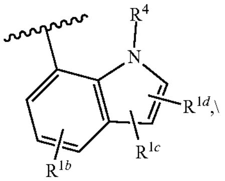
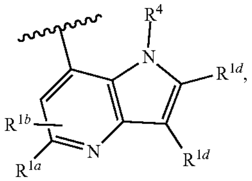
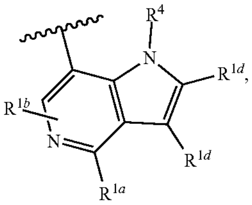
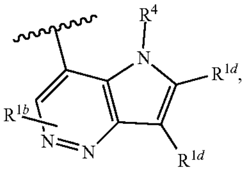
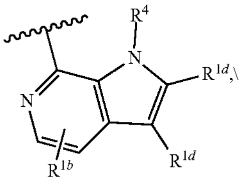
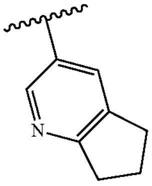
,
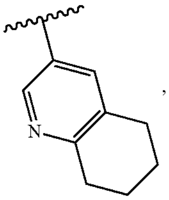
,
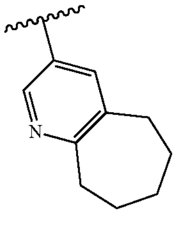
, -continued
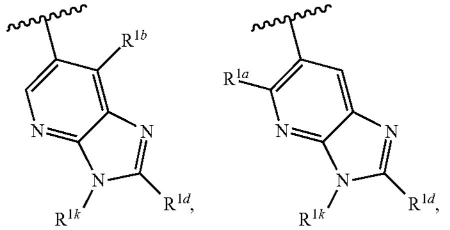
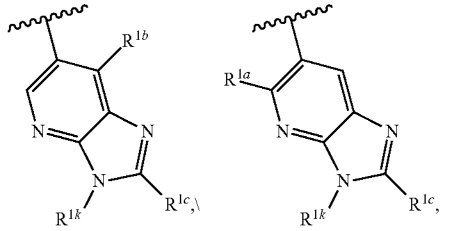
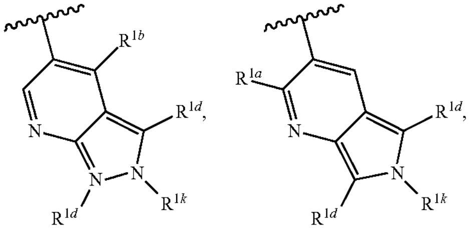
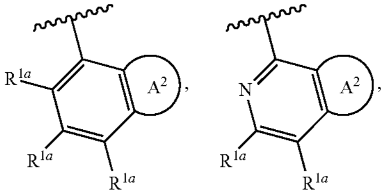
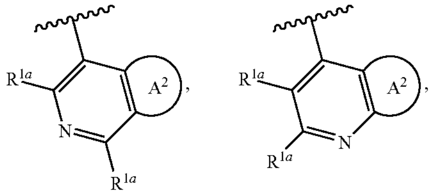
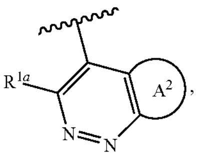
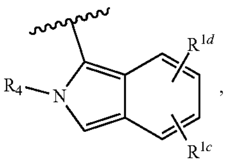
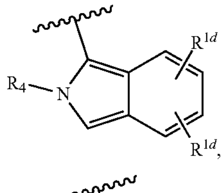
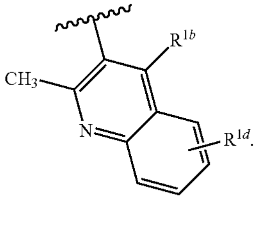
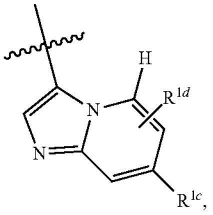
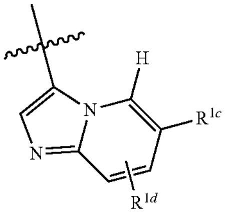
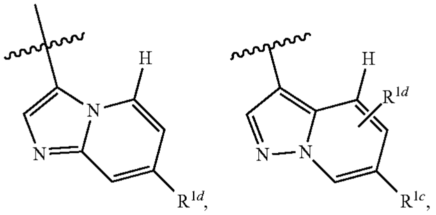
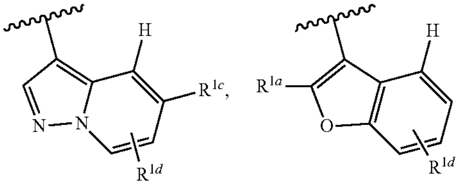
or
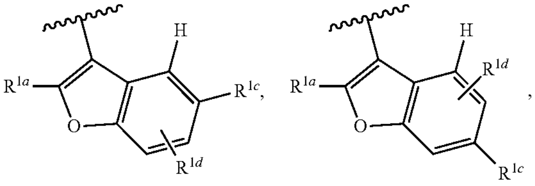
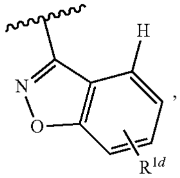
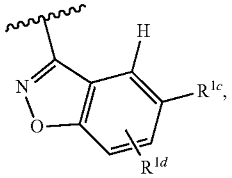
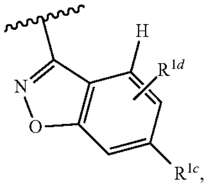
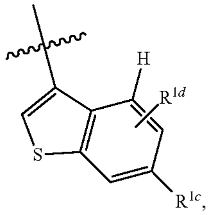
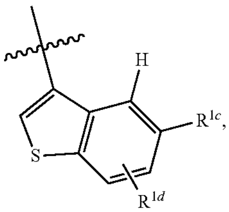
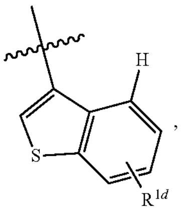
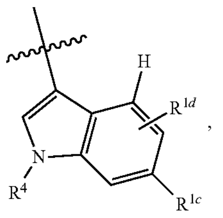
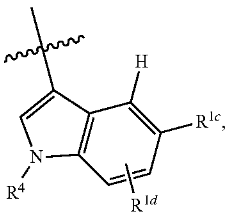
Embodiment 77: The compound according to any one of Embodiments 70-76, wherein $R^{d3}$ is -continued
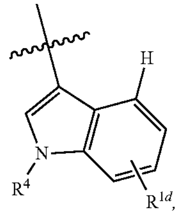
,
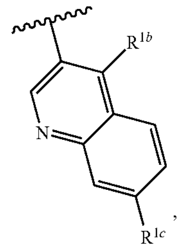
,
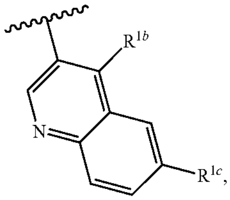
,
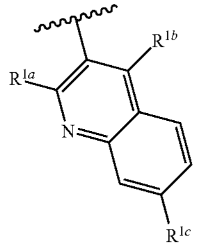
,
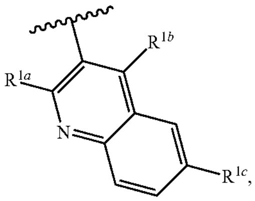
,
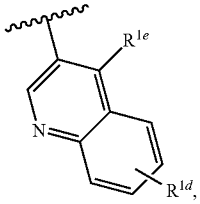
,
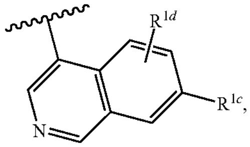
,
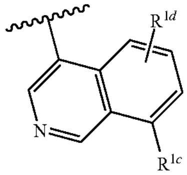
,
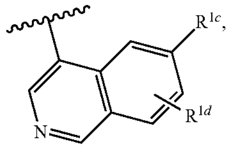
,
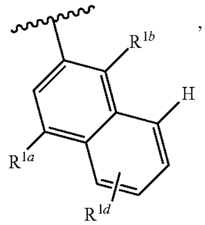
,
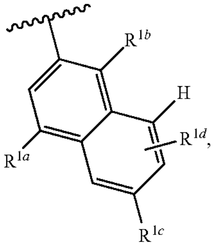
,
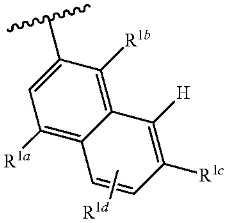
,
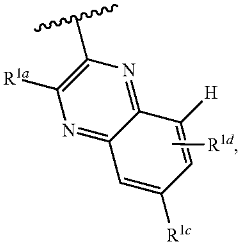
,
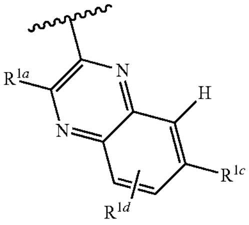
,
-continued
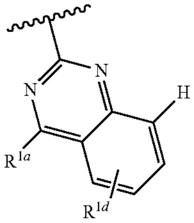
,
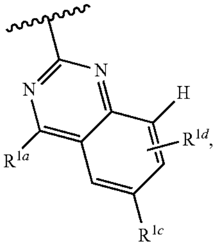
,
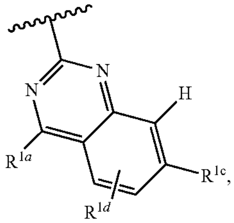
,
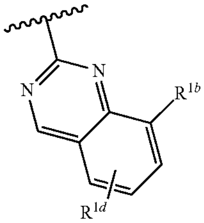
,
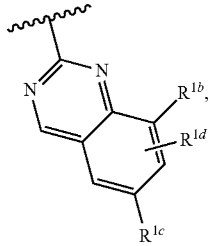
,
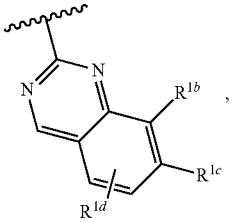
,
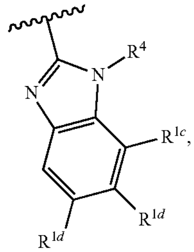
,
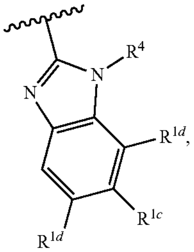
,
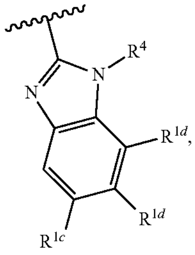
,
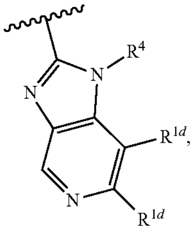
,
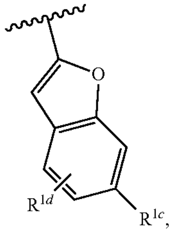
,
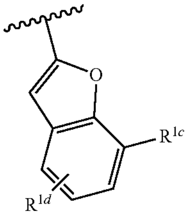
,
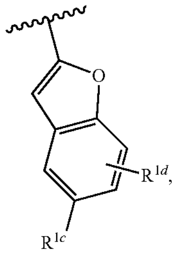
,
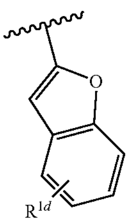
, -continued
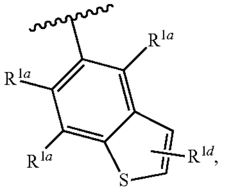
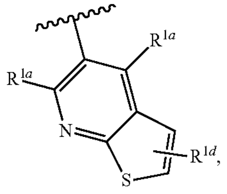
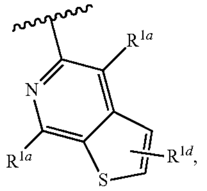
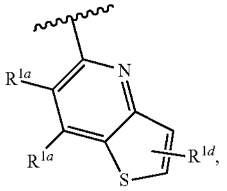
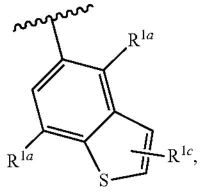
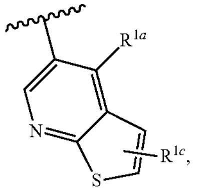
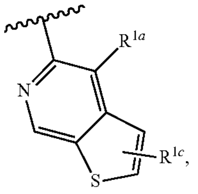
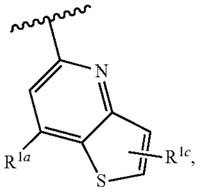
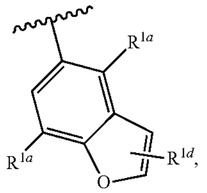
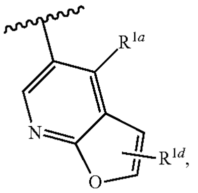
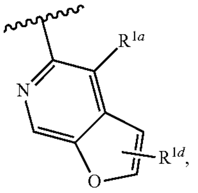
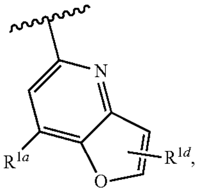
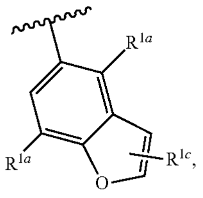
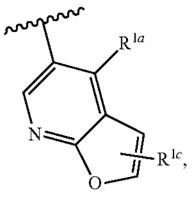
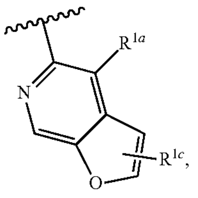
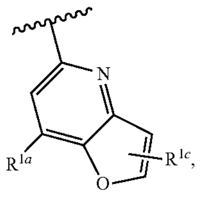
-continued
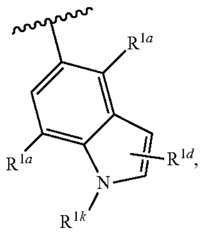
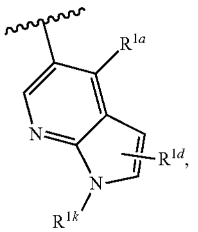
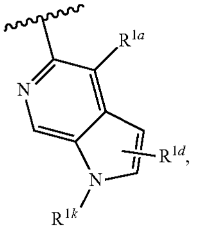
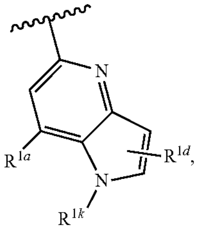
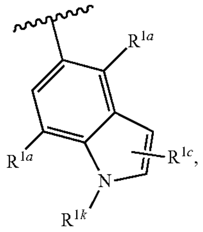
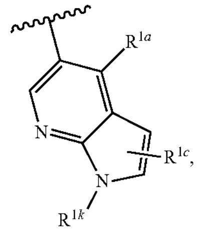
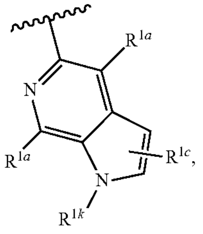
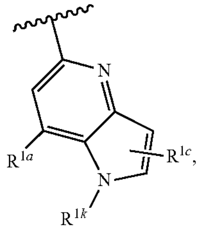
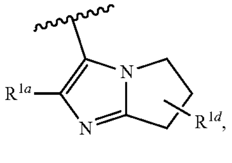
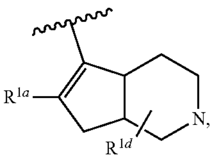
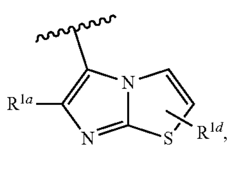
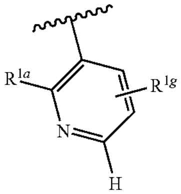
,
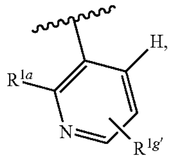
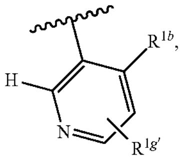
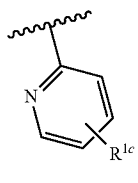
,
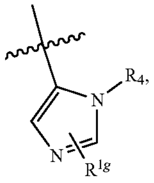

-continued
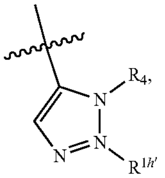
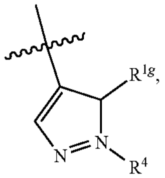
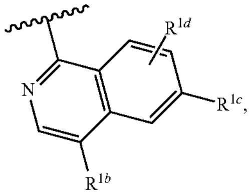
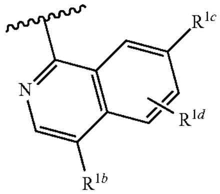
,
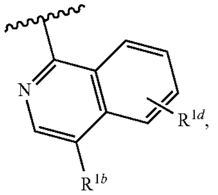
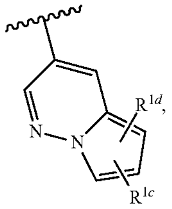
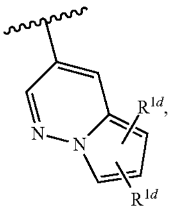
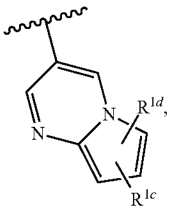
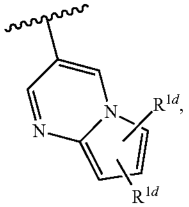
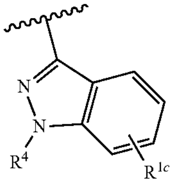
,
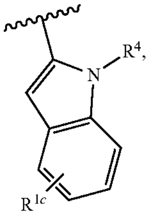
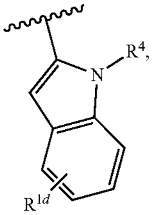
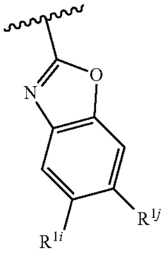
,
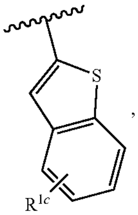
,
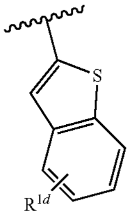
, or
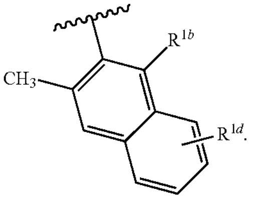
Embodiment 78: The compound according to any one of Embodiments 70-77, wherein the compound has a formula selected from:
(Ia)
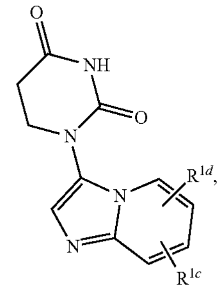
(Ib)
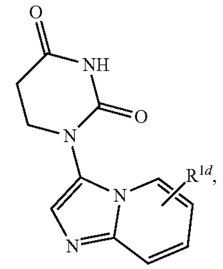
(Ic)
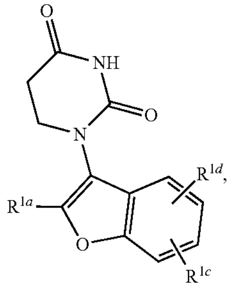
(Id)
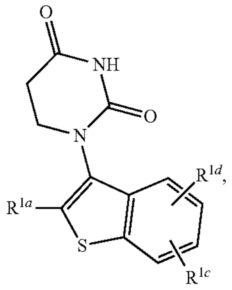
(Ie)
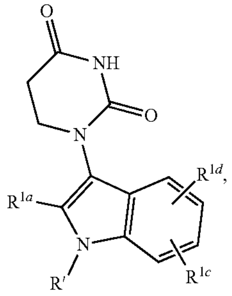

-continued
(If)
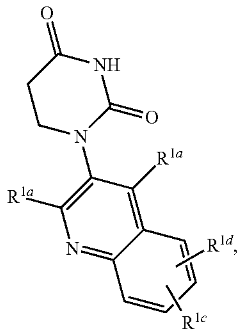
(Ig)
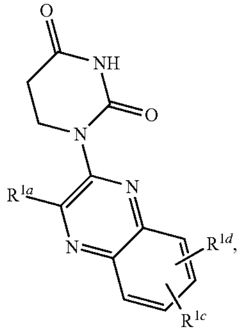
(Ih)
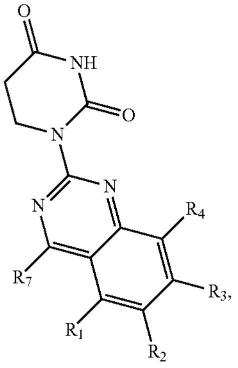
(Ii)
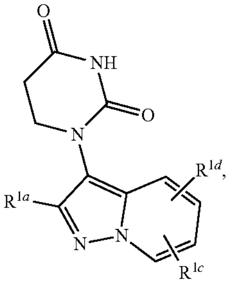
(Ij)
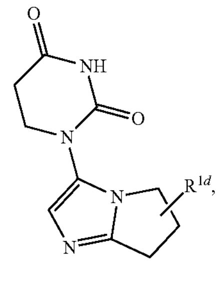
-continued
(Ik)
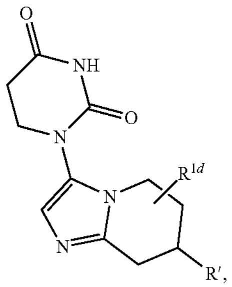
(Il)
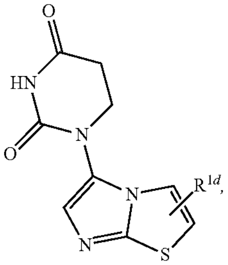
(Im)
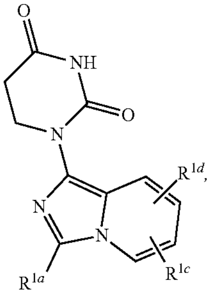
(In)
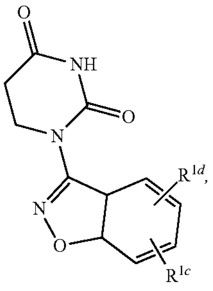
(Io)
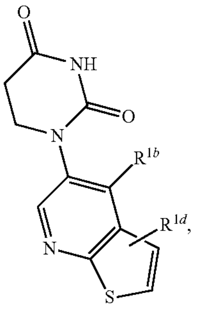

-continued
(Ip)
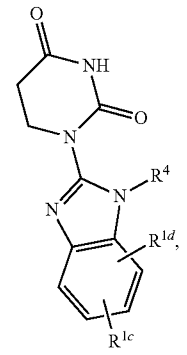
(Ia)
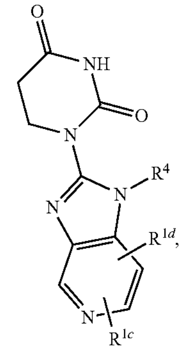
(Ir)
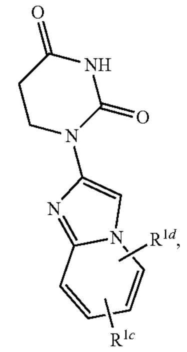
(Is)
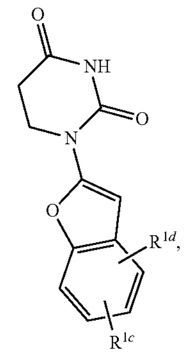
-continued
(It)
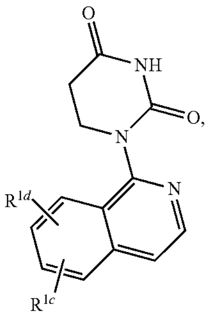
(Iu)
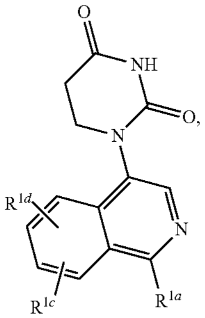
(Iv)
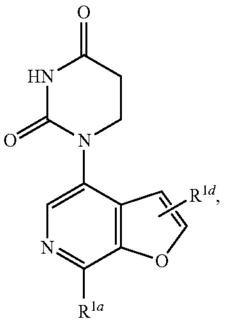
(Iw)
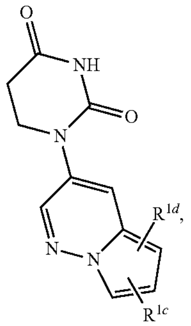
(Ix)
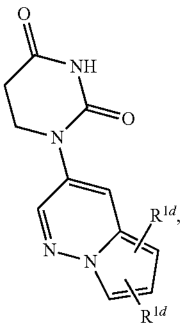

-continued
(Iy)
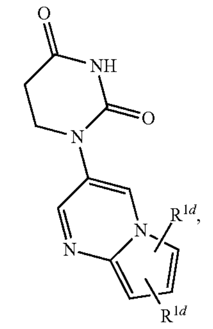
(Iz)
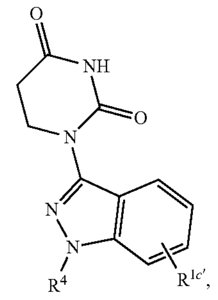
(Iab)
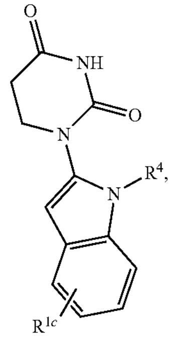
(Iac)
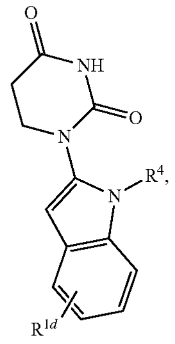
-continued
(Iad)
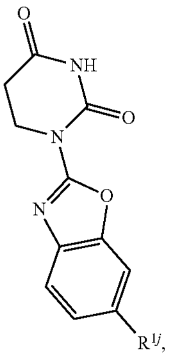
(Iae)
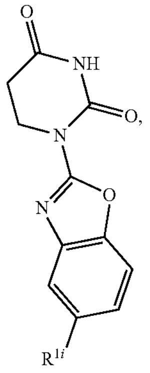
(Iaf)
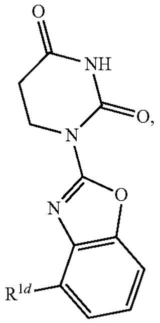
(Iag)
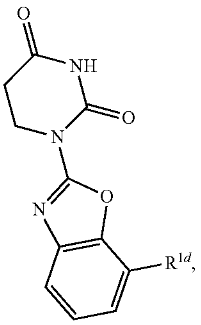

-continued (Iah)

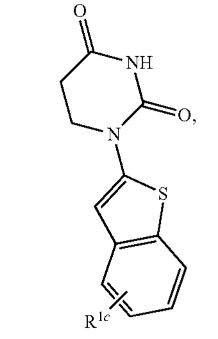

(Iai)

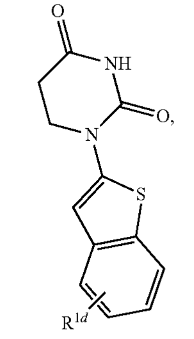

(Iaj)

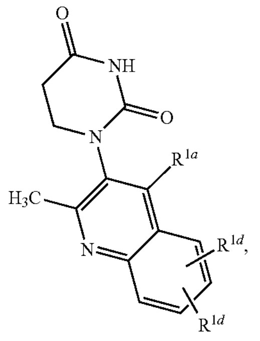

(Iak)

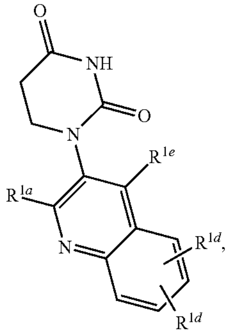

(Ial)

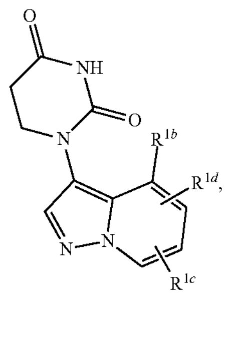

and

-continued (Iam)

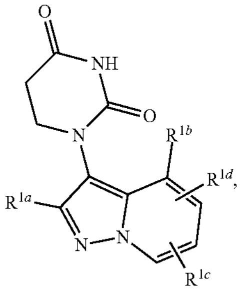

or a pharmaceutically acceptable salt, hydrate, solvate, prodrug, stereoisomer, or tautomer thereof.

Embodiment 79: The compound according to any one of Embodiments 68-78, wherein the compound is selected from:

1-(benzofuran-3-yl)dihydropyrimidine-2,4(1H,3H)-dione;

1-(6-ethynylbenzofuran-3-yl)dihydropyrimidine-2,4(1H,3H)-dione;

1-(6-ethynylbenzofuran-3-yl)dihydropyrimidine-2,4(1H,3H)-dione;

1-(5-iodobenzofuran-3-yl)dihydropyrimidine-2,4(1H,3H)-dione;

1-(6-iodobenzofuran-3-yl)dihydropyrimidine-2,4(1H,3H)-dione;

phenyl (3-(2,4-dioxotetrahydropyrimidin-1(2H)-yl)benzofuran-5-yl)carbamate;

1-(6-chloropyrazolo[1,5-a]pyridin-3-yl)dihydropyrimidine-2,4(1H,3H)-dione;

1-(7-(1-benzyl-1,2,3,6-tetrahydropyridin-4-yl)imidazo[1,2-a]pyridin-3-yl)dihydropyrimidine-2,4(1H,3H)-dione;

1-(7-(1-(4-(tert-butyl)benzoyl)-1,2,3,6-tetrahydropyridin-4-yl)imidazo[1,2-a]pyridin-3-yl)dihydropyrimidine-2,4(1H,3H)-dione;

1-(6-(1-benzylpiperidin-4-yl)imidazo[1,2-a]pyridin-3-yl)dihydropyrimidine-2,4(1H,3H)-dione;

1-(6-(3-(dimethylamino)prop-1-yn-1-yl)benzofuran-3-yl)dihydropyrimidine-2,4(1H,3H)-dione;

N-benzyl-3-(2,4-dioxotetrahydropyrimidin-1(2H)-yl)benzofuran-6-carboxamide;

1-(6-methylbenzo[d]isoxazol-3-yl)dihydropyrimidine-2,4(1H,3H)-dione;

1-(5-chlorobenzo[d]isoxazol-3-yl)dihydropyrimidine-2,4(1H,3H)-dione;

1-(6-(4-methylphenethoxy)benzo[d]isoxazol-3-yl)dihydropyrimidine-2,4(1H,3H)-dione;

1-(6-(1-benzylpiperidin-4-yl)quinolin-3-yl)pyrimidine-2,4(1H,3H)-dione;

1-(7-(1-benzyl-1,2,3,6-tetrahydropyridin-4-yl)imidazo[1,2-a]pyridin-3-yl)pyrimidine-2,4(1H,3H)-dione; and 1-(7-bromoimidazo[1,2-a]pyridin-3-yl)pyrimidine-2,4(1H,3H)-dione;

or a pharmaceutically acceptable salt, hydrate, solvate, prodrug, stereoisomer, or tautomer thereof.

Embodiment 80: A pharmaceutical composition comprising a compound according to any one of Embodiments 68-79, or a pharmaceutically acceptable salt, hydrate, solvate, prodrug, stereoisomer, or tautomer thereof, and a pharmaceutically acceptable carrier or excipient.

Embodiment 81: The pharmaceutical composition according to Embodiment 80 further comprising at least one additional pharmaceutical agent.

Embodiment 82: The pharmaceutical composition according to Embodiment 80 or Embodiment 81 14 for use in the treatment or prevention of a cereblon-mediated disorder, disease, or condition.

Embodiment 83: The pharmaceutical composition of Embodiment 80 or Embodiment 81 for use in the treatment or prevention of a respiratory disorder, a proliferative disorder, an autoimmune disorder, an autoinflammatory disorder, an inflammatory disorder, a neurological disorder, or an infectious disease or disorder.

Embodiment 84: A method of modulating cereblon in a biological sample comprising contacting the sample with a compound according to any one of Embodiments 68-79, or a pharmaceutically acceptable salt, hydrate, solvate, prodrug, stereoisomer, or tautomer thereof.

Embodiment 85: A method of binding to and altering the specificity of a cereblon complex to induce the ubiquitination and degradation of a complex-associated protein selected from the group listed in TABLE 1 in a biological sample, comprising contacting the sample with a compound according to any one of Embodiments 68-79, or a pharmaceutically acceptable salt, hydrate, solvate, prodrug, stereoisomer, or tautomer thereof.

Embodiment 86: A method of treating or preventing a cereblon-mediated disorder, disease, or condition in a subject comprising administering to the subject a compound according to any one of Embodiments 68-79, or a pharmaceutically acceptable salt, hydrate, solvate, prodrug, stereoisomer, or tautomer thereof.

Embodiment 87: The method according to Embodiment 86, wherein the disorder, disease, or condition is a respiratory disorder, a proliferative disorder, an autoimmune disorder, an autoinflammatory disorder, an inflammatory disorder, a neurological disorder, or an infectious disease or disorder.

Embodiment 88: The method according to Embodiment 87, wherein the disorder, disease, or condition is a proliferative disorder.

Embodiment 89: The method according to Embodiment 88, wherein the proliferative disorder is cancer.

Embodiment 90: The method according to Embodiment 87, wherein the disorder, disease, or condition is a neurological disorder.

Embodiment 91: A method of treating or preventing a respiratory disorder, a proliferative disorder, an autoimmune disorder, an autoinflammatory disorder, an inflammatory disorder, a neurological disorder, or an infectious disease or disorder in a subject in need thereof, the method comprising administering to the subject a therapeutically effective amount of a compound according to any one of Embodiments 68-79, or a pharmaceutically acceptable salt, hydrate, solvate, prodrug, stereoisomer, or tautomer thereof.

Embodiment 92: The method according to Embodiment 91, wherein the disorder or disease is a proliferative disorder.

Embodiment 93: The method according to Embodiment 92, wherein the proliferative disorder is cancer.

Embodiment 94: The method according to Embodiment 91, wherein the disorder or disease is a neurological disorder.

Embodiment 95: Use of a compound according to any one of Embodiments 68-79, or a pharmaceutically acceptable salt, hydrate, solvate, prodrug, stereoisomer, or tautomer thereof in the preparation of a medicament for treating or preventing a respiratory disorder, a proliferative disorder, an autoimmune disorder, an autoinflammatory disorder, an inflammatory disorder, a neurological disorder, or an infectious disease or disorder in a subject in need thereof.

Embodiment 96: Use of a compound according to any one of Embodiments 68-79, or a pharmaceutically acceptable salt, hydrate, solvate, prodrug, stereoisomer, or tautomer thereof in the preparation of a medicament for treating or preventing cancer.

Embodiment 97: A method of degrading a target protein in a biological sample comprising contacting the target protein with a compound according to any one of Embodiments 68-79, or a pharmaceutically acceptable salt, hydrate, solvate, prodrug, stereoisomer, or tautomer thereof, wherein the target protein is selected from the group listed in TABLE 1.

Embodiment 98: A method of treating or preventing a target protein-mediated disorder, disease, or condition in a subject comprising administering to the subject a compound according to any one of Embodiments 68-79, or a pharmaceutically acceptable salt, hydrate, solvate, prodrug, stereoisomer, or tautomer thereof.

Embodiment 99: The method according to Embodiment 98, wherein the disorder, disease, or condition is a proliferative disorder.

Embodiment 100: The method according to Embodiment 99, wherein the proliferative disorder is cancer.

Embodiment 101: The method according to Embodiment 98, wherein the disorder, disease, or condition is a neurological disorder.

Embodiment 102: A method of treating or preventing a cancer in a subject comprising administering to the subject a compound according to any one of Embodiments 68-79, or a pharmaceutically acceptable salt, hydrate, solvate, prodrug, stereoisomer, or tautomer thereof.

Embodiment 103: A compound according to any one of Embodiments 68-79, or a pharmaceutically acceptable salt, hydrate, solvate, prodrug, stereoisomer, or tautomer thereof for use in the treatment or prevention of a respiratory disorder, a proliferative disorder, an autoimmune disorder, an autoinflammatory disorder, an inflammatory disorder, a neurological disorder, or an infectious disease or disorder in a subject in need thereof.

Embodiment 104: A compound according to any one of Embodiments 68-79, or a pharmaceutically acceptable salt, hydrate, solvate, prodrug, stereoisomer, or tautomer thereof for use in the treatment or prevention of cancer.

Embodiment 105: Use of a compound according to any one of Embodiments 68-79, or a pharmaceutically acceptable salt, hydrate, solvate, prodrug, stereoisomer, or tautomer thereof in the preparation of a medicament for treating or preventing a target protein-mediated disorder, disease, or condition in a subject.

Embodiment 106: A compound according to any one of Embodiments 68-79, or a pharmaceutically acceptable salt, hydrate, solvate, prodrug, stereoisomer, or tautomer thereof for use in the treatment or prevention of a target protein-mediated disorder, disease, or condition in a subject.

In one embodiment, the Target Protein comprises a beta-hairpin.

In one embodiment, the Target Protein is a beta-turn containing protein. In another embodiment, the beta-turn containing protein is a protein selected from the group listed in Table 1.

In one embodiment, the target protein is selected from the group consisting of:

TABLE 1

| Target Protein Symbol | uniprot name | Target Protein name |
|---|---|---|
| A2M | A2MG_HUMAN | Alpha-2-macroglobulin |
| AADAT | AADAT_HUMAN | Kynurenine/alpha-aminoadipate aminotransferase, mitochondrial |
| AAK1 | AAK1_HUMAN | AP2-associated protein kinase 1 |
| AAMDC | AAMDC_HUMAN | Mth938 domain-containing protein |
| AARS | SYAC_HUMAN | Alanine--tRNA ligase, cytoplasmic |
| AASDHPPT | ADPPT_HUMAN | L-aminoadipate-semialdehyde dehydrogenase-phosphopantetheinyl transferase |
| AASS | AASS_HUMAN | Saccharopine dehydrogenase |
| ABL1 | ABL1_HUMAN | Tyrosine-protein kinase ABL1 |
| ABL2 | ABL2_HUMAN | Tyrosine-protein kinase ABL2 |
| ABLIM2 | ABLM2_HUMAN | Actin-binding LIM protein 2 |
| ACAA1 | THIK_HUMAN | 3-ketoacyl-CoA thiolase, peroxisomal |
| ACAA2 | THIM_HUMAN | 3-ketoacyl-CoA thiolase, mitochondrial |
| ACACA | ACACA_HUMAN | Biotin carboxylase |
| ACACB | ACACB_HUMAN | Biotin carboxylase |
| ACADVL | ACADV_HUMAN | Very long-chain specific acyl-CoA dehydrogenase, mitochondrial |
| ACAP1 | ACAP1_HUMAN | Arf-GAP with coiled-coil, ANK repeat and PH domain-containing protein 1 |
| ACAP2 | ACAP2_HUMAN | Arf-GAP with coiled-coil, ANK repeat and PH domain-containing protein 2 |
| ACAP3 | ACAP3_HUMAN | Arf-GAP with coiled-coil, ANK repeat and PH domain-containing protein 3 |
| ACAT2 | THIC_HUMAN | Acetyl-CoA acetyltransferase, cytosolic |
| ACE | ACE_HUMAN | Angiotensin-converting enzyme, soluble form |
| ACHE | ACES_HUMAN | Acetylcholinesterase |
| ACLY | ACLY_HUMAN | ATP-citrate synthase |
| ACO1 | ACOC_HUMAN | Cytoplasmic aconitate hydratase |
| ACOT12 | ACO12_HUMAN | Acetyl-coenzyme A thioesterase |
| ACOT13 | ACO13_HUMAN | Acyl-coenzyme A thioesterase 13, N-terminally processed |
| ACOT2 | ACOT2_HUMAN | Acyl-coenzyme A thioesterase 2, mitochondrial |
| ACOT4 | ACOT4_HUMAN | Peroxisomal succinyl-coenzyme A thioesterase |
| ACP5 | PPA5_HUMAN | Tartrate-resistant acid phosphatase type 5 |
| ACP6 | PPA6_HUMAN | Lysophosphatidic acid phosphatase type 6 |
| ACSM2A | ACS2A_HUMAN | Acyl-coenzyme A synthetase ACSM2A, mitochondrial |
| ACTB | ACTB_HUMAN | Actin, cytoplasmic 1, N-terminally processed |
| ACTG1 | ACTG_HUMAN | Actin, cytoplasmic 2, N-terminally processed |
| ACVR1 | ACVR1_HUMAN | Activin receptor type-1 |
| ACVR1B | ACV1B_HUMAN | Activin receptor type-1B |
| ACVR2A | AVR2A_HUMAN | Activin receptor type-2A |
| ACVR2B | AVR2B_HUMAN | Activin receptor type-2B |
| ACY1 | ACY1_HUMAN | Aminoacylase-1 |
| ADA2 | ADA2_HUMAN | Adenosine deaminase 2 |
| ADAM10 | ADA10_HUMAN | Disintegrin and metalloproteinase domain-containing protein 10 |
| ADAM17 | ADA17_HUMAN | Disintegrin and metalloproteinase domain-containing protein 17 |
| ADAP1 | ADAP1_HUMAN | Arf-GAP with dual PH domain-containing protein 1 |
| ADAP2 | ADAP2_HUMAN | Arf-GAP with dual PH domain-containing protein 2 |
| ADAR | DSRAD_HUMAN | Double-stranded RNA-specific adenosine deaminase |
| ADARB1 | RED1_HUMAN | Double-stranded RNA-specific editase 1 |
| ADCY10 | ADCYA_HUMAN | Adenylate cyclase type 10 |
| ADCYAP1R1 | PACR_HUMAN | Pituitary adenylate cyclase-activating polypeptide type I receptor |
| ADGRB3 | AGRB3_HUMAN | Adhesion G protein-coupled receptor B3 |
| ADGRL3 | AGRL3_HUMAN | Adhesion G protein-coupled receptor L3 |
| ADIPOQ | ADIPO_HUMAN | Adiponectin |
| ADORA2A | AA2AR_HUMAN | Adenosine receptor A2a |
| ADRB2 | ADRB2_HUMAN | Beta-2 adrenergic receptor |
| ADRM1 | ADRM1_HUMAN | Proteasomal ubiquitin receptor ADRM1 |
| ADSS | PURA2_HUMAN | Adenylosuccinate synthetase isozyme 2 |
| AEBP2 | AEBP2_HUMAN | Zinc finger protein AEBP2 |
| AGA | ASPG_HUMAN | Glycosylasparaginase beta chain |
| AGAP2 | AGAP2_HUMAN | Arf-GAP with GTPase, ANK repeat and PH domain-containing protein 2 |
| AGER | RAGE_HUMAN | Advanced glycosylation end product-specific receptor |
| AGFG1 | AGFG1_HUMAN | Arf-GAP domain and FG repeat-containing protein 1 |
| AGO1 | AGO1_HUMAN | Protein argonaute-1 |
| AGO2 | AGO2_HUMAN | Protein argonaute-2 |
| AGO3 | AGO3_HUMAN | Protein argonaute-3 |

TABLE 1-continued

| Target Protein Symbol | uniprot name | Target Protein name |
|---|---|---|
| AGRP | AGRP_HUMAN | Agouti-related protein |
| AGTR2 | AGTR2_HUMAN | Type-2 angiotensin II receptor |
| AGXT | SPYA_HUMAN | Serine--pyruvate aminotransferase |
| AHCY | SAHH_HUMAN | Adenosylhomocysteinase |
| AHCYL1 | SAHH2_HUMAN | S-adenosylhomocysteine hydrolase-like protein 1 |
| AHCYL2 | SAHH3_HUMAN | Adenosylhomocysteinase 3 |
| AIFM1 | AIFM1_HUMAN | Apoptosis-inducing factor 1, mitochondrial |
| AIM2 | AIM2_HUMAN | Interferon-inducible protein AIM2 |
| AIMP1 | AIMP1_HUMAN | Endothelial monocyte-activating polypeptide 2 |
| AIP | AIP_HUMAN | AH receptor-interacting protein |
| AIRE | AIRE_HUMAN | Autoimmune regulator |
| AK2 | KAD2_HUMAN | Adenylate kinase 2, mitochondrial, N-terminally processed |
| AK3 | KAD3_HUMAN | GTP: AMP phosphotransferase AK3, mitochondrial |
| AK4 | KAD4_HUMAN | Adenylate kinase 4, mitochondrial |
| AKAP13 | AKP13_HUMAN | A-kinase anchor protein 13 |
| AKR1A1 | AK1A1_HUMAN | Aldo-keto reductase family 1 member A1 |
| AKR1B1 | ALDR_HUMAN | Aldo-keto reductase family 1 member B1 |
| AKR1C1 | AK1C1_HUMAN | Aldo-keto reductase family 1 member C1 |
| AKR1C2 | AK1C2_HUMAN | Aldo-keto reductase family 1 member C2 |
| AKR1C3 | AK1C3_HUMAN | Aldo-keto reductase family 1 member C3 |
| AKT1 | AKT1_HUMAN | RAC-alpha serine/threonine-protein kinase |
| AKT2 | AKT2_HUMAN | RAC-beta serine/threonine-protein kinase |
| AKT3 | AKT3_HUMAN | RAC-gamma serine/threonine-protein kinase |
| ALAS2 | HEM0_HUMAN | 5-aminolevulinate synthase, erythroid-specific, mitochondrial |
| ALCAM | CD166_HUMAN | CD166 antigen |
| ALDH1A2 | AL1A2_HUMAN | Retinal dehydrogenase 2 |
| ALDH1L1 | AL1L1_HUMAN | Cytosolic 10-formyltetrahydrofolate dehydrogenase |
| ALDH2 | ALDH2_HUMAN | Aldehyde dehydrogenase, mitochondrial |
| ALDH5A1 | SSDH_HUMAN | Succinate-semialdehyde dehydrogenase, mitochondrial |
| ALDH7A1 | AL7A1_HUMAN | Alpha-aminoadipic semialdehyde dehydrogenase |
| ALDOB | ALDOB_HUMAN | Fructose-bisphosphate aldolase B |
| ALK | ALK_HUMAN | ALK tyrosine kinase receptor |
| ALKBH8 | ALKB8_HUMAN | Alkylated DNA repair protein alkB homolog 8 |
| ALOX12 | LOX12_HUMAN | Arachidonate 12-lipoxygenase, 12S-type |
| ALOX15B | LX15B_HUMAN | Arachidonate 15-lipoxygenase B |
| ALOX5 | LOX5_HUMAN | Arachidonate 5-lipoxygenase |
| AMBP | AMBP_HUMAN | Trypstatin |
| AMD1 | DCAM_HUMAN | S-adenosylmethionine decarboxylase beta chain |
| AMFR | AMFR_HUMAN | E3 ubiquitin-protein ligase AMFR |
| AMT | GCST_HUMAN | Aminomethyltransferase, mitochondrial |
| AMY1A\|AMY1B\|AMY1C | AMY1_HUMAN | Alpha-amylase 1 |
| AMY2A | AMYP_HUMAN | Pancreatic alpha-amylase |
| ANAPC1 | APC1_HUMAN | Anaphase-promoting complex subunit 1 |
| ANAPC4 | APC4_HUMAN | Anaphase-promoting complex subunit 4 |
| ANGPT1 | ANGP1_HUMAN | Angiopoietin-1 |
| ANGPT2 | ANGP2_HUMAN | Angiopoietin-2 |
| ANGPTL3 | ANGL3_HUMAN | ANGPTL3(17-224) |
| ANGPTL4 | ANGL4_HUMAN | ANGPTL4 C-terminal chain |
| ANK1 | ANK1_HUMAN | Ankyrin-1 |
| ANK2 | ANK2_HUMAN | Ankyrin-2 |
| ANKFY1 | ANFY1_HUMAN | Rabankyrin-5 |
| ANKMY1 | ANKY1_HUMAN | Ankyrin repeat and MYND domain-containing protein 1 |
| ANKMY2 | ANKY2_HUMAN | Ankyrin repeat and MYND domain-containing protein 2 |
| ANKRA2 | ANRA2_HUMAN | Ankyrin repeat family A protein 2 |
| ANKRD27 | ANR27_HUMAN | Ankyrin repeat domain-containing protein 27 |
| ANLN | ANLN_HUMAN | Anillin |
| ANO10 | ANO10_HUMAN | Anoctamin-10 |
| ANOS1 | KALM_HUMAN | Anosmin-1 |
| ANPEP | AMPN_HUMAN | Aminopeptidase N |
| ANTXR1 | ANTR1_HUMAN | Anthrax toxin receptor 1 |
| AOAH | AOAH_HUMAN | Acyloxyacyl hydrolase large subunit |
| AOC1 | AOC1_HUMAN | Amiloride-sensitive amine oxidase [copper-containing] |
| AOC3 | AOC3_HUMAN | Membrane primary amine oxidase |
| AOX1 | AOXA_HUMAN | Aldehyde oxidase |
| AP1S3 | AP1S3_HUMAN | AP-1 complex subunit sigma-3 |
| AP2B1 | AP2B1_HUMAN | AP-2 complex subunit beta |
| AP4B1 | AP4B1_HUMAN | AP-4 complex subunit beta-1 |

TABLE 1-continued

| Target Protein Symbol | uniprot name | Target Protein name |
|---|---|---|
| AP4M1 | AP4M1_HUMAN | AP-4 complex subunit mu-1 |
| APAF1 | APAF_HUMAN | Apoptotic protease-activating factor 1 |
| APBB1 | APBB1_HUMAN | Amyloid-beta A4 precursor protein-binding family B member 1 |
| APBB3 | APBB3_HUMAN | Amyloid-beta A4 precursor protein-binding family B member 3 |
| APCS | SAMP_HUMAN | Serum amyloid P-component(1-203) |
| APEX1 | APEX1_HUMAN | DNA-(apurinic or apyrimidinic site) lyase, mitochondrial |
| APIP | MTNB_HUMAN | Methylthioribulose-1-phosphate dehydratase |
| APLF | APLF_HUMAN | Aprataxin and PNK-like factor |
| APLNR | APJ_HUMAN | Apelin receptor |
| APLP2 | APLP2_HUMAN | Amyloid-like protein 2 |
| APOBEC3A | ABC3A_HUMAN | DNA dC->dU-editing enzyme APOBEC-3A |
| APOD | APOD_HUMAN | Apolipoprotein D |
| APOH | APOH_HUMAN | Beta-2-glycoprotein 1 |
| APOM | APOM_HUMAN | Apolipoprotein M |
| APP | A4_HUMAN | C31 |
| APPL1 | DP13A_HUMAN | DCC-interacting protein 13-alpha |
| APRT | APT_HUMAN | Adenine phosphoribosyltransferase |
| APTX | APTX_HUMAN | Aprataxin |
| AQR | AQR_HUMAN | RNA helicase aquarius |
| AR | ANDR_HUMAN | Androgen receptor |
| ARAF | ARAF_HUMAN | Serine/threonine-protein kinase A-Raf |
| ARAP1 | ARAP1_HUMAN | Arf-GAP with Rho-GAP domain, ANK repeat and PH domain-containing protein 1 |
| ARAP3 | ARAP3_HUMAN | Arf-GAP with Rho-GAP domain, ANK repeat and PH domain-containing protein 3 |
| ARF1 | ARF1_HUMAN | ADP-ribosylation factor 1 |
| ARF6 | ARF6_HUMAN | ADP-ribosylation factor 6 |
| ARFGAP1 | ARFG1_HUMAN | ADP-ribosylation factor GTPase-activating protein 1 |
| ARFGAP2 | ARFG2_HUMAN | ADP-ribosylation factor GTPase-activating protein 2 |
| ARFGAP3 | ARFG3_HUMAN | ADP-ribosylation factor GTPase-activating protein 3 |
| ARHGAP10 | RHG10_HUMAN | Rho GTPase-activating protein 10 |
| ARHGAP11A | RHGBA_HUMAN | Rho GTPase-activating protein 11A |
| ARHGAP26 | RHG26_HUMAN | Rho GTPase-activating protein 26 |
| ARHGAP27 | RHG27_HUMAN | Rho GTPase-activating protein 27 |
| ARHGAP9 | RHG09_HUMAN | Rho GTPase-activating protein 9 |
| ARHGEF12 | ARHGC_HUMAN | Rho guanine nucleotide exchange factor 12 |
| ARHGEF16 | ARHGG_HUMAN | Rho guanine nucleotide exchange factor 16 |
| ARHGEF18 | ARHGI_HUMAN | Rho guanine nucleotide exchange factor 18 |
| ARHGEF2 | ARHG2_HUMAN | Rho guanine nucleotide exchange factor 2 |
| ARHGEF28 | ARG28_HUMAN | Rho guanine nucleotide exchange factor 28 |
| ARHGEF4 | ARHG4_HUMAN | Rho guanine nucleotide exchange factor 4 |
| ARID4A | ARI4A_HUMAN | AT-rich interactive domain-containing protein 4A |
| ARIH1 | ARI1_HUMAN | E3 ubiquitin-protein ligase ARIH1 |
| ARNT | ARNT_HUMAN | Aryl hydrocarbon receptor nuclear translocator |
| ARNTL2 | BMAL2_HUMAN | Aryl hydrocarbon receptor nuclear translocator-like protein 2 |
| ARSB | ARSB_HUMAN | Arylsulfatase B |
| ASAH1 | ASAH1_HUMAN | Acid ceramidase subunit beta |
| ASAH2 | ASAH2_HUMAN | Neutral ceramidase soluble form |
| ASAP1 | ASAP1_HUMAN | Arf-GAP with SH3 domain, ANK repeat and PH domain-containing protein 1 |
| ASAP3 | ASAP3_HUMAN | Arf-GAP with SH3 domain, ANK repeat and PH domain-containing protein 3 |
| ASB11 | ASB11_HUMAN | Ankyrin repeat and SOCS box protein 11 |
| ASB9 | ASB9_HUMAN | Ankyrin repeat and SOCS box protein 9 |
| ASH1L | ASH1L_HUMAN | Histone-lysine N-methyltransferase ASH1L |
| ASH2L | ASH2L_HUMAN | Set1/Ash2 histone methyltransferase complex subunit ASH2 |
| ASPA | ACY2_HUMAN | Aspartoacylase |
| ASRGL1 | ASGL1_HUMAN | Isoaspartyl peptidase/L-asparaginase beta chain |
| ASS1 | ASSY_HUMAN | Argininosuccinate synthase |
| ASTN2 | ASTN2_HUMAN | Astrotactin-2 |
| ASXL1 | ASXL1_HUMAN | Putative Polycomb group protein ASXL1 |
| ASXL2 | ASXL2_HUMAN | Putative Polycomb group protein ASXL2 |
| ASXL3 | ASXL3_HUMAN | Putative Polycomb group protein ASXL3 |
| ATG101 | ATGA1_HUMAN | Autophagy-related protein 101 |
| ATG13 | ATG13_HUMAN | Autophagy-related protein 13 |
| ATG16L1 | A16L1_HUMAN | Autophagy-related protein 16-1 |
| ATG5 | ATG5_HUMAN | Autophagy protein 5 |
| ATL1 | ATLA1_HUMAN | Atlastin-1 |
| ATL3 | ATLA3_HUMAN | Atlastin-3 |
| ATM | ATM_HUMAN | Serine-protein kinase ATM |

TABLE 1-continued

| Target Protein Symbol | uniprot name | Target Protein name |
|---|---|---|
| ATP7A | ATP7A_HUMAN | Copper-transporting ATPase 1 |
| ATP7B | ATP7B_HUMAN | WND/140 kDa |
| ATR | ATR_HUMAN | Serine/threonine-protein kinase ATR |
| ATRX | ATRX_HUMAN | Transcriptional regulator ATRX |
| ATXN1 | ATX1_HUMAN | Ataxin-1 |
| AURKA | AURKA_HUMAN | Aurora kinase A |
| AXL | UFO_HUMAN | Tyrosine-protein kinase receptor UFO |
| AZGP1 | ZA2G_HUMAN | Zinc-alpha-2-glycoprotein |
| AZU1 | CAP7_HUMAN | Azurocidin |
| B2M | B2MG_HUMAN | Beta-2-microglobulin form pI 5.3 |
| B4GALT1 | B4GT1_HUMAN | Processed beta-1,4-galactosyltransferase 1 |
| BACE1 | BACE1_HUMAN | Beta-secretase 1 |
| BACE2 | BACE2_HUMAN | Beta-secretase 2 |
| BAK1 | BAK_HUMAN | Bcl-2 homologous antagonist/killer |
| BARD1 | BARD1_HUMAN | BRCA1-associated RING domain protein 1 |
| BAX | BAX_HUMAN | Apoptosis regulator BAX |
| BAZ2A | BAZ2A_HUMAN | Bromodomain adjacent to zinc finger domain protein 2A |
| BBS9 | PTHB1_HUMAN | Protein PTHB1 |
| BCAM | BCAM_HUMAN | Basal cell adhesion molecule |
| BCAT1 | BCAT1_HUMAN | Branched-chain-amino-acid aminotransferase, cytosolic |
| BCAT2 | BCAT2_HUMAN | Branched-chain-amino-acid aminotransferase, mitochondrial |
| BCHE | CHLE_HUMAN | Cholinesterase |
| BCL11A | BC11A_HUMAN | B-cell lymphoma/leukemia 11A |
| BCL11B | BC11B_HUMAN | B-cell lymphoma/leukemia 11B |
| BCL3 | BCL3_HUMAN | B-cell lymphoma 3 protein |
| BCL6 | BCL6_HUMAN | B-cell lymphoma 6 protein |
| BCL6B | BCL6B_HUMAN | B-cell CLL/lymphoma 6 member B protein |
| BCR | BCR_HUMAN | Breakpoint cluster region protein |
| BDNF | BDNF_HUMAN | Brain-derived neurotrophic factor |
| BECN1 | BECN1_HUMAN | Beclin-1-C 37 kDa |
| BHMT | BHMT1_HUMAN | Betaine--homocysteine S-methyltransferase 1 |
| BIRC2 | BIRC2_HUMAN | Baculoviral IAP repeat-containing protein 2 |
| BIRC3 | BIRC3_HUMAN | Baculoviral IAP repeat-containing protein 3 |
| BIRC6 | BIRC6_HUMAN | Baculoviral IAP repeat-containing protein 6 |
| BIRC7 | BIRC7_HUMAN | Baculoviral IAP repeat-containing protein 7 30 kDa subunit |
| BIRC8 | BIRC8_HUMAN | Baculoviral IAP repeat-containing protein 8 |
| BLMH | BLMH_HUMAN | Bleomycin hydrolase |
| BMI1 | BMI1_HUMAN | Polycomb complex protein BMI-1 |
| BMP2K | BMP2K_HUMAN | BMP-2-inducible protein kinase |
| BMPR1A | BMR1A_HUMAN | Bone morphogenetic protein receptor type-1A |
| BMPR1B | BMR1B_HUMAN | Bone morphogenetic protein receptor type-1B |
| BMPR2 | BMPR2_HUMAN | Bone morphogenetic protein receptor type-2 |
| BMX | BMX_HUMAN | Cytoplasmic tyrosine-protein kinase BMX |
| BNC2 | BNC2_HUMAN | Zinc finger protein basonuclin-2 |
| BOC | BOC_HUMAN | Brother of CDO |
| BOLA3 | BOLA3_HUMAN | BolA-like protein 3 |
| BPI | BPI_HUMAN | Bactericidal permeability-increasing protein |
| BPIFA1 | BPIA1_HUMAN | BPI fold-containing family A member 1 |
| BRAF | BRAF_HUMAN | Serine/threonine-protein kinase B-raf |
| BRAP | BRAP_HUMAN | BRCA1-associated protein |
| BRD1 | BRD1_HUMAN | Bromodomain-containing protein 1 |
| BRF1 | TF3B_HUMAN | Transcription factor IIIB 90 kDa subunit |
| BRF2 | BRF2_HUMAN | Transcription factor IIIB 50 kDa subunit |
| BROX | BROX_HUMAN | BRO1 domain-containing protein BROX |
| BSG | BASI_HUMAN | Basigin |
| BSN | BSN_HUMAN | Protein bassoon |
| BSPRY | BSPRY_HUMAN | B box and SPRY domain-containing protein |
| BTBD2 | BTBD2_HUMAN | BTB/POZ domain-containing protein 2 |
| BTG2 | BTG2_HUMAN | Protein BTG2 |
| BTK | BTK_HUMAN | Tyrosine-protein kinase BTK |
| BTN3A1 | BT3A1_HUMAN | Butyrophilin subfamily 3 member A1 |
| BTN3A2 | BT3A2_HUMAN | Butyrophilin subfamily 3 member A2 |
| BTN3A3 | BT3A3_HUMAN | Butyrophilin subfamily 3 member A3 |
| BTRC | FBW1A_HUMAN | F-box/WD repeat-containing protein 1A |
| BUD31 | BUD31_HUMAN | Protein BUD31 homolog |
| C11orf54 | CK054_HUMAN | Ester hydrolase C11orf54 |
| C11orf68 | CK068_HUMAN | UPF0696 protein C11orf68 |
| C1QA | C1QA_HUMAN | Complement C1q subcomponent subunit A |
| C1QB | C1QB_HUMAN | Complement C1q subcomponent subunit B |
| C1QBP | C1QBP_HUMAN | Complement component 1 Q subcomponent-binding protein, mitochondrial |
| C1QC | C1QC_HUMAN | Complement C1q subcomponent subunit C |
| C1QTNF5 | C1QT5_HUMAN | Complement C1q tumor necrosis factor-related protein 5 |

TABLE 1-continued

| Target Protein Symbol | uniprot name | Target Protein name |
|---|---|---|
| C1R | C1R_HUMAN | Complement C1r subcomponent light chain |
| C1S | C1S_HUMAN | Complement C1s subcomponent light chain |
| C2 | CO2_HUMAN | Complement C2a fragment |
| C2CD2L | C2C2L_HUMAN | Phospholipid transfer protein C2CD2L |
| C3 | CO3_HUMAN | Complement C3c alpha' chain fragment 2 |
| C4A | CO4A_HUMAN | Complement C4 gamma chain |
| C4B\|C4B_2 | CO4B_HUMAN | Complement C4 gamma chain |
| C4BPA | C4BPA_HUMAN | C4b-binding protein alpha chain |
| C5 | CO5_HUMAN | Complement C5 alpha' chain |
| C6 | CO6_HUMAN | Complement component C6 |
| C7 | CO7_HUMAN | Complement component C7 |
| C8A | CO8A_HUMAN | Complement component C8 alpha chain |
| C8B | CO8B_HUMAN | Complement component C8 beta chain |
| C8G | CO8G_HUMAN | Complement component C8 gamma chain |
| C9 | CO9_HUMAN | Complement component C9b |
| CA2 | CAH2_HUMAN | Carbonic anhydrase 2 |
| CA6 | CAH6_HUMAN | Carbonic anhydrase 6 |
| CABP1 | CABP1_HUMAN | Calcium-binding protein 1 |
| CACNG2 | CCG2_HUMAN | Voltage-dependent calcium channel gamma-2 subunit |
| CALCOCO2 | CACO2_HUMAN | Calcium-binding and coiled-coil domain-containing protein 2 |
| CALM1 | CALM1_HUMAN | Calmodulin-1 |
| CALM2 | CALM2_HUMAN | Calmodulin-2 |
| CAMK1D | KCC1D_HUMAN | Calcium/calmodulin-dependent protein kinase type 1D |
| CAMK1G | KCC1G_HUMAN | Calcium/calmodulin-dependent protein kinase type 1G |
| CAMK2A | KCC2A_HUMAN | Calcium/calmodulin-dependent protein kinase type II subunit alpha |
| CAMK2B | KCC2B_HUMAN | Calcium/calmodulin-dependent protein kinase type II subunit beta |
| CAMK2D | KCC2D_HUMAN | Calcium/calmodulin-dependent protein kinase type II subunit delta |
| CAMKK1 | KKCC1_HUMAN | Calcium/calmodulin-dependent protein kinase kinase 1 |
| CAMKK2 | KKCC2_HUMAN | Calcium/calmodulin-dependent protein kinase kinase 2 |
| CANT1 | CANT1_HUMAN | Soluble calcium-activated nucleotidase 1 |
| CAPN15 | CAN15_HUMAN | Calpain-15 |
| CAPN2 | CAN2_HUMAN | Calpain-2 catalytic subunit |
| CAPN9 | CAN9_HUMAN | Calpain-9 |
| CAPNS1 | CPNS1_HUMAN | Calpain small subunit 1 |
| CAPRIN2 | CAPR2_HUMAN | Caprin-2 |
| CARHSP1 | CHSP1_HUMAN | Calcium-regulated heat-stable protein 1 |
| CARM1 | CARM1_HUMAN | Histone-arginine methyltransferase CARM1 |
| CASK | CSKP_HUMAN | Peripheral plasma membrane protein CASK |
| CASP1 | CASP1_HUMAN | Caspase-1 subunit p10 |
| CASP2 | CASP2_HUMAN | Caspase-2 subunit p12 |
| CASP3 | CASP3_HUMAN | Caspase-3 subunit p12 |
| CASP6 | CASP6_HUMAN | Caspase-6 subunit p11 |
| CASP7 | CASP7_HUMAN | Caspase-7 subunit p11 |
| CASP8 | CASP8_HUMAN | Caspase-8 subunit p10 |
| CASP9 | CASP9_HUMAN | Caspase-9 subunit p10 |
| CASR | CASR_HUMAN | Extracellular calcium-sensing receptor |
| CAT | CATA_HUMAN | Catalase |
| CBFA2T2 | MTG8R_HUMAN | Protein CBFA2T2 |
| CBFA2T3 | MTG16_HUMAN | Protein CBFA2T3 |
| CBFB | PEBB_HUMAN | Core-binding factor subunit beta |
| CBL | CBL_HUMAN | E3 ubiquitin-protein ligase CBL |
| CBLB | CBLB_HUMAN | E3 ubiquitin-protein ligase CBL-B |
| CBLC | CBLC_HUMAN | E3 ubiquitin-protein ligase CBL-C |
| CBLL1 | HAKAI_HUMAN | E3 ubiquitin-protein ligase Hakai |
| CBS | CBS_HUMAN | Cystathionine beta-synthase |
| CCL13 | CCL13_HUMAN | C-C motif chemokine 13, short chain |
| CCL14 | CCL14_HUMAN | HCC-1(9-74) |
| CCL17 | CCL17_HUMAN | C-C motif chemokine 17 |
| CCL18 | CCL18_HUMAN | CCL18(4-69) |
| CCL19 | CCL19_HUMAN | C-C motif chemokine 19 |
| CCL23 | CCL23_HUMAN | CCL23(30-99) |
| CCL24 | CCL24_HUMAN | C-C motif chemokine 24 |
| CCL26 | CCL26_HUMAN | C-C motif chemokine 26 |
| CCL8 | CCL8_HUMAN | MCP-2(6-76) |
| CCNB1IP1 | CIP1_HUMAN | E3 ubiquitin-protein ligase CCNB1IP1 |
| CCNT2 | CCNT2_HUMAN | Cyclin-T2 |
| CCR2 | CCR2_HUMAN | C-C chemokine receptor type 2 |
| CCR5 | CCR5_HUMAN | C-C chemokine receptor type 5 |
| CCS | CCS_HUMAN | Copper chaperone for superoxide dismutase |

TABLE 1-continued

| Target Protein Symbol | uniprot name | Target Protein name |
|---|---|---|
| CCT5 | TCPE_HUMAN | T-complex protein 1 subunit epsilon |
| CD19 | CD19_HUMAN | B-lymphocyte antigen CD19 |
| CD1A | CD1A_HUMAN | T-cell surface glycoprotein CD1a |
| CD1B | CD1B_HUMAN | T-cell surface glycoprotein CD1b |
| CD1C | CD1C_HUMAN | T-cell surface glycoprotein CD1c |
| CD1D | CD1D_HUMAN | Antigen-presenting glycoprotein CD1d |
| CD1E | CD1E_HUMAN | T-cell surface glycoprotein CD1e, soluble |
| CD2 | CD2_HUMAN | T-cell surface antigen CD2 |
| CD207 | CLC4K_HUMAN | C-type lectin domain family 4 member K |
| CD22 | CD22_HUMAN | B-cell receptor CD22 |
| CD226 | CD226_HUMAN | CD226 antigen |
| CD2AP | CD2AP_HUMAN | CD2-associated protein |
| CD302 | CD302_HUMAN | CD302 antigen |
| CD320 | CD320_HUMAN | CD320 antigen |
| CD33 | CD33_HUMAN | Myeloid cell surface antigen CD33 |
| CD36 | CD36_HUMAN | Platelet glycoprotein 4 |
| CD4 | CD4_HUMAN | T-cell surface glycoprotein CD4 |
| CD44 | CD44_HUMAN | CD44 antigen |
| CD48 | CD48_HUMAN | CD48 antigen |
| CD5 | CD5_HUMAN | T-cell surface glycoprotein CD5 |
| CD55 | DAF_HUMAN | Complement decay-accelerating factor |
| CD58 | LFA3_HUMAN | Lymphocyte function-associated antigen 3 |
| CD74 | HG2A_HUMAN | HLA class II histocompatibility antigen gamma chain |
| CD86 | CD86_HUMAN | T-lymphocyte activation antigen CD86 |
| CD96 | TACT_HUMAN | T-cell surface protein tactile |
| CDA | CDD_HUMAN | Cytidine deaminase |
| CDC20 | CDC20_HUMAN | Cell division cycle protein 20 homolog |
| CDC40 | PRP17_HUMAN | Pre-mRNA-processing factor 17 |
| CDC42BPA | MRCKA_HUMAN | Serine/threonine-protein kinase MRCK alpha |
| CDC42BPB | MRCKB_HUMAN | Serine/threonine-protein kinase MRCK beta |
| CDC42BPG | MRCKG_HUMAN | Serine/threonine-protein kinase MRCK gamma |
| CDC45 | CDC45_HUMAN | Cell division control protein 45 homolog |
| CDH1 | CADH1_HUMAN | E-Cad/CTF3 |
| CDH13 | CAD13_HUMAN | Cadherin-13 |
| CDH23 | CAD23_HUMAN | Cadherin-23 |
| CDH3 | CADH3_HUMAN | Cadherin-3 |
| CDHR2 | CDHR2_HUMAN | Cadherin-related family member 2 |
| CDK1 | CDK1_HUMAN | Cyclin-dependent kinase 1 |
| CDK12 | CDK12_HUMAN | Cyclin-dependent kinase 12 |
| CDK13 | CDK13_HUMAN | Cyclin-dependent kinase 13 |
| CDK16 | CDK16_HUMAN | Cyclin-dependent kinase 16 |
| CDK2 | CDK2_HUMAN | Cyclin-dependent kinase 2 |
| CDK4 | CDK4_HUMAN | Cyclin-dependent kinase 4 |
| CDK5 | CDK5_HUMAN | Cyclin-dependent-like kinase 5 |
| CDK6 | CDK6_HUMAN | Cyclin-dependent kinase 6 |
| CDK7 | CDK7_HUMAN | Cyclin-dependent kinase 7 |
| CDK9 | CDK9_HUMAN | Cyclin-dependent kinase 9 |
| CDKL1 | CDKL1_HUMAN | Cyclin-dependent kinase-like 1 |
| CDKL2 | CDKL2_HUMAN | Cyclin-dependent kinase-like 2 |
| CDKL3 | CDKL3_HUMAN | Cyclin-dependent kinase-like 3 |
| CDKN2A | CDN2A_HUMAN | Cyclin-dependent kinase inhibitor 2A |
| CDKN2C | CDN2C_HUMAN | Cyclin-dependent kinase 4 inhibitor C |
| CDKN2D | CDN2D_HUMAN | Cyclin-dependent kinase 4 inhibitor D |
| CDO1 | CDO1_HUMAN | Cysteine dioxygenase type 1 |
| CDYL | CDYL_HUMAN | Chromodomain Y-like protein |
| CDYL2 | CDYL2_HUMAN | Chromodomain Y-like protein 2 |
| CEACAM5 | CEAM5_HUMAN | Carcinoembryonic antigen-related cell adhesion molecule 5 |
| CEACAM7 | CEAM7_HUMAN | Carcinoembryonic antigen-related cell adhesion molecule 7 |
| CEBPA | CEBPA_HUMAN | CCAAT/enhancer-binding protein alpha |
| CEL | CEL_HUMAN | Bile salt-activated lipase |
| CELF6 | CELF6_HUMAN | CUGBP Elav-like family member 6 |
| CEP104 | CE104_HUMAN | Centrosomal protein of 104 kDa |
| CEP170 | CE170_HUMAN | Centrosomal protein of 170 kDa |
| CES1 | EST1_HUMAN | Liver carboxylesterase 1 |
| CETP | CETP_HUMAN | Cholesteryl ester transfer protein |
| CFB | CFAB_HUMAN | Complement factor B Bb fragment |
| CFD | CFAD_HUMAN | Complement factor D |
| CFH | CFAH_HUMAN | Complement factor H |
| CFI | CFAI_HUMAN | Complement factor I light chain |
| CFP | PROP_HUMAN | Properdin |
| CFTR | CFTR_HUMAN | Cystic fibrosis transmembrane conductance regulator |
| CGA | GLHA_HUMAN | Glycoprotein hormones alpha chain |
| CHAMP1 | CHAP1_HUMAN | Chromosome alignment-maintaining phosphoprotein 1 |

TABLE 1-continued

| Target Protein Symbol | uniprot name | Target Protein name |
|---|---|---|
| CHD1 | CHD1_HUMAN | Chromodomain-helicase-DNA-binding protein 1 |
| CHD4 | CHD4_HUMAN | Chromodomain-helicase-DNA-binding protein 4 |
| CHD6 | CHD6_HUMAN | Chromodomain-helicase-DNA-binding protein 6 |
| CHD7 | CHD7_HUMAN | Chromodomain-helicase-DNA-binding protein 7 |
| CHD8 | CHD8_HUMAN | Chromodomain-helicase-DNA-binding protein 8 |
| CHEK1 | CHK1_HUMAN | Serine/threonine-protein kinase Chk1 |
| CHFR | CHFR_HUMAN | E3 ubiquitin-protein ligase CHFR |
| CHID1 | CHID1_HUMAN | Chitinase domain-containing protein 1 |
| CHN1 | CHIN_HUMAN | N-chimaerin |
| CHN2 | CHIO_HUMAN | Beta-chimaerin |
| CHRM1 | ACM1_HUMAN | Muscarinic acetylcholine receptor M1 |
| CHRNA1 | ACHA_HUMAN | Acetylcholine receptor subunit alpha |
| CHRNA2 | ACHA2_HUMAN | Neuronal acetylcholine receptor subunit alpha-2 |
| CHRNA3 | ACHA3_HUMAN | Neuronal acetylcholine receptor subunit alpha-3 |
| CHRNA4 | ACHA4_HUMAN | Neuronal acetylcholine receptor subunit alpha-4 |
| CHRNA7 | ACHA7_HUMAN | Neuronal acetylcholine receptor subunit alpha-7 |
| CHRNA9 | ACHA9_HUMAN | Neuronal acetylcholine receptor subunit alpha-9 |
| CHRNB2 | ACHB2_HUMAN | Neuronal acetylcholine receptor subunit beta-2 |
| CHUK | IKKA_HUMAN | Inhibitor of nuclear factor kappa-B kinase subunit alpha |
| CIAO1 | CIAO1_HUMAN | Probable cytosolic iron-sulfur protein assembly protein CIAO1 |
| CIDEA | CIDEA_HUMAN | Cell death activator CIDE-A |
| CIDEB | CIDEB_HUMAN | Cell death activator CIDE-B |
| CKB | KCRB_HUMAN | Creatine kinase B-type |
| CKM | KCRM_HUMAN | Creatine kinase M-type |
| CKMT1A\|CKMT1B | KCRU_HUMAN | Creatine kinase U-type, mitochondrial |
| CKMT2 | KCRS_HUMAN | Creatine kinase S-type, mitochondrial |
| CLDN2 | CLD2_HUMAN | Claudin-2 |
| CLDN4 | CLD4_HUMAN | Claudin-4 |
| CLEC2A | CLC2A_HUMAN | C-type lectin domain family 2 member A |
| CLEC2D | CLC2D_HUMAN | C-type lectin domain family 2 member D |
| CLEC4D | CLC4D_HUMAN | C-type lectin domain family 4 member D |
| CLEC4E | CLC4E_HUMAN | C-type lectin domain family 4 member E |
| CLEC4M | CLC4M_HUMAN | C-type lectin domain family 4 member M |
| CLEC6A | CLC6A_HUMAN | C-type lectin domain family 6 member A |
| CLEC9A | CLC9A_HUMAN | C-type lectin domain family 9 member A |
| CLK1 | CLK1_HUMAN | Dual specificity protein kinase CLK1 |
| CLK2 | CLK2_HUMAN | Dual specificity protein kinase CLK2 |
| CLK3 | CLK3_HUMAN | Dual specificity protein kinase CLK3 |
| CLPP | CLPP_HUMAN | ATP-dependent Clp protease proteolytic subunit, mitochondrial |
| CLPX | CLPX_HUMAN | ATP-dependent Clp protease ATP-binding subunit clpX-like, mitochondrial |
| CLTC | CLH1_HUMAN | Clathrin heavy chain 1 |
| CMA1 | CMA1_HUMAN | Chymase |
| CNBP | CNBP_HUMAN | Cellular nucleic acid-binding protein |
| CNDP2 | CNDP2_HUMAN | Cytosolic non-specific dipeptidase |
| CNNM2 | CNNM2_HUMAN | Metal transporter CNNM2 |
| CNNM3 | CNNM3_HUMAN | Metal transporter CNNM3 |
| CNOT4 | CNOT4_HUMAN | CCR4-NOT transcription complex subunit 4 |
| CNOT7 | CNOT7_HUMAN | CCR4-NOT transcription complex subunit 7 |
| CNP | CN37_HUMAN | 2',3'-cyclic-nucleotide 3'-phosphodiesterase |
| CNR2 | CNR2_HUMAN | Cannabinoid receptor 2 |
| CNTFR | CNTFR_HUMAN | Ciliary neurotrophic factor receptor subunit alpha |
| CNTN1 | CNTN1_HUMAN | Contactin-1 |
| CNTN2 | CNTN2_HUMAN | Contactin-2 |
| CNTN3 | CNTN3_HUMAN | Contactin-3 |
| CNTN5 | CNTN5_HUMAN | Contactin-5 |
| COL10A1 | COAA1_HUMAN | Collagen alpha-1(X) chain |
| COL1A1 | CO1A1_HUMAN | Collagen alpha-1(I) chain |
| COL20A1 | COKA1_HUMAN | Collagen alpha-1(XX) chain |
| COL3A1 | CO3A1_HUMAN | Collagen alpha-1(III) chain |
| COL4A1 | CO4A1_HUMAN | Arresten |
| COL4A2 | CO4A2_HUMAN | Canstatin |
| COL4A3 | CO4A3_HUMAN | Tumstatin |
| COL4A4 | CO4A4_HUMAN | Collagen alpha-4(IV) chain |
| COL4A5 | CO4A5_HUMAN | Collagen alpha-5(IV) chain |
| COLEC11 | COL11_HUMAN | Collectin-11 |
| COLEC12 | COL12_HUMAN | Collectin-12 |
| COMP | COMP_HUMAN | Cartilage oligomeric matrix protein |
| COP1 | COP1_HUMAN | E3 ubiquitin-protein ligase COP1 |
| COPG1 | COPG1_HUMAN | Coatomer subunit gamma-1 |
| COPS3 | CSN3_HUMAN | COP9 signalosome complex subunit 3 |
| COPS4 | CSN4_HUMAN | COP9 signalosome complex subunit 4 |
| COQ8A | COQ8A_HUMAN | Atypical kinase COQ8A, mitochondrial |
| COX5B | COX5B_HUMAN | Cytochrome c oxidase subunit 5B, mitochondrial |
| CPA1 | CBPA1_HUMAN | Carboxypeptidase A1 |

TABLE 1-continued

| Target Protein Symbol | uniprot name | Target Protein name |
|---|---|---|
| CPB1 | CBPB1_HUMAN | Carboxypeptidase B |
| CPD | CBPD_HUMAN | Carboxypeptidase D |
| CPM | CBPM_HUMAN | Carboxypeptidase M |
| CPN1 | CBPN_HUMAN | Carboxypeptidase N catalytic chain |
| CPOX | HEM6_HUMAN | Oxygen-dependent coproporphyrinogen-III oxidase, mitochondrial |
| CPS1 | CPSM_HUMAN | Carbamoyl-phosphate synthase [ammonia], mitochondrial |
| CPSF1 | CPSF1_HUMAN | Cleavage and polyadenylation specificity factor subunit 1 |
| CPSF3 | CPSF3_HUMAN | Cleavage and polyadenylation specificity factor subunit 3 |
| CPSF4 | CPSF4_HUMAN | Cleavage and polyadenylation specificity factor subunit 4 |
| CPSF6 | CPSF6_HUMAN | Cleavage and polyadenylation specificity factor subunit 6 |
| CPSF7 | CPSF7_HUMAN | Cleavage and polyadenylation specificity factor subunit 7 |
| CR1 | CR1_HUMAN | Complement receptor type 1 |
| CR2 | CR2_HUMAN | Complement receptor type 2 |
| CRABP2 | RABP2_HUMAN | Cellular retinoic acid-binding protein 2 |
| CRBN | CRBN_HUMAN | Protein cereblon |
| CREBBP | CBP_HUMAN | CREB-binding protein |
| CRHR1 | CRFR1_HUMAN | Corticotropin-releasing factor receptor 1 |
| CRK | CRK_HUMAN | Adapter molecule crk |
| CRKL | CRKL_HUMAN | Crk-like protein |
| CRP | CRP_HUMAN | C-reactive protein(1-205) |
| CRTAM | CRTAM_HUMAN | Cytotoxic and regulatory T-cell molecule |
| CRYAB | CRYAB_HUMAN | Alpha-crystallin B chain |
| CRYM | CRYM_HUMAN | Ketimine reductase mu-crystallin |
| CS | CISY_HUMAN | Citrate synthase, mitochondrial |
| CSAD | CSAD_HUMAN | Cysteine sulfinic acid decarboxylase |
| CSDE1 | CSDE1_HUMAN | Cold shock domain-containing protein E1 |
| CSF1R | CSF1R_HUMAN | Macrophage colony-stimulating factor 1 receptor |
| CSF3R | CSF3R_HUMAN | Granulocyte colony-stimulating factor receptor |
| CSK | CSK_HUMAN | Tyrosine-protein kinase CSK |
| CSNK1A1 | KC1A_HUMAN | Casein kinase I isoform alpha |
| CSNK1D | KC1D_HUMAN | Casein kinase I isoform delta |
| CSNK1E | KC1E_HUMAN | Casein kinase I isoform epsilon |
| CSNK1G3 | KC1G3_HUMAN | Casein kinase I isoform gamma-3 |
| CSRP3 | CSRP3_HUMAN | Cysteine and glycine-rich protein 3 |
| CST3 | CYTC_HUMAN | Cystatin-C |
| CSTF1 | CSTF1_HUMAN | Cleavage stimulation factor subunit 1 |
| CSTF2 | CSTF2_HUMAN | Cleavage stimulation factor subunit 2 |
| CTCF | CTCF_HUMAN | Transcriptional repressor CTCF |
| CTCFL | CTCFL_HUMAN | Transcriptional repressor CTCFL |
| CTLA4 | CTLA4_HUMAN | Cytotoxic T-lymphocyte protein 4 |
| CTPS1 | PYRG1_HUMAN | CTP synthase 1 |
| CTPS2 | PYRG2_HUMAN | CTP synthase 2 |
| CTRC | CTRC_HUMAN | Chymotrypsin-C |
| CTSA | PPGB_HUMAN | Lysosomal protective protein 20 kDa chain |
| CTSC | CATC_HUMAN | Dipeptidyl peptidase 1 light chain |
| CTSD | CATD_HUMAN | Cathepsin D heavy chain |
| CTSE | CATE_HUMAN | Cathepsin E form II |
| CUL4B | CUL4B_HUMAN | Cullin-4B |
| CUL5 | CUL5_HUMAN | Cullin-5 |
| CUL7 | CUL7_HUMAN | Cullin-7 |
| CUL9 | CUL9_HUMAN | Cullin-9 |
| CUTC | CUTC_HUMAN | Copper homeostasis protein cutC homolog |
| CWC27 | CWC27_HUMAN | Spliceosome-associated protein CWC27 homolog |
| CWF19L2 | C19L2_HUMAN | CWF19-like protein 2 |
| CXADR | CXAR_HUMAN | Coxsackievirus and adenovirus receptor |
| CXCL10 | CXL10_HUMAN | CXCL10(1-73) |
| CXCL2 | CXCL2_HUMAN | GRO-beta(5-73) |
| CXCL5 | CXCL5_HUMAN | ENA-78(9-78) |
| CXCL8 | IL8_HUMAN | IL-8(9-77) |
| CXCR4 | CXCR4_HUMAN | C-X-C chemokine receptor type 4 |
| CYC1 | CY1_HUMAN | Cytochrome c1, heme protein, mitochondrial |
| CYHR1 | CYHR1_HUMAN | Cysteine and histidine-rich protein 1 |
| CYLD | CYLD_HUMAN | Ubiquitin carboxyl-terminal hydrolase CYLD |
| CYP51A1 | CP51A_HUMAN | Lanosterol 14-alpha demethylase |
| CYP7A1 | CP7A1_HUMAN | Cholesterol 7-alpha-monooxygenase |
| CYTH3 | CYH3_HUMAN | Cytohesin-3 |
| CZIB | CZIB_HUMAN | CXXC motif containing zinc binding protein |
| DAG1 | DAG1_HUMAN | Beta-dystroglycan |
| DAPK1 | DAPK1_HUMAN | Death-associated protein kinase 1 |
| DAPK2 | DAPK2_HUMAN | Death-associated protein kinase 2 |
| DAPK3 | DAPK3_HUMAN | Death-associated protein kinase 3 |

TABLE 1-continued

| Target Protein Symbol | uniprot name | Target Protein name |
|---|---|---|
| DARS2 | SYDM_HUMAN | Aspartate--tRNA ligase, mitochondrial |
| DAW1 | DAW1_HUMAN | Dynein assembly factor with WDR repeat domains 1 |
| DBH | DOPO_HUMAN | Soluble dopamine beta-hydroxylase |
| DBNL | DBNL_HUMAN | Drebrin-like protein |
| DCAF1 | DCAF1_HUMAN | DDB1- and CUL4-associated factor 1 |
| DCC | DCC_HUMAN | Netrin receptor DCC |
| DCDC2 | DCDC2_HUMAN | Doublecortin domain-containing protein 2 |
| DCLK1 | DCLK1_HUMAN | Serine/threonine-protein kinase DCLK1 |
| DCLRE1A | DCR1A_HUMAN | DNA cross-link repair 1A protein |
| DCLRE1B | DCR1B_HUMAN | 5' exonuclease Apollo |
| DCTN1 | DCTN1_HUMAN | Dynactin subunit 1 |
| DCTN5 | DCTN5_HUMAN | Dynactin subunit 5 |
| DCUN1D1 | DCNL1_HUMAN | DCN1-like protein 1 |
| DCX | DCX_HUMAN | Neuronal migration protein doublecortin |
| DDAH1 | DDAH1_HUMAN | N(G),N(G)-dimethylarginine dimethylaminohydrolase 1 |
| DDB1 | DDB1_HUMAN | DNA damage-binding protein 1 |
| DDB2 | DDB2_HUMAN | DNA damage-binding protein 2 |
| DDI1 | DDI1_HUMAN | Protein DDI1 homolog 1 |
| DDI2 | DDI2_HUMAN | Protein DDI1 homolog 2 |
| DDR1 | DDR1_HUMAN | Epithelial discoidin domain-containing receptor 1 |
| DDX1 | DDX1_HUMAN | ATP-dependent RNA helicase DDX1 |
| DDX39B | DX39B_HUMAN | Spliceosome RNA helicase DDX39B |
| DDX41 | DDX41_HUMAN | Probable ATP-dependent RNA helicase DDX41 |
| DDX58 | DDX58_HUMAN | Probable ATP-dependent RNA helicase DDX58 |
| DDX59 | DDX59_HUMAN | Probable ATP-dependent RNA helicase DDX59 |
| DEAF1 | DEAF1_HUMAN | Deformed epidermal autoregulatory factor 1 homolog |
| DEFA1\|DEFA1B | DEF1_HUMAN | Neutrophil defensin 2 |
| DEFB4A\|DEFB4B | DFB4A_HUMAN | Beta-defensin 4A |
| DESI1 | DESI1_HUMAN | Desumoylating isopeptidase 1 |
| DFFA | DFFA_HUMAN | DNA fragmentation factor subunit alpha |
| DFFB | DFFB_HUMAN | DNA fragmentation factor subunit beta |
| DGKE | DGKE_HUMAN | Diacylglycerol kinase epsilon |
| DGKI | DGKI_HUMAN | Diacylglycerol kinase iota |
| DGKK | DGKK_HUMAN | Diacylglycerol kinase kappa |
| DGKQ | DGKQ_HUMAN | Diacylglycerol kinase theta |
| DGKZ | DGKZ_HUMAN | Diacylglycerol kinase zeta |
| DHFR | DYR_HUMAN | Dihydrofolate reductase |
| DHX16 | DHX16_HUMAN | Pre-mRNA-splicing factor ATP-dependent RNA helicase DHX16 |
| DHX58 | DHX58_HUMAN | Probable ATP-dependent RNA helicase DHX58 |
| DHX8 | DHX8_HUMAN | ATP-dependent RNA helicase DHX8 |
| DHX9 | DHX9_HUMAN | ATP-dependent RNA helicase A |
| DICER1 | DICER_HUMAN | Endoribonuclease Dicer |
| DIS3 | RRP44_HUMAN | Exosome complex exonuclease RRP44 |
| DIXDC1 | DIXC1_HUMAN | Dixin |
| DLAT | ODP2_HUMAN | Dihydrolipoyllysine-residue acetyltransferase component of pyruvate dehydrogenase complex, mitochondrial |
| DLD | DLDH_HUMAN | Dihydrolipoyl dehydrogenase, mitochondrial |
| DLG5 | DLG5_HUMAN | Disks large homolog 5 |
| DLL1 | DLL1_HUMAN | Delta-like protein 1 |
| DLL4 | DLL4_HUMAN | Delta-like protein 4 |
| DMC1 | DMC1_HUMAN | Meiotic recombination protein DMC1/LIM15 homolog |
| DMGDH | M2GD_HUMAN | Dimethylglycine dehydrogenase, mitochondrial |
| DMPK | DMPK_HUMAN | Myotonin-protein kinase |
| DNAJA1 | DNJA1_HUMAN | DnaJ homolog subfamily A member 1 |
| DNAJA3 | DNJA3_HUMAN | DnaJ homolog subfamily A member 3, mitochondrial |
| DNAJB1 | DNJB1_HUMAN | DnaJ homolog subfamily B member 1 |
| DNAJC24 | DJC24_HUMAN | DnaJ homolog subfamily C member 24 |
| DNLZ | DNLZ_HUMAN | DNL-type zinc finger protein |
| DNMT1 | DNMT1_HUMAN | DNA (cytosine-5)-methyltransferase 1 |
| DNMT3A | DNM3A_HUMAN | DNA (cytosine-5)-methyltransferase 3A |
| DNMT3B | DNM3B_HUMAN | DNA (cytosine-5)-methyltransferase 3B |
| DNMT3L | DNM3L_HUMAN | DNA (cytosine-5)-methyltransferase 3-like |
| DNPEP | DNPEP_HUMAN | Aspartyl aminopeptidase |
| DOK2 | DOK2_HUMAN | Docking protein 2 |
| DPAGT1 | GPT_HUMAN | UDP-N-acetylglucosamine--dolichyl-phosphate N-acetylglucosaminephosphotransferase |
| DPF1 | DPF1_HUMAN | Zinc finger protein neuro-d4 |
| DPF2 | REQU_HUMAN | Zinc finger protein ubi-d4 |
| DPF3 | DPF3_HUMAN | Zinc finger protein DPF3 |
| DPP10 | DPP10_HUMAN | Inactive dipeptidyl peptidase 10 |
| DPP3 | DPP3_HUMAN | Dipeptidyl peptidase 3 |

TABLE 1-continued

| Target Protein Symbol | uniprot name | Target Protein name |
|---|---|---|
| DPP4 | DPP4_HUMAN | Dipeptidyl peptidase 4 soluble form |
| DPP6 | DPP6_HUMAN | Dipeptidyl aminopeptidase-like protein 6 |
| DPP8 | DPP8_HUMAN | Dipeptidyl peptidase 8 |
| DPP9 | DPP9_HUMAN | Dipeptidyl peptidase 9 |
| DRD2 | DRD2_HUMAN | D(2) dopamine receptor |
| DRD3 | DRD3_HUMAN | D(3) dopamine receptor |
| DROSHA | RNC_HUMAN | Ribonuclease 3 |
| DSC1 | DSC1_HUMAN | Desmocollin-1 |
| DSC2 | DSC2_HUMAN | Desmocollin-2 |
| DSG2 | DSG2_HUMAN | Desmoglein-2 |
| DSG3 | DSG3_HUMAN | Desmoglein-3 |
| DSP | DESP_HUMAN | Desmoplakin |
| DTD1 | DTD1_HUMAN | D-aminoacyl-tRNA deacylase 1 |
| DTX3 | DTX3_HUMAN | Probable E3 ubiquitin-protein ligase DTX3 |
| DTX3L | DTX3L_HUMAN | E3 ubiquitin-protein ligase DTX3L |
| DUSP14 | DUS14_HUMAN | Dual specificity protein phosphatase 14 |
| DVL2 | DVL2_HUMAN | Segment polarity protein dishevelled homolog DVL-2 |
| DYNC1H1 | DYHC1_HUMAN | Cytoplasmic dynein 1 heavy chain 1 |
| DYNC1I2 | DC1I2_HUMAN | Cytoplasmic dynein 1 intermediate chain 2 |
| DYNC2H1 | DYHC2_HUMAN | Cytoplasmic dynein 2 heavy chain 1 |
| DYNLRB1 | DLRB1_HUMAN | Dynein light chain roadblock-type 1 |
| DYRK1A | DYR1A_HUMAN | Dual specificity tyrosine-phosphorylation-regulated kinase 1A |
| DYRK2 | DYRK2_HUMAN | Dual specificity tyrosine-phosphorylation-regulated kinase 2 |
| DYRK3 | DYRK3_HUMAN | Dual specificity tyrosine-phosphorylation-regulated kinase 3 |
| DYSF | DYSF_HUMAN | Dysferlin |
| DZANK1 | DZAN1_HUMAN | Double zinc ribbon and ankyrin repeat-containing protein 1 |
| E4F1 | E4F1_HUMAN | Transcription factor E4F1 |
| EBF1 | COE1_HUMAN | Transcription factor COE1 |
| ECE1 | ECE1_HUMAN | Endothelin-converting enzyme 1 |
| ECI1 | ECI1_HUMAN | Enoyl-CoA delta isomerase 1, mitochondrial |
| EDA | EDA_HUMAN | Ectodysplasin-A, secreted form |
| EDC3 | EDC3_HUMAN | Enhancer of mRNA-decapping protein 3 |
| EDNRB | EDNRB_HUMAN | Endothelin receptor type B |
| EEA1 | EEA1_HUMAN | Early endosome antigen 1 |
| EED | EED_HUMAN | Polycomb protein EED |
| EEF1G | EF1G_HUMAN | Elongation factor 1-gamma |
| EEFSEC | SELB_HUMAN | Selenocysteine-specific elongation factor |
| EFEMP2 | FBLN4_HUMAN | EGF-containing fibulin-like extracellular matrix protein 2 |
| EFL1 | EFL1_HUMAN | Elongation factor-like GTPase 1 |
| EFTUD2 | U5S1_HUMAN | 116 kDa U5 small nuclear ribonucleoprotein component |
| EGFR | EGFR_HUMAN | Epidermal growth factor receptor |
| EGLN1 | EGLN1_HUMAN | Egl nine homolog 1 |
| EGR1 | EGR1_HUMAN | Early growth response protein 1 |
| EGR2 | EGR2_HUMAN | E3 SUMO-protein ligase EGR2 |
| EGR3 | EGR3_HUMAN | Early growth response protein 3 |
| EGR4 | EGR4_HUMAN | Early growth response protein 4 |
| EHMT1 | EHMT1_HUMAN | Histone-lysine N-methyltransferase EHMT1 |
| EHMT2 | EHMT2_HUMAN | Histone-lysine N-methyltransferase EHMT2 |
| EIF1 | EIF1_HUMAN | Eukaryotic translation initiation factor 1 |
| EIF1AD | EIF1A_HUMAN | Probable RNA-binding protein EIF1AD |
| EIF2AK2 | E2AK2_HUMAN | Interferon-induced, double-stranded RNA-activated protein kinase |
| EIF2AK3 | E2AK3_HUMAN | Eukaryotic translation initiation factor 2-alpha kinase 3 |
| EIF2B1 | EI2BA_HUMAN | Translation initiation factor eIF-2B subunit alpha |
| EIF2B2 | EI2BB_HUMAN | Translation initiation factor eIF-2B subunit beta |
| EIF2B4 | EI2BD_HUMAN | Translation initiation factor eIF-2B subunit delta |
| EIF2D | EIF2D_HUMAN | Eukaryotic translation initiation factor 2D |
| EIF2S1 | IF2A_HUMAN | Eukaryotic translation initiation factor 2 subunit 1 |
| EIF3B | EIF3B_HUMAN | Eukaryotic translation initiation factor 3 subunit B |
| EIF3E | EIF3E_HUMAN | Eukaryotic translation initiation factor 3 subunit E |
| EIF3G | EIF3G_HUMAN | Eukaryotic translation initiation factor 3 subunit G |
| EIF4EBP2 | 4EBP2_HUMAN | Eukaryotic translation initiation factor 4E-binding protein 2 |
| EIF4G1 | IF4G1_HUMAN | Eukaryotic translation initiation factor 4 gamma 1 |
| EIF5 | IF5_HUMAN | Eukaryotic translation initiation factor 5 |
| EIF5A | IF5A1_HUMAN | Eukaryotic translation initiation factor 5A-1 |
| ELAC1 | RNZ1_HUMAN | Zinc phosphodiesterase ELAC protein 1 |
| ELAVL1 | ELAV1_HUMAN | ELAV-like protein 1 |
| ELAVL4 | ELAV4_HUMAN | ELAV-like protein 4 |
| ELF5 | ELF5_HUMAN | ETS-related transcription factor Elf-5 |

TABLE 1-continued

| Target Protein Symbol | uniprot name | Target Protein name |
|---|---|---|
| ELK1 | ELK1_HUMAN | ETS domain-containing protein Elk-1 |
| ELK4 | ELK4_HUMAN | ETS domain-containing protein Elk-4 |
| ELL | ELL_HUMAN | RNA polymerase II elongation factor ELL |
| ELOC | ELOC_HUMAN | Elongin-C |
| EMILIN1 | EMIL1_HUMAN | EMILIN-1 |
| EML1 | EMAL1_HUMAN | Echinoderm microtubule-associated protein-like 1 |
| ENO1 | ENOA_HUMAN | Alpha-enolase |
| ENO2 | ENOG_HUMAN | Gamma-enolase |
| ENO3 | ENOB_HUMAN | Beta-enolase |
| ENPEP | AMPE_HUMAN | Glutamyl aminopeptidase |
| EP300 | EP300_HUMAN | Histone acetyltransferase p300 |
| EPAS1 | EPAS1_HUMAN | Endothelial PAS domain-containing protein 1 |
| EPB41 | 41_HUMAN | Protein 4.1 |
| EPB41L3 | E41L3_HUMAN | Band 4.1-like protein 3, N-terminally processed |
| EPCAM | EPCAM_HUMAN | Epithelial cell adhesion molecule |
| EPDR1 | EPDR1_HUMAN | Mammalian ependymin-related protein 1 |
| EPHA2 | EPHA2_HUMAN | Ephrin type-A receptor 2 |
| EPHA3 | EPHA3_HUMAN | Ephrin type-A receptor 3 |
| EPHA4 | EPHA4_HUMAN | Ephrin type-A receptor 4 |
| EPHA5 | EPHA5_HUMAN | Ephrin type-A receptor 5 |
| EPHB4 | EPHB4_HUMAN | Ephrin type-B receptor 4 |
| EPM2A | EPM2A_HUMAN | Laforin |
| EPOR | EPOR_HUMAN | Erythropoietin receptor |
| EPRS | SYEP_HUMAN | Proline--tRNA ligase |
| EPS8L1 | ES8L1_HUMAN | Epidermal growth factor receptor kinase substrate 8-like protein 1 |
| EPS8L2 | ES8L2_HUMAN | Epidermal growth factor receptor kinase substrate 8-like protein 2 |
| EPS8L3 | ES8L3_HUMAN | Epidermal growth factor receptor kinase substrate 8-like protein 3 |
| ERAP1 | ERAP1_HUMAN | Endoplasmic reticulum aminopeptidase 1 |
| ERAP2 | ERAP2_HUMAN | Endoplasmic reticulum aminopeptidase 2 |
| ERBB2 | ERBB2_HUMAN | Receptor tyrosine-protein kinase erbB-2 |
| ERBB3 | ERBB3_HUMAN | Receptor tyrosine-protein kinase erbB-3 |
| ERCC6L2 | ER6L2_HUMAN | DNA excision repair protein ERCC-6-like 2 |
| ERCC8 | ERCC8_HUMAN | DNA excision repair protein ERCC-8 |
| ERG | ERG_HUMAN | Transcriptional regulator ERG |
| ERN1 | ERN1_HUMAN | Endoribonuclease |
| ERVK-10 | GAK10_HUMAN | Endogenous retrovirus group K member 10 Gag polyprotein |
| ERVK-19 | GAK19_HUMAN | Endogenous retrovirus group K member 19 Gag polyprotein |
| ERVK-21 | GAK21_HUMAN | Endogenous retrovirus group K member 21 Gag polyprotein |
| ERVK-24 | GAK24_HUMAN | Endogenous retrovirus group K member 24 Gag polyprotein |
| ERVK-5 | GAK5_HUMAN | Endogenous retrovirus group K member 5 Gag polyprotein |
| ERVK-6 | GAK6_HUMAN | Endogenous retrovirus group K member 6 Gag polyprotein |
| ERVK-7 | GAK7_HUMAN | Endogenous retrovirus group K member 7 Gag polyprotein |
| ERVK-8 | GAK8_HUMAN | Endogenous retrovirus group K member 8 Gag polyprotein |
| ERVK-9 | POK9_HUMAN | Reverse transcriptase/ribonuclease H |
| ERVK-9 | GAK9_HUMAN | Endogenous retrovirus group K member 9 Gag polyprotein |
| ESCO1 | ESCO1_HUMAN | N-acetyltransferase ESCO1 |
| ESCO2 | ESCO2_HUMAN | N-acetyltransferase ESCO2 |
| ESRRA | ERR1_HUMAN | Steroid hormone receptor ERR 1 |
| ESRRB | ERR2_HUMAN | Steroid hormone receptor ERR2 |
| ESRRG | ERR3_HUMAN | Estrogen-related receptor gamma |
| ETF1 | ERF1_HUMAN | Eukaryotic peptide chain release factor subunit 1 |
| ETFB | ETFB_HUMAN | Electron transfer flavoprotein subunit beta |
| EVPL | EVPL_HUMAN | Envoplakin |
| EWSR1 | EWS_HUMAN | RNA-binding protein EWS |
| EXO1 | EXO1_HUMAN | Exonuclease 1 |
| EXOG | EXOG_HUMAN | Nuclease EXOG, mitochondrial |
| EXOSC2 | EXOS2_HUMAN | Exosome complex component RRP4 |
| EXOSC4 | EXOS4_HUMAN | Exosome complex component RRP41 |
| EXOSC5 | EXOS5_HUMAN | Exosome complex component RRP46 |
| EXOSC7 | EXOS7_HUMAN | Exosome complex component RRP42 |
| EXOSC9 | EXOS9_HUMAN | Exosome complex component RRP45 |
| EZH2 | EZH2_HUMAN | Histone-lysine N-methyltransferase EZH2 |
| EZR | EZRI_HUMAN | Ezrin |
| F10 | FA10_HUMAN | Activated factor Xa heavy chain |
| F11 | FA11_HUMAN | Coagulation factor XIa light chain |
| F11R | JAM1_HUMAN | Junctional adhesion molecule A |

TABLE 1-continued

| Target Protein Symbol | uniprot name | Target Protein name |
|---|---|---|
| F12 | FA12_HUMAN | Coagulation factor XIIa light chain |
| F13A1 | F13A_HUMAN | Coagulation factor XIIIA chain |
| F2 | THRB_HUMAN | Thrombin heavy chain |
| F2R | PAR1_HUMAN | Proteinase-activated receptor 1 |
| F2RL1 | PAR2_HUMAN | Proteinase-activated receptor 2, alternate cleaved 2 |
| F3 | TF_HUMAN | Tissue factor |
| F5 | FA5_HUMAN | Coagulation factor V light chain |
| F7 | FA7_HUMAN | Factor VII heavy chain |
| F8 | FA8_HUMAN | Factor VIIIa light chain |
| F9 | FA9_HUMAN | Coagulation factor IXa heavy chain |
| FABP1 | FABPL_HUMAN | Fatty acid-binding protein, liver |
| FABP2 | FABPI_HUMAN | Fatty acid-binding protein, intestinal |
| FABP5 | FABP5_HUMAN | Fatty acid-binding protein 5 |
| FABP6 | FABP6_HUMAN | Gastrotropin |
| FAF1 | FAF1_HUMAN | FAS-associated factor 1 |
| FAIM | FAIM1_HUMAN | Fas apoptotic inhibitory molecule 1 |
| FAM3C | FAM3C_HUMAN | Protein FAM3C |
| FAM83A | FA83A_HUMAN | Protein FAM83A |
| FAM83B | FA83B_HUMAN | Protein FAM83B |
| FAN1 | FAN1_HUMAN | Fanconi-associated nuclease 1 |
| FANCF | FANCF_HUMAN | Fanconi anemia group F protein |
| FANCL | FANCL_HUMAN | E3 ubiquitin-protein ligase FANCL |
| FAP | SEPR_HUMAN | Antiplasmin-cleaving enzyme FAP, soluble form |
| FARSB | SYFB_HUMAN | Phenylalanine--tRNA ligase beta subunit |
| FASN | FAS_HUMAN | Oleoyl-[acyl-camer-protein] hydrolase |
| FBL | FBRL_HUMAN | rRNA 2'-O-methyltransferase fibrillarin |
| FBN1 | FBN1_HUMAN | Asprosin |
| FBP1 | F16P1_HUMAN | Fructose-1,6-bisphosphatase 1 |
| FBP2 | F16P2_HUMAN | Fructose-1,6-bisphosphatase isozyme 2 |
| FBXL19 | FXL19_HUMAN | F-box/LRR-repeat protein 19 |
| FBXO3 | FBX3_HUMAN | F-box only protein 3 |
| FBXO31 | FBX31_HUMAN | F-box only protein 31 |
| FBXO43 | FBX43_HUMAN | F-box only protein 43 |
| FBXW7 | FBXW7_HUMAN | F-box/WD repeat-containing protein 7 |
| FCER2 | FCER2_HUMAN | Low affinity immunoglobulin epsilon Fc receptor soluble form |
| FCGRT | FCGRN_HUMAN | IgG receptor FcRn large subunit p51 |
| FCHSD2 | FCSD2_HUMAN | F-BAR and double SH3 domains protein 2 |
| FCN1 | FCN1_HUMAN | Ficolin-1 |
| FCN3 | FCN3_HUMAN | Ficolin-3 |
| FDX1 | ADX_HUMAN | Adrenodoxin, mitochondrial |
| FDX2 | FDX2_HUMAN | Ferredoxin-2, mitochondrial |
| FEN1 | FEN1_HUMAN | Flap endonuclease 1 |
| FER | FER_HUMAN | Tyrosine-protein kinase Fer |
| FES | FES_HUMAN | Tyrosine-protein kinase Fes/Fps |
| FEV | FEV_HUMAN | Protein FEV |
| FEZF1 | FEZF1_HUMAN | Fez family zinc finger protein 1 |
| FEZF2 | FEZF2_HUMAN | Fez family zinc finger protein 2 |
| FFAR1 | FFAR1_HUMAN | Free fatty acid receptor 1 |
| FGA | FIBA_HUMAN | Fibrinogen alpha chain |
| FGB | FIBB_HUMAN | Fibrinogen beta chain |
| FGD1 | FGD1_HUMAN | FYVE, RhoGEF and PH domain-containing protein 1 |
| FGD2 | FGD2_HUMAN | FYVE, RhoGEF and PH domain-containing protein 2 |
| FGD3 | FGD3_HUMAN | FYVE, RhoGEF and PH domain-containing protein 3 |
| FGD4 | FGD4_HUMAN | FYVE, RhoGEF and PH domain-containing protein 4 |
| FGD5 | FGD5_HUMAN | FYVE, RhoGEF and PH domain-containing protein 5 |
| FGD6 | FGD6_HUMAN | FYVE, RhoGEF and PH domain-containing protein 6 |
| FGF1 | FGF1_HUMAN | Fibroblast growth factor 1 |
| FGF10 | FGF10_HUMAN | Fibroblast growth factor 10 |
| FGF12 | FGF12_HUMAN | Fibroblast growth factor 12 |
| FGF13 | FGF13_HUMAN | Fibroblast growth factor 13 |
| FGF18 | FGF18_HUMAN | Fibroblast growth factor 18 |
| FGF19 | FGF19_HUMAN | Fibroblast growth factor 19 |
| FGF2 | FGF2_HUMAN | Fibroblast growth factor 2 |
| FGF20 | FGF20_HUMAN | Fibroblast growth factor 20 |
| FGF23 | FGF23_HUMAN | Fibroblast growth factor 23 C-terminal peptide |
| FGF4 | FGF4_HUMAN | Fibroblast growth factor 4 |
| FGF8 | FGF8_HUMAN | Fibroblast growth factor 8 |
| FGF9 | FGF9_HUMAN | Fibroblast growth factor 9 |
| FGFR1 | FGFR1_HUMAN | Fibroblast growth factor receptor 1 |
| FGFR2 | FGFR2_HUMAN | Fibroblast growth factor receptor 2 |
| FGFR3 | FGFR3_HUMAN | Fibroblast growth factor receptor 3 |

TABLE 1-continued

| Target Protein Symbol | uniprot name | Target Protein name |
|---|---|---|
| FGFR4 | FGFR4_HUMAN | Fibroblast growth factor receptor 4 |
| FGG | FIBG_HUMAN | Fibrinogen gamma chain |
| FH | FUMH_HUMAN | Fumarate hydratase, mitochondrial |
| FHL2 | FHL2_HUMAN | Four and a half LIM domains protein 2 |
| FHL3 | FHL3_HUMAN | Four and a half LIM domains protein 3 |
| FHOD1 | FHOD1_HUMAN | FH1/FH2 domain-containing protein 1 |
| FIBCD1 | FBCD1_HUMAN | Fibrinogen C domain-containing protein 1 |
| FIZ1 | FIZ1_HUMAN | Flt3-interacting zinc finger protein 1 |
| FKBP14 | FKB14_HUMAN | Peptidyl-prolyl cis-trans isomerase FKBP14 |
| FKBP1A | FKB1A_HUMAN | Peptidyl-prolyl cis-trans isomerase FKBP1A |
| FKBP3 | FKBP3_HUMAN | Peptidyl-prolyl cis-trans isomerase FKBP3 |
| FKBP4 | FKBP4_HUMAN | Peptidyl-prolyl cis-trans isomerase FKBP4, N-terminally processed |
| FKBP5 | FKBP5_HUMAN | Peptidyl-prolyl cis-trans isomerase FKBP5 |
| FKBP8 | FKBP8_HUMAN | Peptidyl-prolyl cis-trans isomerase FKBP8 |
| FLU | FLI1_HUMAN | Friend leukemia integration 1 transcription factor |
| FLNA | FLNA_HUMAN | Filamin-A |
| FLNB | FLNB_HUMAN | Filamin-B |
| FLNC | FLNC_HUMAN | Filamin-C |
| FLT1 | VGFR1_HUMAN | Vascular endothelial growth factor receptor 1 |
| FLT3 | FLT3_HUMAN | Receptor-type tyrosine-protein kinase FLT3 |
| FLT4 | VGFR3_HUMAN | Vascular endothelial growth factor receptor 3 |
| FLYWCH1 | FWCH1_HUMAN | FLYWCH-type zinc finger-containing protein 1 |
| FMR1 | FMR1_HUMAN | Synaptic functional regulator FMR1 |
| FN1 | FINC_HUMAN | Ugl-Y3 |
| FNDC3A | FND3A_HUMAN | Fibronectin type-III domain-containing protein 3A |
| FNTB | FNTB_HUMAN | Protein farnesyltransferase subunit beta |
| FOLH1 | FOLH1_HUMAN | Glutamate carboxypeptidase 2 |
| FOXO3 | FOXO3_HUMAN | Forkhead box protein O3 |
| FOXP2 | FOXP2_HUMAN | Forkhead box protein P2 |
| FOXP3 | FOXP3_HUMAN | Forkhead box protein P3 41 kDa form |
| FRS2 | FRS2_HUMAN | Fibroblast growth factor receptor substrate 2 |
| FRS3 | FRS3_HUMAN | Fibroblast growth factor receptor substrate 3 |
| FSCN1 | FSCN1_HUMAN | Fascin |
| FST | FST_HUMAN | Follistatin |
| FSTL3 | FSTL3_HUMAN | Follistatin-related protein 3 |
| FTO | FTO_HUMAN | Alpha-ketoglutarate-dependent dioxygenase FTO |
| FURIN | FURIN_HUMAN | Furin |
| FUS | FUS_HUMAN | RNA-binding protein FUS |
| FUT8 | FUT8_HUMAN | Alpha-(1,6)-fucosyltransferase |
| FXN | FRDA_HUMAN | Frataxin mature form |
| FXR1 | FXR1_HUMAN | Fragile X mental retardation syndrome-related protein 1 |
| FXR2 | FXR2_HUMAN | Fragile X mental retardation syndrome-related protein 2 |
| FYB1 | FYB1_HUMAN | FYN-binding protein 1 |
| FYCO1 | FYCO1_HUMAN | FYVE and coiled-coil domain-containing protein 1 |
| FYN | FYN_HUMAN | Tyrosine-protein kinase Fyn |
| FZD4 | FZD4_HUMAN | Frizzled-4 |
| FZR1 | FZR1_HUMAN | Fizzy-related protein homolog |
| G2E3 | G2E3_HUMAN | G2/M phase-specific E3 ubiquitin-protein ligase |
| G3BP1 | G3BP1_HUMAN | Ras GTPase-activating protein-binding protein 1 |
| GAA | LYAG_HUMAN | 70 kDa lysosomal alpha-glucosidase |
| GABBR1 | GABR1_HUMAN | Gamma-aminobutyric acid type B receptor subunit 1 |
| GABRA1 | GBRA1_HUMAN | Gamma-aminobutyric acid receptor subunit alpha-1 |
| GABRA5 | GBRA5_HUMAN | Gamma-aminobutyric acid receptor subunit alpha-5 |
| GABRB2 | GBRB2_HUMAN | Gamma-aminobutyric acid receptor subunit beta-2 |
| GABRB3 | GBRB3_HUMAN | Gamma-aminobutyric acid receptor subunit beta-3 |
| GABRG2 | GBRG2_HUMAN | Gamma-aminobutyric acid receptor subunit gamma-2 |
| GAD1 | DCE1_HUMAN | Glutamate decarboxylase 1 |
| GAD2 | DCE2_HUMAN | Glutamate decarboxylase 2 |
| GAK | GAK_HUMAN | Cyclin-G-associated kinase |
| GALM | GALM_HUMAN | Aldose 1-epimerase |
| GALNS | GALNS_HUMAN | N-acetylgalactosamine-6-sulfatase |
| GALNT10 | GLT10_HUMAN | Polypeptide N-acetylgalactosaminyltransferase 10 |
| GALNT4 | GALT4_HUMAN | Polypeptide N-acetylgalactosaminyltransferase 4 |
| GALNT7 | GALT7_HUMAN | N-acetylgalactosaminyltransferase 7 |
| GALT | GALT_HUMAN | Galactose-1-phosphate uridylyltransferase |
| GARS | GARS_HUMAN | Glycine--tRNA ligase |
| GART | PUR2_HUMAN | Phosphoribosylglycinamide formyltransferase |
| GAS7 | GAS7_HUMAN | Growth arrest-specific protein 7 |
| GATA1 | GATA1_HUMAN | Erythroid transcription factor |

TABLE 1-continued

| Target Protein Symbol | uniprot name | Target Protein name |
|---|---|---|
| GATA2 | GATA2_HUMAN | Endothelial transcription factor GATA-2 |
| GATA3 | GATA3_HUMAN | Trans-acting T-cell-specific transcription factor GATA-3 |
| GATA4 | GATA4_HUMAN | Transcription factor GATA-4 |
| GATA5 | GATA5_HUMAN | Transcription factor GATA-5 |
| GATA6 | GATA6_HUMAN | Transcription factor GATA-6 |
| GBA | GLCM_HUMAN | Lysosomal acid glucosylceramidase |
| GBA3 | GBA3_HUMAN | Cytosolic beta-glucosidase |
| GBE1 | GLGB_HUMAN | 1,4-alpha-glucan-branching enzyme |
| GCA | GRAN_HUMAN | Grancalcin |
| GCGR | GLR_HUMAN | Glucagon receptor |
| GCK | HXK4_HUMAN | Glucokinase |
| GDF15 | GDF15_HUMAN | Growth/differentiation factor 15 |
| GDF2 | GDF2_HUMAN | Growth/differentiation factor 2 |
| GEMIN5 | GEMI5_HUMAN | Gem-associated protein 5 |
| GEMIN7 | GEMI7_HUMAN | Gem-associated protein 7 |
| GFI1 | GFI1_HUMAN | Zinc finger protein Gfi-1 |
| GFI1B | GFI1B_HUMAN | Zinc finger protein Gfi-1b |
| GFM1 | EFGM_HUMAN | Elongation factor G, mitochondrial |
| GFRA3 | GFRA3_HUMAN | GDNF family receptor alpha-3 |
| GGCT | GGCT_HUMAN | Gamma-glutamylcyclotransferase |
| GGT1 | GGT1_HUMAN | Glutathione hydrolase 1 light chain |
| GHR | GHR_HUMAN | Growth hormone-binding protein |
| GINS2 | PSF2_HUMAN | DNA replication complex GINS protein PSF2 |
| GIPC2 | GIPC2_HUMAN | PDZ domain-containing protein GIPC2 |
| GLDN | GLDN_HUMAN | Gliomedin shedded ectodomain |
| GLI4 | GLI4_HUMAN | Zinc finger protein GLI4 |
| GLIPR2 | GAPR1_HUMAN | Golgi-associated plant pathogenesis-related protein 1 |
| GLIS2 | GLIS2_HUMAN | Zinc finger protein GLIS2 |
| GLO1 | LGUL_HUMAN | Lactoylglutathione lyase |
| GLOD4 | GLOD4_HUMAN | Glyoxalase domain-containing protein 4 |
| GLP1R | GLP1R_HUMAN | Glucagon-like peptide 1 receptor |
| GLRA1 | GLRA1_HUMAN | Glycine receptor subunit alpha-1 |
| GLRA3 | GLRA3_HUMAN | Glycine receptor subunit alpha-3 |
| GLS | GLSK_HUMAN | Glutaminase kidney isoform, mitochondrial |
| GLS2 | GLSL_HUMAN | Glutaminase liver isoform, mitochondrial |
| GLUD1 | DHE3_HUMAN | Glutamate dehydrogenase 1, mitochondrial |
| GMDS | GMDS_HUMAN | GDP-mannose 4,6 dehydratase |
| GMFG | GMFG_HUMAN | Glia maturation factor gamma |
| GNB1 | GBB1_HUMAN | Guanine nucleotide-binding protein G(I)/G(S)/G(T) subunit beta-1 |
| GNE | GLCNE_HUMAN | N-acetylmannosamine kinase |
| GNPDA1 | GNPI1_HUMAN | Glucosamine-6-phosphate isomerase 1 |
| GNPNAT1 | GNA1_HUMAN | Glucosamine 6-phosphate N-acetyltransferase |
| GOT1 | AATC_HUMAN | Aspartate aminotransferase, cytoplasmic |
| GOT2 | AATM_HUMAN | Aspartate aminotransferase, mitochondrial |
| GPD1 | GPDA_HUMAN | Glycerol-3-phosphate dehydrogenase [NAD(+)], cytoplasmic |
| GPD1L | GPD1L_HUMAN | Glycerol-3-phosphate dehydrogenase 1-like protein |
| GPI | G6PI_HUMAN | Glucose-6-phosphate isomerase |
| GPIHBP1 | HDBP1_HUMAN | Glycosylphosphatidylinositol-anchored high density lipoprotein-binding protein 1 |
| GPT2 | ALAT2_HUMAN | Alanine aminotransferase 2 |
| GPX1 | GPX1_HUMAN | Glutathione peroxidase 1 |
| GPX2 | GPX2_HUMAN | Glutathione peroxidase 2 |
| GPX4 | GPX4_HUMAN | Phospholipid hydroperoxide glutathione peroxidase |
| GPX7 | GPX7_HUMAN | Glutathione peroxidase 7 |
| GPX8 | GPX8_HUMAN | Probable glutathione peroxidase 8 |
| GRAP2 | GRAP2_HUMAN | GRB2-related adapter protein 2 |
| GRB10 | GRB10_HUMAN | Growth factor receptor-bound protein 10 |
| GRB14 | GRB14_HUMAN | Growth factor receptor-bound protein 14 |
| GRB2 | GRB2_HUMAN | Growth factor receptor-bound protein 2 |
| GRB7 | GRB7_HUMAN | Growth factor receptor-bound protein 7 |
| GRIA2 | GRIA2_HUMAN | Glutamate receptor 2 |
| GRIK1 | GRIK1_HUMAN | Glutamate receptor ionotropic, kainate 1 |
| GRIK2 | GRIK2_HUMAN | Glutamate receptor ionotropic, kainate 2 |
| GRIN2A | NMDE1_HUMAN | Glutamate receptor ionotropic, NMDA 2A |
| GRK2 | ARBK1_HUMAN | Beta-adrenergic receptor kinase 1 |
| GRK4 | GRK4_HUMAN | G protein-coupled receptor kinase 4 |
| GRK5 | GRK5_HUMAN | G protein-coupled receptor kinase 5 |
| GRK6 | GRK6_HUMAN | G protein-coupled receptor kinase 6 |
| GRM1 | GRM1_HUMAN | Metabotropic glutamate receptor 1 |
| GRM2 | GRM2_HUMAN | Metabotropic glutamate receptor 2 |
| GRM3 | GRM3_HUMAN | Metabotropic glutamate receptor 3 |
| GRM5 | GRM5_HUMAN | Metabotropic glutamate receptor 5 |

TABLE 1-continued

| Target Protein Symbol | uniprot name | Target Protein name |
|---|---|---|
| GRM7 | GRM7_HUMAN | Metabotropic glutamate receptor 7 |
| GRM8 | GRM8_HUMAN | Metabotropic glutamate receptor 8 |
| GRN | GRN_HUMAN | Granulin-7 |
| GSK3B | GSK3B_HUMAN | Glycogen synthase kinase-3 beta |
| GSN | GELS_HUMAN | Gelsolin |
| GSPT1 | ERF3A_HUMAN | Eukaryotic peptide chain release factor GTP-binding subunit ERF3A |
| GSR | GSHR_HUMAN | Glutathione reductase, mitochondrial |
| GSTO1 | GSTO1_HUMAN | Glutathione S-transferase omega-1 |
| GTF2B | TF2B_HUMAN | Transcription initiation factor IIB |
| GTF2E1 | T2EA_HUMAN | General transcription factor IIE subunit 1 |
| GTF2F1 | T2FA_HUMAN | General transcription factor IIF subunit 1 |
| GTF2H1 | TF2H1_HUMAN | General transcription factor IIH subunit 1 |
| GTF3A | TF3A_HUMAN | Transcription factor IIIA |
| GUSB | BGLR_HUMAN | Beta-glucuronidase |
| GZF1 | GZF1_HUMAN | GDNF-inducible zinc finger protein 1 |
| GZMB | GRAB_HUMAN | Granzyme B |
| GZMM | GRAM_HUMAN | Granzyme M |
| H2AFY | H2AY_HUMAN | Core histone macro-H2A. 1 |
| H2AFY2 | H2AW_HUMAN | Core histone macro-H2A.2 |
| HADHA | ECHA_HUMAN | Long chain 3-hydroxyacyl-CoA dehydrogenase |
| HASPIN | HASP_HUMAN | Serine/threonine-protein kinase haspin |
| HAT1 | HAT1_HUMAN | Histone acetyltransferase type B catalytic subunit |
| HBP1 | HBP1_HUMAN | HMG box-containing protein 1 |
| HCFC1 | HCFC1_HUMAN | HCF C-terminal chain 6 |
| HCK | HCK_HUMAN | Tyrosine-protein kinase HCK |
| HDAC4 | HDAC4_HUMAN | Histone deacetylase 4 |
| HDAC6 | HDAC6_HUMAN | Histone deacetylase 6 |
| HDAC7 | HDAC7_HUMAN | Histone deacetylase 7 |
| HDHD2 | HDHD2_HUMAN | Haloacid dehalogenase-like hydrolase domain-containing protein 2 |
| HECTD1 | HECD1_HUMAN | E3 ubiquitin-protein ligase HECTD1 |
| HECW1 | HECW1_HUMAN | E3 ubiquitin-protein ligase HECW1 |
| HECW2 | HECW2_HUMAN | E3 ubiquitin-protein ligase HECW2 |
| HERC1 | HERC1_HUMAN | Probable E3 ubiquitin-protein ligase HERC1 |
| HERC2 | HERC2_HUMAN | E3 ubiquitin-protein ligase HERC2 |
| HERVK_113 | GA113_HUMAN | Endogenous retrovirus group K member 113 Gag polyprotein |
| HEXA | HEXA_HUMAN | Beta-hexosaminidase subunit alpha |
| HEXB | HEXB_HUMAN | Beta-hexosaminidase subunit beta chain A |
| HFE | HFE_HUMAN | Hereditary hemochromatosis protein |
| HGD | HGD_HUMAN | Homogentisate 1,2-dioxygenase |
| HGS | HGS_HUMAN | Hepatocyte growth factor-regulated tyrosine kinase substrate |
| HHIP | HHIP_HUMAN | Hedgehog-interacting protein |
| HIC1 | HIC1_HUMAN | Hypermethylated in cancer 1 protein |
| HIC2 | HIC2_HUMAN | Hypermethylated in cancer 2 protein |
| HIF1A | HIF1A_HUMAN | Hypoxia-inducible factor 1-alpha |
| HIF3A | HIF3A_HUMAN | Hypoxia-inducible factor 3-alpha |
| HINFP | HINFP_HUMAN | Histone H4 transcription factor |
| HIRA | HIRA_HUMAN | Protein HIRA |
| HIVEP1 | ZEP1_HUMAN | Zinc finger protein 40 |
| HIVEP2 | ZEP2_HUMAN | Transcription factor HIVEP2 |
| HIVEP3 | ZEP3_HUMAN | Transcription factor HIVEP3 |
| HMCES | HMCES_HUMAN | Abasic site processing protein HMCES |
| HMGCL | HMGCL_HUMAN | Hydroxymethylglutaryl-CoA lyase, mitochondrial |
| HNF4A | HNF4A_HUMAN | Hepatocyte nuclear factor 4-alpha |
| HNF4G | HNF4G_HUMAN | Hepatocyte nuclear factor 4-gamma |
| HNRNPA1 | ROA1_HUMAN | Heterogeneous nuclear ribonucleoprotein A1, N-terminally processed |
| HNRNPA2B1 | ROA2_HUMAN | Heterogeneous nuclear ribonucleoproteins A2/B1 |
| HNRNPAB | ROAA_HUMAN | Heterogeneous nuclear ribonucleoprotein A/B |
| HNRNPD | HNRPD_HUMAN | Heterogeneous nuclear ribonucleoprotein D0 |
| HNRNPH2 | HNRH2_HUMAN | Heterogeneous nuclear ribonucleoprotein H2, N-terminally processed |
| HPD | HPPD_HUMAN | 4-hydroxyphenylpyruvate dioxygenase |
| HPN | HEPS_HUMAN | Serine protease hepsin catalytic chain |
| HRH1 | HRH1_HUMAN | Histamine H1 receptor |
| HS3ST1 | HS3S1_HUMAN | Heparan sulfate glucosamine 3-O-sulfotransferase 1 |
| HS3ST3A1 | HS3SA_HUMAN | Heparan sulfate glucosamine 3-O-sulfotransferase 3A1 |
| HS3ST5 | HS3S5_HUMAN | Heparan sulfate glucosamine 3-O-sulfotransferase 5 |
| HSCB | HSC20_HUMAN | Iron-sulfur cluster co-chaperone protein HscB, mitochondrial |
| HSD17B10 | HCD2_HUMAN | 3-hydroxyacyl-CoA dehydrogenase type-2 |
| HSD17B4 | DHB4_HUMAN | Enoyl-CoA hydratase 2 |

TABLE 1-continued

| Target Protein Symbol | uniprot name | Target Protein name |
|---|---|---|
| HSPA1A | HS71A_HUMAN | Heat shock 70 kDa protein 1A |
| HSPA5 | BIP_HUMAN | Endoplasmic reticulum chaperone BiP |
| HSPA8 | HSP7C_HUMAN | Heat shock cognate 71 kDa protein |
| HSPA9 | GRP75_HUMAN | Stress-70 protein, mitochondrial |
| HSPB1 | HSPB1_HUMAN | Heat shock protein beta-1 |
| HSPB2 | HSPB2_HUMAN | Heat shock protein beta-2 |
| HSPB6 | HSPB6_HUMAN | Heat shock protein beta-6 |
| HSPD1 | CH60_HUMAN | 60 kDa heat shock protein, mitochondrial |
| HSPG2 | PGBM_HUMAN | LG3 peptide |
| HTRA1 | HTRA1_HUMAN | Serine protease HTRA1 |
| HTRA2 | HTRA2_HUMAN | Serine protease HTRA2, mitochondrial |
| HTRA3 | HTRA3_HUMAN | Serine protease HTRA3 |
| HTT | HD_HUMAN | Huntingtin |
| HUS1 | HUS1_HUMAN | Checkpoint protein HUS1 |
| HU WEI | HUWE1_HUMAN | E3 ubiquitin-protein ligase HUWE1 |
| HYAL1 | HYAL1_HUMAN | Hyaluronidase-1 |
| HYDIN | HYDIN_HUMAN | Hydrocephalus-inducing protein homolog |
| ICAM1 | ICAM1_HUMAN | Intercellular adhesion molecule 1 |
| IDE | IDE_HUMAN | Insulin-degrading enzyme |
| IDH3G | IDH3G_HUMAN | Isocitrate dehydrogenase [NAD] subunit gamma, mitochondrial |
| IDO1 | I23O1_HUMAN | Indoleamine 2,3-dioxygenase 1 |
| IDS | IDS_HUMAN | Iduronate 2-sulfatase 14 kDa chain |
| IDUA | IDUA_HUMAN | Alpha-L-iduronidase |
| IFI16 | IF16_HUMAN | Gamma-interferon-inducible protein 16 |
| IFNAR1 | INAR1_HUMAN | Interferon alpha/beta receptor 1 |
| IFNGR1 | INGR1_HUMAN | Interferon gamma receptor 1 |
| IFNGR2 | INGR2_HUMAN | Interferon gamma receptor 2 |
| IFNLR1 | INLR1_HUMAN | Interferon lambda receptor 1 |
| IGF1R | IGF1R_HUMAN | Insulin-like growth factor 1 receptor beta chain |
| IGF2R | MPRI_HUMAN | Cation-independent mannose-6-phosphate receptor |
| IGFBP1 | IBP1_HUMAN | Insulin-like growth factor-binding protein 1 |
| IGFBP4 | IBP4_HUMAN | Insulin-like growth factor-binding protein 4 |
| IGFBP6 | IBP6_HUMAN | Insulin-like growth factor-binding protein 6 |
| IGHA1 | IGHA1_HUMAN | Immunoglobulin heavy constant alpha 1 |
| IGHE | IGHE_HUMAN | Immunoglobulin heavy constant epsilon |
| IGHG1 | IGHG1_HUMAN | Immunoglobulin heavy constant gamma 1 |
| IGHG4 | IGHG4_HUMAN | Immunoglobulin heavy constant gamma 4 |
| IGHM | IGHM_HUMAN | Immunoglobulin heavy constant mu |
| IGHV3-23 | HV323_HUMAN | Immunoglobulin heavy variable 3-23 |
| IGHV3-33 | HV333_HUMAN | Immunoglobulin heavy variable 3-33 |
| IGHV4-59 | HV459_HUMAN | Immunoglobulin heavy variable 4-59 |
| IGKC | IGKC_HUMAN | Immunoglobulin kappa constant |
| IGKV1-33 | KV133_HUMAN | Immunoglobulin kappa variable 1-33 |
| IKBKB | IKKB_HUMAN | Inhibitor of nuclear factor kappa-B kinase subunit beta |
| IKZF1 | IKZF1_HUMAN | DNA-binding protein Ikaros |
| IKZF2 | IKZF2_HUMAN | Zinc finger protein Helios |
| IKZF3 | IKZF3_HUMAN | Zinc finger protein Aiolos |
| IKZF4 | IKZF4_HUMAN | Zinc finger protein Eos |
| IKZF5 | IKZF5_HUMAN | Zinc finger protein Pegasus |
| IL12B | IL12B_HUMAN | Interleukin-12 subunit beta |
| IL13RA2 | I13R2_HUMAN | Interleukin-13 receptor subunit alpha-2 |
| IL17A | IL17_HUMAN | Interleukin-17A |
| IL17F | IL17F_HUMAN | Interleukin-17F |
| IL17RA | I17RA_HUMAN | Interleukin-17 receptor A |
| IL18R1 | IL18R_HUMAN | Interleukin-18 receptor 1 |
| IL18RAP | I18RA_HUMAN | Interleukin-18 receptor accessory protein |
| IL1F10 | IL1FA_HUMAN | Interleukin-1 family member 10 |
| IL1RAP | IL1AP_HUMAN | Interleukin-1 receptor accessory protein |
| IL20RB | I20RB_HUMAN | Interleukin-20 receptor subunit beta |
| IL22RA1 | I22R1_HUMAN | Interleukin-22 receptor subunit alpha-1 |
| IL23R | IL23R_HUMAN | Interleukin-23 receptor |
| IL4R | IL4RA_HUMAN | Soluble interleukin-4 receptor subunit alpha |
| IL5RA | IL5RA_HUMAN | Interleukin-5 receptor subunit alpha |
| IL6R | IL6RA_HUMAN | Interleukin-6 receptor subunit alpha |
| IL6ST | IL6RB_HUMAN | Interleukin-6 receptor subunit beta |
| ILK | ILK_HUMAN | Integrin-linked protein kinase |
| IMPA1 | IMPA1_HUMAN | Inositol monophosphatase 1 |
| INHBA | INHBA_HUMAN | Inhibin beta A chain |
| INKA1 | INKA1_HUMAN | PAK4-inhibitor INKA1 |
| INO80B | IN80B_HUMAN | INO80 complex subunit B |
| INPPL1 | SHIP2_HUMAN | Phosphatidylinositol 3,4,5-trisphosphate 5-phosphatase 2 |
| INSM1 | INSM1_HUMAN | Insulinoma-associated protein 1 |
| INSM2 | INSM2_HUMAN | Insulinoma-associated protein 2 |
| INSR | INSR_HUMAN | Insulin receptor subunit beta |
| INTS11 | INT11_HUMAN | Integrator complex subunit 11 |

TABLE 1-continued

| Target Protein Symbol | uniprot name | Target Protein name |
|---|---|---|
| IPMK | IPMK_HUMAN | Inositol polyphosphate multikinase |
| IQGAP1 | IQGA1_HUMAN | Ras GTPase-activating-like protein IQGAP1 |
| IQGAP2 | IQGA2_HUMAN | Ras GTPase-activating-like protein IQGAP2 |
| IQGAP3 | IQGA3_HUMAN | Ras GTPase-activating-like protein IQGAP3 |
| IQUB | IQUB_HUMAN | IQ and ubiquitin-like domain-containing protein |
| IRAK1 | IRAK1_HUMAN | Interleukin-1 receptor-associated kinase 1 |
| IRAK4 | IRAK4_HUMAN | Interleukin-1 receptor-associated kinase 4 |
| ISCU | ISCU_HUMAN | Iron-sulfur cluster assembly enzyme ISCU, mitochondrial |
| ISG15 | ISG15_HUMAN | Ubiquitin-like protein ISG15 |
| ISG20 | ISG20_HUMAN | Interferon-stimulated gene 20 kDa protein |
| ITCH | ITCH_HUMAN | E3 ubiquitin-protein ligase Itchy homolog |
| ITGA2B | ITA2B_HUMAN | Integrin alpha-IIb light chain, form 2 |
| ITGA4 | ITA4_HUMAN | Integrin alpha-4 |
| ITGA5 | ITA5_HUMAN | Integrin alpha-5 light chain |
| ITGAL | ITAL_HUMAN | Integrin alpha-L |
| ITGAV | ITAV_HUMAN | Integrin alpha-V light chain |
| ITGAX | ITAX_HUMAN | Integrin alpha-X |
| ITGB1 | ITB1_HUMAN | Integrin beta-1 |
| ITGB1BP1 | ITBP1_HUMAN | Integrin beta-1-binding protein 1 |
| ITGB2 | ITB2_HUMAN | Integrin beta-2 |
| ITGB3 | ITB3_HUMAN | Integrin beta-3 |
| ITGB4 | ITB4_HUMAN | Integrin beta-4 |
| ITGB6 | ITB6_HUMAN | Integrin beta-6 |
| ITIH1 | ITIH1_HUMAN | Inter-alpha-trypsin inhibitor heavy chain H1 |
| ITK | ITK_HUMAN | Tyrosine-protein kinase ITK/TSK |
| ITLN1 | ITLN1_HUMAN | Intelectin-1 |
| ITPA | ITPA_HUMAN | Inosine triphosphate pyrophosphatase |
| ITPK1 | ITPK1_HUMAN | Inositol-tetrakisphosphate 1-kinase |
| ITPKA | IP3KA_HUMAN | Inositol-trisphosphate 3-kinase A |
| ITPKC | IP3KC_HUMAN | Inositol-trisphosphate 3-kinase C |
| ITSN1 | ITSN1_HUMAN | Intersectin-1 |
| ITSN2 | ITSN2_HUMAN | Intersectin-2 |
| IYD | IYD1_HUMAN | Iodotyrosine deiodinase 1 |
| JAG1 | JAG1_HUMAN | Protein jagged-1 |
| JAG2 | JAG2_HUMAN | Protein jagged-2 |
| JAK1 | JAK1_HUMAN | Tyrosine-protein kinase JAK1 |
| JAK2 | JAK2_HUMAN | Tyrosine-protein kinase JAK2 |
| JAK3 | JAK3_HUMAN | Tyrosine-protein kinase JAK3 |
| JMJD1C | JHD2C_HUMAN | Probable JmjC domain-containing histone demethylation protein 2C |
| JMJD6 | JMJD6_HUMAN | Bifunctional arginine demethylase and lysyl-hydroxylase JMJD6 |
| JMJD7 | JMJD7_HUMAN | Bifunctional peptidase and (3S)-lysyl hydroxylase JMJD7 |
| KANK1 | KANK1_HUMAN | KN motif and ankyrin repeat domain-containing protein 1 |
| KANK2 | KANK2_HUMAN | KN motif and ankyrin repeat domain-containing protein 2 |
| KARS | SYK_HUMAN | Lysine-tRNA ligase |
| KAT2A | KAT2A_HUMAN | Histone acetyltransferase KAT2A |
| KAT2B | KAT2B_HUMAN | Histone acetyltransferase KAT2B |
| KAT6A | KAT6A_HUMAN | Histone acetyltransferase KAT6A |
| KAT6B | KAT6B_HUMAN | Histone acetyltransferase KAT6B |
| KCMF1 | KCMF1_HUMAN | E3 ubiquitin-protein ligase KCMF1 |
| KCNAB2 | KCAB2_HUMAN | Voltage-gated potassium channel subunit beta-2 |
| KCNH2 | KCNH2_HUMAN | Potassium voltage-gated channel subfamily H member 2 |
| KCNJ11 | KCJ11_HUMAN | ATP-sensitive inward rectifier potassium channel 11 |
| KCTD10 | BACD3_HUMAN | BIB/POZ domain-containing adapter for CUL3-mediated RhoA degradation protein 3 |
| KCTD13 | BACD1_HUMAN | BIB/POZ domain-containing adapter for CUL3-mediated RhoA degradation protein 1 |
| KCTD16 | KCD16_HUMAN | BTB/POZ domain-containing protein KCTD16 |
| KCTD17 | KCD17_HUMAN | BTB/POZ domain-containing protein KCTD17 |
| KCTD5 | KCTD5_HUMAN | BTB/POZ domain-containing protein KCTD5 |
| KCTD9 | KCTD9_HUMAN | BTB/POZ domain-containing protein KCTD9 |
| KDM1A | KDM1A_HUMAN | Lysine-specific histone demethylase 1A |
| KDM1B | KDM1B_HUMAN | Lysine-specific histone demethylase 1B |
| KDM2A | KDM2A_HUMAN | Lysine-specific demethylase 2A |
| KDM2B | KDM2B_HUMAN | Lysine-specific demethylase 2B |
| KDM3A | KDM3A_HUMAN | Lysine-specific demethylase 3A |
| KDM3B | KDM3B_HUMAN | Lysine-specific demethylase 3B |
| KDM4A | KDM4A_HUMAN | Lysine-specific demethylase 4A |
| KDM4B | KDM4B_HUMAN | Lysine-specific demethylase 4B |
| KDM4C | KDM4C_HUMAN | Lysine-specific demethylase 4C |
| KDM5A | KDM5A_HUMAN | Lysine-specific demethylase 5A |

TABLE 1-continued

| Target Protein Symbol | uniprot name | Target Protein name |
|---|---|---|
| KDM5B | KDM5B_HUMAN | Lysine-specific demethylase 5B |
| KDR | VGFR2_HUMAN | Vascular endothelial growth factor receptor 2 |
| KEAP1 | KEAP1_HUMAN | Kelch-like ECH-associated protein 1 |
| KHDC4 | KHDC4_HUMAN | KH homology domain-containing protein 4 |
| KHK | KHK_HUMAN | Ketohexokinase |
| KIAA0391 | MRPP3_HUMAN | Mitochondrial ribonuclease P catalytic subunit |
| KIF11 | KIF11_HUMAN | Kinesin-like protein KIF11 |
| KIF13B | KI13B_HUMAN | Kinesin-like protein KIF13B |
| KIF15 | KIF15_HUMAN | Kinesin-like protein KIF15 |
| KIF18A | KI18A_HUMAN | Kinesin-like protein KIF18A |
| KIF1A | KIF1A_HUMAN | Kinesin-like protein KIF1A |
| KIF1B | KIF1B_HUMAN | Kinesin-like protein KIF1B |
| KIF1C | KIF1C_HUMAN | Kinesin-like protein KIF1C |
| KIF22 | KIF22_HUMAN | Kinesin-like protein KIF22 |
| KIF23 | KIF23_HUMAN | Kinesin-like protein KIF23 |
| KIF2C | KIF2C_HUMAN | Kinesin-like protein KIF2C |
| KIF3B | KIF3B_HUMAN | Kinesin-like protein KIF3B, N-terminally processed |
| KIF3C | KIF3C_HUMAN | Kinesin-like protein KIF3C |
| KIF7 | KIF7_HUMAN | Kinesin-like protein KIF7 |
| KIF9 | KIF9_HUMAN | Kinesin-like protein KIF9 |
| KIFC1 | KIFC1_HUMAN | Kinesin-like protein KIFC1 |
| KIFC3 | KIFC3_HUMAN | Kinesin-like protein KIFC3 |
| KIN | KIN17_HUMAN | DNA/RNA-binding protein KIN17 |
| KIR2DS4 | KI2S4_HUMAN | Killer cell immunoglobulin-like receptor 2DS4 |
| KIRREL3 | KIRR3_HUMAN | Processed kin of IRRE-like protein 3 |
| KIT | KIT_HUMAN | Mast/stem cell growth factor receptor Kit |
| KLB | KLOTB_HUMAN | Beta-klotho |
| KLF1 | KLF1_HUMAN | Krueppel-like factor 1 |
| KLF10 | KLF10_HUMAN | Krueppel-like factor 10 |
| KLHDC2 | KLDC2_HUMAN | Kelch domain-containing protein 2 |
| KLHL11 | KLH11_HUMAN | Kelch-like protein 11 |
| KLHL12 | KLH12_HUMAN | Kelch-like protein 12 |
| KLHL17 | KLH17_HUMAN | Kelch-like protein 17 |
| KLHL40 | KLH40_HUMAN | Kelch-like protein 40 |
| KLHL7 | KLHL7_HUMAN | Kelch-like protein 7 |
| KLK4 | KLK4_HUMAN | Kallikrein-4 |
| KLK6 | KLK6_HUMAN | Kallikrein-6 |
| KLKB1 | KLKB1_HUMAN | Plasma kallikrein light chain |
| KLRD1 | KLRD1_HUMAN | Natural killer cells antigen CD 94 |
| KLRG1 | KLRG1_HUMAN | Killer cell lectin-like receptor subfamily G member 1 |
| KLRG2 | KLRG2_HUMAN | Killer cell lectin-like receptor subfamily G member 2 |
| KLRK1 | NKG2D_HUMAN | NKG2-D type II integral membrane protein |
| KMO | KMO_HUMAN | Kynurenine 3-monooxygenase |
| KMT2A | KMT2A_HUMAN | MLL cleavage product C180 |
| KMT2B | KMT2B_HUMAN | Histone-lysine N-methyltransferase 2B |
| KMT2C | KMT2C_HUMAN | Histone-lysine N-methyltransferase 2C |
| KMT2D | KMT2D_HUMAN | Histone-lysine N-methyltransferase 2D |
| KMT2E | KMT2E_HUMAN | Inactive histone-lysine N-methyltransferase 2E |
| KMT5A | KMT5A_HUMAN | N-lysine methyltransferase KMT5A |
| KREMEN1 | KREM1_HUMAN | Kremen protein 1 |
| KRIT1 | KRIT1_HUMAN | Krev interaction trapped protein 1 |
| KSR2 | KSR2_HUMAN | Kinase suppressor of Ras 2 |
| KYAT1 | KAT1_HUMAN | Kynurenine-oxoglutarate transaminase 1 |
| KYNU | KYNU_HUMAN | Kynureninase |
| L3MBTL2 | LMBL2_HUMAN | Lethal(3)malignant brain tumor-like protein 2 |
| LAMA5 | LAMA5_HUMAN | Laminin subunit alpha-5 |
| LAMP3 | LAMP3_HUMAN | Lysosome-associated membrane glycoprotein 3 |
| LAMTOR2 | LTOR2_HUMAN | Ragulator complex protein LAMTOR2 |
| LAMTOR3 | LTOR3_HUMAN | Ragulator complex protein LAMTOR3 |
| LAMTOR5 | LTOR5_HUMAN | Ragulator complex protein LAMTOR5 |
| LANCL1 | LANC1_HUMAN | Glutathione S-transferase LANCL1 |
| LARP7 | LARP7_HUMAN | La-related protein 7 |
| LARS | SYLC_HUMAN | Leucine-tRNA ligase, cytoplasmic |
| LASPI | LASP1_HUMAN | LIM and SH3 domain protein 1 |
| LBR | LBR_HUMAN | Delta(14)-sterol reductase |
| LCAT | LCAT_HUMAN | Phosphatidylcholine-sterol acyltransferase |
| LCK | LCK_HUMAN | Tyrosine-protein kinase Lck |
| LCN1 | LCN1_HUMAN | Lipocalin-1 |
| LCN15 | LCN15_HUMAN | Lipocalin-15 |
| LCN2 | NGAL_HUMAN | Neutrophil gelatinase-associated lipocalin |
| LDLR | LDLR_HUMAN | Low-density lipoprotein receptor |
| LEO1 | LEO1_HUMAN | RNA polymerase-associated protein LEO1 |
| LEPR | LEPR_HUMAN | Leptin receptor |
| LGALS1 | LEG1_HUMAN | Galectin-1 |
| LGALS2 | LEG2_HUMAN | Galectin-2 |

TABLE 1-continued

| Target Protein Symbol | uniprot name | Target Protein name |
|---|---|---|
| LGALS3 | LEG3_HUMAN | Galectin-3 |
| LGALS4 | LEG4_HUMAN | Galectin-4 |
| LGALS7\|LGALS7B | LEG7_HUMAN | Galectin-7 |
| LGALS8 | LEG8_HUMAN | Galectin-8 |
| LGALS9 | LEG9_HUMAN | Galectin-9 |
| LGI1 | LGI1_HUMAN | Leucine-rich glioma-inactivated protein 1 |
| LGMN | LGMN_HUMAN | Legumain |
| LGR4 | LGR4_HUMAN | Leucine-rich repeat-containing G-protein coupled receptor 4 |
| LIFR | LIFR_HUMAN | Leukemia inhibitory factor receptor |
| LIG1 | DNLI1_HUMAN | DNA ligase 1 |
| LIG3 | DNLI3_HUMAN | DNA ligase 3 |
| LIG4 | DNLI4_HUMAN | DNA ligase 4 |
| LILRA5 | LIRA5_HUMAN | Leukocyte immunoglobulin-like receptor subfamily A member 5 |
| LILRB4 | LIRB4_HUMAN | Leukocyte immunoglobulin-like receptor subfamily B member 4 |
| LIMK1 | LIMK1_HUMAN | LIM domain kinase 1 |
| LIMK2 | LIMK2_HUMAN | LIM domain kinase 2 |
| LIMS1 | LIMS1_HUMAN | LIM and senescent cell antigen-like-containing domain protein 1 |
| LIN28A | LN28A_HUMAN | Protein lin-28 homolog A |
| LIN28B | LN28B_HUMAN | Protein lin-28 homolog B |
| LINGO1 | LIGO1_HUMAN | Leucine-rich repeat and immunoglobulin-like domain-containing nogo receptor-interacting protein 1 |
| LIPF | LIPG_HUMAN | Gastric triacylglycerol lipase |
| LMNB1 | LMNB1_HUMAN | Lamin-B1 |
| LMO2 | RBTN2_HUMAN | Rhombotin-2 |
| LMO4 | LMO4_HUMAN | LIM domain transcription factor LMO4 |
| LNPEP | LCAP_HUMAN | Leucyl-cystinyl aminopeptidase, pregnancy serum form |
| LNX1 | LNX1_HUMAN | E3 ubiquitin-protein ligase LNX |
| LNX2 | LNX2_HUMAN | Ligand of Numb protein X 2 |
| LONP1 | LONM_HUMAN | Lon protease homolog, mitochondrial |
| LONRF3 | LONF3_HUMAN | LON peptidase N-terminal domain and RING finger protein 3 |
| LRBA | LRBA_HUMAN | Lipopolysaccharide-responsive and beige-like anchor protein |
| LRFN5 | LRFN5_HUMAN | Leucine-rich repeat and fibronectin type-III domain-containing protein 5 |
| LRIG1 | LRIG1_HUMAN | Leucine-rich repeats and immunoglobulin-like domains protein 1 |
| LRP1 | LRP1_HUMAN | Low-density lipoprotein receptor-related protein 1 intracellular domain |
| LRP6 | LRP6_HUMAN | Low-density lipoprotein receptor-related protein 6 |
| LRP8 | LRP8_HUMAN | Low-density lipoprotein receptor-related protein 8 |
| LRRC32 | LRC32_HUMAN | Transforming growth factor beta activator LRRC32 |
| LRRC4 | LRRC4_HUMAN | Leucine-rich repeat-containing protein 4 |
| LRRC4C | LRC4C_HUMAN | Leucine-rich repeat-containing protein 4C |
| LRRK2 | LRRK2_HUMAN | Leucine-rich repeat serine/threonine-protein kinase 2 |
| LSM4 | LSM4_HUMAN | U6 snRNA-associated Sm-like protein LSm4 |
| LSM6 | LSM6_HUMAN | U6 snRNA-associated Sm-like protein LSm6 |
| LSM7 | LSM7_HUMAN | U6 snRNA-associated Sm-like protein LSm7 |
| LSM8 | LSM8_HUMAN | U6 snRNA-associated Sm-like protein LSm8 |
| LSS | ERG7_HUMAN | Lanosterol synthase |
| LTF | TRFL_HUMAN | Lactoferroxin-C |
| LXN | LXN_HUMAN | Latexin |
| LY86 | LY86_HUMAN | Lymphocyte antigen 86 |
| LYAR | LYAR_HUMAN | Cell growth-regulating nucleolar protein |
| LYPD6 | LYPD6_HUMAN | Ly6/PLAUR domain-containing protein 6 |
| LYZ | LYSC_HUMAN | Lysozyme C |
| MAD2L1 | MD2L1_HUMAN | Mitotic spindle assembly checkpoint protein MAD2A |
| MAGI1 | MAGI1_HUMAN | Membrane-associated guanylate kinase, WW and PDZ domain-containing protein 1 |
| MAGOH | MGN_HUMAN | Protein mago nashi homolog |
| MAGOHB | MGN2_HUMAN | Protein mago nashi homolog 2 |
| MALT1 | MALT1_HUMAN | Mucosa-associated lymphoid tissue lymphoma translocation protein 1 |
| MAN1B1 | MA1B1_HUMAN | Endoplasmic reticulum mannosyl-oligosaccharide 1,2-alpha-mannosidase |
| MAP2K1 | MP2K1_HUMAN | Dual specificity mitogen-activated protein kinase kinase 1 |
| MAP2K2 | MP2K2_HUMAN | Dual specificity mitogen-activated protein kinase kinase 2 |

TABLE 1-continued

| Target Protein Symbol | uniprot name | Target Protein name |
|---|---|---|
| MAP2K4 | MP2K4_HUMAN | Dual specificity mitogen-activated protein kinase kinase 4 |
| MAP2K5 | MP2K5_HUMAN | Dual specificity mitogen-activated protein kinase kinase 5 |
| MAP2K6 | MP2K6_HUMAN | Dual specificity mitogen-activated protein kinase kinase 6 |
| MAP2K7 | MP2K7_HUMAN | Dual specificity mitogen-activated protein kinase kinase 7 |
| MAP3K10 | M3K10_HUMAN | Mitogen-activated protein kinase kinase kinase 10 |
| MAP3K11 | M3K11_HUMAN | Mitogen-activated protein kinase kinase kinase 11 |
| MAP3K12 | M3K12_HUMAN | Mitogen-activated protein kinase kinase kinase 12 |
| MAP3K14 | M3K14_HUMAN | Mitogen-activated protein kinase kinase kinase 14 |
| MAP3K20 | M3K20_HUMAN | Mitogen-activated protein kinase kinase kinase 20 |
| MAP3K5 | M3K5_HUMAN | Mitogen-activated protein kinase kinase kinase 5 |
| MAP3K7 | M3K7_HUMAN | Mitogen-activated protein kinase kinase kinase 7 |
| MAP3K9 | M3K9_HUMAN | Mitogen-activated protein kinase kinase kinase 9 |
| MAP4K1 | M4K1_HUMAN | Mitogen-activated protein kinase kinase kinase kinase 1 |
| MAP4K3 | M4K3_HUMAN | Mitogen-activated protein kinase kinase kinase kinase 3 |
| MAP4K4 | M4K4_HUMAN | Mitogen-activated protein kinase kinase kinase kinase 4 |
| MAPK1 | MK01_HUMAN | Mitogen-activated protein kinase 1 |
| MAPK10 | MK10_HUMAN | Mitogen-activated protein kinase 10 |
| MAPK12 | MK12_HUMAN | Mitogen-activated protein kinase 12 |
| MAPK13 | MK13_HUMAN | Mitogen-activated protein kinase 13 |
| MAPK14 | MK14_HUMAN | Mitogen-activated protein kinase 14 |
| MAPK3 | MK03_HUMAN | Mitogen-activated protein kinase 3 |
| MAPK7 | MK07_HUMAN | Mitogen-activated protein kinase 7 |
| MAPK8 | MK08_HUMAN | Mitogen-activated protein kinase 8 |
| MAPK9 | MK09_HUMAN | Mitogen-activated protein kinase 9 |
| MAPKAPK2 | MAPK2_HUMAN | MAP kinase-activated protein kinase 2 |
| MAPKAPK3 | MAPK3_HUMAN | MAP kinase-activated protein kinase 3 |
| MARC1 | MARC1_HUMAN | Mitochondrial amidoxime-reducing component 1 |
| MARK1 | MARK1_HUMAN | Serine/threonine-protein kinase MARK1 |
| MARK2 | MARK2_HUMAN | Serine/threonine-protein kinase MARK2 |
| MARK3 | MARK3_HUMAN | MAP/microtubule affinity-regulating kinase 3 |
| MARK4 | MARK4_HUMAN | MAP/microtubule affinity-regulating kinase 4 |
| MARS | SYMC_HUMAN | Methionine-tRNA ligase, cytoplasmic |
| MASP1 | MASP1_HUMAN | Mannan-binding lectin serine protease 1 light chain |
| MASP2 | MASP2_HUMAN | Mannan-binding lectin serine protease 2 B chain |
| MASTL | GWL_HUMAN | Serine/threonine-protein kinase greatwall |
| MATK | MATK_HUMAN | Megakaryocyte-associated tyrosine-protein kinase |
| MAZ | MAZ_HUMAN | Myc-associated zinc finger protein |
| MBD1 | MBD1_HUMAN | Methyl-CpG-binding domain protein 1 |
| MBD2 | MBD2_HUMAN | Methyl-CpG-binding domain protein 2 |
| MBD3 | MBD3_HUMAN | Methyl-CpG-binding domain protein 3 |
| MBD4 | MBD4_HUMAN | Methyl-CpG-binding domain protein 4 |
| MBL2 | MBL2_HUMAN | Mannose-binding protein C |
| MBLAC1 | MBLC1_HUMAN | Metallo-beta-lactamase domain-containing protein 1 |
| MBTD1 | MBTD1_HUMAN | MBT domain-containing protein 1 |
| MCAT | FABD_HUMAN | Malonyl-CoA-acyl carrier protein transacylase, mitochondrial |
| MCEE | MCEE_HUMAN | Methylmalonyl-CoA epimerase, mitochondrial |
| MCOLN1 | MCLN1_HUMAN | Mucolipin-1 |
| MCTS1 | MCTS1_HUMAN | Malignant T-cell-amplified sequence 1 |
| MCU | MCU_HUMAN | Calcium uniporter protein, mitochondrial |
| MDM2 | MDM2_HUMAN | E3 ubiquitin-protein ligase Mdm2 |
| MDP1 | MGDP1_HUMAN | Magnesium-dependent phosphatase 1 |
| ME1 | MAOX_HUMAN | NADP-dependent malic enzyme |
| ME2 | MAOM_HUMAN | NAD-dependent malic enzyme, mitochondrial |
| MECOM | MECOM_HUMAN | Histone-lysine N-methyltransferase MECOM |
| MECP2 | MECP2_HUMAN | Methyl-CpG-binding protein 2 |
| MEFV | MEFV_HUMAN | Pyrin |
| MELK | MELK_HUMAN | Maternal embryonic leucine zipper kinase |
| MEN1 | MEN1_HUMAN | Menin |
| MEP1B | MEP1B_HUMAN | Meprin A subunit beta |
| MERTK | MERTK_HUMAN | Tyrosine-protein kinase Mer |
| MET | MET_HUMAN | Hepatocyte growth factor receptor |
| METAP2 | MAP2_HUMAN | Methionine aminopeptidase 2 |
| METTL16 | MET16_HUMAN | RNA N6-adenosine-methyltransferase METTL16 |
| METTL18 | MET18_HUMAN | Histidine protein methyltransferase 1 homolog |
| MEX3C | MEX3C_HUMAN | RNA-binding E3 ubiquitin-protein ligase MEX3C |
| MGAM | MGA_HUMAN | Glucoamylase |

TABLE 1-continued

| Target Protein Symbol | uniprot name | Target Protein name |
|---|---|---|
| MGLL | MGLL_HUMAN | Monoglyceride lipase |
| MGMT | MGMT_HUMAN | Methylated-DNA--protein-cysteine methyltransferase |
| MIA | MIA_HUMAN | Melanoma-derived growth regulatory protein |
| MIB1 | MIB1_HUMAN | E3 ubiquitin-protein ligase MIB1 |
| MIB2 | MIB2_HUMAN | E3 ubiquitin-protein ligase MIB2 |
| MICAL1 | MICA1_HUMAN | [F-actin]-monooxygenase MICAL1 |
| MICU1 | MICU1_HUMAN | Calcium uptake protein 1, mitochondrial |
| MINDY1 | MINY1_HUMAN | Ubiquitin carboxyl-terminal hydrolase MINDY-1 |
| MKNK1 | MKNK1_HUMAN | MAP kinase-interacting serine/threonine-protein kinase 1 |
| MLH1 | MLH1_HUMAN | DNA mismatch repair protein Mlhl |
| MLLT1 | ENL_HUMAN | Protein ENL |
| MLLT10 | AF10_HUMAN | Protein AF-10 |
| MLLT3 | AF9_HUMAN | Protein AF-9 |
| MLLT6 | AF17_HUMAN | Protein AF-17 |
| MLPH | MELPH_HUMAN | Melanophilin |
| MLST8 | LST8_HUMAN | Target of rapamycin complex subunit LST8 |
| MMAB | MMAB_HUMAN | Corrinoid adenosyltransferase |
| MMADHC | MMAD_HUMAN | Methylmalonic aciduria and homocystinuria type D protein, mitochondrial |
| MME | NEP_HUMAN | Neprilysin |
| MMP1 | MMP1_HUMAN | 27 kDa interstitial collagenase |
| MMP13 | MMP13_HUMAN | Collagenase 3 |
| MMP14 | MMP14_HUMAN | Matrix metalloproteinase-14 |
| MMP2 | MMP2_HUMAN | PEX |
| MMUT | MUTA_HUMAN | Methylmalonyl-CoA mutase, mitochondrial |
| MNAT1 | MAT1_HUMAN | CDK-activating kinase assembly factor MAT1 |
| MPG | 3MG_HUMAN | DNA-3-methyladenine glycosylase |
| MPP7 | MPP7_HUMAN | MAGUK p55 subfamily member 7 |
| MPST | THTM_HUMAN | 3-mercaptopyruvate sulfurtransferase |
| MR1 | HMR1_HUMAN | Major histocompatibility complex class I-related gene protein |
| MRC1 | MRC1_HUMAN | Macrophage mannose receptor 1 |
| MRC2 | MRC2_HUMAN | C-type mannose receptor 2 |
| MRI1 | MTNA_HUMAN | Methylthioribose-1 -phosphate isomerase |
| MRPL13 | RM13_HUMAN | 39S ribosomal protein L13, mitochondrial |
| MRPL18 | RM18_HUMAN | 39S ribosomal protein L18, mitochondrial |
| MRPL24 | RM24_HUMAN | 39S ribosomal protein L24, mitochondrial |
| MRPL28 | RM28_HUMAN | 39S ribosomal protein L28, mitochondrial |
| MRPL3 | RM03_HUMAN | 39S ribosomal protein L3, mitochondrial |
| MRPL30 | RM30_HUMAN | 39S ribosomal protein L30, mitochondrial |
| MRPL32 | RM32_HUMAN | 39S ribosomal protein L32, mitochondrial |
| MRPL35 | RM35_HUMAN | 39S ribosomal protein L35, mitochondrial |
| MRPL43 | RM43_HUMAN | 39S ribosomal protein L43, mitochondrial |
| MRPL45 | RM45_HUMAN | 39S ribosomal protein L45, mitochondrial |
| MRPL46 | RM46_HUMAN | 39S ribosomal protein L46, mitochondrial |
| MRPL47 | RM47_HUMAN | 39S ribosomal protein L47, mitochondrial |
| MRPL49 | RM49_HUMAN | 39S ribosomal protein L49, mitochondrial |
| MRPL53 | RM53_HUMAN | 39S ribosomal protein L53, mitochondrial |
| MRPL55 | RM55_HUMAN | 39S ribosomal protein L55, mitochondrial |
| MRPS18A | RT18A_HUMAN | 39S ribosomal protein S18a, mitochondrial |
| MSH2 | MSH2_HUMAN | DNA mismatch repair protein Msh2 |
| MSH3 | MSH3_HUMAN | DNA mismatch repair protein Msh3 |
| MSH6 | MSH6_HUMAN | DNA mismatch repair protein Msh6 |
| MSL2 | MSL2_HUMAN | E3 ubiquitin-protein ligase MSL2 |
| MSL3 | MS3L1_HUMAN | Male-specific lethal 3 homolog |
| MSMB | MSMB_HUMAN | Beta-microseminoprotein |
| MSN | MOES_HUMAN | Moesin |
| MSRB1 | MSRB1_HUMAN | Methionine-R-sulfoxide reductase B1 |
| MST1R | RON_HUMAN | Macrophage-stimulating protein receptor beta chain |
| MSTN | GDF8_HUMAN | Growth/differentiation factor 8 |
| MT-CO2 | COX2_HUMAN | Cytochrome c oxidase subunit 2 |
| MTERF4 | MTEF4_HUMAN | mTERF domain-containing protein 2 processed |
| MTF1 | MTF1_HUMAN | Metal regulatory transcription factor 1 |
| MTF2 | MTF2_HUMAN | Metal-response element-binding transcription factor 2 |
| MTHFR | MTHR_HUMAN | Methylenetetrahydrofolate reductase |
| MTHFS | MTHFS_HUMAN | 5-formyltetrahydrofolate cyclo-ligase |
| MTIF3 | IF3M_HUMAN | Translation initiation factor IF-3, mitochondrial |
| MTMR1 | MTMR1_HUMAN | Myotubularin-related protein 1 |
| MTMR2 | MTMR2_HUMAN | Myotubularin-related protein 2 |
| MTMR3 | MTMR3_HUMAN | Myotubularin-related protein 3 |
| MTMR4 | MTMR4_HUMAN | Myotubularin-related protein 4 |
| MTOR | MTOR_HUMAN | Serine/threonine-protein kinase mTOR |
| MTPAP | PAPD1_HUMAN | Poly(A) RNA polymerase, mitochondrial |
| MTR | METH_HUMAN | Methionine synthase |

TABLE 1-continued

| Target Protein Symbol | uniprot name | Target Protein name |
|---|---|---|
| MVK | KIME_HUMAN | Mevalonate kinase |
| MYBPC3 | MYPC3_HUMAN | Myosin-binding protein C, cardiac-type |
| MYCBP2 | MYCB2_HUMAN | E3 ubiquitin-protein ligase MYCBP2 |
| MYH10 | MYH10_HUMAN | Myosin-10 |
| MYH14 | MYH14_HUMAN | Myosin-14 |
| MYH7 | MYH7_HUMAN | Myosin-7 |
| MYL3 | MYL3_HUMAN | Myosin light chain 3 |
| MYL6B | MYL6B_HUMAN | Myosin light chain 6B |
| MYLIP | MYLIP_HUMAN | E3 ubiquitin-protein ligase MYLIP |
| MYLK4 | MYLK4_HUMAN | Myosin light chain kinase family member 4 |
| MYNN | MYNN_HUMAN | Myoneurin |
| MYO10 | MYO10_HUMAN | Unconventional myosin-X |
| MYO1C | MYO1C_HUMAN | Unconventional myosin-Ic |
| MYO5C | MYO5C_HUMAN | Unconventional myosin-Vc |
| MYO7A | MYO7A_HUMAN | Unconventional myosin-VIIa |
| MYO7B | MYO7B_HUMAN | Unconventional myosin-VIIb |
| MYOC | MYOC_HUMAN | Myocilin, C-terminal fragment |
| MYOF | MYOF_HUMAN | Myoferlin |
| MYOM1 | MYOM1_HUMAN | Myomesin-1 |
| MYOT | MYOTI_HUMAN | Myotilin |
| MYRF | MYRF_HUMAN | Myelin regulatory factor, C-terminal |
| MYZAP | MYZAP_HUMAN | Myocardial zonula adherens protein |
| MZF1 | MZF1_HUMAN | Myeloid zinc finger 1 |
| NAA10 | NAA10_HUMAN | N-alpha-acetyltransferase 10 |
| NAAA | NAAA_HUMAN | N-acylethanolamine-hydrolyzing acid amidase subunit beta |
| NAALADL1 | NALDL_HUMAN | Aminopeptidase NAALADL1 |
| NABP2 | SOSB1_HUMAN | SOSS complex subunit B1 |
| NAE1 | ULA1_HUMAN | NEDD8-activating enzyme E1 regulatory subunit |
| NAGA | NAGAB_HUMAN | Alpha-N-acetylgalactosaminidase |
| NAGK | NAGK_HUMAN | N-acetyl-D-glucosamine kinase |
| NAIP | BIRC1_HUMAN | Baculoviral IAP repeat-containing protein 1 |
| NAMPT | NAMPT_HUMAN | Nicotinamide phosphoribosyltransferase |
| NANOS1 | NANO1_HUMAN | Nanos homolog 1 |
| NANOS2 | NANO2_HUMAN | Nanos homolog 2 |
| NANOS3 | NANO3_HUMAN | Nanos homolog 3 |
| NARS | SYNC_HUMAN | Asparagine-tRNA ligase, cytoplasmic |
| NCAM1 | NCAM1_HUMAN | Neural cell adhesion molecule 1 |
| NCAM2 | NCAM2_HUMAN | Neural cell adhesion molecule 2 |
| NCF4 | NCF4_HUMAN | Neutrophil cytosol factor 4 |
| NCK1 | NCK1_HUMAN | Cytoplasmic protein NCK1 |
| NCK2 | NCK2_HUMAN | Cytoplasmic protein NCK2 |
| NCL | NUCL_HUMAN | Nucleolin |
| NCOA1 | NCOA1_HUMAN | Nuclear receptor coactivator 1 |
| NCR2 | NCTR2_HUMAN | Natural cytotoxicity triggering receptor 2 |
| NCR3 | NCTR3_HUMAN | Natural cytotoxicity triggering receptor 3 |
| NCR3LG1 | NR3L1_HUMAN | Natural cytotoxicity triggering receptor 3 ligand 1 |
| NDP | NDP_HUMAN | Norrin |
| NDRG2 | NDRG2_HUMAN | Protein NDRG2 |
| NDST1 | NDST1_HUMAN | Heparan sulfate N-sulfotransferase 1 |
| NDUFA2 | NDUA2_HUMAN | NADH dehydrogenase [ubiquinone] 1 alpha subcomplex subunit 2 |
| NDUFS1 | NDUS1_HUMAN | NADH-ubiquinone oxidoreductase 75 kDa subunit, mitochondrial |
| NDUFS4 | NDUS4_HUMAN | NADH dehydrogenase [ubiquinone] iron-sulfur protein 4, mitochondrial |
| NDUFS6 | NDUS6_HUMAN | NADH dehydrogenase [ubiquinone] iron-sulfur protein 6, mitochondrial |
| NDUFV1 | NDUV1_HUMAN | NADH dehydrogenase [ubiquinone] flavoprotein 1, mitochondrial |
| NEB | NEBU_HUMAN | Nebulin |
| NEBL | NEBL_HUMAN | Nebulette |
| NECTIN1 | NECT1_HUMAN | Nectin-1 |
| NECTIN2 | NECT2_HUMAN | Nectin-2 |
| NECTIN3 | NECT3_HUMAN | Nectin-3 |
| NECTIN4 | NECT4_HUMAN | Processed poliovirus receptor-related protein 4 |
| NEDD4 | NEDD4_HUMAN | E3 ubiquitin-protein ligase NEDD4 |
| NEDD4L | NED4L_HUMAN | E3 ubiquitin-protein ligase NEDD4-like |
| NEDD8 | NEDD8_HUMAN | NEDD8 |
| NEIL1 | NEIL1_HUMAN | Endonuclease 8-like 1 |
| NEK1 | NEK1_HUMAN | Serine/threonine-protein kinase Nek1 |
| NEK2 | NEK2_HUMAN | Serine/threonine-protein kinase Nek2 |
| NEK7 | NEK7_HUMAN | Serine/threonine-protein kinase Nek7 |
| NEO1 | NEO1_HUMAN | Neogenin |
| NET1 | ARHG8_HUMAN | Neuroepithelial cell-transforming gene 1 protein |
| NEU2 | NEUR2_HUMAN | Sialidase-2 |
| NEURL1 | NEUL1_HUMAN | E3 ubiquitin-protein ligase NEURL1 |
| NEURL1B | NEU1B_HUMAN | E3 ubiquitin-protein ligase NEURL1B |

TABLE 1-continued

| Target Protein Symbol | uniprot name | Target Protein name |
|---|---|---|
| NEURL4 | NEUL4_HUMAN | Neuralized-like protein 4 |
| NF1 | NF1_HUMAN | Neurofibromin truncated |
| NF2 | MERL_HUMAN | Merlin |
| NFASC | NFASC_HUMAN | Neurofascin |
| NFATC1 | NFAC1_HUMAN | Nuclear factor of activated T-cells, cytoplasmic 1 |
| NFATC2 | NFAC2_HUMAN | Nuclear factor of activated T-cells, cytoplasmic 2 |
| NFE2L2 | NF2L2_HUMAN | Nuclear factor erythroid 2-related factor 2 |
| NFKB1 | NFKB1_HUMAN | Nuclear factor NF-kappa-B p50 subunit |
| NFKB2 | NFKB2_HUMAN | Nuclear factor NF-kappa-B p52 subunit |
| NFKBIA | IKBA_HUMAN | NF-kappa-B inhibitor alpha |
| NFS1 | NFS1_HUMAN | Cysteine desulfurase, mitochondrial |
| NGF | NGF_HUMAN | Beta-nerve growth factor |
| NHLRC2 | NHLC2_HUMAN | NHL repeat-containing protein 2 |
| NKTR | NKTR_HUMAN | NK-tumor recognition protein |
| NLGN1 | NLGN1_HUMAN | Neuroligin-1 |
| NLGN2 | NLGN2_HUMAN | Neuroligin-2 |
| NLGN4X | NLGNX_HUMAN | Neuroligin-4, X-linked |
| NLN | NEUL_HUMAN | Neurolysin, mitochondrial |
| NMRK1 | NRK1_HUMAN | Nicotinamide riboside kinase 1 |
| NMT1 | NMT1_HUMAN | Glycylpeptide N-tetradecanoyltransferase 1 |
| NNMT | NNMT_HUMAN | Nicotinamide N-methyltransferase |
| NOB1 | NOB1_HUMAN | RNA-binding protein NOB1 |
| NOCT | NOCT_HUMAN | Nocturnin |
| NONO | NONO_HUMAN | Non-POU domain-containing octamer-binding protein |
| NOS1 | NOS1_HUMAN | Nitric oxide synthase, brain |
| NOS2 | NOS2_HUMAN | Nitric oxide synthase, inducible |
| NOS3 | NOS3_HUMAN | Nitric oxide synthase, endothelial |
| NOTCH1 | NOTC1_HUMAN | Notch 1 intracellular domain |
| NOTUM | NOTUM_HUMAN | Palmitoleoyl-protein carboxylesterase NOTUM |
| NPC1 | NPC1_HUMAN | NPC intracellular cholesterol transporter 1 |
| NPHP1 | NPHP1_HUMAN | Nephrocystin-1 |
| NPM1 | NPM_HUMAN | Nucleophosmin |
| NPR1 | ANPRA_HUMAN | Atrial natriuretic peptide receptor 1 |
| NPR2 | ANPRB_HUMAN | Atrial natriuretic peptide receptor 2 |
| NPR3 | ANPRC_HUMAN | Atrial natriuretic peptide receptor 3 |
| NPRL2 | NPRL2_HUMAN | GATOR complex protein NPRL2 |
| NPTN | NPTN_HUMAN | Neuroplastin |
| NPY1R | NPY1R_HUMAN | Neuropeptide Y receptor type 1 |
| NR1D1 | NR1D1_HUMAN | Nuclear receptor subfamily 1 group D member 1 |
| NR1D2 | NR1D2_HUMAN | Nuclear receptor subfamily 1 group D member 2 |
| NR1H2 | NR1H2_HUMAN | Oxysterols receptor LXR-beta |
| NR1H3 | NR1H3_HUMAN | Oxysterols receptor LXR-alpha |
| NR1H4 | NR1H4_HUMAN | Bile acid receptor |
| NR1I2 | NR1I2_HUMAN | Nuclear receptor subfamily 1 group I member 2 |
| NR1I3 | NR1I3_HUMAN | Nuclear receptor subfamily 1 group I member 3 |
| NR2C1 | NR2C1_HUMAN | Nuclear receptor subfamily 2 group C member 1 |
| NR2C2 | NR2C2_HUMAN | Nuclear receptor subfamily 2 group C member 2 |
| NR2E1 | NR2E1_HUMAN | Nuclear receptor subfamily 2 group E member 1 |
| NR2E3 | NR2E3_HUMAN | Photoreceptor-specific nuclear receptor |
| NR2F1 | COT1_HUMAN | COUP transcription factor 1 |
| NR2F2 | COT2_HUMAN | COUP transcription factor 2 |
| NR2F6 | NR2F6_HUMAN | Nuclear receptor subfamily 2 group F member 6 |
| NR3C1 | GCR_HUMAN | Glucocorticoid receptor |
| NR3C2 | MCR_HUMAN | Mineralocorticoid receptor |
| NR4A1 | NR4A1_HUMAN | Nuclear receptor subfamily 4 group A member 1 |
| NR4A2 | NR4A2_HUMAN | Nuclear receptor subfamily 4 group A member 2 |
| NR4A3 | NR4A3_HUMAN | Nuclear receptor subfamily 4 group A member 3 |
| NR5A1 | STF1_HUMAN | Steroidogenic factor 1 |
| NR5A2 | NR5A2_HUMAN | Nuclear receptor subfamily 5 group A member 2 |
| NR6A1 | NR6A1_HUMAN | Nuclear receptor subfamily 6 group A member 1 |
| NRCAM | NRCAM_HUMAN | Neuronal cell adhesion molecule |
| NSD1 | NSD1_HUMAN | Histone-lysine N-methyltransferase, H3 lysine-36 and H4 lysine-20 specific |
| NSD2 | NSD2_HUMAN | Histone-lysine N-methyltransferase NSD2 |
| NSD3 | NSD3_HUMAN | Histone-lysine N-methyltransferase NSD3 |
| NSFL1C | NSF1C_HUMAN | NSFL1 cofactor p47 |
| NSMCE1 | NSE1_HUMAN | Non-structural maintenance of chromosomes element 1 homolog |
| NSMCE2 | NSE2_HUMAN | E3 SUMO-protein ligase NSE2 |
| NT5C2 | 5NTC_HUMAN | Cytosolic purine 5'-nucleotidase |
| NT5E | 5NTD_HUMAN | 5'-nucleotidase |
| NTF3 | NTF3_HUMAN | Neurotrophin-3 |
| NTF4 | NTF4_HUMAN | Neurotrophin-4 |
| NTN1 | NET1_HUMAN | Netrin-1 |
| NTNG1 | NTNG1_HUMAN | Netrin-G1 |
| NTNG2 | NTNG2_HUMAN | Netrin-G2 |
| NTPCR | NTPCR_HUMAN | Cancer-related nucleoside-triphosphatase |

TABLE 1-continued

| Target Protein Symbol | uniprot name | Target Protein name |
|---|---|---|
| NTRK1 | NTRK1_HUMAN | High affinity nerve growth factor receptor |
| NTRK2 | NTRK2_HUMAN | BDNF/NT-3 growth factors receptor |
| NTRK3 | NTRK3_HUMAN | NT-3 growth factor receptor |
| NUDT1 | 8ODP_HUMAN | 7,8-dihydro-8-oxoguanine triphosphatase |
| NUDT14 | NUD14_HUMAN | Uridine diphosphate glucose pyrophosphatase |
| NUDT16 | NUD16_HUMAN | U8 snoRNA-decapping enzyme |
| NUDT4 | NUDT4_HUMAN | Diphosphoinositol polyphosphate phosphohydrolase 2 |
| NUDT5 | NUDT5_HUMAN | ADP-sugar pyrophosphatase |
| NUDT6 | NUDT6_HUMAN | Nucleoside diphosphate-linked moiety X motif 6 |
| NUDT7 | NUDT7_HUMAN | Peroxisomal coenzyme A diphosphatase NUDT7 |
| NUDT9 | NUDT9_HUMAN | ADP-ribose pyrophosphatase, mitochondrial |
| NUMB | NUMB_HUMAN | Protein numb homolog |
| NUP133 | NU133_HUMAN | Nuclear pore complex protein Nup133 |
| NUP155 | NU155_HUMAN | Nuclear pore complex protein Nup155 |
| NUP160 | NU160_HUMAN | Nuclear pore complex protein Nup160 |
| NUP214 | NU214_HUMAN | Nuclear pore complex protein Nup214 |
| NUP37 | NUP37_HUMAN | Nucleoporin Nup37 |
| NUP43 | NUP43_HUMAN | Nucleoporin Nup43 |
| NUP50 | NUP50_HUMAN | Nuclear pore complex protein Nup50 |
| NUP54 | NUP54_HUMAN | Nucleoporin p54 |
| NUP98 | NUP98_HUMAN | Nuclear pore complex protein Nup96 |
| NXF1 | NXF1_HUMAN | Nuclear RNA export factor 1 |
| OAS1 | OAS1_HUMAN | 2'-5'-oligoadenylate synthase 1 |
| OASL | OASL_HUMAN | 2'-5'-oligoadenylate synthase-like protein |
| OAT | OAT_HUMAN | Ornithine aminotransferase, renal form |
| OBP2A | OBP2A_HUMAN | Odorant-binding protein 2a |
| OBSCN | OBSCN_HUMAN | Obscurin |
| OBSL1 | OBSL1_HUMAN | Obscurin-like protein 1 |
| OLFM1 | NOE1_HUMAN | Noelin |
| OPCML | OPCM_HUMAN | Opioid-binding protein/cell adhesion molecule |
| OPRK1 | OPRK_HUMAN | Kappa-type opioid receptor |
| OPTN | OPTN_HUMAN | Optineurin |
| ORC2 | ORC2_HUMAN | Origin recognition complex subunit 2 |
| ORM1 | A1AG1_HUMAN | Alpha-1-acid glycoprotein 1 |
| ORM2 | A1AG2_HUMAN | Alpha-1-acid glycoprotein 2 |
| OS9 | OS9_HUMAN | Protein OS-9 |
| OSBPL11 | OSB11_HUMAN | Oxysterol-binding protein-related protein 11 |
| OSBPL1A | OSBL1_HUMAN | Oxysterol-binding protein-related protein 1 |
| OSBPL2 | OSBL2_HUMAN | Oxysterol-binding protein-related protein 2 |
| OSBPL8 | OSBL8_HUMAN | Oxysterol-binding protein-related protein 8 |
| OSR1 | OSR1_HUMAN | Protein odd-skipped-related 1 |
| OSR2 | OSR2_HUMAN | Protein odd-skipped-related 2 |
| OSTF1 | OSTF1_HUMAN | Osteoclast-stimulating factor 1 |
| OTUD1 | OTUD1_HUMAN | OTU domain-containing protein 1 |
| OVOL1 | OVOL1_HUMAN | Putative transcription factor Ovo-like 1 |
| OVOL2 | OVOL2_HUMAN | Transcription factor Ovo-like 2 |
| OVOL3 | OVOL3_HUMAN | Putative transcription factor ovo-like protein 3 |
| OXCT1 | SCOT1_HUMAN | Succinyl-CoA: 3-ketoacid coenzyme A transferase 1, mitochondrial |
| OXSM | OXSM_HUMAN | 3-oxoacyl-[acyl-carrier-protein] synthase, mitochondrial |
| OXSR1 | OXSR1_HUMAN | Serine/threonine-protein kinase OSR1 |
| P2RX3 | P2RX3_HUMAN | P2X purinoceptor 3 |
| P2RY1 | P2RY1_HUMAN | P2Y purinoceptor 1 |
| PABPC1 | PABP1_HUMAN | Polyadenylate-binding protein 1 |
| PACSIN1 | PACN1_HUMAN | Protein kinase C and casein kinase substrate in neurons protein 1 |
| PACSIN2 | PACN2_HUMAN | Protein kinase C and casein kinase substrate in neurons protein 2 |
| PADI2 | PADI2_HUMAN | Protein-arginine deiminase type-2 |
| PADI4 | PADI4_HUMAN | Protein-arginine deiminase type-4 |
| PAF1 | PAF1_HUMAN | RNA polymerase II-associated factor 1 homolog |
| PAIP1 | PAIP1_HUMAN | Polyadenylate-binding protein-interacting protein 1 |
| PAK1 | PAK1_HUMAN | Serine/threonine-protein kinase PAK 1 |
| PAK2 | PAK2_HUMAN | PAK-2p34 |
| PAK3 | PAK3_HUMAN | Serine/threonine-protein kinase PAK 3 |
| PAK4 | PAK4_HUMAN | Serine/threonine-protein kinase PAK 4 |
| PAK5 | PAK5_HUMAN | Serine/threonine-protein kinase PAK 5 |
| PAK6 | PAK6_HUMAN | Serine/threonine-protein kinase PAK 6 |
| PALB2 | PALB2_HUMAN | Partner and localizer of BRCA2 |
| PALLD | PALLD_HUMAN | Palladin |
| PANK1 | PANK1_HUMAN | Pantothenate kinase 1 |
| PANK2 | PANK2_HUMAN | Pantothenate kinase 2, mitochondrial |
| PANK3 | PANK3_HUMAN | Pantothenate kinase 3 |
| PAPSS1 | PAPS1_HUMAN | Adenylyl-sulfate kinase |
| PARD3 | PARD3_HUMAN | Partitioning defective 3 homolog |

TABLE 1-continued

| Target Protein Symbol | uniprot name | Target Protein name |
|---|---|---|
| PARD6A | PAR6A_HUMAN | Partitioning defective 6 homolog alpha |
| PARP1 | PARP1_HUMAN | Poly [ADP-ribose] polymerase 1 |
| PARP10 | PAR10_HUMAN | Protein mono-ADP-ribosyltransferase PARP10 |
| PARP11 | PAR11_HUMAN | Protein mono-ADP-ribosyltransferase PARP11 |
| PARP14 | PAR14_HUMAN | Protein mono-ADP-ribosyltransferase PARP14 |
| PARP15 | PAR15_HUMAN | Protein mono-ADP-ribosyltransferase PARP15 |
| PASK | PASK_HUMAN | PAS domain-containing serine/threonine-protein kinase |
| PATJ | INADL_HUMAN | InaD-like protein |
| PATZ1 | PATZ1_HUMAN | POZ-, AT hook-, and zinc finger-containing protein 1 |
| PAX5 | PAX5_HUMAN | Paired box protein Pax-5 |
| PAX6 | PAX6_HUMAN | Paired box protein Pax-6 |
| PBRM1 | PB1_HUMAN | Protein polybromo-1 |
| PC | PYC_HUMAN | Pyruvate carboxylase, mitochondrial |
| PCBD2 | PHS2_HUMAN | Pterin-4-alpha-carbinolamine dehydratase 2 |
| PCDH1 | PCDH1_HUMAN | Protocadherin-1 |
| PCDH15 | PCD15_HUMAN | Protocadherin-15 |
| PCDH7 | PCDH7_HUMAN | Protocadherin-7 |
| PCDH9 | PCDH9_HUMAN | Protocadherin-9 |
| PCDHGB3 | PCDGF_HUMAN | Protocadherin gamma-B3 |
| PCGF2 | PCGF2_HUMAN | Polycomb group RING finger protein 2 |
| PCGF5 | PCGF5_HUMAN | Polycomb group RING finger protein 5 |
| PCK1 | PCKGC_HUMAN | Phosphoenolpyruvate carboxykinase, cytosolic [GTP] |
| PCMT1 | PIMT_HUMAN | Protein-L-isoaspartate(D-aspartate) O-methyltransferase |
| PCNA | PCNA_HUMAN | Proliferating cell nuclear antigen |
| PCOLCE | PCOC1_HUMAN | Procollagen C-endopeptidase enhancer 1 |
| PCSK9 | PCSK9_HUMAN | Proprotein convertase subtilisin/kexin type 9 |
| PCTP | PPCT_HUMAN | Phosphatidylcholine transfer protein |
| PDCD1 | PDCD1_HUMAN | Programmed cell death protein 1 |
| PDCD11 | RRP5_HUMAN | Protein RRP5 homolog |
| PDCD2 | PDCD2_HUMAN | Programmed cell death protein 2 |
| PDCD6 | PDCD6_HUMAN | Programmed cell death protein 6 |
| PDE4B | PDE4B_HUMAN | cAMP-specific 3',5'-cyclic phosphodiesterase 4B |
| PDE4D | PDE4D_HUMAN | cAMP-specific 3',5'-cyclic phosphodiesterase 4D |
| PDE5A | PDE5A_HUMAN | cGMP-specific 3',5'-cyclic phosphodiesterase |
| PDE6D | PDE6D_HUMAN | Retinal rod rhodopsin-sensitive cGMP 3',5'-cyclic phosphodiesterase subunit delta |
| PDF | DEFM_HUMAN | Peptide deformylase, mitochondrial |
| PDGFRB | PGFRB_HUMAN | Platelet-derived growth factor receptor beta |
| PDIA3 | PDIA3_HUMAN | Protein disulfide-isomerase A3 |
| PDK2 | PDK2_HUMAN | [Pyruvate dehydrogenase (acetyl-transferring)] kinase isozyme 2, mitochondrial |
| PDK4 | PDK4_HUMAN | [Pyruvate dehydrogenase (acetyl-transferring)] kinase isozyme 4, mitochondrial |
| PDLIM1 | PDLI1_HUMAN | PDZ and LIM domain protein 1 |
| PDXK | PDXK_HUMAN | Pyridoxal kinase |
| PDZD3 | NHRF4_HUMAN | Na(+)/H(+) exchange regulatory cofactor NHE-RF4 |
| PDZRN3 | PZRN3_HUMAN | E3 ubiquitin-protein ligase PDZRN3 |
| PDZRN4 | PZRN4_HUMAN | PDZ domain-containing RING finger protein 4 |
| PEG10 | PEG10_HUMAN | Retrotransposon-derived protein PEG10 |
| PEG3 | PEG3_HUMAN | Paternally-expressed gene 3 protein |
| PELI2 | PELI2_HUMAN | E3 ubiquitin-protein ligase pellino homolog 2 |
| PEPD | PEPD_HUMAN | Xaa-Pro dipeptidase |
| PEX2 | PEX2_HUMAN | Peroxisome biogenesis factor 2 |
| PEX5 | PEX5_HUMAN | Peroxisomal targeting signal 1 receptor |
| PF4 | PLF4_HUMAN | Platelet factor 4, short form |
| PF4V1 | PF4V_HUMAN | Platelet factor 4 variant(6-74) |
| PFKFB1 | F261_HUMAN | Fructose-2,6-bisphosphatase |
| PGA4 | PEPA4_HUMAN | Pepsin A-4 |
| PGAM5 | PGAM5_HUMAN | Serine/threonine-protein phosphatase PGAM5, mitochondrial |
| PGC | PEPC_HUMAN | Gastricsin |
| PGD | 6PGD_HUMAN | 6-phosphogluconate dehydrogenase, decarboxylating |
| PGK1 | PGK1_HUMAN | Phosphoglycerate kinase 1 |
| PGLYRP3 | PGRP3_HUMAN | Peptidoglycan recognition protein 3 |
| PGLYRP4 | PGRP4_HUMAN | Peptidoglycan recognition protein 4 |
| PGM1 | PGM1_HUMAN | Phosphoglucomutase-1 |
| PGR | PRGR_HUMAN | Progesterone receptor |
| PHC1 | PHC1_HUMAN | Polyhomeotic-like protein 1 |
| PHC2 | PHC2_HUMAN | Polyhomeotic-like protein 2 |
| PHC3 | PHC3_HUMAN | Polyhomeotic-like protein 3 |
| PHF1 | PHF1_HUMAN | PHD finger protein 1 |
| PHF14 | PHF14_HUMAN | PHD finger protein 14 |

TABLE 1-continued

| Target Protein Symbol | uniprot name | Target Protein name |
|---|---|---|
| PHF19 | PHF19_HUMAN | PHD finger protein 19 |
| PHF20 | PHF20_HUMAN | PHD finger protein 20 |
| PHF20L1 | P20L1_HUMAN | PHD finger protein 20-like protein 1 |
| PHF23 | PHF23_HUMAN | PHD finger protein 23 |
| PHF5A | PHF5A_HUMAN | PHD finger-like domain-containing protein 5A |
| PHF6 | PHF6_HUMAN | PHD finger protein 6 |
| PHF7 | PHF7_HUMAN | PHD finger protein 7 |
| PHKG2 | PHKG2_HUMAN | Phosphorylase b kinase gamma catalytic chain, liver/testis isoform |
| PHRF1 | PHRF1_HUMAN | PHD and RING finger domain-containing protein 1 |
| PI4K2A | P4K2A_HUMAN | Phosphatidylinositol 4-kinase type 2-alpha |
| PI4K2B | P4K2B_HUMAN | Phosphatidylinositol 4-kinase type 2-beta |
| PI4KA | PI4KA_HUMAN | Phosphatidylinositol 4-kinase alpha |
| PI4KB | PI4KB_HUMAN | Phosphatidylinositol 4-kinase beta |
| PIAS3 | PIAS3_HUMAN | E3 SUMO-protein ligase PIAS3 |
| PIF1 | PIF1_HUMAN | ATP-dependent DNA helicase PIF1 |
| PIGR | PIGR_HUMAN | Secretory component |
| PIH1D1 | PIHD1_HUMAN | PIH1 domain-containing protein 1 |
| PIK3C3 | PK3C3_HUMAN | Phosphatidylinositol 3-kinase catalytic subunit type 3 |
| PIK3CA | PK3CA_HUMAN | Phosphatidylinositol 4,5-bisphosphate 3-kinase catalytic subunit alpha isoform |
| PIK3CD | PK3CD_HUMAN | Phosphatidylinositol 4,5-bisphosphate 3-kinase catalytic subunit delta isoform |
| PIK3CG | PK3CG_HUMAN | Phosphatidylinositol 4,5-bisphosphate 3-kinase catalytic subunit gamma isoform |
| PIK3R1 | P85A_HUMAN | Phosphatidylinositol 3-kinase regulatory subunit alpha |
| PIKFYVE | FYV1_HUMAN | 1-phosphatidylinositol 3-phosphate 5-kinase |
| PILRA | PILRA_HUMAN | Paired immunoglobulin-like type 2 receptor alpha |
| PILRB | PILRB_HUMAN | Paired immunoglobulin-like type 2 receptor beta |
| PIM1 | PIM1_HUMAN | Serine/threonine-protein kinase pim-1 |
| PIM2 | PIM2_HUMAN | Serine/threonine-protein kinase pim-2 |
| PIN1 | PIN1_HUMAN | Peptidyl-prolyl cis-trans isomerase NIMA-interacting 1 |
| PIN4 | PIN4_HUMAN | Peptidyl-prolyl cis-trans isomerase NIMA-interacting 4 |
| PIP4K2B | PI42B_HUMAN | Phosphatidylinositol 5-phosphate 4-kinase type-2 beta |
| PIR | PIR_HUMAN | Pirin |
| PITPNA | PIPNA_HUMAN | Phosphatidylinositol transfer protein alpha isoform |
| PITRM1 | PREP_HUMAN | Presequence protease, mitochondrial |
| PIWIL1 | PIWL1_HUMAN | Piwi-like protein 1 |
| PIWIL2 | PIWL2_HUMAN | Piwi-like protein 2 |
| PKD1 | PKD1_HUMAN | Polycystin-1 |
| PKD2 | PKD2_HUMAN | Polycystin-2 |
| PKD2L1 | PK2L1_HUMAN | Polycystic kidney disease 2-like 1 protein |
| PKLR | KPYR_HUMAN | Pyruvate kinase PKLR |
| PKM | KPYM_HUMAN | Pyruvate kinase PKM |
| PKMYT1 | PMYT1_HUMAN | Membrane-associated tyrosine- and threonine-specific cdc2-inhibitory kinase |
| PKN1 | PKN1_HUMAN | Serine/threonine-protein kinase N1 |
| PKN2 | PKN2_HUMAN | Serine/threonine-protein kinase N2 |
| PLA2G2E | PA2GE_HUMAN | Group IIE secretory phospholipase A2 |
| PLA2G4A | PA24A_HUMAN | Lysophospholipase |
| PLA2G4D | PA24D_HUMAN | Cytosolic phospholipase A2 delta |
| PLAA | PLAP_HUMAN | Phospholipase A-2-activating protein |
| PLAG1 | PLAG1_HUMAN | Zinc finger protein PLAG1 |
| PLAGL1 | PLAL1_HUMAN | Zinc finger protein PLAGL1 |
| PLAGL2 | PLAL2_HUMAN | Zinc finger protein PLAGL2 |
| PLAU | UROK_HUMAN | Urokinase-type plasminogen activator chain B |
| PLAUR | UPAR_HUMAN | Urokinase plasminogen activator surface receptor |
| PLCG1 | PLCG1_HUMAN | 1-phosphatidylinositol 4,5-bisphosphate phosphodiesterase gamma-1 |
| PLCG2 | PLCG2_HUMAN | 1-phosphatidylinositol 4,5-bisphosphate phosphodiesterase gamma-2 |
| PLEC | PLEC_HUMAN | Plectin |
| PLEKHB2 | PKHB2_HUMAN | Pleckstrin homology domain-containing family B member 2 |
| PLEKHF1 | PKHF1_HUMAN | Pleckstrin homology domain-containing family F member 1 |
| PLEKHF2 | PKHF2_HUMAN | Pleckstrin homology domain-containing family F member 2 |
| PLEKHM3 | PKHM3_HUMAN | Pleckstrin homology domain-containing family M member 3 |
| PLG | PLMN_HUMAN | Plasmin light chain B |
| PLK1 | PLK1_HUMAN | Serine/threonine-protein kinase PLK1 |

TABLE 1-continued

| Target Protein Symbol | uniprot name | Target Protein name |
|---|---|---|
| PLK2 | PLK2__HUMAN | Serine/threonine-protein kinase PLK2 |
| PLK3 | PLK3__HUMAN | Serine/threonine-protein kinase PLK3 |
| PLK4 | PLK4__HUMAN | Serine/threonine-protein kinase PLK4 |
| PLRG1 | PLRG1__HUMAN | Pleiotropic regulator 1 |
| PLXNA4 | PLXA4__HUMAN | Plexin-A4 |
| PLXNB1 | PLXB1__HUMAN | Plexin-B1 |
| PLXNB2 | PLXB2__HUMAN | Plexin-B2 |
| PLXNC1 | PLXC1__HUMAN | Plexin-C1 |
| PLXND1 | PLXD1__HUMAN | Plexin-D1 |
| PMS2 | PMS2__HUMAN | Mismatch repair endonuclease PMS2 |
| PNLIP | LIPP__HUMAN | Pancreatic triacylglycerol lipase |
| PNLIPRP1 | LIPR1__HUMAN | Inactive pancreatic lipase-related protein 1 |
| PNLIPRP2 | LIPR2__HUMAN | Pancreatic lipase-related protein 2 |
| PNMA3 | PNMA3__HUMAN | Paraneoplastic antigen Ma3 |
| PNPO | PNPO__HUMAN | Pyridoxine-5'-phosphate oxidase |
| PNPT1 | PNPT1__HUMAN | Polyribonucleotide nucleotidyltransferase 1, mitochondrial |
| POGLUT2 | PLGT2__HUMAN | Protein O-glucosyltransferase 2 |
| POLA1 | DPOLA__HUMAN | DNA polymerase alpha catalytic subunit |
| POLB | DPOLB__HUMAN | DNA polymerase beta |
| POLE2 | DPOE2__HUMAN | DNA polymerase epsilon subunit 2 |
| POLG | DPOG1__HUMAN | DNA polymerase subunit gamma-1 |
| POLG2 | DPOG2__HUMAN | DNA polymerase subunit gamma-2, mitochondrial |
| POLH | POLH__HUMAN | DNA polymerase eta |
| POLL | DPOLL__HUMAN | DNA polymerase lambda |
| POLM | DPOLM__HUMAN | DNA-directed DNA/RNA polymerase mu |
| POLN | DPOLN__HUMAN | DNA polymerase nu |
| POLQ | DPOLQ__HUMAN | DNA polymerase theta |
| POLR1B | RPA2__HUMAN | DNA-directed RNA polymerase I subunit RPA2 |
| POLR2A | RPB1__HUMAN | DNA-directed RNA polymerase II subunit RPB1 |
| POLR2B | RPB2__HUMAN | DNA-directed RNA polymerase II subunit RPB2 |
| POLR2E | RPAB1__HUMAN | DNA-directed RNA polymerases I, II, and III subunit RPABC1 |
| POLR2G | RPB7__HUMAN | DNA-directed RNA polymerase II subunit RPB7 |
| POLR2I | RPB9__HUMAN | DNA-directed RNA polymerase II subunit RPB9 |
| POLR2K | RPAB4__HUMAN | DNA-directed RNA polymerases I, II, and III subunit RPABC4 |
| POLR2L | RPAB5__HUMAN | DNA-directed RNA polymerases I, II, and III subunit RPABC5 |
| POLR3B | RPC2__HUMAN | DNA-directed RNA polymerase III subunit RPC2 |
| POLR3C | RPC3__HUMAN | DNA-directed RNA polymerase III subunit RPC3 |
| POLR3K | RPC10__HUMAN | DNA-directed RNA polymerase III subunit RPC10 |
| POLRMT | RPOM__HUMAN | DNA-directed RNA polymerase, mitochondrial |
| POMGNT1 | PMGT1__HUMAN | Protein O-linked-mannose beta-1,2-N-acetylglucosaminyltransferase 1 |
| POP1 | POP1__HUMAN | Ribonucleases P/MRP protein subunit POP1 |
| POP5 | POP5__HUMAN | Ribonuclease P/MRP protein subunit POP5 |
| POR | NCPR__HUMAN | NADPH--cytochrome P450 reductase |
| POSTN | POSTN__HUMAN | Periostin |
| POT1 | POTE1__HUMAN | Protection of telomeres protein 1 |
| PPA1 | IPYR__HUMAN | Inorganic pyrophosphatase |
| PPARA | PPARA__HUMAN | Peroxisome proliferator-activated receptor alpha |
| PPARD | PPARD__HUMAN | Peroxisome proliferator-activated receptor delta |
| PPARG | PPARG__HUMAN | Peroxisome proliferator-activated receptor gamma |
| PPBP | CXCL7__HUMAN | Neutrophil-activating peptide 2(1-63) |
| PPIA | PPIA__HUMAN | Peptidyl-prolyl cis-trans isomerase A, N-terminally processed |
| PPIE | PPIE__HUMAN | Peptidyl-prolyl cis-trans isomerase E |
| PPIL1 | PPIL1__HUMAN | Peptidyl-prolyl cis-trans isomerase-like 1 |
| PPIL3 | PPIL3__HUMAN | Peptidyl-prolyl cis-trans isomerase-like 3 |
| PPL | PEPL__HUMAN | Periplakin |
| PPM1K | PPM1K__HUMAN | Protein phosphatase 1K, mitochondrial |
| PPME1 | PPME1__HUMAN | Protein phosphatase methylesterase 1 |
| PPOX | PPOX__HUMAN | Protoporphyrinogen oxidase |
| PPP1R13L | IASPP__HUMAN | RelA-associated inhibitor |
| PPP2R2A | 2ABA__HUMAN | Serine/threonine-protein phosphatase 2A 55 kDa regulatory subunit B alpha isoform |
| PPP3CA | PP2BA__HUMAN | Serine/threonine-protein phosphatase 2B catalytic subunit alpha isoform |
| PPP3CB | PP2BB__HUMAN | Serine/threonine-protein phosphatase 2B catalytic subunit beta isoform |
| PRDM1 | PRDM1__HUMAN | PR domain zinc finger protein 1 |
| PRDM10 | PRD10__HUMAN | PR domain zinc finger protein 10 |
| PRDM11 | PRD11__HUMAN | PR domain-containing protein 11 |
| PRDM12 | PRD12__HUMAN | PR domain zinc finger protein 12 |
| PRDM13 | PRD13__HUMAN | PR domain zinc finger protein 13 |
| PRDM14 | PRD14__HUMAN | PR domain zinc finger protein 14 |
| PRDM15 | PRD15__HUMAN | PR domain zinc finger protein 15 |

TABLE 1-continued

| Target Protein Symbol | uniprot name | Target Protein name |
|---|---|---|
| PRDM16 | PRD16_HUMAN | Histone-lysine N-methyltransferase PRDM16 |
| PRDM2 | PRDM2_HUMAN | PR domain zinc finger protein 2 |
| PRDM5 | PRDM5_HUMAN | PR domain zinc finger protein 5 |
| PRDM6 | PRDM6_HUMAN | Putative histone-lysine N-methyltransferase PRDM6 |
| PRDM9 | PRDM9_HUMAN | Histone-lysine N-methyltransferase PRDM9 |
| PRDX1 | PRDX1_HUMAN | Peroxiredoxin-1 |
| PRDX2 | PRDX2_HUMAN | Peroxiredoxin-2 |
| PRDX3 | PRDX3_HUMAN | Thioredoxin-dependent peroxide reductase, mitochondrial |
| PRDX4 | PRDX4_HUMAN | Peroxiredoxin-4 |
| PRDX5 | PRDX5_HUMAN | Peroxiredoxin-5, mitochondrial |
| PRDX6 | PRDX6_HUMAN | Peroxiredoxin-6 |
| PREB | PREB_HUMAN | Prolactin regulatory element-binding protein |
| PREP | PPCE_HUMAN | Prolyl endopeptidase |
| PREX2 | PREX2_HUMAN | Phosphatidylinositol 3,4,5-trisphosphate-dependent Rac exchanger 2 protein |
| PRG2 | PRG2_HUMAN | Eosinophil granule major basic protein |
| PRIM1 | PRI1_HUMAN | DNA primase small subunit |
| PRIMPOL | PRIPO_HUMAN | DNA-directed primase/polymerase protein |
| PRKAA1 | AAPK1_HUMAN | 5'-AMP-activated protein kinase catalytic subunit alpha-1 |
| PRKAA2 | AAPK2_HUMAN | 5'-AMP-activated protein kinase catalytic subunit alpha-2 |
| PRKAB1 | AAKB1_HUMAN | 5'-AMP-activated protein kinase subunit beta-1 |
| PRKAB2 | AAKB2_HUMAN | 5'-AMP-activated protein kinase subunit beta-2 |
| PRKACA | KAPCA_HUMAN | cAMP-dependent protein kinase catalytic subunit alpha |
| PRKAG1 | AAKG1_HUMAN | 5'-AMP-activated protein kinase subunit gamma-1 |
| PRKCA | KPCA_HUMAN | Protein kinase C alpha type |
| PRKCB | KPCB_HUMAN | Protein kinase C beta type |
| PRKCD | KPCD_HUMAN | Protein kinase C delta type catalytic subunit |
| PRKCE | KPCE_HUMAN | Protein kinase C epsilon type |
| PRKCG | KPCG_HUMAN | Protein kinase C gamma type |
| PRKCH | KPCL_HUMAN | Protein kinase C eta type |
| PRKCI | KPCI_HUMAN | Protein kinase C iota type |
| PRKCQ | KPCT_HUMAN | Protein kinase C theta type |
| PRKD1 | KPCD1_HUMAN | Serine/threonine-protein kinase D1 |
| PRKD2 | KPCD2_HUMAN | Serine/threonine-protein kinase D2 |
| PRKD3 | KPCD3_HUMAN | Serine/threonine-protein kinase D3 |
| PRKDC | PRKDC_HUMAN | DNA-dependent protein kinase catalytic subunit |
| PRKG1 | KGP1_HUMAN | cGMP-dependent protein kinase 1 |
| PRKN | PRKN_HUMAN | E3 ubiquitin-protein ligase parkin |
| PRLR | PRLR_HUMAN | Prolactin receptor |
| PRMT5 | ANM5_HUMAN | Protein arginine N-methyltransferase 5, N-terminally processed |
| PRNP | PRIO_HUMAN | Major prion protein |
| PROS1 | PROS_HUMAN | Vitamin K-dependent protein S |
| PROZ | PROZ_HUMAN | Vitamin K-dependent protein Z |
| PRPF19 | PRP19_HUMAN | Pre-mRNA-processing factor 19 |
| PRPF38A | PR38A_HUMAN | Pre-mRNA-splicing factor 38A |
| PRPF4 | PRP4_HUMAN | U4/U6 small nuclear ribonucleoprotein Prp4 |
| PRPF40A | PR40A_HUMAN | Pre-mRNA-processing factor 40 homolog A |
| PRPF8 | PRP8_HUMAN | Pre-mRNA-processing-splicing factor 8 |
| PRPSAP1 | KPRA_HUMAN | Phosphoribosyl pyrophosphate synthase-associated protein 1 |
| PSAT1 | SERC_HUMAN | Phosphoserine aminotransferase |
| PSMA1 | PSA1_HUMAN | Proteasome subunit alpha type-1 |
| PSMA2 | PSA2_HUMAN | Proteasome subunit alpha type-2 |
| PSMA3 | PSA3_HUMAN | Proteasome subunit alpha type-3 |
| PSMA4 | PSA4_HUMAN | Proteasome subunit alpha type-4 |
| PSMA5 | PSA5_HUMAN | Proteasome subunit alpha type-5 |
| PSMA6 | PSA6_HUMAN | Proteasome subunit alpha type-6 |
| PSMA7 | PSA7_HUMAN | Proteasome subunit alpha type-7 |
| PSMB1 | PSB1_HUMAN | Proteasome subunit beta type-1 |
| PSMB10 | PSB10_HUMAN | Proteasome subunit beta type-10 |
| PSMB2 | PSB2_HUMAN | Proteasome subunit beta type-2 |
| PSMB3 | PSB3_HUMAN | Proteasome subunit beta type-3 |
| PSMB4 | PSB4_HUMAN | Proteasome subunit beta type-4 |
| PSMB5 | PSB5_HUMAN | Proteasome subunit beta type-5 |
| PSMB6 | PSB6_HUMAN | Proteasome subunit beta type-6 |
| PSMB7 | PSB7_HUMAN | Proteasome subunit beta type-7 |
| PSMB8 | PSB8_HUMAN | Proteasome subunit beta type-8 |
| PSMB9 | PSB9_HUMAN | Proteasome subunit beta type-9 |
| PSMC1 | PRS4_HUMAN | 26S proteasome regulatory subunit 4 |
| PSMC4 | PRS6B_HUMAN | 26S proteasome regulatory subunit 6B |
| PSMC5 | PRS8_HUMAN | 26S proteasome regulatory subunit 8 |
| PSMC6 | PRS10_HUMAN | 26S proteasome regulatory subunit 10B |

TABLE 1-continued

| Target Protein Symbol | uniprot name | Target Protein name |
|---|---|---|
| PSMD1 | PSMD1_HUMAN | 26S proteasome non-ATPase regulatory subunit 1 |
| PSMD10 | PSD10_HUMAN | 26S proteasome non-ATPase regulatory subunit 10 |
| PSMD11 | PSD11_HUMAN | 26S proteasome non-ATPase regulatory subunit 11 |
| PSMD12 | PSD12_HUMAN | 26S proteasome non-ATPase regulatory subunit 12 |
| PSMD14 | PSDE_HUMAN | 26S proteasome non-ATPase regulatory subunit 14 |
| PSMD3 | PSMD3_HUMAN | 26S proteasome non-ATPase regulatory subunit 3 |
| PSPC1 | PSPC1_HUMAN | Paraspeckle component 1 |
| PTCRA | PTCRA_HUMAN | Pre T-cell antigen receptor alpha |
| PTGDS | PTGDS_HUMAN | Prostaglandin-H2 D-isomerase |
| PTGER3 | PE2R3_HUMAN | Prostaglandin E2 receptor EP3 subtype |
| PTGS2 | PGH2_HUMAN | Prostaglandin G/H synthase 2 |
| PTK2 | FAK1_HUMAN | Focal adhesion kinase 1 |
| PTK2B | FAK2_HUMAN | Protein-tyrosine kinase 2-beta |
| PTK6 | PTK6_HUMAN | Protein-tyrosine kinase 6 |
| PTPN11 | PTN11_HUMAN | Tyrosine-protein phosphatase non-receptor type 11 |
| PTPN12 | PTN12_HUMAN | Tyrosine-protein phosphatase non-receptor type 12 |
| PTPN13 | PTN13_HUMAN | Tyrosine-protein phosphatase non-receptor type 13 |
| PTPN14 | PTN14_HUMAN | Tyrosine-protein phosphatase non-receptor type 14 |
| PTPN2 | PTN2_HUMAN | Tyrosine-protein phosphatase non-receptor type 2 |
| PTPN23 | PTN23_HUMAN | Tyrosine-protein phosphatase non-receptor type 23 |
| PTPN3 | PTN3_HUMAN | Tyrosine-protein phosphatase non-receptor type 3 |
| PTPN5 | PTN5_HUMAN | Tyrosine-protein phosphatase non-receptor type 5 |
| PTPN6 | PTN6_HUMAN | Tyrosine-protein phosphatase non-receptor type 6 |
| PTPN7 | PTN7_HUMAN | Tyrosine-protein phosphatase non-receptor type 7 |
| PTPRD | PTPRD_HUMAN | Receptor-type tyrosine-protein phosphatase delta |
| PTPRF | PTPRF_HUMAN | Receptor-type tyrosine-protein phosphatase F |
| PTPRM | PTPRM_HUMAN | Receptor-type tyrosine-protein phosphatase mu |
| PTPRR | PTPRR_HUMAN | Receptor-type tyrosine-protein phosphatase R |
| PTPRS | PTPRS_HUMAN | Receptor-type tyrosine-protein phosphatase S |
| PTPRZ1 | PTPRZ_HUMAN | Receptor-type tyrosine-protein phosphatase zeta |
| PTS | PTPS_HUMAN | 6-pyruvoyl tetrahydrobiopterin synthase |
| PUF60 | PUF60_HUMAN | Poly(U)-binding-splicing factor PUF60 |
| PUS7 | PUS7_HUMAN | Pseudouridylate synthase 7 homolog |
| PVR | PVR_HUMAN | Poliovirus receptor |
| PWWP2B | PWP2B_HUMAN | PWWP domain-containing protein 2B |
| PYGL | PYGL_HUMAN | Glycogen phosphorylase, liver form |
| QARS | SYQ_HUMAN | Glutamine-tRNA ligase |
| QPCT | QPCT_HUMAN | Glutaminyl-peptide cyclotransferase |
| QSOX1 | QSOX1_HUMAN | Sulfhydryl oxidase 1 |
| QTRT1 | TGT_HUMAN | Queuine tRNA-ribosyltransferase catalytic subunit |
| RAB3IP | RAB3I_HUMAN | Rab-3 A-interacting protein |
| RABIF | MSS4_HUMAN | Guanine nucleotide exchange factor MSS4 |
| RAC1 | RAC1_HUMAN | Ras-related C3 botulinum toxin substrate 1 |
| RACGAP1 | RGAP1_HUMAN | Rac GTPase-activating protein 1 |
| RACK1 | RACK1_HUMAN | Receptor of activated protein C kinase 1, N-terminally processed |
| RAD18 | RAD1_HUMAN | Cell cycle checkpoint protein RAD1 |
| RAD18 | RAD18_HUMAN | E3 ubiquitin-protein ligase RAD18 |
| RAD51 | RAD51_HUMAN | DNA repair protein RAD51 homolog 1 |
| RAD52 | RAD52_HUMAN | DNA repair protein RAD52 homolog |
| RAE1 | RAE1L_HUMAN | mRNA export factor |
| RAET1L | ULBP6_HUMAN | UL16-binding protein 6 |
| RAF1 | RAF1_HUMAN | RAF proto-oncogene serine/threonine-protein kinase |
| RALGDS | GNDS_HUMAN | Ral guanine nucleotide dissociation stimulator |
| RAN | RAN_HUMAN | GTP-binding nuclear protein Ran |
| RANBP1 | RANG_HUMAN | Ran-specific GTPase-activating protein |
| RANBP2 | RBP2_HUMAN | E3 SUMO-protein ligase RanBP2 |
| RANBP3 | RANB3_HUMAN | Ran-binding protein 3 |
| RANBP9 | RANB9_HUMAN | Ran-binding protein 9 |
| RAP1GAP | RPGP1_HUMAN | Rap1 GTPase-activating protein 1 |
| RAPGEF5 | RPGF5_HUMAN | Rap guanine nucleotide exchange factor 5 |
| RAPGEFL1 | RPGFL_HUMAN | Rap guanine nucleotide exchange factor-like 1 |
| RAPH1 | RAPH1_HUMAN | Ras-associated and pleckstrin homology domains-containing protein 1 |
| RAPSN | RAPSN_HUMAN | 43 kDa receptor-associated protein of the synapse |
| RARA | RARA_HUMAN | Retinoic acid receptor alpha |
| RARB | RARB_HUMAN | Retinoic acid receptor beta |
| RARG | RARG_HUMAN | Retinoic acid receptor gamma |
| RARS | SYRC_HUMAN | Arginine--tRNA ligase, cytoplasmic |
| RASA1 | RASA1_HUMAN | Ras GTPase-activating protein 1 |
| RASGRP1 | GRP1_HUMAN | RAS guanyl-releasing protein 1 |
| RASGRP2 | GRP2_HUMAN | RAS guanyl-releasing protein 2 |
| RASGRP3 | GRP3_HUMAN | Ras guanyl-releasing protein 3 |
| RASGRP4 | GRP4_HUMAN | RAS guanyl-releasing protein 4 |
| RASSF1 | RASF1_HUMAN | Ras association domain-containing protein 1 |
| RASSF5 | RASF5_HUMAN | Ras association domain-containing protein 5 |
| RAVER1 | RAVR1_HUMAN | Ribonucleoprotein PTB-binding 1 |

TABLE 1-continued

| Target Protein Symbol | uniprot name | Target Protein name |
|---|---|---|
| RBAK | RBAK_HUMAN | RB-associated KRAB zinc finger protein |
| RBBP4 | RBBP4_HUMAN | Histone-binding protein RBBP4 |
| RBBP6 | RBBP6_HUMAN | E3 ubiquitin-protein ligase RBBP6 |
| RBBP8 | CTIP_HUMAN | DNA endonuclease RBBP8 |
| RBKS | RBSK_HUMAN | Ribokinase |
| RBM10 | RBM10_HUMAN | RNA-binding protein 10 |
| RBM11 | RBM11_HUMAN | Splicing regulator RBM11 |
| RBM22 | RBM22_HUMAN | Pre-mRNA-splicing factor RBM22 |
| RBM23 | RBM23_HUMAN | Probable RNA-binding protein 23 |
| RBM38 | RBM38_HUMAN | RNA-binding protein 38 |
| RBM39 | RBM39_HUMAN | RNA-binding protein 39 |
| RBM4 | RBM4_HUMAN | RNA-binding protein 4 |
| RBM4B | RBM4B_HUMAN | RNA-binding protein 4B |
| RBM5 | RBM5_HUMAN | RNA-binding protein 5 |
| RBM7 | RBM7_HUMAN | RNA-binding protein 7 |
| RBM8A | RBM8A_HUMAN | RNA-binding protein 8A |
| RBMX2 | RBMX2_HUMAN | RNA-binding motif protein, X-linked 2 |
| RBP4 | RET4_HUMAN | Plasma retinol-binding protein(1-176) |
| RBP5 | RET5_HUMAN | Retinol-binding protein 5 |
| RBPJ | SUH_HUMAN | Recombining binding protein suppressor of hairless |
| RBSN | RBNS5_HUMAN | Rabenosyn-5 |
| RCC1 | RCC1_HUMAN | Regulator of chromosome condensation |
| RCC1L | RCC1L_HUMAN | RCC1-like G exchanging factor-like protein |
| RCC2 | RCC2_HUMAN | Protein RCC2 |
| RCHY1 | ZN363_HUMAN | RING finger and CHY zinc finger domain-containing protein 1 |
| RECQL4 | RECQ4_HUMAN | ATP-dependent DNA helicase Q4 |
| REN | RENI_HUMAN | Renin |
| REPIN1 | REPI1_HUMAN | Replication initiator 1 |
| REST | REST_HUMAN | RE1-silencing transcription factor |
| RET | RET_HUMAN | Extracellular cell-membrane anchored RET cadherin 120 kDa fragment |
| RFFL | RFFL_HUMAN | E3 ubiquitin-protein ligase rififylin |
| RFK | RIFK_HUMAN | Riboflavin kinase |
| RFPL4A | RFPLA_HUMAN | Ret finger protein-like 4A |
| RFWD3 | RFWD3_HUMAN | E3 ubiquitin-protein ligase RFWD3 |
| RFXANK | RFXK_HUMAN | DNA-binding protein RFXANK |
| RGCC | RGCC_HUMAN | Regulator of cell cycle RGCC |
| RGMB | RGMB_HUMAN | RGM domain family member B |
| RGN | RGN_HUMAN | Regucalcin |
| RHEB | RHEB_HUMAN | GTP-binding protein Rheb |
| RHO | OPSD_HUMAN | Rhodopsin |
| RIDA | RIDA_HUMAN | 2-iminobutanoate/2-iminopropanoate deaminase |
| RIMBP2 | RIMB2_HUMAN | RIMS-binding protein 2 |
| RIMBP3 | RIM3A_HUMAN | RIMS-binding protein 3 A |
| RIMS1 | RIMS1_HUMAN | Regulating synaptic membrane exocytosis protein 1 |
| RIMS2 | RIMS2_HUMAN | Regulating synaptic membrane exocytosis protein 2 |
| RIOK1 | RIOK1_HUMAN | Serine/threonine-protein kinase RIO1 |
| RIOK2 | RIOK2_HUMAN | Serine/threonine-protein kinase RIO2 |
| RIPK1 | RIPK1_HUMAN | Receptor-interacting serine/threonine-protein kinase 1 |
| RIPK2 | RIPK2_HUMAN | Receptor-interacting serine/threonine-protein kinase 2 |
| RLBP1 | RLBP1_HUMAN | Retinaldehyde-binding protein 1 |
| RMI2 | RMI2_HUMAN | RecQ-mediated genome instability protein 2 |
| RNASE4 | RNAS4_HUMAN | Ribonuclease 4 |
| RNASEH2B | RNH2B_HUMAN | Ribonuclease H2 subunit B |
| RNASEH2C | RNH2C_HUMAN | Ribonuclease H2 subunit C |
| RNASEL | RN5A_HUMAN | 2-5A-dependent ribonuclease |
| RNF121 | RN121_HUMAN | RING finger protein 121 |
| RNF123 | RN123_HUMAN | E3 ubiquitin-protein ligase RNF123 |
| RNF125 | RN125_HUMAN | E3 ubiquitin-protein ligase RNF125 |
| RNF14 | RNF14_HUMAN | E3 ubiquitin-protein ligase RNF14 |
| RNF166 | RN166_HUMAN | RING finger protein 166 |
| RNF17 | RNF17_HUMAN | RING finger protein 17 |
| RNF170 | RN170_HUMAN | E3 ubiquitin-protein ligase RNF170 |
| RNF175 | RN175_HUMAN | RING finger protein 175 |
| RNF19A | RN19A_HUMAN | E3 ubiquitin-protein ligase RNF19A |
| RNF19B | RN19B_HUMAN | E3 ubiquitin-protein ligase RNF19B |
| RNF2 | RING2_HUMAN | E3 ubiquitin-protein ligase RING2 |
| RNF207 | RN207_HUMAN | RING finger protein 207 |
| RNF208 | RN208_HUMAN | RING finger protein 208 |
| RNF212B | R212B_HUMAN | RING finger protein 212B |
| RNF216 | RN216_HUMAN | E3 ubiquitin-protein ligase RNF216 |
| RNF31 | RNF31_HUMAN | E3 ubiquitin-protein ligase RNF31 |

TABLE 1-continued

| Target Protein Symbol | uniprot name | Target Protein name |
|---|---|---|
| RNF34 | RNF34_HUMAN | E3 ubiquitin-protein ligase RNF34 |
| RNF39 | RNF39_HUMAN | RING finger protein 39 |
| RNF4 | RNF4_HUMAN | E3 ubiquitin-protein ligase RNF4 |
| RNF8 | RNF8_HUMAN | E3 ubiquitin-protein ligase RNF8 |
| RNGTT | MCE1_HUMAN | mRNA guanylyltransferase |
| ROBO1 | ROBO1_HUMAN | Roundabout homolog 1 |
| ROBO2 | ROBO2_HUMAN | Roundabout homolog 2 |
| ROCK1 | ROCK1_HUMAN | Rho-associated protein kinase 1 |
| ROCK2 | ROCK2_HUMAN | Rho-associated protein kinase 2 |
| ROR2 | ROR2_HUMAN | Tyrosine-protein kinase transmembrane receptor ROR2 |
| RORA | RORA_HUMAN | Nuclear receptor ROR-alpha |
| RORB | RORB_HUMAN | Nuclear receptor ROR-beta |
| RORC | RORG_HUMAN | Nuclear receptor ROR-gamma |
| RPA1 | RFA1_HUMAN | Replication protein A 70 kDa DNA-binding subunit, N-terminally processed |
| RPA3 | RFA3_HUMAN | Replication protein A 14 kDa subunit |
| RPGR | RPGR_HUMAN | X-linked retinitis pigmentosa GTPase regulator |
| RPH3A | RP3A_HUMAN | Rabphilin-3A |
| RPH3AL | RPH3L_HUMAN | Rab effector Noc2 |
| RPL11 | RL11_HUMAN | 60S ribosomal protein L11 |
| RPL37 | RL37_HUMAN | 60S ribosomal protein L37 |
| RPL37A | RL37A_HUMAN | 60S ribosomal protein L37a |
| RPL37AP8 | RL37L_HUMAN | Putative 60S ribosomal protein L37a-like protein |
| RPS12 | RS12_HUMAN | 40S ribosomal protein S12 |
| RPS15A | RS15A_HUMAN | 40S ribosomal protein S15a |
| RPS18 | RS18_HUMAN | 40S ribosomal protein S18 |
| RPS19 | RS19_HUMAN | 40S ribosomal protein S19 |
| RPS21 | RS21_HUMAN | 40S ribosomal protein S21 |
| RPS23 | RS23_HUMAN | 40S ribosomal protein S23 |
| RPS24 | RS24_HUMAN | 40S ribosomal protein S24 |
| RPS27A | RS27A_HUMAN | 40S ribosomal protein S27a |
| RPS3A | RS3A_HUMAN | 40S ribosomal protein S3a |
| RPS4X | RS4X_HUMAN | 40S ribosomal protein S4, X isoform |
| RPS4Y1 | RS4Y1_HUMAN | 40S ribosomal protein S4, Y isoform 1 |
| RPS6 | RS6_HUMAN | 40S ribosomal protein S6 |
| RPS6KA1 | KS6A1_HUMAN | Ribosomal protein S6 kinase alpha-1 |
| RPS6KA3 | KS6A3_HUMAN | Ribosomal protein S6 kinase alpha-3 |
| RPS6KA5 | KS6A5_HUMAN | Ribosomal protein S6 kinase alpha-5 |
| RPS6KB1 | KS6B1_HUMAN | Ribosomal protein S6 kinase beta-1 |
| RPS7 | RS7_HUMAN | 40S ribosomal protein S7 |
| RPS8 | RS8_HUMAN | 40S ribosomal protein S8 |
| RPSA | RSSA_HUMAN | 40S ribosomal protein SA |
| RPTOR | RPTOR_HUMAN | Regulatory-associated protein of mTOR |
| RREB1 | RREB1_HUMAN | Ras-responsive element-binding protein 1 |
| RRM1 | RIR1_HUMAN | Ribonucleoside-diphosphate reductase large subunit |
| RRP9 | U3IP2_HUMAN | U3 small nucleolar RNA-interacting protein 2 |
| RSF1 | RSF1_HUMAN | Remodeling and spacing factor 1 |
| RSPO1 | RSPO1_HUMAN | R-spondin-1 |
| RTL3 | RTL3_HUMAN | Retrotransposon Gag-like protein 3 |
| RUFY1 | RUFY1_HUMAN | RUN and FYVE domain-containing protein 1 |
| RUFY2 | RUFY2_HUMAN | RUN and FYVE domain-containing protein 2 |
| RUFY4 | RUFY4_HUMAN | RUN and FYVE domain-containing protein 4 |
| RUNX1T1 | MTG8_HUMAN | Protein CBFA2T1 |
| RUSC1 | RUSC1_HUMAN | RUN and SH3 domain-containing protein 1 |
| RUVBL1 | RUVB1_HUMAN | RuvB-like 1 |
| RUVBL2 | RUVB2_HUMAN | RuvB-like 2 |
| RXRA | RXRA_HUMAN | Retinoic acid receptor RXR-alpha |
| RXRB | RXRB_HUMAN | Retinoic acid receptor RXR-beta |
| RXRG | RXRG_HUMAN | Retinoic acid receptor RXR-gamma |
| RYR2 | RYR2_HUMAN | Ryanodine receptor 2 |
| S100B | S100B_HUMAN | Protein S100-B |
| SACS | SACS_HUMAN | Sacsin |
| SAE1 | SAE1_HUMAN | SUMO-activating enzyme subunit 1, N-terminally processed |
| SALL1 | SALL1_HUMAN | Sal-like protein 1 |
| SALL2 | SALL2_HUMAN | Sal-like protein 2 |
| SALL3 | SALL3_HUMAN | Sal-like protein 3 |
| SALL4 | SALL4_HUMAN | Sal-like protein 4 |
| SAMHD1 | SAMH1_HUMAN | Deoxynucleoside triphosphate triphosphohydrolase SAMHD1 |
| SARS | SYSC_HUMAN | Serine--tRNA ligase, cytoplasmic |
| SAT1 | SAT1_HUMAN | Diamine acetyltransferase 1 |
| SAT2 | SAT2_HUMAN | Diamine acetyltransferase 2 |
| SBDS | SBDS_HUMAN | Ribosome maturation protein SBDS |
| SCARB2 | SCRB2_HUMAN | Lysosome membrane protein 2 |
| SCIN | ADSV_HUMAN | Adseverin |

TABLE 1-continued

| Target Protein Symbol | uniprot name | Target Protein name |
|---|---|---|
| SCLY | SCLY_HUMAN | Selenocysteine lyase |
| SCN2A | SCN2A_HUMAN | Sodium channel protein type 2 subunit alpha |
| SCN3B | SCN3B_HUMAN | Sodium channel subunit beta-3 |
| SCN9A | SCN9A_HUMAN | Sodium channel protein type 9 subunit alpha |
| SCO1 | SCO1_HUMAN | Protein SCO1 homolog, mitochondrial |
| SCP2 | NLTP_HUMAN | Non-specific lipid-transfer protein |
| SCRT1 | SCRT1_HUMAN | Transcriptional repressor scratch 1 |
| SCRT2 | SCRT2_HUMAN | Transcriptional repressor scratch 2 |
| SDCBP | SDCB1_HUMAN | Syntenin-1 |
| SDK2 | SDK2_HUMAN | Protein sidekick-2 |
| SEC13 | SEC13_HUMAN | Protein SEC13 homolog |
| SEC14L2 | S14L2_HUMAN | SEC14-like protein 2 |
| SEC14L3 | S14L3_HUMAN | SEC14-like protein 3 |
| SEC14L4 | S14L4_HUMAN | SEC14-like protein 4 |
| SEC22B | SC22B_HUMAN | Vesicle-trafficking protein SEC22b |
| SEC24A | SC24A_HUMAN | Protein transport protein Sec24A |
| SEC24B | SC24B_HUMAN | Protein transport protein Sec24B |
| SEC24C | SC24C_HUMAN | Protein transport protein Sec24C |
| SEC24D | SC24D_HUMAN | Protein transport protein Sec24D |
| SEH1L | SEH1_HUMAN | Nucleoporin SEH1 |
| SEMA4D | SEM4D_HUMAN | Semaphorin-4D |
| SEMA7A | SEM7A_HUMAN | Semaphorin-7A |
| SEPHS1 | SPS1_HUMAN | Selenide, water dikinase 1 |
| SEPT2 | SEPT2_HUMAN | Septin-2 |
| SERPINA1 | A1AT_HUMAN | Short peptide from AAT |
| SERPINA10 | ZPI_HUMAN | Protein Z-dependent protease inhibitor |
| SERPINA12 | SPA12_HUMAN | Serpin A12 |
| SERPINA3 | AACT_HUMAN | Alpha-1-antichymotrypsin His-Pro-less |
| SERPINA4 | KAIN_HUMAN | Kallistatin |
| SERPINA5 | IPSP_HUMAN | Plasma serine protease inhibitor |
| SERPINA6 | CBG_HUMAN | Corticosteroid-binding globulin |
| SERPINA7 | THBG_HUMAN | Thyroxine-binding globulin |
| SERPINB1 | ILEU_HUMAN | Leukocyte elastase inhibitor |
| SERPINB3 | SPB3_HUMAN | SerpinB3 |
| SERPINC1 | ANT3_HUMAN | Antithrombin-III |
| SERPINE1 | PAI1_HUMAN | Plasminogen activator inhibitor 1 |
| SERPINE2 | GDN_HUMAN | Glia-derived nexin |
| SERPINF1 | PEDF_HUMAN | Pigment epithelium-derived factor |
| SERPING1 | IC1_HUMAN | Plasma protease C1 inhibitor |
| SERPINI1 | NEUS_HUMAN | Neuroserpin |
| SETD2 | SETD2_HUMAN | Histone-lysine N-methyltransferase SETD2 |
| SETD3 | SETD3_HUMAN | Actin-histidine N-methyltransferase |
| SETD7 | SETD7_HUMAN | Histone-lysine N-methyltransferase SETD7 |
| SETDB1 | SETB1_HUMAN | Histone-lysine N-methyltransferase SETDB1 |
| SETMAR | SETMR_HUMAN | Transposon Hsmar1 transposase |
| SF1 | SF01_HUMAN | Splicing factor 1 |
| SF3A2 | SF3A2_HUMAN | Splicing factor 3 A subunit 2 |
| SF3A3 | SF3A3_HUMAN | Splicing factor 3 A subunit 3 |
| SF3B3 | SF3B3_HUMAN | Splicing factor 3B subunit 3 |
| SF3B4 | SF3B4_HUMAN | Splicing factor 3B subunit 4 |
| SFPQ | SFPQ_HUMAN | Splicing factor, proline- and glutamine-rich |
| SFTPD | SFTPD_HUMAN | Pulmonary surfactant-associated protein D |
| SGF29 | SGF29_HUMAN | SAGA-associated factor 29 |
| SGK1 | SGK1_HUMAN | Serine/threonine-protein kinase Sgk1 |
| SGK3 | SGK3_HUMAN | Serine/threonine-protein kinase Sgk3 |
| SGPL1 | SGPL1_HUMAN | Sphingosine-1-phosphate lyase 1 |
| SH2B1 | SH2B1_HUMAN | SH2B adapter protein 1 |
| SH2D1A | SH21A_HUMAN | SH2 domain-containing protein 1A |
| SHARPIN | SHRPN_HUMAN | Sharpin |
| SHMT1 | GLYC_HUMAN | Serine hydroxymethyltransferase, cytosolic |
| SHMT2 | GLYM_HUMAN | Serine hydroxymethyltransferase, mitochondrial |
| SHQ1 | SHQ1_HUMAN | Protein SHQ1 homolog |
| SI | SUIS_HUMAN | Isomaltase |
| SIAH1 | SIAH1_HUMAN | E3 ubiquitin-protein ligase SIAH1 |
| SIAH2 | SIAH2_HUMAN | E3 ubiquitin-protein ligase SIAH2 |
| SIRPA | SHPS1_HUMAN | Tyrosine-protein phosphatase non-receptor type substrate 1 |
| SIRT2 | SIR2_HUMAN | NAD-dependent protein deacetylase sirtuin-2 |
| SIRT5 | SIR5_HUMAN | NAD-dependent protein deacylase sirtuin-5, mitochondrial |
| SKP1 | SKP1_HUMAN | S-phase kinase-associated protein 1 |
| SLA | SLAP1_HUMAN | Src-like-adapter |
| SLA2 | SLAP2_HUMAN | Src-like-adapter 2 |
| SLC4A1 | B3AT_HUMAN | Band 3 anion transport protein |
| SLITRK1 | SLIK1_HUMAN | SLIT and NTRK-like protein 1 |
| SLK | SLK_HUMAN | STE20-like serine/threonine-protein kinase |
| SLMAP | SLMAP_HUMAN | Sarcolemmal membrane-associated protein |
| SLPI | SLPI_HUMAN | Antileukoproteinase |

TABLE 1-continued

| Target Protein Symbol | uniprot name | Target Protein name |
|---|---|---|
| SLU7 | SLU7_HUMAN | Pre-mRNA-splicing factor SLU7 |
| SLURP2 | SLUR2_HUMAN | Secreted Ly-6/uPAR domain-containing protein 2 |
| SLX4 | SLX4_HUMAN | Structure-specific endonuclease subunit SLX4 |
| SMAD4 | SMAD4_HUMAN | Mothers against decapentaplegic homolog 4 |
| SMAP1 | SMAP1_HUMAN | Stromal membrane-associated protein 1 |
| SMAP2 | SMAP2_HUMAN | Stromal membrane-associated protein 2 |
| SMARCA2 | SMCA2_HUMAN | Probable global transcription activator SNF2L2 |
| SMARCA4 | SMCA4_HUMAN | Transcription activator BRG1 |
| SMARCB1 | SNF5_HUMAN | SWI/SNF-related matrix-associated actin-dependent regulator of chromatin subfamily B member 1 |
| SMC2 | SMC2_HUMAN | Structural maintenance of chromosomes protein 2 |
| SMC4 | SMC4_HUMAN | Structural maintenance of chromosomes protein 4 |
| SMG6 | EST1A_HUMAN | Telomerase-binding protein EST1A |
| SMN1\|SMN2 | SMN_HUMAN | Survival motor neuron protein |
| SMNDC1 | SPF30_HUMAN | Survival of motor neuron-related-splicing factor 30 |
| SMO | SMO_HUMAN | Smoothened homolog |
| SMPD3 | NSMA2_HUMAN | Sphingomyelin phosphodiesterase 3 |
| SMS | SPSY_HUMAN | Spermine synthase |
| SMU1 | SMU1_HUMAN | WD40 repeat-containing protein SMU1, N-terminally processed |
| SMURF1 | SMUF1_HUMAN | E3 ubiquitin-protein ligase SMURF1 |
| SMURF2 | SMUF2_HUMAN | E3 ubiquitin-protein ligase SMURF2 |
| SMYD2 | SMYD2_HUMAN | N-lysine methyltransferase SMYD2 |
| SMYD3 | SMYD3_HUMAN | Histone-lysine N-methyltransferase SMYD3 |
| SNAI1 | SNAI1_HUMAN | Zinc finger protein SNAI1 |
| SNAI2 | SNAI2_HUMAN | Zinc finger protein SNAI2 |
| SNAI3 | SNAI3_HUMAN | Zinc finger protein SNAI3 |
| SNAP23 | SNP23_HUMAN | Synaptosomal-associated protein 23 |
| SNAP25 | SNP25_HUMAN | Synaptosomal-associated protein 25 |
| SND1 | SND1_HUMAN | Staphylococcal nuclease domain-containing protein 1 |
| SNIP1 | SNIP1_HUMAN | Smad nuclear-interacting protein 1 |
| SNRK | SNRK_HUMAN | SNF-related serine/threonine-protein kinase |
| SNRNP200 | U520_HUMAN | U5 small nuclear ribonucleoprotein 200 kDa helicase |
| SNRNP40 | SNR40_HUMAN | U5 small nuclear ribonucleoprotein 40 kDa protein |
| SNRNP70 | RU17_HUMAN | U1 small nuclear ribonucleoprotein 70 kDa |
| SNRPB | RSMB_HUMAN | Small nuclear ribonucleoprotein-associated proteins B and B' |
| SNRPD1 | SMD1_HUMAN | Small nuclear ribonucleoprotein Sm D1 |
| SNRPD3 | SMD3_HUMAN | Small nuclear ribonucleoprotein Sm D3 |
| SNRPF | RUXF_HUMAN | Small nuclear ribonucleoprotein F |
| SNRPG | RUXG_HUMAN | Small nuclear ribonucleoprotein G |
| SNUPN | SPN1_HUMAN | Snurportin-1 |
| SNW1 | SNW1_HUMAN | SNW domain-containing protein 1 |
| SNX17 | SNX17_HUMAN | Sorting nexin-17 |
| SNX9 | SNX9_HUMAN | Sorting nexin-9 |
| SOCS2 | SOCS2_HUMAN | Suppressor of cytokine signaling 2 |
| SOD1 | SODC_HUMAN | Superoxide dismutase [Cu—Zn] |
| SOD2 | SODM_HUMAN | Superoxide dismutase [Mn], mitochondrial |
| SORBS3 | VINEX_HUMAN | Vinexin |
| SORCS2 | SORC2_HUMAN | VPS 10 domain-containing receptor SorCS2 |
| SORL1 | SORL_HUMAN | Sortilin-related receptor |
| SORT1 | SORT_HUMAN | Sortilin |
| S0S1 | SOS1_HUMAN | Son of sevenless homolog 1 |
| SP5 | SP5_HUMAN | Transcription factor Sp5 |
| SPDEF | SPDEF_HUMAN | SAM pointed domain-containing Ets transcription factor |
| SPEG | SPEG_HUMAN | Striated muscle preferentially expressed protein kinase |
| SPEN | MINT_HUMAN | Msx2-interacting protein |
| SPHK1 | SPHK1_HUMAN | Sphingosine kinase 1 |
| SPIN1 | SPIN1_HUMAN | Spindlin-1 |
| SPIN3 | SPIN3_HUMAN | Spindlin-3 |
| SPIN4 | SPIN4_HUMAN | Spindlin-4 |
| SPINK1 | ISK1_HUMAN | Serine protease inhibitor Kazal-type 1 |
| SPINK5 | ISK5_HUMAN | Hemofiltrate peptide HF7665 |
| SPINT2 | SPIT2_HUMAN | Kunitz-type protease inhibitor 2 |
| SPIRE1 | SPIR1_HUMAN | Protein spire homolog 1 |
| SPOP | SPOP_HUMAN | Speckle-type POZ protein |
| SPRED1 | SPRE1_HUMAN | Sprouty-related, EVH1 domain-containing protein 1 |
| SPRYD3 | SPRY3_HUMAN | SPRY domain-containing protein 3 |
| SPSB1 | SPSB1_HUMAN | SPRY domain-containing SOCS box protein 1 |
| SPSB2 | SPSB2_HUMAN | SPRY domain-containing SOCS box protein 2 |
| SPSB4 | SPSB4_HUMAN | SPRY domain-containing SOCS box protein 4 |
| SPTBN2 | SPTN2_HUMAN | Spectrin beta chain, non-ery throcy tic 2 |

TABLE 1-continued

| Target Protein Symbol | uniprot name | Target Protein name |
|---|---|---|
| SQLE | ERG1_HUMAN | Squalene monooxygenase |
| SQSTM1 | SQSTM_HUMAN | Sequestosome-1 |
| SRC | SRC_HUMAN | Proto-oncogene tyrosine-protein kinase Src |
| SREK1IP1 | SR1IP_HUMAN | Protein SREK1IP1 |
| SRF | SRF_HUMAN | Serum response factor |
| SRI | SORCN_HUMAN | Sorcin |
| SRM | SPEE_HUMAN | Spermidine synthase |
| SRP68 | SRP68_HUMAN | Signal recognition particle subunit SRP68 |
| SRP9 | SRP09_HUMAN | Signal recognition particle 9 kDa protein |
| SRPK1 | SRPK1_HUMAN | SRSF protein kinase 1 |
| SRPK2 | SRPK2_HUMAN | SRSF protein kinase 2 C-terminal |
| SRRT | SRRT_HUMAN | Serrate RNA effector molecule homolog |
| SRSF1 | SRSF1_HUMAN | Serine/arginine-rich splicing factor 1 |
| SRSF7 | SRSF7_HUMAN | Serine/arginine-rich splicing factor 7 |
| SRXN1 | SRXN1_HUMAN | Sulfiredoxin-1 |
| SSRP1 | SSRP1_HUMAN | FACT complex subunit SSRP1 |
| ST14 | ST14_HUMAN | Suppressor of tumorigenicity 14 protein |
| STAM2 | STAM2_HUMAN | Signal transducing adapter molecule 2 |
| STAR | STAR_HUMAN | Steroidogenic acute regulatory protein, mitochondrial |
| STARD13 | STA13_HUMAN | StAR-related lipid transfer protein 13 |
| STARD3 | STAR3_HUMAN | StAR-related lipid transfer protein 3 |
| STAT1 | STAT1_HUMAN | Signal transducer and activator of transcription 1-alpha/beta |
| STAT6 | STAT6_HUMAN | Signal transducer and activator of transcription 6 |
| STK10 | STK10_HUMAN | Serine/threonine-protein kinase 10 |
| STK11 | STK11_HUMAN | Serine/threonine-protein kinase STK11 |
| STK16 | STK16_HUMAN | Serine/threonine-protein kinase 16 |
| STK17B | ST17B_HUMAN | Serine/threonine-protein kinase 17B |
| STK24 | STK24_HUMAN | Serine/threonine-protein kinase 24 12 kDa subunit |
| STK25 | STK25_HUMAN | Serine/threonine-protein kinase 25 |
| STK26 | STK26_HUMAN | Serine/threonine-protein kinase 26 |
| STK3 | STK3_HUMAN | Serine/threonine-protein kinase 3 20 kDa subunit |
| STK32A | ST32A_HUMAN | Serine/threonine-protein kinase 32A |
| STK38 | STK38_HUMAN | Serine/threonine-protein kinase 38 |
| STK4 | STK4_HUMAN | Serine/threonine-protein kinase 4 18 kDa subunit |
| STMN4 | STMN4_HUMAN | Stathmin-4 |
| STN1 | STN1_HUMAN | CST complex subunit STN1 |
| STRADA | STRAA_HUMAN | STE20-related kinase adapter protein alpha |
| STXBP4 | STXB4_HUMAN | Syntaxin-binding protein 4 |
| SUB1 | TCP4_HUMAN | Activated RNA polymerase II transcriptional coactivator p15 |
| SUCLG1 | SUCA_HUMAN | Succinate--CoA ligase [ADP/GDP-forming] subunit alpha, mitochondrial |
| SUFU | SUFU_HUMAN | Suppressor of fused homolog |
| SUMF1 | SUMF1_HUMAN | Formylglycine-generating enzyme |
| SUMF2 | SUMF2_HUMAN | Inactive C-alpha-formylglycine-generating enzyme 2 |
| SUMO2 | SUMO2_HUMAN | Small ubiquitin-related modifier 2 |
| SUMO3 | SUMO3_HUMAN | Small ubiquitin-related modifier 3 |
| SUPT16H | SP16H_HUMAN | FACT complex subunit SPT16 |
| SUPT5H | SPT5H_HUMAN | Transcription elongation factor SPT5 |
| SUPT6H | SPT6H_HUMAN | Transcription elongation factor SPT6 |
| SUZ12 | SUZ12_HUMAN | Polycomb protein SUZ12 |
| SYK | KSYK_HUMAN | Tyrosine-protein kinase SYK |
| SYN3 | SYN3_HUMAN | Synapsin-3 |
| SYT1 | SYT1_HUMAN | Synaptotagmin-1 |
| SYT13 | SYT13_HUMAN | Sy naptotagmin-13 |
| SYT5 | SYT5_HUMAN | Synaptotagmin-5 |
| TAB1 | TAB1_HUMAN | TGF-beta-activated kinase 1 and MAP3K7-binding protein 1 |
| TAF1 | TAF1_HUMAN | Transcription initiation factor TFIID subunit 1 |
| TAF15 | RBP56_HUMAN | TATA-binding protein-associated factor 2N |
| TAF2 | TAF2_HUMAN | Transcription initiation factor TFIID subunit 2 |
| TAF3 | TAF3_HUMAN | Transcription initiation factor TFIID subunit 3 |
| TAF5 | TAF5_HUMAN | Transcription initiation factor TFIID subunit 5 |
| TAPBP | TPSN_HUMAN | Tapasin |
| TAPBPL | TPSNR_HUMAN | Tapasin-related protein |
| TARDBP | TADBP_HUMAN | TAR DNA-binding protein 43 |
| TARS | SYTC_HUMAN | Threonine--tRNA ligase, cytoplasmic |
| TASP1 | TASP1_HUMAN | Threonine aspartase subunit beta |
| TAT | ATTY_HUMAN | Tyrosine aminotransferase |
| TAX1BP1 | TAXB1_HUMAN | Tax1-binding protein 1 |
| TBK1 | TBK1_HUMAN | Serine/threonine-protein kinase TBK1 |
| TBL1XR1 | TBL1R_HUMAN | F-box-like/WD repeat-containing protein TBL1XR1 |
| TBP | TBP_HUMAN | TATA-box-binding protein |
| TBXA2R | TA2R_HUMAN | Thromboxane A2 receptor |

TABLE 1-continued

| Target Protein Symbol | uniprot name | Target Protein name |
|---|---|---|
| TCEA1 | TCEA1_HUMAN | Transcription elongation factor A protein 1 |
| TCEA2 | TCEA2_HUMAN | Transcription elongation factor A protein 2 |
| TCEA3 | TCEA3_HUMAN | Transcription elongation factor A protein 3 |
| TCERG1 | TCRG1_HUMAN | Transcription elongation regulator 1 |
| TCN2 | TCO2_HUMAN | Transcobalamin-2 |
| TDP1 | TYDP1_HUMAN | Tyrosyl-DNA phosphodiesterase 1 |
| TDRD1 | TDRD1_HUMAN | Tudor domain-containing protein 1 |
| TDRD3 | TDRD3_HUMAN | Tudor domain-containing protein 3 |
| TDRD7 | TDRD7_HUMAN | Tudor domain-containing protein 7 |
| TDRKH | TDRKH_HUMAN | Tudor and KH domain-containing protein |
| TEAD4 | TEAD4_HUMAN | Transcriptional enhancer factor TEF-3 |
| TEK | TIE2_HUMAN | Angiopoietin-1 receptor |
| TEN1 | TEN1L_HUMAN | CST complex subunit TEN1 |
| TENM2 | TEN2_HUMAN | Ten-2 intracellular domain |
| TET2 | TET2_HUMAN | Methylcytosine dioxygenase TET2 |
| TEX13A | TX13A_HUMAN | Testis-expressed protein 13A |
| TF | TRFE_HUMAN | Serotransferrin |
| TFPI | TFPI1_HUMAN | Tissue factor pathway inhibitor |
| TFRC | TFR1_HUMAN | Transferrin receptor protein 1, serum form |
| TGFBI | BGH3_HUMAN | Transforming growth factor-beta-induced protein ig-h3 |
| TGFBR1 | TGFR1_HUMAN | TGF-beta receptor type-1 |
| TGFBR2 | TGFR2_HUMAN | TGF-beta receptor type-2 |
| TGM2 | TGM2_HUMAN | Protein-glutamine gamma-glutamyltransferase 2 |
| TGM3 | TGM3_HUMAN | Protein-glutamine gamma-glutamyltransferase E 27 kDa non-catalytic chain |
| THAP1 | THAP1_HUMAN | THAP domain-containing protein 1 |
| THAP4 | THAP4_HUMAN | THAP domain-containing protein 4 |
| THBS1 | TSP1_HUMAN | Thrombospondin-1 |
| THBS2 | TSP2_HUMAN | Thrombospondin-2 |
| THOP1 | THOP1_HUMAN | Thimet oligopeptidase |
| THRA | THA_HUMAN | Thyroid hormone receptor alpha |
| THRB | THB_HUMAN | Thyroid hormone receptor beta |
| THTPA | THTPA_HUMAN | Thiamine-triphosphatase |
| TIA1 | TIA1_HUMAN | Nucleolysin TIA-1 isoform p40 |
| TIAL1 | TIAR_HUMAN | Nucleolysin TIAR |
| TIAM1 | TIAM1_HUMAN | T-lymphoma invasion and metastasis-inducing protein 1 |
| TIGIT | TIGIT_HUMAN | T-cell immuno receptor with Ig and ITIM domains |
| TIMP2 | TIMP2_HUMAN | Metalloproteinase inhibitor 2 |
| TJP1 | ZO1_HUMAN | Tight junction protein ZO-1 |
| TLE1 | TLE1_HUMAN | Transducin-like enhancer protein 1 |
| TLL1 | TLL1_HUMAN | Tolloid-like protein 1 |
| TLR1 | TLR1_HUMAN | Toll-like receptor 1 |
| TLR2 | TLR2_HUMAN | Toll-like receptor 2 |
| TLR4 | TLR4_HUMAN | Toll-like receptor 4 |
| TMPRSS11E | TM11E_HUMAN | Transmembrane protease serine 11E catalytic chain |
| TMSB4X | TYB4_HUMAN | Hematopoietic system regulatory peptide |
| TMX2 | TMX2_HUMAN | Thioredoxin-related transmembrane protein 2 |
| TNFAIP3 | TNAP3_HUMAN | A20p37 |
| TNFAIP6 | TSG6_HUMAN | Tumor necrosis factor-inducible gene 6 protein |
| TNFRSF10A | TR10A_HUMAN | Tumor necrosis factor receptor superfamily member 10A |
| TNFRSF21 | TNR21_HUMAN | Tumor necrosis factor receptor superfamily member 21 |
| TNFRSF6B | TNF6B_HUMAN | Tumor necrosis factor receptor superfamily member 6B |
| TNFRSF9 | TNR9_HUMAN | Tumor necrosis factor receptor superfamily member 9 |
| TNFSF12 | TNF12_HUMAN | Tumor necrosis factor ligand superfamily member 12, secreted form |
| TNFSF14 | TNF14_HUMAN | Tumor necrosis factor ligand superfamily member 14, soluble form |
| TNIK | TNIK_HUMAN | TRAF2 and NCK-interacting protein kinase |
| TNK2 | ACK1_HUMAN | Activated CDC42 kinase 1 |
| TNKS | TNKS1_HUMAN | Poly [ADP-ribose] polymerase tankyrase-1 |
| TNKS2 | TNKS2_HUMAN | Poly [ADP-ribose] polymerase tankyrase-2 |
| TNNI3K | TNI3K_HUMAN | Serine/threonine-protein kinase TNNI3K |
| TNS2 | TNS2_HUMAN | Tensin-2 |
| TOB1 | TOB1_HUMAN | Protein Tob1 |
| TONSL | TONSL_HUMAN | Tonsoku-like protein |
| TOP1 | TOP1_HUMAN | DNA topoisomerase 1 |
| TOP2A | TOP2A_HUMAN | DNA topoisomerase 2-alpha |
| TOP2B | TOP2B_HUMAN | DNA topoisomerase 2-beta |
| TOPBP1 | TOPB1_HUMAN | DNA topoisomerase 2-binding protein 1 |
| TP53 | P53_HUMAN | Cellular tumor antigen p53 |
| TP53BP1 | TP53B_HUMAN | TP53-binding protein 1 |

TABLE 1-continued

| Target Protein Symbol | uniprot name | Target Protein name |
|---|---|---|
| TP53BP2 | ASPP2_HUMAN | Apoptosis-stimulating of p53 protein 2 |
| TP63 | P63_HUMAN | Tumor protein 63 |
| TP73 | P73_HUMAN | Tumor protein p73 |
| TRAC | TRAC_HUMAN | T cell receptor alpha constant |
| TRAF2 | TRAF2_HUMAN | TNF receptor-associated factor 2 |
| TRAF3 | TRAF3_HUMAN | TNF receptor-associated factor 3 |
| TRAF4 | TRAF4_HUMAN | TNF receptor-associated factor 4 |
| TRAF6 | TRAF6_HUMAN | TNF receptor-associated factor 6 |
| TRAFD1 | TRAD1_HUMAN | TRAF-type zinc finger domain-containing protein 1 |
| TRAP1 | TRAP1_HUMAN | Heat shock protein 75 kDa, mitochondrial |
| TRAPPC4 | TPPC4_HUMAN | Trafficking protein particle complex subunit 4 |
| TRAV12-2 | TVAL2_HUMAN | T cell receptor alpha variable 12-2 |
| TRAV12-3 | TVAL3_HUMAN | T cell receptor alpha variable 12-3 |
| TRAV21 | TVA21_HUMAN | T cell receptor alpha variable 21 |
| TRAV22 | TVA22_HUMAN | T cell receptor alpha variable 22 |
| TRAV24 | TVA24_HUMAN | T cell receptor alpha variable 24 |
| TRAV29DV5 | TVA29_HUMAN | T cell receptor alpha variable 29/delta variable 5 |
| TRBC1 | TRBC1_HUMAN | T cell receptor beta constant 1 |
| TRBC2 | TRBC2_HUMAN | T cell receptor beta constant 2 |
| TRBV12-4 | TVBL4_HUMAN | T cell receptor beta variable 12-4 |
| TRBV19 | TVB19_HUMAN | T cell receptor beta variable 19 |
| TRBV5-1 | TVB51_HUMAN | T cell receptor beta variable 5-1 |
| TRBV6-5 | TVB65_HUMAN | T cell receptor beta variable 6-5 |
| TREM1 | TREM1_HUMAN | Triggering receptor expressed on myeloid cells 1 |
| TREM2 | TREM2_HUMAN | Triggering receptor expressed on myeloid cells 2 |
| TREML1 | TRML1_HUMAN | Trem-like transcript 1 protein |
| TRERF1 | TREF1_HUMAN | Transcriptional-regulating factor 1 |
| TRGC2 | TRGC2_HUMAN | T cell receptor gamma constant 2 |
| TRIB1 | TRIB1_HUMAN | Tribbles homolog 1 |
| TRIM10 | TRI10_HUMAN | Tripartite motif-containing protein 10 |
| TRIM14 | TRI14_HUMAN | Tripartite motif-containing protein 14 |
| TRIM15 | TRI15_HUMAN | Tripartite motif-containing protein 15 |
| TRIM21 | RO52_HUMAN | E3 ubiquitin-protein ligase TRIM21 |
| TRIM22 | TRI22_HUMAN | E3 ubiquitin-protein ligase TRIM22 |
| TRIM23 | TRI23_HUMAN | E3 ubiquitin-protein ligase TRIM23 |
| TRIM25 | TRI25_HUMAN | E3 ubiquitin/ISG15 ligase TRIM25 |
| TRIM29 | TRI29_HUMAN | Tripartite motif-containing protein 29 |
| TRIM3 | TRIM3_HUMAN | Tripartite motif-containing protein 3 |
| TRIM31 | TRI31_HUMAN | E3 ubiquitin-protein ligase TRIM31 |
| TRIM32 | TRI32_HUMAN | E3 ubiquitin-protein ligase TRIM32 |
| TRIM33 | TRI33_HUMAN | E3 ubiquitin-protein ligase TRIM33 |
| TRIM34 | TRI34_HUMAN | Tripartite motif-containing protein 34 |
| TRIM38 | TRI38_HUMAN | E3 ubiquitin-protein ligase TRIM38 |
| TRIM39 | TRI39_HUMAN | E3 ubiquitin-protein ligase TRIM39 |
| TRIM44 | TRI44_HUMAN | Tripartite motif-containing protein 44 |
| TRIM5 | TRIM5_HUMAN | Tripartite motif-containing protein 5 |
| TRIM50 | TRI50_HUMAN | E3 ubiquitin-protein ligase TRIM50 |
| TRIM58 | TRI58_HUMAN | E3 ubiquitin-protein ligase TRIM58 |
| TRIM6 | TRIM6_HUMAN | Tripartite motif-containing protein 6 |
| TRIM65 | TRI65_HUMAN | Tripartite motif-containing protein 65 |
| TRIM67 | TRI67_HUMAN | Tripartite motif-containing protein 67 |
| TRIM68 | TRI68_HUMAN | E3 ubiquitin-protein ligase TRIM68 |
| TRIM7 | TRIM7_HUMAN | E3 ubiquitin-protein ligase TRIM7 |
| TRIM72 | TRI72_HUMAN | Tripartite motif-containing protein 72 |
| TRIM73 | TRI73_HUMAN | Tripartite motif-containing protein 73 |
| TRIM74 | TRI74_HUMAN | Tripartite motif-containing protein 74 |
| TRIM9 | TRIM9_HUMAN | E3 ubiquitin-protein ligase TRIM9 |
| TRIO | TRIO_HUMAN | Triple functional domain protein |
| TRIP10 | CIP4_HUMAN | Cdc42-interacting protein 4 |
| TRIP6 | TRIP6_HUMAN | Thyroid receptor-interacting protein 6 |
| TRMT112 | TR112_HUMAN | Multifunctional methyltransferase subunit TRM112-like protein |
| TRMT61B | TR61B_HUMAN | tRNA (adenine(58)-N(1))-methyltransferase, mitochondrial |
| TRNAU1AP | TSAP1_HUMAN | tRNA selenocysteine 1-associated protein 1 |
| TRNT1 | TRNT1_HUMAN | CCA tRNA nucleotidyltransferase 1, mitochondrial |
| TRPA1 | TRPA1_HUMAN | Transient receptor potential cation channel subfamily A member 1 |
| TRPC3 | TRPC3_HUMAN | Short transient receptor potential channel 3 |
| TRPC6 | TRPC6_HUMAN | Short transient receptor potential channel 6 |
| TRPM2 | TRPM2_HUMAN | Transient receptor potential cation channel subfamily M member 2 |
| TRPM4 | TRPM4_HUMAN | Transient receptor potential cation channel subfamily M member 4 |

TABLE 1-continued

| Target Protein Symbol | uniprot name | Target Protein name |
|---|---|---|
| TRPS1 | TRPS1_HUMAN | Zinc finger transcription factor Trps1 |
| TRPV2 | TRPV2_HUMAN | Transient receptor potential cation channel subfamily V member 2 |
| TRPV3 | TRPV3_HUMAN | Transient receptor potential cation channel subfamily V member 3 |
| TRPV4 | TRPV4_HUMAN | Transient receptor potential cation channel subfamily V member 4 |
| TRPV6 | TRPV6_HUMAN | Transient receptor potential cation channel subfamily V member 6 |
| TSG101 | TS101_HUMAN | Tumor susceptibility gene 101 protein |
| TSHZ1 | TSH1_HUMAN | Teashirt homolog 1 |
| TSHZ2 | TSH2_HUMAN | Teashirt homolog 2 |
| TSHZ3 | TSH3_HUMAN | Teashirt homolog 3 |
| TSR1 | TSR1_HUMAN | Pre-rRNA-processing protein TSR1 homolog |
| TTBK1 | TTBK1_HUMAN | Tau-tubulin kinase 1 |
| TTN | TITIN_HUMAN | Titin |
| TTR | TTHY_HUMAN | Transthyretin |
| TUB | TUB_HUMAN | Tubby protein homolog |
| TUBA1B | TBA1B_HUMAN | Detyrosinated tubulin alpha-1B chain |
| TUBGCP4 | GCP4_HUMAN | Gamma-tubulin complex component 4 |
| TUFM | EFTU_HUMAN | Elongation factor Tu, mitochondrial |
| TULP1 | TULP1_HUMAN | Tubby-related protein 1 |
| TUT1 | STPAP_HUMAN | Speckle targeted PIP5K1A-regulated poly(A) polymerase |
| TUT4 | TUT4_HUMAN | Terminal uridylyltransferase 4 |
| TUT7 | TUT7_HUMAN | Terminal uridylyltransferase 7 |
| TXK | TXK_HUMAN | Tyrosine-protein kinase TXK |
| TXNDC12 | TXD12_HUMAN | Thioredoxin domain-containing protein 12 |
| TXNDC17 | TXD17_HUMAN | Thioredoxin domain-containing protein 17 |
| TXNL1 | TXNL1_HUMAN | Thioredoxin-like protein 1 |
| TXNRD1 | TRXR1_HUMAN | Thioredoxin reductase 1, cytoplasmic |
| TYK2 | TYK2_HUMAN | Non-receptor tyrosine-protein kinase TYK2 |
| TYMP | TYPH_HUMAN | Thymidine phosphorylase |
| TYMS | TYSY_HUMAN | Thymidylate synthase |
| TYRO3 | TYRO3_HUMAN | Tyrosine-protein kinase receptor TYRO3 |
| U2AF2 | U2AF2_HUMAN | Splicing factor U2AF 65 kDa subunit |
| UAP1 | UAP1_HUMAN | UDP-N-acetylglucosamine pyrophosphorylase |
| UBA2 | SAE2_HUMAN | SUMO-activating enzyme subunit 2 |
| UBA52 | RL40_HUMAN | 60S ribosomal protein L40 |
| UBASH3A | UBS3A_HUMAN | Ubiquitin-associated and SH3 domain-containing protein A |
| UBASH3B | UBS3B_HUMAN | Ubiquitin-associated and SH3 domain-containing protein B |
| UBB | UBB_HUMAN | Ubiquitin |
| UBC | UBC_HUMAN | Ubiquitin |
| UBE2H | UBE2H_HUMAN | Ubiquitin-conjugating enzyme E2 H |
| UBE2K | UBE2K_HUMAN | Ubiquitin-conjugating enzyme E2 K |
| UBE2U | UBE2U_HUMAN | Ubiquitin-conjugating enzyme E2 U |
| UBE2V1 | UB2V1_HUMAN | Ubiquitin-conjugating enzyme E2 variant 1 |
| UBE2V2 | UB2V2_HUMAN | Ubiquitin-conjugating enzyme E2 variant 2 |
| UBE3A | UBE3A_HUMAN | Ubiquitin-protein ligase E3A |
| UBE4B | UBE4B_HUMAN | Ubiquitin conjugation factor E4 B |
| UBL3 | UBL3_HUMAN | Ubiquitin-like protein 3 |
| UBL5 | UBL5_HUMAN | Ubiquitin-like protein 5 |
| UBR3 | UBR3_HUMAN | E3 ubiquitin-protein ligase UBR3 |
| UBR5 | UBR5_HUMAN | E3 ubiquitin-protein ligase UBR5 |
| UBXN4 | UBXN4_HUMAN | UBX domain-containing protein 4 |
| UBXN7 | UBXN7_HUMAN | UBX domain-containing protein 7 |
| UFM1 | UFM1_HUMAN | Ubiquitin-fold modifier 1 |
| UGP2 | UGPA_HUMAN | UTP-glucose-1-phosphate uridylyltransferase |
| UHRF1 | UHRF1_HUMAN | E3 ubiquitin-protein ligase UHRF1 |
| UHRF2 | UHRF2_HUMAN | E3 ubiquitin-protein ligase UHRF2 |
| ULBP3 | ULBP3_HUMAN | UL16-binding protein 3 |
| UMPS | UMPS_HUMAN | Orotidine 5'-phosphate decarboxylase |
| UNC119 | U119A_HUMAN | Protein unc-119 homolog A |
| UNC13A | UN13A_HUMAN | Protein unc-13 homolog A |
| UNC13B | UN13B_HUMAN | Protein unc-13 homolog B |
| UNC13C | UN13C_HUMAN | Protein unc-13 homolog C |
| UNC5A | UNC5A_HUMAN | Netrin receptor UNC5A |
| UPB1 | BUP1_HUMAN | Beta-ureidopropionase |
| UPF1 | RENT1_HUMAN | Regulator of nonsense transcripts 1 |
| UPF3A | REN3A_HUMAN | Regulator of nonsense transcripts 3A |
| UPF3B | REN3B_HUMAN | Regulator of nonsense transcripts 3B |
| UQCRC1 | QCR1_HUMAN | Cytochrome b-c1 complex subunit 1, mitochondrial |
| UQCRC2 | QCR2_HUMAN | Cytochrome b-c1 complex subunit 2, mitochondrial |
| UQCRFS1 | UCRI_HUMAN | Cytochrome b-c1 complex subunit 9 |

TABLE 1-continued

| Target Protein Symbol | uniprot name | Target Protein name |
|---|---|---|
| UROD | DCUP_HUMAN | Uroporphyrinogen decarboxylase |
| USP13 | UBP13_HUMAN | Ubiquitin carboxyl-terminal hydrolase 13 |
| USP14 | UBP14_HUMAN | Ubiquitin carboxyl-terminal hydrolase 14 |
| USP15 | UBP15_HUMAN | Ubiquitin carboxyl-terminal hydrolase 15 |
| USP16 | UBP16_HUMAN | Ubiquitin carboxyl-terminal hydrolase 16 |
| USP2 | UBP2_HUMAN | Ubiquitin carboxyl-terminal hydrolase 2 |
| USP20 | UBP20_HUMAN | Ubiquitin carboxyl-terminal hydrolase 20 |
| USP21 | UBP21_HUMAN | Ubiquitin carboxyl-terminal hydrolase 21 |
| USP22 | UBP22_HUMAN | Ubiquitin carboxyl-terminal hydrolase 22 |
| USP25 | UBP25_HUMAN | Ubiquitin carboxyl-terminal hydrolase 25 |
| USP37 | UBP37_HUMAN | Ubiquitin carboxyl-terminal hydrolase 37 |
| USP39 | SNUT2_HUMAN | U4/U6.U5 tri-snRNP-associated protein 2 |
| USP4 | UBP4_HUMAN | Ubiquitin carboxyl-terminal hydrolase 4 |
| USP44 | UBP44_HUMAN | Ubiquitin carboxyl-terminal hydrolase 44 |
| USP45 | UBP45_HUMAN | Ubiquitin carboxyl-terminal hydrolase 45 |
| USP49 | UBP49_HUMAN | Ubiquitin carboxyl-terminal hydrolase 49 |
| USP5 | UBP5_HUMAN | Ubiquitin carboxyl-terminal hydrolase 5 |
| USP7 | UBP7_HUMAN | Ubiquitin carboxyl-terminal hydrolase 7 |
| VAV1 | VAV_HUMAN | Proto-oncogene vav |
| VAV2 | VAV2_HUMAN | Guanine nucleotide exchange factor VAV2 |
| VAV3 | VAV3_HUMAN | Guanine nucleotide exchange factor VAV3 |
| VCPKMT | MT21D_HUMAN | Protein-lysine methyltransferase METTL21D |
| VDAC1 | VDAC1_HUMAN | Voltage-dependent anion-selective channel protein 1 |
| VDR | VDR_HUMAN | Vitamin D3 receptor |
| VEGFA | VEGFA_HUMAN | Vascular endothelial growth factor A |
| VEZF1 | VEZF1_HUMAN | Vascular endothelial zinc finger 1 |
| VHL | VHL_HUMAN | von Hippel-Lindau disease tumor suppressor |
| VLDLR | VLDLR_HUMAN | Very low-density lipoprotein receptor |
| VNN1 | VNN1_HUMAN | Pantetheinase |
| VPS11 | VPS11_HUMAN | Vacuolar protein sorting-associated protein 11 homolog |
| VPS25 | VPS25_HUMAN | Vacuolar protein-sorting-associated protein 25 |
| VPS26A | VP26A_HUMAN | Vacuolar protein sorting-associated protein 26A |
| VPS36 | VPS36_HUMAN | Vacuolar protein-sorting-associated protein 36 |
| VRK1 | VRK1_HUMAN | Serine/threonine-protein kinase VRK1 |
| VRK2 | VRK2_HUMAN | Serine/threonine-protein kinase VRK2 |
| VRK3 | VRK3_HUMAN | Inactive serine/threonine-protein kinase VRK3 |
| VSIG4 | VSIG4_HUMAN | V-set and immunoglobulin domain-containing protein 4 |
| VTCN1 | VTCN1_HUMAN | V-set domain-containing T-cell activation inhibitor 1 |
| VWF | VWF_HUMAN | von Willebrand antigen 2 |
| WAS | WASP_HUMAN | Wiskott-Aldrich syndrome protein |
| WBP4 | WBP4_HUMAN | WW domain-binding protein 4 |
| WDFY1 | WDFY1_HUMAN | WD repeat and FYVE domain-containing protein 1 |
| WDFY2 | WDFY2_HUMAN | WD repeat and FYVE domain-containing protein 2 |
| WDFY3 | WDFY3_HUMAN | WD repeat and FYVE domain-containing protein 3 |
| WDHD1 | WDHD1_HUMAN | WD repeat and HMG-box DNA-binding protein 1 |
| WDR12 | WDR12_HUMAN | Ribosome biogenesis protein WDR12 |
| WDR20 | WDR20_HUMAN | WD repeat-containing protein 20 |
| WDR33 | WDR33_HUMAN | pre-mRNA 3' end processing protein WDR33 |
| WDR45B | WIPI3_HUMAN | WD repeat domain phosphoinositide-interacting protein 3 |
| WDR48 | WDR48_HUMAN | WD repeat-containing protein 48 |
| WDR5 | WDR5_HUMAN | WD repeat-containing protein 5 |
| WDR61 | WDR61_HUMAN | WD repeat-containing protein 61, N-terminally processed |
| WDR77 | MEP50_HUMAN | Methylosome protein 50 |
| WDR92 | WDR92_HUMAN | WD repeat-containing protein 92 |
| WEE1 | WEE1_HUMAN | Wee1-like protein kinase |
| WEE2 | WEE2_HUMAN | Wee1-like protein kinase 2 |
| WIF1 | WIF1_HUMAN | Wnt inhibitory factor 1 |
| WIZ | WIZ_HUMAN | Protein Wiz |
| WNK1 | WNK1_HUMAN | Serine/threonine-protein kinase WNK1 |
| WNK3 | WNK3_HUMAN | Serine/threonine-protein kinase WNK3 |
| WRNIP1 | WRIP1_HUMAN | ATPase WRNIP1 |
| WWOX | WWOX_HUMAN | WW domain-containing oxidoreductase |
| WWP2 | WWP2_HUMAN | NEDD4-like E3 ubiquitin-protein ligase WWP2 |
| XAF1 | XAF1_HUMAN | XIAP-associated factor 1 |
| XCL1 | XCL1_HUMAN | Lymphotactin |
| XDH | XDH_HUMAN | Xanthine oxidase |
| XIAP | XIAP_HUMAN | E3 ubiquitin-protein ligase XIAP |
| XPA | XPA_HUMAN | DNA repair protein complementing XP-A cells |
| XPO1 | XPO1_HUMAN | Exportin-1 |
| XPO5 | XPO5_HUMAN | Exportin-5 |
| XRCC6 | XRCC6_HUMAN | X-ray repair cross-complementing protein 6 |
| YAP1 | YAP1_HUMAN | Transcriptional coactivator YAP1 |

TABLE 1-continued

| Target Protein Symbol | uniprot name | Target Protein name |
|---|---|---|
| YBX1 | YBOX1_HUMAN | Nuclease-sensitive element-binding protein 1 |
| YEATS4 | YETS4_HUMAN | YEATS domain-containing protein 4 |
| YES1 | YES_HUMAN | Tyrosine-protein kinase Yes |
| YTHDC1 | YTDC1_HUMAN | YTH domain-containing protein 1 |
| YTHDC2 | YTDC2_HUMAN | 3'-5' RNA helicase YTHDC2 |
| YTHDF1 | YTHD1_HUMAN | YTH domain-containing family protein 1 |
| YTHDF2 | YTHD2_HUMAN | YTH domain-containing family protein 2 |
| YY1 | TYY1_HUMAN | Transcriptional repressor protein YY1 |
| YY2 | TYY2_HUMAN | Transcription factor YY2 |
| ZAP70 | ZAP70_HUMAN | Tyrosine-protein kinase ZAP-70 |
| ZBBX | ZBBX_HUMAN | Zinc finger B-box domain-containing protein 1 |
| ZBED2 | ZBED2_HUMAN | Zinc finger BED domain-containing protein 2 |
| ZBED3 | ZBED3_HUMAN | Zinc finger BED domain-containing protein 3 |
| ZBED4 | ZBED4_HUMAN | Zinc finger BED domain-containing protein 4 |
| ZBTB1 | ZBTB1_HUMAN | Zinc finger and BTB domain-containing protein 1 |
| ZBTB10 | ZBT10_HUMAN | Zinc finger and BTB domain-containing protein 10 |
| ZBTB11 | ZBT11_HUMAN | Zinc finger and BTB domain-containing protein 11 |
| ZBTB12 | ZBT12_HUMAN | Zinc finger and BTB domain-containing protein 12 |
| ZBTB14 | ZBT14_HUMAN | Zinc finger and BTB domain-containing protein 14 |
| ZBTB16 | ZBT16_HUMAN | Zinc finger and BTB domain-containing protein 16 |
| ZBTB17 | ZBT17_HUMAN | Zinc finger and BTB domain-containing protein 17 |
| ZBTB18 | ZBT18_HUMAN | Zinc finger and BTB domain-containing protein 18 |
| ZBTB2 | ZBTB2_HUMAN | Zinc finger and BTB domain-containing protein 2 |
| ZBTB21 | ZBT21_HUMAN | Zinc finger and BTB domain-containing protein 21 |
| ZBTB24 | ZBT24_HUMAN | Zinc finger and BTB domain-containing protein 24 |
| ZBTB25 | ZBT25_HUMAN | Zinc finger and BTB domain-containing protein 25 |
| ZBTB26 | ZBT26_HUMAN | Zinc finger and BTB domain-containing protein 26 |
| ZBTB3 | ZBTB3_HUMAN | Zinc finger and BTB domain-containing protein 3 |
| ZBTB32 | ZBT32_HUMAN | Zinc finger and BTB domain-containing protein 32 |
| ZBTB33 | KAISO_HUMAN | Transcriptional regulator Kaiso |
| ZBTB34 | ZBT34_HUMAN | Zinc finger and BTB domain-containing protein 34 |
| ZBTB37 | ZBT37_HUMAN | Zinc finger and BTB domain-containing protein 37 |
| ZBTB38 | ZBT38_HUMAN | Zinc finger and BTB domain-containing protein 38 |
| ZBTB39 | ZBT39_HUMAN | Zinc finger and BTB domain-containing protein 39 |
| ZBTB4 | ZBTB4_HUMAN | Zinc finger and BTB domain-containing protein 4 |
| ZBTB40 | ZBT40_HUMAN | Zinc finger and BTB domain-containing protein 40 |
| ZBTB41 | ZBT41_HUMAN | Zinc finger and BTB domain-containing protein 41 |
| ZBTB42 | ZBT42_HUMAN | Zinc finger and BTB domain-containing protein 42 |
| ZBTB43 | ZBT43_HUMAN | Zinc finger and BTB domain-containing protein 43 |
| ZBTB44 | ZBT44_HUMAN | Zinc finger and BTB domain-containing protein 44 |
| ZBTB45 | ZBT45_HUMAN | Zinc finger and BTB domain-containing protein 45 |
| ZBTB46 | ZBT46_HUMAN | Zinc finger and BTB domain-containing protein 46 |
| ZBTB47 | ZBT47_HUMAN | Zinc finger and BTB domain-containing protein 47 |
| ZBTB48 | TZAP_HUMAN | Telomere zinc finger-associated protein |
| ZBTB49 | ZBT49_HUMAN | Zinc finger and BTB domain-containing protein 49 |
| ZBTB5 | ZBTB5_HUMAN | Zinc finger and BTB domain-containing protein 5 |
| ZBTB6 | ZBTB6_HUMAN | Zinc finger and BTB domain-containing protein 6 |
| ZBTB7A | ZBT7A_HUMAN | Zinc finger and BTB domain-containing protein 7A |
| ZBTB7B | ZBT7B_HUMAN | Zinc finger and BTB domain-containing protein 7B |
| ZBTB8A | ZBT8A_HUMAN | Zinc finger and BTB domain-containing protein 8A |
| ZBTB8B | ZBT8B_HUMAN | Zinc finger and BTB domain-containing protein 8B |
| ZBTB9 | ZBTB9_HUMAN | Zinc finger and BTB domain-containing protein 9 |
| ZC2HC1A | ZC21A_HUMAN | Zinc finger C2HC domain-containing protein 1A |
| ZC2HC1B | ZC21B_HUMAN | Zinc finger C2HC domain-containing protein 1B |
| ZC2HC1C | ZC21C_HUMAN | Zinc finger C2HC domain-containing protein 1C |
| ZC3H7A | Z3H7A_HUMAN | Zinc finger CCCH domain-containing protein 7A |
| ZC3H7B | Z3H7B_HUMAN | Zinc finger CCCH domain-containing protein 7B |
| ZCCHC12 | ZCH12_HUMAN | Zinc finger CCHC domain-containing protein 12 |
| ZCCHC13 | ZCH13_HUMAN | Zinc finger CCHC domain-containing protein 13 |
| ZCCHC14 | ZCH14_HUMAN | Zinc finger CCHC domain-containing protein 14 |
| ZCCHC17 | NO40_HUMAN | Nucleolar protein of 40 kDa |
| ZCCHC18 | ZCC18_HUMAN | Zinc finger CCHC domain-containing protein 18 |
| ZCCHC2 | ZCHC2_HUMAN | Zinc finger CCHC domain-containing protein 2 |
| ZCCHC23 | ZCH23_HUMAN | Zinc finger CCHC domain-containing protein 23 |
| ZCCHC3 | ZCHC3_HUMAN | Zinc finger CCHC domain-containing protein 3 |
| ZCCHC4 | ZCHC4_HUMAN | rRNA N6-adenosine-methyltransferase ZCCHC4 |
| ZCCHC8 | ZCHC8_HUMAN | Zinc finger CCHC domain-containing protein 8 |
| ZCCHC9 | ZCHC9_HUMAN | Zinc finger CCHC domain-containing protein 9 |
| ZCRB1 | ZCRB1_HUMAN | Zinc finger CCHC-type and RNA-binding motif-containing protein 1 |
| ZDHHC17 | ZDH17_HUMAN | Palmitoyltransferase ZDHHC17 |
| ZDHHC20 | ZDH20_HUMAN | Palmitoyltransferase ZDHHC20 |
| ZEB1 | ZEB1_HUMAN | Zinc finger E-box-binding homeobox 1 |
| ZEB2 | ZEB2_HUMAN | Zinc finger E-box-binding homeobox 2 |

TABLE 1-continued

| Target Protein Symbol | uniprot name | Target Protein name |
|---|---|---|
| ZFAND4 | ZFAN4_HUMAN | AN1-type zinc finger protein 4 |
| ZFAT | ZFAT_HUMAN | Zinc finger protein ZFAT |
| ZFHX2 | ZFHX2_HUMAN | Zinc finger homeobox protein 2 |
| ZFHX3 | ZFHX3_HUMAN | Zinc finger homeobox protein 3 |
| ZFHX4 | ZFHX4_HUMAN | Zinc finger homeobox protein 4 |
| ZFP1 | ZFP1_HUMAN | Zinc finger protein 1 homolog |
| ZFP14 | ZFP14_HUMAN | Zinc finger protein 14 homolog |
| ZFP2 | ZFP2_HUMAN | Zinc finger protein 2 homolog |
| ZFP28 | ZFP28_HUMAN | Zinc finger protein 28 homolog |
| ZFP3 | ZFP3_HUMAN | Zinc finger protein 3 homolog |
| ZFP30 | ZFP30_HUMAN | Zinc finger protein 30 homolog |
| ZFP37 | ZFP37_HUMAN | Zinc finger protein 37 homolog |
| ZFP41 | ZFP41_HUMAN | Zinc finger protein 41 homolog |
| ZFP42 | ZFP42_HUMAN | Zinc finger protein 42 homolog |
| ZFP57 | ZFP57_HUMAN | Zinc finger protein 57 homolog |
| ZFP62 | ZFP62_HUMAN | Zinc finger protein 62 homolog |
| ZFP64 | ZF64B_HUMAN | Zinc finger protein 64 |
| ZFP69 | ZFP69_HUMAN | Zinc finger protein 69 homolog |
| ZFP69B | ZF69B_HUMAN | Zinc finger protein 69 homolog B |
| ZFP82 | ZFP82_HUMAN | Zinc finger protein 82 homolog |
| ZFP90 | ZFP90_HUMAN | Zinc finger protein 90 homolog |
| ZFP91 | ZFP91_HUMAN | E3 ubiquitin-protein ligase ZFP91 |
| ZFP92 | ZFP92_HUMAN | Zinc finger protein 92 homolog |
| ZFPM1 | FOG1_HUMAN | Zinc finger protein ZFPM1 |
| ZFPM2 | FOG2_HUMAN | Zinc finger protein ZFPM2 |
| ZFX | ZFX_HUMAN | Zinc finger X-chromosomal protein |
| ZFY | ZFY_HUMAN | Zinc finger Y-chromosomal protein |
| ZFYVE1 | ZFYV1_HUMAN | Zinc finger FYVE domain-containing protein 1 |
| ZFYVE16 | ZFY16_HUMAN | Zinc finger FYVE domain-containing protein 16 |
| ZFYVE19 | ANCHR_HUMAN | Abscission/NoCut checkpoint regulator |
| ZFYVE21 | ZFY21_HUMAN | Zinc finger FYVE domain-containing protein 21 |
| ZFYVE26 | ZFY26_HUMAN | Zinc finger FYVE domain-containing protein 26 |
| ZFYVE27 | ZFY27_HUMAN | Protrudin |
| ZFYVE28 | LST2_HUMAN | Lateral signaling target protein 2 homolog |
| ZFYVE9 | ZFYV9_HUMAN | Zinc finger FYVE domain-containing protein 9 |
| ZG16 | ZG16_HUMAN | Zymogen granule membrane protein 16 |
| ZG16B | ZG16B_HUMAN | Zymogen granule protein 16 homolog B |
| ZIC1 | ZIC1_HUMAN | Zinc finger protein ZIC 1 |
| ZIC2 | ZIC2_HUMAN | Zinc finger protein ZIC 2 |
| ZIC5 | ZIC5_HUMAN | Zinc finger protein ZIC 5 |
| ZIK1 | ZIK1_HUMAN | Zinc finger protein interacting with ribonucleoprotein K |
| ZIM2 | ZIM2_HUMAN | Zinc finger imprinted 2 |
| ZIM3 | ZIM3_HUMAN | Zinc finger imprinted 3 |
| ZKSCAN1 | ZKSC1_HUMAN | Zinc finger protein with KRAB and SCAN domains 1 |
| ZKSCAN2 | ZKSC2_HUMAN | Zinc finger protein with KRAB and SCAN domains 2 |
| ZKSCAN3 | ZKSC3_HUMAN | Zinc finger protein with KRAB and SCAN domains 3 |
| ZKSCAN4 | ZKSC4_HUMAN | Zinc finger protein with KRAB and SCAN domains 4 |
| ZKSCAN5 | ZKSC5_HUMAN | Zinc finger protein with KRAB and SCAN domains 5 |
| ZKSCAN7 | ZKSC7_HUMAN | Zinc finger protein with KRAB and SCAN domains 7 |
| ZKSCAN8 | ZKSC8_HUMAN | Zinc finger protein with KRAB and SCAN domains 8 |
| ZMAT1 | ZMAT1_HUMAN | Zinc finger matrin-type protein 1 |
| ZMYM1 | ZMYM1_HUMAN | Zinc finger MYM-type protein 1 |
| ZMYM2 | ZMYM2_HUMAN | Zinc finger MYM-type protein 2 |
| ZMYM3 | ZMYM3_HUMAN | Zinc finger MYM-type protein 3 |
| ZMYM4 | ZMYM4_HUMAN | Zinc finger MYM-type protein 4 |
| ZMYM5 | ZMYM5_HUMAN | Zinc finger MYM-type protein 5 |
| ZMYM6 | ZMYM6_HUMAN | Zinc finger MYM-type protein 6 |
| ZMYND11 | ZMY11_HUMAN | Zinc finger MYND domain-containing protein 11 |
| ZNF10 | ZNF10_HUMAN | Zinc finger protein 10 |
| ZNF100 | ZN100_HUMAN | Zinc finger protein 100 |
| ZNF101 | ZN101_HUMAN | Zinc finger protein 101 |
| ZNF106 | ZN106_HUMAN | Zinc finger protein 106 |
| ZNF107 | ZN107_HUMAN | Zinc finger protein 107 |
| ZNF112 | ZN112_HUMAN | Zinc finger protein 112 |
| ZNF114 | ZN114_HUMAN | Zinc finger protein 114 |
| ZNF117 | ZN117_HUMAN | Zinc finger protein 117 |
| ZNF12 | ZNF12_HUMAN | Zinc finger protein 12 |
| ZNF121 | ZN121_HUMAN | Zinc finger protein 121 |
| ZNF124 | ZN124_HUMAN | Zinc finger protein 124 |
| ZNF132 | ZN132_HUMAN | Zinc finger protein 132 |

TABLE 1-continued

| Target Protein Symbol | uniprot name | Target Protein name |
|---|---|---|
| ZNF133 | ZN133_HUMAN | Zinc finger protein 133 |
| ZNF134 | ZN134_HUMAN | Zinc finger protein 134 |
| ZNF135 | ZN135_HUMAN | Zinc finger protein 135 |
| ZNF136 | ZN136_HUMAN | Zinc finger protein 136 |
| ZNF137P | ZN137_HUMAN | Putative zinc finger protein 137 |
| ZNF138 | ZN138_HUMAN | Zinc finger protein 138 |
| ZNF14 | ZNF14_HUMAN | Zinc finger protein 14 |
| ZNF140 | ZN140_HUMAN | Zinc finger protein 140 |
| ZNF141 | ZN141_HUMAN | Zinc finger protein 141 |
| ZNF142 | ZN142_HUMAN | Zinc finger protein 142 |
| ZNF143 | ZN143_HUMAN | Zinc finger protein 143 |
| ZNF146 | OZF_HUMAN | Zinc finger protein OZF |
| ZNF148 | ZN148_HUMAN | Zinc finger protein 148 |
| ZNF154 | ZN154_HUMAN | Zinc finger protein 154 |
| ZNF155 | ZN155_HUMAN | Zinc finger protein 155 |
| ZNF157 | ZN157_HUMAN | Zinc finger protein 157 |
| ZNF16 | ZNF16_HUMAN | Zinc finger protein 16 |
| ZNF160 | ZN160_HUMAN | Zinc finger protein 160 |
| ZNF165 | ZN165_HUMAN | Zinc finger protein 165 |
| ZNF169 | ZN169_HUMAN | Zinc finger protein 169 |
| ZNF17 | ZNF17_HUMAN | Zinc finger protein 17 |
| ZNF174 | ZN174_HUMAN | Zinc finger protein 174 |
| ZNF175 | ZN175_HUMAN | Zinc finger protein 175 |
| ZNF177 | ZN177_HUMAN | Zinc finger protein 177 |
| ZNF18 | ZNF18_HUMAN | Zinc finger protein 18 |
| ZNF180 | ZN180_HUMAN | Zinc finger protein 180 |
| ZNF181 | ZN181_HUMAN | Zinc finger protein 181 |
| ZNF182 | ZN182_HUMAN | Zinc finger protein 182 |
| ZNF184 | ZN184_HUMAN | Zinc finger protein 184 |
| ZNF189 | ZN189_HUMAN | Zinc finger protein 189 |
| ZNF19 | ZNF19_HUMAN | Zinc finger protein 19 |
| ZNF195 | ZN195_HUMAN | Zinc finger protein 195 |
| ZNF197 | ZN197_HUMAN | Zinc finger protein 197 |
| ZNF2 | ZNF2_HUMAN | Zinc finger protein 2 |
| ZNF20 | ZNF20_HUMAN | Zinc finger protein 20 |
| ZNF200 | ZN200_HUMAN | Zinc finger protein 200 |
| ZNF202 | ZN202_HUMAN | Zinc finger protein 202 |
| ZNF205 | ZN205_HUMAN | Zinc finger protein 205 |
| ZNF207 | ZN207_HUMAN | BUB3-interacting and GLEBS motif-containing protein ZNF207 |
| ZNF208 | ZN208_HUMAN | Zinc finger protein 208 |
| ZNF211 | ZN211_HUMAN | Zinc finger protein 211 |
| ZNF212 | ZN212_HUMAN | Zinc finger protein 212 |
| ZNF213 | ZN213_HUMAN | Zinc finger protein 213 |
| ZNF214 | ZN214_HUMAN | Zinc finger protein 214 |
| ZNF215 | ZN215_HUMAN | Zinc finger protein 215 |
| ZNF217 | ZN217_HUMAN | Zinc finger protein 217 |
| ZNF219 | ZN219_HUMAN | Zinc finger protein 219 |
| ZNF22 | ZNF22_HUMAN | Zinc finger protein 22 |
| ZNF221 | ZN221_HUMAN | Zinc finger protein 221 |
| ZNF222 | ZN222_HUMAN | Zinc finger protein 222 |
| ZNF223 | ZN223_HUMAN | Zinc finger protein 223 |
| ZNF224 | ZN224_HUMAN | Zinc finger protein 224 |
| ZNF225 | ZN225_HUMAN | Zinc finger protein 225 |
| ZNF226 | ZN226_HUMAN | Zinc finger protein 226 |
| ZNF227 | ZN227_HUMAN | Zinc finger protein 227 |
| ZNF229 | ZN229_HUMAN | Zinc finger protein 229 |
| ZNF23 | ZNF23_HUMAN | Zinc finger protein 23 |
| ZNF230 | ZN230_HUMAN | Zinc finger protein 230 |
| ZNF232 | ZN232_HUMAN | Zinc finger protein 232 |
| ZNF233 | ZN233_HUMAN | Zinc finger protein 233 |
| ZNF234 | ZN234_HUMAN | Zinc finger protein 234 |
| ZNF235 | ZN235_HUMAN | Zinc finger protein 235 |
| ZNF236 | ZN236_HUMAN | Zinc finger protein 236 |
| ZNF239 | ZN239_HUMAN | Zinc finger protein 239 |
| ZNF24 | ZNF24_HUMAN | Zinc finger protein 24 |
| ZNF248 | ZN248_HUMAN | Zinc finger protein 248 |
| ZNF25 | ZNF25_HUMAN | Zinc finger protein 25 |
| ZNF250 | ZN250_HUMAN | Zinc finger protein 250 |
| ZNF251 | ZN251_HUMAN | Zinc finger protein 251 |
| ZNF253 | ZN253_HUMAN | Zinc finger protein 253 |
| ZNF254 | ZN254_HUMAN | Zinc finger protein 254 |
| ZNF256 | ZN256_HUMAN | Zinc finger protein 256 |
| ZNF257 | ZN257_HUMAN | Zinc finger protein 257 |
| ZNF26 | ZNF26_HUMAN | Zinc finger protein 26 |
| ZNF260 | ZN260_HUMAN | Zinc finger protein 260 |
| ZNF263 | ZN263_HUMAN | Zinc finger protein 263 |
| ZNF264 | ZN264_HUMAN | Zinc finger protein 264 |

TABLE 1-continued

| Target Protein Symbol | uniprot name | Target Protein name |
|---|---|---|
| ZNF266 | ZN266_HUMAN | Zinc finger protein 266 |
| ZNF267 | ZN267_HUMAN | Zinc finger protein 267 |
| ZNF268 | ZN268_HUMAN | Zinc finger protein 268 |
| ZNF273 | ZN273_HUMAN | Zinc finger protein 273 |
| ZNF274 | ZN274_HUMAN | Neurotrophin receptor-interacting factor homolog |
| ZNF275 | ZN275_HUMAN | Zinc finger protein 275 |
| ZNF276 | ZN276_HUMAN | Zinc finger protein 276 |
| ZNF28 | ZNF28_HUMAN | Zinc finger protein 28 |
| ZNF282 | ZN282_HUMAN | Zinc finger protein 282 |
| ZNF283 | ZN283_HUMAN | Zinc finger protein 283 |
| ZNF284 | ZN284_HUMAN | Zinc finger protein 284 |
| ZNF285 | ZN285_HUMAN | Zinc finger protein 285 |
| ZNF286A | Z286A_HUMAN | Zinc finger protein 286A |
| ZNF286B | Z286B_HUMAN | Putative zinc finger protein 286B |
| ZNF287 | ZN287_HUMAN | Zinc finger protein 287 |
| ZNF296 | ZN296_HUMAN | Zinc finger protein 296 |
| ZNF3 | ZNF3_HUMAN | Zinc finger protein 3 |
| ZNF30 | ZNF30_HUMAN | Zinc finger protein 30 |
| ZNF300 | ZN300_HUMAN | Zinc finger protein 300 |
| ZNF302 | ZN302_HUMAN | Zinc finger protein 302 |
| ZNF304 | ZN304_HUMAN | Zinc finger protein 304 |
| ZNF311 | ZN311_HUMAN | Zinc finger protein 311 |
| ZNF316 | ZN316_HUMAN | Zinc finger protein 316 |
| ZNF317 | ZN317_HUMAN | Zinc finger protein 317 |
| ZNF319 | ZN319_HUMAN | Zinc finger protein 319 |
| ZNF32 | ZNF32_HUMAN | Zinc finger protein 32 |
| ZNF320 | ZN320_HUMAN | Zinc finger protein 320 |
| ZNF322 | ZN322_HUMAN | Zinc finger protein 322 |
| ZNF324 | Z324A_HUMAN | Zinc finger protein 324A |
| ZNF324B | Z324B_HUMAN | Zinc finger protein 324B |
| ZNF329 | ZN329_HUMAN | Zinc finger protein 329 |
| ZNF330 | ZN330_HUMAN | Zinc finger protein 330 |
| ZNF331 | ZN331_HUMAN | Zinc finger protein 331 |
| ZNF333 | ZN333_HUMAN | Zinc finger protein 333 |
| ZNF334 | ZN334_HUMAN | Zinc finger protein 334 |
| ZNF335 | ZN335_HUMAN | Zinc finger protein 335 |
| ZNF337 | ZN337_HUMAN | Zinc finger protein 337 |
| ZNF33A | ZN33A_HUMAN | Zinc finger protein 33A |
| ZNF33B | ZN33B_HUMAN | Zinc finger protein 33B |
| ZNF34 | ZNF34_HUMAN | Zinc finger protein 34 |
| ZNF341 | ZN341_HUMAN | Zinc finger protein 341 |
| ZNF343 | ZN343_HUMAN | Zinc finger protein 343 |
| ZNF345 | ZN345_HUMAN | Zinc finger protein 345 |
| ZNF347 | ZN347_HUMAN | Zinc finger protein 347 |
| ZNF35 | ZNF35_HUMAN | Zinc finger protein 35 |
| ZNF350 | ZN350_HUMAN | Zinc finger protein 350 |
| ZNF354A | Z354A_HUMAN | Zinc finger protein 354A |
| ZNF354B | Z354B_HUMAN | Zinc finger protein 354B |
| ZNF354C | Z354C_HUMAN | Zinc finger protein 354C |
| ZNF355P | Z355P_HUMAN | Putative zinc finger protein 355P |
| ZNF358 | ZN358_HUMAN | Zinc finger protein 358 |
| ZNF362 | ZN362_HUMAN | Zinc finger protein 362 |
| ZNF365 | ZN365_HUMAN | Protein ZNF365 |
| ZNF366 | ZN366_HUMAN | Zinc finger protein 366 |
| ZNF37A | ZN37A_HUMAN | Zinc finger protein 37A |
| ZNF382 | ZN382_HUMAN | Zinc finger protein 382 |
| ZNF383 | ZN383_HUMAN | Zinc finger protein 383 |
| ZNF391 | ZN391_HUMAN | Zinc finger protein 391 |
| ZNF394 | ZN394_HUMAN | Zinc finger protein 394 |
| ZNF396 | ZN396_HUMAN | Zinc finger protein 396 |
| ZNF397 | ZN397_HUMAN | Zinc finger protein 397 |
| ZNF398 | ZN398_HUMAN | Zinc finger protein 398 |
| ZNF404 | ZN404_HUMAN | Zinc finger protein 404 |
| ZNF407 | ZN407_HUMAN | Zinc finger protein 407 |
| ZNF408 | ZN408_HUMAN | Zinc finger protein 408 |
| ZNF41 | ZNF41_HUMAN | Zinc finger protein 41 |
| ZNF410 | ZN410_HUMAN | Zinc finger protein 410 |
| ZNF415 | ZN415_HUMAN | Zinc finger protein 415 |
| ZNF416 | ZN416_HUMAN | Zinc finger protein 416 |
| ZNF417 | ZN417_HUMAN | Zinc finger protein 417 |
| ZNF418 | ZN418_HUMAN | Zinc finger protein 418 |
| ZNF419 | ZN419_HUMAN | Zinc finger protein 419 |
| ZNF420 | ZN420_HUMAN | Zinc finger protein 420 |
| ZNF423 | ZN423_HUMAN | Zinc finger protein 423 |
| ZNF425 | ZN425_HUMAN | Zinc finger protein 425 |
| ZNF426 | ZN426_HUMAN | Zinc finger protein 426 |
| ZNF429 | ZN429_HUMAN | Zinc finger protein 429 |
| ZNF43 | ZNF43_HUMAN | Zinc finger protein 43 |

TABLE 1-continued

| Target Protein Symbol | uniprot name | Target Protein name |
|---|---|---|
| ZNF430 | ZN430_HUMAN | Zinc finger protein 430 |
| ZNF431 | ZN431_HUMAN | Zinc finger protein 431 |
| ZNF432 | ZN432_HUMAN | Zinc finger protein 432 |
| ZNF433 | ZN433_HUMAN | Zinc finger protein 433 |
| ZNF436 | ZN436_HUMAN | Zinc finger protein 436 |
| ZNF439 | ZN439_HUMAN | Zinc finger protein 439 |
| ZNF44 | ZNF44_HUMAN | Zinc finger protein 44 |
| ZNF440 | ZN440_HUMAN | Zinc finger protein 440 |
| ZNF441 | ZN441_HUMAN | Zinc finger protein 441 |
| ZNF442 | ZN442_HUMAN | Zinc finger protein 442 |
| ZNF443 | ZN443_HUMAN | Zinc finger protein 443 |
| ZNF444 | ZN444_HUMAN | Zinc finger protein 444 |
| ZNF445 | ZN445_HUMAN | Zinc finger protein 445 |
| ZNF446 | ZN446_HUMAN | Zinc finger protein 446 |
| ZNF449 | ZN449_HUMAN | Zinc finger protein 449 |
| ZNF45 | ZNF45_HUMAN | Zinc finger protein 45 |
| ZNF451 | ZN451_HUMAN | E3 SUMO-protein ligase ZNF451 |
| ZNF454 | ZN454_HUMAN | Zinc finger protein 454 |
| ZNF460 | ZN460_HUMAN | Zinc finger protein 460 |
| ZNF461 | ZN461_HUMAN | Zinc finger protein 461 |
| ZNF462 | ZN462_HUMAN | Zinc finger protein 462 |
| ZNF467 | ZN467_HUMAN | Zinc finger protein 467 |
| ZNF468 | ZN468_HUMAN | Zinc finger protein 468 |
| ZNF469 | ZN469_HUMAN | Zinc finger protein 469 |
| ZNF470 | ZN470_HUMAN | Zinc finger protein 470 |
| ZNF471 | ZN471_HUMAN | Zinc finger protein 471 |
| ZNF473 | ZN473_HUMAN | Zinc finger protein 473 |
| ZNF474 | ZN474_HUMAN | Zinc finger protein 474 |
| ZNF479 | ZN479_HUMAN | Zinc finger protein 479 |
| ZNF48 | ZNF48_HUMAN | Zinc finger protein 48 |
| ZNF480 | ZN480_HUMAN | Zinc finger protein 480 |
| ZNF483 | ZN483_HUMAN | Zinc finger protein 483 |
| ZNF484 | ZN484_HUMAN | Zinc finger protein 484 |
| ZNF485 | ZN485_HUMAN | Zinc finger protein 485 |
| ZNF486 | ZN486_HUMAN | Zinc finger protein 486 |
| ZNF487 | ZN487_HUMAN | Putative zinc finger protein 487 |
| ZNF490 | ZN490_HUMAN | Zinc finger protein 490 |
| ZNF491 | ZN491_HUMAN | Zinc finger protein 491 |
| ZNF492 | ZN492_HUMAN | Zinc finger protein 492 |
| ZNF493 | ZN493_HUMAN | Zinc finger protein 493 |
| ZNF496 | ZN496_HUMAN | Zinc finger protein 496 |
| ZNF497 | ZN497_HUMAN | Zinc finger protein 497 |
| ZNF500 | ZN500_HUMAN | Zinc finger protein 500 |
| ZNF501 | ZN501_HUMAN | Zinc finger protein 501 |
| ZNF502 | ZN502_HUMAN | Zinc finger protein 502 |
| ZNF506 | ZN506_HUMAN | Zinc finger protein 506 |
| ZNF507 | ZN507_HUMAN | Zinc finger protein 507 |
| ZNF510 | ZN510_HUMAN | Zinc finger protein 510 |
| ZNF512 | ZN512_HUMAN | Zinc finger protein 512 |
| ZNF512B | Z512B_HUMAN | Zinc finger protein 512B |
| ZNF514 | ZN514_HUMAN | Zinc finger protein 514 |
| ZNF516 | ZN516_HUMAN | Zinc finger protein 516 |
| ZNF517 | ZN517_HUMAN | Zinc finger protein 517 |
| ZNF518A | Z518A_HUMAN | Zinc finger protein 518A |
| ZNF518B | Z518B_HUMAN | Zinc finger protein 518B |
| ZNF519 | ZN519_HUMAN | Zinc finger protein 519 |
| ZNF521 | ZN521_HUMAN | Zinc finger protein 521 |
| ZNF524 | ZN524_HUMAN | Zinc finger protein 524 |
| ZNF525 | ZN525_HUMAN | Zinc finger protein 525 |
| ZNF526 | ZN526_HUMAN | Zinc finger protein 526 |
| ZNF527 | ZN527_HUMAN | Zinc finger protein 527 |
| ZNF528 | ZN528_HUMAN | Zinc finger protein 528 |
| ZNF529 | ZN529_HUMAN | Zinc finger protein 529 |
| ZNF530 | ZN530_HUMAN | Zinc finger protein 530 |
| ZNF532 | ZN532_HUMAN | Zinc finger protein 532 |
| ZNF534 | ZN534_HUMAN | Zinc finger protein 534 |
| ZNF536 | ZN536_HUMAN | Zinc finger protein 536 |
| ZNF540 | ZN540_HUMAN | Zinc finger protein 540 |
| ZNF541 | ZN541_HUMAN | Zinc finger protein 541 |
| ZNF542P | ZN542_HUMAN | Putative zinc finger protein 542 |
| ZNF543 | ZN543_HUMAN | Zinc finger protein 543 |
| ZNF544 | ZN544_HUMAN | Zinc finger protein 544 |
| ZNF546 | ZN546_HUMAN | Zinc finger protein 546 |
| ZNF547 | ZN547_HUMAN | Zinc finger protein 547 |
| ZNF548 | ZN548_HUMAN | Zinc finger protein 548 |
| ZNF549 | ZN549_HUMAN | Zinc finger protein 549 |
| ZNF550 | ZN550_HUMAN | Zinc finger protein 550 |
| ZNF551 | ZN551_HUMAN | Zinc finger protein 551 |

TABLE 1-continued

| Target Protein Symbol | uniprot name | Target Protein name |
|---|---|---|
| ZNF552 | ZN552_HUMAN | Zinc finger protein 552 |
| ZNF554 | ZN554_HUMAN | Zinc finger protein 554 |
| ZNF555 | ZN555_HUMAN | Zinc finger protein 555 |
| ZNF556 | ZN556_HUMAN | Zinc finger protein 556 |
| ZNF557 | ZN557_HUMAN | Zinc finger protein 557 |
| ZNF558 | ZN558_HUMAN | Zinc finger protein 558 |
| ZNF559 | ZN559_HUMAN | Zinc finger protein 559 |
| ZNF56 | ZNF56_HUMAN | Putative zinc finger protein 56 |
| ZNF560 | ZN560_HUMAN | Zinc finger protein 560 |
| ZNF561 | ZN561_HUMAN | Zinc finger protein 561 |
| ZNF562 | ZN562_HUMAN | Zinc finger protein 562 |
| ZNF563 | ZN563_HUMAN | Zinc finger protein 563 |
| ZNF564 | ZN564_HUMAN | Zinc finger protein 564 |
| ZNF565 | ZN565_HUMAN | Zinc finger protein 565 |
| ZNF566 | ZN566_HUMAN | Zinc finger protein 566 |
| ZNF567 | ZN567_HUMAN | Zinc finger protein 567 |
| ZNF568 | ZN568_HUMAN | Zinc finger protein 568 |
| ZNF569 | ZN569_HUMAN | Zinc finger protein 569 |
| ZNF57 | ZNF57_HUMAN | Zinc finger protein 57 |
| ZNF570 | ZN570_HUMAN | Zinc finger protein 570 |
| ZNF571 | ZN571_HUMAN | Zinc finger protein 571 |
| ZNF572 | ZN572_HUMAN | Zinc finger protein 572 |
| ZNF573 | ZN573_HUMAN | Zinc finger protein 573 |
| ZNF574 | ZN574_HUMAN | Zinc finger protein 574 |
| ZNF575 | ZN575_HUMAN | Zinc finger protein 575 |
| ZNF576 | ZN576_HUMAN | Zinc finger protein 576 |
| ZNF577 | ZN577_HUMAN | Zinc finger protein 577 |
| ZNF578 | ZN578_HUMAN | Zinc finger protein 578 |
| ZNF579 | ZN579_HUMAN | Zinc finger protein 579 |
| ZNF580 | ZN580_HUMAN | Zinc finger protein 580 |
| ZNF581 | ZN581_HUMAN | Zinc finger protein 581 |
| ZNF582 | ZN582_HUMAN | Zinc finger protein 582 |
| ZNF583 | ZN583_HUMAN | Zinc finger protein 583 |
| ZNF584 | ZN584_HUMAN | Zinc finger protein 584 |
| ZNF585A | Z585A_HUMAN | Zinc finger protein 585A |
| ZNF585B | Z585B_HUMAN | Zinc finger protein 585B |
| ZNF586 | ZN586_HUMAN | Zinc finger protein 586 |
| ZNF587 | ZN587_HUMAN | Zinc finger protein 587 |
| ZNF587B | Z587B_HUMAN | Zinc finger protein 587B |
| ZNF589 | ZN589_HUMAN | Zinc finger protein 589 |
| ZNF592 | ZN592_HUMAN | Zinc finger protein 592 |
| ZNF594 | ZN594_HUMAN | Zinc finger protein 594 |
| ZNF595 | ZN595_HUMAN | Zinc finger protein 595 |
| ZNF596 | ZN596_HUMAN | Zinc finger protein 596 |
| ZNF597 | ZN597_HUMAN | Zinc finger protein 597 |
| ZNF599 | ZN599_HUMAN | Zinc finger protein 599 |
| ZNF600 | ZN600_HUMAN | Zinc finger protein 600 |
| ZNF605 | ZN605_HUMAN | Zinc finger protein 605 |
| ZNF606 | ZN606_HUMAN | Zinc finger protein 606 |
| ZNF607 | ZN607_HUMAN | Zinc finger protein 607 |
| ZNF610 | ZN610_HUMAN | Zinc finger protein 610 |
| ZNF611 | ZN611_HUMAN | Zinc finger protein 611 |
| ZNF613 | ZN613_HUMAN | Zinc finger protein 613 |
| ZNF614 | ZN614_HUMAN | Zinc finger protein 614 |
| ZNF615 | ZN615_HUMAN | Zinc finger protein 615 |
| ZNF616 | ZN616_HUMAN | Zinc finger protein 616 |
| ZNF618 | ZN618_HUMAN | Zinc finger protein 618 |
| ZNF619 | ZN619_HUMAN | Zinc finger protein 619 |
| ZNF620 | ZN620_HUMAN | Zinc finger protein 620 |
| ZNF621 | ZN621_HUMAN | Zinc finger protein 621 |
| ZNF623 | ZN623_HUMAN | Zinc finger protein 623 |
| ZNF624 | ZN624_HUMAN | Zinc finger protein 624 |
| ZNF625 | ZN625_HUMAN | Zinc finger protein 625 |
| ZNF626 | ZN626_HUMAN | Zinc finger protein 626 |
| ZNF627 | ZN627_HUMAN | Zinc finger protein 627 |
| ZNF628 | ZN628_HUMAN | Zinc finger protein 628 |
| ZNF629 | ZN629_HUMAN | Zinc finger protein 629 |
| ZNF630 | ZN630_HUMAN | Zinc finger protein 630 |
| ZNF639 | ZN639_HUMAN | Zinc finger protein 639 |
| ZNF641 | ZN641_HUMAN | Zinc finger protein 641 |
| ZNF644 | ZN644_HUMAN | Zinc finger protein 644 |
| ZNF646 | ZN646_HUMAN | Zinc finger protein 646 |
| ZNF648 | ZN648_HUMAN | Zinc finger protein 648 |
| ZNF649 | ZN649_HUMAN | Zinc finger protein 649 |
| ZNF652 | ZN652_HUMAN | Zinc finger protein 652 |
| ZNF653 | ZN653_HUMAN | Zinc finger protein 653 |
| ZNF654 | ZN654_HUMAN | Zinc finger protein 654 |
| ZNF655 | ZN655_HUMAN | Zinc finger protein 655 |

TABLE 1-continued

| Target Protein Symbol | uniprot name | Target Protein name |
|---|---|---|
| ZNF658 | ZN658_HUMAN | Zinc finger protein 658 |
| ZNF658B | Z658B_HUMAN | Zinc finger protein 658B |
| ZNF66 | ZNF66_HUMAN | Putative zinc finger protein 66 |
| ZNF660 | ZN660_HUMAN | Zinc finger protein 660 |
| ZNF662 | ZN662_HUMAN | Zinc finger protein 662 |
| ZNF664 | ZN664_HUMAN | Zinc finger protein 664 |
| ZNF665 | ZN665_HUMAN | Zinc finger protein 665 |
| ZNF667 | ZN667_HUMAN | Zinc finger protein 667 |
| ZNF668 | ZN668_HUMAN | Zinc finger protein 668 |
| ZNF669 | ZN669_HUMAN | Zinc finger protein 669 |
| ZNF670 | ZN670_HUMAN | Zinc finger protein 670 |
| ZNF671 | ZN671_HUMAN | Zinc finger protein 671 |
| ZNF672 | ZN672_HUMAN | Zinc finger protein 672 |
| ZNF674 | ZN674_HUMAN | Zinc finger protein 674 |
| ZNF675 | ZN675_HUMAN | Zinc finger protein 675 |
| ZNF676 | ZN676_HUMAN | Zinc finger protein 676 |
| ZNF677 | ZN677_HUMAN | Zinc finger protein 677 |
| ZNF678 | ZN678_HUMAN | Zinc finger protein 678 |
| ZNF679 | ZN679_HUMAN | Zinc finger protein 679 |
| ZNF680 | ZN680_HUMAN | Zinc finger protein 680 |
| ZNF681 | ZN681_HUMAN | Zinc finger protein 681 |
| ZNF682 | ZN682_HUMAN | Zinc finger protein 682 |
| ZNF683 | ZN683_HUMAN | Tissue-resident T-cell transcription regulator protein ZNF683 |
| ZNF684 | ZN684_HUMAN | Zinc finger protein 684 |
| ZNF687 | ZN687_HUMAN | Zinc finger protein 687 |
| ZNF688 | ZN688_HUMAN | Zinc finger protein 688 |
| ZNF689 | ZN689_HUMAN | Zinc finger protein 689 |
| ZNF69 | ZNF69_HUMAN | Zinc finger protein 69 |
| ZNF691 | ZN691_HUMAN | Zinc finger protein 691 |
| ZNF692 | ZN692_HUMAN | Zinc finger protein 692 |
| ZNF695 | ZN695_HUMAN | Zinc finger protein 695 |
| ZNF696 | ZN696_HUMAN | Zinc finger protein 696 |
| ZNF697 | ZN697_HUMAN | Zinc finger protein 697 |
| ZNF699 | ZN699_HUMAN | Zinc finger protein 699 |
| ZNF7 | ZNF7_HUMAN | Zinc finger protein 7 |
| ZNF70 | ZNF70_HUMAN | Zinc finger protein 70 |
| ZNF700 | ZN700_HUMAN | Zinc finger protein 700 |
| ZNF701 | ZN701_HUMAN | Zinc finger protein 701 |
| ZNF702P | ZN702_HUMAN | Putative zinc finger protein 702 |
| ZNF705A | Z705A_HUMAN | Zinc finger protein 705A |
| ZNF705B | Z705B_HUMAN | Putative zinc finger protein 705B |
| ZNF705D | Z705D_HUMAN | Zinc finger protein 705D |
| ZNF705E | Z705E_HUMAN | Putative zinc finger protein 705E |
| ZNF705F | Z705F_HUMAN | Zinc finger protein 705F |
| ZNF707 | ZN707_HUMAN | Zinc finger protein 707 |
| ZNF708 | ZN708_HUMAN | Zinc finger protein 708 |
| ZNF709 | ZN709_HUMAN | Zinc finger protein 709 |
| ZNF71 | ZNF71_HUMAN | Endothelial zinc finger protein induced by tumor necrosis factor alpha |
| ZNF710 | ZN710_HUMAN | Zinc finger protein 710 |
| ZNF711 | ZN711_HUMAN | Zinc finger protein 711 |
| ZNF713 | ZN713_HUMAN | Zinc finger protein 713 |
| ZNF714 | ZN714_HUMAN | Zinc finger protein 714 |
| ZNF716 | ZN716_HUMAN | Zinc finger protein 716 |
| ZNF717 | ZN717_HUMAN | Zinc finger protein 717 |
| ZNF718 | ZN718_HUMAN | Zinc finger protein 718 |
| ZNF721 | ZN721_HUMAN | Zinc finger protein 721 |
| ZNF723 | ZN723_HUMAN | Zinc finger protein 723 |
| ZNF724 | ZN724_HUMAN | Zinc finger protein 724 |
| ZNF726 | ZN726_HUMAN | Zinc finger protein 726 |
| ZNF726P1 | ZNF67_HUMAN | Putative zinc finger protein 726P1 |
| ZNF727 | ZN727_HUMAN | Putative zinc finger protein 727 |
| ZNF728 | ZN728_HUMAN | Zinc finger protein 728 |
| ZNF729 | ZN729_HUMAN | Zinc finger protein 729 |
| ZNF73 | ZNF73_HUMAN | Zinc finger protein 73 |
| ZNF730 | ZN730_HUMAN | Putative zinc finger protein 730 |
| ZNF732 | ZN732_HUMAN | Zinc finger protein 732 |
| ZNF735 | ZN735_HUMAN | Putative zinc finger protein 735 |
| ZNF736 | ZN736_HUMAN | Zinc finger protein 736 |
| ZNF737 | ZN737_HUMAN | Zinc finger protein 737 |
| ZNF74 | ZNF74_HUMAN | Zinc finger protein 74 |
| ZNF746 | ZN746_HUMAN | Zinc finger protein 746 |
| ZNF749 | ZN749_HUMAN | Zinc finger protein 749 |
| ZNF75A | ZN75A_HUMAN | Zinc finger protein 75A |
| ZNF75CP | ZN75C_HUMAN | Putative zinc finger protein 75C |
| ZNF75D | ZN75D_HUMAN | Zinc finger protein 75D |
| ZNF76 | ZNF76_HUMAN | Zinc finger protein 76 |

TABLE 1-continued

| Target Protein Symbol | uniprot name | Target Protein name |
|---|---|---|
| ZNF761 | ZN761_HUMAN | Zinc finger protein 761 |
| ZNF763 | ZN763_HUMAN | Zinc finger protein 763 |
| ZNF764 | ZN764_HUMAN | Zinc finger protein 764 |
| ZNF765 | ZN765_HUMAN | Zinc finger protein 765 |
| ZNF766 | ZN766_HUMAN | Zinc finger protein 766 |
| ZNF768 | ZN768_HUMAN | Zinc finger protein 768 |
| ZNF77 | ZNF77_HUMAN | Zinc finger protein 77 |
| ZNF770 | ZN770_HUMAN | Zinc finger protein 770 |
| ZNF771 | ZN771_HUMAN | Zinc finger protein 771 |
| ZNF772 | ZN772_HUMAN | Zinc finger protein 772 |
| ZNF773 | ZN773_HUMAN | Zinc finger protein 773 |
| ZNF774 | ZN774_HUMAN | Zinc finger protein 774 |
| ZNF775 | ZN775_HUMAN | Zinc finger protein 775 |
| ZNF776 | ZN776_HUMAN | Zinc finger protein 776 |
| ZNF777 | ZN777_HUMAN | Zinc finger protein 777 |
| ZNF778 | ZN778_HUMAN | Zinc finger protein 778 |
| ZNF780A | Z780A_HUMAN | Zinc finger protein 780A |
| ZNF780B | Z780B_HUMAN | Zinc finger protein 780B |
| ZNF781 | ZN781_HUMAN | Zinc finger protein 781 |
| ZNF782 | ZN782_HUMAN | Zinc finger protein 782 |
| ZNF784 | ZN784_HUMAN | Zinc finger protein 784 |
| ZNF785 | ZN785_HUMAN | Zinc finger protein 785 |
| ZNF786 | ZN786_HUMAN | Zinc finger protein 786 |
| ZNF787 | ZN787_HUMAN | Zinc finger protein 787 |
| ZNF789 | ZN789_HUMAN | Zinc finger protein 789 |
| ZNF79 | ZNF79_HUMAN | Zinc finger protein 79 |
| ZNF790 | ZN790_HUMAN | Zinc finger protein 790 |
| ZNF791 | ZN791_HUMAN | Zinc finger protein 791 |
| ZNF792 | ZN792_HUMAN | Zinc finger protein 792 |
| ZNF793 | ZN793_HUMAN | Zinc finger protein 793 |
| ZNF799 | ZN799_HUMAN | Zinc finger protein 799 |
| ZNF8 | ZNF8_HUMAN | Zinc finger protein 8 |
| ZNF80 | ZNF80_HUMAN | Zinc finger protein 80 |
| ZNF800 | ZN800_HUMAN | Zinc finger protein 800 |
| ZNF805 | ZN805_HUMAN | Zinc finger protein 805 |
| ZNF806 | ZN806_HUMAN | Zinc finger protein 806 |
| ZNF808 | ZN808_HUMAN | Zinc finger protein 808 |
| ZNF81 | ZNF81_HUMAN | Zinc finger protein 81 |
| ZNF813 | ZN813_HUMAN | Zinc finger protein 813 |
| ZNF814 | ZN814_HUMAN | Zinc finger protein 814 |
| ZNF816 | ZN816_HUMAN | Zinc finger protein 816 |
| ZNF818P | ZN818_HUMAN | Putative zinc finger protein 818 |
| ZNF821 | ZN821_HUMAN | Zinc finger protein 821 |
| ZNF823 | ZN823_HUMAN | Zinc finger protein 823 |
| ZNF826P | ZN826_HUMAN | Putative zinc finger protein 826 |
| ZNF827 | ZN827_HUMAN | Zinc finger protein 827 |
| ZNF829 | ZN829_HUMAN | Zinc finger protein 829 |
| ZNF83 | ZNF83_HUMAN | Zinc finger protein 83 |
| ZNF831 | ZN831_HUMAN | Zinc finger protein 831 |
| ZNF833P | ZN833_HUMAN | Putative zinc finger protein 833 |
| ZNF835 | ZN835_HUMAN | Zinc finger protein 835 |
| ZNF836 | ZN836_HUMAN | Zinc finger protein 836 |
| ZNF837 | ZN837_HUMAN | Zinc finger protein 837 |
| ZNF84 | ZNF84_HUMAN | Zinc finger protein 84 |
| ZNF840P | ZN840_HUMAN | Putative zinc finger protein 840 |
| ZNF841 | ZN841_HUMAN | Zinc finger protein 841 |
| ZNF843 | ZN843_HUMAN | Zinc finger protein 843 |
| ZNF844 | ZN844_HUMAN | Zinc finger protein 844 |
| ZNF845 | ZN845_HUMAN | Zinc finger protein 845 |
| ZNF846 | ZN846_HUMAN | Zinc finger protein 846 |
| ZNF85 | ZNF85_HUMAN | Zinc finger protein 85 |
| ZNF850 | ZN850_HUMAN | Zinc finger protein 850 |
| ZNF852 | ZN852_HUMAN | Zinc finger protein 852 |
| ZNF853 | ZN853_HUMAN | Zinc finger protein 853 |
| ZNF860 | ZN860_HUMAN | Zinc finger protein 860 |
| ZNF861P | ZN861_HUMAN | Putative zinc finger protein 861 |
| ZNF865 | ZN865_HUMAN | Zinc finger protein 865 |
| ZNF875 | ZN875_HUMAN | Zinc finger protein 875 |
| ZNF876P | Z876P_HUMAN | Putative zinc finger protein 876 |
| ZNF878 | ZN878_HUMAN | Zinc finger protein 878 |
| ZNF879 | ZN879_HUMAN | Zinc finger protein 879 |
| ZNF880 | ZN880_HUMAN | Zinc finger protein 880 |
| ZNF883 | ZN883_HUMAN | Zinc finger protein 883 |
| ZNF888 | ZN888_HUMAN | Zinc finger protein 888 |
| ZNF891 | ZN891_HUMAN | Zinc finger protein 891 |
| ZNF90 | ZNF90_HUMAN | Zinc finger protein 90 |
| ZNF91 | ZNF91_HUMAN | Zinc finger protein 91 |
| ZNF92 | ZNF92_HUMAN | Zinc finger protein 92 |

TABLE 1-continued

| Target Protein Symbol | uniprot name | Target Protein name |
|---|---|---|
| ZNF93 | ZNF93_HUMAN | Zinc finger protein 93 |
| ZNF98 | ZNF98_HUMAN | Zinc finger protein 98 |
| ZNF99 | ZNF99_HUMAN | Zinc finger protein 99 |
| ZNHIT1 | ZNHI1_HUMAN | Zinc finger HIT domain-containing protein 1 |
| ZNHIT6 | BCD1_HUMAN | Box C/D snoRNA protein 1 |
| ZNRD1 | RPA12_HUMAN | DNA-directed RNA polymerase I subunit RPA12 |
| ZRANB1 | ZRAN1_HUMAN | Ubiquitin thioesterase ZRANB1 |
| ZRANB2 | ZRAB2_HUMAN | Zinc finger Ran-binding domain-containing protein 2 |
| ZSCAN1 | ZSCA1_HUMAN | Zinc finger and SCAN domain-containing protein 1 |
| ZSCAN10 | ZSC10_HUMAN | Zinc finger and SCAN domain-containing protein 10 |
| ZSCAN12 | ZSC12_HUMAN | Zinc finger and SCAN domain-containing protein 12 |
| ZSCAN16 | ZSC16_HUMAN | Zinc finger and SCAN domain-containing protein 16 |
| ZSCAN18 | ZSC18_HUMAN | Zinc finger and SCAN domain-containing protein 18 |
| ZSCAN2 | ZSCA2_HUMAN | Zinc finger and SCAN domain-containing protein 2 |
| ZSCAN20 | ZSC20_HUMAN | Zinc finger and SCAN domain-containing protein 20 |
| ZSCAN21 | ZSC21_HUMAN | Zinc finger and SCAN domain-containing protein 21 |
| ZSCAN22 | ZSC22_HUMAN | Zinc finger and SCAN domain-containing protein 22 |
| ZSCAN23 | ZSC23_HUMAN | Zinc finger and SCAN domain-containing protein 23 |
| ZSCAN25 | ZSC25_HUMAN | Zinc finger and SCAN domain-containing protein 25 |
| ZSCAN26 | ZSC26_HUMAN | Zinc finger and SCAN domain-containing protein 26 |
| ZSCAN29 | ZSC29_HUMAN | Zinc finger and SCAN domain-containing protein 29 |
| ZSCAN30 | ZSC30_HUMAN | Zinc finger and SCAN domain-containing protein 30 |
| ZSCAN31 | ZSC31_HUMAN | Zinc finger and SCAN domain-containing protein 31 |
| ZSCAN32 | ZSC32_HUMAN | Zinc finger and SCAN domain-containing protein 32 |
| ZSCAN5A | ZSA5A_HUMAN | Zinc finger and SCAN domain-containing protein 5A |
| ZSCAN5C | ZSA5C_HUMAN | Putative zinc finger and SCAN domain-containing protein 5C |
| ZSCAN9 | ZSC9_HUMAN | Zinc finger and SCAN domain-containing protein 9 |
| ZUP1 | ZUP1_HUMAN | Zinc finger-containing ubiquitin peptidase 1 |
| ZWILCH | ZWILC_HUMAN | Protein zwilch homolog |
| ZZZ3 | ZZZ3_HUMAN | ZZ-type zinc finger-containing protein 3 |

In another embodiment of the disclosure, the compounds of the present disclosure are enantiomers. In some embodiments the compounds are the (S)-enantiomer. In other embodiments, the compounds are the (R)-enantiomer. In yet other embodiments, the compounds of the present disclosure may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the disclosure, and pharmaceutically acceptable salts, hydrates, solvates, stereoisomers, and prodrugs thereof may exist in their tautomeric form (for example, as an amide or imino ether). All such tautomeric forms are contemplated herein as part of the present disclosure.

The compounds of the disclosure may contain asymmetric or chiral centers and, therefore, exist in different stereoisomeric forms. It is intended that all stereoisomeric forms of the compounds of the disclosure as well as mixtures thereof, including racemic mixtures, form part of the present disclosure. In addition, the present disclosure embraces all geometric and positional isomers. For example, if a compound of the disclosure incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the disclosure may be atropisomers (e.g., substituted biaryls) and are considered as part of this disclosure. Enantiomers can also be separated by use of a chiral HPLC column.

It is also possible that the compounds of the disclosure may exist in different tautomeric forms, and all such forms are embraced within the scope of the disclosure and chemical structures and names. Also, for example, all keto-enol and imine-enamine forms of the compounds are included in the disclosure.

All stereoisomers (for example, geometric isomers, optical isomers, and the like) of the present compounds (including those of the salts, solvates, esters, and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or is admixed, for example, as racemates or with all other, or other selected, stereoisomers.

The chiral centers of the compounds of the disclosure can have the S or R configuration as defined by the IUPAC 1974 Recommendations. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

The use of the terms "salt", "solvate", "ester," "prodrug", and the like, is intended to equally apply to the salt, solvate, ester, and prodrug of enantiomers, stereoisomers, rotamers, tautomers, positional isomers, racemates, or prodrugs of the inventive compounds.

The compounds of the disclosure may form salts which are also within the scope of this disclosure. Reference to a compound of the Formula herein is generally understood to include reference to salts thereof, unless otherwise indicated.

The compounds and intermediates may be isolated and used as the compound per se. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, and, such as $^{2}H$, $^{3}H$, $^{11}C$, $^{13}C$, $^{14}C$, $^{15}N$, $^{18}F$, $^{31}P$ $^{32}P$, respectively. The disclosure includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$, $^{11}C$ or labeled compound may be particularly desirable for PET or SPECT studies.

Further, substitution with heavier isotopes, particularly deuterium (i.e., $^{2}H$ or D) may afford certain therapeutic advantages resulting from greater metabolic stability, for example, increased in vivo half-life, reduced dosage requirements, reduced CYP450 inhibition (competitive or time dependent) or an improvement in therapeutic index. For example, substitution with deuterium may modulate undesirable side effects of the undeuterated compound, such as competitive CYP450 inhibition, time dependent CYP450 inactivation, etc. It is understood that deuterium in this context is regarded as a substituent in compounds of the present disclosure. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present disclosure can generally be prepared by conventional techniques known to those skilled in the art or by carrying out the procedures disclosed in the schemes or in the examples and preparations described below using an appropriate isotopically-labeled reagent in place of the non-isotopically labeled reagent.

Pharmaceutically acceptable solvates in accordance with the disclosure include those wherein the solvent of crystallization may be isotopically substituted, e.g., $D_2O$, $d_6$-acetone, $d_6$-DMSO.

In some embodiments, the degradation of a target protein is measured by $EC_{50}$.

Potency of can be determined by $EC_{50}$ value. A compound with a lower $EC_{50}$ value, as determined under substantially similar degradation conditions, is a more potent degrader relative to a compound with a higher $EC_{50}$ value. In some embodiments, the substantially similar conditions comprise determining degradation of protein levels in cells expressing the specific protein, or a fragment of any thereof.

The disclosure is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

E. Methods of Using Compounds of Formula (I)

Compounds and compositions described herein are generally useful for the modulation of CRBN. Another aspect of the disclosure relates to a method of modulating a target protein in a subject in need thereof, the method comprising administering to the subject a therapeutically effective amount of a compound disclosed herein, or a pharmaceutically acceptable salt, hydrate, solvate, prodrug, stereoisomer, or tautomer thereof or a pharmaceutical composition comprising a compound disclosed herein, or a pharmaceutically acceptable salt, hydrate, solvate, prodrug, stereoisomer, or tautomer thereof. In one embodiment, the target protein is a target protein selected from one of the target proteins listed in Table 1.

In another aspect, the disclosure relates to a method of inhibiting a target protein in a subject in need thereof, the method comprising administering to the subject a therapeutically effective amount of a compound disclosed herein, or a pharmaceutically acceptable salt, hydrate, solvate, prodrug, stereoisomer, or tautomer thereof or a pharmaceutical composition comprising a compound disclosed herein, or a pharmaceutically acceptable salt, hydrate, solvate, prodrug, stereoisomer, or tautomer thereof. In one embodiment, the target protein is a target protein selected from one of the target proteins listed in Table 1.

Another aspect of the disclosure relates to a method of modulating or inhibiting a target protein in a subject in need thereof, the method comprising administering to the subject a therapeutically effective amount of a compound disclosed herein, or a pharmaceutically acceptable salt, hydrate, solvate, prodrug, stereoisomer, or tautomer thereof or a pharmaceutical composition comprising a compound disclosed herein, or a pharmaceutically acceptable salt, hydrate, solvate, prodrug, stereoisomer, or tautomer thereof. In one embodiment, the target protein is a target protein selected from one of the target proteins listed in Table 1.

In another aspect, the disclosure relates to a method of treating or preventing a respiratory disorder, a proliferative disorder, an autoimmune disorder, an autoinflammatory disorder, an inflammatory disorder, a neurological disorder, and an infectious disease or disorder mediated by a target protein in a subject in need thereof, the method comprising administering to the subject a therapeutically effective amount of a compound disclosed herein, or a pharmaceutically acceptable salt, hydrate, solvate, prodrug, stereoisomer, or tautomer thereof or a pharmaceutical composition comprising a compound disclosed herein, or a pharmaceutically acceptable salt, hydrate, solvate, prodrug, stereoisomer, or tautomer thereof. In one embodiment, the disorder is mediated by a target protein listed in Table 1.

Another aspect of the disclosure relates to a method of treating or preventing a cancer in a subject in need thereof, the method comprising administering to the subject a therapeutically effective amount of a compound disclosed herein, or a pharmaceutically acceptable salt, hydrate, solvate, prodrug, stereoisomer, or tautomer thereof or a pharmaceutical composition comprising a compound disclosed herein, or a pharmaceutically acceptable salt, hydrate, solvate, prodrug, stereoisomer, or tautomer thereof.

In another aspect, the disclosure provides compounds of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in inhibiting or modulating a target protein in a subject in need thereof. In one embodiment, the target protein is a target protein selected from one of the target proteins listed in Table 1.

Another aspect of the disclosure relates to a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in inhibiting a target protein in a subject in need thereof. In one embodiment, the target protein is a target protein selected from one of the target proteins listed in Table 1.

In another aspect, the disclosure provides pharmaceutical compositions comprising compounds of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in inhibiting or modulating a target protein in a subject in need thereof. In one embodiment, the target protein is a target protein selected from one of the target proteins listed in Table 1.

Another aspect of the disclosure relates to a pharmaceutical composition comprising a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in inhibiting a target protein in a subject in need thereof. In one embodiment, the target protein is a target protein selected from one of the target proteins listed in Table 1.

In another aspect, the disclosure relates to a pharmaceutical composition comprising a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, and a pharmaceutically acceptable carrier, for use in inhibiting a target protein in a subject in need thereof. In one embodiment, the target protein is a target protein selected from one of the target proteins listed in Table 1.

Another aspect of the disclosure relates to a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in treating or preventing a respiratory disorder, a proliferative disorder, an autoimmune disorder, an autoinflammatory disorder, an inflammatory disorder, a neurological disorder, and an infectious disease or disorder mediated by a target protein in a subject in need thereof. In one embodiment, the disorder is mediated by a target protein listed in Table 1.

In another aspect, the disclosure relates to a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in treating or preventing a cancer in a subject in need thereof. In one embodiment, the cancer is mediated by a target protein listed in Table 1

Another aspect of the disclosure relates to a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, in the manufacture of a medicament for inhibiting or modulating a target protein in a subject in need thereof. In one embodiment, the target protein is a target protein selected from one of the target proteins listed in Table 1.

In another aspect, the disclosure relates to the use of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, in the manufacture of a medicament for inhibiting a target protein in a subject in need thereof. In one embodiment, the target protein is a target protein selected from one of the target proteins listed in Table 1.

Another aspect of the disclosure relates to the use of a pharmaceutical composition comprising a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, and a pharmaceutically acceptable carrier, in the manufacture of a medicament for treating a Target Protein-mediated disorder, disease, or condition in a subject in need thereof. In one embodiment, the Target Protein-mediated disorder, disease, or condition is selected from a respiratory disorder, a proliferative disorder, an autoimmune disorder, an autoinflammatory disorder, an inflammatory disorder, a neurological disorder, and an infectious disease or disorder. In one aspect, the proliferative disorder is a cancer.

In another aspect, the disclosure relates to the use of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, in the manufacture of a medicament for treating or preventing a cancer mediated by a target protein in a subject in need thereof. In one embodiment, the cancer is mediated by a target protein listed in Table 1.

Another aspect of the disclosure relates to a method for treating or preventing a cancer mediated by a target protein in a subject in need thereof comprising administering a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, to the subject. In one embodiment, the cancer is mediated by a target protein listed in Table 1.

In another aspect, the disclosure relates to the use of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, in the manufacture of a medicament for treating or preventing a respiratory disorder, a proliferative disorder, an autoimmune disorder, an autoinflammatory disorder, an inflammatory disorder, a neurological disorder, and an infectious disease or disorder in a subject in need thereof. In one embodiment, the disorder is mediated by a target protein listed in Table 1.

Another aspect of the disclosure relates to a method of treating or preventing a disorder in a subject in need thereof, the method comprising administering to the subject a therapeutically effective amount of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof.

In another aspect, the disclosure relates to the use of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof in the manufacture of a medicament for treating or preventing a disorder in a subject in need thereof.

Another aspect of the disclosure relates to a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in the treatment or prevention a disorder in a subject in need thereof.

In another aspect, the disclosure provides a method for inducing degradation of a Target Protein, e.g., a Target protein in Table 1, in a subject in need thereof, the method comprising administering to the subject a therapeutically effective amount of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof.

Another aspect of the disclosure relates to a method of inhibiting, reducing, or eliminating the activity of a Target Protein, e.g., a Target protein in Table 1, the method comprising administering to the subject a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof.

In another aspect, the disclosure provides a method of treating or preventing a cancer in a subject in need thereof, the method comprising administering to the subject a therapeutically effective amount of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof.

In another aspect, the disclosure provides a method of treating or preventing a cancer mediated by a Target protein, e.g., a Target protein in Table 1, in a subject in need thereof, the method comprising administering to the subject a therapeutically effective amount of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof.

Another aspect of the disclosure relates to compounds of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or pharmaceutical compositions comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in modulating a Target protein in a subject in need thereof.

In another aspect, the disclosure provides compounds of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or pharmaceutical compositions comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in inhibiting a Target protein in a subject in need thereof.

Another aspect of the disclosure relates to of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or pharmaceutical compositions comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in treating or preventing a cancer in a subject in need thereof.

In another aspect, the disclosure provides compounds of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or pharmaceutical compositions comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, for use in treating or preventing a cancer mediated by a Target protein, e.g., a Target protein in Table 1, in a subject in need thereof.

In another aspect, the disclosure provides a use of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, in the manufacture of a medicament for modulating a Target protein, e.g., a Target protein in Table 1, in a subject in need thereof.

Another aspect of the disclosure relates to a use of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, in the manufacture of a medicament for inhibiting a Target protein, e.g., a Target protein in Table 1, in a subject in need thereof.

In another aspect, the disclosure provides a use of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, in the manufacture of a medicament for treating or preventing a cancer mediated by a Target protein, e.g., a Target protein in Table 1, in a subject in need thereof.

Another aspect of the disclosure relates to use of a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, or a pharmaceutical composition comprising a compound of Formula ((I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, in the manufacture of a medicament for treating or preventing a cancer in a subject in need thereof.

The disclosed compounds of the disclosure can be administered in effective amounts to treat a disorder and/or prevent the development thereof in subjects.

Compounds of the application can be administered in therapeutically effective amounts in a combinational therapy with one or more therapeutic agents (pharmaceutical combinations) or modalities, e.g., non-drug therapies. For example, synergistic effects can occur with other anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

F. Combination Therapy

Combination therapy includes the administration of the subject compounds in further combination with other biologically active ingredients (such as, but not limited to, a second and different antineoplastic agent, an antiproliferative agent, anticancer agent, immunomodulatory agent, an anti-inflammatory agent, a neurological treatment agent, an anti-viral agent, an anti-fungal agent, anti-parasitic agent, an antibiotic, or a general anti-infective agent) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

Another embodiment is a pharmaceutical combination comprising a compound of Formula (I), (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu), (Iv), (Iw), (Ix), (Iy), (Iz), (Iaa), (Iab), (Iac), (Iad), (Iae), (Iaf), (Iag), (Iah), (Iai), (Iaj), (Iak), (Ial), or (Iam), or Compounds I-1 to I-18, or a pharmaceutically acceptable salt, hydrate, solvate, prodrug, stereoisomer, or tautomer thereof, and one or more additional therapeutic agent(s) or pharmaceutical agent(s) for simultaneous, separate or sequential use in therapy.

In another embodiment, the additional therapeutic agent is selected from the group consisting of: an antiproliferative agent, anticancer agent, immunomodulatory agent, an anti-inflammatory agent, a neurological treatment agent, an anti-viral agent, an anti-fungal agent, anti-parasitic agent, an antibiotic, and a general anti-infective agent.

In another embodiment, the additional therapeutic agent is selected from the group consisting of: a second a target protein inhibitor.

G. Administration, Pharmaceutical Compositions, and Dosing of Compounds of Formula (I)

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, com oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride, and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes, and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles, and multilamellar vesicles. Liposomes can be formed from a variety of phospholipids, containing cholesterol, stearylamine or phosphatidylcholines.

In some embodiments, a film of lipid components is hydrated with an aqueous solution of drug to a form lipid layer encapsulating the drug, as described in U.S. Pat. No. 5,262,564, which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In one embodiment, the disclosure provides a kit comprising two or more separate pharmaceutical compositions, at least one of which contains a compound of the present disclosure. In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

The dosage regimen utilizing the disclosed compound is selected in accordance with a variety of factors including type, species, age, weight, sex, and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3rd edition, John Wiley & Sons). These groups are removed at a convenient stage of the compound synthesis using methods that are readily apparent to those skilled in the art.

Those skilled in the art will recognize if a stereocenter exists in the compounds of the present disclosure. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Analytical Methods, Materials, and Instrumentation

Unless otherwise noted, reagents and solvents were used as received from commercial suppliers. Proton nuclear magnetic resonance (NMR) spectra were obtained on either Bruker Avance spectrometer or Varian Oxford 400 MHz spectrometer unless otherwise noted. Spectra are given in ppm (δ) and coupling constants, J, are reported in Hertz. Tetramethylsilane (TMS) was used as an internal standard. Chemical shifts are reported in ppm relative to dimethyl sulfoxide (δ 2.50), methanol (δ 3.31), chloroform (δ 7.26) or other solvent as indicated in NMR spectral data. A small amount of the dry sample (2-5 mg) is dissolved in an appropriate deuterated solvent (1 mL). The chemical names were generated using ChemBioDraw Ultra v14 from CambridgeSoft.

LC/MS conditions: Liquid chromatograpy (LC) analysis were performed using a Waters System (Column: Waters Acquity UPLC BEH C18 1.7 um, 2.1×30 mm (Part #: 186002349); flow rate: 1 mL/min; temperature: 55° C. (column temp); mobile phase compositions: A) 0.05% formic acid in water, B) 0.04% formic acid in methanol.

Mass spectra (ESI-MS) were collected using a Waters System (Acquity UPLC and a Micromass ZQ mass spectrometer) or Agilent-1260 Infinity (6120 Quadrupole); all masses reported are the m/z of the protonated parent ions unless recorded otherwise. The sample was dissolved in acquirable solvent such as MeCN, DMSO, or MeOH and was injected directly into the column using an automated sample handler. Abbreviations used in the following examples and elsewhere herein are:

aq. aqueous
Bn benzyl
BnBr benzylbromide
Boc tert-butyloxycarbonyl
br broad
brs broad singlet
CDI 1,1'-carbonyldiimidazole
d doublet
DCM dichloromethane
dd doublet of doublets
ddd doublet of doublet of doublets
DIAD diisopropyl azodicarboxylate
DIPEA N,N-diisopropylethylamine
DMA dimethylacetamide
DMF N,N-dimethylformamide
DMSO dimethylsulfoxide
dq doublet of quartets
dt doublet of triplets
dtd doublet of triplet of doublets
$EC_{50}$ half maximal effective concentration (relative)
Et ethyl
EtOAc ethyl acetate
EtOH ethanol or ethyl alcohol $Et_3N$ triethylamine
equiv equivalents
h, hr, or hrs hour(s)
hept heptet
HATU 1-[Bis(dimethylamino)methylene]-1H-1,2,3-triazolo[4,5-b]pyridinium 3-oxid hexafluorophosphate
HPLC high performance liquid chromatography
HRMS high resonance mass spectrometry
g gram
i-Pr isopropyl
i-PrOH or IPA isopropanol or isopropyl alcohol
$i\text{-}Pr_2NEt$ N,N-diisopropylethylamine
Me methyl
MeCN acetonitrile
MeOH methanol
m multiplet
M molar
mg milligram
MHz megahertz
min minutes
mL milliliter
mmol millimole
MS mass spectrometry
$NaBH(OAc)_3$ sodium triacetoxyborohydride
NIS N-iodosuccinimide
NMR nuclear magnetic resonance
PMB para-methoxybenzyl
PMB-Cl 4-methoxybenzyl chloride
p-TsOH para-toluenesulfonic acid
q quartet
quint quintet
quintd quintet of doublets
rt room temperature
Rt retention time
s singlet
sat. saturated
t-Bu tert-butyl
t triplet
t-BuONa sodium tert-butoxide
tdd triplet of doublet of doublets
TBAF tetra-n-butylammonium fluoride
TBAI tetrabutylammonium iodide
TEA triethylamine
TFA trifluoroacetic acid
TFE 2,2,2-trifluoroethanol
TfOH trifluoromethanesulfonic acid
THF tetrahydrofuran
ttd triplet of triplet of doublets
UPLC Ultra-Performance Liquid Chromatography
X-Phos Pd G1 2-Dicyclohexylphosphino-2',4',6'-triisopropyl-1,1'-biphenyl)[2-(2-aminoethyl)phenyl)]palladium(II) chloride
XPhos Pd-G2 Chloro(2-dicyclohexylphosphino-2',4',6'-triisopropyl-1,1'-biphenyl)[2-(2'-amino-1,1'-biphenyl)] palladium(II)

Example 1: 1-(Benzofuran-3-yl)dihydropyrimidine-2,4(1H,3H)-dione

3-Bromobenzofuran (I-1)

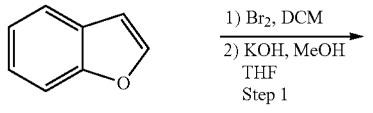

1-1a

-continued

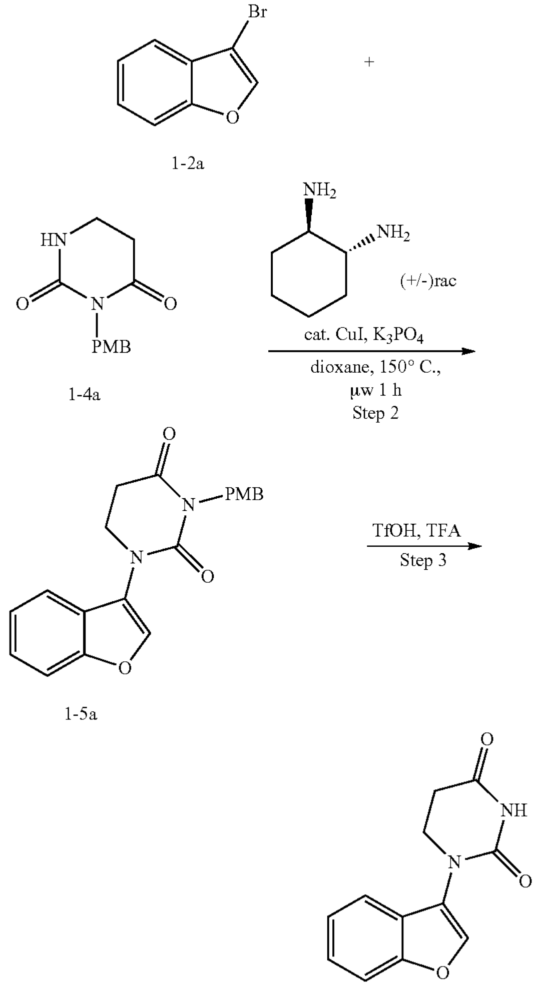

1-2a 1-4a 1-5a 1-1

Step 1. 3-Bromobenzofuran (1-2a)

To a solution of benzofuran (1-1a, 0.466 mL, 4.23 mmol) in DCM (10 mL), bromine (0.434 mL, 8.47 mmol) was added then stirred at room temperature for 15 minutes. The reaction was quenched with aqueous sodium thiosulfate then extracted with DCM. The organic phases were combined, dried over $Na_2SO_4$, filtered, then concentrated to dryness. The crude residue was dissolved into 10 mL THF and then a solution of KOH (237 mg, 4.23 mmol) in 2 mL MeOH was added. The resultant mixture was stirred at room temperature for 30 minutes. The reaction mixture was diluted with $H_2O$ and extracted with EtOAc (3×10 mL). The combined organic phases were dried over $Na_2SO_4$, filtered, and concentrated to dryness. Silica gel chromatography (heptane) affords the desired product 1-2a as an oil (500 mg, 60% yield). $^1H$ NMR (400 MHz, chloroform-d) δ 7.67 (s, 1H), 7.59-7.55 (m, 1H), 7.54-7.48 (m, 1H), 7.36 (dqd, J=8.5, 7.3, 1.3 Hz, 2H).

Preparation of 3-(4-Methoxybenzyl)dihydropyrimidine-2,4(1H,3H)-dione (1-4a)

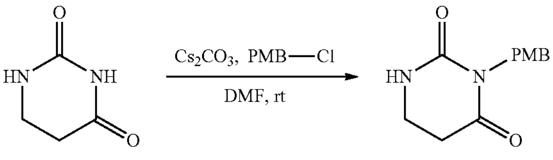

1-3a 1-4a

To a suspension of dihydrouracil (1-3a, 4.64 g, 40.7 mmol) in DMF (100 mL) was added PMB-Cl (7.17 mL, 52.9 mmol) and $Cs_2CO_3$ (15.9 g, 48.8 mmol) and the resulting mixture was stirred at room temperature overnight. The reaction mixture was filtered, washed with DMF, and concentrated to dryness. Water was then added to dissolve residual $Cs_2CO_3$ and to precipitate the product. The mixture was filtered and the resulting solid was washed with water, 1:1 EtOAc/heptane (2×), and DCM (1×) and then dried under vacuum filtration for 20 minutes to provide the desired product 1-4a as a white solid (5.20 g, 55% yield). $^1H$ NMR (400 MHz, DMSO-$d_6$) δ 7.81 (s, 1H), 7.24-7.10 (m, 2H), 6.92-6.78 (m, 2H), 4.71 (s, 2H), 3.71 (s, 3H), 3.21 (td, J=6.8, 2.7 Hz, 2H), 2.62 (t, J=6.8 Hz, 2H). MS $[M+H]^+$=235.2.

Step 2. 1-(Benzofuran-3-yl)-3-(4-methoxybenzyl) dihydropyrimidine-2,4(1H,3H)-dione (1-5a)

To a microwave vial containing 1-2a (70.0 mg, 0.355 mmol), 1-4a (108 mg, 0.462 mmol), CuI (33.8 mg, 0.178 mmol), and $K_3PO_4$ (151 mg, 0.711 mmol) was added dioxane (2.5 mL). (+/−)-trans Cyclohexyl diamine (0.021 mL, 0.178 mmol) was then added and nitrogen gas was bubbled through the resulting mixture for 5 minutes. The vial was sealed and heated in the microwave at 150° C. for 1 hr (Biotage microwave). The reaction mixture was filtered through Celite® filter aid and the pad was washed with MeOH. The filtrate was concentrated to dryness and the resulting residue was purified by silica gel chromatography, eluting with 2% MeOH/DCM, to afford 1-5a (90 mg, 72% yield). MS $[M+H]^+$=351.2.

Step 3. 1-(Benzofuran-3-yl)dihydropyrimidine-2,4 (1H,3H)-dione (I-1)

To 1-5a (50 mg, 0.14 mmol) dissolved in TFA (1.0 mL) was added TfOH (0.5 mL) and the resulting mixture was stirred at room temperature for 30 minutes. The reaction mixture was then quenched with MeOH and concentrated to dryness. The crude residue was purified by reverse phase HPLC (MeCN/$H_2O$ with formic acid modifier) to afford I-1 (9 mg, 26% yield). $^1H$ NMR (400 MHz, methanol-$d_4$) δ 7.93 (s, 1H), 7.60 (ddd, J=7.8, 1.5, 0.7 Hz, 1H), 7.50 (dt, J=8.3, 0.9 Hz, 1H), 7.35 (ddd, J=8.4, 7.2, 1.4 Hz, 1H), 7.28 (td, J=7.5, 1.0 Hz, 1H), 3.94 (t, J=6.7 Hz, 2H), 2.88 (t, J=6.7 Hz, 2H). MS $[M+H]^+$=231.3.

Example 2: 1-(5-Methylbenzofuran-3-yl)dihydropyrimidine-2,4(1H,3H)-dione (I-3)

I-3

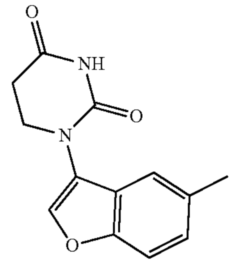

The title compound was prepared according to the procedure described for compound I-1 in Example 1 starting from 5-methylbenzofuran (300 mg, 2.26 mmol) in place of 1-1a, to afford the desired I-3 as a white solid (15 mg, 3% yield). $^1H$ NMR (300 MHz, DMSO-$d_6$): δ 10.50 (brs, 1H), 8.04 (s, 1H), 7.45 (d, J=11 Hz, 1H), 7.36 (s, 1H), 7.14 (d, J=12 Hz, 1H), 3.80 (t, J=8.4 Hz, 2H), 2.75 (t, J=9.0 Hz, 2H), 2.37 (s, 3H). MS $[M+H]^+$=245.1.

Example 3: Phenyl (3-(2,4-dioxotetrahydropyrimidin-1(2H)-yl)benzofuran-5-yl)carbamate (I-6)

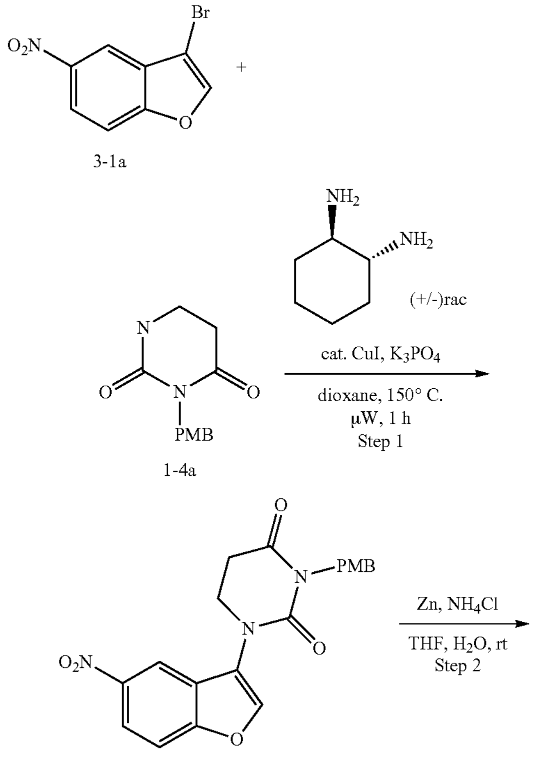

3-1a
1-4a
3-2a

-continued

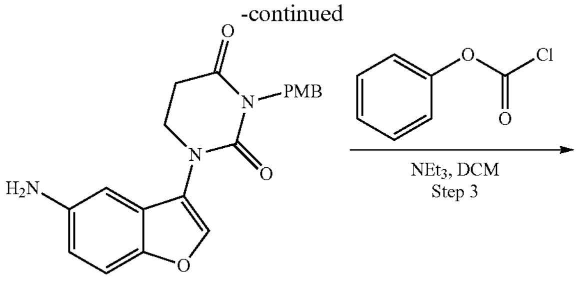

3-3a

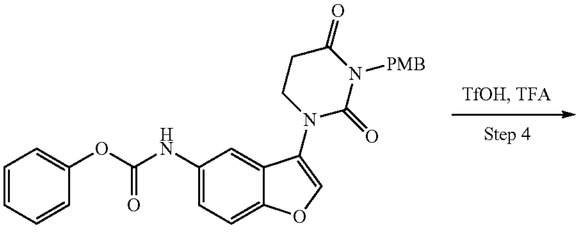

3-4a

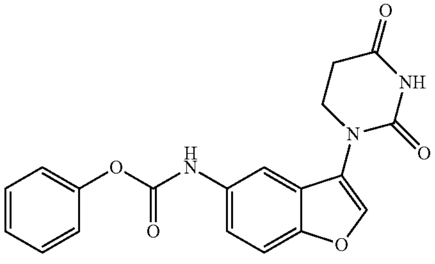

I-6

Preparation of 3-Bromo-5-nitrobenzofuran (3-1a)

3-1a was prepared according to the procedure described for 1-2a in Example 1 starting from 5-nitrobenzofuran. $^1H$ NMR (400 MHz, acetone-$d_6$) δ 8.47 (d, J=2.4 Hz, 1H), 8.42-8.37 (m, 1H), 8.35 (s, 1H), 7.90 (d, J=8.8 Hz, 1H).

Step 1. 3-(4-Methoxybenzyl)-1-(5-nitrobenzofuran-3-yl)dihydropyrimidine-2,4(1H,3H)-dione (3-2a)

3-2a was prepared according to the procedure described for 1-5a in Example 1 starting from 3-1a (2 g, 8.26 mmol) and 1-4a (2.5 g, 10.75 mmol). The crude material was purified by silica gel chromatography, eluting with 50% EtOAc/hexane, to afford 3-2a (1.75 g, 55% yield). MS $[M+H]^+$=396.1.

Step 2. 1-(5-aminobenzofuran-3-yl)-3-(4-methoxybenzyl)dihydropyrimidine-2,4(1H,3H)-dione (3-3a)

To a stirred solution of 3-2a (1.50 g, 3.79 mmol) in THF (20 mL) was added a solution of $NH_4Cl$ (aq) (2.43 g, 53.5 mmol). Zn (1.49 g, 22.8 mmol) was then added portion-wise at room temperature and the resulting mixture was stirred at room temperature for 1 hour. The reaction mixture was then filtered through a Celite® pad. The filtrate was diluted with water then extracted with EtOAc (2×). The combined organic phases were washed with water and brine, dried over $Na_2SO_4$, filtered, and concentrated to dryness to afford crude 3-3a (1.48 g, 4.0 mmol). The crude material was carried onto the next step without purification. MS $[M+H]^+$=366.0.

Step 3. Phenyl (3-(3-(4-methoxybenzyl)-2,4-dioxotetrahydropyrimidin-1(2H)-yl)benzofuran-5-yl)carbamate (3-4a)

To a solution of 3-3a (150 mg, 0.41 mmol) in DCM (5 mL) was added $Et_3N$ (0.11 mL, 0.82 mmol). Phenyl chloroformate (0.1 mL, 0.73 mmol) was added and the resulting mixture was stirred at room temperature for 16 hours. The reaction mixture was then concentrated to dryness and the crude material was purified by silica gel chromatography, eluting with 35% EtOAc/heptane, to afford 3-4a as a yellow solid (80 mg, 40% yield). MS $[M+H]^+$=484.2.

Step 4. Phenyl (3-(2,4-dioxotetrahydropyrimidin-1(2H)-yl)benzofuran-5-yl)carbamate (I-6)

To a stirred solution of 3-4a (80 mg, 0.39 mmol) in TFA (0.5 mL) was added TfOH (0.2 mL) dropwise over 5 min at 0° C. The resulting mixture was then removed from the ice bath and stirred at room temperature for 40 min. The reaction mixture was quenched with sat. aq. $NaHCO_3$ solution, diluted with water then extracted with EtOAc (3×). The combined organic phases were dried over $Na_2SO_4$, filtered, then concentrated to dryness. The crude residue was then purified by reverse phase HPLC (MeCN/$H_2O$ with 0.1% formic acid modifier) to afford the title compound I-6 as a white solid (9 mg, 15% yield). $^1H$ NMR (400 MHz, DMSO-$d_6$): δ 10.57 (s, 1H), 10.30 (s, 1H), 8.11 (s, 1H), 7.80 (s, 1H), 7.56 (d, J=8.4 Hz, 1H), 7.43-7.41 (m, 3H), 7.23-7.21 (m, 3H), 3.82 (t, J=9.0 Hz, 2H), 2.75 (t, J=8.5 Hz, 2H). MS $[M+H]^+$=366.1.

Example 4: 1-(5-Iodobenzofuran-3-yl)dihydropyrimidine-2,4(1H,3H)-dione (I-4)

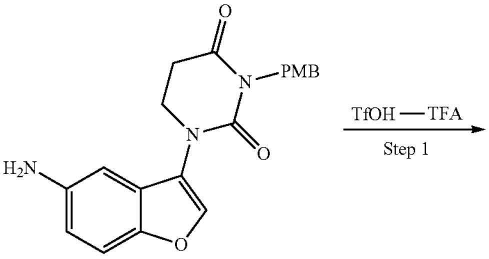

3-3a

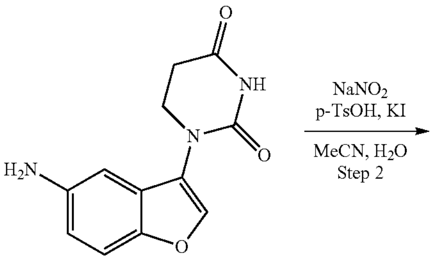

4-1a

-continued

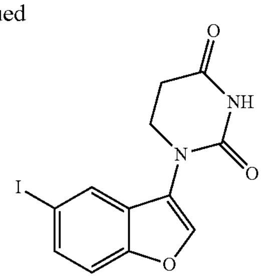

I-4

Step 1. 1-(5-Aminobenzofuran-3-yl)dihydropyrimidine-2,4(1H,3H)-dione (4-1a)

TFA (2 mL) was added to 3-3a (220 mg, 0.60 mmol). TfOH (1 mL) was then added at 0° C. over 5 minutes and the resulting mixture was then stirred at 0° C. for 2 hours. The reaction mixture was concentrated to dryness. The crude residue was slowly neutralized with sat. aq. $NaHCO_3$ solution then extracted with EtOAc (3×). The combined organic phases were then washed with water and brine, dried over $Na_2SO_4$, filtered, and concentrated to dryness. The resulting residue was purified by silica gel chromatography, eluting with 3% MeOH/DCM, to afford 4-1a as a brown solid (90 mg, 61% yield). MS $[M+H]^+$=246.0.

Step 2. 1-(5-Iodobenzofuran-3-yl)dihydropyrimidine-2,4(1H,3H)-dione (I-4)

To a stirred solution of 4-1a (90 mg, 0.37 mmol) in MeCN (3 mL) was added p-TsOH (209 mg, 1.1 mmol) and the resulting mixture was then cooled in an ice bath for 15 minutes. A solution of KI (152 mg, 0.92 mmol) and $NaNO_2$ (50 mg, 0.73 mmol) in $H_2O$ (3 mL) was then added dropwise at about 0° C. and stirring was continued at about 0° C. for 1 hour. The reaction mixture was quenched with sat. aq. $NaHCO_3$ solution at 0° C. then extracted with EtOAc (3×). The combined organic phases were washed with water and brine, dried over $Na_2SO_4$, filtered, and concentrated to dryness. The crude residue was then purified by silica gel chromatography, eluting with 0.5% MeOH/DCM, to afford an impure material. The material was further purified by reverse phase HPLC (MeCN/$H_2O$ with 0.1% formic acid modifier) to afford I-4 as an off-white solid (17 mg, 13% yield). $^1H$ NMR (400 MHz, DMSO-$d_6$): δ 10.6 (s, 1H), 8.11 (s, 1H), 7.99 (d, J=1.6 Hz, 1H), 7.65-7.61 (m, 1H), 7.46 (d, J=8.0 Hz, 1H), 3.82 (t, J=6.4 Hz, 2H), 2.77 (t, J=6.1 Hz, 2H).

Example 5: 1-(6-Iodobenzofuran-3-yl)dihydropyrimidine-2,4(1H,3H)-dione (I-5)

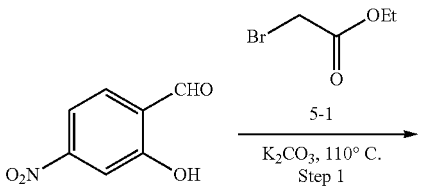

5-1a

-continued

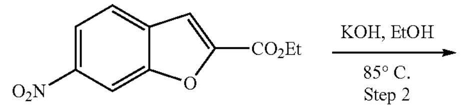

5-2a

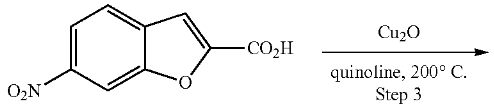

5-3a

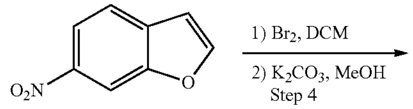

5-4a

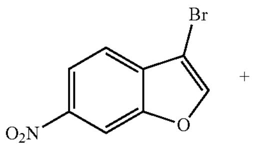

5-5a

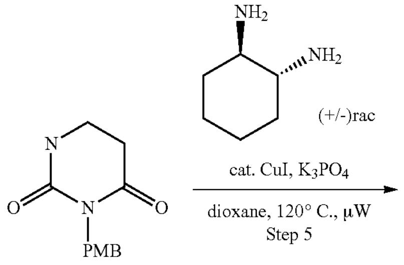

1-4a

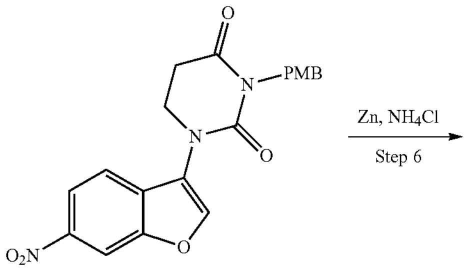

5-6a

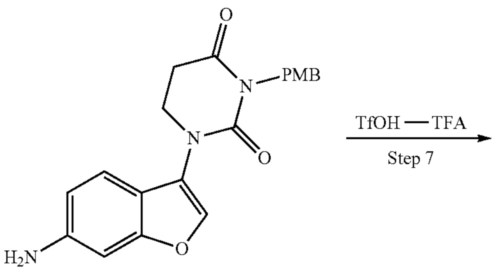

5-7a

-continued

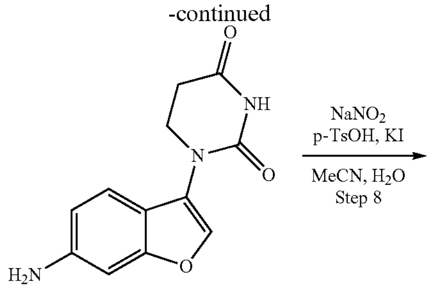

5-8a

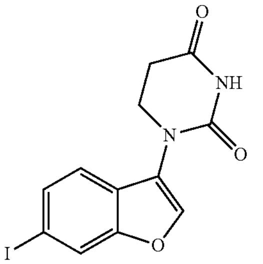

I-5

Step 1. Ethyl 5-nitrobenzofuran-2-carboxylate (5-2a)

To a solution of 5-1a (2.50 g, 15.0 mmol) in DMF at room temperature was added ethyl bromoacetate (5-1, 2.0 mL, 18.0 mmol) followed by $K_2CO_3$ (6.20 g, 44.9 mmol). The resulting mixture was then heated at 110° C. for 1 hour. The reaction mixture was poured into ice water and extracted with EtOAc (2×). The combined organic phases were washed with brine, dried over $Na_2SO_4$, filtered, and concentrated to dryness to afford 5-2a (2.50 g, 71%). The obtained product was carried onto the next step without purification.

Step 2. 5-Nitrobenzofuran-2-carboxylic Acid (5-3a)

To a solution of 5-2a (2.50 g, 10.6 mmol) in EtOH (20 mL) was added KOH (1.19 g, 21.3 mmol) at room temperature and the resulting mixture was then heated at 85° C. for 2 hours. The reaction mixture was then cooled to room temperature and concentrated to dryness. The obtained residue was acidified with 6N HCl. The resulting suspension was filtered and the solid was washed with water (2×) and then dried under vacuum filtration to afford 5-3a (1.40 g, 63%). The material was carried onto the next step without purification.

Step 3. 5-Nitrobenzofuran (5-4a)

To a solution of 5-3a (1.4 g 6.8 mmol) in quinoline (20 mL) was added $Cu_2O$ (0.10 g, 0.68 mmol) and the resulting mixture was then heated at 200° C. for 2 hours. The reaction mixture was then cooled to room temperature and filtered through Celite® filter aid. The filtrate was diluted with water and extracted with EtOAc (2×100 mL). The combined organic phases were washed with 6N HCl (2×50 mL), dried over $Na_2SO_4$, filtered, and concentrated to dryness. The resulting residue was purified by silica gel chromatography, eluting with 3% EtOAc/hexanes, to afford 5-4a (0.72 g, 65% yield).

Step 4 to 8. 1-(5-Iodobenzofuran-3-yl)dihydropyrimidine-2,4(1H,3H)-dione (I-5)

The title compound I-5 was prepared according to the procedure described in Example 1, Step 1, Example 3, Steps 1 and 2, and Example 4, Steps 1 and 2 starting from 5-4a (0.72 g, 4.40 mmol). I-5 was obtained as an off-white solid (34 mg, 0.095 mmol). $^1H$ NMR (400 MHz, DMSO-$d_6$): δ 10.57 (s, 1H), 8.10 (s, 1H), 8.05 (d, J=1.2 Hz, 1H), 7.61 (dd, J=11.2, 1.1 Hz, 1H), 7.43 (d, J=11.2 Hz, 1H), 3.83 (t, J=8.8 Hz, 2H), 2.79-2.74 (t, J=8.8 Hz, 2H). MS $[M+H]^+$=356.9.

Example 6: 1-(6-Ethynylbenzofuran-3-yl)dihydropyrimidine-2,4(1H,3H)-dione (I-2)

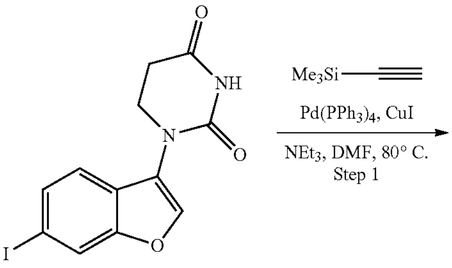

I-5

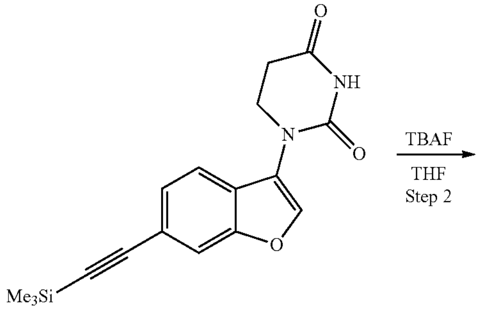

6-1a

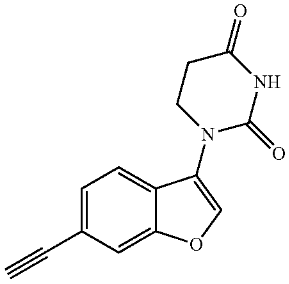

I-2

Step 1. 1-(6-((Trimethylsilyl)ethynyl)benzofuran-3-yl)dihydropyrimidine-2,4(1H,3H)-dione (6-1a)

To a degassed solution of I-5 (120 mg, 0.34 mmol) in DMF (5 mL) was added $Pd(PPh_3)_4$ (27 mg, 0.20 mmol) and $NEt_3$ (0.240 mL, 1.68 mmol) and the resulting mixture was degassed for 5 minutes with nitrogen gas. CuI (6.4 mg, 0.034 mmol) and ethynyltrimethylsilane (0.24 mL, 1.68 mmol) were then added and the reaction mixture was then heated at 80° C. for 16 hours under an atmosphere of nitrogen. The reaction mixture was cooled to room temperature and partitioned between EtOAc and water. The phases were separated and the aqueous layer was extracted with EtOAc (2×10 mL). The combined organic phases were washed with water and brine, dried over $Na_2SO_4$, filtered, and concentrated to dryness. The resulting residue was purified by silica gel chromatography, eluting with 60-65% EtOAc/hexane, to afford 6-1a (80 mg, 73% yield). MS $[M+H]^+$=327.1

Step 2. 1-(6-Ethynylbenzofuran-3-yl)dihydropyrimidine-2,4(1H,3H)-dione (I-2)

To a solution of 6-1a (60 mg, 0.18 mmol) in THF (5 mL) was added TBAF (1M in THF) (0.27 mL, 0.28 mmol) at 0° C. and the resulting mixture was then stirred at about 0° C. for 1 hour. The reaction mixture was then quenched with ice water and extracted with EtOAc (2×10 mL). The combined organic phases were dried over $Na_2SO_4$, filtered, and concentrated to dryness. The resulting residue was purified by silica gel chromatography, eluting with 55% EtOAc/hexanes to afford I-2 as a white solid (18 mg, 54% yield). $^1H$ NMR (300 MHz, DMSO-$d_6$): δ 10.57 (s, 1H), 8.23 (s, 1H), 7.76 (s, 1H), 7.61 (d, J=7.2 Hz, 1H), 7.37 (d, J=7.3 Hz, 1H), 4.24 (s, 1H), 3.84 (t, J=6.6 Hz, 2H), 2.77 (t, J=6.6 Hz, 2H). MS $[M+H]^+$=255.1.

Example 7: 1-(7-(1-Benzyl-1,2,3,6-tetrahydropyridin-4-yl)imidazo[1,2-a]pyridin-3-yl)dihydropyrimidine-2,4(1H,3H)-dione (I-8)

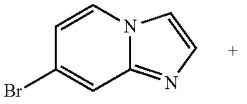

7-1a

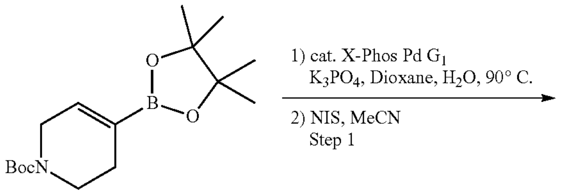

7-2a

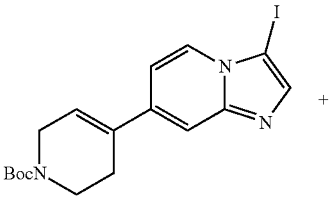

7-3a

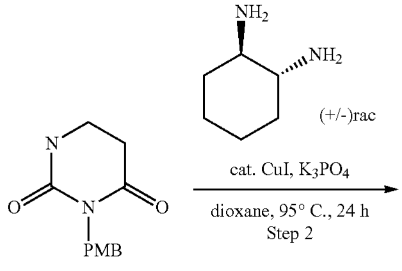

1-4a

-continued

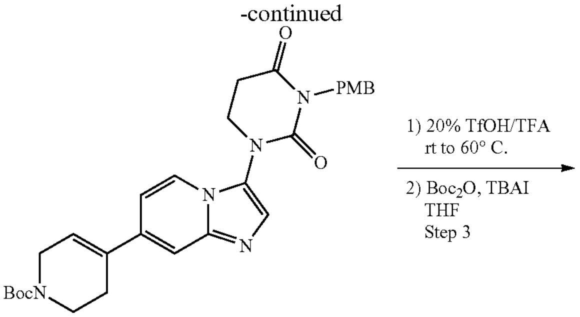

7-4a

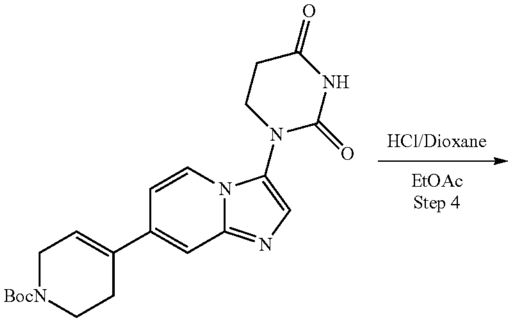

7-5a

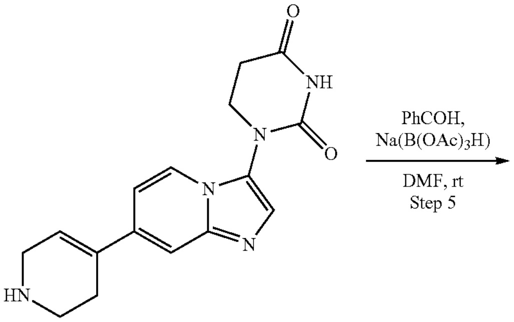

7-6a

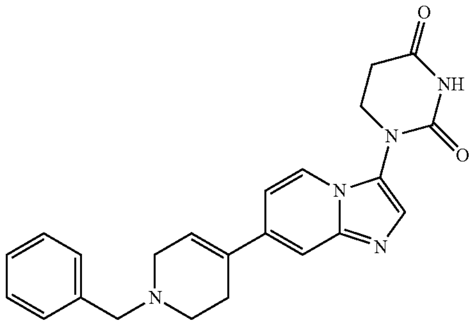

I-8

Step 1. tert-Butyl 4-(3-iodoimidazo[1,2-a]pyridin-7-yl)-3,6-dihydropyridine-1(2H)-carboxylate (7-3a)

To a 40 mL vial charged with 7-1a (504 mg, 2.56 mmol), boronate ester 7-2a (958 mg, 3.10 mmol), $K_3PO_4$ (814 mg, 3.84 mmol), and X-Phos Pd G1 (56 mg, 0.076 mmol) was added dioxane (25 mL) and $H_2O$ (1 mL, 55.5 mmol) and the resulting mixture was sealed (pressure release cap) and heated at 90° C. for 16 hours. The reaction mixture was cooled to room temperature, diluted with water (10 mL) and then filtered through Celite® filter aid. The Celite® pad was washed with EtOAc washes (50 mL) and the filtrate was then separated. The aqueous layer was extracted with EtOAc (15 mL). The combined organic phases were washed with brine, dried, over $Na_2SO_4$, filtered, and concentrated to dryness to provide the intermediate product as a brown oil (766 mg, 100%). MS $[M+H]^+$=300.1 The brown oil (766 mg, 2.56 mmol) was dissolved in MeCN (25 mL) and NIS (600 mg, 2.67 mmol) was then added portion wise over 5 min. The resulting mixture was stirred at room temperature for 30 minutes and then concentrated to dryness to afford a brown oil. The oil was purified by silica gel chromatography, eluting with 0-100% EtOAc/heptane, to provide a yellow-orange solid. 5% $K_2CO_3$ solution was added to the solid and the resulting mixture was sonicated for 1 minute. The mixture was filtered and the yellow solid was washed several times with water and then heptane. The solid was dried under vacuum filtration for 15 minutes, collected and stored under high vacuum to provide 7-3a (680 mg, 63% yield over 2 steps). $^1$H NMR (400 MHz, chloroform-d) δ 8.14 (d, J=6.3 Hz, 1H), 7.86-7.66 (m, 2H), 7.23 (s, 1H), 6.38 (s, 1H), 4.17 (d, J 13.7 Hz, 2H), 3.70 (t, J=5.6 Hz, 2H), 2.60 (s, 2H), 1.52 (s, 9H).

Step 2. tert-Butyl 4-(3-(3-(4-methoxybenzyl)-2,4-dioxotetrahydropyrimidin-1(2H)-yl)imidazo[1,2-a]pyridin-7-yl)-3,6-dihydropyridine-1(2H)-carboxylate (7-4a)

To a vial containing 7-3a (366 mg, 0.861 mmol), 1-4a (255 mg, 1.09 mmol), $K_3PO_4$ (350 mg, 1.65 mmol), and CuI (32.7 mg, 0.172 mmol) and under an atmosphere nitrogen was added dioxane (6 mL). Rac-trans-cyclohexane-1,2-diamine (19.7 mg, 0.172 mmol) was then added via micropipette and the resulting mixture was sealed (pressure relief cap) and heated at 95° C. overnight. The reaction mixture was cooled to room temperature and filtered through Celite® filter aid, washing the pad with EtOAc (3×15 mL). The filtrate was washed with water (10 mL) and brine (10 mL). The organic phase was dried over $Na_2SO_4$, filtered, and concentrated to dryness. The resulting brown residue was dissolved in MeCN (10 mL) and NIS (60 mg, 0.267 mmol) was added. The resulting mixture was stirred at room temperature for 1 hour. The reaction mixture was diluted with EtOAc (15 mL) and then quenched with 50% aq. sodium thiosulfate solution (5 mL) and water (5 mL). The phases were separated and the aqueous phase was extracted with EtOAc (20 mL). The combined organic phases were washed with brine, dried over $Na_2SO_4$, filtered, and concentrated to dryness affording a brown oil. The residue was then purified by silica gel chromatography, eluting with 0-6% MeOH/DCM, to afford 7-4a as a brown solid (240 mg, 52% yield). MS $[M+H]^+$=532.2

Step 3. tert-Butyl 4-(3-(2,4-dioxotetrahydropyrimidin-1(2H)-yl)imidazo[1,2-a]pyridin-7-yl)-3,6-dihydropyridine-1(2H)-carboxylate (7-5a)

To 7-4a (240 mg, 0.451 mmol) was added 20% TfOH in TFA (5 mL) and the resulting mixture was heated at 60° C. for 1 hour. The reaction mixture was cooled to room temperature and concentrated in vacuo to remove TFA. The resulting red residue was dissolved in water (5 mL) and then stirred at room temperature for 5 minutes. The mixture was filtered with water washes (2×5 mL). The aqueous phase was then neutralized with solid $NaHCO_3$ to ~pH 7. THF (10 mL) was added to the aqueous mixture followed by the addition of Boc-anhydride (245 μL, 1.054 mmol) and TBAI (33.4 mg, 0.090 mmol). The reaction mixture was stirred at room temperature for 1 hour and then diluted with EtOAc (15 mL). The phases were separated and the aqueous phase was extracted with EtOAc (2×15 mL). The combined organic phases were dried over $Na_2SO_4$, filtered, and concentrated to dryness. The resulting solid was purified by silica gel chromatography, eluting with 1% $Et_3N$/EtOAc, to afford 7-5a as an off-white solid (105 mg, 58% yield). $^1$H NMR (400 MHz, DMSO-$d_6$) δ 10.66 (s, 1H), 8.24 (d, J=7.2 Hz, 1H), 7.54 (s, 1H), 7.51 (s, 1H), 7.18 (dd, J=7.3, 1.6 Hz, 1H), 6.43 (bs, 1H), 4.05 (bs, 2H), 3.80 (t, J=6.7 Hz, 2H), 3.57 (t, J=5.5 Hz, 2H), 2.83 (t, J=6.6 Hz, 2H), 2.54 (bs, 2H), 1.44 (s, 9H). MS $[M+H]^+$=412.1.

Step 4. tert-Butyl 1-(7-(1,2,3,6-tetrahydropyridin-4-yl)imidazo[1,2-a]pyridin-3-yl)dihydropyrimidine-2,4 (1H,3H)-dione (7-6a)

To a room temperature suspension of 7-5a (90 mg, 0.219 mmol) in EtOAc (1.5 mL) was added HCl (4N in dioxane) (1.5 mL, 6.00 mmol) and the resulting mixture was then stirred at room temperature for 1 hour. The reaction mixture was concentrated to dryness to provide 7-6a as an off-white solid (90 mg, 100% yield), which was carried onto the next step without purification. MS $[M+H]^+$=312.1.

Step 5. tert-Butyl 1-(7-(1,2,3,6-tetrahydropyridin-4-yl)imidazo[1,2-a]pyridin-3-yl)dihydropyrimidine-2,4 (1H,3H)-dione (I-8)

To a room temperature suspension of 7-6a (37 mg, 0.106 mmol) in DMF (1 mL) was added $NaBH(OAc)_3$ (44 mg, 0.208 mmol). Benzaldehyde (0.017 mL, 0.168 mmol) was then added and the resulting mixture stirred at room temperature for 1 hour. After 1 hour, 70% conversion to the desired product was observed. An additional 1 equivalent of $NaBH(OAc)_3$ and benzaldehyde was added and the reaction mixture was stirred at room temperature for 2 hours after which time >95% conversion to the desired product was observed. The reaction mixture was slowly quenched with sat. aq. $NaHCO_3$ solution (5 mL) and then extracted with EtOAc (3×10 mL). The combined organic phases were washed with brine. Silica gel (5 g) was added to the organic phase and then concentrated to dryness. The silica gel solid was then stored under high vacuum overnight. The product was purified by silica gel flash chromatography, eluting with 3:1 EtOAc/EtOH followed by 3:1 EtOAc/EtOH with 0.1% $Et_3N$ as a modifier, to afford the desired product I-8 as an off-white solid (21 mg, 47% yield). $^1$H NMR (400 MHz, DMSO-$d_6$) δ 10.66 (s, 1H), 8.21 (d, J=7.3 Hz, 1H), 7.52 (s, 1H), 7.47 (s, 1H), 7.41-7.33 (m, 4H), 7.29 (d, J=6.0 Hz, 1H), 7.17 (dd, J=7.4, 1.8 Hz, 1H), 6.44 (d, J=3.7 Hz, 1H), 3.79 (t, J=6.7 Hz, 2H), 3.66 (s, 2H), 3.22-3.06 (m, 2H), 2.82 (t, J=6.7 Hz, 2H), 2.72 (bs, 2H), 2.57 (bs, 2H). MS $[M+H]^+$=402.4.

Example 8: 1-(7-(1-(4-(tert-Butyl)benzoyl)-1,2,3,6-tetrahydropyridin-4-yl)imidazo[1,2-a]pyridin-3-yl) dihydropyrimidine-2,4(1H,3H)-dione (I-9)

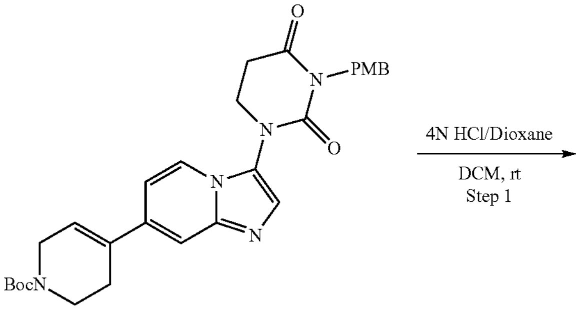

7-4a

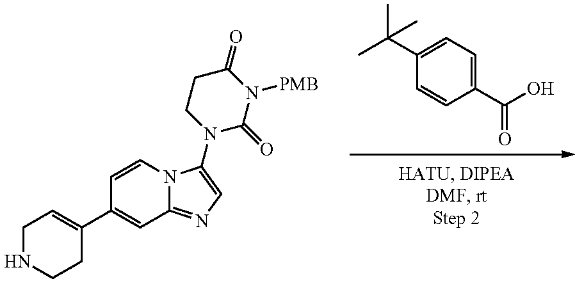

8-1a

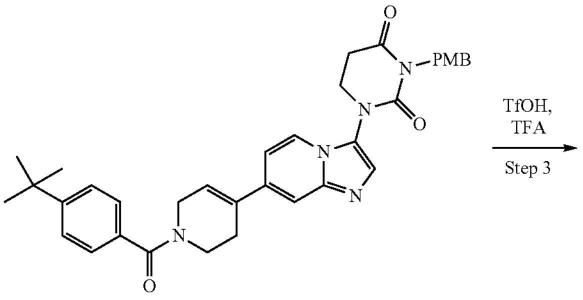

8-2a

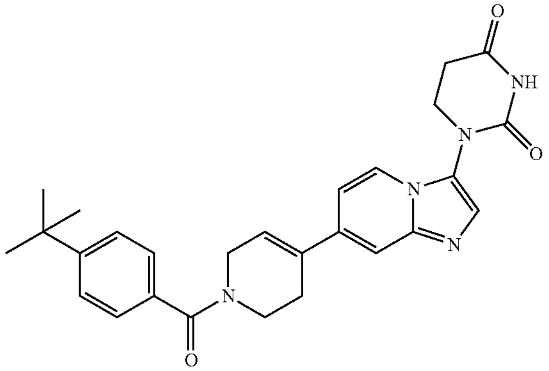

I-9

Step 1. 3-(4-Methoxybenzyl)-1-(7-(1,2,3,6-tetrahydropyridin-4-yl)imidazo[1,2-a]pyridin-3-yl)dihydropyrimidine-2,4(1H,3H)-dione (8-1a)

To a stirred solution of 7-4a (3.90 g, 7.34 mmol) in DCM (10 mL) was added 4N HCl in dioxane (5.0 mL) at 0° C. and the resulting mixture was stirred at room temperature for 16 hours. The reaction mixture was concentrated under reduced pressure to afford the 8-1a as a yellow solid (3.20 g, 93% yield), which was carried onto the next step without purification. MS $[M+H]^+$=432.2.

Step 2. 1-(7-(1-(4-(tert-Butyl)benzoyl)-1,2,3,6-tetrahydropyridin-4-yl)imidazo[1,2-a]pyridin-3-yl)-3-(4-methoxybenzyl)dihydropyrimidine-2,4(1H,3H)-dione (8-2a)

To a stirred solution of 8-1a (250 mg, 0.70 mmol) in DMF (5.0 mL) was added DIPEA (0.38 mL, 2.13 mmol), 4-(tert-butyl)benzoic acid (139 mg, 0.78 mmol), and HATU (404.0 mg, 1.06 mmol) and the resulting mixture was then stirred at room temperature overnight. Water was added and the mixture was extracted with DCM. The organic phase was separated, dried over $Na_2SO_4$, and concentrated to dryness to afford a light brown solid. The obtained solid was purified by silica gel chromatography, eluting with 5% MeOH/DCM, to afford 8-2a as an off-white solid (200 mg, 47% yield). MS $[M+H]^+$=592.0.

Step 3. 1-(7-(1-(4-(tert-Butyl)benzoyl)-1,2,3,6-tetrahydropyridin-4-yl)imidazo[1,2-a]pyridin-3-yl)dihydropyrimidine-2,4(1H,3H)-dione (I-9)

To a stirred solution of 8-2a (200 mg, 0.33 mmol) in TFA (4.0 mL) was added TfOH (1.0 mL) and the resulting mixture was stirred for 18 hours at room temperature. The reaction mixture was then concentrated to dryness. The resulting residue was diluted with 10% MeOH in DCM and washed with sat aq. $NaHCO_3$ solution. The phases were separated and the organic phase was dried over $Na_2SO_4$, filtered, and concentrated to dryness. The residue was then purified by silica gel chromatography, eluting with 10% MeOH/DCM, to afford I-9 as a brown solid (70 mg, 35% yield). $^1$H NMR ($CDCl_3$, 400 MHz): 7.81 (s, 1H), 7.73 (d, J=6.8 Hz, 1H, d), 7.56 (1H, s), 7.54 (s, 1H), 7.46-7.39 (m, 3H), 7.03-6.99 (bs, 1H), 6.36 (s, 1H), 4.43 (s, 1H), 4.42 (bs, 1H), 4.00 (bs, 1H), 3.92 (t, J=6.9 Hz, 2H), 3.70 (bs, 2H), 2.95 (t, J=6.9 Hz, 2H), 2.61 (bs, 2H), 1.34 (S, 9H). MS $[M+H]^+$=472.0.

Example 9: 1-(6-(1-Benzylpiperidin-4-yl)imidazo[1,2-a]pyridin-3-yl)dihydropyrimidine-2,4(1H,3H)-dione (I-10)

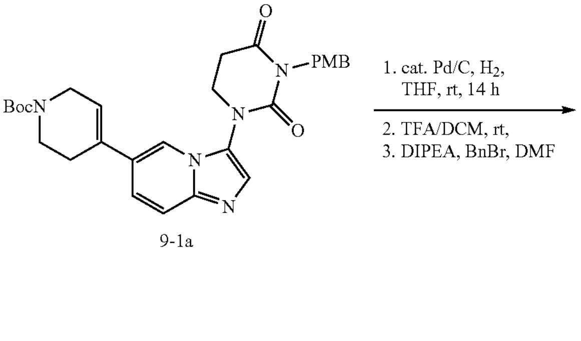

9-1a

-continued

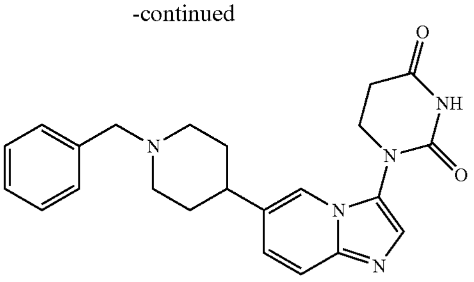

I-10

Intermediate 9-1a was synthesized according to the procedure described for the synthesis of 7-4a in Example 7, Step 2 starting from 6-bromoimidazo[1,2-a]pyridine (369 mg, 1.97 mmol) to provide 9-1a as a brown amorphous solid (204 mg, 0.34 mmol). MS $[M+H]^+$=532.3.

To a room temperature solution of 9-1a (74 mg, 0.18 mmol) in THF, was added Pd/C (25 mg, 0.023 mmol) and the resulting mixture was purged with hydrogen gas for 5 minutes and stirred under an atmosphere of hydrogen using a gas balloon overnight. The reaction mixture was then purged with nitrogen gas and filtered through Celite® filter aid, washing the pad with DCM (60 mL). The filtrate was concentrated to dryness and the resulting residue was dissolved in DCM (1.5 mL). TFA (300 μL, 3.89 mmol) was added and the reaction mixture was stirred at room temperature for 30 minutes and then concentrated to dryness. The resulting residue was stored under high vacuum for 1 hour and dissolved in DMF (1.5 mL). DIPEA (117 μL, 0.668 mmol) was added followed by addition of BnBr (22 μL, 0.187 mmol). The reaction mixture was stirred at room temperature for 20 minutes and then quenched with 1N HCl (3 mL) and filtered. The aqueous mixture was washed with EtOAc (2×5 mL) and DCM (2×5 mL), neutralized to a pH of 7 with solid $NaHCO_3$, and then extracted with EtOAc (4×10 mL). The combined organic phases were then dried over $Na_2SO_4$, filtered, and concentrated to dryness. The resulting residue was purified by silica gel chromatography, eluting with 0-20% IPA/DCM, to afford the desired product I-10 as a cream-colored solid (26 mg, 32% yield, broad peak at 20% IPA/DCM). $^1$H NMR (400 MHz, DMSO-$d_6$) δ 10.62 (s, 1H), 8.10 (s, 1H), 7.52 (d, J=8.1 Hz, 2H), 7.38-7.24 (m, 6H), 3.78 (t, J=6.7 Hz, 2H), 3.58-3.42 (m, 2H), 3.07-2.78 (m, 4H), 1.86-1.64 (m, 5H). MS $[M+H]^+$=404.2.

Example 10: 1-(6-Chloropyrazolo[1,5-a]pyridin-3-yl)dihydropyrimidine-2,4(1H,3H)-dione (I-7)

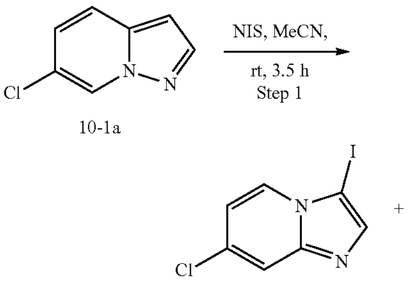

10-1a 10-2a

+

-continued

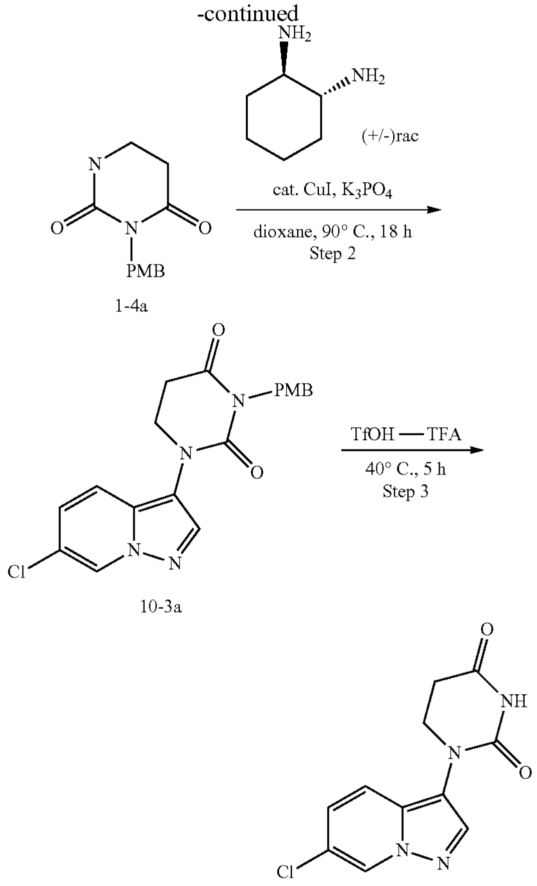

1-4a 10-3a

I-7

Step 1. 6-Chloro-3-iodopyrazolo[1,5-a]pyridine (10-2a)

To a stirred solution of 10-1a (500 mg, 3.28 mmol) in MeCN (16.4 mL) was added NIS (737 mg, 3.28 mmol) and the resulting mixture was stirred at room temperature for 3.5 hours. The reaction mixture was concentrated onto silica gel. The crude material was purified by silica gel chromatography, eluting with 0-10% EtOAc/heptane, to afford 10-2a as an off-white solid (796 mg, 87% yield). $^1$H NMR (400 MHz, DMSO-$d_6$) δ 9.12 (dd, J=1.7, 0.6 Hz, 1H), 8.16 (s, 1H), 7.59-7.53 (m, 1H), 7.38 (dd, J=9.4, 1.8 Hz, 1H). MS $[M+H]^+$=279.0.

Step 2. 1-(6-Chloropyrazolo[1,5-a]pyridin-3-yl)dihydropyrimidine-2,4(1H,3H)-dione (10-3a)

Nitrogen gas was bubbled through a stirred suspension of 10-2a (0.796 g, 2.86 mmol), 3-(4-methoxybenzyl)dihydropyrimidine-2,4(1H,3H)-dione (1-4a, 1 g, 4.29 mmol), CuI (136 mg, 0.715 mmol), and $K_3PO_4$ (1.52 g, 7.15 mmol) in dioxane (14.3 mL). (+/−)-trans-1,2-Diaminocyclohexane (86 μL, 0.715 mmol) was then added and the resulting mixture was sparged with nitrogen for a further 5 minutes before it as capped and heated at 90° C. for ~18 hours. The reaction mixture was then allowed to cool to room temperature and diluted with water (100 mL). 28% $NH_4OH$ (aq) (5 mL) was added and the resulting mixture was extracted with EtOAc (2×100 mL). The combined organic phases were dried over $MgSO_4$, filtered, and concentrated in vacuo to afford a brown oily residue. The crude material was pre-adsorbed onto silica gel and purified by silica gel flash chromatography, eluting with 0-5% MeOH/DCM, to afford a brown solid. The solid was sonicated in DCM (10 mL) and the resulting suspension was left to slurry at room temperature for 2 hours. The resulting solid was removed by vacuum filtration and washed with small amounts of DCM. The filtrate was concentrated in vacuo to afford 10-3a as a pale brown foam (1.04 g, 71% yield at 75% purity). $^1$H NMR (400 MHz, DMSO-$d_6$) δ 9.00 (dd, J=1.8, 0.8 Hz, 1H), 8.11 (s, 1H), 7.62 (dd, J=9.6, 0.9 Hz, 1H), 7.32 (dd, J=9.5, 1.8 Hz, 1H), 7.27-7.21 (m, 2H), 6.89-6.85 (m, 2H), 4.82 (s, 2H), 3.81 (t, J=6.7 Hz, 2H), 3.72 (s, 3H), 2.96 (t, J=6.8 Hz, 2H). MS $[M+H]^+$=385.1.

Step 3. 1-(6-Chloropyrazolo[1,5-a]pyridin-3-yl)dihydropyrimidine-2,4(1H,3H)-dione (I-7)

To a vial containing 10-3a (200 mg, 0.39 mmol) was added 10% TfOH in TFA (2.3 mL) and the resulting solution was stirred at 40° C. for ~6 hours. The reaction mixture was cooled in an ice bath and then quenched by the dropwise addition (over about an hour) of saturated $NaHCO_3$(aq) (100 mL). The reaction mixture was diluted with water (50 mL) and extracted with a 4:1 mixture of DCM:iPrOH (50 mL). The organic phase was separated, dried over $MgSO_4$, filtered, and concentrated in vacuo to afford an orange/brown solid. The crude material was pre-adsorbed onto silica gel and purified by silica gel flash chromatography, eluting with 1-6% MeOH/DCM, to afford I-7 as a pale brown/tan solid (92 mg, 87% yield). $^1$H NMR (400 MHz, DMSO-$d_6$) δ 10.47 (s, 1H), 8.99 (dd, J=1.7, 0.7 Hz, 1H), 8.09 (s, 1H), 7.66 (dd, J=9.5, 0.9 Hz, 1H), 7.31 (dd, J=9.5, 1.8 Hz, 1H), 3.78 (t, J=6.7 Hz, 2H), 2.77 (t, J=6.7 Hz, 2H). MS $[M+H]^+$=265.2.

Example 11: 1-(6-(3-(dimethylamino)prop-1-yn-1-yl)benzofuran-3-yl)dihydropyrimidine-2,4(1H,3H)-dione (I-11)

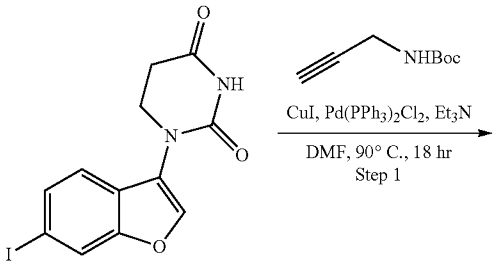

I-5

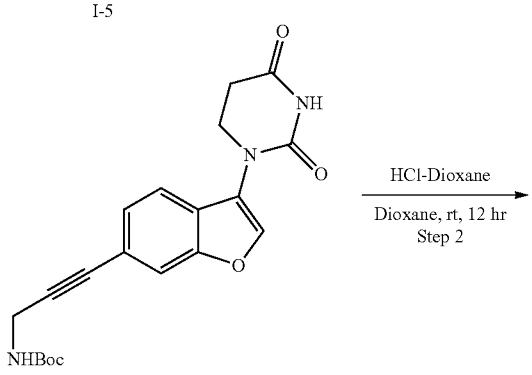

11-1

-continued

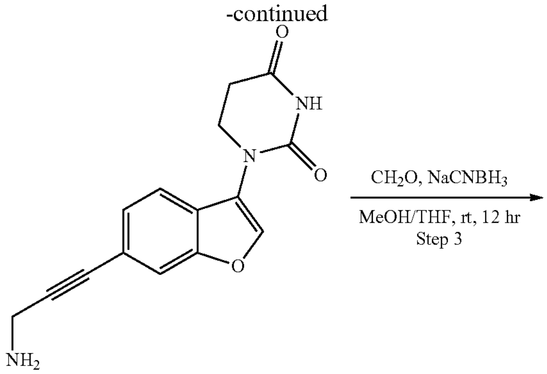

11-2

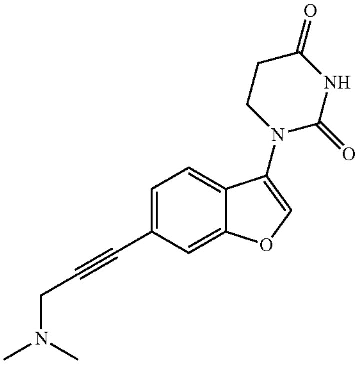

I-11

Step 1. tert-Butyl (3-(3-(2,4-dioxotetrahydropyrimidin-1(2H)-yl)benzofuran-6-yl)prop-2-yn-1-yl)carbamate (11-1)

I-5 (150 mg, 0.42 mmol, Example 5) was dissolved in DMF (3 mL) and the resulting mixture was degassed with argon gas for 10 min. CuI (8.0 mg, 0.042 mmol), Pd(PPh)$_2Cl_2$ (15 mg, 0.021 mmol), $Et_3N$ (0.58 mL, 4.2 mmol) and N-Boc propargyl amine (71.9 mg, 0.46 mmol) were then added and the resulting mixture was degassed with argon for 5 min and then heated at 90° C. for 18 h. The reaction mixture was then concentrated to dryness under high vacuum and EtOAc was added to the resulting solid mass. The crude material was purified via silica gel chromatography, eluting with 70-80% EtOAc/hexane, to afford 11-1 as a white solid (96 mg, 90% purity, 59% yield). MS $[M+H]^+$=384.2.

Step 2. 1-(6-(3-Aminoprop-1-yn-1-yl)benzofuran-3-yl)dihydropyrimidine-2,4(1H,3H)-dione (11-2)

To a stirred solution of 11-1 in dioxane (5 mL) at 0° C. was added HCl (4N in dioxane, 1 mL) and the resulting mixture was stirred at room temperature overnight. The reaction mixture was then concentrated under reduced pressure. The crude product was washed with MeCN, EtOAc, and $CHCl_3$ to afford 11-2 as a solid (50 mg, 94% purity, 66% yield) which was carried onto the next step without further purification. MS $[M+H]^+$=284.1.

Step 3. 1-(6-(3-(Dimethylamino)prop-1-yn-1-yl)benzofuran-3-yl)dihydropyrimidine-2,4(1H,3H)-dione (I-11)

To a stirred solution of 11-2 (70 mg, 85% purity, 0.21 mmol) in MeOH/THF (1:1 mixture, 2 mL) at room temperature was added $NaCNBH_3$ (20.6 mg, 0.32 mmol) and the resulting mixture was stirred at room temperature for 5 min. Formaldehyde (0.01 mL, 37% in $H_2O$, 0.67 mmol) was then added and the reaction mixture was then stirred at room temperature overnight. The reaction mixture was concentrated to dryness. The resulting residue was purified by silica gel chromatography, eluting with 10% MeOH/DCM, to afford I-11 as solid (40 mg, 67% yield). $^1$H NMR (400 MHz, $CDCl_3$): δ 7.91 (s, 1H), 7.80 (s, 1H), 7.59 (s, 1H), 7.43 (m, 1H), 7.35 (m, 1H), 3.95-3.89 (m, 2H), 3.50 (s, 2H), 2.91-2.89 (m, 2H), 2.40 (s, 6H). MS $[M+H]^+$=312.2.

Example 12: N-benzyl-3-(2,4-dioxotetrahydropyrimidin-1(2H)-yl)benzofuran-6-carboxamide (I-12)

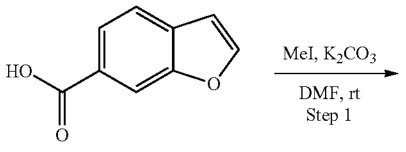

12-1

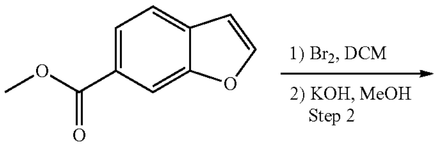

12-2

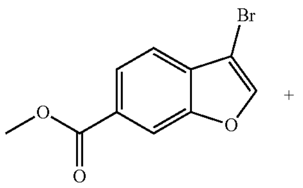

12-3

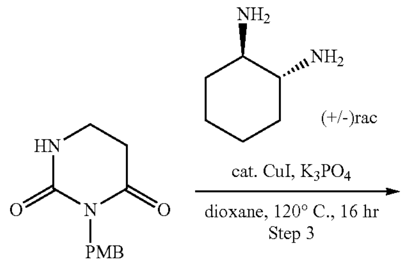

1-4a

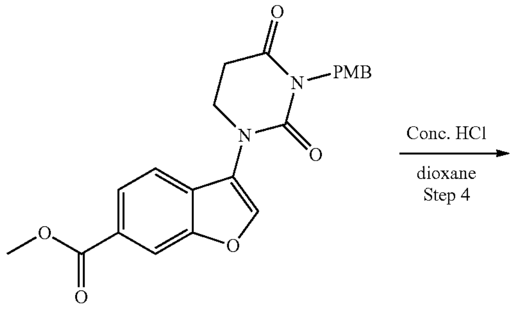

12-4

-continued

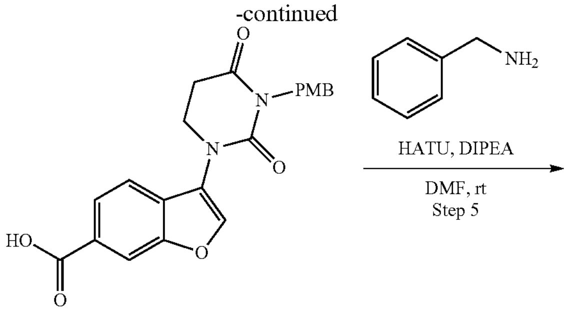

12-5

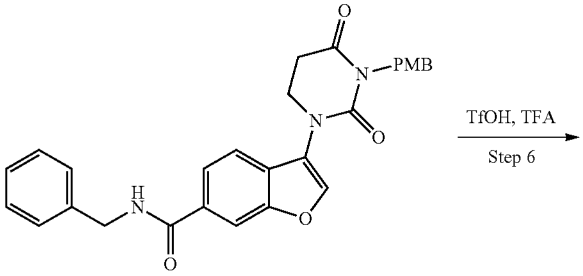

12-6

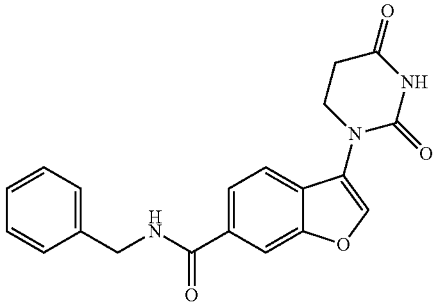

I-12

Step 1. Methyl benzofuran-6-carboxylate (12-2)

To a stirred solution of benzofuran-6-carboxylic acid (12-1, 4 g, 24.7 mmol) in DMF (50 mL) was added MeI (2.3 mL, 37.0 mmol) followed by $K_2CO_3$ (6.8 g, 49.3 mmol) under an atmosphere of nitrogen at 0° C. and the resulting mixture was allowed to stir and warm up to room temperature over 16 h. The reaction mixture was then diluted with EtOAc and water. The phases were separated and the aqueous phase was extracted with EtOAc (2×50 mL). The combined organic phases were washed with brine (2×50 mL), dried over $Na_2SO_4$, filtered, and concentrated to dryness to afford crude 12-2, which was taken onto the next step without further purification. $^1$H NMR (300 MHz, DMSO-$d_6$): δ 8.21 (d, J=1.8 Hz, 1H), 8.1 (bs, 1H), 7.87 (dd, J=8.1, 1.8 Hz, 1H), 7.75 (d, J=8.1 Hz, 1H), 7.07-7.06 (m, 1H), 3.85 (s, 3H).

Step 2. Methyl 3-bromobenzofuran-6-carboxylate (12-3)

12-3 was prepared according to the procedure described for 1-2a in Example 1 starting from 12-2 (2.5 g, 14.2 mmol) and using $K_2CO_3$ instead of KOH to afford 12-3 (2.6 g, 72% yield). $^1$H NMR (300 MHz, DMSO-$d_6$): δ 8.53 (s, 1H), 8.21 (s, 1H), 7.97 (d, J=8.1 Hz, 1H), 7.67 (d, J=8.4 Hz, 1H), 3.88 (s, 3H).

Step 3. Methyl 3-(3-(4-methoxybenzyl)-2,4-dioxotetrahydropyrimidin-1(2H)-yl)benzofuran-6-carboxylate (12-4)

12-4 was prepared according to the procedure described for 1-5a in Example 1 starting from 12-3 (1.3 g, 5.1 mmol) and 1-4a (1.6 g, 6.6 mmol). The crude material was purified by silica gel chromatography eluting with 50% EtOAc/hexane to afford 12-4 as a yellow oil (0.9 g, 43% yield). MS $[M+H]^+$=409.1.

Step 4. 3-(3-(4-methoxybenzyl)-2,4-dioxotetrahydropyrimidin-1(2H)-yl)benzofuran-6-carboxylic Acid (12-5)

To a solution of 12-4 (0.5 g, 1.2 mmol) in dioxane (5 mL) was added concentrated HCl (5 mL) at 0° C. and the resulting mixture was then stirred at 50° C. for 40 h (monitored by TLC). The reaction mixture was then concentrated to dryness. The crude material was purified by silica gel chromatography eluting with 4-5% MeOH/DCM to afford 12-5 (0.42 g, 40% purity by LC-MS), which was taken onto next step without further purification. MS $[M+H]^+$=394.9.

Step 5. N-benzyl-3-(3-(4-methoxybenzyl)-2,4-dioxotetrahydropyrimidin-1(2H)-yl)benzofuran-6-carboxamide (12-6)

To a stirred solution of 12-5 (0.1 g, 40% purity) in DMF (5 mL) were added benzyl amine (0.03 mL, 0.3 mmol) and HATU (0.14 g, 0.38 mmol) followed by DIPEA (0.22 mL, 1.26 mmol) at rt and the resulting mixture was stirred at rt for 16 h. The reaction mixture was then concentrated to dryness in vacuo. The resulting residue was purified by silica gel chromatography eluting with 60% EtOAc/heptane, to afford 12-6 (0.14 g, ca. 29% purity by LC-MS), which was taken onto next step without further purification. MS $[M+H]^+$=484.2.

Step 6N-benzyl-3-(2,4-dioxotetrahydropyrimidin-1(2H)-yl)benzofuran-6-carboxamide (I-12)

Final deprotection was done according to the procedure described for I-6 in Example 3 starting from 12-6 (0.14 g, 29% purity) to afford I-12 as a yellow solid (20 mg, 99% purity). $^1H$ NMR (400 MHz, DMSO-$d_6$): δ 10.59 (s, 1H), 9.14 (t, J=5.6 Hz, 1H), 8.27 (s, 1H), 8.13 (s, 1H), 7.86 (dd, J=8.0, 1.2 Hz, 1H), 7.69 (d, J=8.4 Hz, 1H), 7.34-7.33 (m, 4H), 7.26-7.23 (m, 1H), 4.52 (d, J=6.0 Hz, 2H), 3.87 (t, J 6.4 Hz, 2H), 2.78 (t, J=6.6 Hz, 2H). MS $[M+H]^+$=363.8.

Example 13: 1-(6-Methylbenzo[d]isoxazol-3-yl)dihydropyrimidine-2,4(1H,3H)-dione (I-13)

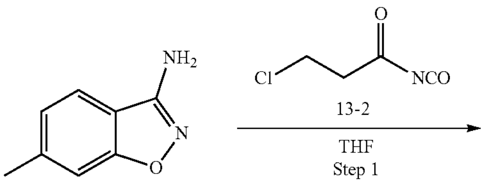

13-1
13-2

-continued

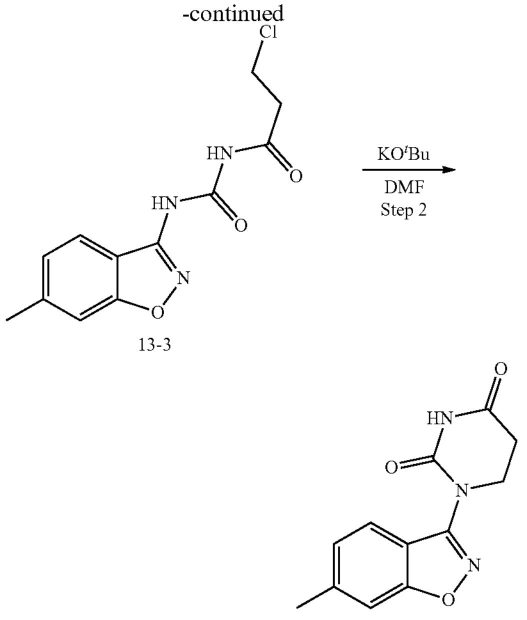

13-3
I-13

Step 1. 3-Chloro-N-((6-methylbenzo[d]isoxazol-3-yl)carbamoyl)propanamide (13-3)

A solution of 3-chloropropanoyl isocyanate (13-2, 0.45 g, 3.4 mmol; see Bioorg. Med. Chem. 2009, 17, 3873-3878) in THF (2 mL) was added dropwise to a solution of 6-methylbenzo[d]isoxazol-3-amine (13-1, 0.25 g, 1.7 mmol) in THF (Volume: 8.4 ml) at rt and the resulting mixture was stirred at rt for 15 min. The reaction mixture was then diluted with EtOAc and quenched with water. The phases were separated and the organic phase was washed with brine, dried over $Na_2SO_4$, filtered, and concentrated to provide crude 3-chloro-N-((6-methylbenzo[d]isoxazol-3-yl)carbamoyl)propanamide (13-3) as a white solid which was used in the next step without further purification. MS $[M+H]^+$=282.2.

Step 2. 1-(6-Methylbenzo[d]isoxazol-3-yl)dihydropyrimidine-2,4(1H,3H)-dione (I-13)

Potassium tert-butoxide (284 mg, 2.53 mmol) was added to a solution of crude 3-chloro-N-((6-methylbenzo[d]isoxazol-3-yl)carbamoyl)propanamide (13-3, 475 mg, 1.687 mmol) in DMF (17 mL) at rt and the resulting mixture was stirred at rt for 5 min. The reaction mixture was then diluted with EtOAc and quenched with ~1.5 mL of 2N aqueous HCl solution. Water was added and the phases were separated. The aqueous phase was extracted with EtOAc and the combined organic phases were washed with water and brine and then dried over $Na_2SO_4$, filtered, and concentrated in vacuo. The crude product was dissolved in DMSO and purified by reverse-phase HPLC ($MeCN/H_2O$ with 0.1% TFA modifier) to provide the trifluoroacetate salt of 1-(6-methylbenzo[d]isoxazol-3-yl)dihydropyrimidine-2,4(1H,3H)-dione (I-13, 5.5 mg, 15 umol, 1% yield). MS m/z [M+H]*=246.2. $^1H$ NMR (400 MHz, DMSO-$d_6$) δ 10.85 (s, 1H), 7.66-7.55 (m, 2H), 7.48 (dd, J=8.7, 1.7 Hz, 1H), 4.05 (t, J=6.6 Hz, 2H), 2.79 (t, J=6.6 Hz, 2H), 2.42 (s, 3H).

Example 14: 1-(5-Chlorobenzo[d]isoxazol-3-yl) dihydropyrimidine-2,4(1H,3H)-dione (I-14)

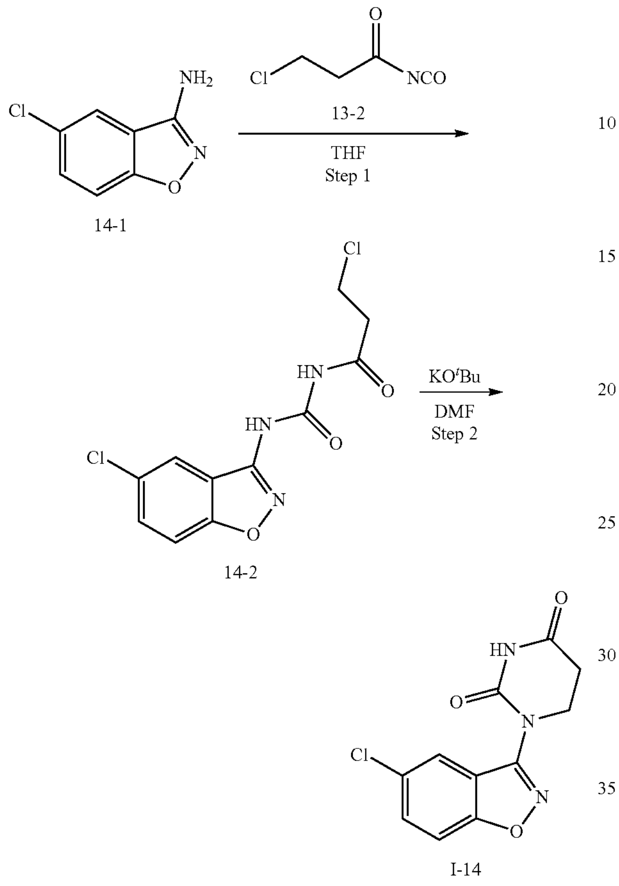

Step 1. 3-Chloro-N-((5-chlorobenzo[d]isoxazol-3-yl)carbamoyl)propanamide (14-2)

A solution of 3-chloropropanoyl isocyanate (13-2, 0.40 g, 3.0 mmol; see Bioorg. Med. Chem. 2009, 17, 3873-3878) in THF (2 mL) was added dropwise to a solution of 5-chlorobenzo[d]isoxazol-3-amine (14-1, 0.25 g, 1.7 mmol) in THF (Volume: 7.4 ml) at rt and the resulting mixture was stirred at rt for 15 min. The reaction mixture was then diluted with EtOAc and quenched with water. The phases were separated and the organic phase was washed with brine, dried over $Na_2SO_4$, filtered, and concentrated to give crude 3-chloro-N-((5-chlorobenzo[d]isoxazol-3-yl)carbamoyl) propanamide (14-2) as a white solid, which was used in the next step without further purification. MS $[M+H]^+$=302.1.

Step 2. 1-(5-chlorobenzo[d]isoxazol-3-yl)dihydro-pyrimidine-2,4(1H,3H)-dione (I-14)

Potassium tert-butoxide (250 mg, 2.23 mmol) was added to a solution of crude 3-chloro-N-((5-chlorobenzo[d]isoxazol-3-yl)carbamoyl)propanamide (14-2, 448 mg, 1.48 mmol) in DMF (14 mL) at rt and the resulting mixture was stirred at rt for 5 min. The reaction mixture was then diluted with EtOAc and quenched with ~1.5 mL of 2N aqueous HCl solution. Water was added and the phases were separated. The aqueous phase was extracted with EtOAc and the combined organic phases were washed with water and brine, and then dried over $Na_2SO_4$, filtered, and concentrated in vacuo. The crude product was dissolved in DMSO and purified by reverse-phase HPLC ($MeCN/H_2O$ with 0.1% TFA modifier) to provide the trifluoroacetate salt of 1-(5-chlorobenzo[d]isoxazol-3-yl)dihydropyrimidine-2,4(1H, 3H)-dione (I-14, 16 mg, 39 umol, 3% yield). MS $[M+H]^+$ 266.2. $^1H$ NMR (400 MHz, DMSO-$d_6$) δ 10.91 (s, 1H), 7.92 (dd, J=2.1, 0.7 Hz, 1H), 7.85-7.77 (m, 1H), 7.70 (ddd, J=9.0, 2.2, 0.6 Hz, 1H), 4.07 (t, J=6.6 Hz, 2H), 2.79 (t, J=6.6 Hz, 2H).

Example 15: 1-(6-(4-Methylphenethoxy)benzo[d] isoxazol-3-yl)dihydropyrimidine-2,4(1H,3H)-dione (I-15)

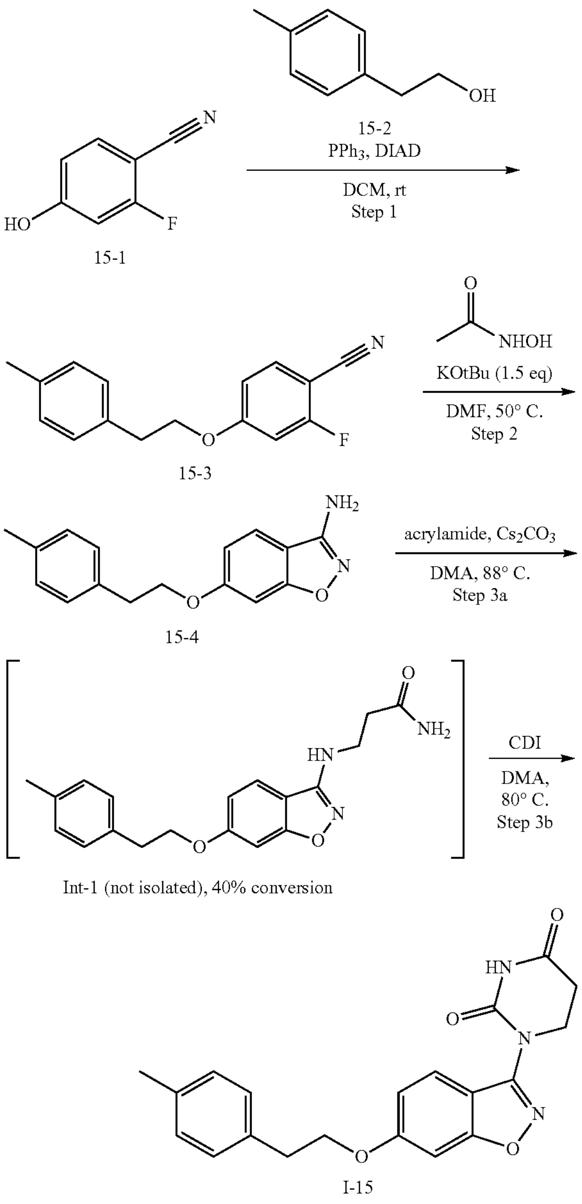

Step 1. 2-Fluoro-4-(4-methylphenethoxy)benzonitrile (15-3)

2-fluoro-4-hydroxybenzonitrile (15~1, 155 mg, 1.13 mmol) was dissolved in DCM (10 mL). 2-(p-tolyl)ethan-1-ol (15-2, 0.2 mL, 1.43 mmol) was then added via micropipette followed by addition of $PPh_3$ (384 mg, 1.464 mmol). The reaction mixture was stirred at room temperature for 5 min then a solution of DIAD (0,273 mL, 1.32 mmol) in DCM (5 ml) was then added dropwise via addition funnel After complete addition, the reaction mixture was stirred at room temperature for 5 min (TLC control) and then concentrated to dryness. The resulting residue was purified by silica gel chromatography, eluting with 0-25% EtOAc/heptane, to afford 15-3 as a white solid (282 mg 98% yield). $^1H$ NMR (400 MHz, $CDCl_3$) δ 7.49 (Id, 8.8, 7.4 Hz), 7.17-7.12 (m 4H) 6.74 (dd, J=8.8, 2.5 Hz, 1H). 668 (dd, J=11.2, 2.4 Hz, 1H), 4.18 (t, J=6.9 Hz, 2H), 3.07 (t, J=7.0 Hz, 2H), 2.34 (s, 3H).

Step 2. 6-(4-Methylphenethoxy)benzo[d]isoxazol-3-amine (15-4)

KO$^t$Bu (200 mg, 1.782 mmol) was weighed in a vial and then dry DMF (8 mL) was added followed by N-hydroxyacetamide (129 mg, 1,718 mmol) and the resulting mixture was stirred at room temperature for 30 min. A solution of 15-3 (277 mg, 1.085 mmol) in DMF (3 mL) was then added to the suspension all at once. The reaction mixture was then heated at 50° C. overnight (75% conversion) and was then quenched with sat. aq. $NH_4Cl$ solution (10 mL) and diluted with water (5 mL). The mixture was extracted with EtOAc (2×20 mL). The combined organic phases were washed with water (2×10 mL) and brine (10 mL), dried over $Na_2SO_4$, filtered, and concentrated to dryness. The resulting colorless oil was purified by silica gel chromatography, eluting with 0-45% EtOAc/heptane, to afford 154 as a white solid (156 rug, 54% yield). MS $[M+H]^+$=269.2.

Step 3a and 3b. 1-(6-(4-Methylphenethoxy)benzo[d]isoxazol-3-yl)dihydropyrimidine-2,4(1H,3H)-dione (1-15)

A mixture of 15-4 (101 mg, 0.376 mmol), acrylamide (36 mg, 0.506 mmol), and $Cs_2CO_3$ (251 mg, 0.770 mmol) in DMA (3.5 mL) was heated at 88° C. for 24 hrs. 40% conversion to Int-1 (MS $[M+H]^+$=340) was observed along with 10-15% bisalkylation (MS $[M+H]^+$=411.3), The resulting mixture was cooled to room temperature and then CDT (122 Mg. 0.753 mmol) was added all at once. The reaction mixture was then heated at 80° C. for 2.5 hrs and then cooled to room temperature, diluted with EtOAc (10 mL) and filtered through Celite® Filter aid with EtOAc wash (10 mL). The organic phase was washed with 1N HCl (2×10 mL), water (2×10 mL) and brine (10 mL), dried over $Na_2SO_4$, filtered, and concentrated to dryness. The resulting yellow oil was purified by silica gel chromatography, eluting with 0-20% EtOAc/DCM, to afford 1-15 as a white solid (12 mg, 8% yield). H NMR (400 MHz, DMSO-$d_6$) δ 10.86 (s, 1H), 7.69 (d, J=8.9 Hz, 1H), 7.27 (d, J=2.2 Hz, 1H), 7.22 (d, 7.9 Hz, 2H), 7.12 (d, J=7.8 Hz, 2H), 6.93 (dd, J=9.0, 2.1 Hz, 1H), 4.27 t, J=68 Hz, 2H), 4.03 (t, J=6.6 Hz, 2H), 3.03 (t, J=6.8 Hz, 2H), 2.78 (d, J=6.6 Hz, 2H), 2.27 (s, 3H). MS $[M+H]^+$=366.4.

Example 16: 1-(6-(1-benzylpiperidin-4-yl)quinolin-3-yl)pyrimidine-2,4(1H,3H)-dione (I-16)

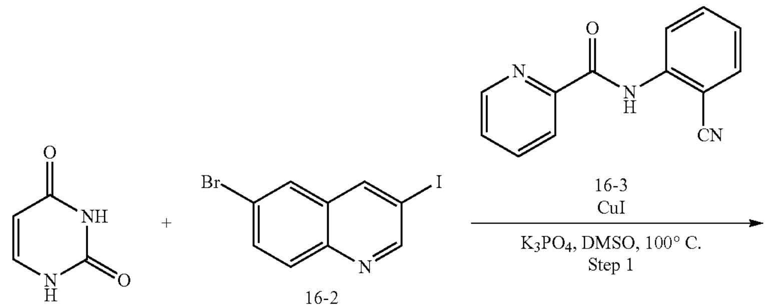

16-1 16-2

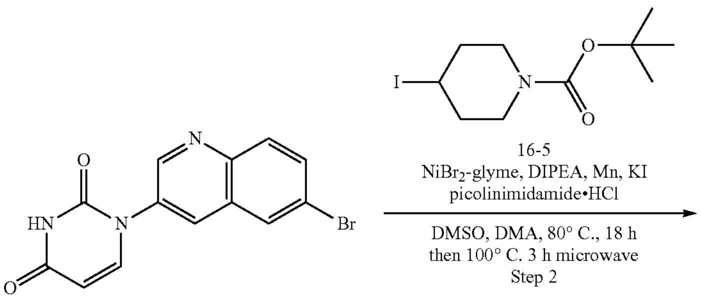

16-4

-continued

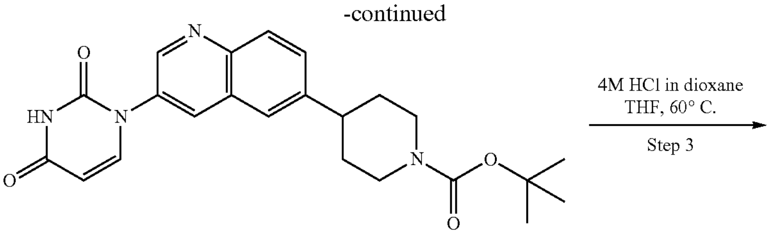

16-6

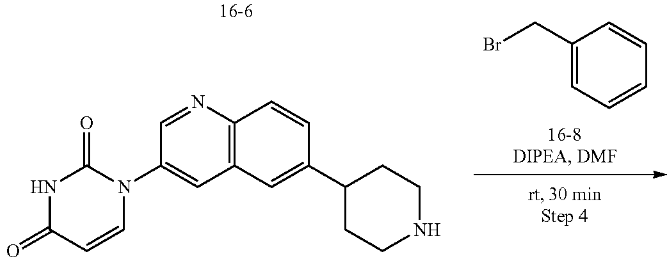

16-7

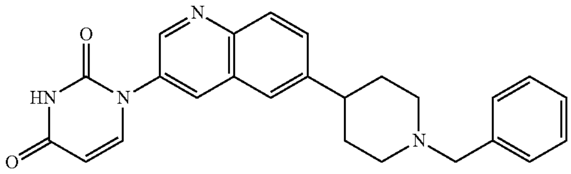

I-16

Step 1. 1-(6-Bromoquinolin-3-yl)pyrimidine-2,4 (1H,3H)-dione (16-4)

To a 10 mL-20 mL microwave vial was added N-(2-cyanophenyl)picolinamide (16-3, 134 mg, 0.599 mmol), pyrimidine-2,4(1H,3H)-dione (16-1, 403 mg, 3.59 mmol), 6-bromo-3-iodoquinoline (16-2, 1000 mg, 2.99 mmol), CuI (57 mg, 0.30 mmol), $K_3PO_4$ (1335 mg, 6.29 mmol) and DMSO (15 mL). Nitrogen gas was bubbled through the resulting mixture for 3 min and then it was sealed and sonicated. The resulting mixture was microwaved for 20 h at 100° C. and the solids were filtered off and washed with acetone. The solids were then washed with water and acetone once more and then dried under reduced pressure to provide product 16-4 (756 mg, 2.139 mmol, 71.4% yield). $^1$H NMR (400 MHz, DMSO-$d_6$) δ 8.93 (d, J=2.5 Hz, 1H), 8.33-8.20 (m, 2H), 7.96 (d, J=8.9 Hz, 1H), 7.85 (dd, J=8.9, 2.3 Hz, 1H), 7.49 (d, J=7.6 Hz, 1H), 5.46 (d, J=7.6 Hz, 1H). MS $[M+H]^+$=318.9.

Step 2 tert-butyl 4-(3-(2,4-dioxo-3,4-dihydropyrimidin-1(2H)-yl)quinolin-6-yl)piperidine-1-carboxylate (16-6)

To a 40 mL dram vial was added 1-(6-bromoquinolin-3-yl)pyrimidine-2,4(1H,3H)-dione (16-4, 430 mg, 1.35 mmol), tert-butyl 4-iodopiperidine-1-carboxylate (16-5, 547 mg, 1.76 mmol), $NiBr_2$.glyme (42 mg, 0.14 mmol), picolinimidamide·HCl (21 mg, 0.14 mmol), manganese (223 mg, 4.05 mmol), and KI (337 mg, 2.027 mmol). DMA (10 mL) was then added, followed by DIPEA (24 ul, 0.14 mmol) and the resulting mixture was degassed with nitrogen for 1 min, and then vigorously stirred for 18 h at 80° C. The reaction mixture was transferred to a 10-20 mL microwave vessel, DMSO (2 mL) was added and nitrogen gas was bubbled into the mixture for 1 min. The vial was then microwaved for 3 h at 100° C. The reaction mixture was filtered through a pad of Celite® filter aid and washed with EtOAc, and the filtrate was poured into water (200 mL). After stirring the resulting aqueous mixture for 20 min, the organic phase was separated. The aqueous phase was extracted with EtOAc (×2) and the combined organic phases were concentrated under reduced pressure and azeotroped with heptane. The crude material was purified by silica gel flash chromatography eluting with 0-100% EtOAc in heptane to provide product 16-6 (30 mg, 0.071 mmol, 5% yield) as a yellow oil. $^1$H NMR (400 MHz, DMSO-$d_6$) δ 11.61 (d, J=2.2 Hz, 1H), 8.88 (d, J=2.4 Hz, 1H), 8.41 (d, J=2.5 Hz, 1H), 8.03 (d, J=8.7 Hz, 1H), 7.91-7.84 (m, 2H), 7.78 (dd, J=8.8, 2.0 Hz, 1H), 5.79 (dd, J=7.9, 2.3 Hz, 1H), 4.13 (d, J=12.8 Hz, 2H), 2.91 (m, 3H), 1.88 (d, J=12.8 Hz, 2H), 1.68-1.52 (m, 2H), 1.43 (s, 9H). MS $[M+H]^+$=423.5.

Step 3. 1-(6-(Piperidin-4-yl)quinolin-3-yl)pyrimidine-2,4(1H,3H)-dione hydrochloride Salt (16-7)

To a solution of tert-butyl 4-(3-(2,4-dioxo-3,4-dihydropyrimidin-1(2H)-yl)quinolin-6-yl)piperidine-1-carboxylate (16-6, 562 mg, 1.33 mmol) in THF (10 mL) was added a 4M HCl solution in dioxane (3.0 mL, 13 mmol) and the resulting mixture was stirred for 3 h at 60° C. The solvents were removed under reduced pressure. Water was then added and the resulting aqueous mixture was lyophilized to dryness to provide product 16-7, which was used in the next step without further purification. MS $[M+H]^+$=323.3.

Step 4. 1-(6-(1-Benzylpiperidin-4-yl)quinolin-3-yl) pyrimidine-2,4(1H,3H)-dione (I-16)

To a solution of 1-(6-(piperidin-4-yl)quinolin-3-yl)pyrimidine-2,4(1H,3H)-dione-HCl salt (16-7, 477 mg, 1.33 mmol) in DMF (10 mL) was added DIPEA (700 μL, 3.99 mmol), followed by benzyl bromide (16-8, 190 μL, 1.6 mmol) and the resulting mixture was stirred at for 30 min at rt. The reaction mixture was diluted with EtOAc and washed with brine. The aqueous phase was extracted with EtOAc (x2) and the combined organic phases were dried over $Na_2SO_4$, filtered, and concentrated. The crude material was purified by silica gel flash chromatography eluting with 0-100% EtOAc in heptane and then 0-20% MeOH in DCM to provide the desired product I-16 (58 mg, 0.13 mmol, 10% yield). $^1$H NMR (400 MHz, DMSO-$d_6$) δ 11.60 (s, 1H), 8.87 (d, J=2.4 Hz, 1H), 8.39 (d, J=2.5 Hz, 1H), 8.01 (d, J=8.7 Hz, 1H), 7.93-7.83 (m, 2H), 7.78 (dd, J=8.7, 2.0 Hz, 1H), 7.34 (d, J=4.4 Hz, 4H), 7.29-7.16 (m, 2H), 5.78 (dd, J=7.9, 1.6 Hz, 1H), 3.53 (s, 2H), 2.96 (d, J=11.1 Hz, 2H), 2.80-2.68 (m, 1H), 2.11 (dd, J=12.5, 9.8 Hz, 2H), 1.90-1.66 (m, 4H). MS $[M+H]^+$=413.5.

Example 17: 1-(7-Bromoimidazo[1,2-a]pyridin-3-yl)pyrimidine-2,4(1H,3H)-dione (I-18) and 1-(7-(1-benzyl-1,2,3,6-tetrahydropyridin-4-yl)imidazo[1,2-a]pyridin-3-yl)pyrimidine-2,4(1H,3H)-dione (I-17)

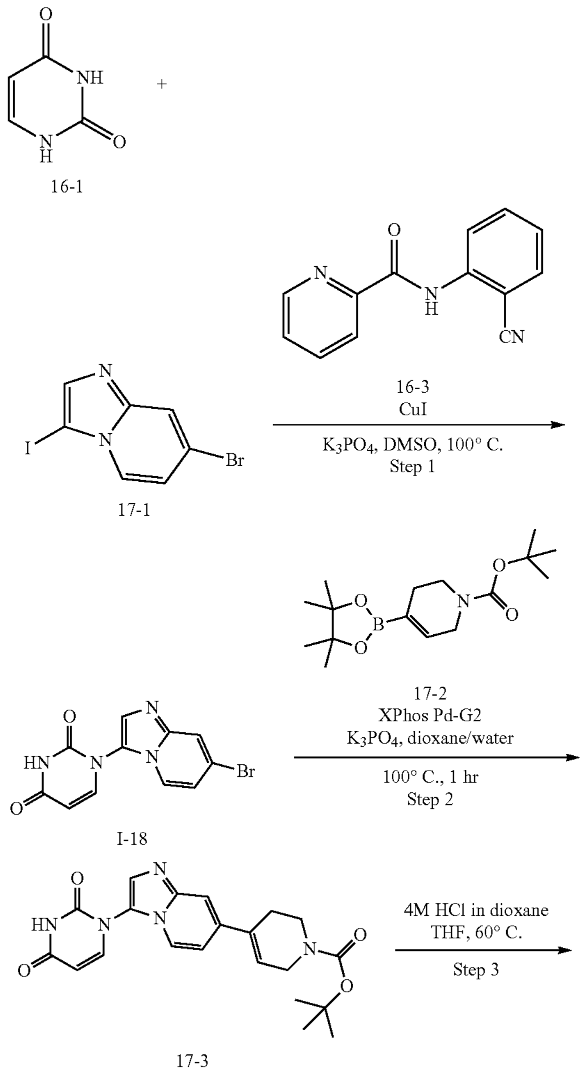

-continued

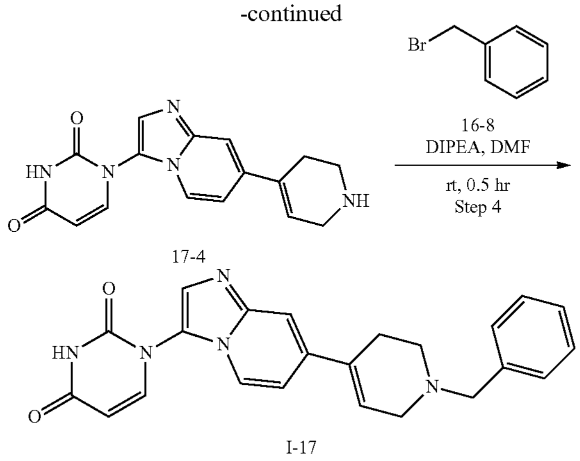

Step 1. 1-(7-Bromoimidazo[1,2-a]pyridin-3-yl)pyrimidine-2,4(1H,3H)-dione (I-18)

To a 0.5 mL-2 mL microwave vial was added pyrimidine-2,4(1H,3H)-dione (16-1, 21 mg, 0.19 mmol), 7-bromo-3-iodoimidazo[1,2-a]pyridine (17-1, 50 mg, 0.16 mmol), N-(2-cyanophenyl)picolinamide (16-3, prepared according to J. Org. Chem. 2019, 84, 4873-4892)(6 mg, 0.03 mmol, 20 mol %), CuI (3.0 mg, 0.015 mmol, 10 mol %) and $K_3PO_4$ (69 mg, 0.33 mmol) followed by DMSO (1.5 mL) and the resulting mixture was degassed with nitrogen and then microwaved for 16 h at 100° C. The reaction mixture was diluted with a mixture of DMSO:water:MeCN (~0.5 mL, v/v/v=1:1:1) and the solids were filtered. The filtrate was directly purified by reverse phase HPLC (ACN/$H_2O$+5 mM $NH_4OH$ at 75 ml/min; 1.5 mL injection; Column: Waters XBridge C18 OBD 30×100 mm) to provide the desired product I-18 (8.0 mg, 0.025 mmol, 16% yield) as a white solid. $^1$H NMR (400 MHz, DMSO-$d_6$) δ 8.05 (s, 1H), 7.95 (d, J=1.9 Hz, 1H), 7.61 (s, 1H), 7.38 (d, J=7.7 Hz, 1H), 7.12 (dd, J=7.3, 1.9 Hz, 1H), 5.52 (d, J=7.6 Hz, 1H). MS $[M+H]^+$=308.9.

Step 2. tert-Butyl 4-(3-(2,4-dioxo-3,4-dihydropyrimidin-1(2H)-yl)imidazo[1,2-a]pyridin-7-yl)-3,6-dihydropyridine-1(2H)-carboxylate (17-3)

To a 2 mL-5 mL microwave vial was added 1-(7-bromoimidazo[1,2-a]pyridin-3-yl)pyrimidine-2,4(1H,3H)-dione (I-18, 373 mg, 0.607 mmol), tert-butyl 4-(4,4,5,5-tetramethyl-1,3,2-dioxaborolan-2-yl)-3,6-dihydropyridine-1(2H)-carboxylate (17-2, 244 mg, 0.789 mmol), XPhos Pd-G2 (24 mg, 0.030 mmol), and $K_3PO_4$ (516 mg, 2.43 mmol) followed by dioxane (3 mL) and water (0.5 mL) and the resulting mixture was microwaved for 1 h at 100° C. The reaction mixture was then poured into saturated aqueous sodium bicarbonate solution (50 mL) and extracted with DCM (x2). The organic phases were combined and concentrated. The crude material was purified by silica gel flash chromatography eluting with 0-100% EtOAc in heptane and then 0-20% MeOH in DCM to afford the desired product 17-3 (64 mg, 0.16 mmol, 26% yield) as a cream colored solid. $^1$H NMR (400 MHz, DMSO-$d_6$) δ 11.65 (d, J=2.1 Hz, 1H), 8.30 (d, J=7.4 Hz, 1H), 7.76-7.61 (m, 2H), 7.57 (s, 1H), 7.21 (d, J=7.2 Hz, 1H), 6.46 (br s, 1H), 5.83-5.73 (m, 1H), 4.08 (d, J=17.6 Hz, 2H), 3.57 (t, J=5.5 Hz, 2H), 1.44 (d, J=3.9 Hz, 11H). MS $[M+H]^+$=410.5.

Step 3. 1-(7-(1,2,3,6-Tetrahydropyridin-4-yl)imidazo[1,2-a]pyridin-3-yl)pyrimidine-2,4(1H,3H)-dione (17-4)

To a suspension of tert-butyl 4-(3-(2,4-dioxo-3,4-dihydropyrimidin-1(2H)-yl)imidazo[1,2-a]pyridin-7-yl)-3,6-dihydropyridine-1(2H)-carboxylate (17-3, 24 mg, 0.059 mmol) in THF (3 mL) was added 4M HCl in dioxane (0.15 mL, 0.59 mmol) and the resulting mixture was heated for 18 h at 60° C. The reaction mixture was then allowed to warm to room temperature and concentrated under reduced pressure. Acetone was added to the crude material and the solids were filtered off. The solids were washed with diethyl ether and dried to provide desired product 17-4 (24 mg, 0.044 mmol, 75% yield) which was carried onto the next step without purification. $^1$H NMR (400 MHz, DMSO-$d_6$) δ 11.80 (d, J=2.1 Hz, 1H), 9.38 (s, 2H), 8.80 (d, J=7.4 Hz, 1H), 8.31 (s, 1H), 7.87 (s, 1H), 7.67 (t, J=7.4 Hz, 2H), 5.87 (dd, J=7.9, 2.2 Hz, 1H), 3.85 (br s, 2H), 3.67-3.57 (m, 2H), 3.37 (d, J=13.4 Hz, 2H), 2.79 (s, 1H). MS $[M+H]^+$=310.1.

Step 4. 1-(7-(1-Benzyl-1,2,3,6-tetrahydropyridin-4-yl)imidazo[1,2-a]pyridin-3-yl)pyrimidine-2,4(1H,3H)-dione (I-17)

To a solution of 1-(7-(1,2,3,6-tetrahydropyridin-4-yl)imidazo[1,2-a]pyridin-3-yl)pyrimidine-2,4(1H,3H)-dione (17-4, 24 mg, 0.063 mmol) in DMF (0.6 mL), was added DIPEA (44 µL, 0.25 mmol) followed by benzyl bromide (16-8, 12 µL, 0.094 mmol) and the resulting mixture was stirred for 30 min at rt. The reaction mixture was diluted with MeCN: water:DMSO (0.8 mL, v/v/v=1:1:1) and then purified by reverse phase HPLC (ACN/$H_2O$+5 mM $NH_4OH$ at 75 ml/min; 1.5 mL injection, Column: Waters XBridge C18 OBD 30×100 mm) to afford product I-17 (3 mg, 7 µmol, 11% yield). $^1$H NMR (400 MHz, DMSO-$d_6$) δ 11.64 (d, J=2.3 Hz, 1H), 8.27 (d, J=7.2 Hz, 1H), 7.75-7.66 (m, 2H), 7.53 (d, J=1.6 Hz, 1H), 7.39-7.30 (m, 4H), 7.27 (dt, J=5.6, 3.0 Hz, 1H), 7.20 (dd, J=7.4, 1.8 Hz, 1H), 6.49-6.44 (m, 1H), 5.76 (dd, J=7.9, 2.1 Hz, 1H), 3.60 (s, 2H), 3.12 (q, J=2.9 Hz, 2H), 2.66 (d, J=5.9 Hz, 2H), 2.58-2.53 (m, 2H). MS $[M+H]^+$=400.2.

Biological Assays and Data

The activity of a compound according to the present disclosure can be assessed by the following in vitro methods.

Example 18: Prolabel Quantification of IKZF1, GSPT1, or SALL4 protein levels in GripTite™ 293 MSR Cell line The Prolabel system from DiscoverX was used to develop high-throughput and quantitative assays to measure changes in IKZF1, GSPT1, and SALL4 protein levels in response to compounds. The prolabel tag is derived from the alpha fragment of beta galactosidase and has the following protein sequence: mssnslavvlgrrdwenpgvtglnrlaahppfaswrnseeartdrpsqqlrsinge (SEQ ID NO. 1). The complementary fragment of beta-galactosidase (from DiscoverX), is added to the prolabel tag to form an active beta galactosidase enzyme whose activity can be precisely measured. In this way, the levels of a fusion protein with the prolabel tag can be quantified in cell lysates.

Lentiviral vectors, based on the Invitrogen pLenti6.2/V5 DEST backbone, were constructed that placed the prolabel tag upstream of IKZF1, GSPT1, or SALL4 and expressed the fusion protein from a CMV promoter.

To ensure moderate and consistent expression of the prolabel fusion proteins across all cells in the population, stable cell lines were constructed from cells expressing a single copy of the construct. Lentivirus packaged with the constructs was made using the Virapower kit from Invitrogen. Strongly adherent 293GT cell, GripTite 293 MSR cells from Thermo Fisher Scientific (Catalog number: R79507), were infected with the virus at low multiplicity of infection and selected by 5 µg/mL blasticidin for 2 weeks.

The levels of prolabel tagged fusion proteins in compound treated cell lines were measured as follows:

Day 1, Cells were diluted to $1.0\times10^6$ cells/mL in normal growth medium. 17.5 µL of cells were plated in each well of a solid white 384 well plate. Plates were incubated overnight in a 37° C. tissue culture incubator.

Day 2, Serial dilutions of compounds were made in 384 well plates from 10 mM stocks. 15 µL of DMSO was added to each well of a 384 well plate. In the first column, 15 µL of stock compound was added. The solution was mixed and 15 µL was transferred to the next column. This was repeated until 20 two-fold dilutions were prepared. 2.5 µL of the diluted compounds were transferred into 60 µL of cell culture medium in another 384 well plate, and mixed well. 2.5 µL of this mixture was added to the plated cells. The final DMSO concentration was 0.5% and the highest concentration of compound was 50 µM. Plates were incubated overnight (e.g., about 14 h, 18 h, or 24 h) in a 37° C. tissue culture incubator.

Day 3, Plates were removed from the incubator and allowed to equilibrate at room temperature for 30 minutes. Prolabel substrate (DiscoverX PathHunter Prolabel Detection Kit, User manual: 93-0180) was added as described by the manufacturers protocols. Plates were incubated at room temperature for three hours and luminescence was read using an Envision reader (Perkin Elmer) Data was analyzed and visualized using the Spotfire software package.

Table 2 shows Ikaros (IKZF1) degradation activity of representative compounds in the disclosure in Pro-label assays in GripTite™ 293 MSR Cell line, ($EC_{50}$, and % degradation at 10 µM).

TABLE 2

| Cmpd No. | IKZF1 $EC_{50}$ (µM) | IKZF1 % protein reduction at 10 µM, 24 h | Cmpd No. | IKZF1 $EC_{50}$ (µM) | IKZF1 % protein reduction at 10 µM, 24 h |
|---|---|---|---|---|---|
| I-1 | 0.057 | 75% | I-3 | 0.016 | >90% |
| I-6 | 0.120 | 75% | I-12 | >20 | — |
| I-4 | 0.051 | 60% | I-13 | 0.006 | >90% |
| I-5 | 0.130 | >90% | I-14 | 0.025 | >90% |
| I-2 | 0.060 | >90% | I-15 | 0.63 | 80% |
| I-8 | 0.041 | >90% | I-16 | >20 | — |
| I-7 | 0.006 | >90% | I-17 | 0.43 | 80% |
| I-11 | 0.046 | >90% | I-18 | — | 40% |

Table 3 shows G1 to S phase transition 1 protein (GSPT1) degradation activity of representative compounds of the disclosure in Pro-label assays in GripTite™ 293 MSR Cell line, ($EC_{50}$, and % degradation at 10 µM).

TABLE 3

| Cmpd No. | GSPT1 $EC_{50}$ (μM) | GSPT1 % protein reduction at 10 μM, 24 h |
|---|---|---|
| I-9 | 0.170 | 80% |
| I-10 | 0.170 | 80% |

Table 4 shows Spalt Like Transcription Factor 4 (SALL4) degradation activity of representative compounds of the disclosure in Pro-label assays in GripTite™ 293 MSR Cell line, ($EC_{50}$, and % degradation at 101 μM).

TABLE 4

| Cmpd No. | SALL4 $EC_{50}$ (μM) | SALL4 % protein Reduction at 10 μM, 24 h |
|---|---|---|
| I-5 | — | 60% |
| I-10 | — | 60% |

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound or a pharmaceutically acceptable salt of Formula (I):

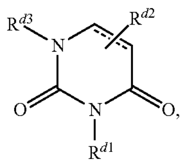

(I)

or a pharmaceutically acceptable salt, hydrate, solvate, stereoisomer, or tautomer thereof, wherein:

$\overline{\cdots}$ is a single bond or a double bond;

$R^{d1}$ is H, —$CH_2OC(O)R^{15}$, —$CH_2OP(O)OHOR^{15}$, or —$CH_2OP(O)(R^{15})_2$;

$R^{d2}$ is H, $C_{1-6}$ alkyl, halogen, $C_{1-6}$ haloalkyl, or $C_{1-6}$ heteroalkyl;

$R^{d3}$ is

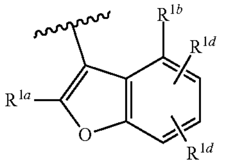

or

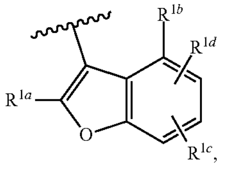

$R^{1a}$ and $R^{1b}$ are each independently H, $C_{1-3}$ alkyl, $C_{1-3}$ haloalkyl, $C_{1-3}$ alkoxy, $C_{1-3}$ haloalkoxy, —$NH_2$, —NH($C_{1-3}$ alkyl), —N($C_{1-3}$ alkyl)$_2$, —CN, F, or Cl;

$R^{1c}$ is $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)O$C_{1-6}$ alkyl, —$(CH_2)_{0-4}$—C(O) $NH_2$, —$(CH_2)_{0-4}$—C(O) NH($R^{13}$), —$(CH_2)_{0-4}$—C(O) N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3(CH_2)_{0-4}$—$C_{3-7}$ carbocyclyl, —$(CH_2)_{0-4}NR^3$ $(CH_2)_{0-4}$-5- to 7-membered heterocyclyl comprising 1-3 heteroatoms selected from O, N, and S, —$(CH_2)_{0-4}NR^3$ $(CH_2)_{0-4}$—$C_{6-10}$ aryl, —$(CH_2)_{0-4}NR^3$ $(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S;

each $R^{1d}$ is independently is selected from H, $C_{1-6}$ alkyl, $C_{2-6}$ alkenyl, $C_{2-6}$ alkynyl, $C_{1-6}$ haloalkyl, $C_{1-6}$ alkoxy, $C_{1-3}$ haloalkoxy, halogen, CN, —C(O)OH, —C(O)O$C_{1-6}$ alkyl, —$(CH_2)_{0-4}$—C(O) $NH_2$, —$(CH_2)_{0-4}$—C(O) NH($R^{13}$), —$(CH_2)_{0-4}$—C(O) N$(R^{13})_2$, —$(CH_2)_{0-6}$—$C_{3-7}$ carbocyclyl, —$(CH_2)_{0-6}$-5- to 7-membered heterocyclyl comprising 1-3 heteroatoms selected from O, N, and S, —$(CH_2)_{0-6}$ $C_{6-10}$ aryl, —$(CH_2)_{0-6}$-5- or 6-membered heteroaryl comprising 1-3 heteroatoms selected from O, N, and S, —$(CH_2)_{0-4}NR^3$ $(CH_2)_{0-4}$—$C_{3-7}$ carbocyclyl, —$(CH_2)_{0-4}NR^3$ $(CH_2)_{0-4}$-5- to 7-membered heterocyclyl comprising 1-3 heteroatoms selected from O, N, and S, —$(CH_2)_{0-4}NR^3$ $(CH_2)_{0-4}$—$C_{6-10}$ aryl, —$(CH_2)_{0-4}NR^3$ $(CH_2)_{0-4}$-5- or 6-membered heteroaryl comprising 1-3 heteroatoms selected from O, N, and S, —$(CH_2)_{0-4}$—$NR^3C(O)$—$C_{3-7}$ carbocyclyl, —$(CH_2)_{0-4}$—$NR^3C(O)$-5- to 7-membered heterocyclyl comprising 1-3 heteroatoms selected from O, N, and S, —$(CH_2)_{0-4}$—$NR^3C(O)$—$C_{6-10}$ aryl, —$(CH_2)_{0-4}$—$NR^3C(O)$-5- or 6-membered heteroaryl comprising 1-3 heteroatoms selected from O, N, and S, —$NR^3C(O)O(CH_2)_{0-4}$—$C_{3-7}$ carbocyclyl, —$NR^3C(O)O(CH_2)_{0-4}$-5- to 7-membered heterocyclyl comprising 1-3 heteroatoms selected from O, N, and S, —$NR^3C(O)O(CH_2)_{0-4}$—$C_{6-10}$ aryl, or —$NR^3C(O)O(CH_2)_{0-4}$-5- or 6-membered heteroaryl comprising 1-3 heteroatoms selected from O, N, and S;

each $R^3$ is independently H or $C_{1-6}$ alkyl;

each $R^{13}$ is independently $C_{1-6}$ alkyl, $C_{1-6}$ haloalkyl, $C_{6-10}$ aryl, or a 5- or 6-membered heteroaryl comprising 1-3 heteroatoms selected from O, N, and S, wherein the alkyl is optionally substituted with one to two $C_{1-6}$ alkoxy and the aryl and heteroaryl are optionally substituted with one to three $R^{14}$; and each $R^{14}$ is independently $C_{1-6}$ alkyl, $C_{1-6}$ haloalkyl, $C_{1-6}$ alkoxy, $C_{1-3}$ haloalkoxy, halogen, $C_{6-10}$ aryl, or a 5- or 6-membered heteroaryl comprising 1-3 heteroatoms selected from O, N, and S.

2. The compound of claim 1 or a pharmaceutically acceptable salt, hydrate, solvate, stereoisomer, or tautomer thereof, wherein $R^{d1}$ is H and $\overline{\cdots}$ is a single bond.

3. The compound of claim 1 or a pharmaceutically acceptable salt, hydrate, solvate, stereoisomer, or tautomer thereof, wherein $R^{d2}$ is H and ⎓ is a single bond.

4. The compound of claim 1 or a pharmaceutically acceptable salt, hydrate, solvate, stereoisomer, or tautomer thereof, wherein $R^{d1}$ and $R^{d2}$ are each independently H and ⎓ is a single bond.

5. The compound of claim 1 or a pharmaceutically acceptable salt, hydrate, solvate, stereoisomer, or tautomer thereof, wherein said compound is of Formula (Ic)

(Ic)

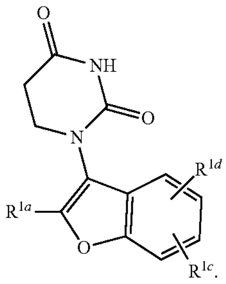

6. The compound of claim 5 or a pharmaceutically acceptable salt, hydrate, solvate, stereoisomer, or tautomer thereof, wherein $R^{1d}$ is H.

7. A compound selected from the group consisting of:

1-(benzofuran-3-yl)dihydropyrimidine-2,4 (1H,3H)-dione;

1-(6-ethynylbenzofuran-3-yl)dihydropyrimidine-2,4 (1H, 3H)-dione;

1-(5-methylbenzofuran-3-yl)dihydropyrimidine-2,4 (1H, 3H)-dione;

1-(5-iodobenzofuran-3-yl)dihydropyrimidine-2,4 (1H, 3H)-dione;

1-(6-iodobenzofuran-3-yl)dihydropyrimidine-2,4 (1H, 3H)-dione;

phenyl (3-(2,4-dioxotetrahydropyrimidin-1 (2H)-yl)benzofuran-5-yl) carbamate;

1-(6-(3-(dimethylamino) prop-1-yn-1-yl)benzofuran-3-yl)dihydropyrimidine-2,4 (1H,3H)-dione; and N-benzyl-3-(2,4-dioxotetrahydropyrimidin-1 (2H)-yl) benzofuran-6-carboxamide;

or a pharmaceutically acceptable salt thereof.

8. A pharmaceutical composition comprising a compound according to claim 1, or a pharmaceutically acceptable salt thereof, and a pharmaceutically acceptable carrier or excipient.

9. The pharmaceutical composition according to claim 8 further comprising at least one additional pharmaceutical agent.

* * * * *